United States Patent
Makings et al.

(10) Patent No.: US 8,367,691 B2
(45) Date of Patent: *Feb. 5, 2013

(54) MODULATORS OF MUSCARINIC RECEPTORS

(75) Inventors: Lewis R. Makings, Encinitas, CA (US); Miguel Garcia-Guzman Blanco, San Diego, CA (US); Dennis J. Hurley, San Marcos, CA (US); Ioana Drutu, La Jolla, CA (US); Gabriel Raffai, Tucson, AZ (US); Daniele M. Bergeron, La Mesa, CA (US); Akiko Nakatani, San Diego, CA (US); Andreas P. Termin, Encinitas, CA (US); Alina Silina, San Diego, CA (US)

(73) Assignee: Vertex Pharmaceutical Incorporated, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/794,202

(22) Filed: Jun. 4, 2010

(65) Prior Publication Data

US 2010/0311746 A1    Dec. 9, 2010

Related U.S. Application Data

(60) Division of application No. 11/359,960, filed on Feb. 22, 2006, now Pat. No. 7,786,141, which is a continuation-in-part of application No. 11/208,386, filed on Aug. 19, 2005, now Pat. No. 7,879,834.

(60) Provisional application No. 60/602,731, filed on Aug. 19, 2004.

(51) Int. Cl.
*A61K 31/44* (2006.01)
*C07D 471/00* (2006.01)

(52) U.S. Cl. .................................. 514/278; 546/85

(58) Field of Classification Search ........................ None
See application file for complete search history.

(56) References Cited

U.S. PATENT DOCUMENTS

| | | | |
|---|---|---|---|
| 3,654,287 A | 4/1972 | Dykstra | |
| 3,666,764 A | 5/1972 | Campbell et al. | |
| 3,959,475 A | 5/1976 | Bauer et al. | |
| 3,962,259 A | 6/1976 | Bauer et al. | |
| 4,233,307 A | 11/1980 | Ono et al. | |
| 4,349,549 A | 9/1982 | Roszkowski et al. | |
| 4,558,049 A | 12/1985 | Bernardi et al. | |
| 4,612,121 A | 9/1986 | Hermansson | |
| 5,091,387 A | 2/1992 | Evans et al. | |
| 5,219,860 A | 6/1993 | Chambers et al. | |
| 5,324,733 A | 6/1994 | Billington et al. | |
| 5,457,207 A | 10/1995 | Efange et al. | |
| 5,536,716 A | 7/1996 | Chen et al. | |
| 5,576,321 A | 11/1996 | Krushinski, Jr. et al. | |
| 5,578,593 A | 11/1996 | Chen et al. | |
| 5,614,523 A | 3/1997 | Audia et al. | |
| 5,627,196 A | 5/1997 | Audia et al. | |
| 5,652,235 A | 7/1997 | Chen et al. | |
| 5,658,921 A | 8/1997 | Perregaard et al. | |
| 5,665,725 A | 9/1997 | Moltzen et al. | |
| 5,693,643 A | 12/1997 | Gilbert et al. | |
| 5,741,789 A | 4/1998 | Hibschman et al. | |
| 5,789,402 A | 8/1998 | Audia et al. | |
| 5,817,679 A | 10/1998 | Shen et al. | |
| 5,885,999 A | 3/1999 | Elliott et al. | |
| 6,013,652 A | 1/2000 | Maccoss et al. | |
| 6,130,217 A | 10/2000 | Arnold et al. | |
| 6,166,040 A | 12/2000 | Fairhurst et al. | |
| 6,294,534 B1 | 9/2001 | Nargund et al. | |
| 6,316,437 B1 | 11/2001 | Hoffman | |
| 6,326,375 B1 | 12/2001 | Fukami et al. | |
| 6,436,962 B1 | 8/2002 | Hoffman et al. | |
| 6,566,367 B2 | 5/2003 | Bakthavatchalam et al. | |
| 6,713,487 B2 | 3/2004 | Yu et al. | |
| 6,720,324 B2 | 4/2004 | Marzabadi et al. | |
| 6,828,440 B2 | 12/2004 | Goehring et al. | |
| 6,869,960 B2 | 3/2005 | Ito et al. | |
| 6,943,199 B2 | 9/2005 | DeLombaert et al. | |
| 7,045,527 B2 | 5/2006 | Chen et al. | |
| 7,205,417 B2 | 4/2007 | Fukami et al. | |
| 7,279,471 B2 | 10/2007 | Mueller et al. | |
| 7,351,706 B2 | 4/2008 | Bissantz et al. | |
| 7,491,715 B2 | 2/2009 | Ek et al. | |
| 7,858,635 B2 * | 12/2010 | Makings et al. | ............... 514/278 |
| 2002/0188124 A1 | 12/2002 | Fukami et al. | |
| 2003/0036652 A1 | 2/2003 | Bakthavatchalam et al. | |
| 2003/0158219 A1 | 8/2003 | Ito et al. | |
| 2004/0054177 A1 | 3/2004 | Otake et al. | |
| 2004/0072847 A1 | 4/2004 | Bakthavatchalam et al. | |
| 2004/0122074 A1 | 6/2004 | Dow et al. | |
| 2004/0142956 A1 | 7/2004 | Chen et al. | |
| 2004/0204397 A1 | 10/2004 | Chaturvedula et al. | |

(Continued)

FOREIGN PATENT DOCUMENTS

CN    1535967 A    10/2004
EP    0070171 A1    1/1983

(Continued)

OTHER PUBLICATIONS

Abdel-Madid, A., et al., "Reductive Amination of Aldehydes and Ketones with Sodium Tracetoxyborohydride. Studies on Direct and Indirect Reductive Amination Procedures1", J. Org. Chem. (1996) vol. 61, pp. 3849-3862.

Bignan, G., et al., "Preparation of 3-Spirocyclic Indolin-2-ones as Ligands for the ORL-1 Receptor," Bioorganic and Medicinal Chem. Lett, (2005) vol. 15, pp. 5022-5026.

Butera, J., et al., "Recent Approaches to the Treatment of Urinary Incontinence: A Survey of Patent Activity from 1995 to 1998," Expert Opinion on Therapeutic Patents (1998) vol. 8, No. 8, pp. 1017-1035.

Bymaster, F., et al., "Xanomiline: A Selective Muscarinic Agonist for the Treatment of Alzheimer's Disease," Drug Development Research (1997) vol. 40, pp. 158-170.

Caufield, M.P., et al., "International Union of Pharmacology. XVII. Classification of Muscarinic Acetylcholine Receptors," Pharmacol. Rev., (1998) vol. 50, No. 2, pp. 279-290.

(Continued)

*Primary Examiner* — Noble Jarrell
(74) *Attorney, Agent, or Firm* — Honigman Miller Schwartz and Cohn LLP; Christopher C. Forbes; Jonathan P. O'Brien

(57) ABSTRACT

The present invention relates to modulators of muscarinic receptors. The present invention also provides compositions comprising such modulators, and methods therewith for treating muscarinic receptor mediated diseases.

5 Claims, No Drawings

U.S. PATENT DOCUMENTS

| | | |
|---|---|---|
| 2005/0033048 A1 | 2/2005 | Bakthavatchalam et al. |
| 2005/0143372 A1 | 6/2005 | Ghosh et al. |
| 2005/0153998 A1 | 7/2005 | Ito et al. |
| 2005/0176703 A1 | 8/2005 | Gabriel et al. |
| 2005/0215576 A1 | 9/2005 | Degnan et al. |
| 2005/0261332 A1 | 11/2005 | DiStefano et al. |
| 2006/0019962 A1 | 1/2006 | Makings et al. |
| 2006/0040964 A1 | 2/2006 | Bakthavatchalam et al. |
| 2006/0058778 A1 | 3/2006 | Arcusa Villacampa et al. |
| 2006/0106045 A1 | 5/2006 | Hughes et al. |
| 2006/0111380 A1 | 5/2006 | Otake et al. |
| 2006/0173027 A1 | 8/2006 | Marzabadi et al. |
| 2006/0183904 A1 | 8/2006 | Guo et al. |
| 2006/0211722 A1 | 9/2006 | Jiao et al. |
| 2006/0217372 A1 | 9/2006 | Blanco-Pillado et al. |
| 2006/0270673 A1 | 11/2006 | Duggan et al. |
| 2007/0043023 A1 | 2/2007 | Makings et al. |
| 2007/0149502 A1 | 6/2007 | Chaturvedula et al. |
| 2007/0254903 A1 | 11/2007 | Boatman et al. |
| 2008/0171753 A1 | 7/2008 | Jitsuoka et al. |

FOREIGN PATENT DOCUMENTS

| | | |
|---|---|---|
| EP | 0414289 A1 | 2/1991 |
| EP | 0444945 A2 | 9/1991 |
| EP | 0486280 A2 | 5/1992 |
| GB | 1575800 | 10/1980 |
| GB | 2308064 A | 6/1997 |
| JP | 59059685 A | 4/1984 |
| JP | 2001/278886 | 10/2001 |
| JP | 2002/316987 | 10/2002 |
| WO | 94/22846 A1 | 10/1994 |
| WO | 95/11029 A1 | 4/1995 |
| WO | 95/14025 A1 | 5/1995 |
| WO | 95/28389 A1 | 10/1995 |
| WO | 97/41878 A1 | 11/1997 |
| WO | 97/41879 A1 | 11/1997 |
| WO | 99/06434 A1 | 2/1999 |
| WO | 99/32489 A1 | 7/1999 |
| WO | 00/06146 A1 | 2/2000 |
| WO | 00/06153 A1 | 2/2000 |
| WO | 00/06545 A1 | 2/2000 |
| WO | 00/38720 A1 | 7/2000 |
| WO | 01/02386 A1 | 1/2001 |
| WO | 01/22919 A2 | 4/2001 |
| WO | 01/29027 A1 | 4/2001 |
| WO | 01/45707 A1 | 6/2001 |
| WO | 01/64213 A1 | 9/2001 |
| WO | 02/094825 A1 | 11/2002 |
| WO | 03/095427 A1 | 11/2003 |
| WO | 2004/010942 A2 | 2/2004 |
| WO | 2004/010943 A2 | 2/2004 |
| WO | 2004/011427 A2 | 2/2004 |
| WO | 2005/065779 A1 | 7/2005 |
| WO | 2006/001958 A2 | 1/2006 |

OTHER PUBLICATIONS

Caufield, M.P., "Muscarinic Receptors-Characterization, Coupling and Function," Pharmac. Ther. (1993) vol. 58, pp. 319-379.

Chambers, Mark S., et al., "Spiropiperidines as High-Affinity, Selective s Ligands," Journal of Medicinal Chemistry (1992) vol. 35, No. 11, pp. 2033-2039.

Cheng, Y., et al., "Solid Phase Synthesis of Spiroindoline," Tet. Lett. (1997) vol. 38, No. 9, pp. 1497-1500.

Chiavarelli, S., et al., "Ricerche nella serle della 4-feniipiperidina. Nota v. Derivati della 4,4'-spiro-(1"metilpiperidin)-1,2,3,4,-tetraidroisochinolina," Gazzetta Chimica Italiana (1960) vol. 90, pp. 189-195.

Custers, F., et al., "Vesamicol and Some of its Derivatives: Questionable Ligands for Selectively Labeling Acetylcholine Transporters in Rat Brain," Eur. Jour. of Pharm. (1997) vol. 338, pp. 177-183.

deLaszlo, S.E., et al., "A Nonpeptidic Agonist Ligand of the Human C5A Receptor: Synthesis, Binding Affinity Optimization and Functional Characterization," Bioorganic and Medicinal Chem. Lett. (1997) vol. 7, No. 2, pp. 213-218.

Dhar, T.G. Murali, et al., "Design and Synthesis of Novel a1a Adrenoceptor-selective Antagonists," Journal of Medicinal Chemistry (1999) vol. 42, No. 23, pp. 4778-4793.

Efange, S.M.N., et al., "(+)-p-([18F]Fluorobenzyl)Spirotrozamicol {(+)-[18F]Spiro-FBT}: Synthesis and Biological Evaluation of a High-Affinity Ligand for the Vesicular Acetylcholine Transporter (VAChT)," Nuclear Medicine and Biology (1999) vol. 26, pp. 189-192.

Efange, S.M.N., et al., "Comparative Tissue Distribution of Conformationally Restricted Radioiodinated Vesamicol Receptor Ligands," Nuclear Medicine and Biology (1995) vol. 22, No. 4, pp. 437-444.

Efange, S.M.N., et al., "Spirovesamicols: Conformationally Restricted Analogs of 2-(4-Phenylpiperidino) Cyclohexnol (Vesamicol, AH5183) as Potential Modulators of Presynaptic Cholinergic Function," Journal of Medicinal Chemistry (1994) vol. 37, No. 16, pp. 2574-2582.

Efange, S.M.N., et al., "N-Hydroxyalkyl Derivatives of 3β-Phenyltropane and Methylspiro[1H-indoline-3,4'-piperidine]: Vesamicol Analogues with Affinity of Monoamine Transporters," J. Med. Chem. (1997) vol. 40, pp. 3905-3914.

Efange, S.M.N., et al., "Vesamicol Analogs as Sigma Ligands. Molecular Determinants of Selectivity at the Vesamicol Receptor," Biochem. Pharm. (1995) vol. 49, No. 6, pp. 791-797.

Evans, Ben E., et al., "Orally Active, Nonpeptide Oxytocin Antagonists," Journal of Medicinal Chemistry (1992) vol. 35, No. 21, pp. 3919-3927.

Felder, C., et al., "Therapeutic Opportunities for Muscarinic Receptors in the Central Nervous System," J. Med. Chem. (2000) vol. 43, No. 23, pp. 4333-4353.

Freireich, et al., "Quantitative Comparison of Toxicity of Anticancer Agents in Mouse, Rat, Hamster, Dog, Monkey and Man," Cancer Chemother, Rep. (1966) vol. 50, pp. 219-244.

Hulme, E.C., et al., "Muscarinic Receptor Subtypes," Annu. Rev. Pharmacol. Toxicol. (1990) vol. 30, pp. 633-673.

Kim, Dooseop, et al., "Discovery of Human CCR5 Antagonists Containing Hydantoins for the Treatment of HIV-1 Infection," Bioorganic and Medicinal Chem. Lett. (2001) vol. 11, pp. 3099-3102.

Maligres, P.E., et al., "Synthesis of the Orally Active Spiroindoline-Based Growth Hormone Secretagogue, MK-677," Tetrahedron (1997) vol. 53, No. 32, pp. 10983-10992.

Malmstrom, R.E., et al., "Pharmacology of H 394/84, a Dihydropyridine Neuropeptide Y Y1 Receptor Antagonist, in Vivo," Eur. Jour. of Pharm. (2001) vol. 418, pp. 95-104.

Matier, W., et al., "Novel Cyclizations and Ring-Opening Reactions of 3-Phenylindene Derivatives," J. Org. Chem. (1971) vol. 36, No. 5, pp. 650-654.

Moltzen, Ejner K., et al., "s Ligands with Subnanomolar Affinity and Preference for the s2 Binding Site," Journal of Medicinal Chemistry (1995) vol. 38, No. 11, pp. 2009-2017.

Morrow, D.F., et al., "Synthesis of Some New 17-Spiro-Substituted Steroids," J. Med. Chem. (1967) vol. 10, No. 2, pp. 133-138.

Nargund, R., et al., "Peptidomimetic Growth Hormone Secretagogues: Synthesis and Biological Activities of Analogs Varied at the Indole Nucleus of the Prototypical Spiropiperidine L-162,752," Bioorganic and Medicinal Chem. Lett. (1996) vol. 6, No. 14, pp. 1731-1736.

Nargund, R., et al., "Synthesis and Biological Activities of Camphor-Based Non-Peptide Growth Hormone Secretagogues," Bioorganic and Medicinal Chem. Lett. (1996) vol. 6, No. 11, pp. 1265-1270.

Oprea, T., et al., "Is There a Difference Between Leads and Drugs? A Historical Perspective," J. Chem. Inf. Comput. Sci. (2001) vol. 41, pp. 1308-1315.

Pasternak, A., et al., "Potent, Orally Bioavailable Somatostatin Agonists: Good Absorption Achieved by Urea Backbone Cyclization," Bioorganic and Medicinal Chem. Lett. (1999) vol. 9, pp. 491-496.

Patchett, A.A., et al., "The Synthesis of 17β-Amino-17 a-(2'-carboxyethyl)androstane Lacatama1," J. Org. Chem. (1962) vol. 27, pp. 3822-3828.

Pettibone, D.J., et al., "Identification of an Orally Active, Nonpeptidyl Oxytocin Antagonist," Journal of Pharm. and Experimental Therap. (1993) vol. 264, No. 1, pp. 308-314.

Reimann, E., et al., "Synthese und Pharmakologische Pr fung Holologer und Hydroxylierter 3,4-Dihydro-1'-methyispiro [naphthalin-(2H),4'-piperidine]," Archiv. Der. Pharmazie, VCH Verlagsgesellschaft MBH, Weinheim, DE, (1990) vol. 323, pp. 35-39.

Rubin, B.K., et al., "Novel Medications for Asthma: A Look into the Future," Exper. Opinion on Investigational Drugs (2007) vol. 16, No. 6, pp. 889-897.

Takemoto, T., et al., "Asymmetric Synthesis of Enantiomerically Pure Spiro[((2S)-hydroxy)indane-1,4'-piperidine]," Tetrahedron Asymmetry (1999) vol. 10, pp. 1787-1793.

Tata, J., et al., "The Synthesis and Activity of Spiroindine Growth Hormone Secretagogues," Bioorganic and Medicinal Chem. Lett. (1997) vol. 7, No. 6, pp. 663-668.

Williams, P., et al., "1-(((7,7-Dimethyl-2(S)-(2(S)-amino-4-(methylsulfonyl)butyramido)bicyclo[2.2.1]-heptan-1(S)-yl) methyl)sulfonyl)-4-2(2-methylphenyl)piperazine (L-368,899): An Orally Bioavailable, Non-Peptide Oxytocin Antagonist with Potential Utility for Managing Preterm Labor," J. Med. Chem. (1994) vol. 37, pp. 555-571.

Yang, Lihu, et al., "Potent 3-Spiropiperidine Growth Hormone Secretagogues," Bioorganic & Medicinal Chemistry Letters (1998) vol. 8, No. 1, pp. 107-112.

Yang, Lihu, et al., "The Design and Synthesis of non-peptide Somatostatin Receptor Agonists," Peptides for the New Millennium, Proceedings of the American Peptide Symposium, 16th, Minneapolis, MN, Jun. 26-Jul. 1999 (2000), Meeting Date 1999, pp. 250-252.

* cited by examiner

MODULATORS OF MUSCARINIC RECEPTORS

CLAIM OF PRIORITY

This application is divisional of U.S. patent application Ser. No. 11/359,960, filed on Feb. 22, 2006, which is a continuation-in-part of U.S. patent application Ser. No. 11/208,386 filed on Aug. 19, 2005, which claims the benefit of U.S. provisional patent application No. 60/602,731, filed on Aug. 19, 2004, all of which are hereby incorporated by reference.

TECHNICAL FIELD OF THE INVENTION

The present invention relates to modulators of muscarinic receptors. The present invention also provides compositions comprising such modulators, and methods therewith for treating muscarinic receptor mediated diseases.

BACKGROUND OF THE INVENTION

The neurotransmitter acetylcholine binds to two types of cholinergic receptors: the ionotropic family of nicotinic receptors and the metabotropic family of muscarinic receptors. Muscarinic receptors belong to the large superfamily of plasma membrane-bound G protein coupled receptors (GPCRs). To date, five subtypes of muscarinic receptors ($M_1$-$M_5$) have been cloned and sequenced from a variety of species, and show a remarkably high degree of homology across species and receptor subtype. These $M_1$-$M_5$ muscarinic receptors are predominantly expressed within the parasympathetic nervous system which exerts excitatory and inhibitory control over the central and peripheral tissues and participate in a number of physiologic functions, including heart rate, arousal, cognition, sensory processing, and motor control.

Muscarinic agonists such as muscarine and pilocarpine, and antagonists, such as atropine have been known for over a century, but little progress has been made in the discovery of receptor subtype-selective compounds, thereby making it difficult to assign specific functions to the individual receptors. See, e.g., DeLapp, N. et al., "Therapeutic Opportunities for Muscarinic Receptors in the Central Nervous System," *J. Med. Chem.*, 43(23), pp. 4333-4353 (2000); Hulme, E. C. et al., "Muscarinic Receptor Subtypes," *Ann. Rev. Pharmacol. Toxicol.*, 30, pp. 633-673 (1990); Caulfield, M. P. et al., "Muscarinic Receptors—Characterization, Coupling, and Function," *Pharmacal. Ther.*, 58, pp. 319-379 (1993); Caulfield, M. P. et al., International Union of Pharmacology. XVII. "Classification of Muscarinic Acetylcholine Receptors," *Pharmacol. Rev.*, 50, pp. 279-290 (1998), the disclosures of which are incorporated herein by reference.

The Muscarinic family of receptors is the target of a large number of pharmacological agents used for various diseases, including leading drugs for COPD, asthma, urinary incontinence, glaucoma, Alzheimer's (AchE inhibitors). Despite the large therapeutic value of this family, cholinergic drugs are limited by the lack of selectivity of these agents, with significant activation of the parasympathetic autonomous system and elevated incidence of adverse effects. The molecular cloning of the muscarinic receptors and the identification of the physiological role of specific isoforms using knock-out mice, has recently delineated novel opportunities for selective muscarinic ligands, and has helped to define the selectivity profile that is required for enhanced efficacy and reduced side effects.

There is a need for modulators of muscarinic receptors $M_1$-$M_5$. There is also a need for methods for treating muscarinic receptor-mediated diseases.

There is also a need for modulators of muscarinic receptors that are selective as to subtypes $M_1$-$M_5$.

SUMMARY OF THE INVENTION

The present invention provides methods of modulating activity of a muscarinic receptor using compounds of formula (I):

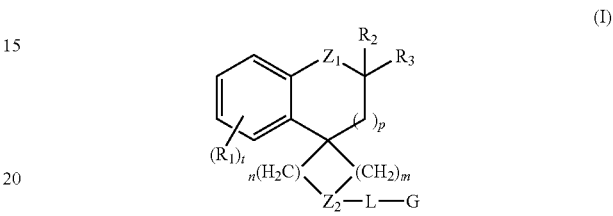

and pharmaceutically acceptable salts thereof.

Each of $R_1$, $R_2$, $R_3$ is independently $Q_1$ or $Q_2$, or $R_2$ and $R_3$ together form oxo.

$Z_1$ is —C($Q_1$)$_2$-, —C(H)($Q_1$)-, —C(H)($Q_5$)-, —C(O)—, —CH$_2$—, —N($Q_1$)-, —N($Q_2$)-, or O.

$Z_2$ is N.

L is a bond, an aliphatic group, $C_3$-$C_6$ cycloaliphatic, —O—, —S(O)$_z$—, —S(O)$_z$—($C_1$-$C_4$)alkyl-, —C(O)N($Q_2$)-, or —S(O)$_z$N($Q_2$)-, in which the aliphatic group is optionally substituted with 1-3 of oxo, $Q_1$, or $Q_2$.

G is a monocycloaliphatic group, a monocycloheteroaliphatic group, adamantyl, or a bicyclic or a tricyclic group of the formula (III)

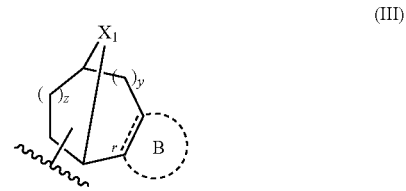

in which the monocycloaliphatic group, the monocycloheteroalipahtic group, the adamantyl, and the bicyclic or tricyclic group are connected to L via any ring atom including those in $X_1$ and ring B, and the monocycloaliphatic, the monocycloheteroaliphatic, the bicyclic, and the tricyclic groups are optionally substituted with 1-3 of oxo, =N—O$Q_4$, fluorine, $Q_2$, —C(O)—$X_2$-aliphatic in which $X_2$ is absent, —O—, —NH—, —NQ$_2$-, or —S(O)$_z$— and the aliphatic group is optionally substituted with 1-3 substituents independently selected from $Q_3$; bond r is a single or double bond and when ring B is present, bond r is fused with B; ring B, when present, is a 5-6 membered cycloaliphatic or heterocyclic ring; and ring B is optionally substituted with 1-3 of oxo, $Q_1$, or $Q_2$.

$X_1$ is —(CH$_2$)$_i$—, —O—, —S—, —N($Q_2$)-, —N(C(O)—$X_2$-aliphatic)- in which $X_2$ is absent, —O—, —NH—, —NQ$_2$-, or —S(O)$_z$— and the aliphatic group is optionally substituted with 1-3 substituents independently selected from $Q_3$;

Each $Q_1$ is independently halo, —CN, —NO$_2$, —O$Q_2$, —S(O)$_z$$Q_2$, —S(O)$_z$N($Q_2$)$_2$, —N($Q_2$)$_2$, —C(O)O$Q_2$, —C(O)-Q$_2$, —C(O)N(Q$_2$)$_2$, —C(O)N(Q$_2$)(OQ$_2$), —N(Q$_2$)C(O)-Q$_2$, —N(Q$_2$)C(O)N(Q$_2$)$_2$, —N(Q$_2$)C(O)O-Q$_2$, —N(Q$_2$)S(O)$_z$-Q$_2$ or aliphatic optionally including 1-3 substituents independently selected from Q$_2$ or Q$_3$.

Each Q$_2$ is independently H, aliphatic, cycloaliphatic, aryl, arylalkyl, heterocyclic, or heteroaryl ring, each optionally substituted with 1-3 substituents independently selected from Q$_3$. In several examples, Q$_2$ is a heteroaryl ring optionally substituted with 1-3 of Q$_3$. In other examples, Q$_2$ is a pyrazole-yl, a thiadiazole-yl, or a pyrazine-yl, each of which is optionally substituted with 1-3 of C$_{1-4}$ aliphatic.

Each Q$_3$ is halo, oxo, CN, NO$_2$, CF$_3$, OCF$_3$, OH, —S(O)$_z$Q$_4$, —N(Q$_4$)$_2$, —COOQ$_4$, —C(O)Q$_4$, —OQ$_4$ or C$_1$-C$_4$ alkyl optionally substituted with 1-3 halo, oxo, —CN, —NO$_2$, —CF$_3$, —OCF$_3$, —OH, —SH, —S(O)$_z$H, —NH$_2$, or —COOH.

Each Q$_4$ is aliphatic, cycloaliphatic, aryl, aralkyl, heterocycloaliphatic, heteroaralky, or heteroaryl, each optionally including 1-3 substituents selected from halo, oxo, CN, NO$_2$, CF$_3$, OCF$_3$, OH, SH, —S(O)$_z$H, —NH$_2$, or COOH.

Each Q$_5$ is a heterocyclic ring optionally substituted with 1-3 substituents selected from halo, C$_1$-C$_4$alkyl, oxo, CN, NO$_2$, CF$_3$, OCF$_3$, OH, SH, —S(O)$_z$H, —NH$_2$, COOH; and each i is independently 1, 2, or 3; each m and n is independently 1, 2, 3, or 4 provided that m+n is at least 4; each p is 0 or 1; each y is independently 0 or 1; t is 1 to 4; and each z is independently 0, 1, or 2.

Additional aspects of the present invention provide compounds of formula (II), pharmaceutical compositions that are useful modulators of muscarinic receptors, and methods of treating muscarinic receptor mediated diseases using compounds of formulae (I and II).

Advantageously, the compounds of the invention are generally selective for M$_1$ and M$_4$ muscarinic receptors. Unexpectedly, the compounds of the invention exhibit increased activity and/or efficacy for M$_1$ and/or M$_4$ muscarinic receptors relative to other muscarinic receptors.

DETAILED DESCRIPTION OF THE INVENTION

As used herein, the following definitions shall apply unless otherwise indicated.

I. Definitions

For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "muscarinic receptor," without a prefix specifying the receptor subtype, refers to one or more of the five receptor subtypes M$_1$-M$_5$.

The term "modulating" as used herein means increasing or decreasing, e.g. activity, by a measurable amount. Compounds that modulate muscarinic activity by increasing the activity of the muscarinic receptors are called agonists. Compounds that modulate muscarinic activity by decreasing the activity of the muscarinic receptors are called antagonists. An agonist interacts with a muscarinic receptor to increase the ability of the receptor to transduce an intracellular signal in response to endogenous ligand binding. An antagonist interacts with a muscarinic receptor and competes with the endogenous ligand(s) or substrate(s) for binding site(s) on the receptor to decrease the ability of the receptor to transduce an intracellular signal in response to endogenous ligand binding.

The phrase "treating or reducing the severity of a muscarinic receptor mediated disease" refers both to treatments for diseases that are directly caused by muscarinic activities and alleviation of symptoms of diseases not directly caused by muscarinic activities. Examples of diseases whose symptoms may be affected by muscarinic activity include, but are not limited to, CNS derived pathologies including cognitive disorders, Attention Deficit Hyperactivity Disorder (ADHD), obesity, Alzheimer's disease, various dementias such as vascular dementia, psychosis including schizophrenia, mania, bipolar disorders, pain conditions including acute and chronic syndromes, Huntington's Chorea, Friederich's ataxia, Gilles de la Tourette's Syndrome, Downs Syndrome, Pick disease, clinical depression, Parkinson's disease, peripheral disorders such as reduction of intra ocular pressure in Glaucoma and treatment of dry eyes and dry mouth including Sjögren's Syndrome, bradhycardia, gastric acid secretion, asthma, GI disturbances and wound healing.

As described herein, compounds of the invention may optionally be substituted with one or more substituents, such as are illustrated generally above, or as exemplified by particular classes, subclasses, and species of the invention.

As used herein the term "aliphatic" encompasses the terms alkyl, alkenyl, alkynyl, each of which being optionally substituted as set forth below.

As used herein, an "alkyl" group refers to a saturated aliphatic hydrocarbon group containing 1-8 (e.g., 1-6 or 1-4) carbon atoms. An alkyl group can be straight or branched. Examples of alkyl groups include, but are not limited to, methyl, ethyl, propyl, isopropyl, butyl, isobutyl, sec-butyl, tert-butyl, n-pentyl, n-heptyl, or 2-ethylhexyl. An alkyl group can be substituted (i.e., optionally substituted) with one or more substituents such as halo, cycloaliphatic [e.g., cycloalkyl or cycloalkenyl], heterocycloaliphatic [e.g., heterocycloalkyl or heterocycloalkenyl], aryl, heteroaryl, alkoxy, aroyl, heteroaroyl, acyl [e.g., (aliphatic)carbonyl, (cycloaliphatic)carbonyl, or (heterocycloaliphatic)carbonyl], nitro, cyano, amido [e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl], amino [e.g., aliphaticamino, cycloaliphaticamino, or heterocycloaliphaticamino], sulfonyl [e.g., aliphatic-SO$_2$—], sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroarylalkoxy, alkoxycarbonyl, alkylcarbonyloxy, or hydroxy. Without limitation, some examples of substituted alkyls include carboxyalkyl (such as HOOC-alkyl, alkoxycarbonylalkyl, and alkylcarbonyloxyalkyl), cyanoalkyl, hydroxyalkyl, alkoxyalkyl, acylalkyl, aralkyl, (alkoxyaryl)alkyl, (sulfonylamino)alkyl (such as (alkyl-SO$_2$-amino)alkyl), aminoalkyl, amidoalkyl, (cycloaliphatic)alkyl, or haloalkyl.

As used herein, an "alkenyl" group refers to an aliphatic carbon group that contains 2-8 (e.g., 2-6 or 2-4) carbon atoms and at least one double bond. Like an alkyl group, an alkenyl group can be straight or branched. Examples of an alkenyl group include, but are not limited to, allyl, isoprenyl, 2-butenyl, and 2-hexenyl. An alkenyl group can be optionally substituted with one or more substituents such as halo, cycloaliphatic [e.g., cycloalkyl or cycloalkenyl], heterocycloaliphatic [e.g., heterocycloalkyl or heterocycloalkenyl], aryl, heteroaryl, alkoxy, aroyl, heteroaroyl, acyl [e.g., (aliphatic)carbonyl, (cycloaliphatic)carbonyl, or (heterocycloaliphatic)carbonyl], nitro, cyano, amido [e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl], amino [e.g., aliphaticamino, cycloaliphaticamino, heterocycloaliphaticamino, or aliphaticsulfonylamino], sulfonyl [e.g., alkyl-$SO_2$—, cycloaliphatic-$SO_2$—, or aryl-$SO_2$—], sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroaralkoxy, alkoxycarbonyl, alkylcarbonyloxy, or hydroxy. Without limitation, some examples of substituted alkenyls include cyanoalkenyl, alkoxyalkenyl, acylalkenyl, hydroxyalkenyl, aralkenyl, (alkoxyaryl)alkenyl, (sulfonylamino)alkenyl (such as (alkyl-$SO_2$-amino)alkenyl), aminoalkenyl, amidoalkenyl, (cycloaliphatic)alkenyl, or haloalkenyl.

As used herein, an "alkynyl" group refers to an aliphatic carbon group that contains 2-8 (e.g., 2-6 or 2-4) carbon atoms and has at least one triple bond. An alkynyl group can be straight or branched. Examples of an alkynyl group include, but are not limited to, propargyl and butynyl. An alkynyl group can be optionally substituted with one or more substituents such as aroyl, heteroaroyl, alkoxy, cycloalkyloxy, heterocycloalkyloxy, aryloxy, heteroaryloxy, aralkyloxy, nitro, carboxy, cyano, halo, hydroxy, sulfo, mercapto, sulfanyl [e.g., aliphaticsulfanyl or cycloaliphaticsulfanyl], sulfinyl [e.g., aliphaticsulfinyl or cycloaliphaticsulfinyl], sulfonyl [e.g., aliphatic-$SO_2$—, aliphaticamino-$SO_2$—, or cycloaliphatic-$SO_2$—], amido [e.g., aminocarbonyl, alkyl aminocarbonyl, alkylcarbonylamino, cycloalkylaminocarbonyl, heterocycloalkylaminocarbonyl, cycloalkylcarbonylamino, arylaminocarbonyl, arylcarbonylamino, aralkylcarbonylamino, (heterocycloalkyl)carbonylamino, (cycloalkylalkyl)carbonylamino, heteroaralkylcarbonylamino, heteroarylcarbonylamino or heteroarylaminocarbonyl], urea, thiourea, sulfamoyl, sulfamide, alkoxycarbonyl, alkylcarbonyloxy, cycloaliphatic, heterocycloaliphatic, aryl, heteroaryl, acyl [e.g., (cycloaliphatic)carbonyl or (heterocycloaliphatic)carbonyl], amino [e.g., aliphaticamino], sulfoxy, oxo, carboxy, carbamoyl, (cycloaliphatic)oxy, (heterocycloaliphatic)oxy, or (heteroaryl)alkoxy.

As used herein, an "amido" encompasses both "aminocarbonyl" and "carbonylamino". These terms when used alone or in connection with another group refers to an amido group such as —N($R^X$)—C(O)—$R^Y$ or —C(O)—N($R^X$)$_2$, when used terminally, and —C(O)—N($R^X$)— or —N($R^X$)—C(O)— when used internally, wherein $R^X$ and $R^Y$ are defined below. Examples of amido groups include alkylamido (such as alkylcarbonylamino or alkylaminocarbonyl), (heterocycloaliphatic)amido, (heteroaralkyl)amido, (heteroaryl)amido, (heterocycloalkyl)alkylamido, arylamido, aralkylamido, (cycloalkyl)alkylamido, or cycloalkylamido.

As used herein, an "amino" group refers to —$NR^XR^Y$ wherein each of $R^X$ and $R^Y$ is independently hydrogen, alkyl, cycloaliphatic, (cycloaliphatic)aliphatic, aryl, araliphatic, heterocycloaliphatic, (heterocycloaliphatic)aliphatic, heteroaryl, carboxy, sulfanyl, sulfanyl, sulfonyl, (aliphatic)carbonyl, (cycloaliphatic)carbonyl, ((cycloaliphatic)aliphatic)carbonyl, arylcarbonyl, (araliphatic)carbonyl, (heterocycloaliphatic)carbonyl, ((heterocycloaliphatic)aliphatic)carbonyl, (heteroaryl)carbonyl, or (heteroaraliphatic) carbonyl, each of which being defined herein and being optionally substituted. Examples of amino groups include alkylamino, dialkylamino, or arylamino. When the term "amino" is not the terminal group (e.g., alkylcarbonylamino), it is represented by —$NR^X$—. $R^X$ has the same meaning as defined above.

As used herein, an "aryl" group used alone or as part of a larger moiety as in "aralkyl", "aralkoxy", or "aryloxyalkyl" refers to monocyclic (e.g., phenyl); bicyclic (e.g., indenyl, naphthalenyl, tetrahydronaphthyl, tetrahydroindenyl); and tricyclic (e.g., fluorenyl tetrahydrofluorenyl, or tetrahydroanthracenyl, anthracenyl) ring systems in which the monocyclic ring system is aromatic or at least one of the rings in a bicyclic or tricyclic ring system is aromatic. The bicyclic and tricyclic groups include benzofused 2-3 membered carbocyclic rings. For example, a benzofused group includes phenyl fused with two or more $C_{4-8}$ carbocyclic moieties. An aryl is optionally substituted with one or more substituents including aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic)oxy; aryloxy; heteroaryloxy; (araliphatic)oxy; (heteroaraliphatic)oxy; aroyl; heteroaroyl; amino; oxo (on a non-aromatic carbocyclic ring of a benzofused bicyclic or tricyclic aryl); nitro; carboxy; amido; acyl [e.g., aliphaticcarbonyl; (cycloaliphatic)carbonyl; ((cycloaliphatic)aliphatic)carbonyl; (araliphatic)carbonyl; (heterocycloaliphatic)carbonyl; ((heterocycloaliphatic)aliphatic)carbonyl; or (heteroaraliphatic) carbonyl]; sulfonyl [e.g., aliphatic-$SO_2$— or amino-$SO_2$—]; sulfinyl [e.g., aliphatic-S(O)— or cycloaliphatic-S(O)—]; sulfanyl [e.g., aliphatic-S—]; cyano; halo; hydroxy; mercapto; sulfoxy; urea; thiourea; sulfamoyl; sulfamide; or carbamoyl. Alternatively, an aryl can be unsubstituted.

Non-limiting examples of substituted aryls include haloaryl [e.g., mono-, di (such as p,m-dihaloaryl), and (trihalo)aryl]; (carboxy)aryl [e.g., (alkoxycarbonyl)aryl, ((aralkyl)carbonyloxy)aryl, and (alkoxycarbonyl)aryl]; (amido)aryl [e.g., (aminocarbonyl)aryl, (((alkylamino)alkyl)aminocarbonyl)aryl, (alkylcarbonyl)aminoaryl, (arylaminocarbonyl)aryl, and (((heteroaryl)amino)carbonyl)aryl]; aminoaryl [e.g., ((alkylsulfonyl)amino)aryl or ((dialkyl)amino)aryl]; (cyanoalkyl)aryl; (alkoxy)aryl; (sulfamoyl)aryl [e.g., (aminosulfonyl)aryl]; (alkylsulfonyl)aryl; (cyano)aryl; (hydroxyalkyl)aryl; ((alkoxy)alkyl)aryl; (hydroxy)aryl, ((carboxy) alkyl)aryl; (((dialkyl)amino)alkyl)aryl; (nitroalkyl)aryl; (((alkylsulfonyl)amino)alkyl)aryl; ((heterocycloaliphatic) carbonyl)aryl; ((alkylsulfonyl)alkyl)aryl; (cyanoalkyl)aryl; (hydroxyalkyl)aryl; (alkylcarbonyl)aryl; alkylaryl; (trihaloalkyl)aryl; p-amino-m-alkoxycarbonylaryl; p-amino-m-cyanoaryl; p-halo-m-aminoaryl; or (m-(heterocycloaliphatic)-o-(alkyl))aryl.

As used herein, an "araliphatic" such as an "aralkyl" group refers to an aliphatic group (e.g., a $C_{1-4}$ alkyl group) that is substituted with an aryl group. "Aliphatic," "alkyl," and "aryl" are defined herein. An example of an araliphatic such as an aralkyl group is benzyl.

As used herein, an "aralkyl" group refers to an alkyl group (e.g., a $C_{1-4}$ alkyl group) that is substituted with an aryl group. Both "alkyl" and "aryl" have been defined above. An example of an aralkyl group is benzyl. An aralkyl is optionally substituted with one or more substituents such as aliphatic [e.g., alkyl, alkenyl, or alkynyl, including carboxyalkyl, hydroxyalkyl, or haloalkyl such as trifluoromethyl], cycloaliphatic [e.g., cycloalkyl or cycloalkenyl], (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, amido [e.g., aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, or heteroaralkylcarbonylamino], cyano, halo, hydroxy, acyl, mercapto, alkylsulfanyl, sulfoxy, urea, thiourea, sulfamoyl, sulfamide, oxo, or carbamoyl.

As used herein, a "bicyclic ring system" includes 8-12 (e.g., 9, 10, or 11) membered structures that form two rings, wherein the two rings have at least one atom in common (e.g., 2 atoms in common). Bicyclic ring systems include bicycloaliphatics (e.g., bicycloalkyl or bicycloalkenyl), bicycloheteroaliphatics, bicyclic aryls, and bicyclic heteroaryls.

As used herein, a "cycloaliphatic" group encompasses a "cycloalkyl" group and a "cycloalkenyl" group, each of which being optionally substituted as set forth below.

As used herein, a "cycloalkyl" group refers to a saturated carbocyclic mono- or bicyclic (fused or bridged) ring of 3-10 (e.g., 5-10) carbon atoms. Examples of cycloalkyl groups include cyclopropyl, cyclobutyl, cyclopentyl, cyclohexyl, cycloheptyl, adamantyl, norbornyl, cubyl, octahydro-indenyl, decahydro-naphthyl, bicyclo[3.2.1]octyl, bicyclo[2.2.2]octyl, bicyclo[3.3.1]nonyl, bicyclo[3.3.2.]decyl, bicyclo[2.2.2]octyl, adamantyl, azacycloalkyl, or ((aminocarbonyl)cycloalkyl)cycloalkyl. A "cycloalkenyl" group, as used herein, refers to a non-aromatic carbocyclic ring of 3-10 (e.g., 4-8) carbon atoms having one or more double bonds. Examples of cycloalkenyl groups include cyclopentenyl, 1,4-cyclohexa-di-enyl, cycloheptenyl, cyclooctenyl, hexahydro-indenyl, octahydro-naphthyl, cyclohexenyl, cyclopentenyl, bicyclo[2.2.2]octenyl, or bicyclo[3.3.1]nonenyl. A cycloalkyl or cycloalkenyl group can be optionally substituted with one or more substituents such as aliphatic [e.g., alkyl, alkenyl, or alkynyl], cycloaliphatic, (cycloaliphatic)aliphatic, heterocycloaliphatic, (heterocycloaliphatic)aliphatic, aryl, heteroaryl, alkoxy, (cycloaliphatic)oxy, (heterocycloaliphatic)oxy, aryloxy, heteroaryloxy, (araliphatic)oxy, (heteroaraliphatic)oxy, aroyl, heteroaroyl, amino, amido [e.g., (aliphatic)carbonylamino, (cycloaliphatic)carbonylamino, ((cycloaliphatic)aliphatic)carbonylamino, (aryl)carbonylamino, (araliphatic)carbonylamino, (heterocycloaliphatic)carbonylamino, ((heterocycloaliphatic)aliphatic)carbonylamino, (heteroaryl)carbonylamino, or (heteroaraliphatic)carbonylamino], nitro, carboxy [e.g., HOOC—, alkoxycarbonyl, or alkylcarbonyloxy], acyl [e.g., (cycloaliphatic)carbonyl, ((cycloaliphatic)aliphatic)carbonyl, (araliphatic)carbonyl, (heterocycloaliphatic)carbonyl, ((heterocycloaliphatic)aliphatic)carbonyl, or (heteroaraliphatic)carbonyl], cyano, halo, hydroxy, mercapto, sulfonyl [e.g., alkyl-$SO_2$— and aryl-$SO_2$—], sulfinyl [e.g., alkyl-S(O)—], sulfanyl [e.g., alkyl-S—], sulfoxy, urea, thiourea, sulfamoyl, sulfamide, oxo, or carbamoyl.

As used herein, "cyclic moiety" includes cycloaliphatic, heterocycloaliphatic, aryl, or heteroaryl, each of which has been defined previously.

As used herein, the term "heterocycloaliphatic" encompasses a heterocycloalkyl group and a heterocycloalkenyl group, each of which being optionally substituted as set forth below.

As used herein, a "heterocycloalkyl" group refers to a 3-10 membered mono- or bicyclic (fused or bridged) (e.g., 5- to 10-membered mono- or bicyclic) saturated ring structure, in which one or more of the ring atoms is a heteroatom (e.g., N, O, S, or combinations thereof). Examples of a heterocycloalkyl group include piperidyl, piperazyl, tetrahydropyranyl, tetrahydrofuryl, 1,4-dioxolanyl, 1,4-dithianyl, 1,3-dioxolanyl, oxazolidyl, isoxazolidyl, morpholinyl, thiomorpholyl, octahydrobenzofuryl, octahydrochromenyl, octahydrothiochromenyl, octahydroindolyl, octahydropyrindinyl, decahydroquinolinyl, octahydrobenzo[b]thiopheneyl, 2-oxa-bicyclo[2.2.2]octyl, 1-aza-bicyclo[2.2.2]octyl, 3-aza-bicyclo[3.2.1]octyl, and 2,6-dioxa-tricyclo[3.3.1.0$^{3.7}$]nonyl. A monocyclic heterocycloalkyl group can be fused with a phenyl moiety such as tetrahydroisoquinoline. A "heterocycloalkenyl" group, as used herein, refers to a mono- or bicyclic (e.g., 5- to 10-membered mono- or bicyclic) non-aromatic ring structure having one or more double bonds, and wherein one or more of the ring atoms is a heteroatom (e.g., N, O, or S). Monocyclic and bicycloheteroaliphatics are numbered according to standard chemical nomenclature.

A heterocycloalkyl or heterocycloalkenyl group can be optionally substituted with one or more substituents such as aliphatic [e.g., alkyl, alkenyl, or alkynyl], cycloaliphatic, (cycloaliphatic)aliphatic, heterocycloaliphatic, (heterocycloaliphatic)aliphatic, aryl, heteroaryl, alkoxy, (cycloaliphatic)oxy, (heterocycloaliphatic)oxy, aryloxy, heteroaryloxy, (araliphatic)oxy, (heteroaraliphatic)oxy, aroyl, heteroaroyl, amino, amido [e.g., (aliphatic)carbonylamino, (cycloaliphatic)carbonylamino, ((cycloaliphatic)aliphatic)carbonylamino, (aryl)carbonylamino, (araliphatic)carbonylamino, (heterocycloaliphatic)carbonylamino, ((heterocycloaliphatic)aliphatic)carbonylamino, (heteroaryl)carbonylamino, or (heteroaraliphatic)carbonylamino], nitro, carboxy [e.g., HOOC—, alkoxycarbonyl, or alkylcarbonyloxy], acyl [e.g., (cycloaliphatic)carbonyl, ((cycloaliphatic)aliphatic)carbonyl, (araliphatic)carbonyl, (heterocycloaliphatic)carbonyl, ((heterocycloaliphatic)aliphatic)carbonyl, or (heteroaraliphatic)carbonyl], nitro, cyano, halo, hydroxy, mercapto, sulfonyl [e.g., alkylsulfonyl or arylsulfonyl], sulfinyl [e.g., alkylsulfinyl], sulfanyl [e.g., alkylsulfanyl], sulfoxy, urea, thiourea, sulfamoyl, sulfamide, oxo, or carbamoyl.

A "heteroaryl" group, as used herein, refers to a monocyclic, bicyclic, or tricyclic ring system having 4 to 15 ring atoms wherein one or more of the ring atoms is a heteroatom (e.g., N, O, S, or combinations thereof) and in which the monocyclic ring system is aromatic or at least one of the rings in the bicyclic or tricyclic ring systems is aromatic. A heteroaryl group includes a benzofused ring system having 2 to 3 rings. For example, a benzofused group includes benzo fused with one or two 4 to 8 membered heterocycloaliphatic moieties (e.g., indolizyl, indolyl, isoindolyl, 3H-indolyl, indolinyl, benzo[b]furyl, benzo[b]thiophenyl, quinolinyl, or isoquinolinyl). Some examples of heteroaryl are azetidinyl, pyridyl, 1H-indazolyl, furyl, pyrrolyl, thienyl, thiazolyl, oxazolyl, imidazolyl, tetrazolyl, benzofuryl, isoquinolinyl, benzthiazolyl, xanthene, thioxanthene, phenothiazine, dihydroindole, benzo[1,3]dioxole, benzo[b]furyl, benzo[b]thiophenyl, indazolyl, benzimidazolyl, benzthiazolyl, puryl, cinnolyl, quinolyl, quinazolyl, cinnolyl, phthalazyl, quinazolyl, quinoxalyl, isoquinolyl, 4H-quinolizyl, benzo-1,2,5-thiadiazolyl, or 1,8-naphthyridyl.

Without limitation, monocyclic heteroaryls include furyl, thiophenyl, 2H-pyrrolyl, pyrrolyl, oxazolyl, thazolyl, imidazolyl, pyrazolyl, isoxazolyl, isothiazolyl, 1,3,4-thiadiazolyl, 2H-pyranyl, 4-H-pranyl, pyridyl, pyridazyl, pyrimidyl, pyrazolyl, pyrazyl, or 1,3,5-triazyl. Monocyclic heteroaryls are numbered according to standard chemical nomenclature.

Without limitation, bicyclic heteroaryls include indolizyl, indolyl, isoindolyl, 3H-indolyl, indolinyl, benzo[b]furyl, benzo[b]thiophenyl, quinolinyl, isoquinolinyl, indolizyl, isoindolyl, indolyl, benzo[b]furyl, bexo[b]thiophenyl, indazolyl, benzimidazyl, benzthiazolyl, purinyl, 4H-quinolizyl, quinolyl, isoquinolyl, cinnolyl, phthalazyl, quinazolyl, quinoxalyl, 1,8-naphthyridyl, or pteridyl. Bicyclic heteroaryls are numbered according to standard chemical nomenclature.

A heteroaryl is optionally substituted with one or more substituents such as aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic) oxy; aryloxy; heteroaryloxy; (araliphatic)oxy; (heteroaraliphatic)oxy; aroyl; heteroaroyl; amino; oxo (on a non-aromatic carbocyclic or heterocyclic ring of a bicyclic or tricyclic heteroaryl); carboxy; amido; acyl [e.g., aliphaticcarbonyl; (cycloaliphatic)carbonyl; ((cycloaliphatic)aliphatic) carbonyl; (araliphatic)carbonyl; (heterocycloaliphatic)carbonyl; ((heterocycloaliphatic)aliphatic)carbonyl; or (heteroaraliphatic)carbonyl]; sulfonyl [e.g., aliphaticsulfonyl or aminosulfonyl]; sulfinyl [e.g., aliphaticsulfinyl]; sulfanyl [e.g., aliphaticsulfanyl]; nitro; cyano; halo; hydroxy; mercapto; sulfoxy; urea; thiourea; sulfamoyl; sulfamide; or carbamoyl. Alternatively, a heteroaryl can be unsubstituted.

Non-limiting examples of substituted heteroaryls include (halo)heteroaryl [e.g., mono- and di-(halo)heteroaryl]; (carboxy)heteroaryl [e.g., (alkoxycarbonyl)heteroaryl]; cyano-heteroaryl; aminoheteroaryl [e.g., ((alkylsulfonyl)amino)heteroaryl and ((dialkyl)amino)heteroaryl]; (amido)heteroaryl [e.g., aminocarbonylheteroaryl, ((alkylcarbonyl)amino)heteroaryl, ((((alkyl)amino)alkyl)aminocarbonyl)heteroaryl, (((heteroaryl)amino)carbonyl)heteroaryl, ((heterocycloaliphatic)carbonyl)heteroaryl, and ((alkylcarbonyl) amino)heteroaryl]; (cyanoalkyl)heteroaryl; (alkoxy)heteroaryl; (sulfamoyl)heteroaryl [e.g., (aminosulfonyl) heteroaryl]; (sulfonyl)heteroaryl [e.g., (alkylsulfonyl) heteroaryl]; (hydroxyalkyl)heteroaryl; (alkoxyalkyl) heteroaryl; (hydroxy)heteroaryl; ((carboxy)alkyl)heteroaryl; (((dialkyl)amino)alkyl]heteroaryl; (heterocycloaliphatic) heteroaryl; (cycloaliphatic)heteroaryl; (nitroalkyl)heteroaryl; (((alkylsulfonyl)amino)alkyl)heteroaryl; ((alkylsulfonyl)alkyl)heteroaryl; (cyanoalkyl)heteroaryl; (acyl) heteroaryl [e.g., (alkylcarbonyl)heteroaryl]; (alkyl) heteroaryl, and (haloalkyl)heteroaryl [e.g., trihaloalkylheteroaryl].

A "heteroaraliphatic (such as a heteroaralkyl group) as used herein, refers to an aliphatic group (e.g., a $C_{1-4}$ alkyl group) that is substituted with a heteroaryl group. "Aliphatic," "alkyl," and "heteroaryl" have been defined above.

A "heteroaralkyl" group, as used herein, refers to an alkyl group (e.g., a $C_{1-4}$ alkyl group) that is substituted with a heteroaryl group. Both "alkyl" and "heteroaryl" have been defined above. A heteroaralkyl is optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, an "acyl" group refers to a formyl group or $R^X$—C(O)— (such as -alkyl-C(O)—, also referred to as "alkylcarbonyl") where $R^X$ and "alkyl" have been defined previously. Acetyl and pivaloyl are examples of acyl groups.

As used herein, an "aroyl" or "heteroaroyl" refers to an aryl-C(O)— or a heteroaryl-C(O)—. The aryl and heteroaryl portion of the aroyl or heteroaroyl is optionally substituted as previously defined.

As used herein, an "alkoxy" group refers to an alkyl-O— group where "alkyl" has been defined previously.

As used herein, a "carbamoyl" group refers to a group having the structure —O—O—$NR^XR^Y$ or —$NR^X$—CO—O—$R^Z$ wherein $R^X$ and $R^Y$ have been defined above and $R^Z$ can be aliphatic, aryl, aralphatic, heterocycloaliphatic, heteroaryl, or heteroaraliphatic.

As used herein, a "carboxy" group refers to —COOH, —COOR$^X$, —OC(O)H, —OC(O)R$^X$ when used as a terminal group; or —OC(O)— or —C(O)O— when used as an internal group.

As used herein, a "haloaliphatic" group refers to an aliphatic group substituted with 1-3 halogen. For instance, the term haloalkyl includes the group —$CF_3$.

As used herein, a "mercapto" group refers to —SH.

As used herein, a "sulfo" group refers to —$SO_3H$ or —$SO_3R^X$ when used terminally or —$S(O)_3$— when used internally.

As used herein; a "sulfamide" group refers to the structure —$NR^X$—$S(O)_2$—$NR^YR^Z$ when used terminally and —$NR^X$—$S(O)_2$—$NR^Y$— when used internally, wherein $R^X$, $R^Y$, and $R^Z$ have been defined above.

As used herein, a "sulfamoyl" group refers to the structure —$S(O)_2$—$NR^XR^Y$ or —$NR^X$—$S(O)_2$—$R^Z$ when used terminally; or —$S(O)_2$—$NR^X$— or —$NR^X$—$S(O)_2$— when used internally, wherein $R^X$, $R^Y$, and $R^Z$ are defined above.

As used herein a "sulfanyl" group refers to —S—$R^X$ when used terminally and —S— when used internally, wherein $R^X$ has been defined above. Examples of sulfanyls include aliphatic-S—, cycloaliphatic-S—, aryl-S—, or the like.

As used herein a "sulfinyl" group refers to —S(O)—$R^X$ when used terminally and —S(O)— when used internally, wherein $R^X$ has been defined above. Exemplary sulfinyl groups include aliphatic-S(O)—, aryl-S(O)—, (cycloaliphatic(aliphatic))-S(O)—, cycloalkyl-S(O)—, heterocycloaliphatic-S(O)—, heteroaryl-S(O)—, or the like.

As used herein, a "sulfonyl" group refers to —$S(O)_2$—$R^X$ when used terminally and —$S(O)_2$— when used internally, wherein $R^X$ has been defined above. Exemplary sulfonyl groups include aliphatic-$S(O)_2$—, aryl-$S(O)_2$—, (cycloaliphatic(aliphatic))-$S(O)_2$—, cycloaliphatic-$S(O)_2$—, heterocycloaliphatic-$S(O)_2$—, heteroaryl-$S(O)_2$—, (cycloaliphatic(amido(aliphatic)))-$S(O)_2$— or the like.

As used herein, a "sulfoxy" group refers to —O—SO—$R^X$ or —SO—O—$R^X$, when used terminally and —O—S(O)— or —S(O)—O— when used internally, where $R^X$ has been defined above.

As used herein, a "halogen" or "halo" group refers to fluorine, chlorine, bromine or iodine.

As used herein, an "alkoxycarbonyl," which is encompassed by the term carboxy, used alone or in connection with another group refers to a group such as alkyl-O—C(O)—.

As used herein, an "alkoxyalkyl" refers to an alkyl group such as alkyl-O-alkyl-, wherein alkyl has been defined above.

As used herein, a "carbonyl" refer to —C(O)—.

As used herein, an "oxo" refers to =O.

As used herein, an "aminoalkyl" refers to the structure $(R^X)_2$N-alkyl-.

As used herein, a "cyanoalkyl" refers to the structure (NC)-alkyl-.

As used herein, a "urea" group refers to the structure —NR$^X$—CO—NR$^Y$R$^Z$ and a "thiourea" group refers to the structure —NR$^X$—CS—NR$^Y$R$^Z$ when used terminally and —NR$^X$—CO—NR$^Y$— or —NR$^X$—CS—NR$^Y$— when used internally, wherein R$^X$, R$^Y$, and R$^Z$ have been defined above.

As used herein, a "guanidine" group refers to the structure —N=C(N(R$^X$R$^Y$))N(R$^X$R$^Y$) wherein R$^X$ and R$^Y$ have been defined above.

As used herein, the term "amidino" group refers to the structure —C=(NR$^X$)N(R$^X$R$^Y$) wherein R$^X$ and R$^Y$ have been defined above.

In general, the term "vicinal" refers to the placement of substituents on a group that includes two or more carbon atoms, wherein the substituents are attached to adjacent carbon atoms.

In general, the term "geminal" refers to the placement of substituents on a group that includes two or more carbon atoms, wherein the substituents are attached to the same carbon atom.

The terms "terminally" and "internally" refer to the location of a group within a substituent. A group is terminal when the group is present at the end of the substituent not further bonded to the rest of the chemical structure. Carboxyalkyl, i.e., R$^X$O(O)C-alkyl is an example of a carboxy group used terminally. A group is internal when the group is present in the middle of a substituent to at the end of the substituent bound to the rest of the chemical structure. Alkylcarboxy (e.g., alkyl-C(O)O— or alkyl-OC(O)—) and alkylcarboxyaryl (e.g., alkyl-C(O)O-aryl- or alkyl-O(CO)-aryl-) are examples of carboxy groups used internally.

As used herein, the term "amidino" group refers to the structure —C=(NR$^X$)N(R$^X$R$^Y$) wherein R$^X$ and R$^Y$ have been defined above.

As used herein, "cyclic group" includes mono-, bi-, and tri-cyclic ring systems including cycloaliphatic, heterocycloaliphatic, aryl, or heteroaryl, each of which has been previously defined.

As used herein, a "bridged bicyclic ring system" refers to a bicyclic heterocyclicalipahtic ring system or bicyclic cycloaliphatic ring system in which the rings are bridged. Examples of bridged bicyclic ring systems include, but are not limited to, adamantanyl, norbornanyl, bicyclo[3.2.1]octyl, bicyclo[2.2.2]octyl, bicyclo[3.3.1]nonyl, bicyclo[3.2.3] nonyl, 2-oxa-bicyclo[2.2.2]octyl, 1-aza-bicyclo[2.2.2]octyl, 3-aza-bicyclo[3.2.1]octyl, and 2,6-dioxa-tricyclo[3.3.1.03,7] nonyl. A bridged bicyclic ring system can be optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, an "aliphatic chain" refers to a branched or straight aliphatic group (e.g., alkyl groups, alkenyl groups, or alkynyl groups). A straight aliphatic chain has the structure —[CH$_2$]$_v$—, where v is 1-6. A branched aliphatic chain is a straight aliphatic chain that is substituted with one or more aliphatic groups. A branched aliphatic chain has the structure —[CHQ]$_v$- where Q is hydrogen or an aliphatic group; however, Q shall be an aliphatic group in at least one instance. The term aliphatic chain includes alkyl chains, alkenyl chains, and alkynyl chains, where alkyl, alkenyl, and alkynyl are defined above.

The phrase "optionally substituted" is used interchangeably with the phrase "substituted or unsubstituted." As described herein, compounds of the invention can optionally be substituted with one or more substituents, such as are illustrated generally above, or as exemplified by particular classes, subclasses, and species of the invention. As described herein, the variables in formula I and other variables contained encompass specific groups, such as alkyl and aryl. Unless otherwise noted, each of the specific groups for the variables in formula I and other variables contained therein can be optionally substituted with one or more substituents described herein. Each substituent of a specific group is further optionally substituted with one to three of halo, cyano, oxo, alkoxy, hydroxy, amino, nitro, aryl, haloalkyl, and alkyl. For instance, an alkyl group can be substituted with alkylsulfanyl and the alkylsulfanyl can be optionally substituted with one to three of halo, cyano, oxo, alkoxy, hydroxy, amino, nitro, aryl, haloalkyl, and alkyl. As an additional example, the cycloalkyl portion of a (cycloalkyl)carbonylamino can be optionally substituted with one to three of halo, cyano, alkoxy, hydroxy, nitro, haloalkyl, and alkyl. When two alkoxy groups are bound to the same atom or adjacent atoms, the two alkoxy groups can form a ring together with the atom(s) to which they are bound.

In general, the term "substituted," whether preceded by the term "optionally" or not, refers to the replacement of hydrogen radicals in a given structure with the radical of a specified substituent. Specific substituents are described above in the definitions and below in the description of compounds and examples thereof. Unless otherwise indicated, an optionally substituted group can have a substituent at each substitutable position of the group, and when more than one position in any given structure can be substituted with more than one substituent selected from a specified group, the substituent can be either the same or different at every position. A ring substituent, such as a heterocycloalkyl, can be bound to another ring, such as a cycloalkyl, to form a spiro-bicyclic ring system, e.g., both rings share one common atom. As one of ordinary skill in the art will recognize, combinations of substituents envisioned by this invention are those combinations that result in the formation of stable or chemically feasible compounds.

The phrase "stable or chemically feasible," as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

As used herein, an effective amount is defined as the amount required to confer a therapeutic effect on the treated patient, and is typically determined based on age, surface area, weight, and condition of the patient. The interrelationship of dosages for animals and humans (based on milligrams per meter squared of body surface) is described by Freireich et al., *Cancer Chemother. Rep.*, 50: 219 (1966). Body surface area may be approximately determined from height and weight of the patient. See, e.g., Scientific Tables, Geigy Pharmaceuticals, Ardsley, N.Y., 537 (1970). As used herein, "patient" refers to a mammal, including a human.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this invention. Such compounds are useful, for example, as analytical tools or probes in biological assays.

II. Compounds

The present invention provides methods of modulating muscarinic receptor activity using compounds of formulae (I and II), described above, that are useful in modulating activity of a muscarinic receptor.

Methods of modulating muscarinic receptors according to one aspect of the present invention involve compounds of formula (I):

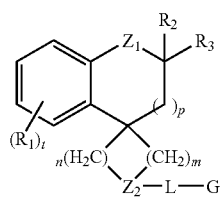
(I)

or pharmaceutically acceptable salts thereof.

Each of $R_1$, $R_2$, $R_3$ is independently $Q_1$ or $Q_2$, or $R_2$ and $R_3$ together form oxo.

$Z_1$ is —C$(Q_1)_2$-, —C(H)$(Q_1)$-, —C(H)$(Q_5)$-, —C(O)—, —CH$_2$—, —N$(Q_1)$-, —N$(Q_2)$-, or O.

$Z_2$ is N.

L is a bond, an aliphatic group, $C_3$-$C_6$ cycloaliphatic, —O—, —S(O)$_z$—, —S(O)$_z$—$(C_1$-$C_4)$alkyl-, —C(O)N$(Q_2)$-, or —S(O)$_z$N$(Q_2)$-, in which the aliphatic group is optionally substituted with 1-3 of oxo, $Q_1$, or $Q_2$.

G is a monocycloaliphatic group, a monocycloheteroaliphatic group, adamantyl, or a bicyclic or a tricyclic group of the formula (III)

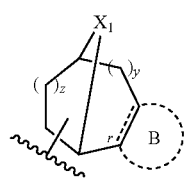
(III)

in which the monocycloaliphatic group, the monocycloheteroalipahtic group, the adamantyl, and the bicyclic or tricyclic group are connected to L via any ring atom including those in $X_1$ and ring B, and the monocycloaliphatic, the monocycloheteroaliphatic, the bicyclic, and the tricyclic groups are optionally substituted with 1-3 of oxo, =N—O$Q_4$, fluorine, $Q_2$, —C(O)—$X_2$-aliphatic in which $X_2$ is absent, —O—, —NH—, —N$Q_2$-, or —S(O)$_z$— and the aliphatic group is optionally substituted with 1-3 substituents independently selected from $Q_3$; bond r is a single or double bond and when ring B is present, bond r is fused with B; ring B, when present, is a 5-6 membered cycloaliphatic or heterocyclic ring; and ring B is optionally substituted with 1-3 of oxo, $Q_1$, or $Q_2$.

$X_1$ is —(CH$_2$)$_i$—, —O—, —S—, —N$(Q_2)$-, —N(C(O)—$X_2$-aliphatic)- in which $X_2$ is absent, —O—, —NH—, —N$Q_2$-, or —S(O)$_z$— and the aliphatic group is optionally substituted with 1-3 substituents independently selected from $Q_3$.

Each $Q_1$ is independently halo, —CN, —NO$_2$, —O$Q_2$, —S(O)$_z$$Q_2$, —S(O)$_z$N$(Q_2)_2$, —N$(Q_2)_2$, —C(O)O$Q_2$, —C(O)-$Q_2$, —C(O)N$(Q_2)_2$, —C(O)N$(Q_2)$(O$Q_2$), —N$(Q_2)$C(O)-$Q_2$, —N$(Q_2)$C(O)N$(Q_2)_2$, —N$(Q_2)$C(O)O-$Q_2$, —N$(Q_2)$S(O)$_z$-$Q_2$ or aliphatic optionally including 1-3 substituents independently selected from $Q_2$ or $Q_3$.

Each $Q_2$ is independently H, aliphatic, cycloaliphatic, aryl, arylalkyl, heterocyclic, or heteroaryl ring, each optionally including 1-3 substituents independently selected from $Q_3$.

Each $Q_3$ is halo, oxo, CN, NO$_2$, CF$_3$, OCF$_3$, OH, —S(O)$_z$$Q_4$, —N$(Q_4)_2$, —COO$Q_4$, —C(O)$Q_4$, —O$Q_4$, or $C_1$-$C_4$ alkyl optionally substituted with 1-3 of halo, oxo, —CN, —NO$_2$, —CF$_3$, —OCF$_3$, —OH, —SH, —S(O)$_z$H, —NH$_2$, or —COOH.

Each $Q_4$ is aliphatic, cycloaliphatic, aryl, aralkyl, heterocyclic, heteroaralyl, or heteroaryl ring, each optionally substituted with 1-3 substituents selected from halo, oxo, CN, NO$_2$, CF$_3$, —OCF$_3$, —OH, —SH, —S(O)$_z$H, —NH$_2$, —COOH.

Each $Q_5$ is a heterocyclic ring optionally substituted with 1-3 substituents selected from halo, $C_1$-$C_4$ alkyl, oxo, CN, NO$_2$, CF$_3$, OCF$_3$, OH, SH, —S(O)$_z$H, —NH$_2$, COOH; and each i is independently 1, 2, or 3.

Each m and n is independently 1, 2, 3, or 4 provided that m+n is at least 4.

Each p is 0 or 1.

Each y is independently 0 or 1; each t is 1 to 4; and each z is independently 0, 1, or 2.

Another aspect of the invention provides compounds of formula (II) including:

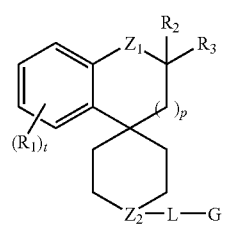
(II)

or pharmaceutically acceptable salts thereof.

Each of $R_1$, $R_2$, $R_3$ is independently $Q_1$ or $Q_2$, or $R_2$ and $R_3$ together form oxo.

$Z_1$ is —C$(Q_1)_2$-, —C(H)$(Q_1)$-, —C(H)$(Q_5)$-, —C(O)—, —CH$_2$—, —N$(Q_1)$-, —N$(Q_2)$-, or O.

$Z_2$ is N.

L is a bond, an aliphatic group, $C_3$-$C_6$ cycloaliphatic, —O—, —S(O)$_z$—, —S(O)$_z$—$(C_1$-$C_4)$alkyl-, —C(O)N$(Q_2)$-, or —S(O)$_z$N$(Q_2)$-, in which the aliphatic group is optionally substituted with 1-3 of oxo, $Q_1$, or $Q_2$.

G is a monocycloaliphatic group, a monocycloheteroaliphatic group, adamantyl, or a bicyclic or a tricyclic group of formula (III)

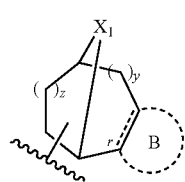

(III)

in which the monocycloaliphatic group, the monocycloheteroaliphatic group, the adamantyl, and the bicyclic or tricyclic group are connected to L via any ring atom including those in $X_1$ and ring B, and the monocycloaliphatic, the monocycloheteroaliphatic, the bicyclic, and the tricyclic groups are optionally substituted with 1-3 of oxo, =N—$OQ_4$, fluorine, $Q_2$, —C(O)—$X_2$-aliphatic in which $X_2$ is absent, —O—, —NH—, —$NQ_2$-, or —S(O)$_z$— and the aliphatic group is optionally substituted with 1-3 substituents independently selected from $Q_3$; bond r is a single or double bond and when ring B is present, bond r is fused with B; ring B, when present, is a 5-6 membered cycloaliphatic or heterocyclic ring, and is optionally substituted with 1-3 of oxo, $Q_1$, or $Q_2$.

$X_1$ is —$(CH_2)_i$—, —O—, —S—, —N($Q_2$)-, —N(C(O)—$X_2$-aliphatic)- in which $X_2$ is absent, —O—, —NH—, —$NQ_2$-, or —S(O)$_z$— and the aliphatic group is optionally substituted with 1-3 substituents independently selected from $Q_3$.

Each $Q_1$ is independently halo, —CN, —$NO_2$, —$OQ_2$, —S(O)$_z$$Q_2$, —S(O)$_z$N($Q_2$)$_2$, —N($Q_2$)$_2$, —C(O)$OQ_2$, —C(O)-$Q_2$, —C(O)N($Q_2$)$_2$, —C(O)N($Q_2$)($OQ_2$), —N($Q_2$)C(O)-$Q_2$, —N($Q_2$)C(O)N($Q_2$)$_2$, —N($Q_2$)C(O)O-$Q_2$, —N($Q_2$)S(O)$_z$-$Q_2$ or aliphatic optionally including 1-3 substituents independently selected from $Q_2$ or $Q_3$.

Each $Q_2$ is independently H, aliphatic, cycloaliphatic, aryl, arylalkyl, heterocyclic, or heteroaryl ring, each optionally substituted with 1-3 substituents independently selected from $Q_3$.

Each $Q_3$ is halo, oxo, —CN, —$NO_2$, —$CF_3$, —$OCF_3$, —OH, —S(O)$_z$$Q_4$, —N($Q_4$)$_2$, —$COOQ_4$, —C(O)$Q_4$, —$OQ_4$, or $C_1$-$C_4$alkyl optionally substituted with 1-3 halo, oxo, —CN, —$NO_2$, —$CF_3$, —$OCF_3$, —OH, —SH, —S(O)$_z$H, —$NH_2$, or —COOH.

Each $Q_4$ is aliphatic, cycloaliphatic, aryl, aralkyl, heterocycloaliphatic, heteroaralky, or heteroaryl, each optionally including 1-3 substituents selected from halo, oxo, CN, $NO_2$, $CF_3$, $OCF_3$, OH, SH, —S(O)$_z$H, —$NH_2$, or COOH.

Each $Q_5$ is a heterocyclic ring optionally substituted with 1-3 substituents selected from halo, oxo, $C_1$-$C_4$alkyl, —CN, —$NO_2$, —$CF_3$, —$OCF_3$, —OH, —SH, —S(O)$_z$H, —$NH_2$, and —COOH.

Each i is independently 1, 2, or 3.
Each p is 0 or 1.
Each y is independently 0 or 1.
Each z is independently 0, 1, or 2.

III. Specific Embodiments a. Substituent G

G is a monocycloaliphatic group, a monocycloheteroaliphatic group, adamantyl, or a bicyclic or a tricyclic group of formula (III)

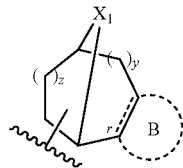

(III)

in which the monocycloaliphatic group, the monocycloheteroaliphatic group, the adamantyl, and the bicyclic or tricyclic group are connected to L via any ring atom including those in $X_1$ and ring B, and the monocycloaliphatic, the monocycloheteroaliphatic, the bicyclic, and the tricyclic groups are optionally substituted with 1-3 of oxo, =N—$OQ_4$, fluorine, $Q_2$, —C(O)—$X_2$-aliphatic in which $X_2$ is absent, —O—, —NH—, —$NQ_2$-, or —S(O)$_z$— and the aliphatic group is optionally substituted with 1-3 substituents independently selected from Q; bond r is a single or double bond and when ring B is present, bond r is fused with B; ring B, when present, is a 5-6 membered cycloaliphatic or heterocyclic ring, and is optionally substituted with 1-3 of oxo, $Q_1$, or $Q_2$.

In certain embodiments, G is an optionally substituted monocycloaliphatic group.

In several embodiments, G is an optionally substituted cycloaliphatic. In examples of this embodiment, G is an optionally substituted monocycloaliphatic. Specific examples of G include, but are not limited to, 5 to 8 membered monocycloalkyls or a 5 to 8 membered monocycloalkenyls. In other examples, G can be an optionally substituted cyclopentyl, cyclopentenyl, cyclohexyl, cyclohexenyl, cycloheptyl, or cyclooctyl.

In several embodiments, G is optionally substituted with $Q_2$, or —C(O)—$X_2$-aliphatic, where $X_2$ is absent, —O—, —NH—, or —$NQ_2$-, and the aliphatic group is optionally substituted with 1-3 substituents independently selected from $Q_3$. In examples of these embodiments, G can be substituted with carbonyl, sulfonyl, alkoxy, combinations thereof, or the like.

In several embodiments, G is optionally substituted with 1 to 3 of carbonyl, sulfonyl, or combinations thereof. Examples of G include, but are not limited to, alkoxycarbonyl, aliphaticcarbonyl (e.g., alkylcarbonyl, alkenylcarbonyl, or alkynylcarbonyl), aliphatic, alkoxyalkoxycarbonyl, cycloalkoxycarbonyl, heterocycloalkoxycarbonyl, aminoaliphatic, aliphaticamino, arylcarbonyl, or heteroarylcarbonyl, each of which is optionally substituted.

In several embodiments, G is substituted with alkyl, aryl, haloalkyl, alkoxycarbonyl, or alkoxyamino.

In several embodiments, G is selected from

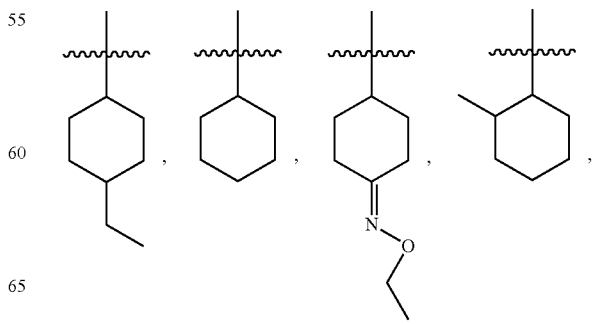

-continued

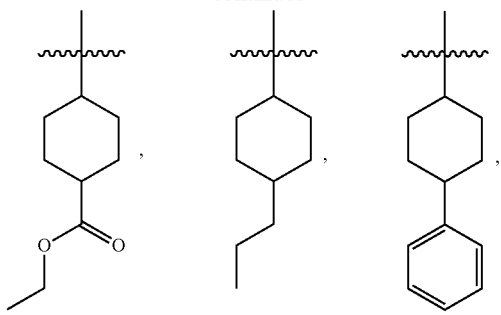

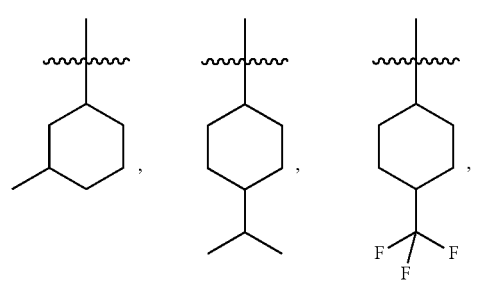

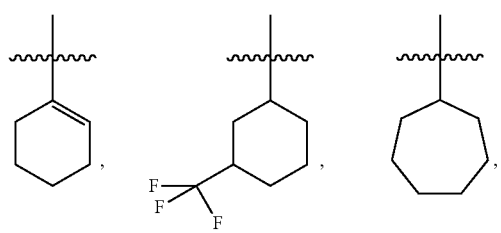

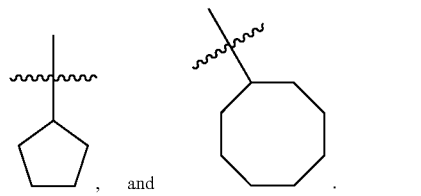

In several embodiments, G is an optionally substituted monoheterocycloaliphatic group. Examples of G include, but are not limited to, optionally substituted 5 to 7 membered monoheterocycloaliphatic groups.

In several embodiments, G includes at least 1 nitrogen atom. G can be substituted with 1 to 3 substituents independently selected from $Q_2$, and —C(O)—$X_2$-aliphatic, where $X_2$ is absent, —O—, —NH—, or —N$Q_2$-, and the aliphatic group is optionally substituted with 1-3 substituents independently selected from $Q_3$.

In several embodiments, G is optionally substituted with 1 to 2 substituents independently selected from alkoxycarbonyl, alkynyloxycarbonyl, alkoxyalkoxycarbonyl, haloalkoxycarbonyl, heterocycloalkoxycarbonyl, and cycloalkoxycarbonyl.

In other embodiments, G is one selected from

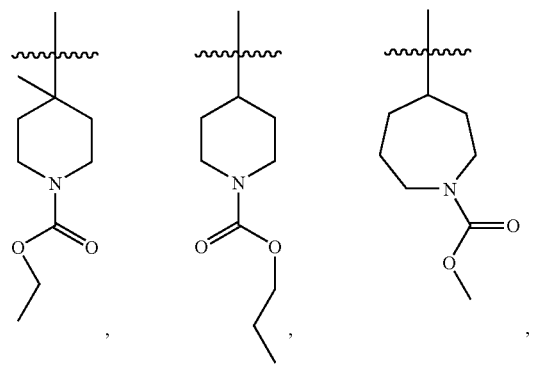

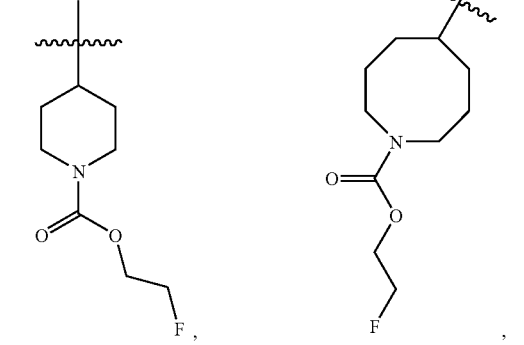

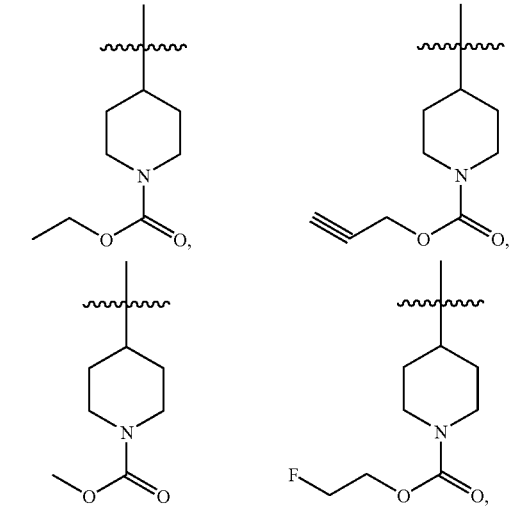

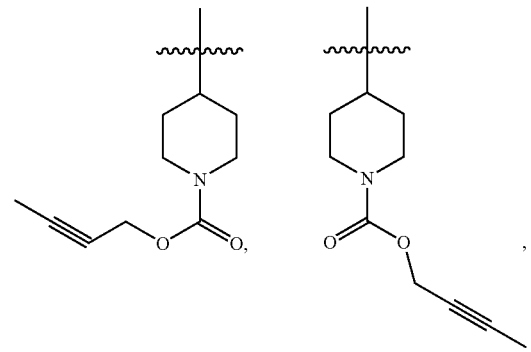

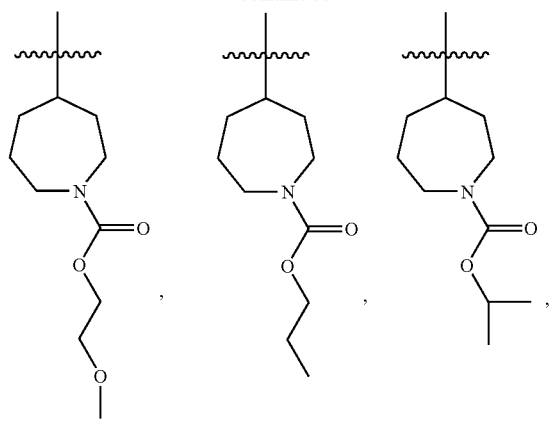
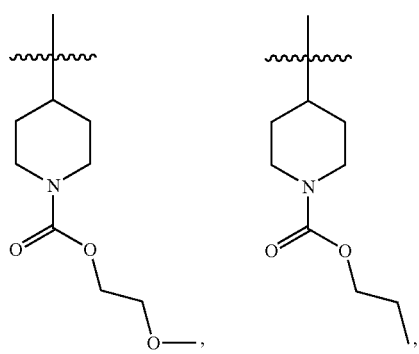
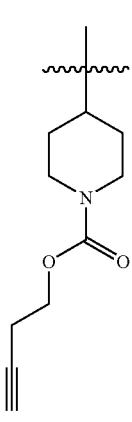
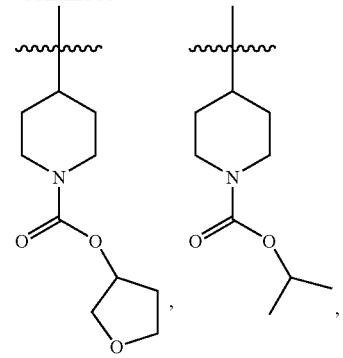
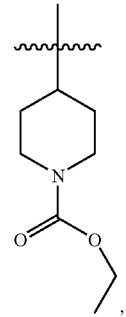
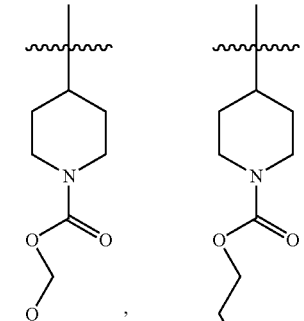
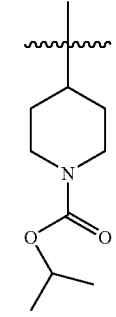
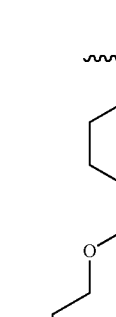
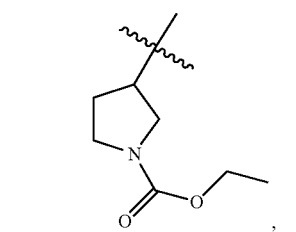
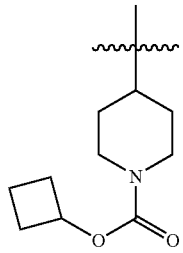
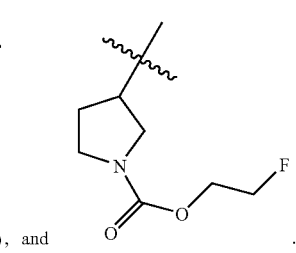

In several embodiments, G includes at least one O atom. In several examples, G is optionally substituted with 1 to 3 substituents independently selected from independently selected from alkoxycarbonyl, alkynyloxycarbonyl, alkoxyalkoxycarbonyl, haloalkoxycarbonyl, heterocycloalkoxycarbonyl, and cycloalkoxycarbonyl. In other examples, G is unsubstituted.

In several embodiments, G is one selected from

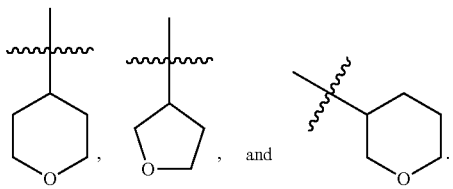

In other embodiments, G is an optionally substituted bicyclic group of formula (III). In one group of examples, ring B is absent from the bicyclic group of formula (III).

In several embodiments, $X_1$ is —$(CH)_{2i}$—.

In several alternative embodiments, the bicyclic group of formula (III) includes 7 to 9 ring atoms. In specific examples, G is an optionally substituted bicyclo[2.2.1]heptyl, bicyclo[3.2.1]octyl, bicyclo[3.3.1]nonyl, bicyclo[2.2.2]octyl, or bicyclo[2.2.1]heptanyl. In yet another group of the examples, G can be substituted with 1 to 3 substituents independently selected from $Q_2$, and —C(O)—$X_2$-aliphatic, where $X_2$ is absent, —O—, —NH—, or —$NQ_2$-, and the aliphatic group is optionally substituted with 1-3 substituents independently selected from $Q_3$.

In several embodiments, G is one selected from

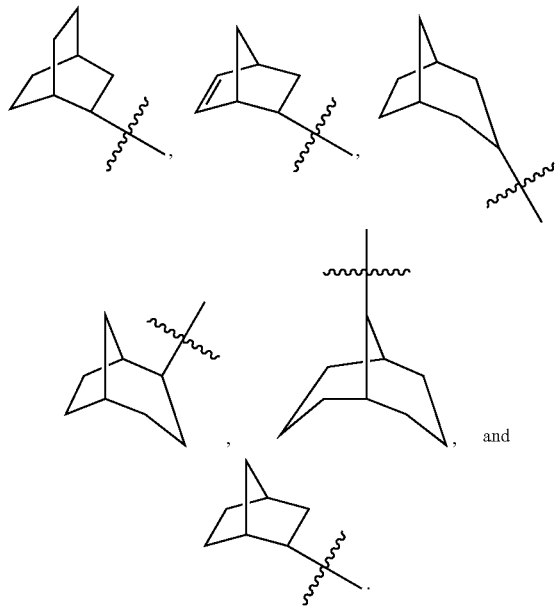

In other embodiments, G is optionally substituted adamantly.

In several embodiments, $X_1$ is —N($Q_2$)- or —N(C(O)—$X_2$-aliphatic), where $X_2$ is absent, —O—, —NH—, or —$NQ_2$-, and the aliphatic group is optionally substituted with 1-3 substituents independently selected from Q. In one group of examples, G is an optionally substituted tropane.

In other examples, G is substituted with $Q_2$, and —C(O)—$X_2$-aliphatic, where $X_2$ is absent, —O—, —NH—, or —$NQ_2$-, and the aliphatic group is optionally substituted with 1-3 substituents independently selected from $Q_3$.

In several embodiments, G is substituted with alkoxycarbonyl, alkoxyalkoxycarbonyl, heterocycloalkoxycarbonyl, cycloalkoxycarbonyl, alkoxyaryloxycarbonyl, alkylaminocarbonyl, haloalkoxycarbonyl, alkynyloxycarbonyl, or heterocycloalkylalkoxycarbonyl.

In several embodiments, G is one selected from

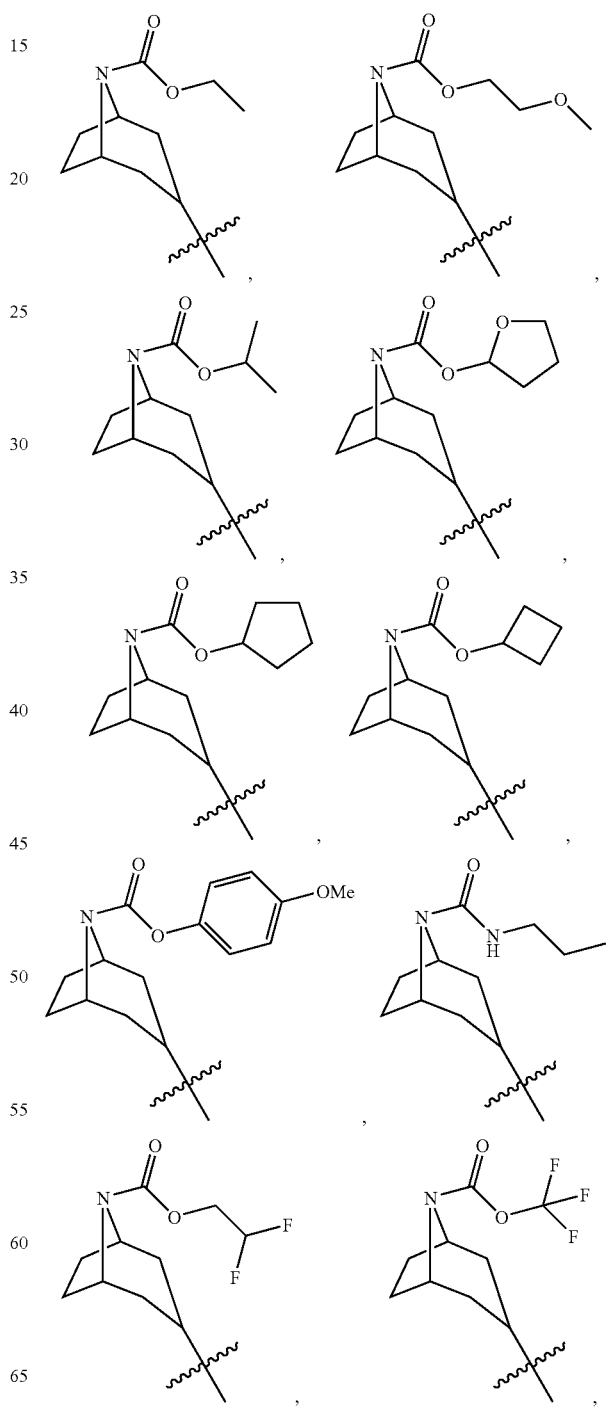

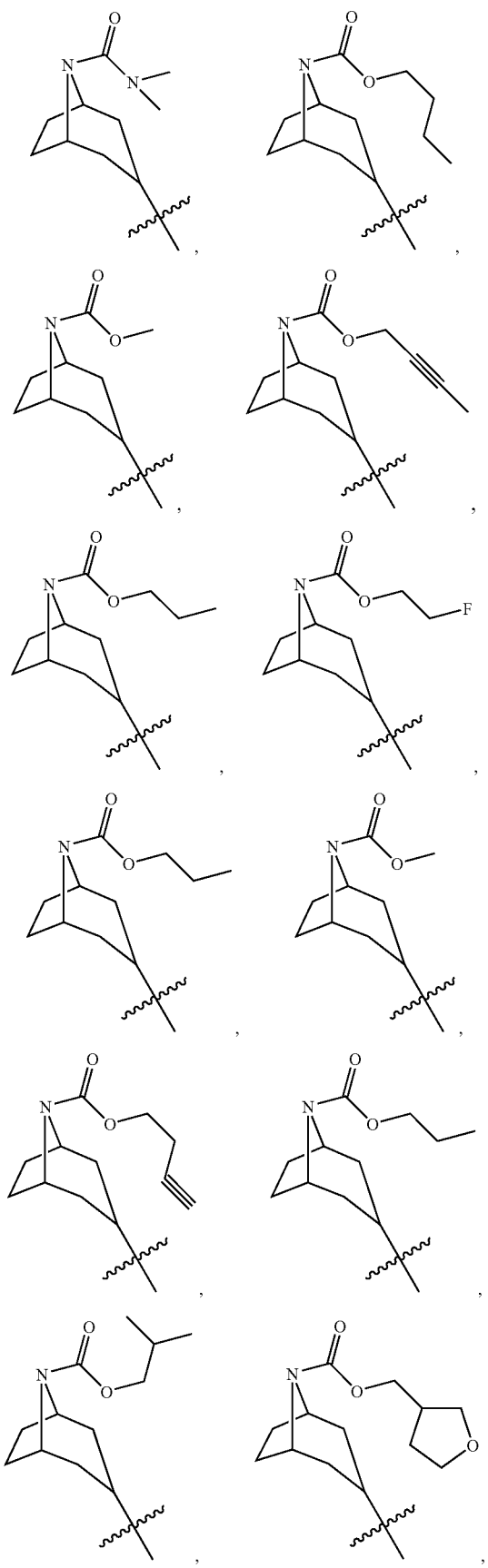

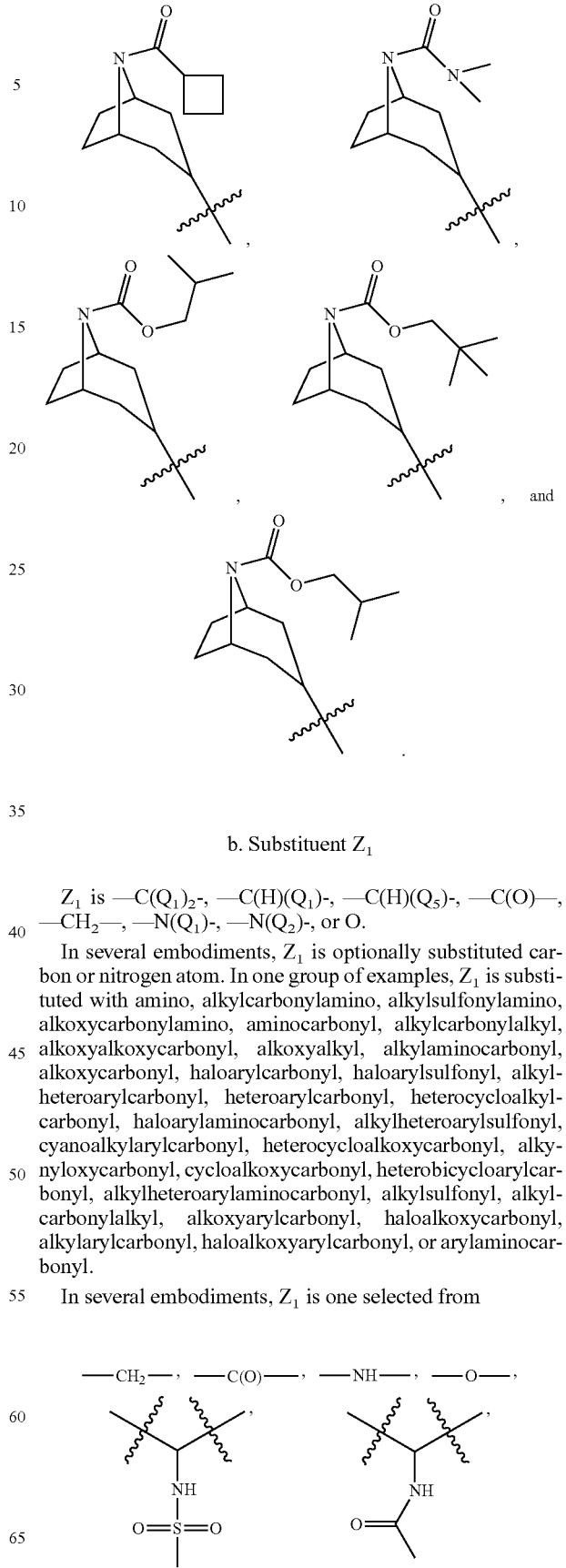

b. Substituent $Z_1$ $Z_1$ is —C($Q_1$)$_2$-, —C(H)($Q_1$)-, —C(H)($Q_5$)-, —C(O)—, —CH$_2$—, —N($Q_1$)-, —N($Q_2$)-, or O.

In several embodiments, $Z_1$ is optionally substituted carbon or nitrogen atom. In one group of examples, $Z_1$ is substituted with amino, alkylcarbonylamino, alkylsulfonylamino, alkoxycarbonylamino, aminocarbonyl, alkylcarbonylalkyl, alkoxyalkoxycarbonyl, alkoxyalkyl, alkylaminocarbonyl, alkoxycarbonyl, haloarylcarbonyl, haloarylsulfonyl, alkylheteroarylcarbonyl, heteroarylcarbonyl, heterocycloalkylcarbonyl, haloarylaminocarbonyl, alkylheteroarylsulfonyl, cyanoalkylarylcarbonyl, heterocycloalkoxycarbonyl, alkynyloxycarbonyl, cycloalkoxycarbonyl, heterobicycloarylcarbonyl, alkylheteroarylaminocarbonyl, alkylsulfonyl, alkylcarbonylalkyl, alkoxyarylcarbonyl, haloalkoxycarbonyl, alkylarylcarbonyl, haloalkoxyarylcarbonyl, or arylaminocarbonyl.

In several embodiments, $Z_1$ is one selected from

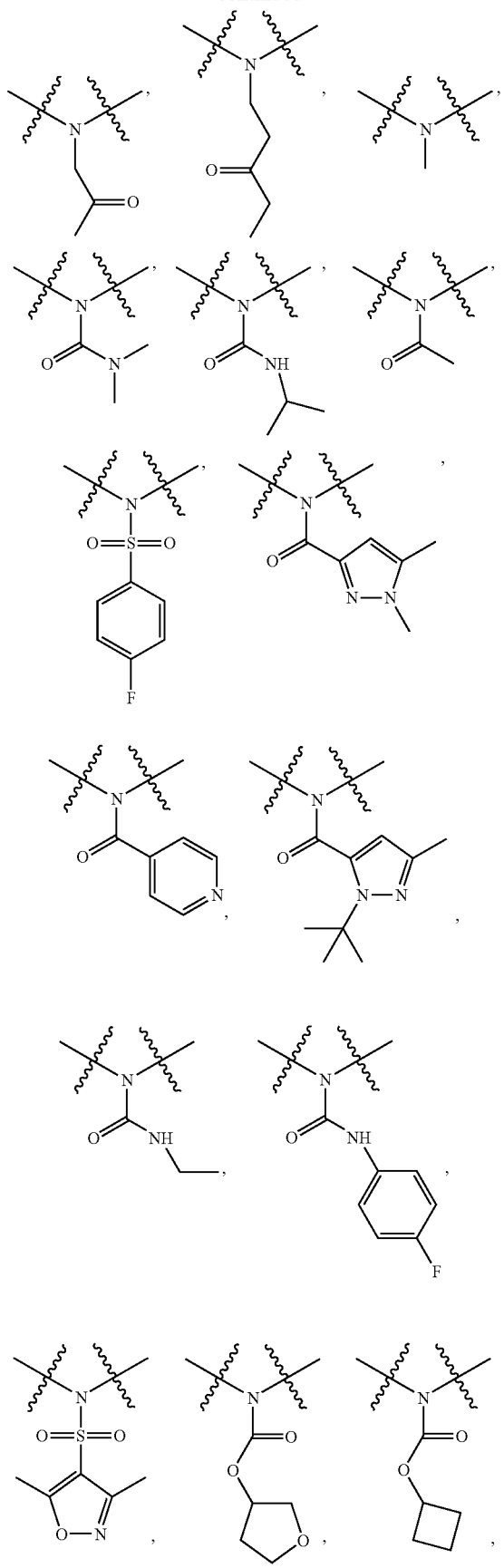
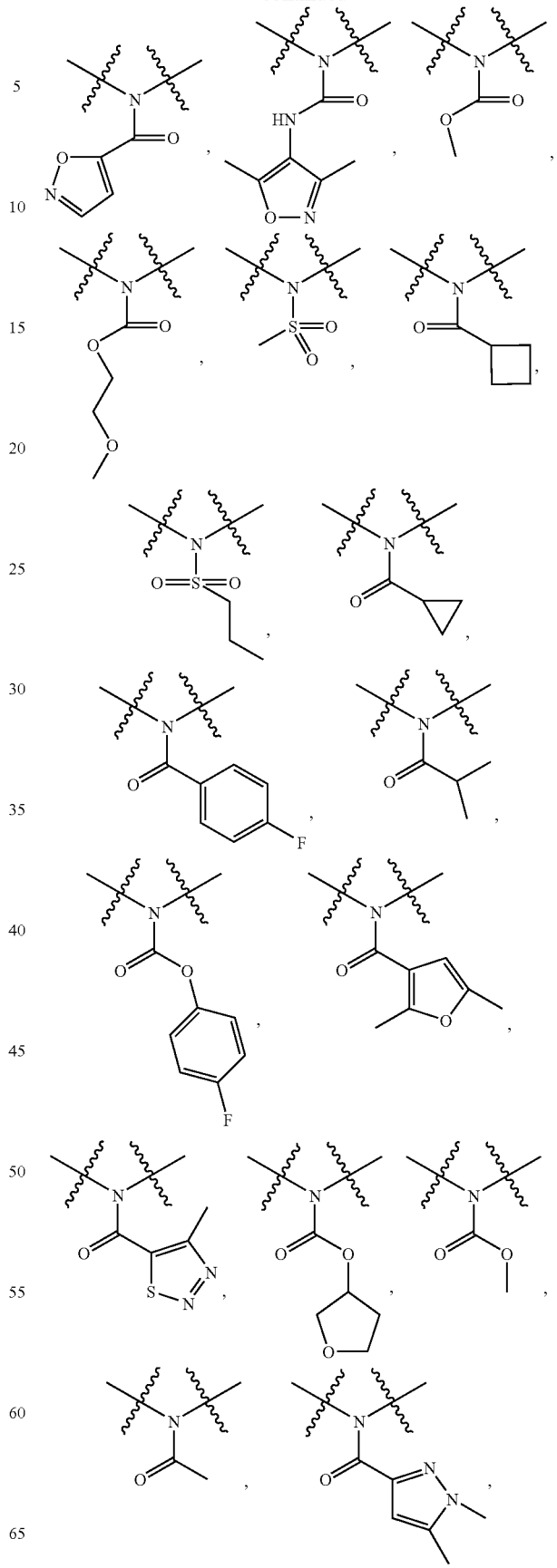

-continued
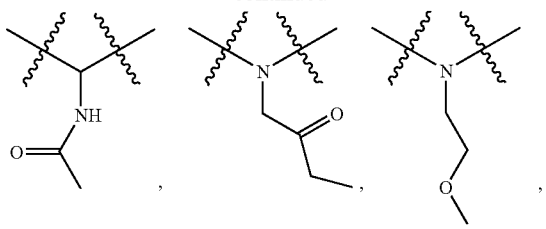
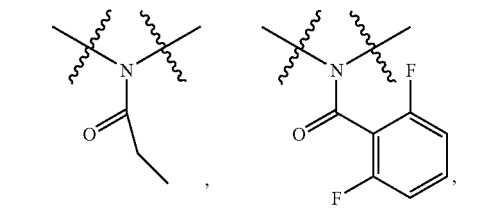
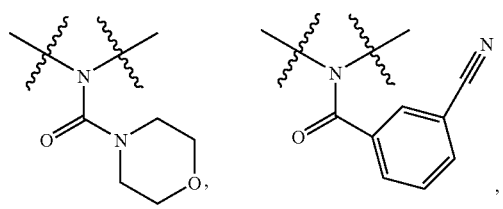
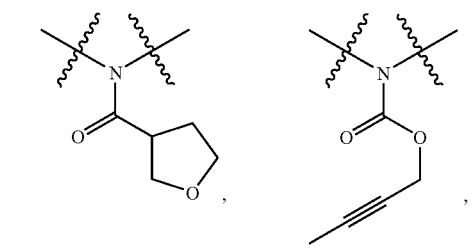
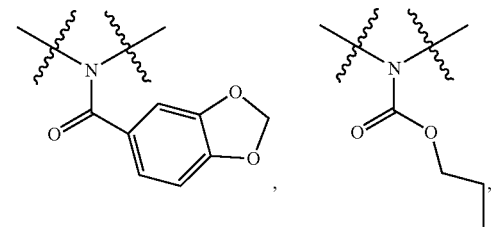
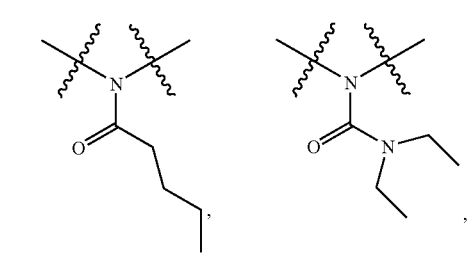
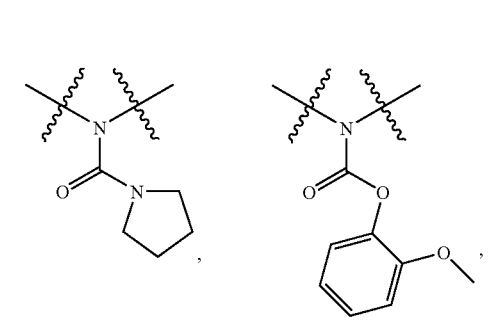
-continued
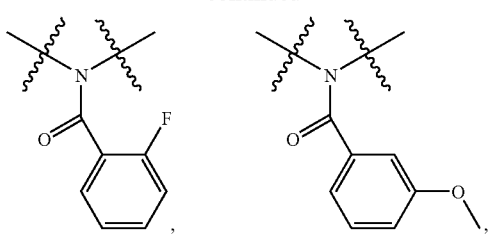
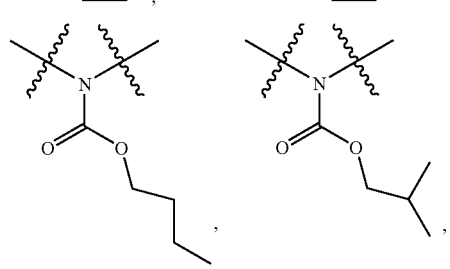
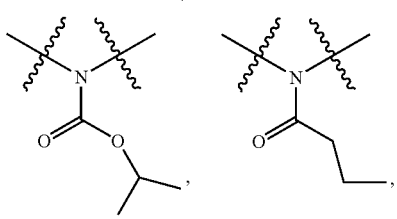
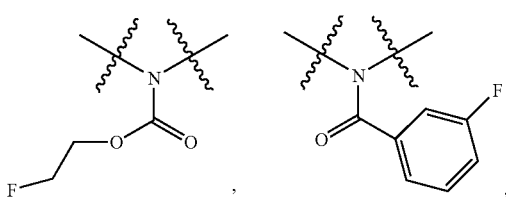
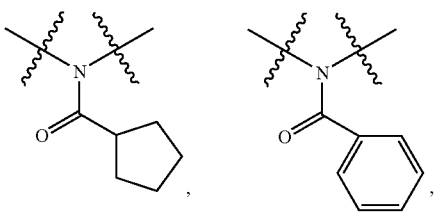
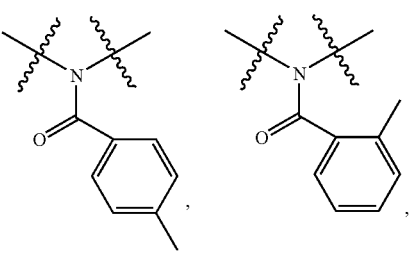
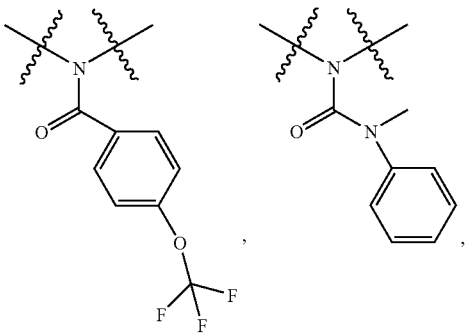

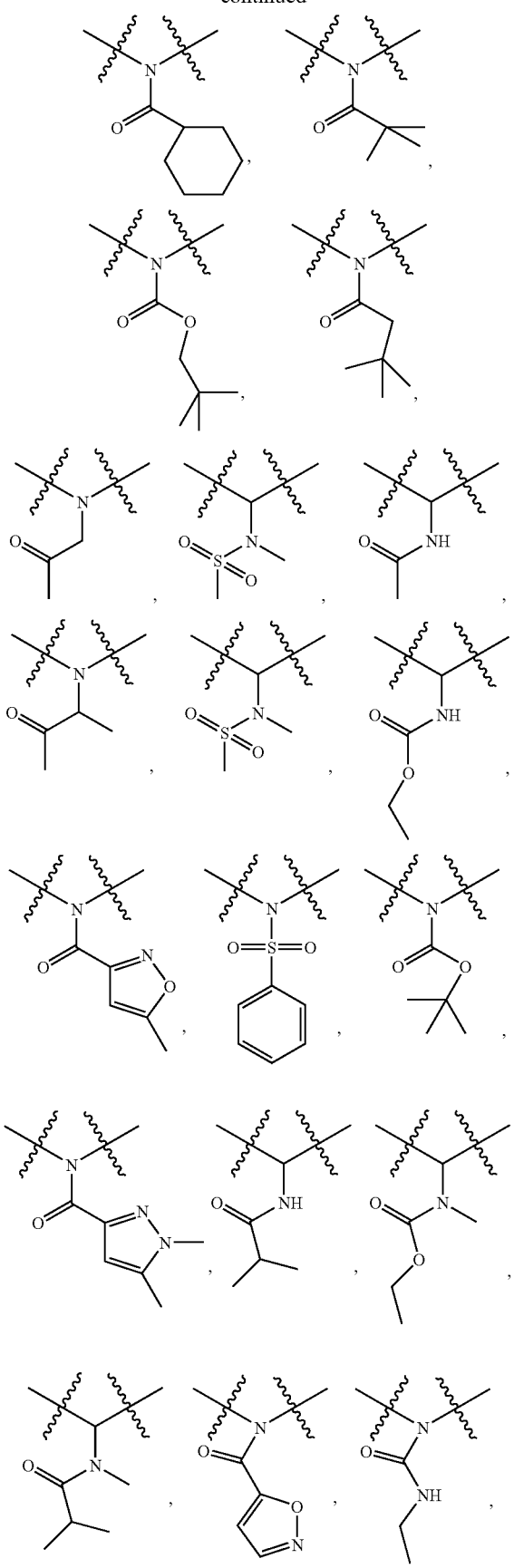
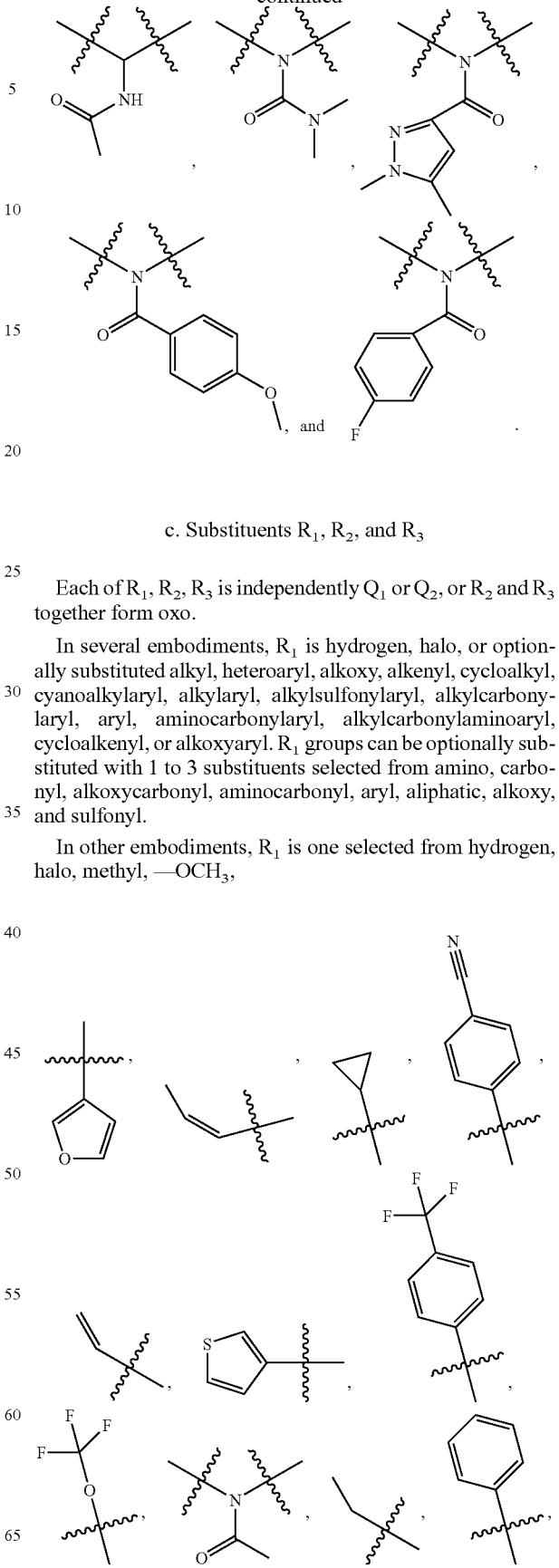

c. Substituents $R_1$, $R_2$, and $R_3$

Each of $R_1$, $R_2$, $R_3$ is independently $Q_1$ or $Q_2$, or $R_2$ and $R_3$ together form oxo.

In several embodiments, $R_1$ is hydrogen, halo, or optionally substituted alkyl, heteroaryl, alkoxy, alkenyl, cycloalkyl, cyanoalkylaryl, alkylaryl, alkylsulfonylaryl, alkylcarbonylaryl, aryl, aminocarbonylaryl, alkylcarbonylaminoaryl, cycloalkenyl, or alkoxyaryl. $R_1$ groups can be optionally substituted with 1 to 3 substituents selected from amino, carbonyl, alkoxycarbonyl, aminocarbonyl, aryl, aliphatic, alkoxy, and sulfonyl.

In other embodiments, $R_1$ is one selected from hydrogen, halo, methyl, —$OCH_3$, -continued

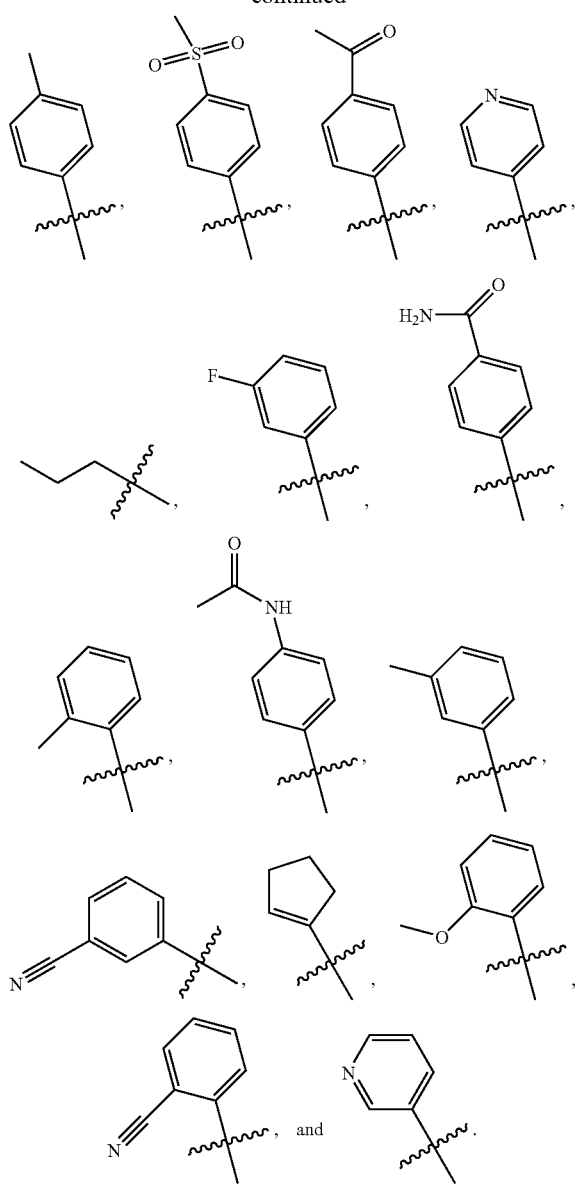

In several embodiments, $R_2$ and $R_3$ are independently hydrogen, alkyl, arylalkyl, or $R_2$ and $R_3$ together form an oxo or amino.

In still other embodiments, $R_2$ and $R_3$ are independently hydrogen, alkyl, or $R_2$ and $R_3$ together form an oxo.

d. L Groups

L is a bond, an aliphatic group, $C_3$-$C_6$ cycloaliphatic, —O—, —S(O)$_z$—, —S(O)$_z$—($C_1$-$C_4$)alkyl-, —C(O)N($Q_2$)-, or —S(O)$_z$N($Q_2$)-, in which the aliphatic group is optionally substituted with 1-3 of oxo, $Q_1$, or $Q_2$. In some embodiments, L is a bond or an aliphatic group in which the aliphatic group is optionally substituted with 1-3 of oxo, $Q_1$, or $Q_2$. In other embodiments, L is a bond. In still further embodiments, L is an aliphatic group optionally substituted with 1-3 of oxo, $Q_1$, or $Q_2$. L is $CH_2$.

e. Combinations of Embodiments

Other embodiments include any combination of the aforementioned substituents G, $Z_1$, L, $R_1$, $R_2$, and $R_3$.

f. Excluded Compounds

In several embodiments, when $Z_1$ is —$CH_2$— or —N($CH_3$)—, L is a bond, and G is an optionally substituted monocycloaliphatic, an optionally substituted monocycloheteroalipahtic group, or a norbornanyl group, then the $R_1$ substituent on the indane or indole is other than H.

In several embodiments, when L is —C(O)—$CH_2$— and $Z_1$ is —N($Q_1$)-, and $Q_1$ on $Z_1$ is —S(O)$_2$-optionally substituted phenyl, then the $R_1$ substituent on the indole is other than H.

In several embodiments, when L is —S(O)$_2$—($C_1$-$C_4$) alkyl-, $Z_1$ is —$CH_2$—, then the $R_1$ substituent on the indane or tetrahydronaphthyl is other than H.

In several embodiments, when L is —S(O)$_2$—($C_1$-$C_4$) alkyl-, $R_2$ and $R_3$ form =O, $Z_1$ is —N($Q_1$)-, and $Q_1$ is aliphatic or —S(O)$_2$-aliphatic, then the $R_1$ substituent on the indole is other than H.

In several embodiments, when L is aliphatic, and $R_2$ and $R_3$ form =O, and $Z_1$ is —N($Q_1$)-, $Q_1$ is aliphatic, G is a substituted monocycloheteroaliphatic group, then the $R_1$ substituent on the indole is other than H.

In certain embodiments, L is not —S(O)$_2$—($C_1$-$C_4$)alkyl-.

g. Specific Embodiments

Specific compounds of formulae (I or II) are shown below in Table 1.

TABLE 1

Exemplary compounds of formula I.

| 1 | 2 |
|---|---|
| 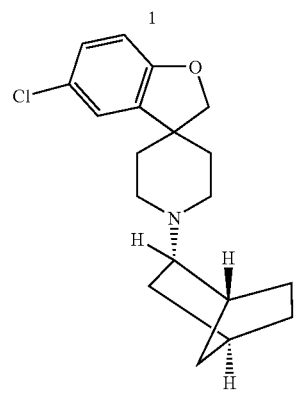 | 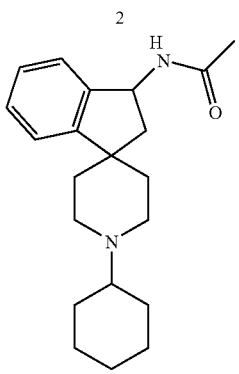 |

TABLE 1-continued
Exemplary compounds of formula I.
3
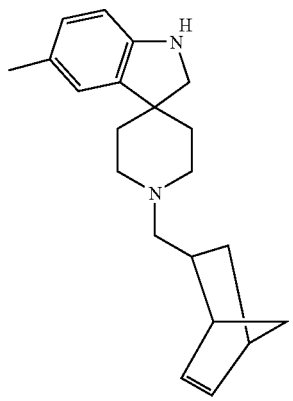
4
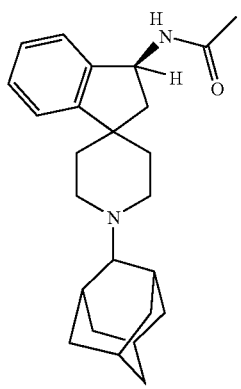
5
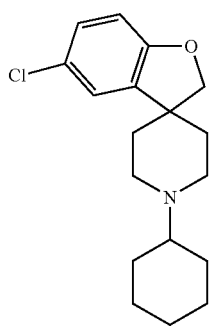 [SMILES: Clc1ccc2c(c1)C1(CCN(C3CCCCC3)CC1)CO2]
6
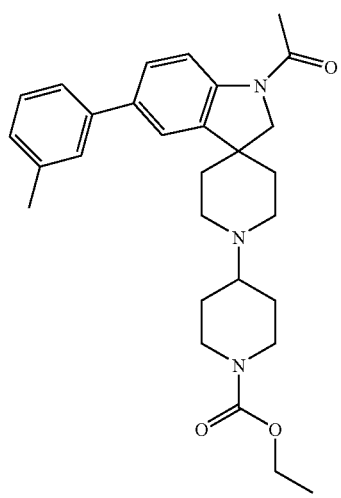
7
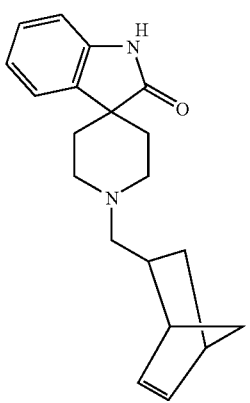
8
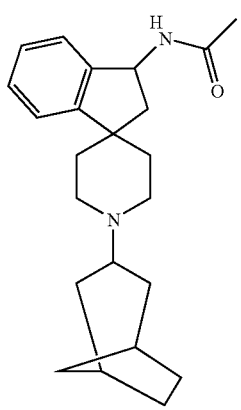

TABLE 1-continued
Exemplary compounds of formula I.
9
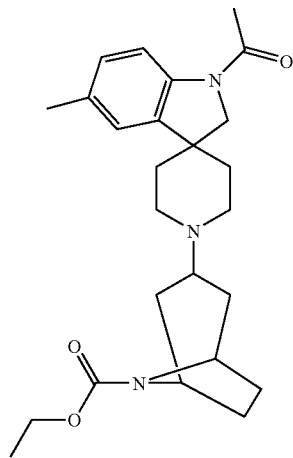 [SMILES: CCOC(=O)N1C2CCC1CC(N1CCC3(CC1)CN(C(C)=O)c1ccc(C)cc13)C2]
10
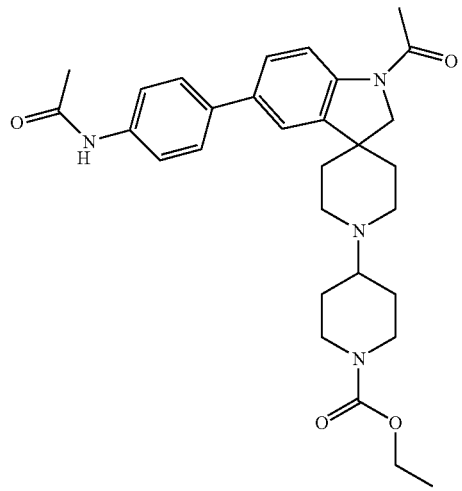
11
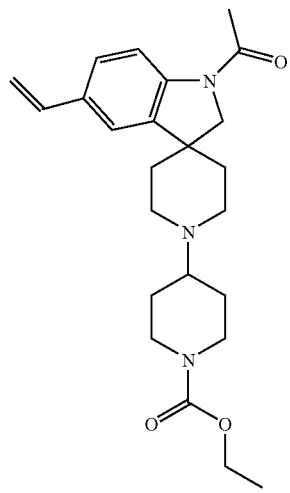 [SMILES: C=Cc1ccc2c(c1)C1(CCN(C3CCN(C(=O)OCC)CC3)CC1)CN2C(C)=O]
12
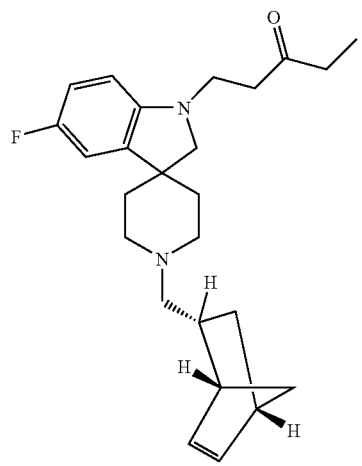 [SMILES: CCC(=O)CCN1CC2(CCN(C[C@@H]3C[C@H]4C=C[C@H]3C4)CC2)c2cc(F)ccc21]
13
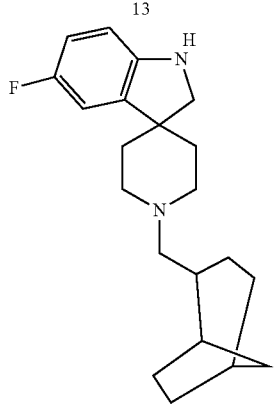
14
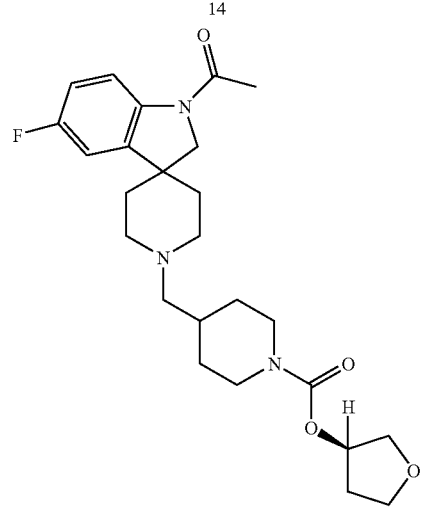

TABLE 1-continued
Exemplary compounds of formula I.
15
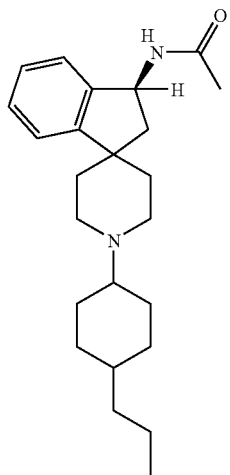
16
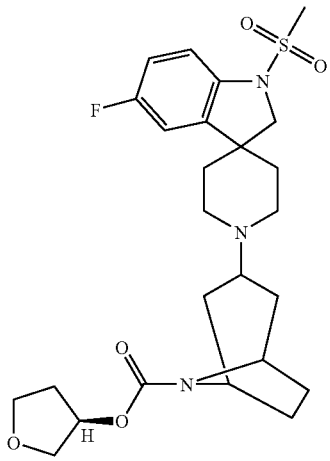
17
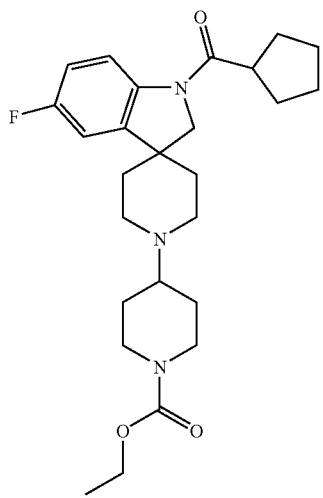 [SMILES: CCOC(=O)N1CCC(N2CCC3(CC2)CN(C(=O)C2CCCC2)c2ccc(F)cc23)CC1]
18
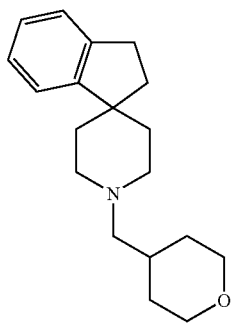 [SMILES: c1ccc2c(c1)CCC21CCN(CC2CCOCC2)CC1]
19
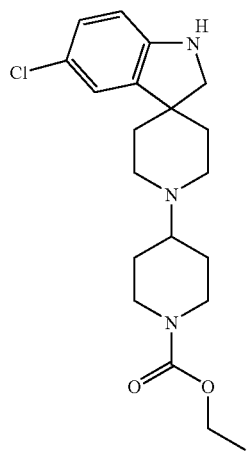
20
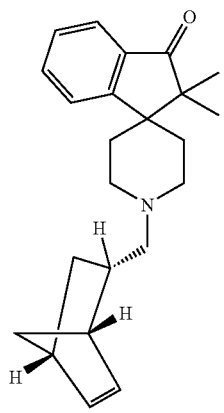 [SMILES: CC1(C)C(=O)c2ccccc2C12CCN(C[C@H]1C[C@@H]3C=C[C@@H]1C3)CC2]

TABLE 1-continued
Exemplary compounds of formula I.
21
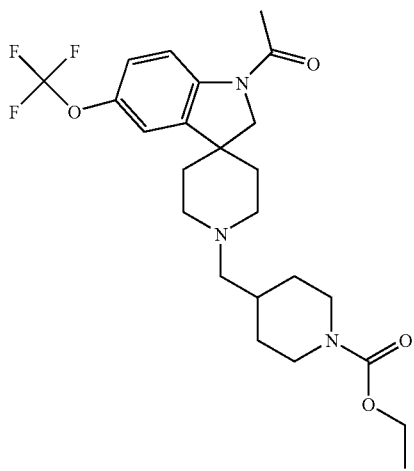 [SMILES: CCOC(=O)N1CCC(CN2CCC3(CC2)CN(C(C)=O)c2ccc(OC(F)(F)F)cc23)CC1]
22
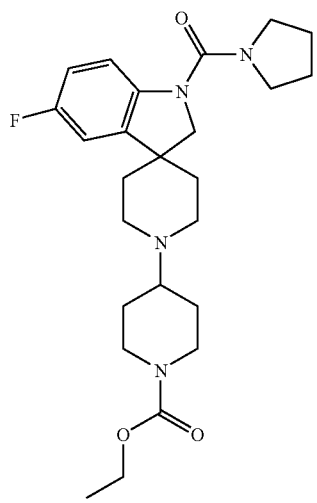 [SMILES: CCOC(=O)N1CCC(N2CCC3(CC2)CN(C(=O)N2CCCC2)c2ccc(F)cc23)CC1]
23
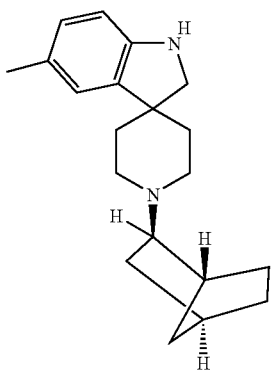
24
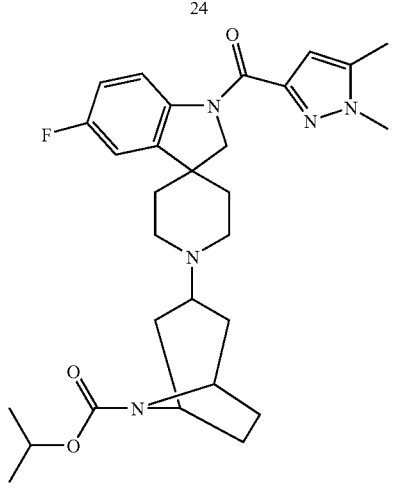
25
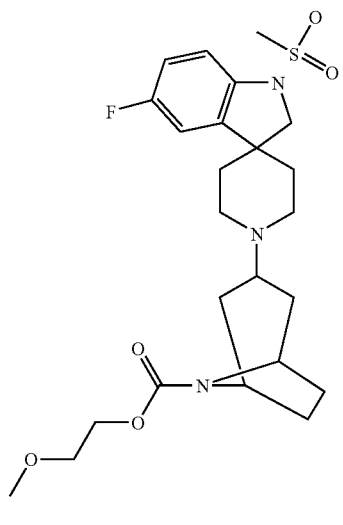
26
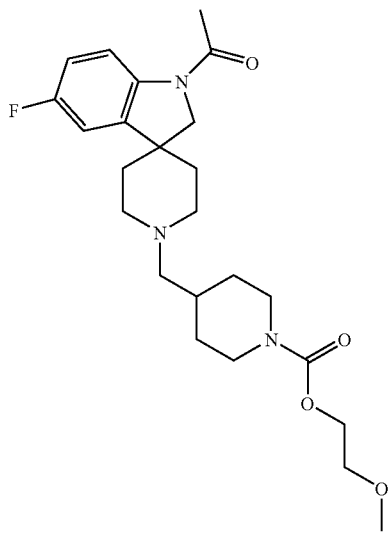 [SMILES: COCCOC(=O)N1CCC(CN2CCC3(CC2)CN(C(C)=O)c2ccc(F)cc23)CC1]

TABLE 1-continued
Exemplary compounds of formula I.
27
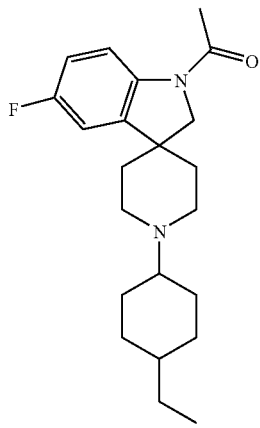 [SMILES: CCC1CCC(N2CCC3(CC2)CN(C(C)=O)c2ccc(F)cc23)CC1]
28
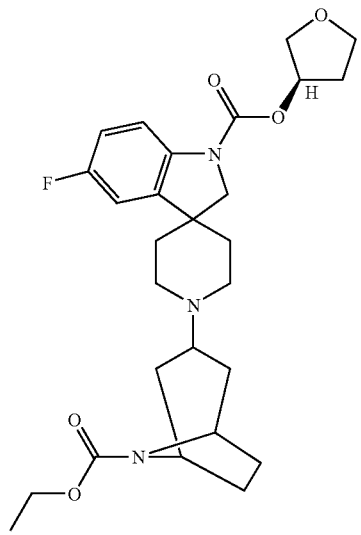
29
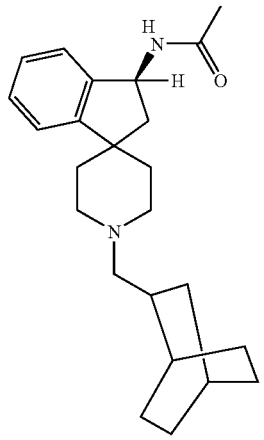
30
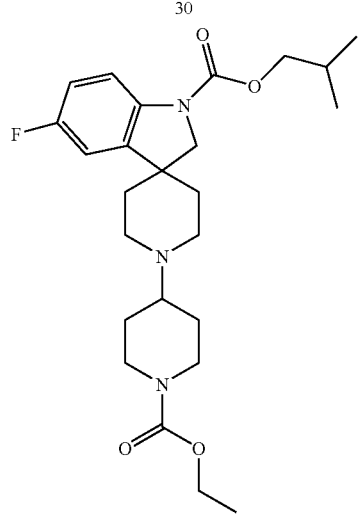
31
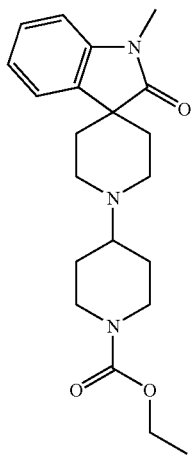 [SMILES: CCOC(=O)N1CCC(N2CCC3(CC2)C(=O)N(C)c2ccccc23)CC1]
32
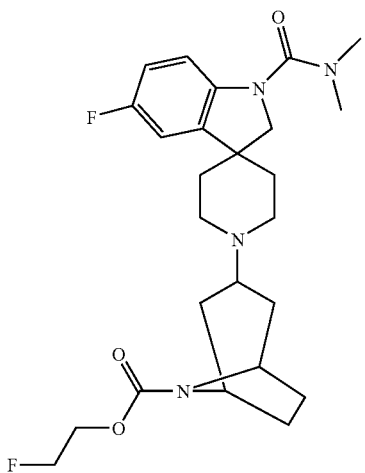 [SMILES: CN(C)C(=O)N1CC2(CCN(C3CC4CCC(C3)N4C(=O)OCCF)CC2)c2cc(F)ccc21]

TABLE 1-continued
Exemplary compounds of formula I.
33
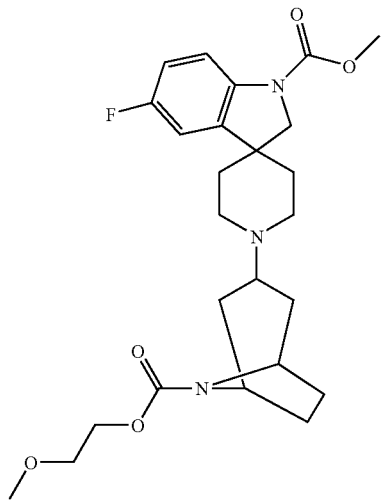
34
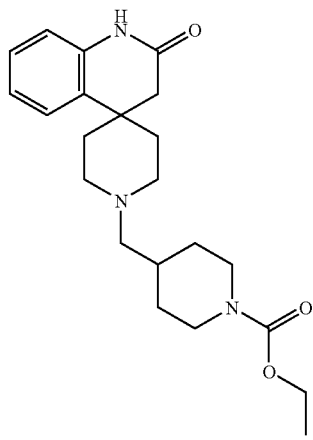 [SMILES: CCOC(=O)N1CCC(CN2CCC3(CC2)CC(=O)Nc2ccccc23)CC1]
35
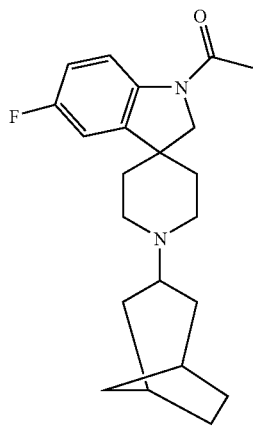 [SMILES: CC(=O)N1CC2(CCN(C3CC4CCC(C4)C3)CC2)c2cc(F)ccc21]
36
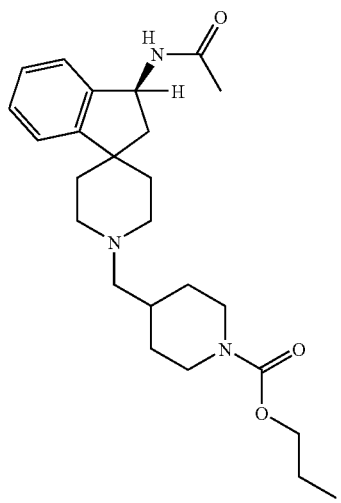
37
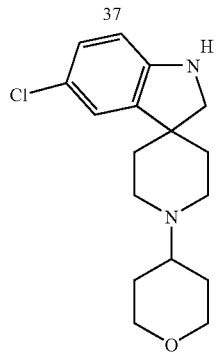
38
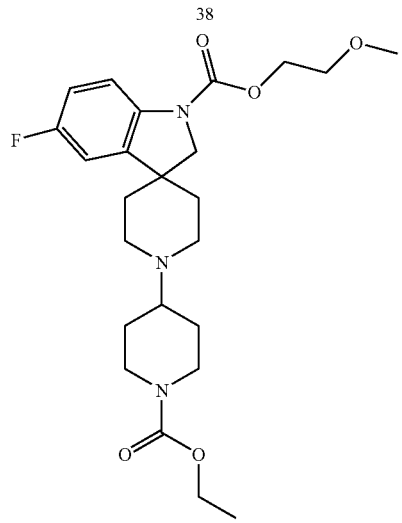

TABLE 1-continued
Exemplary compounds of formula I.
39
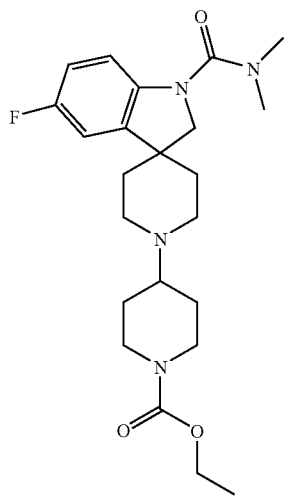
40
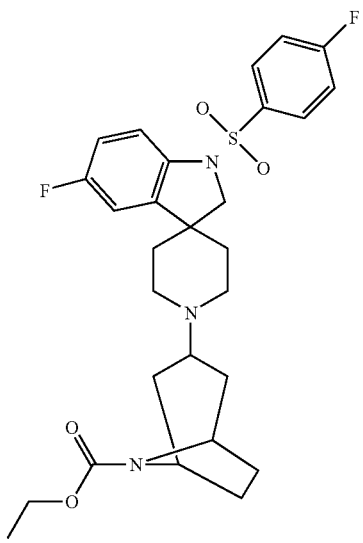
41
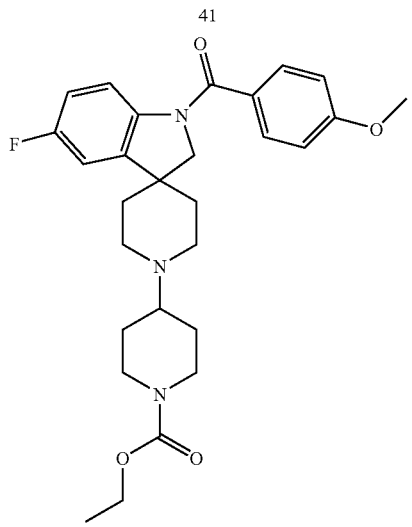
42
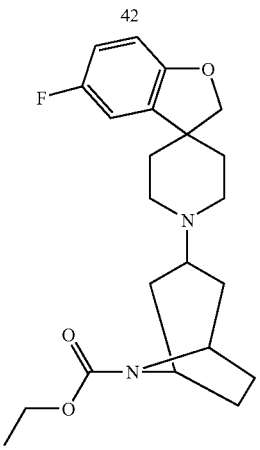
43
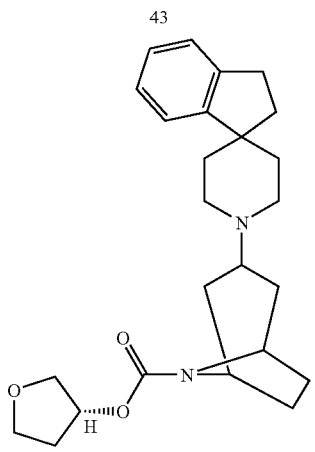
44
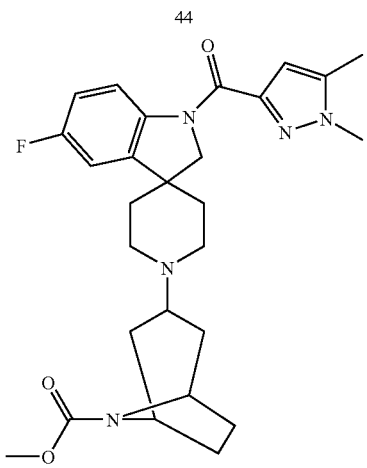

TABLE 1-continued
Exemplary compounds of formula I.
45
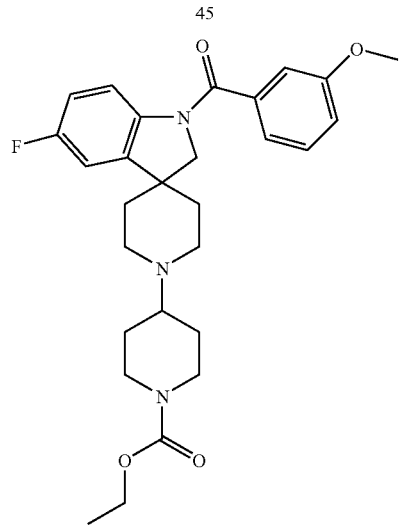
46
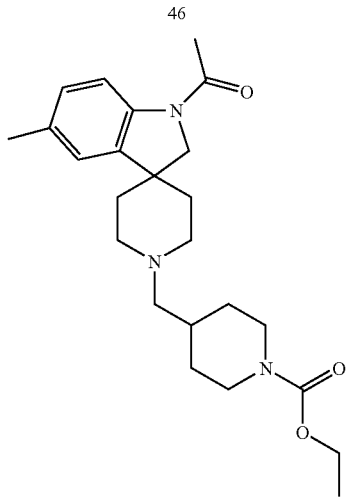
47
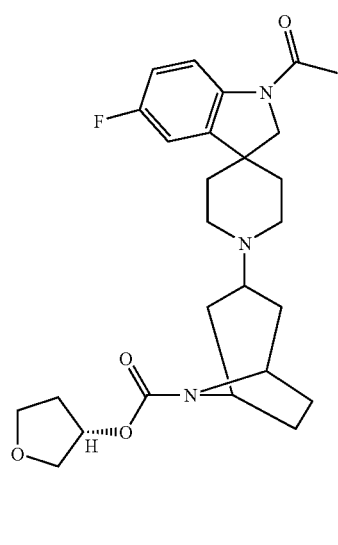
48
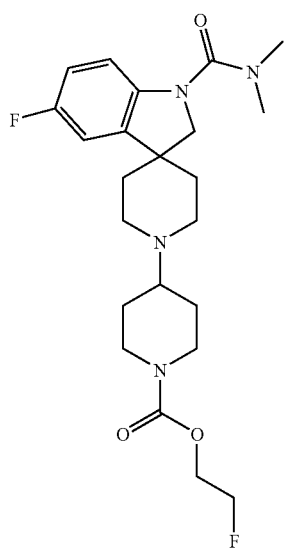

TABLE 1-continued
Exemplary compounds of formula I.
49
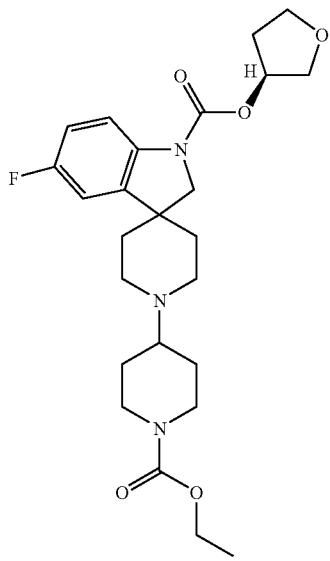
50
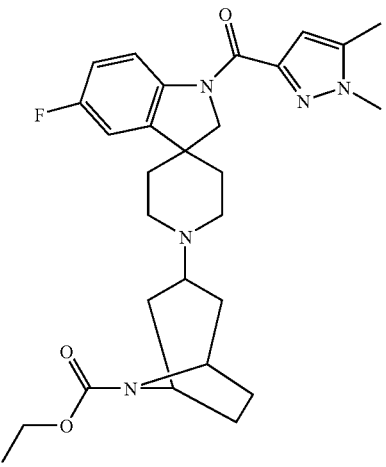 [SMILES: CCOC(=O)N1C2CCC1CC(N1CCC3(CC1)CN(C(=O)c1cc(C)n(C)n1)c1ccc(F)cc13)C2]
51
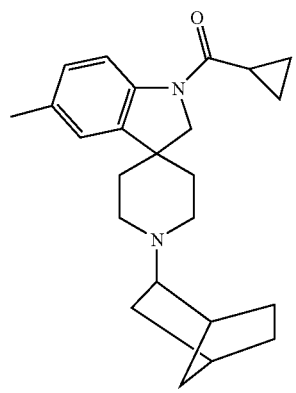 [SMILES: Cc1ccc2c(c1)C1(CCN(C3CC4CCC3C4)CC1)CN2C(=O)C1CC1]
52
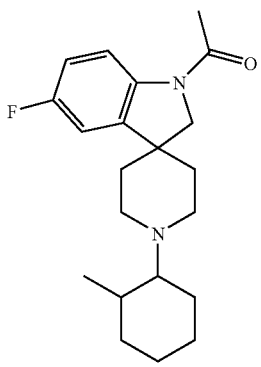 [SMILES: CC(=O)N1CC2(CCN(C3CCCCC3C)CC2)c2cc(F)ccc21]
53
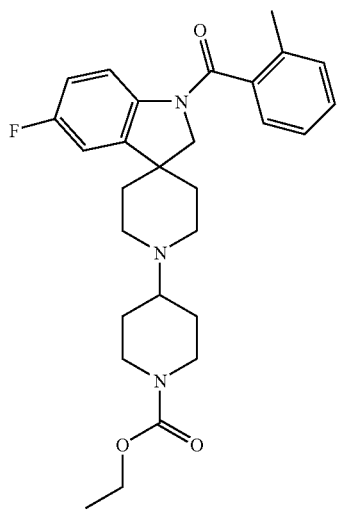 [SMILES: CCOC(=O)N1CCC(N2CCC3(CC2)CN(C(=O)c2ccccc2C)c2ccc(F)cc23)CC1]
54
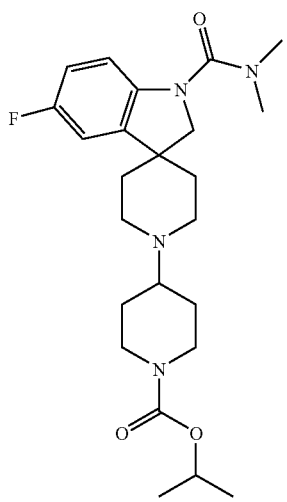 [SMILES: CC(C)OC(=O)N1CCC(N2CCC3(CC2)CN(C(=O)N(C)C)c2ccc(F)cc23)CC1]

TABLE 1-continued
Exemplary compounds of formula I.
55
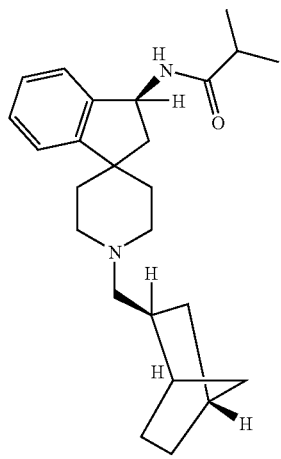
56
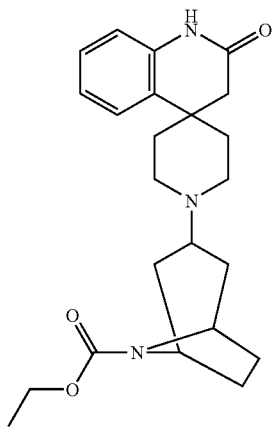 [SMILES: CCOC(=O)N1C2CCC1CC(N1CCC3(CC1)CC(=O)Nc1ccccc13)C2]
57
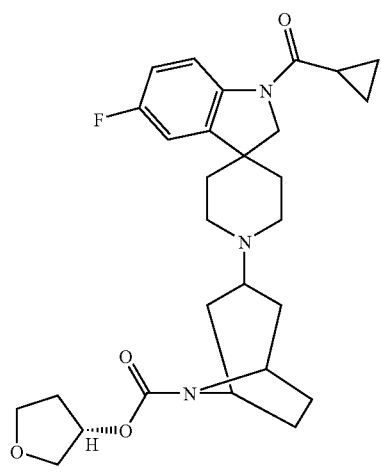
58
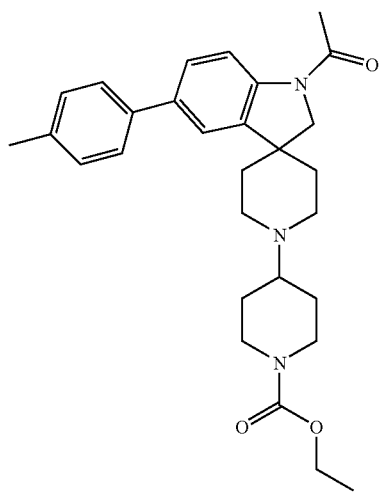 [SMILES: CCOC(=O)N1CCC(N2CCC3(CC2)CN(C(C)=O)c2ccc(-c4ccc(C)cc4)cc23)CC1]
59
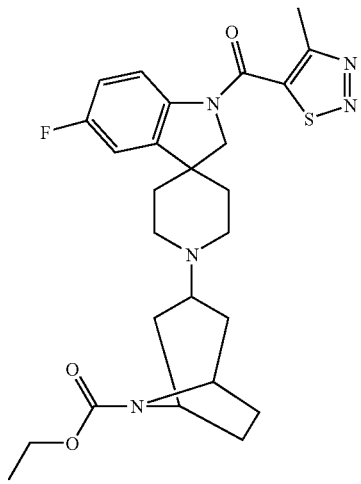 [SMILES: CCOC(=O)N1C2CCC1CC(N1CCC3(CC1)CN(C(=O)c1snnc1C)c1ccc(F)cc13)C2]
60
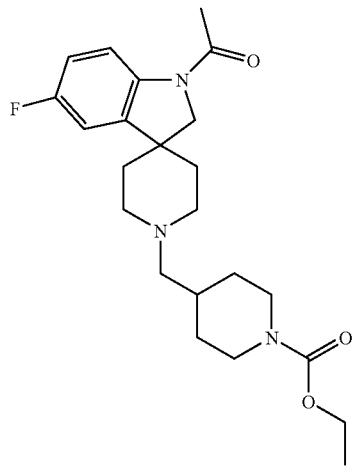

TABLE 1-continued
Exemplary compounds of formula I.
61
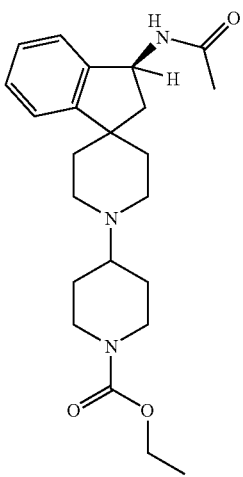
62
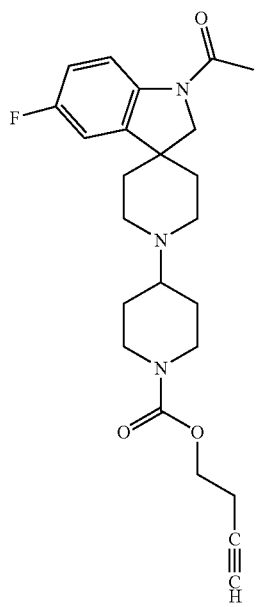 [SMILES: C#CCCOC(=O)N1CCC(N2CCC3(CC2)CN(C(C)=O)c2ccc(F)cc23)CC1]
63
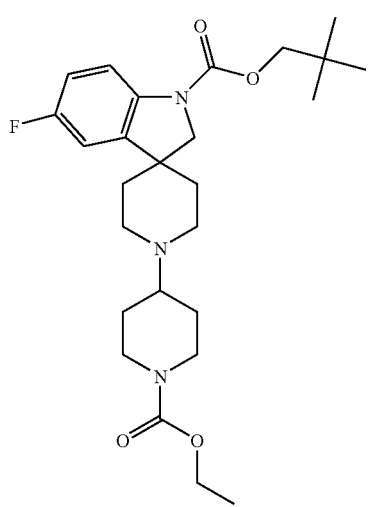 [SMILES: CCOC(=O)N1CCC(N2CCC3(CC2)CN(C(=O)OCC(C)(C)C)c2ccc(F)cc23)CC1]
64
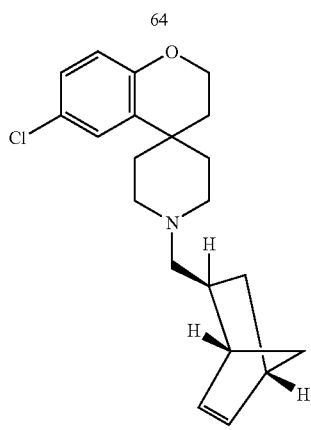

TABLE 1-continued
Exemplary compounds of formula I.
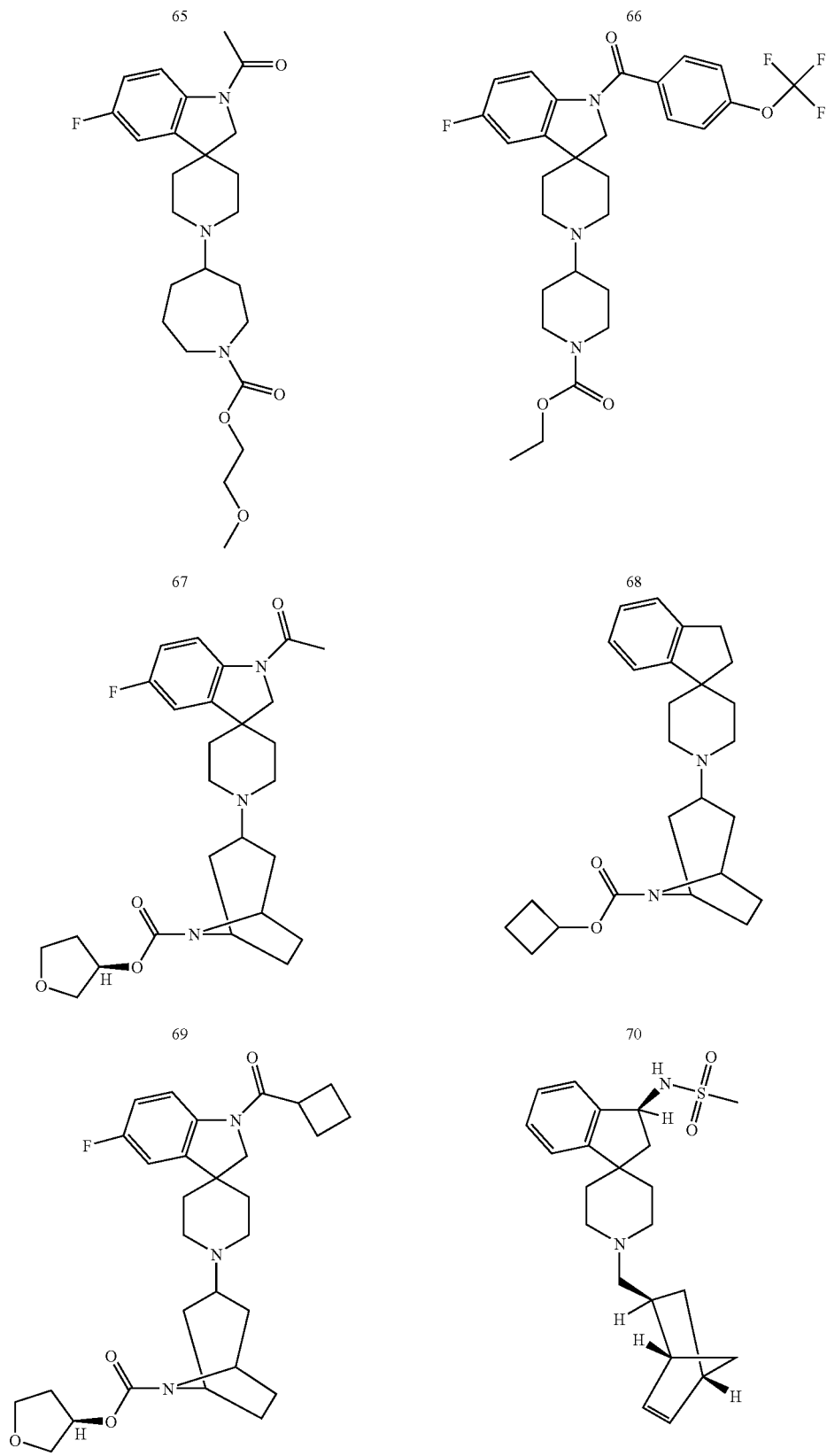

TABLE 1-continued
Exemplary compounds of formula I.
71
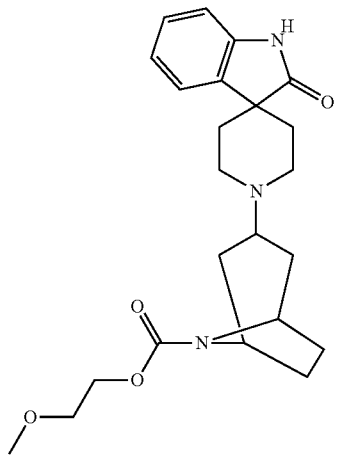
72
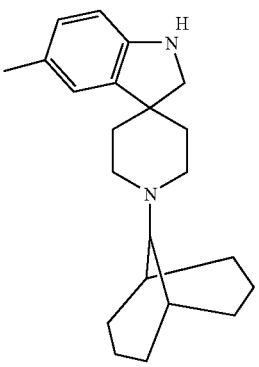
73
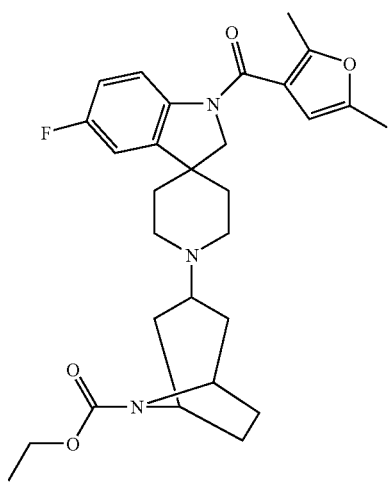 [SMILES: CCOC(=O)N1C2CCC1CC(N1CCC3(CC1)CN(C(=O)c1cc(C)oc1C)c1ccc(F)cc13)C2]
74
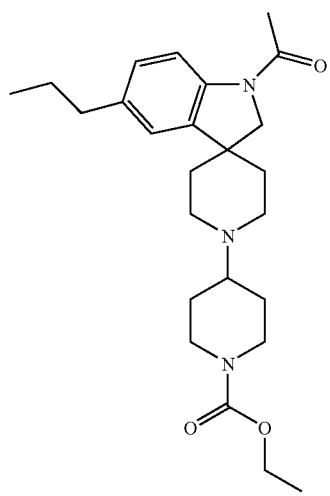 [SMILES: CCCc1ccc2c(c1)C1(CCN(C3CCN(C(=O)OCC)CC3)CC1)CN2C(C)=O]
75
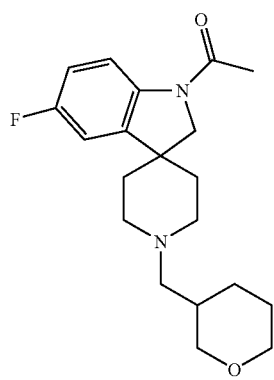 [SMILES: CC(=O)N1CC2(CCN(CC3CCCOC3)CC2)c2cc(F)ccc21]
76
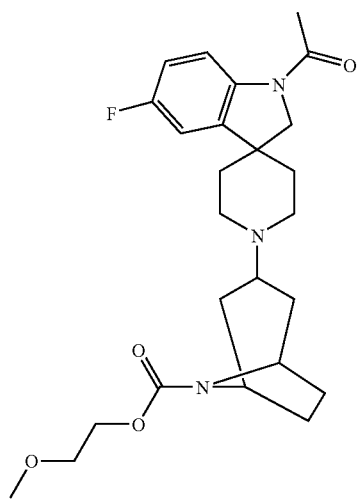 [SMILES: COCCOC(=O)N1C2CCC1CC(N1CCC3(CC1)CN(C(C)=O)c1ccc(F)cc13)C2]

TABLE 1-continued
Exemplary compounds of formula I.
77
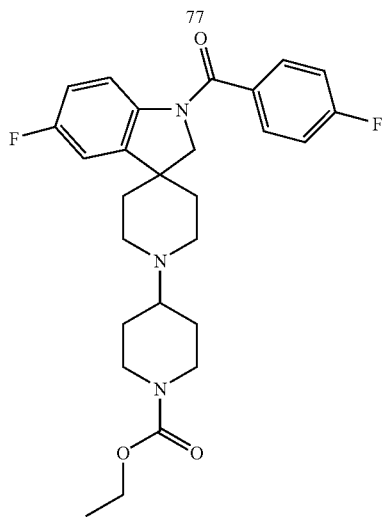
78
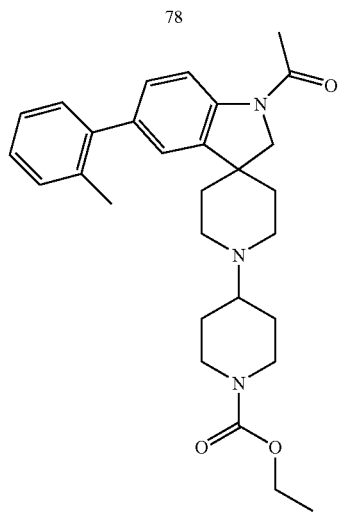
79
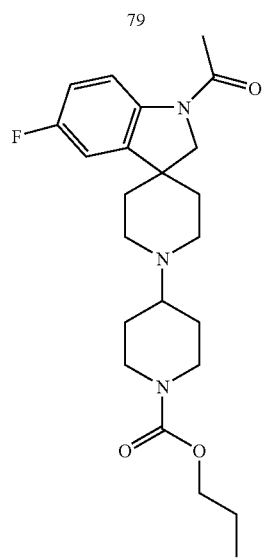
80
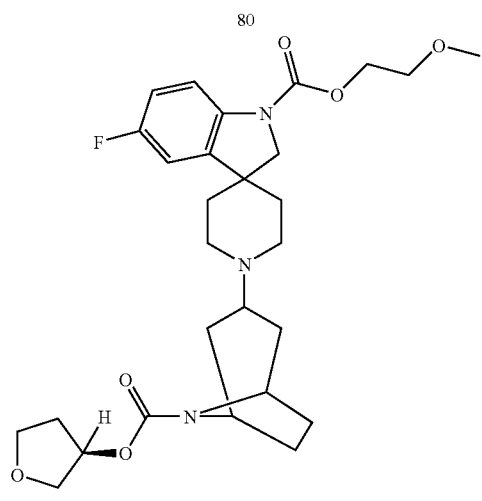
81
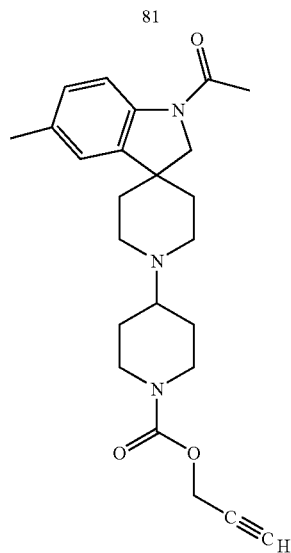
82
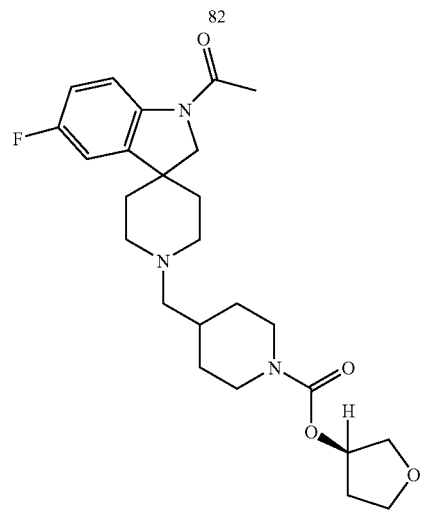

TABLE 1-continued
Exemplary compounds of formula I.
83
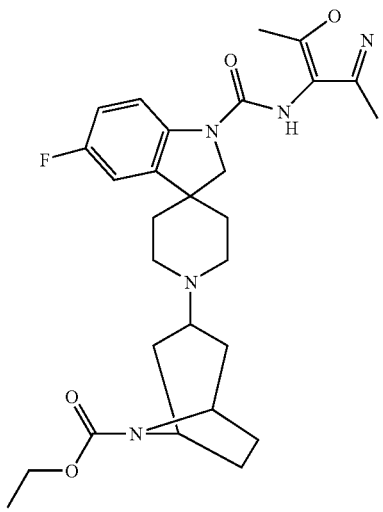
84
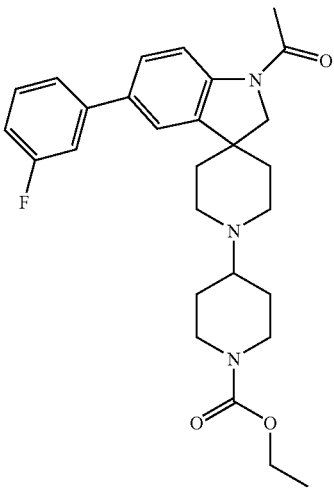 [SMILES: CCOC(=O)N1CCC(N2CCC3(CC2)CN(C(C)=O)c2ccc(-c4cccc(F)c4)cc23)CC1]
85
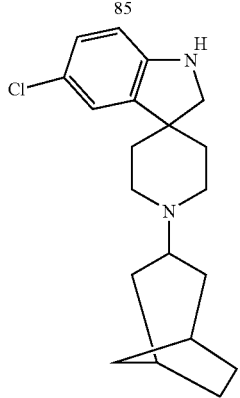
86
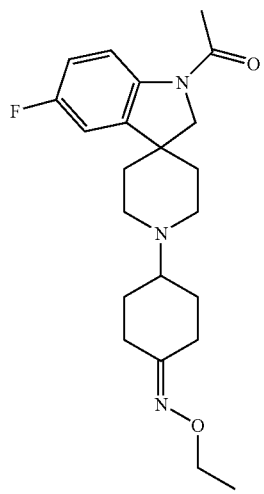 [SMILES: CCON=C1CCC(N2CCC3(CC2)CN(C(C)=O)c2ccc(F)cc23)CC1]
87
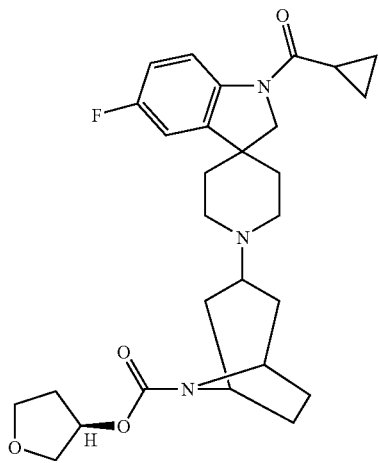
88
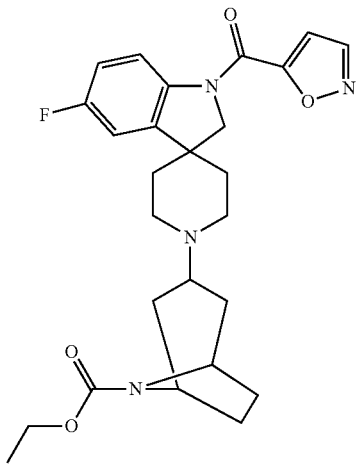 [SMILES: CCOC(=O)N1C2CCC1CC(N1CCC3(CC1)CN(C(=O)c1ccno1)c1ccc(F)cc13)C2]

TABLE 1-continued
Exemplary compounds of formula I.
89
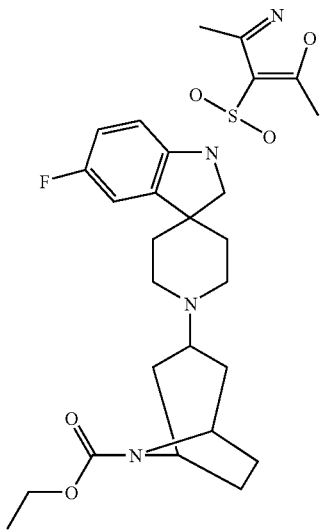
90
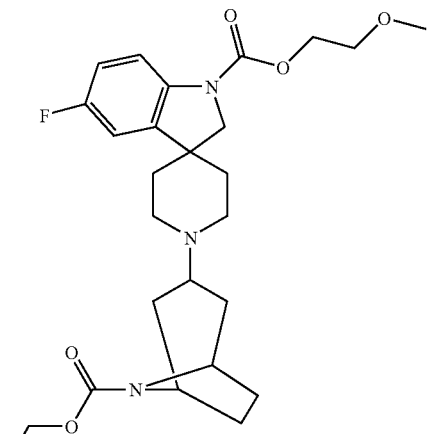
91
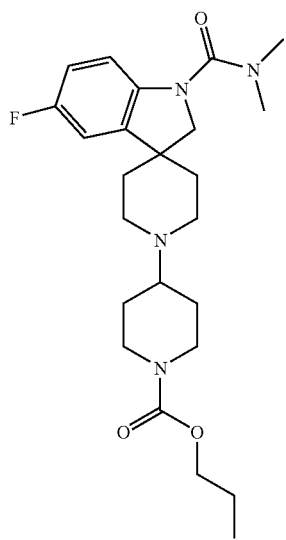 [SMILES: CCCOC(=O)N1CCC(N2CCC3(CC2)CN(C(=O)N(C)C)c2ccc(F)cc23)CC1]
92
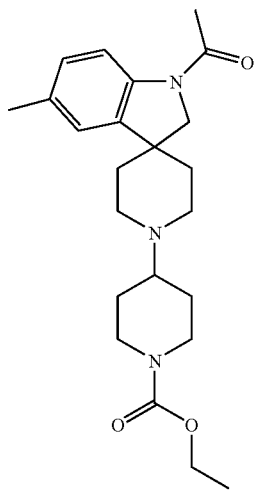 [SMILES: CCOC(=O)N1CCC(N2CCC3(CC2)CN(C(C)=O)c2ccc(C)cc23)CC1]

TABLE 1-continued
Exemplary compounds of formula I.
93
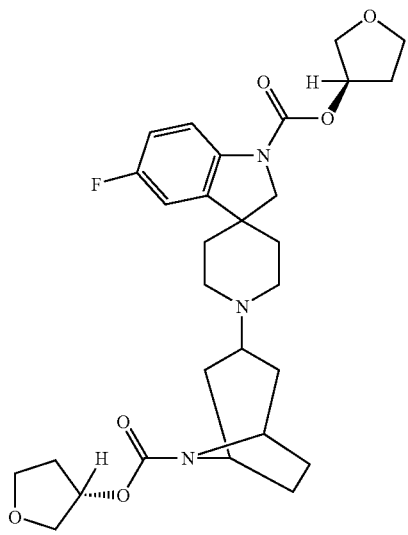 [SMILES: O=C(O[C@@H]1CCOC1)N1CC2(CCN(C3CC4CCC(C3)N4C(=O)O[C@H]3CCOC3)CC2)c2cc(F)ccc21]
94
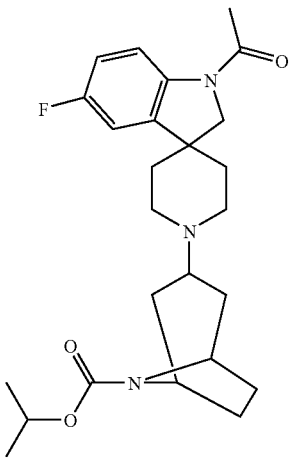 [SMILES: CC(=O)N1CC2(CCN(C3CC4CCC(C3)N4C(=O)OC(C)C)CC2)c2cc(F)ccc21]
95
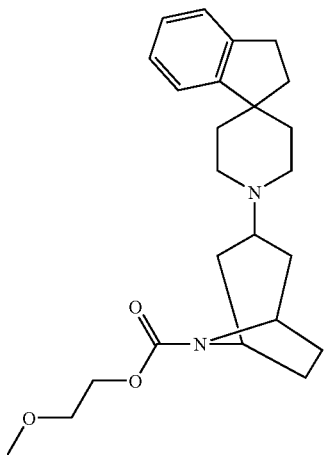 [SMILES: COCCOC(=O)N1C2CCC1CC(N1CCC3(CCc4ccccc43)CC1)C2]
96
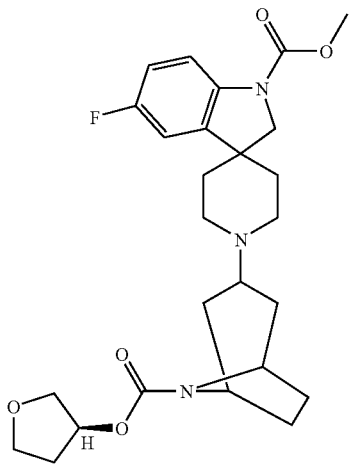
97
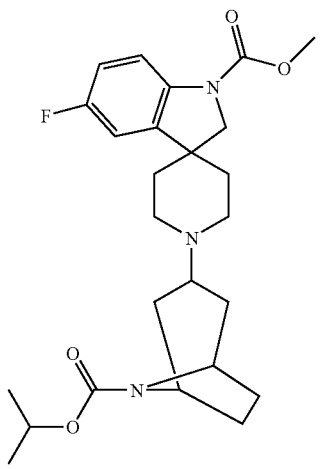 [SMILES: COC(=O)N1CC2(CCN(C3CC4CCC(C3)N4C(=O)OC(C)C)CC2)c2cc(F)ccc21]
98
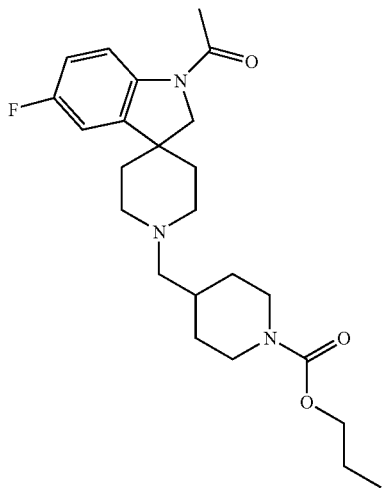 [SMILES: CCCOC(=O)N1CCC(CN2CCC3(CC2)CN(C(C)=O)c2ccc(F)cc23)CC1]

TABLE 1-continued
Exemplary compounds of formula I.
99
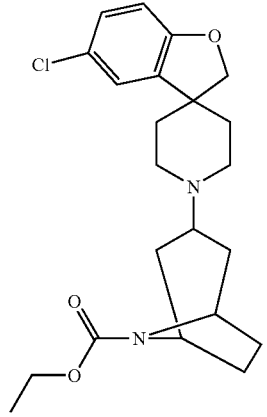
100
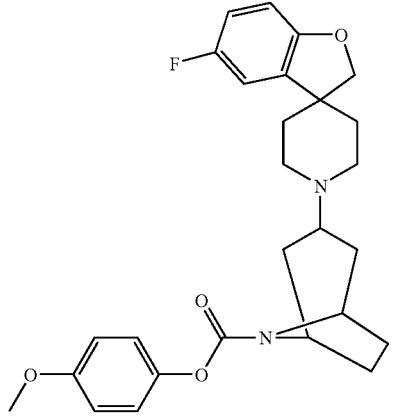 [SMILES: COc1ccc(OC(=O)N2C3CCC2CC(N2CCC4(CC2)COc2ccc(F)cc24)C3)cc1]
101
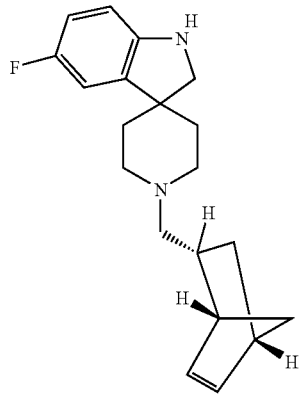
102
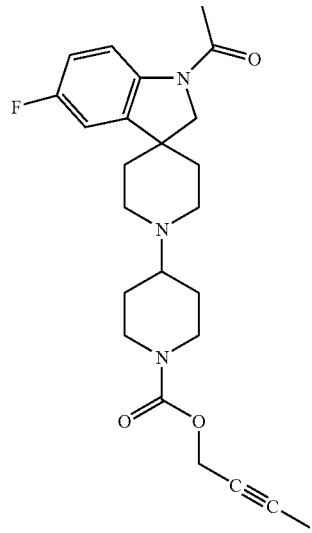 [SMILES: CC#CCOC(=O)N1CCC(N2CCC3(CC2)CN(C(C)=O)c2ccc(F)cc23)CC1]
103
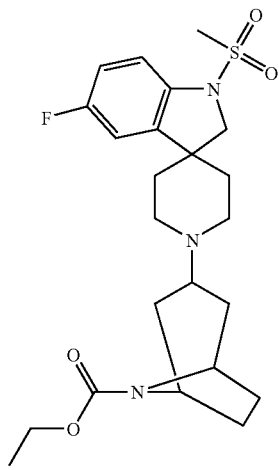 [SMILES: CCOC(=O)N1C2CCC1CC(N1CCC3(CC1)CN(S(C)(=O)=O)c1ccc(F)cc13)C2]
104
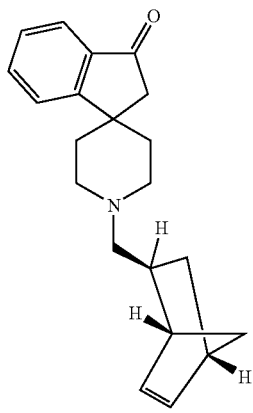 [SMILES: O=C1CC2(CCN(C[C@H]3C[C@H]4C=C[C@H]3C4)CC2)c2ccccc21]

TABLE 1-continued
Exemplary compounds of formula I.
105
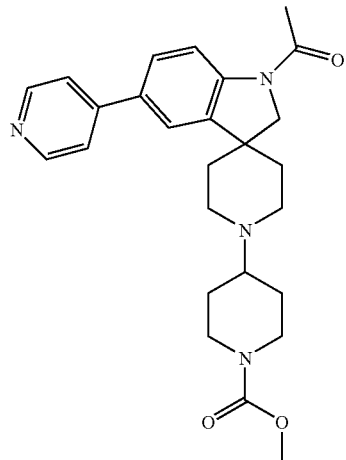
106
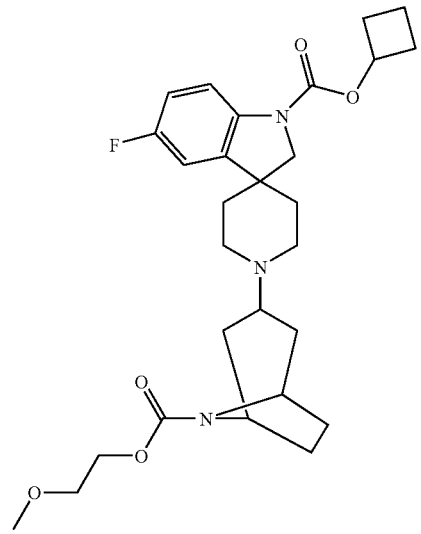 [SMILES: COCCOC(=O)N1C2CCC1CC(N1CCC3(CC1)CN(C(=O)OC1CCC1)c1ccc(F)cc13)C2]
107
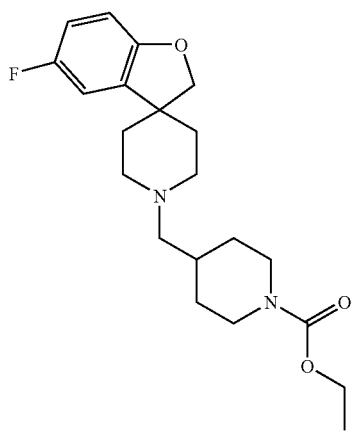 [SMILES: CCOC(=O)N1CCC(CN2CCC3(CC2)COc2ccc(F)cc23)CC1]
108
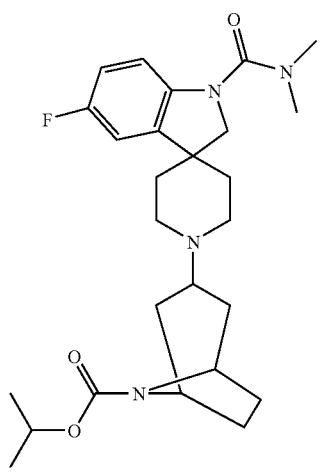 [SMILES: CC(C)OC(=O)N1C2CCC1CC(N1CCC3(CC1)CN(C(=O)N(C)C)c1ccc(F)cc13)C2]
109
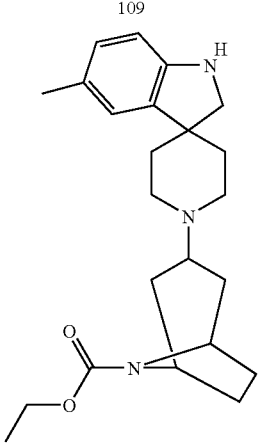
110
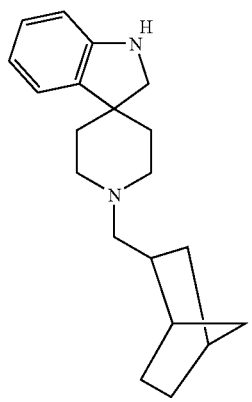

TABLE 1-continued
Exemplary compounds of formula I.
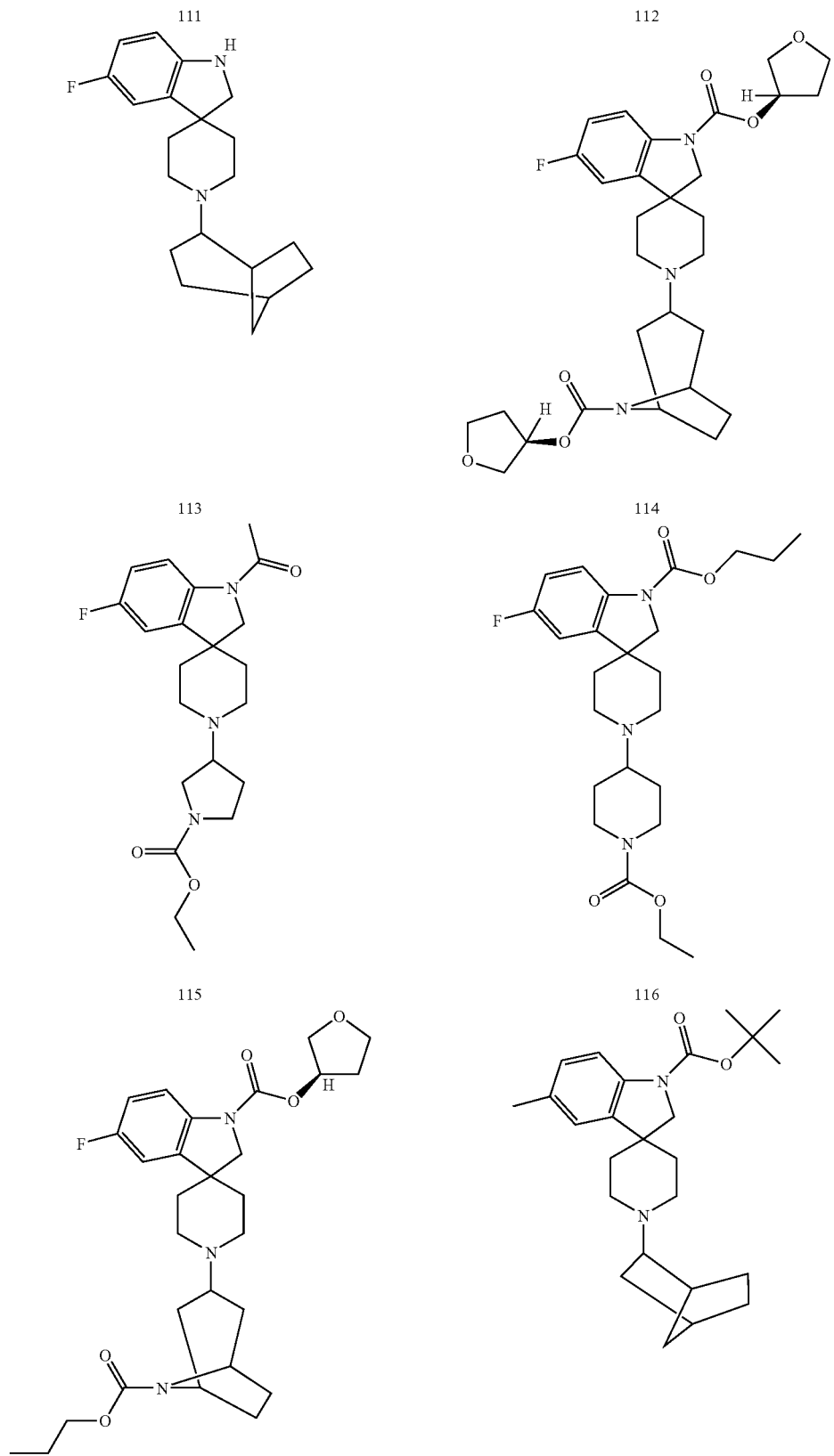

TABLE 1-continued
Exemplary compounds of formula I.
117
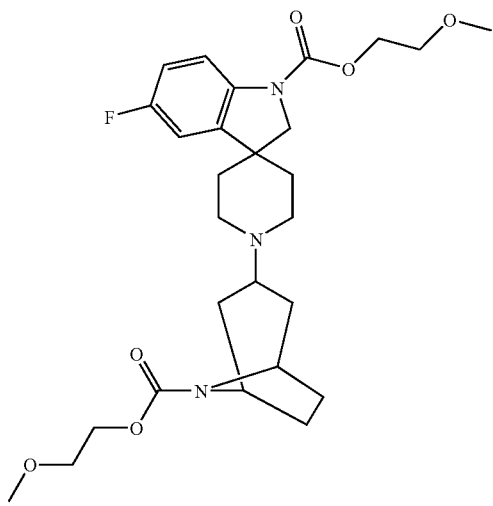
118
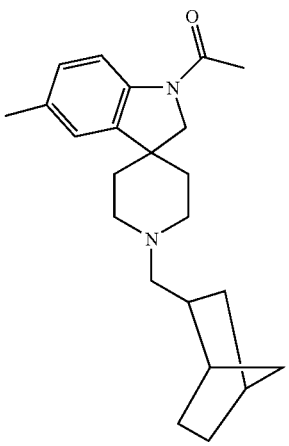 [SMILES: CC(=O)N1CC2(CCN(CC3CC4CCC3C4)CC2)c2cc(C)ccc21]
119
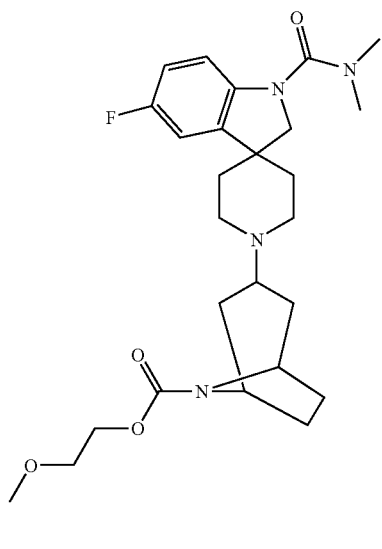
120
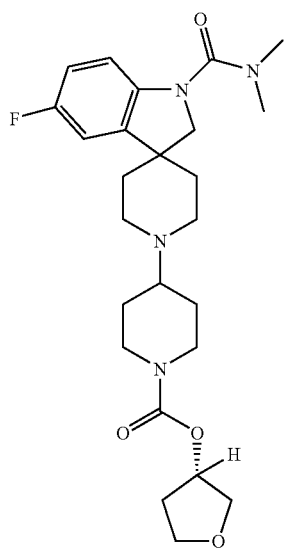 [SMILES: CN(C)C(=O)N1CC2(CCN(C3CCN(C(=O)O[C@H]4CCOC4)CC3)CC2)c2cc(F)ccc21]
122
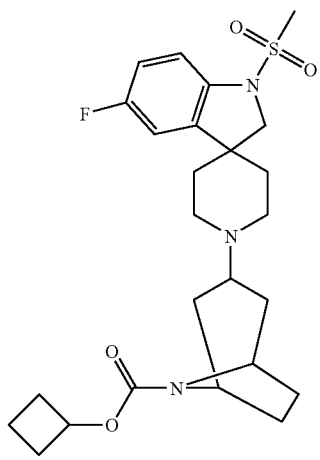 [SMILES: CS(=O)(=O)N1CC2(CCN(C3CC4CCC(C3)N4C(=O)OC3CCC3)CC2)c2cc(F)ccc21]
123
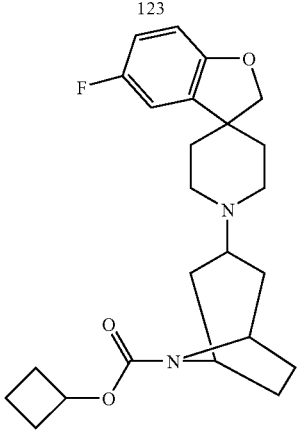

TABLE 1-continued
Exemplary compounds of formula I.
124
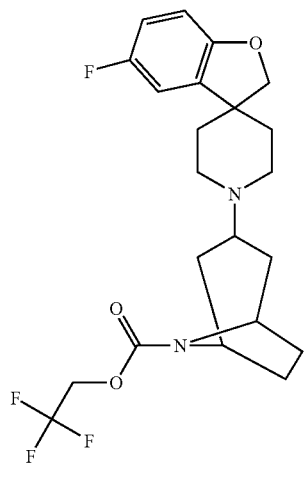 [SMILES: O=C(OCC(F)(F)F)N1C2CCC1CC(N1CCC3(CC1)COc1ccc(F)cc13)C2]
125
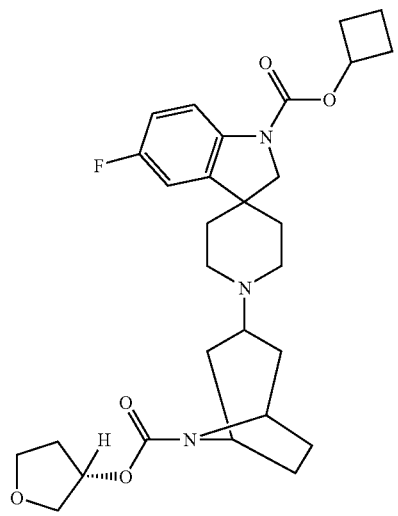 [SMILES: O=C(OC1CCC1)N1CC2(CCN(C3CC4CCC(C3)N4C(=O)O[C@H]3CCOC3)CC2)c2cc(F)ccc21]
126
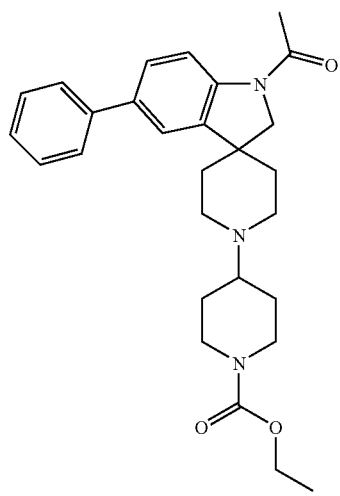 [SMILES: CCOC(=O)N1CCC(N2CCC3(CC2)CN(C(C)=O)c2ccc(-c4ccccc4)cc23)CC1]
127
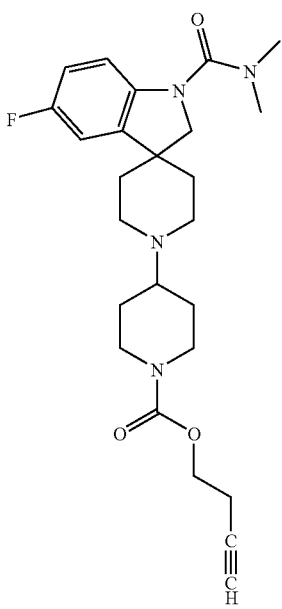 [SMILES: C#CCCOC(=O)N1CCC(N2CCC3(CC2)CN(C(=O)N(C)C)c2ccc(F)cc23)CC1]

TABLE 1-continued
Exemplary compounds of formula I.
128
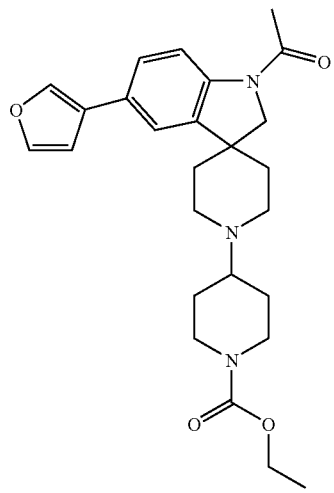 [SMILES: CCOC(=O)N1CCC(N2CCC3(CC2)CN(C(C)=O)c2ccc(-c4ccoc4)cc23)CC1]
129
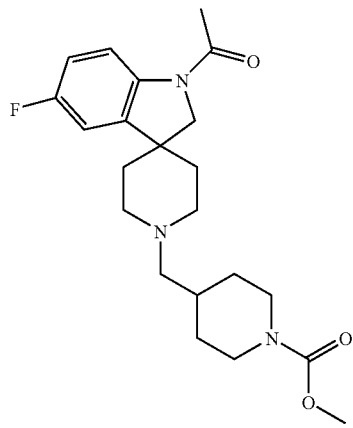 [SMILES: COC(=O)N1CCC(CN2CCC3(CC2)CN(C(C)=O)c2ccc(F)cc23)CC1]
130
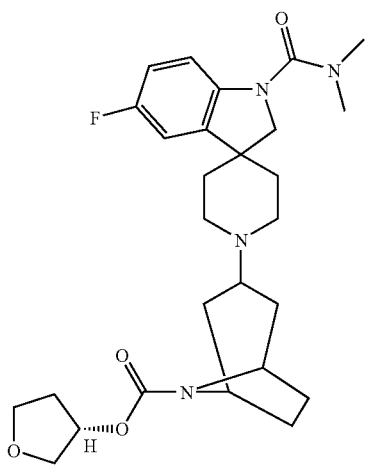
131
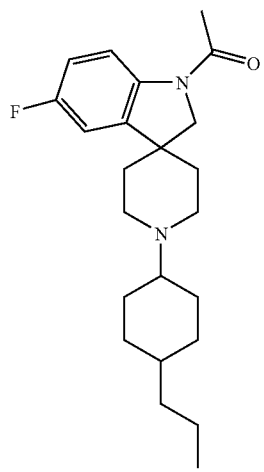 [SMILES: CCCC1CCC(N2CCC3(CC2)CN(C(C)=O)c2ccc(F)cc23)CC1]
132
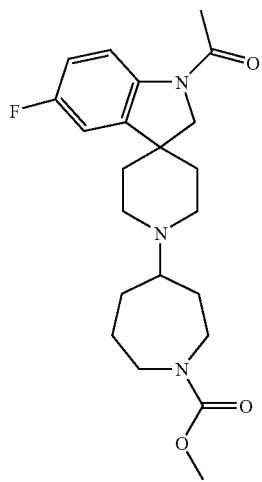 [SMILES: COC(=O)N1CCCC(N2CCC3(CC2)CN(C(C)=O)c2ccc(F)cc23)CC1]
133
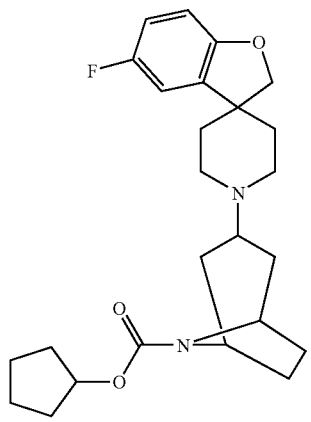 [SMILES: O=C(OC1CCCC1)N1C2CCC1CC(N1CCC3(CC1)COc1ccc(F)cc13)C2]

TABLE 1-continued
Exemplary compounds of formula I.
134
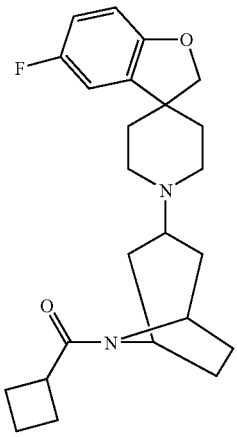 [SMILES: O=C(C1CCC1)N1C2CCC1CC(N1CCC3(CC1)COc1ccc(F)cc13)C2]
135
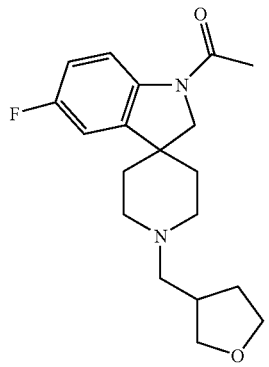 [SMILES: CC(=O)N1CC2(CCN(CC3CCOC3)CC2)c2cc(F)ccc21]
136
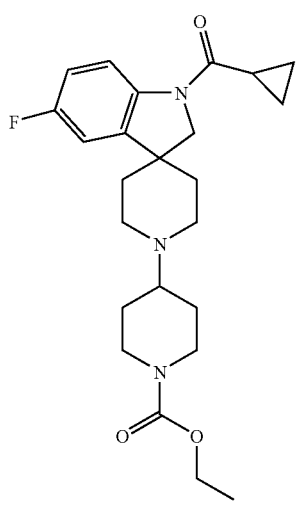 [SMILES: CCOC(=O)N1CCC(N2CCC3(CC2)CN(C(=O)C2CC2)c2ccc(F)cc23)CC1]
137
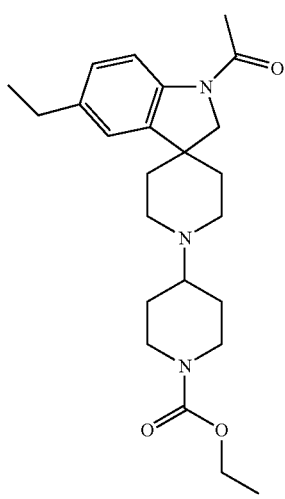 [SMILES: CCOC(=O)N1CCC(N2CCC3(CC2)CN(C(C)=O)c2ccc(CC)cc23)CC1]
138
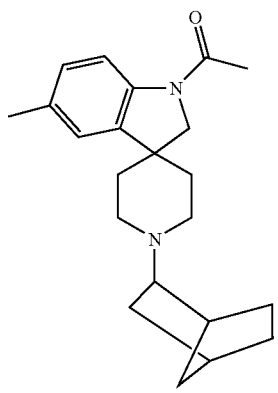 [SMILES: CC(=O)N1CC2(CCN(C3CC4CCC3C4)CC2)c2cc(C)ccc21]
139
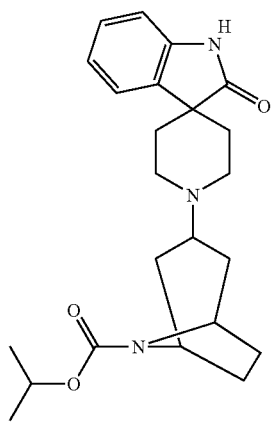

TABLE 1-continued
Exemplary compounds of formula I.
140
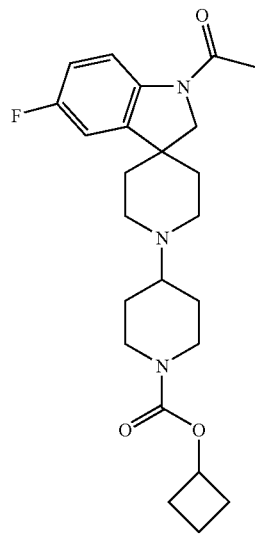 [SMILES: CC(=O)N1CC2(CCN(C3CCN(C(=O)OC4CCC4)CC3)CC2)c2cc(F)ccc21]
141
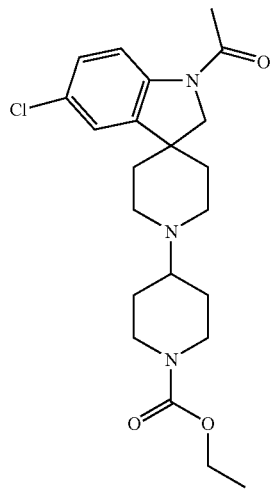 [SMILES: CCOC(=O)N1CCC(N2CCC3(CC2)CN(C(C)=O)c2ccc(Cl)cc23)CC1]
142
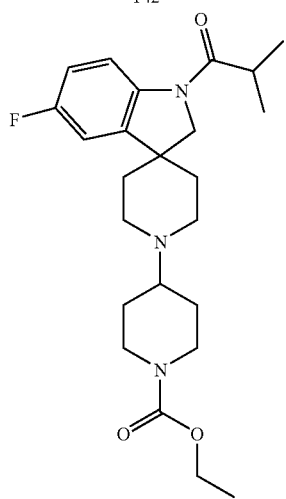
143
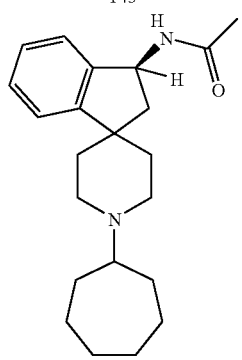
144
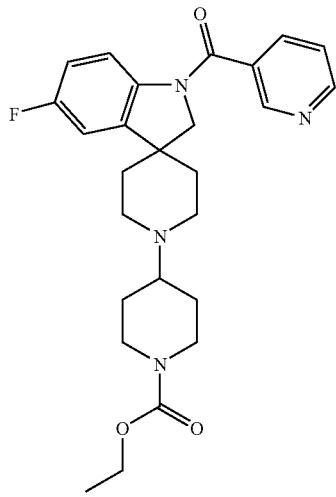 [SMILES: CCOC(=O)N1CCC(N2CCC3(CC2)CN(C(=O)c2cccnc2)c2ccc(F)cc23)CC1]
145
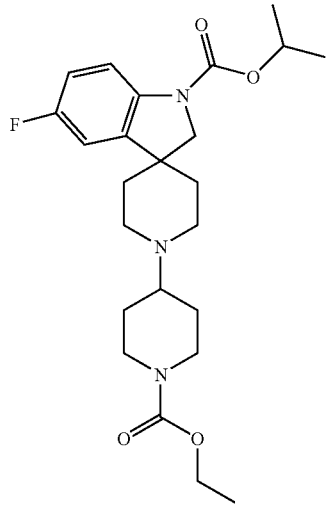 [SMILES: CCOC(=O)N1CCC(N2CCC3(CC2)CN(C(=O)OC(C)C)c2ccc(F)cc23)CC1]

TABLE 1-continued
Exemplary compounds of formula I.
146
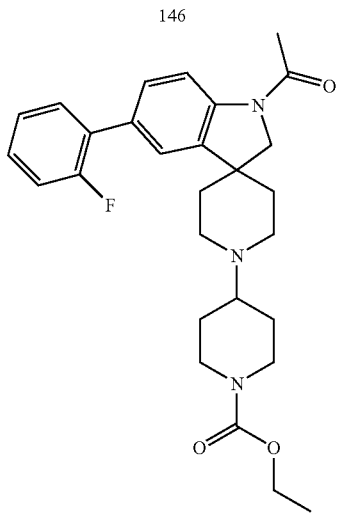
147
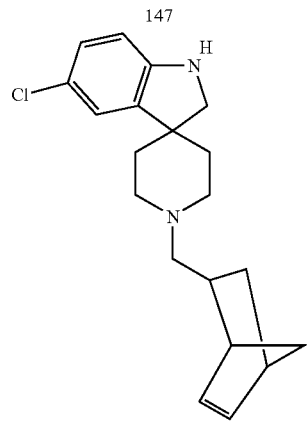
148
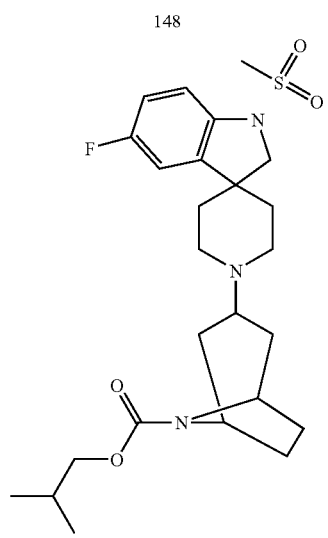
149
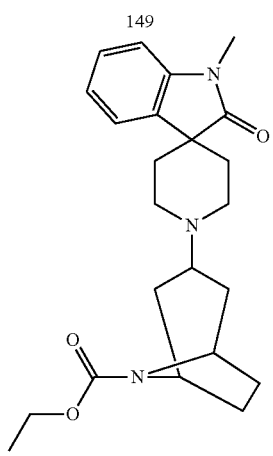
150
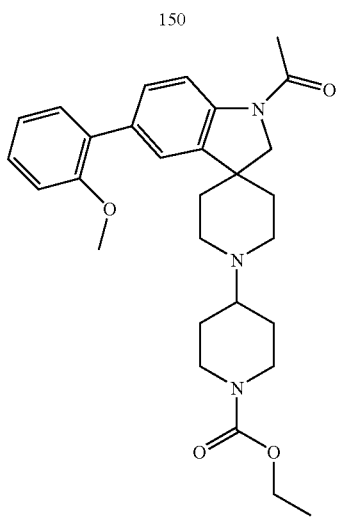
151
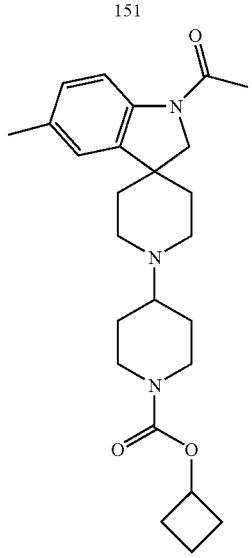

TABLE 1-continued
Exemplary compounds of formula I.
152
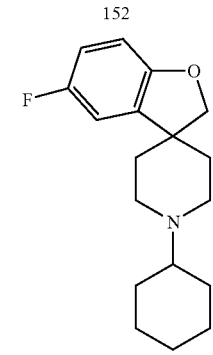
153
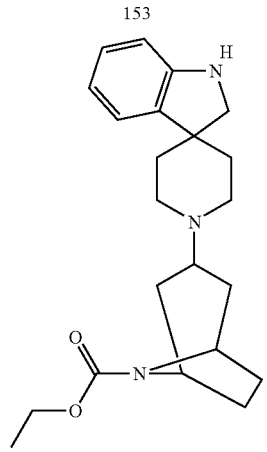
154
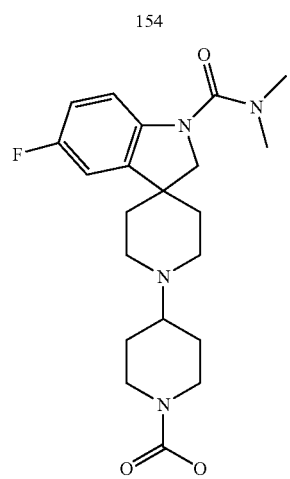
155
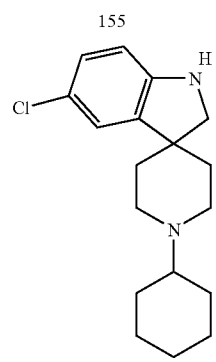
156
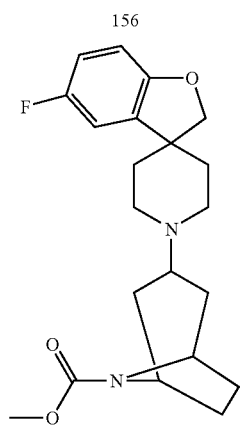
157
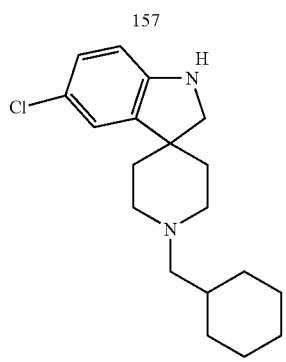

TABLE 1-continued
Exemplary compounds of formula I.
158
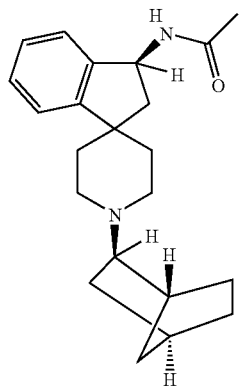
159
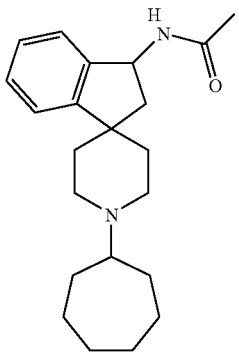
160
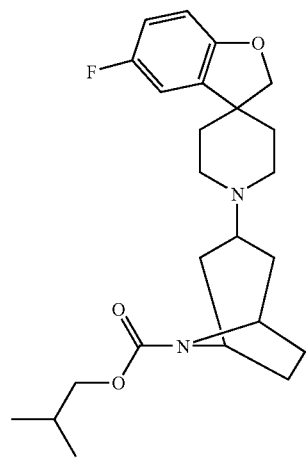 [SMILES: CC(C)COC(=O)N1C2CCC1CC(N1CCC3(CC1)COc1ccc(F)cc13)C2]
161
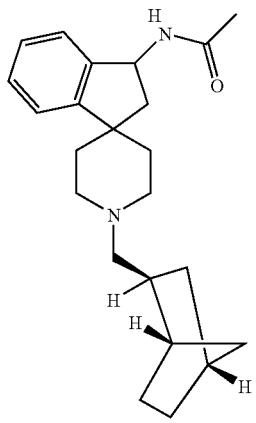
162
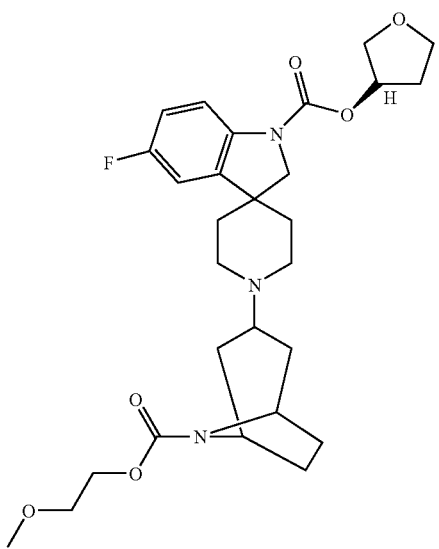
163
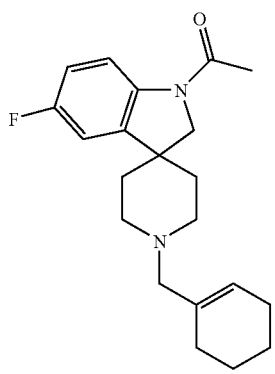 [SMILES: CC(=O)N1CC2(CCN(CC3=CCCCC3)CC2)c2cc(F)ccc21]

TABLE 1-continued
Exemplary compounds of formula I.
164
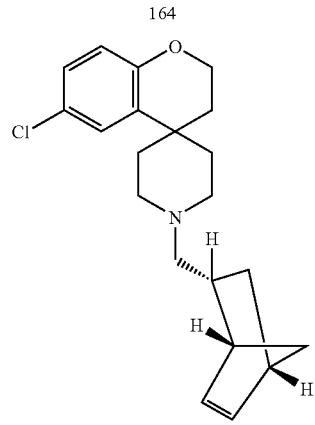
165
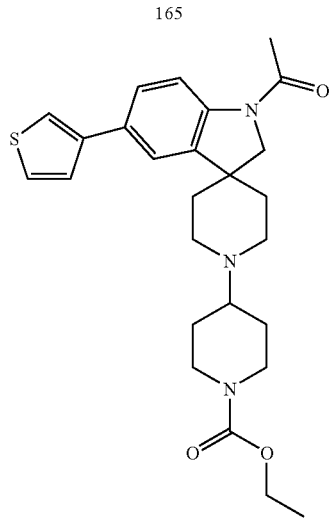
166
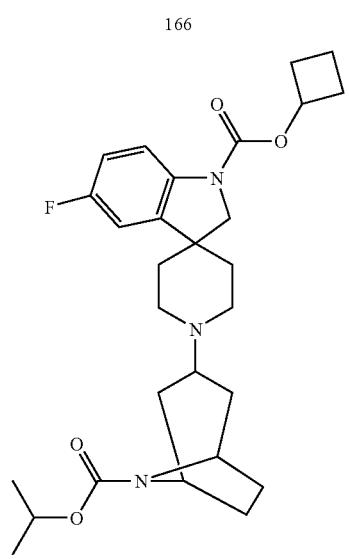
167
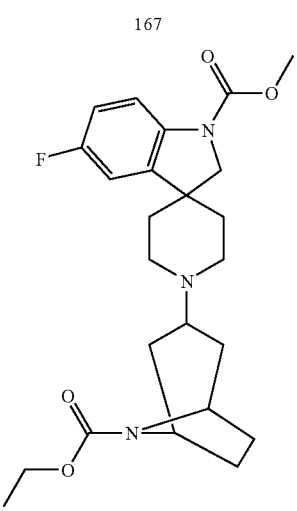

TABLE 1-continued
Exemplary compounds of formula I.
168
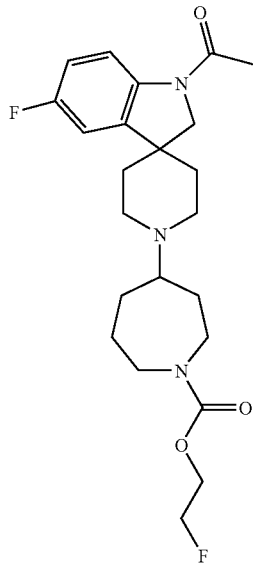 [SMILES: CC(=O)N1CC2(CCN(C3CCCN(C(=O)OCCF)CC3)CC2)c2cc(F)ccc21]
169
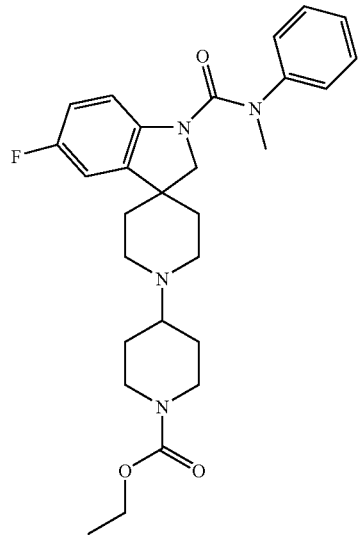 [SMILES: CCOC(=O)N1CCC(N2CCC3(CC2)CN(C(=O)N(C)c2ccccc2)c2ccc(F)cc23)CC1]
170
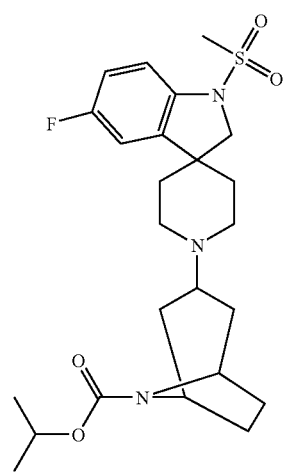 [SMILES: CC(C)OC(=O)N1C2CCC1CC(N1CCC3(CC1)CN(S(C)(=O)=O)c1ccc(F)cc13)C2]
171
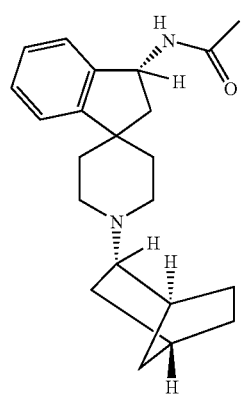

TABLE 1-continued
Exemplary compounds of formula I.
172
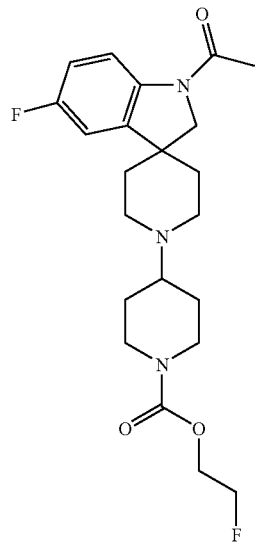 [SMILES: CC(=O)N1CC2(CCN(C3CCN(C(=O)OCCF)CC3)CC2)c2cc(F)ccc21]
173
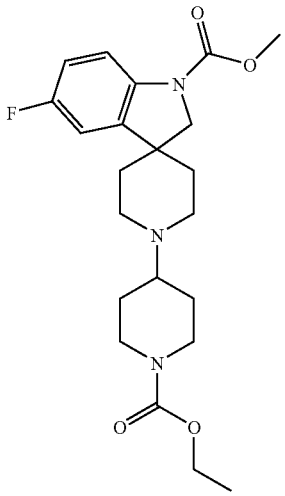 [SMILES: CCOC(=O)N1CCC(N2CCC3(CC2)CN(C(=O)OC)c2ccc(F)cc23)CC1]
174
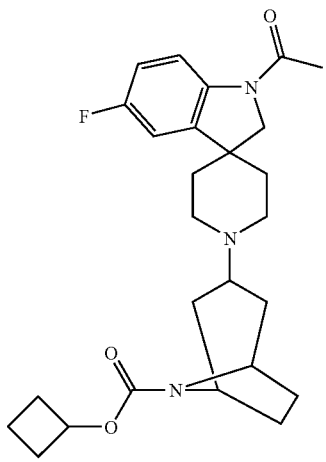 [SMILES: CC(=O)N1CC2(CCN(C3CC4CCC(C3)N4C(=O)OC3CCC3)CC2)c2cc(F)ccc21]
175
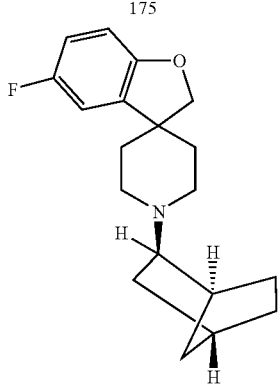
176
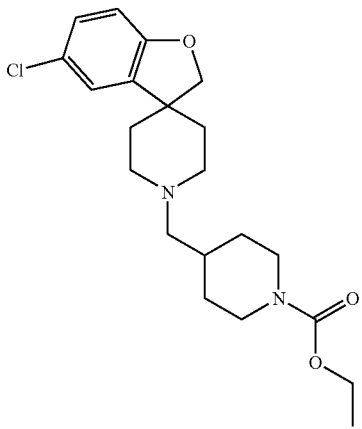 [SMILES: CCOC(=O)N1CCC(CN2CCC3(CC2)COc2ccc(Cl)cc23)CC1]
177
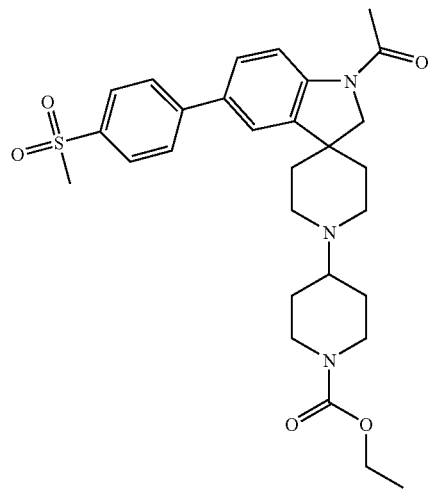 [SMILES: CCOC(=O)N1CCC(N2CCC3(CC2)CN(C(C)=O)c2ccc(-c4ccc(S(C)(=O)=O)cc4)cc23)CC1]

TABLE 1-continued
Exemplary compounds of formula I.
178
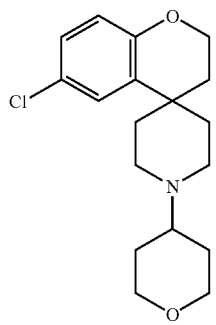 [SMILES: Clc1ccc2c(c1)C1(CCO2)CCN(C2CCOCC2)CC1]
179
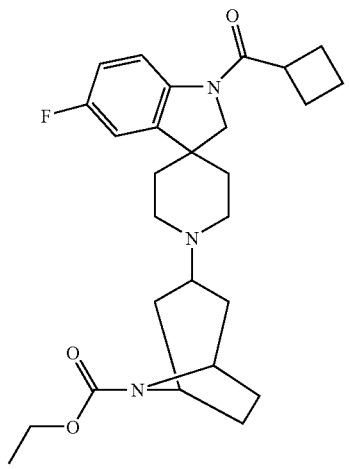 [SMILES: CCOC(=O)N1C2CCC1CC(N1CCC3(CC1)CN(C(=O)C1CCC1)c1ccc(F)cc13)C2]
180
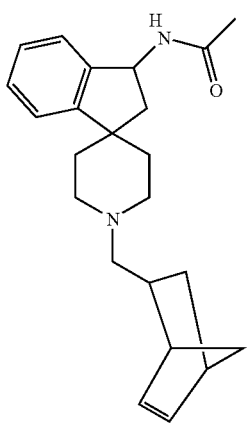
181
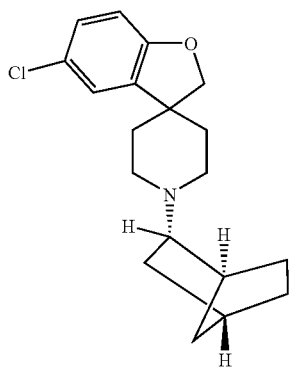 [SMILES: Clc1ccc2c(c1)C1(CCN([C@H]3C[C@@H]4CC[C@H]3C4)CC1)CO2]
182
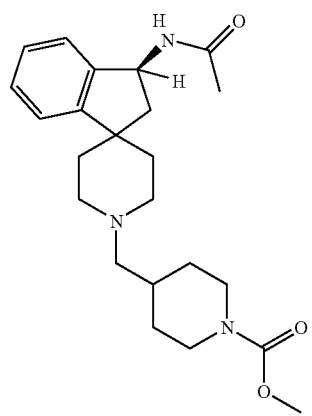
183
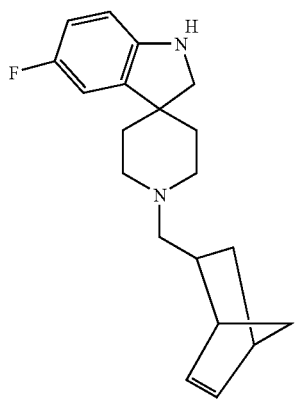

TABLE 1-continued
Exemplary compounds of formula I.
184
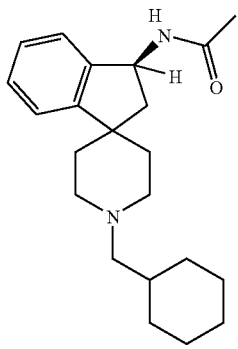
185
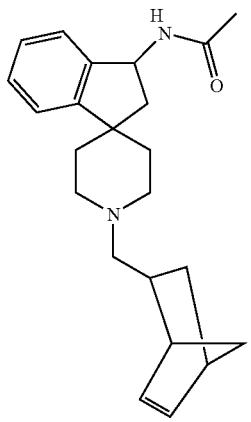
186
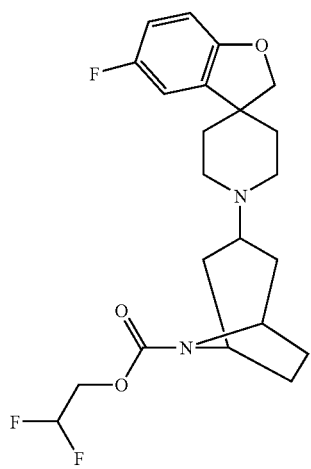 [SMILES: O=C(OCC(F)F)N1C2CCC1CC(N1CCC3(CC1)COc1ccc(F)cc13)C2]
187
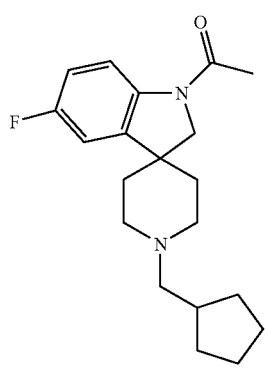 [SMILES: CC(=O)N1CC2(CCN(CC3CCCC3)CC2)c2cc(F)ccc21]
188
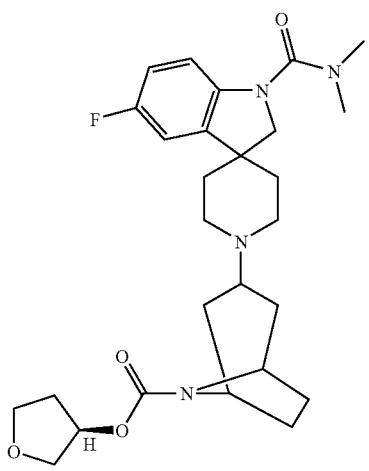
189
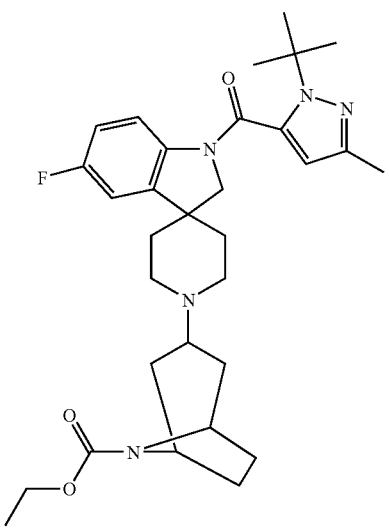 [SMILES: CCOC(=O)N1C2CCC1CC(N1CCC3(CC1)CN(C(=O)c1cc(C)nn1C(C)(C)C)c1ccc(F)cc13)C2]

TABLE 1-continued
Exemplary compounds of formula I.
190
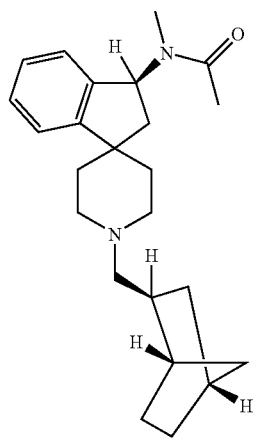 [SMILES: CC(=O)N(C)[C@H]1CC2(CCN(C[C@H]3C[C@H]4CC[C@H]3C4)CC2)c2ccccc21]
191
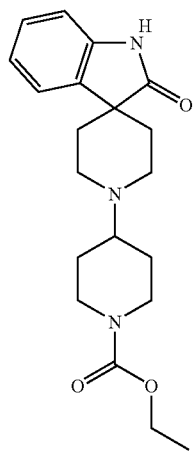
192
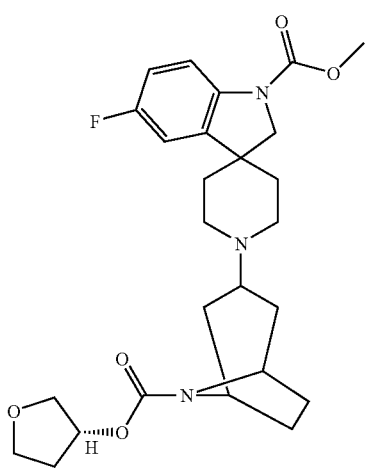
193
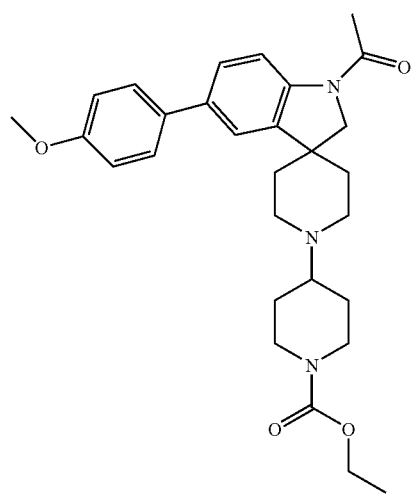 [SMILES: CCOC(=O)N1CCC(N2CCC3(CC2)CN(C(C)=O)c2ccc(-c4ccc(OC)cc4)cc23)CC1]
194
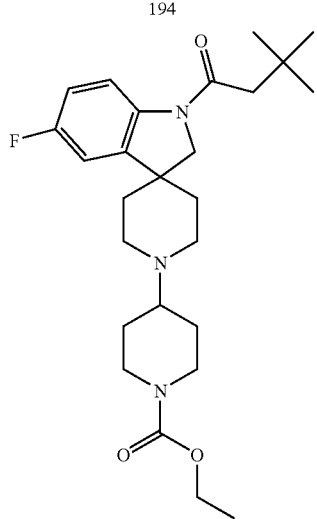
195
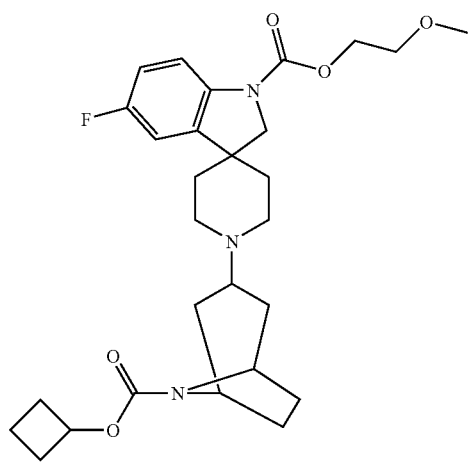 [SMILES: COCCOC(=O)N1CC2(CCN(C3CC4CCC(C3)N4C(=O)OC3CCC3)CC2)c2cc(F)ccc21]

TABLE 1-continued
Exemplary compounds of formula I.
196
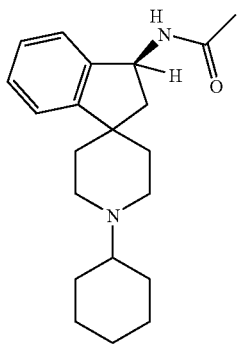
197
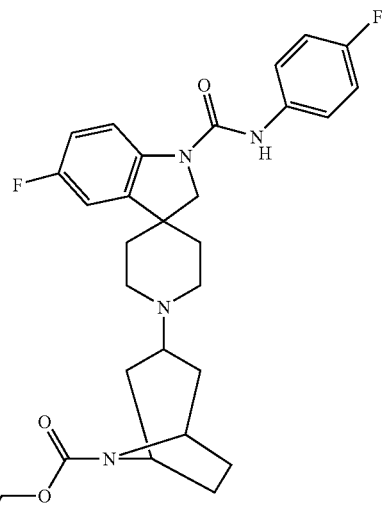
198
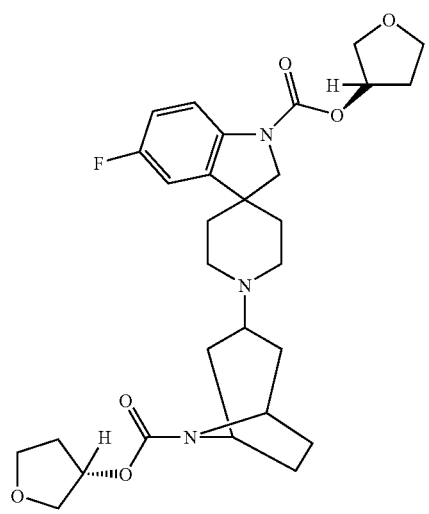
199
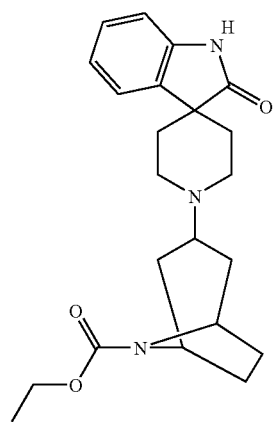

TABLE 1-continued
Exemplary compounds of formula I.
200
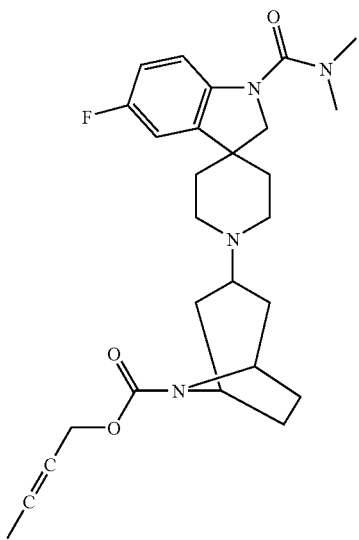 [SMILES: CC=CCOC(=O)N1C2CCC1CC(N1CCC3(CC1)CN(C(=O)N(C)C)c1ccc(F)cc13)C2]
202
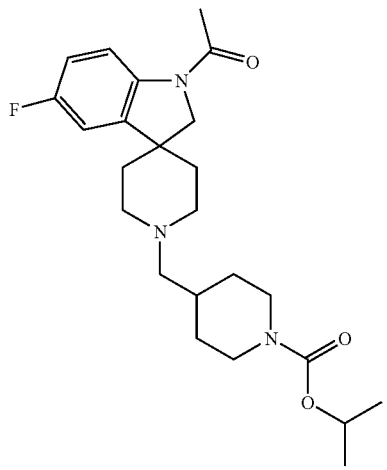 [SMILES: CC(=O)N1CC2(CCN(CC3CCN(C(=O)OC(C)C)CC3)CC2)c2cc(F)ccc21]
203
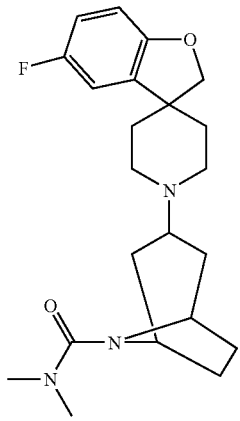 [SMILES: CN(C)C(=O)N1C2CCC1CC(N1CCC3(CC1)COc1ccc(F)cc13)C2]
204
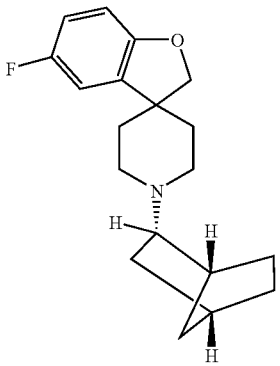 [SMILES: Fc1ccc2c(c1)C1(CCN([C@H]3C[C@@H]4CC[C@@H]3C4)CC1)CO2]
205
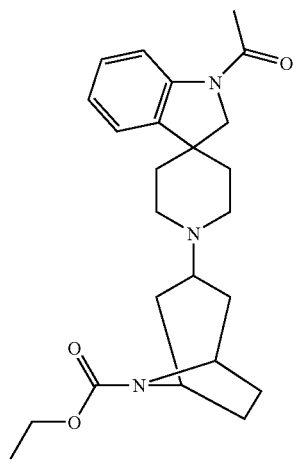 [SMILES: CCOC(=O)N1C2CCC1CC(N1CCC3(CC1)CN(C(C)=O)c1ccccc13)C2]
206
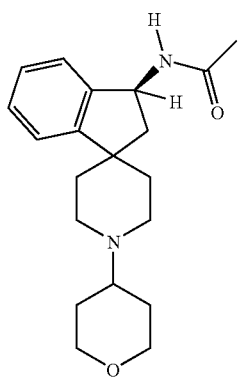 [SMILES: CC(=O)N[C@H]1CC2(CCN(C3CCOCC3)CC2)c2ccccc21]

TABLE 1-continued
Exemplary compounds of formula I.
207
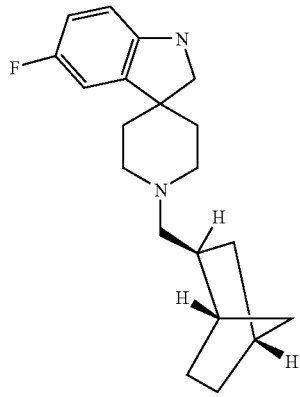 [SMILES: Fc1ccc2c(c1)C1(CCN(C[C@H]3C[C@H]4CC[C@H]3C4)CC1)CN2]
208
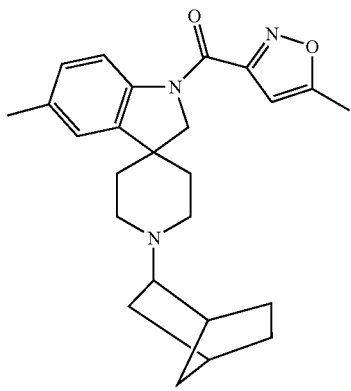
209
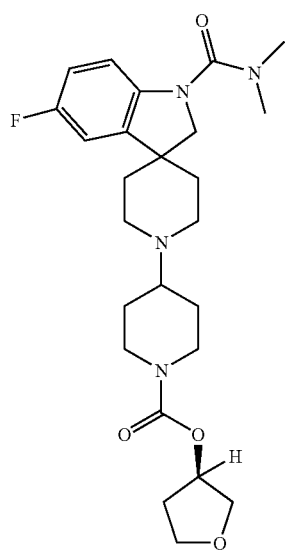 [SMILES: CN(C)C(=O)N1CC2(CCN(C3CCN(C(=O)O[C@@H]4CCOC4)CC3)CC2)c2cc(F)ccc21]
210
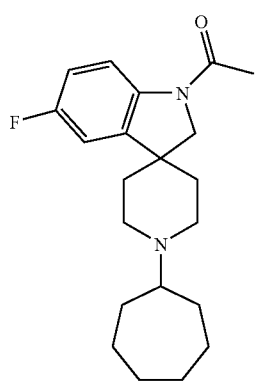 [SMILES: CC(=O)N1CC2(CCN(C3CCCCCC3)CC2)c2cc(F)ccc21]
211
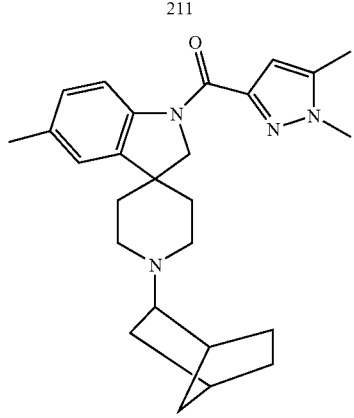
212
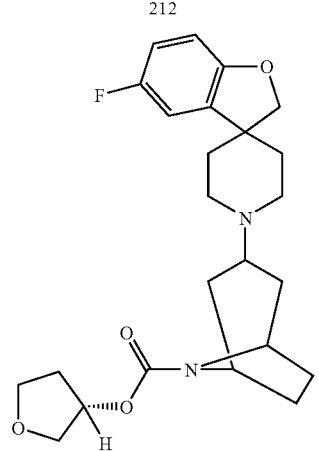

TABLE 1-continued
Exemplary compounds of formula I.
213
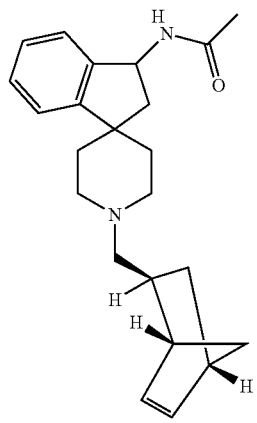
214
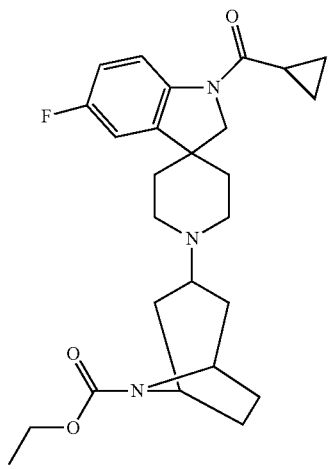 [SMILES: CCOC(=O)N1C2CCC1CC(N1CCC3(CC1)CN(C(=O)C1CC1)c1ccc(F)cc13)C2]
215
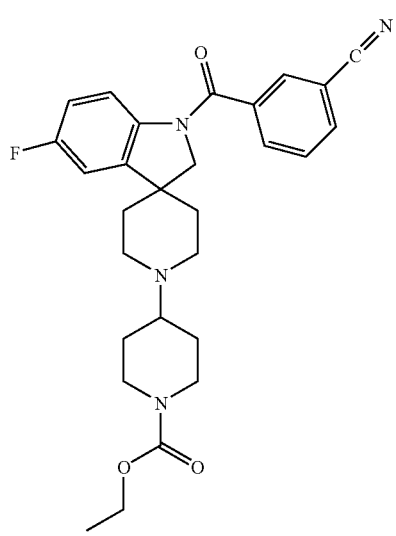 [SMILES: CCOC(=O)N1CCC(N2CCC3(CC2)CN(C(=O)c2cccc(C=N)c2)c2ccc(F)cc23)CC1]
216
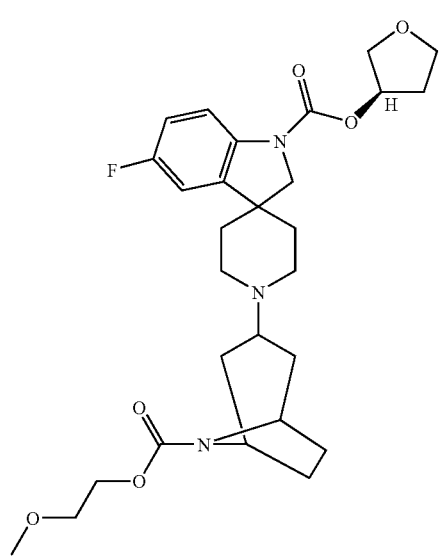
217
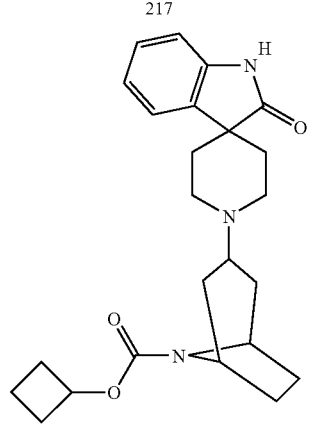
218
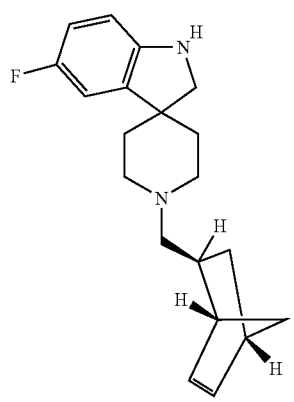

TABLE 1-continued
Exemplary compounds of formula I.
219
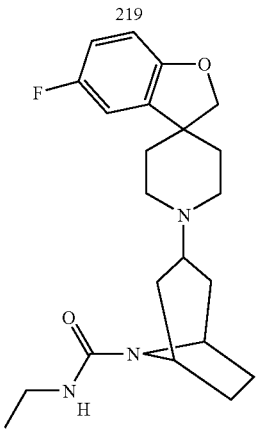
220
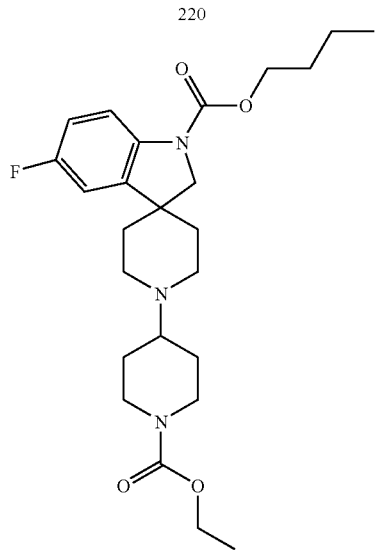
221
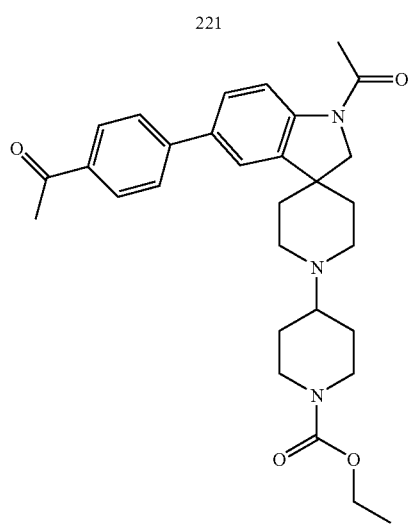
222
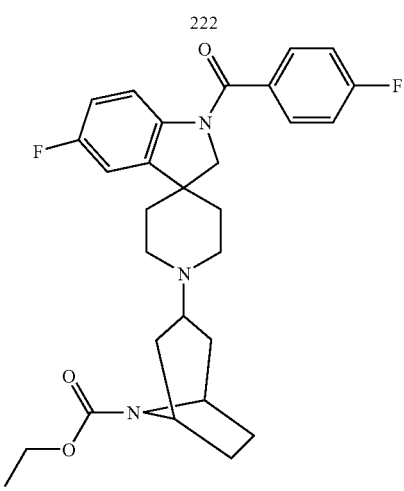
223
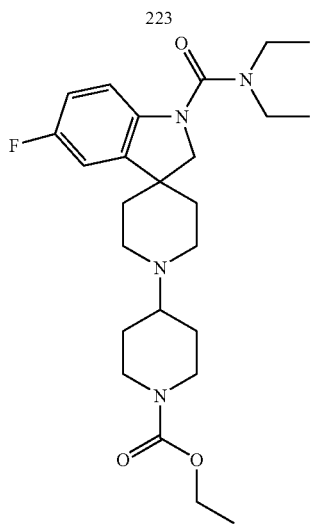
224
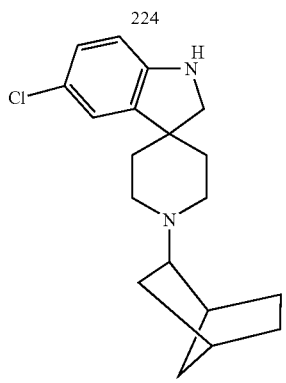

TABLE 1-continued
Exemplary compounds of formula I.
225
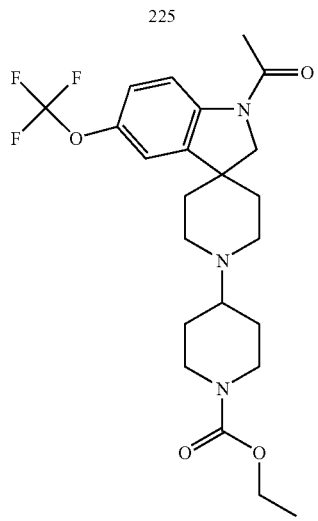
226
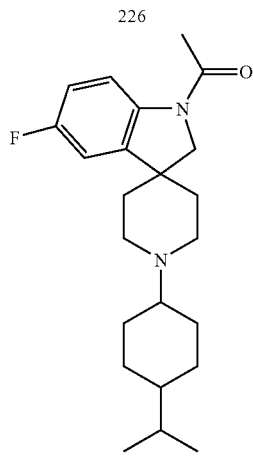
227
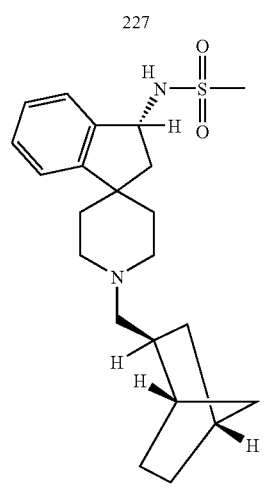
228
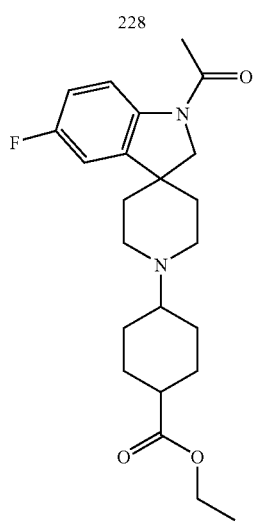
229
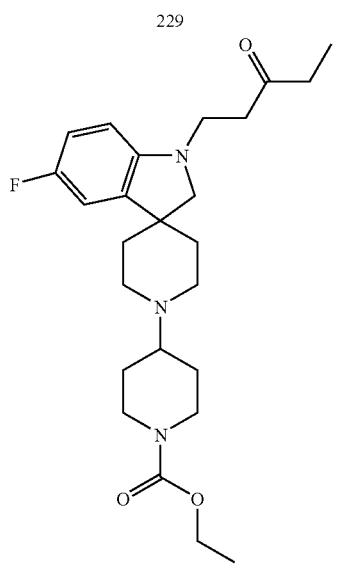
230
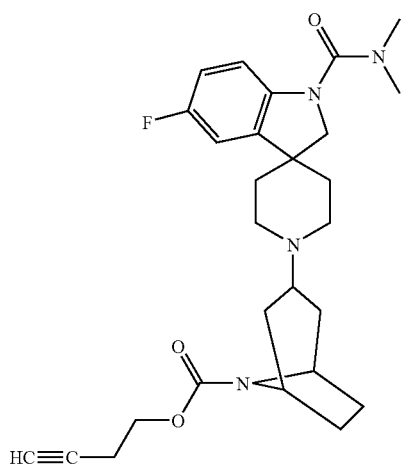 [SMILES: C#CCCOC(=O)N1C2CCC1CC(N1CCC3(CC1)CN(C(=O)N(C)C)c1ccc(F)cc13)C2]

US 8,367,691 B2
113                                                                                                   114
TABLE 1-continued
Exemplary compounds of formula I.
231
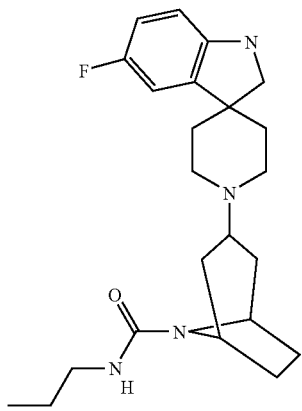
232
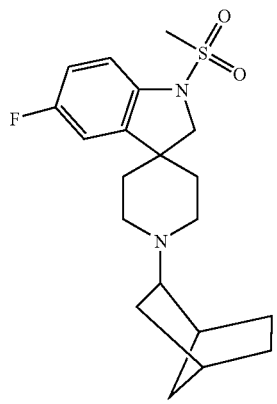 [SMILES: CS(=O)(=O)N1CC2(CCN(C3CC4CCC3C4)CC2)c2cc(F)ccc21]
233
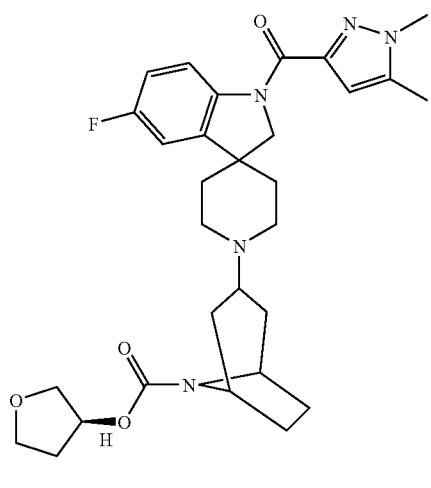
234
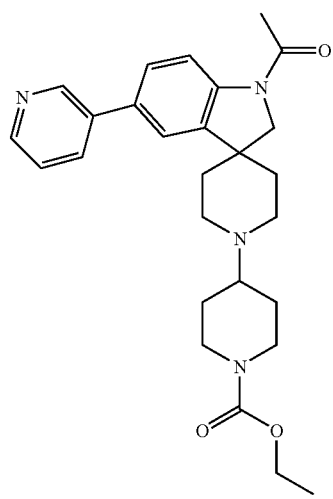 [SMILES: CCOC(=O)N1CCC(N2CCC3(CC2)CN(C(C)=O)c2ccc(-c4cccnc4)cc23)CC1]
235
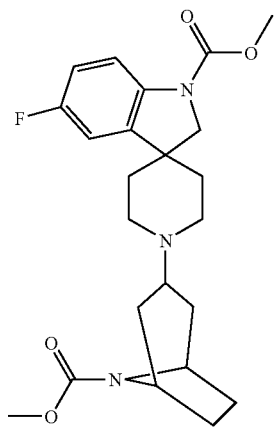
236
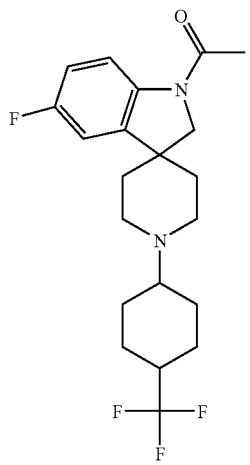 [SMILES: CC(=O)N1CC2(CCN(C3CCC(C(F)(F)F)CC3)CC2)c2cc(F)ccc21]

TABLE 1-continued
Exemplary compounds of formula I.
237
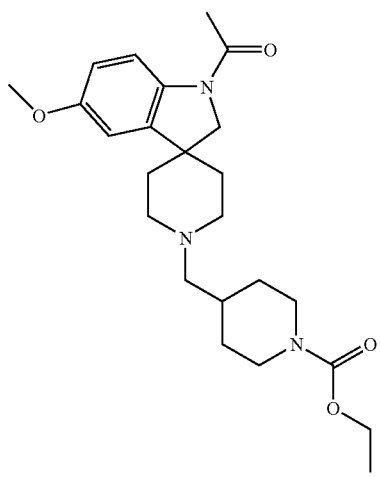 [SMILES: CCOC(=O)N1CCC(CN2CCC3(CC2)CN(C(C)=O)c2ccc(OC)cc23)CC1]
238
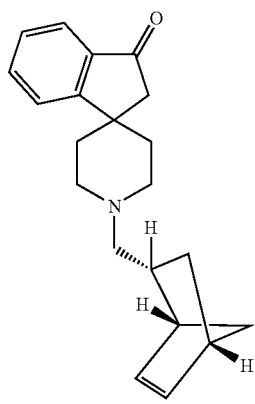 [SMILES: O=C1CC2(CCN(C[C@@H]3C[C@H]4C=C[C@H]3C4)CC2)c2ccccc21]
239
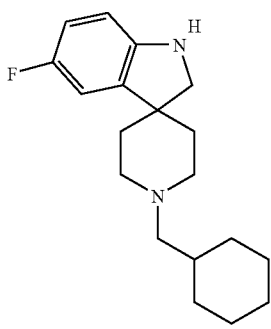
240
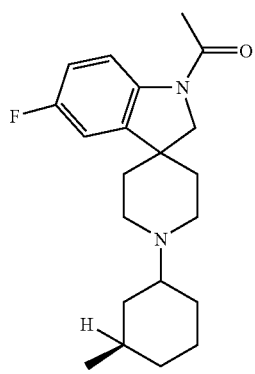 [SMILES: CC(=O)N1CC2(CCN(C3CCC[C@@H](C)C3)CC2)c2cc(F)ccc21]
241
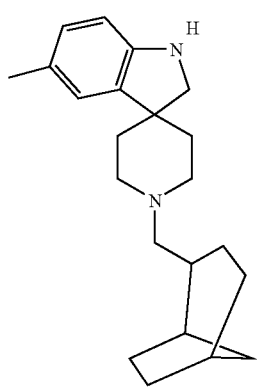
242
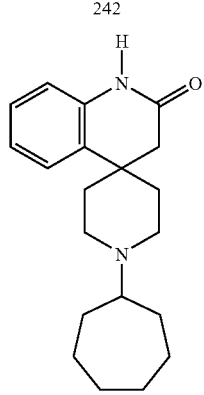

TABLE 1-continued
Exemplary compounds of formula I.
243
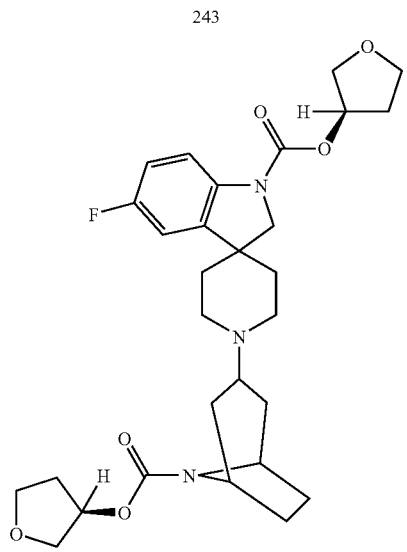
244
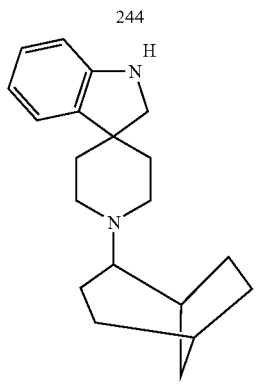
245
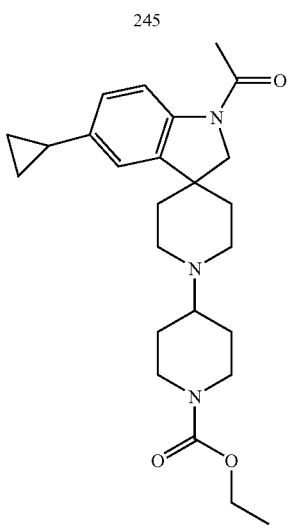
246
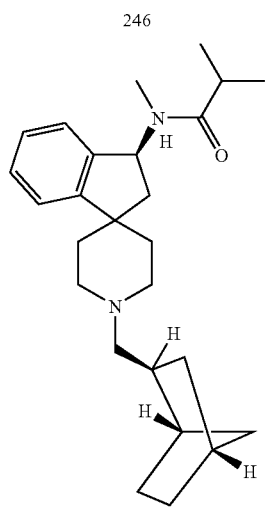
247
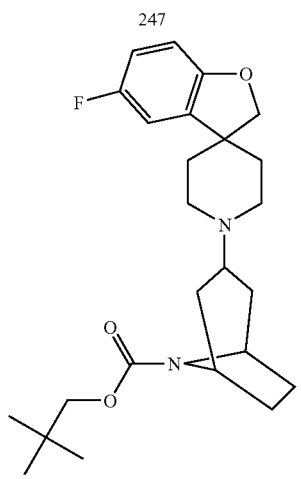
248
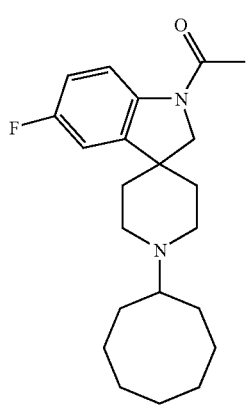 [SMILES: CC(=O)N1CC2(CCN(C3CCCCCCC3)CC2)c2cc(F)ccc21]

TABLE 1-continued
Exemplary compounds of formula I.
249
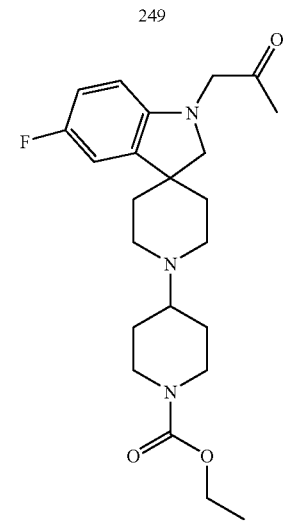
250
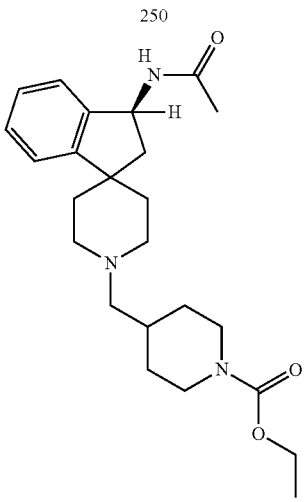
251
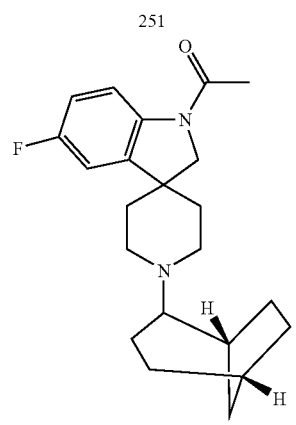
252
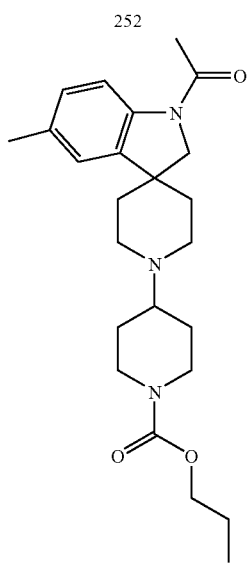
253
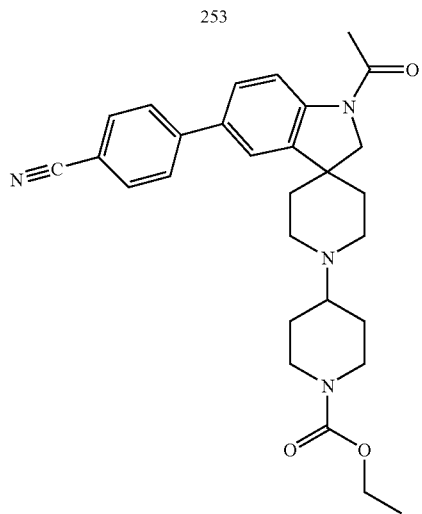
254
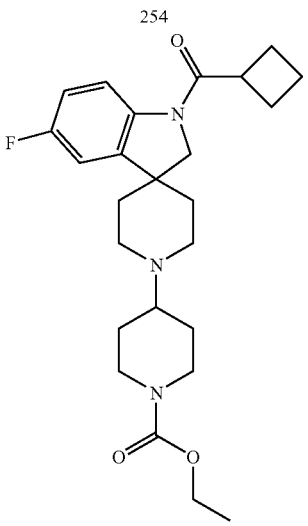

TABLE 1-continued
Exemplary compounds of formula I.
255
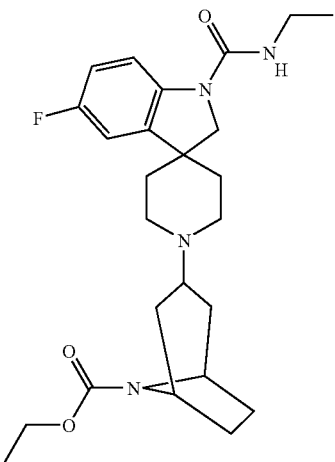
256
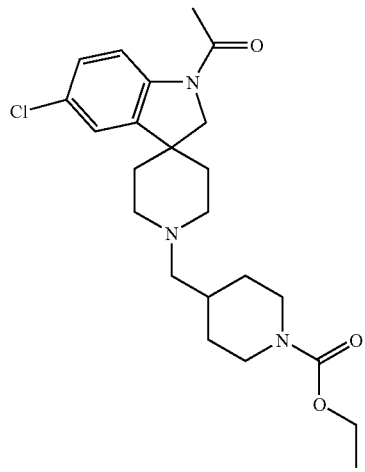 [SMILES: CCOC(=O)N1CCC(CN2CCC3(CC2)CN(C(C)=O)c2ccc(Cl)cc23)CC1]
257
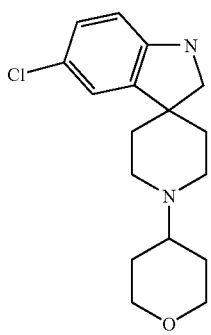 [SMILES: Clc1ccc2c(c1)C1(CCN(C3CCOCC3)CC1)CN2]
258
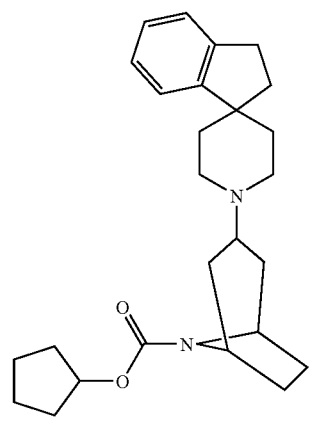 [SMILES: O=C(OC1CCCC1)N1C2CCC1CC(N1CCC3(CCc4ccccc43)CC1)C2]
259
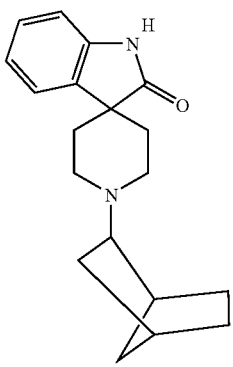
260
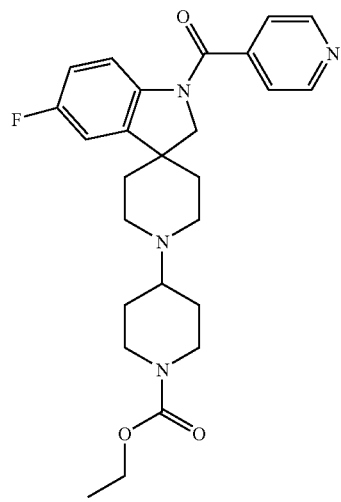 [SMILES: CCOC(=O)N1CCC(N2CCC3(CC2)CN(C(=O)c2ccncc2)c2ccc(F)cc23)CC1]

TABLE 1-continued
Exemplary compounds of formula I.
261
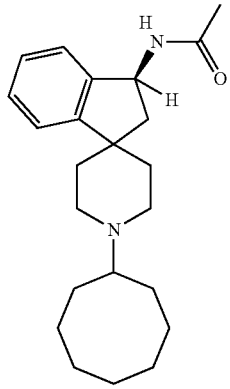
262
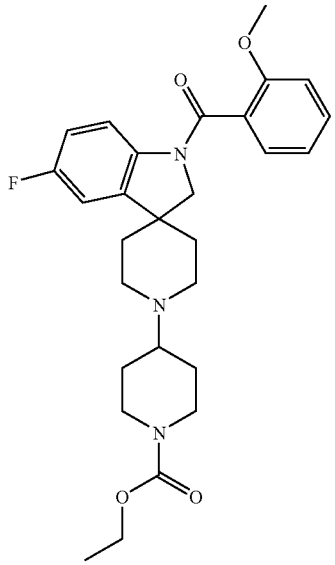 [SMILES: CCOC(=O)N1CCC(N2CCC3(CC2)CN(C(=O)c2ccccc2OC)c2ccc(F)cc23)CC1]
263
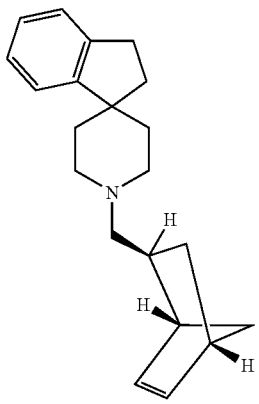 [SMILES: C1=C[C@H]2C[C@H]1C[C@@H]2CN1CCC2(CCc3ccccc32)CC1]
264
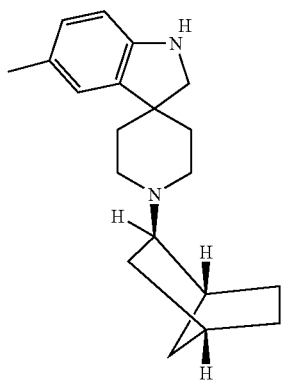
265
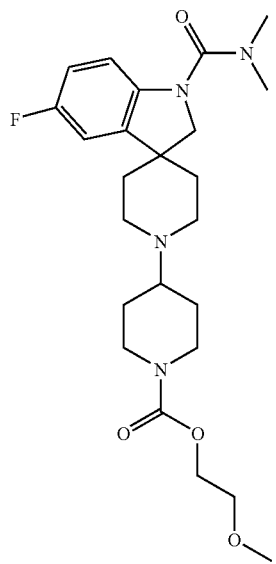 [SMILES: COCCOC(=O)N1CCC(N2CCC3(CC2)CN(C(=O)N(C)C)c2ccc(F)cc23)CC1]
266
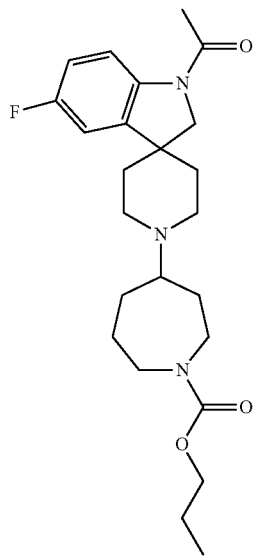 [SMILES: CCCOC(=O)N1CCCC(N2CCC3(CC2)CN(C(C)=O)c2ccc(F)cc23)CC1]

TABLE 1-continued
Exemplary compounds of formula I.
267
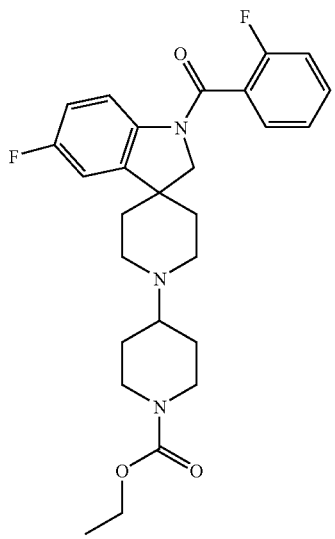 [SMILES: CCOC(=O)N1CCC(N2CCC3(CC2)CN(C(=O)c2ccccc2F)c2ccc(F)cc23)CC1]
268
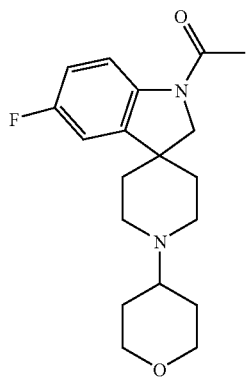 [SMILES: CC(=O)N1CC2(CCN(C3CCOCC3)CC2)c2cc(F)ccc21]
269
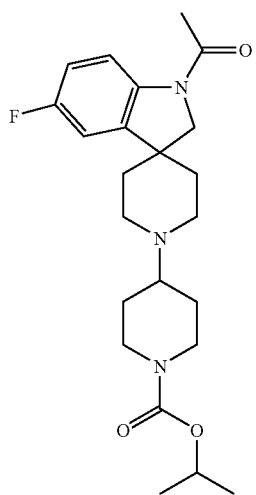 [SMILES: CC(=O)N1CC2(CCN(C3CCN(C(=O)OC(C)C)CC3)CC2)c2cc(F)ccc21]
270
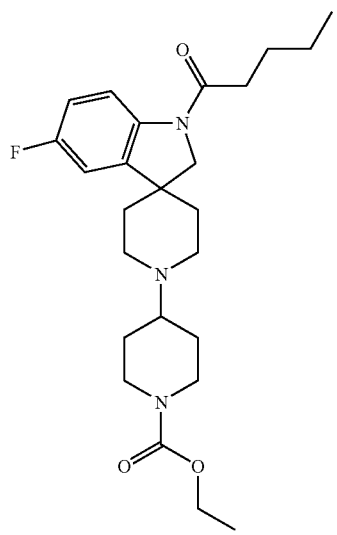
271
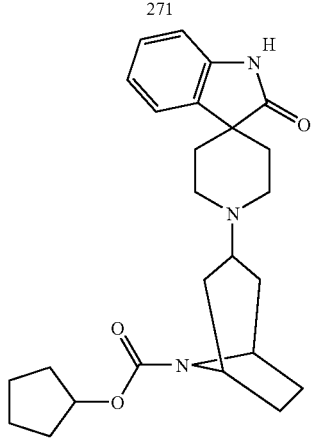
272
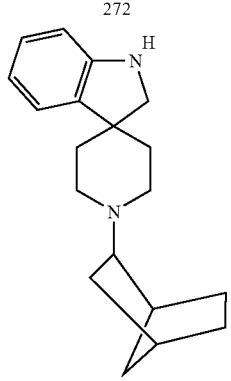

TABLE 1-continued
Exemplary compounds of formula I.
273
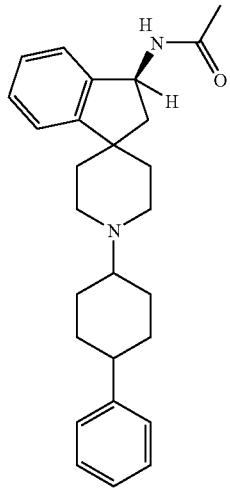
274
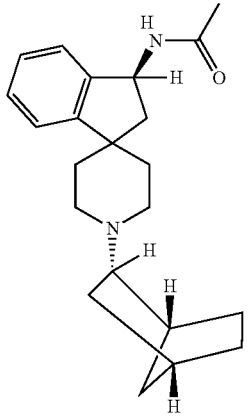
275
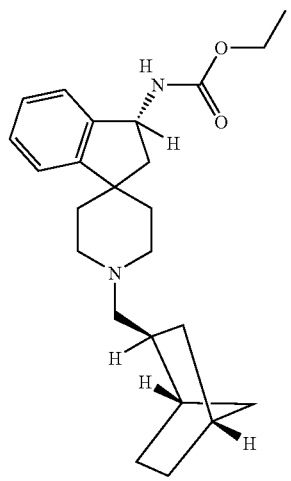
276
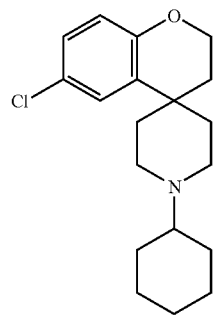 [SMILES: Clc1ccc2c(c1)C1(CCO2)CCN(C2CCCCC2)CC1]
277
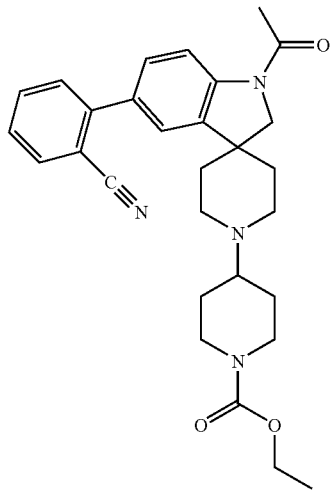 [SMILES: CCOC(=O)N1CCC(N2CCC3(CC2)CN(C(C)=O)c2ccc(-c4ccccc4C#N)cc23)CC1]
278
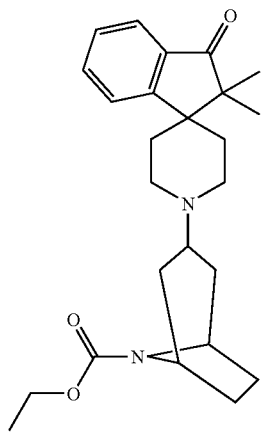 [SMILES: CCOC(=O)N1C2CCC1CC(N1CCC3(CC1)c1ccccc1C(=O)C3(C)C)C2]

TABLE 1-continued
Exemplary compounds of formula I.
279
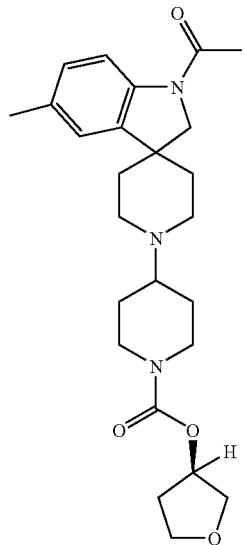 [SMILES: CC(=O)N1CC2(CCN(C3CCN(C(=O)O[C@@H]4CCOC4)CC3)CC2)c2cc(C)ccc21]
280
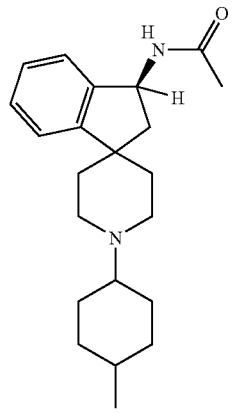
281
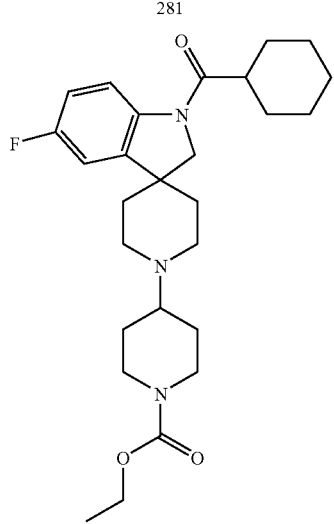
282
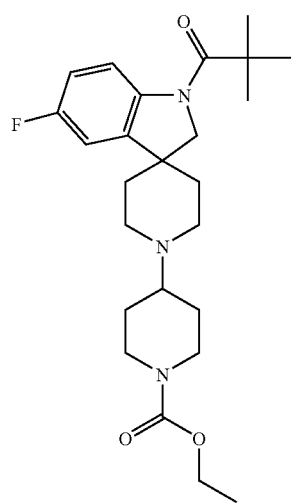 [SMILES: CCOC(=O)N1CCC(N2CCC3(CC2)CN(C(=O)C(C)(C)C)c2ccc(F)cc23)CC1]

TABLE 1-continued
Exemplary compounds of formula I.
283
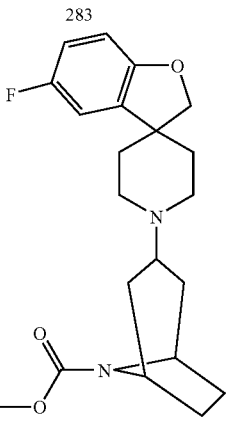
284
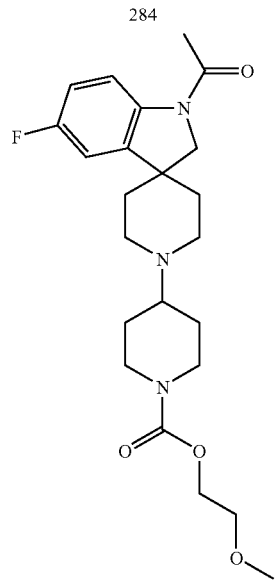
285
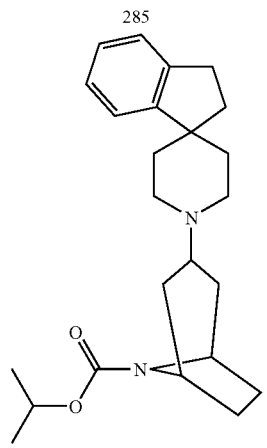
286
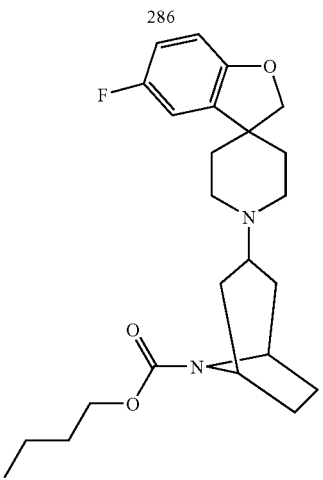
287
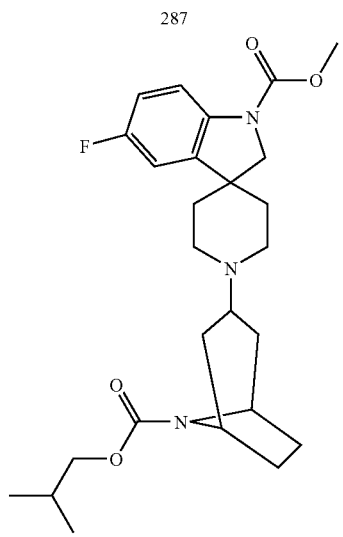
288
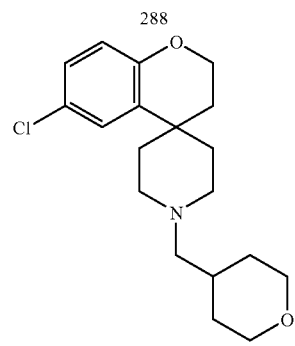

TABLE 1-continued
Exemplary compounds of formula I.
289
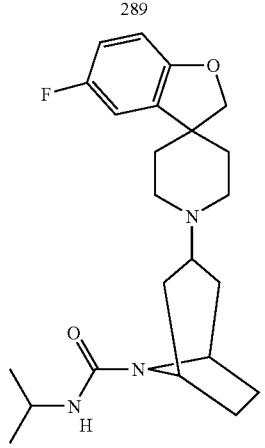
290
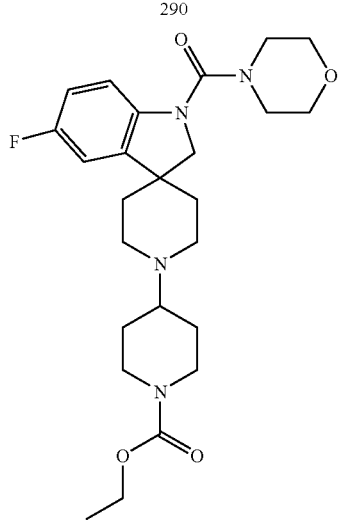
291
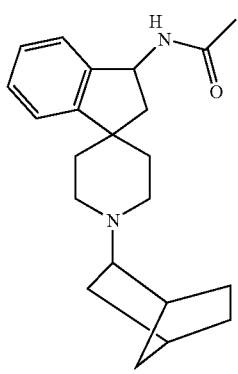
292
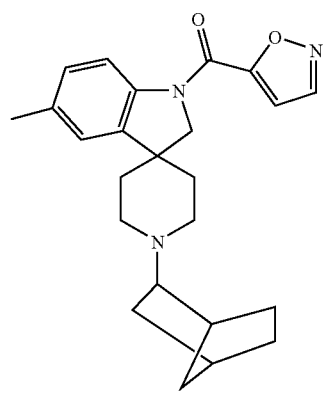 [SMILES: Cc1ccc2c(c1)C1(CCN(C3CC4CCC3C4)CC1)CN2C(=O)c1ccno1]
293
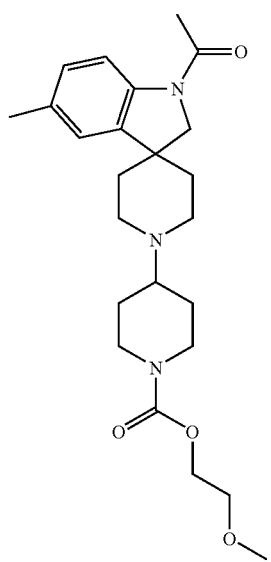
294
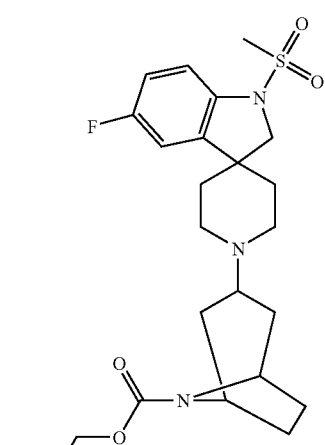

TABLE 1-continued
Exemplary compounds of formula I.
295
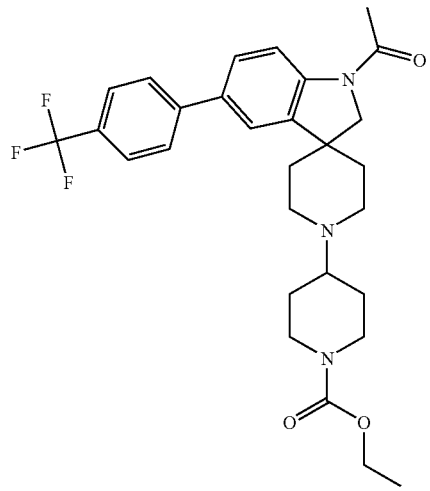 [SMILES: CCOC(=O)N1CCC(N2CCC3(CC2)CN(C(C)=O)c2ccc(-c4ccc(C(F)(F)F)cc4)cc23)CC1]
296
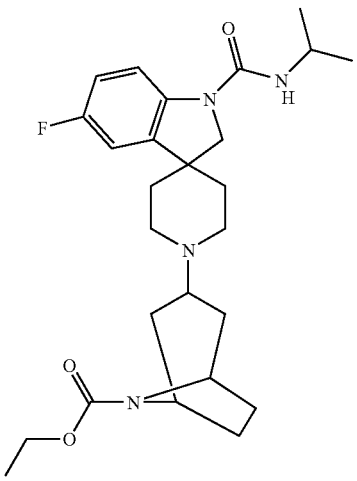
297
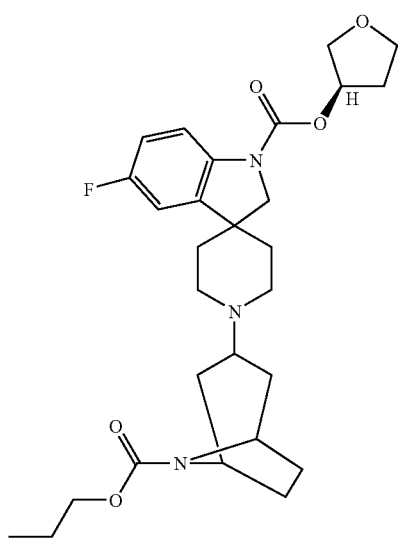
298
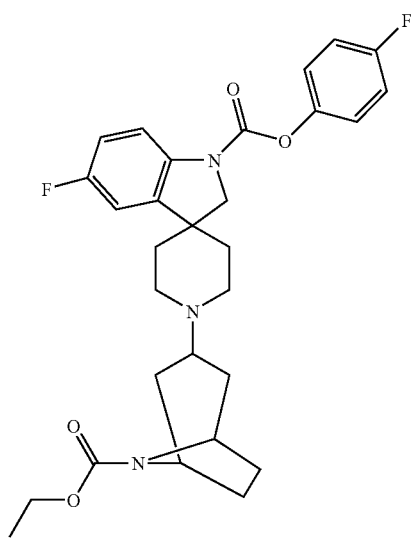 [SMILES: CCOC(=O)N1C2CCC1CC(N1CCC3(CC1)CN(C(=O)Oc1ccc(F)cc1)c1ccc(F)cc13)C2]
299
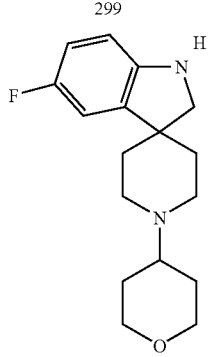
300
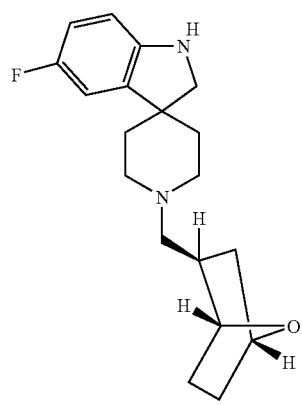

TABLE 1-continued
Exemplary compounds of formula I.
301
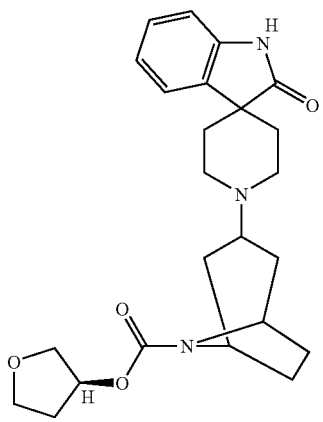
302
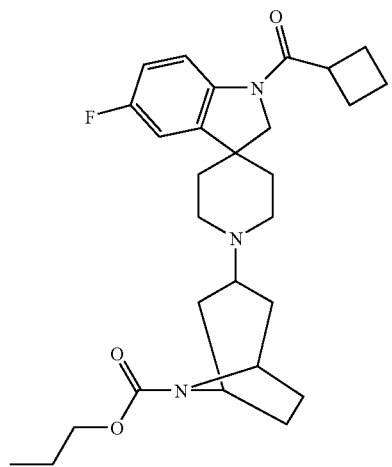 [SMILES: CCCOC(=O)N1C2CCC1CC(N1CCC3(CC1)CN(C(=O)C1CCC1)c1ccc(F)cc13)C2]
303
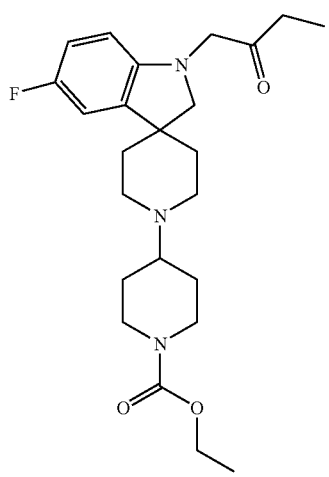 [SMILES: CCOC(=O)N1CCC(N2CCC3(CC2)CN(CC(=O)CC)c2ccc(F)cc23)CC1]
304
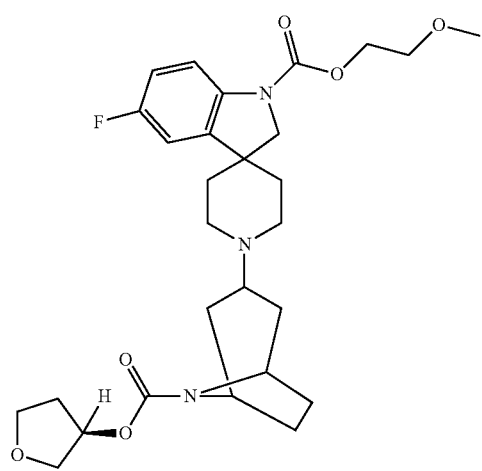 [SMILES: COCCOC(=O)N1CC2(CCN(C3CC4CCC(C3)N4C(=O)O[C@@H]3CCOC3)CC2)c2cc(F)ccc21]
305
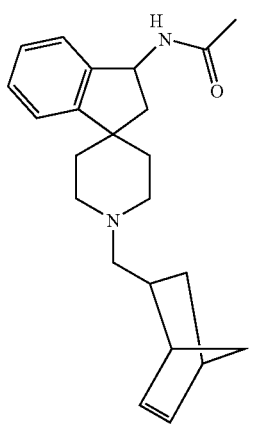
306
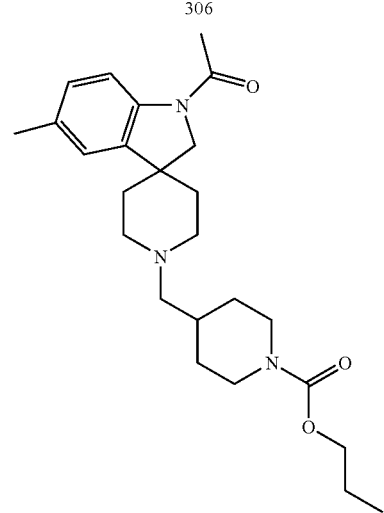

TABLE 1-continued
Exemplary compounds of formula I.
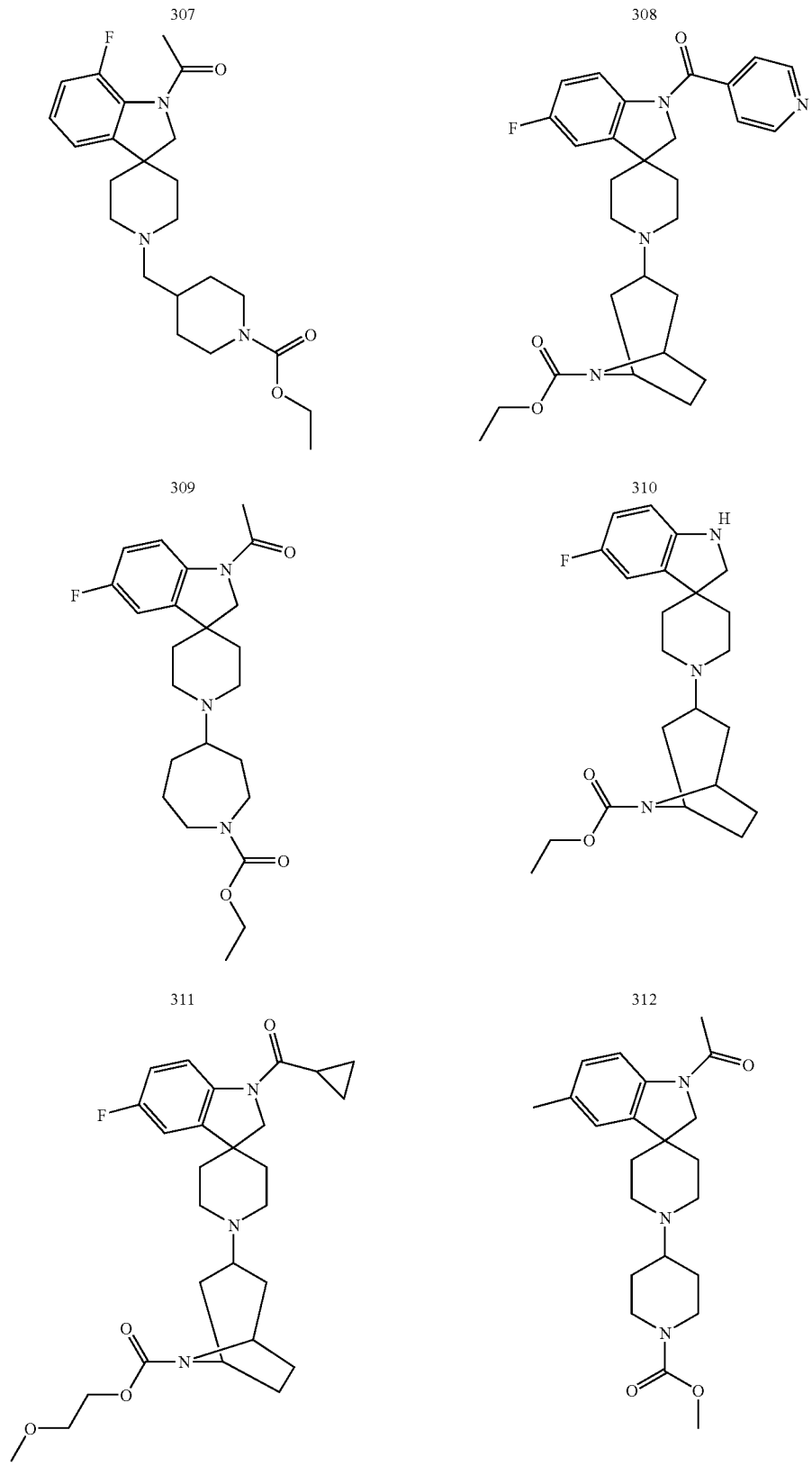

TABLE 1-continued
Exemplary compounds of formula I.
313
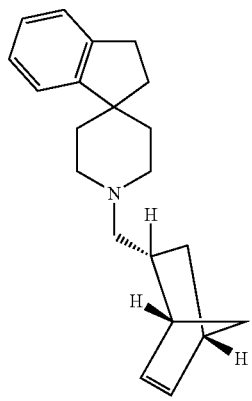 [SMILES: C1=C[C@H]2C[C@H]1C[C@H]2CN1CCC2(CCc3ccccc32)CC1]
314
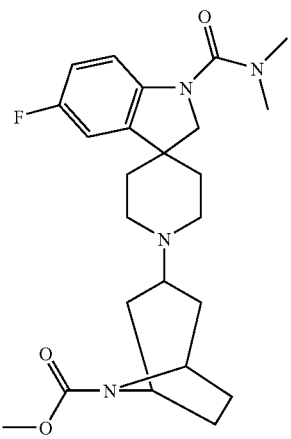
315
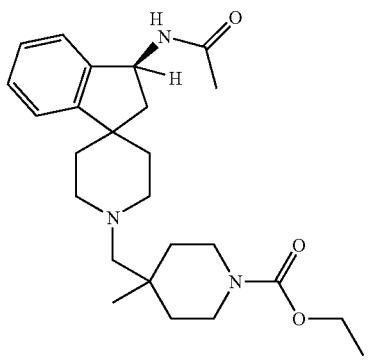
316
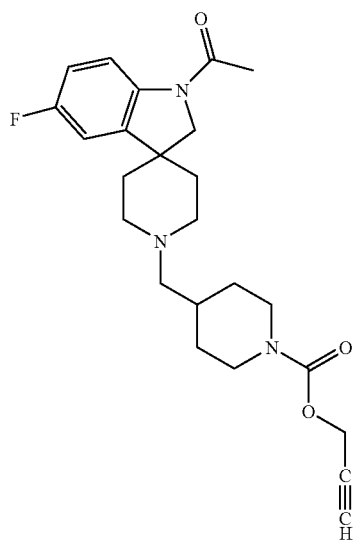 [SMILES: C#CCOC(=O)N1CCC(CN2CCC3(CC2)CN(C(C)=O)c2ccc(F)cc23)CC1]
317
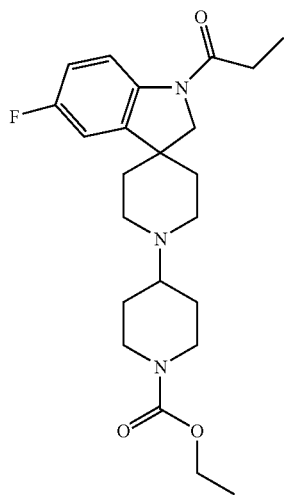 [SMILES: CCOC(=O)N1CCC(N2CCC3(CC2)CN(C(=O)CC)c2ccc(F)cc23)CC1]
318
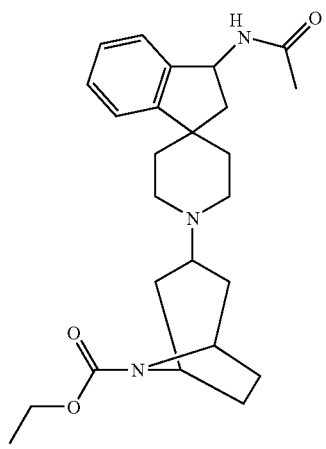

TABLE 1-continued
Exemplary compounds of formula I.
319
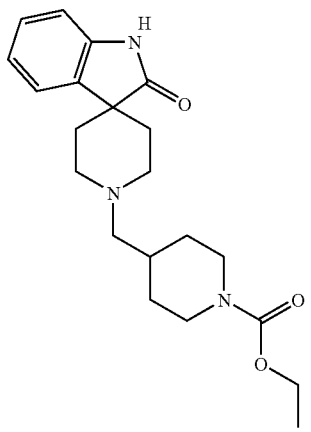
320
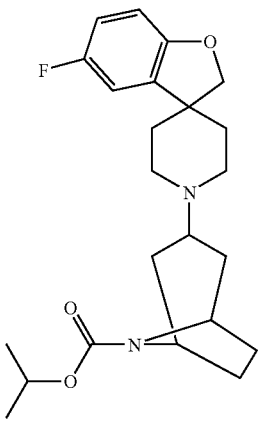 [SMILES: CC(C)OC(=O)N1C2CCC1CC(N1CCC3(CC1)COc1ccc(F)cc13)C2]
321
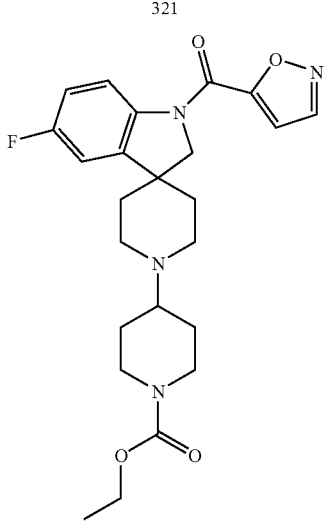
322
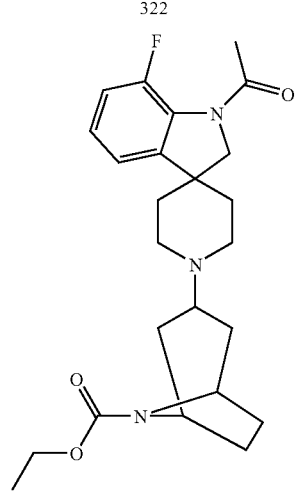
323
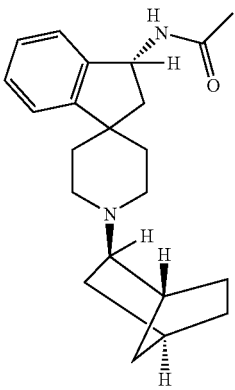
324
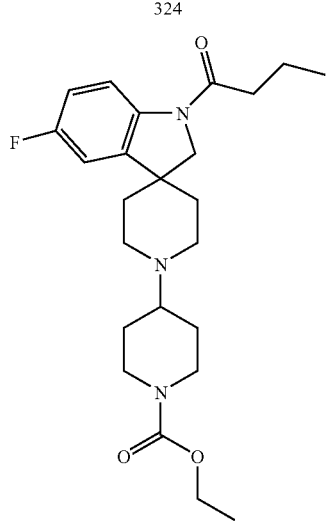

TABLE 1-continued
Exemplary compounds of formula I.
325
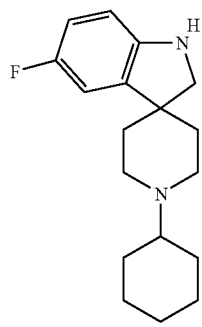
326
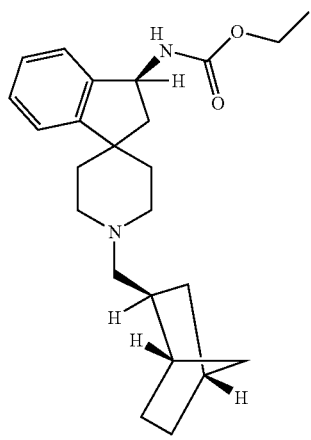
327
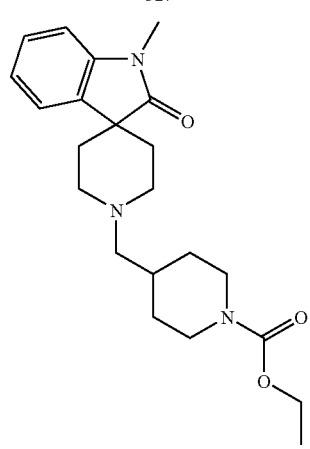
328
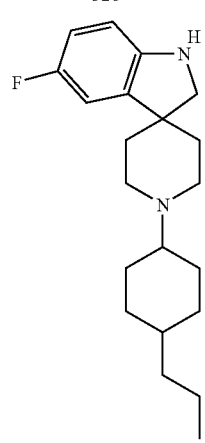
329
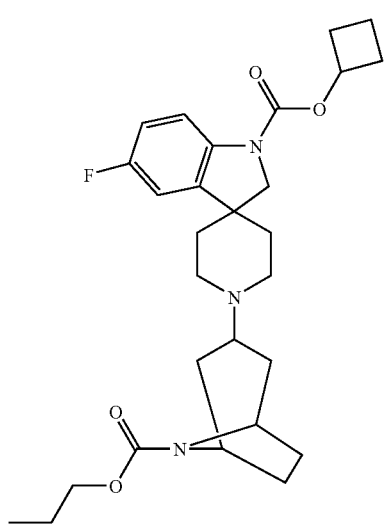 [SMILES: CCCOC(=O)N1C2CCC1CC(N1CCC3(CC1)CN(C(=O)OC1CCC1)c1ccc(F)cc13)C2]
330
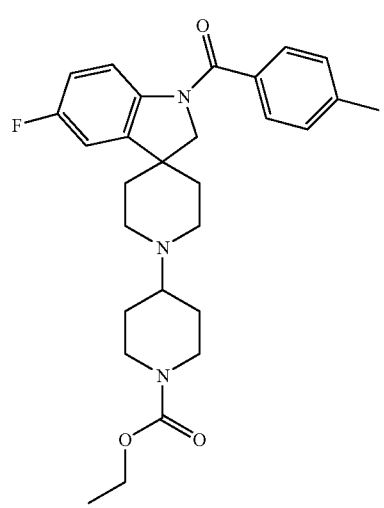 [SMILES: CCOC(=O)N1CCC(N2CCC3(CC2)CN(C(=O)c2ccc(C)cc2)c2ccc(F)cc23)CC1]

TABLE 1-continued
Exemplary compounds of formula I.
331
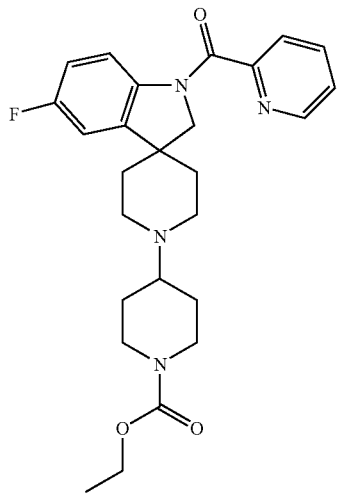 [SMILES: CCOC(=O)N1CCC(N2CCC3(CC2)CN(C(=O)c2ccccn2)c2ccc(F)cc23)CC1]
332
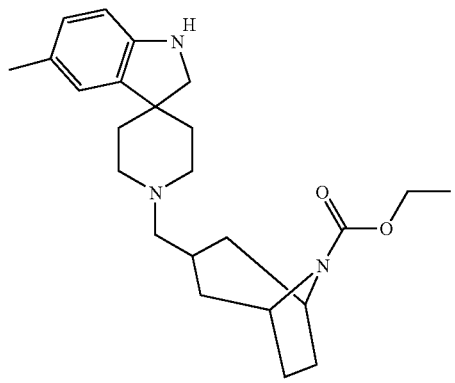
333
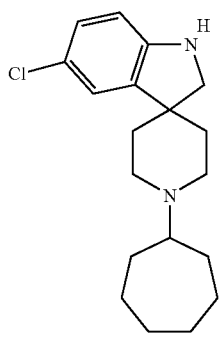
334
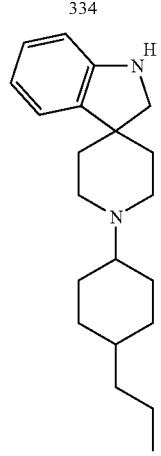
335
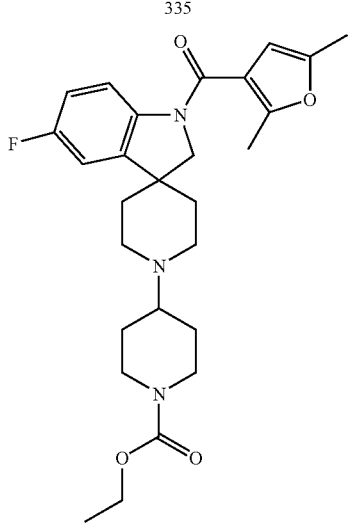
336
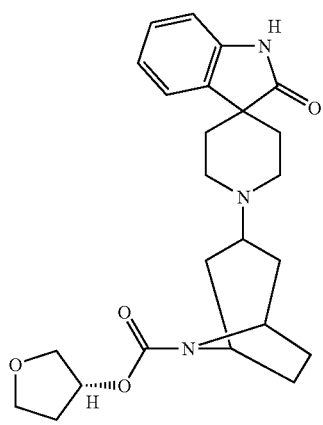

TABLE 1-continued
Exemplary compounds of formula I.
337
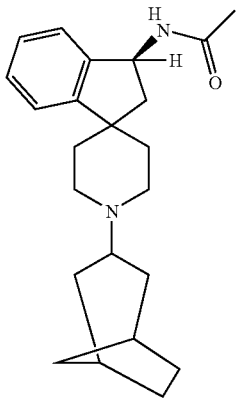
338
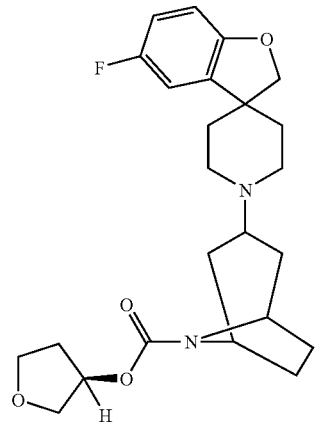 [SMILES: O=C(O[C@@H]1CCOC1)N1C2CCC1CC(N1CCC3(CC1)COc1ccc(F)cc13)C2]
339
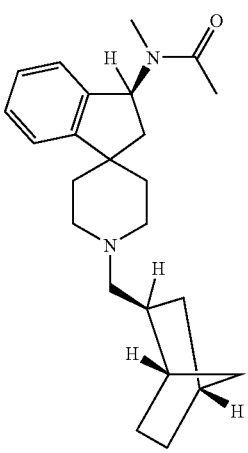 [SMILES: CC(=O)N(C)[C@H]1CC2(CCN(C[C@H]3C[C@H]4CC[C@H]3C4)CC2)c2ccccc21]
340
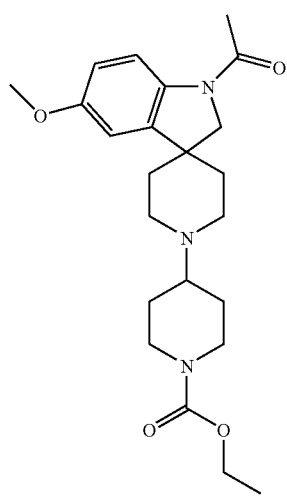
341
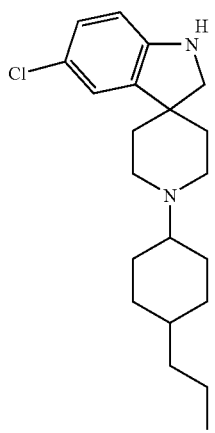
342
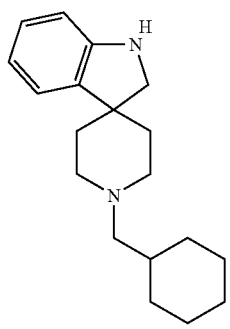

TABLE 1-continued
Exemplary compounds of formula I.
343
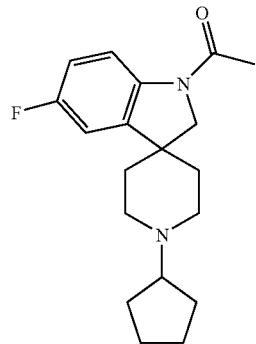 [SMILES: CC(=O)N1CC2(CCN(C3CCCC3)CC2)c2cc(F)ccc21]
344
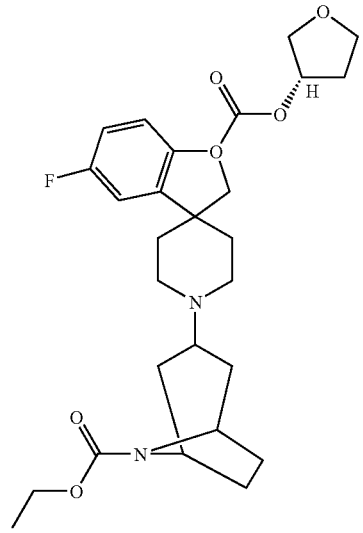
345
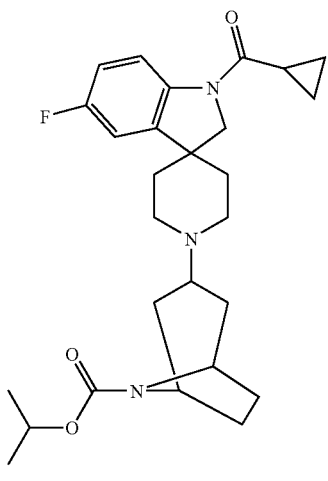 [SMILES: CC(C)OC(=O)N1C2CCC1CC(N1CCC3(CC1)CN(C(=O)C1CC1)c1ccc(F)cc13)C2]
346
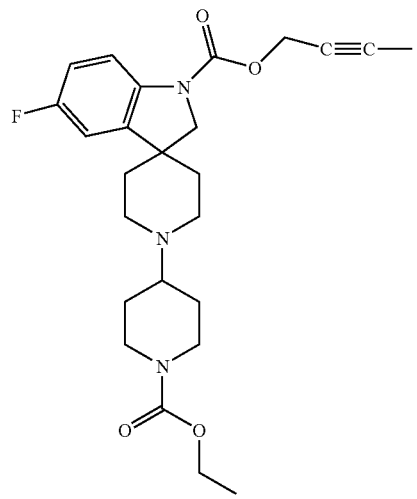 [SMILES: CC#CCOC(=O)N1CC2(CCN(C3CCN(C(=O)OCC)CC3)CC2)c2cc(F)ccc21]
347
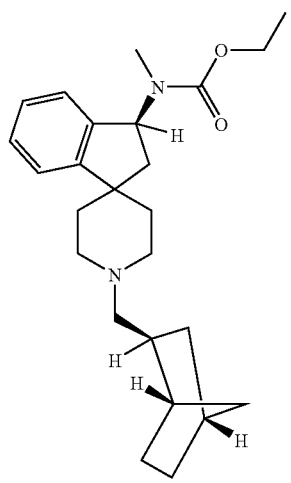 [SMILES: CCOC(=O)N(C)[C@H]1CC2(CCN(C[C@H]3C[C@H]4CC[C@H]3C4)CC2)c2ccccc21]
348
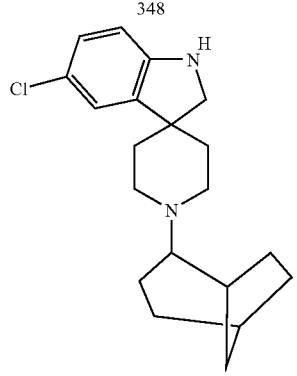

TABLE 1-continued
Exemplary compounds of formula I.
349
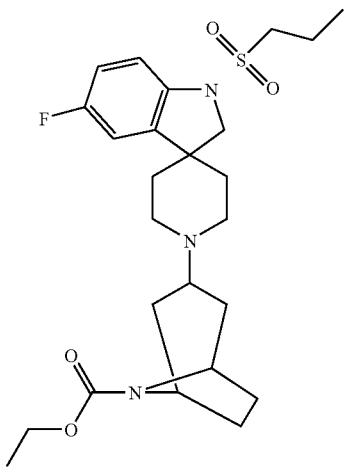
350
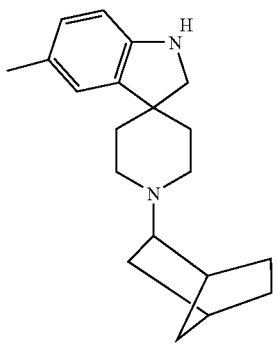
351
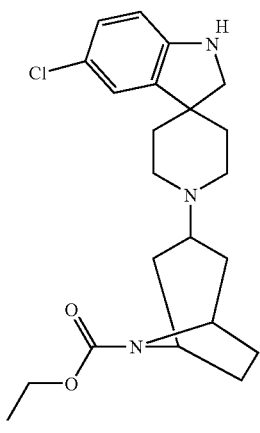
352
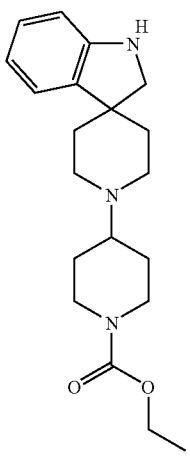
353
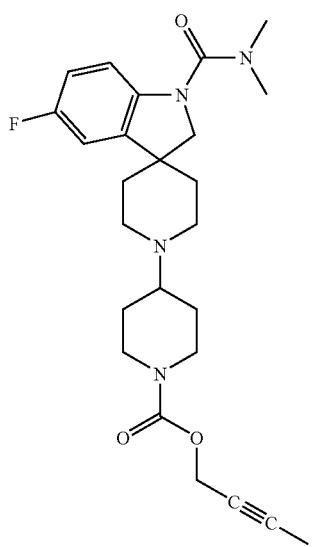
354
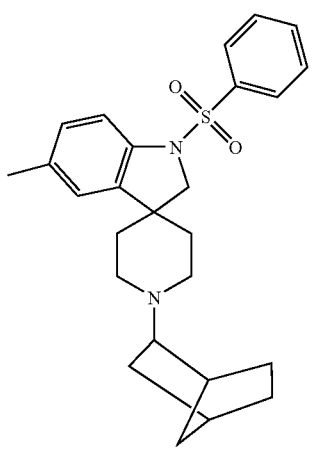 [SMILES: Cc1ccc2c(c1)C1(CCN(C3CC4CCC3C4)CC1)CN2S(=O)(=O)c1ccccc1]

TABLE 1-continued
Exemplary compounds of formula I.
355
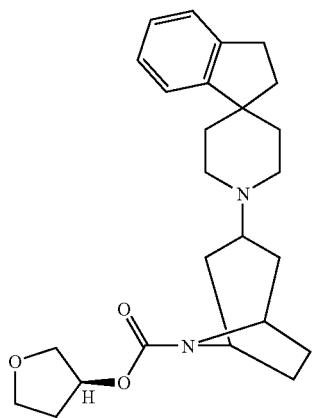
356
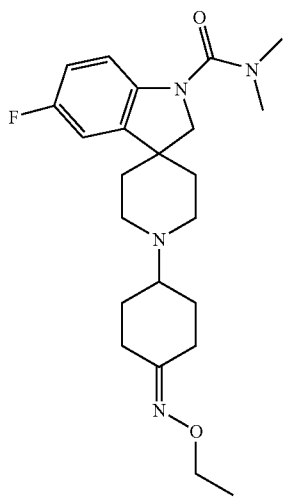 [SMILES: CCON=C1CCC(N2CCC3(CC2)CN(C(=O)N(C)C)c2ccc(F)cc23)CC1]
357
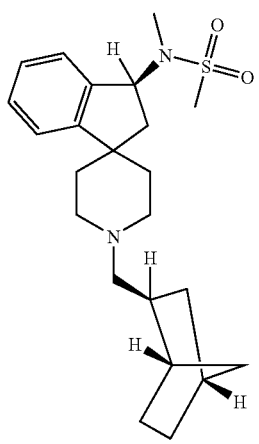 [SMILES: CN([C@H]1CC2(CCN(C[C@H]3C[C@H]4CC[C@H]3C4)CC2)c2ccccc21)S(C)(=O)=O]
358
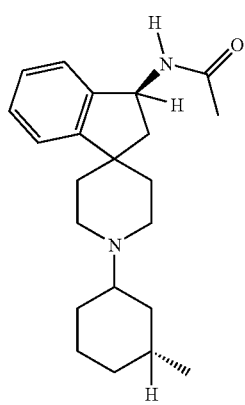 [SMILES: CC(=O)N[C@H]1CC2(CCN(C3CCC[C@@H](C)C3)CC2)c2ccccc21]
359
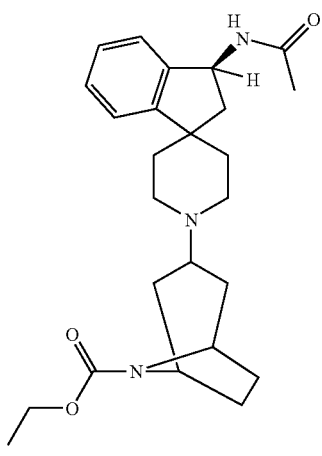
360
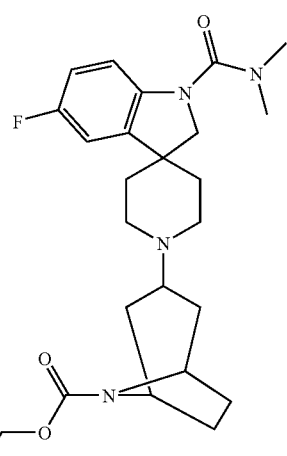

TABLE 1-continued
Exemplary compounds of formula I.
361
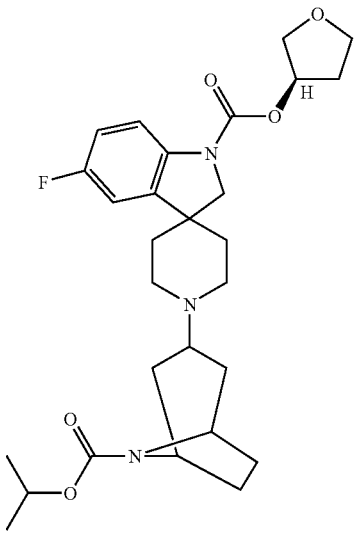
362
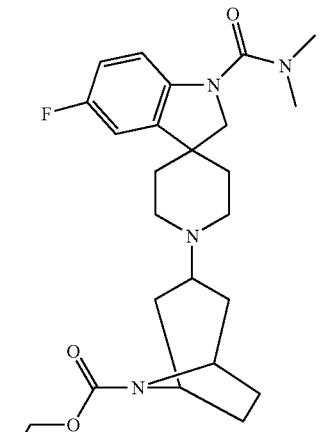
363
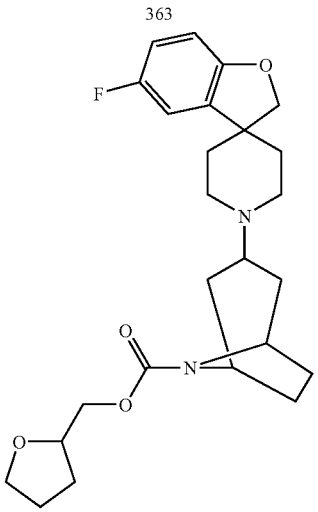
364
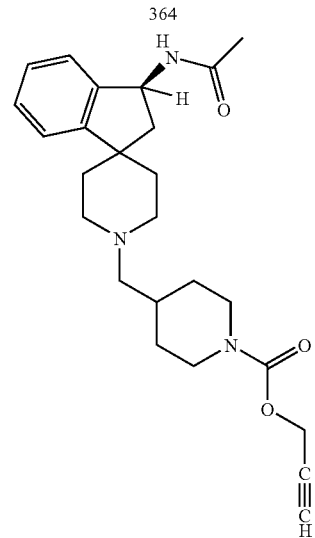
365
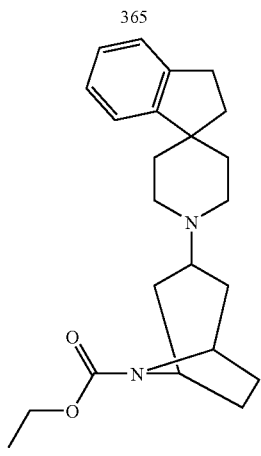
366
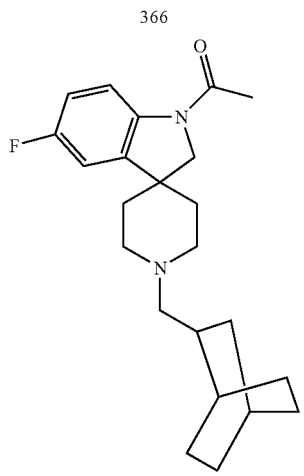

TABLE 1-continued
Exemplary compounds of formula I.
367
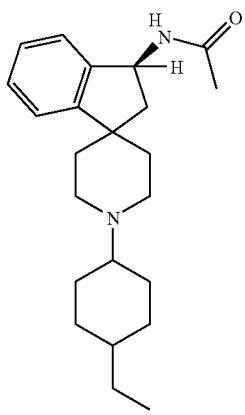
368
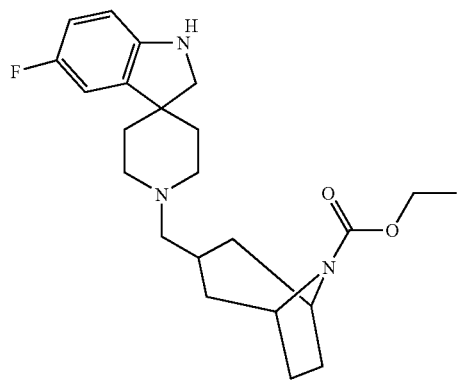
369
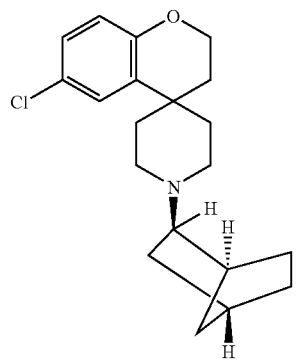 [SMILES: Clc1ccc2c(c1)C1(CCO2)CCN([C@@H]2C[C@@H]3CC[C@H]2C3)CC1]
370
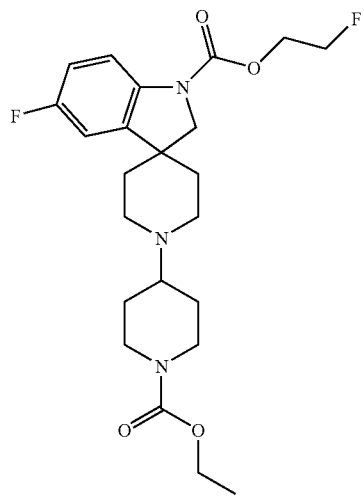 [SMILES: CCOC(=O)N1CCC(N2CCC3(CC2)CN(C(=O)OCCF)c2ccc(F)cc23)CC1]
371
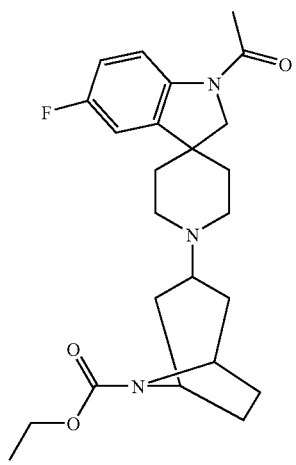
372
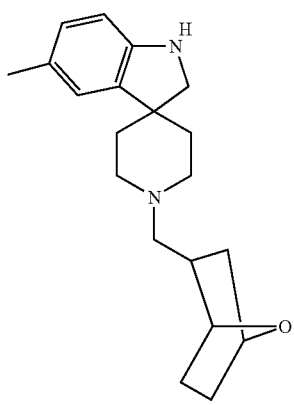

TABLE 1-continued
Exemplary compounds of formula I.
373
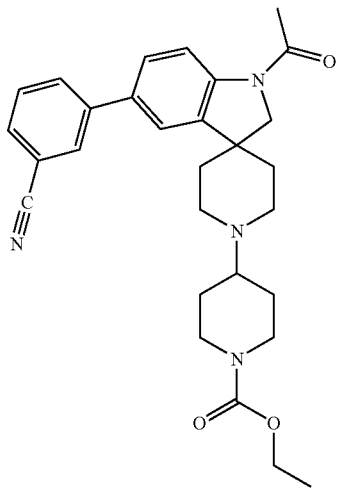 [SMILES: CCOC(=O)N1CCC(N2CCC3(CC2)CN(C(C)=O)c2ccc(-c4cccc(C#N)c4)cc23)CC1]
374
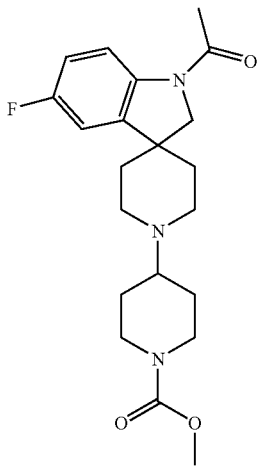 [SMILES: COC(=O)N1CCC(N2CCC3(CC2)CN(C(C)=O)c2ccc(F)cc23)CC1]
375
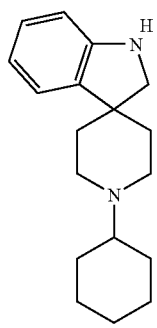
376
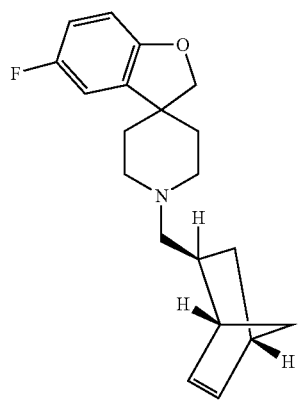 [SMILES: Fc1ccc2c(c1)C1(CCN(C[C@H]3C[C@H]4C=C[C@H]3C4)CC1)CO2]
377
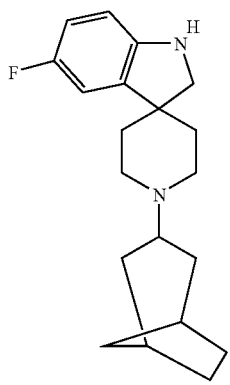
378
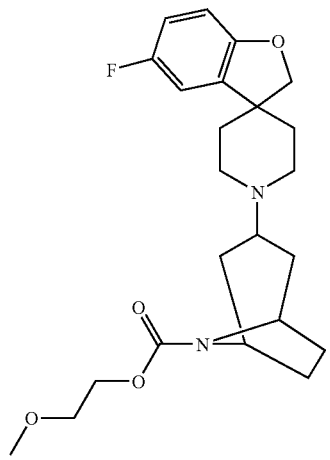 [SMILES: COCCOC(=O)N1C2CCC1CC(N1CCC3(CC1)COc1ccc(F)cc13)C2]

TABLE 1-continued
Exemplary compounds of formula I.
379
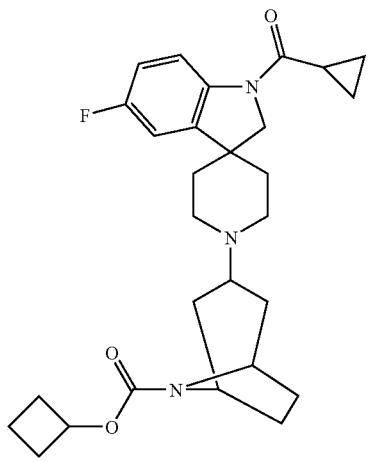 [SMILES: O=C(C1CC1)N1CC2(CCN(C3CC4CCC(C3)N4C(=O)OC3CCC3)CC2)c2cc(F)ccc21]
380
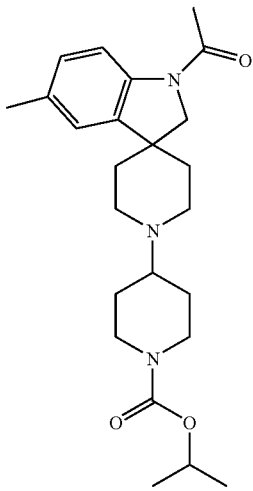 [SMILES: CC(=O)N1CC2(CCN(C3CCN(C(=O)OC(C)C)CC3)CC2)c2cc(C)ccc21]
381
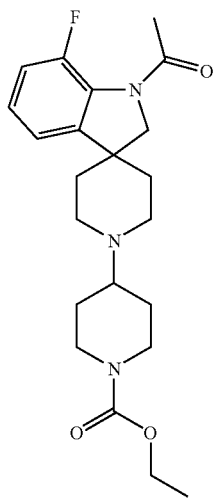 [SMILES: CCOC(=O)N1CCC(N2CCC3(CC2)CN(C(C)=O)c2c(F)cccc23)CC1]
382
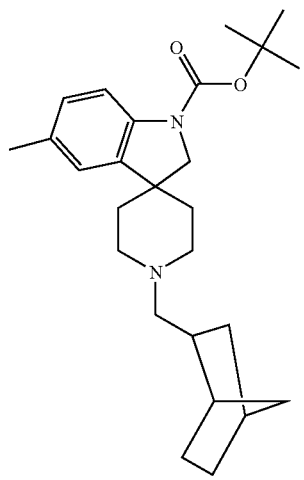 [SMILES: Cc1ccc2c(c1)C1(CCN(CC3CC4CCC3C4)CC1)CN2C(=O)OC(C)(C)C]
383
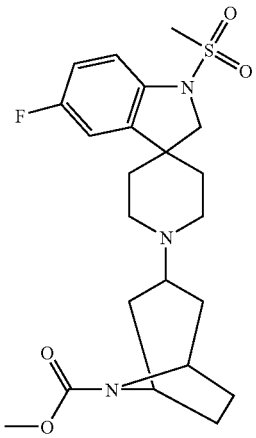 [SMILES: COC(=O)N1C2CCC1CC(N1CCC3(CC1)CN(S(C)(=O)=O)c1ccc(F)cc13)C2]
384
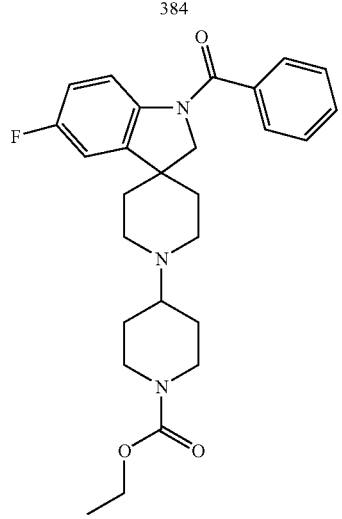

TABLE 1-continued
Exemplary compounds of formula I.
385
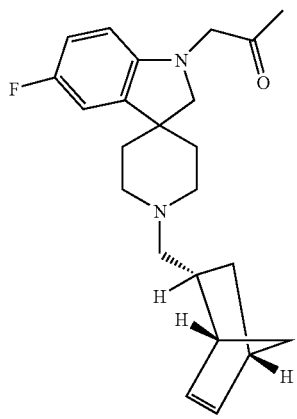 [SMILES: CC(=O)CN1CC2(CCN(C[C@@H]3C[C@H]4C=C[C@H]3C4)CC2)c2cc(F)ccc21]
386
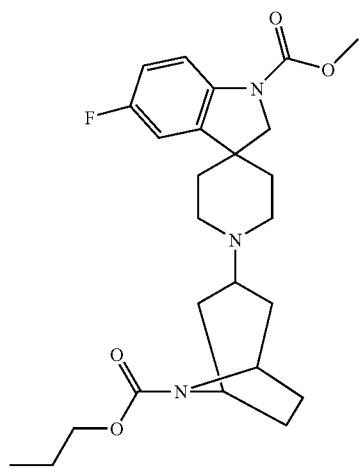 [SMILES: CCCOC(=O)N1C2CCC1CC(N1CCC3(CC1)CN(C(=O)OC)c1ccc(F)cc13)C2]
387
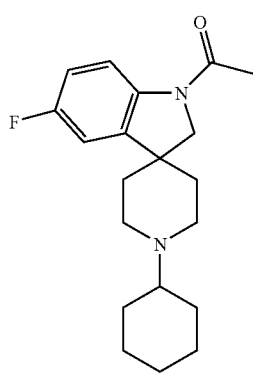 [SMILES: CC(=O)N1CC2(CCN(C3CCCCC3)CC2)c2cc(F)ccc21]
388
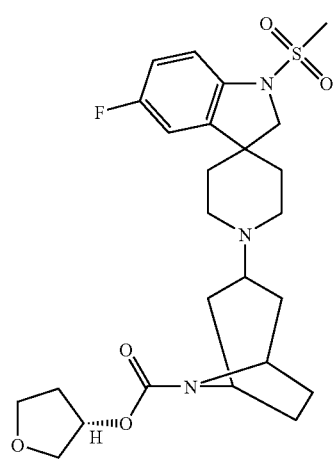
389
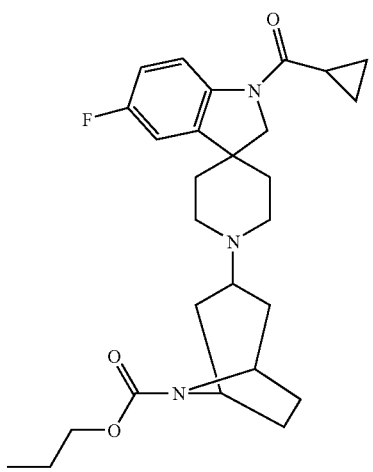 [SMILES: CCCOC(=O)N1C2CCC1CC(N1CCC3(CC1)CN(C(=O)C1CC1)c1ccc(F)cc13)C2]
390
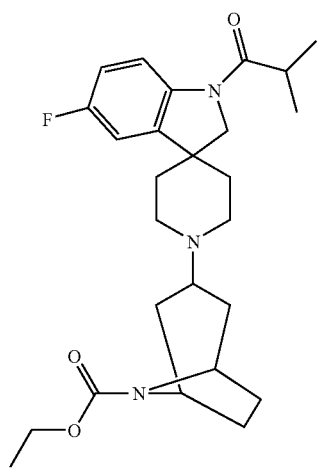 [SMILES: CCOC(=O)N1C2CCC1CC(N1CCC3(CC1)CN(C(=O)C(C)C)c1ccc(F)cc13)C2]

TABLE 1-continued
Exemplary compounds of formula I.
391
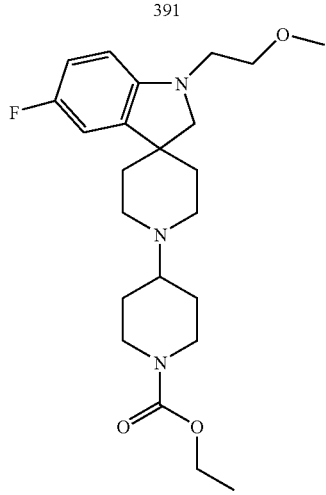
392
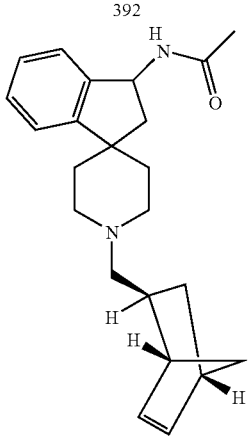
393
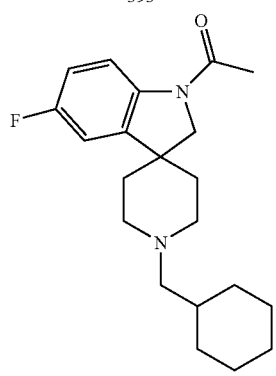
394
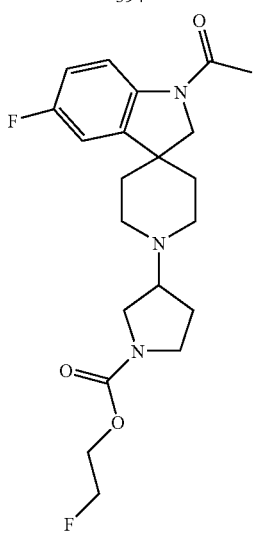
395
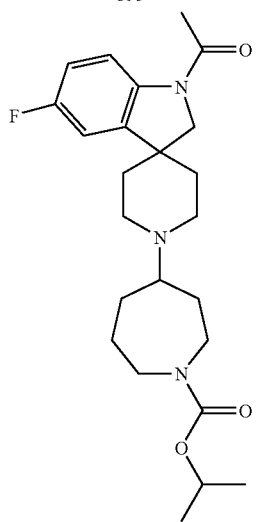
396
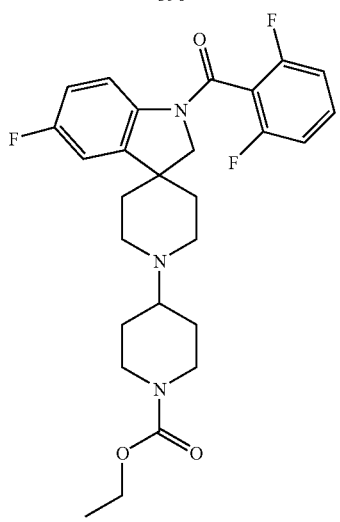

TABLE 1-continued
Exemplary compounds of formula I.
397
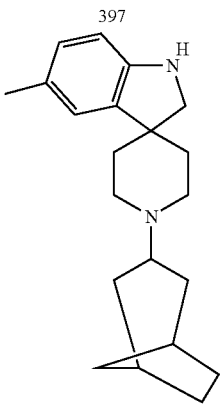
398
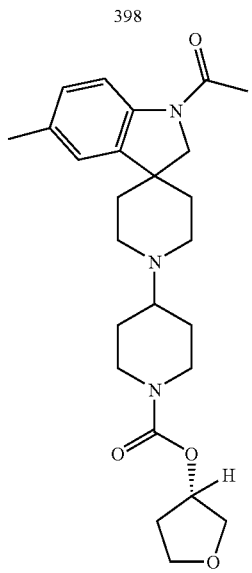
399
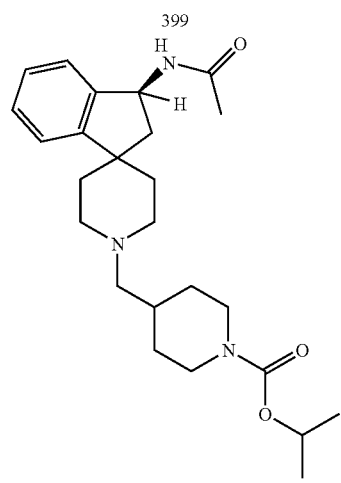
400
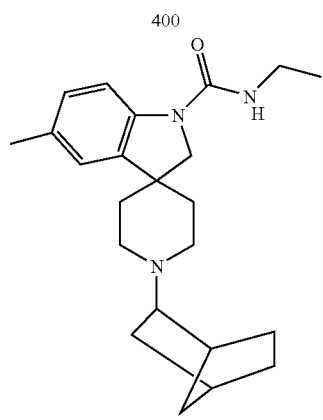
401
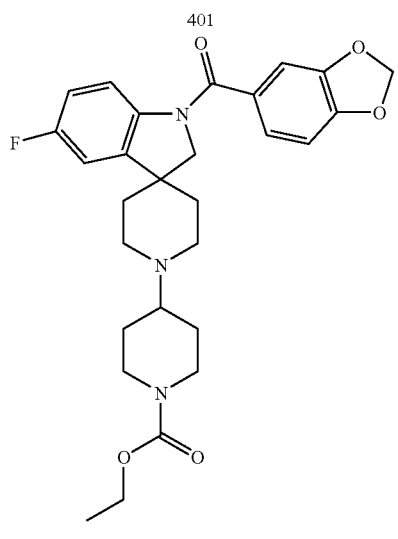
402
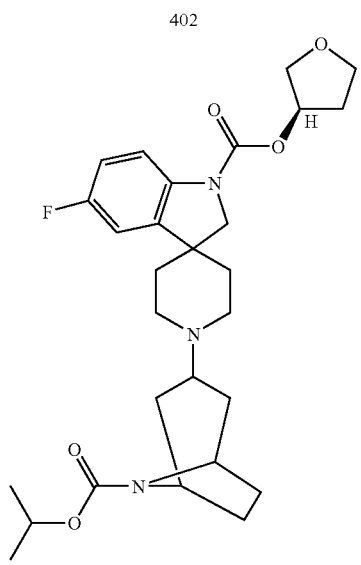

TABLE 1-continued
Exemplary compounds of formula I.
403
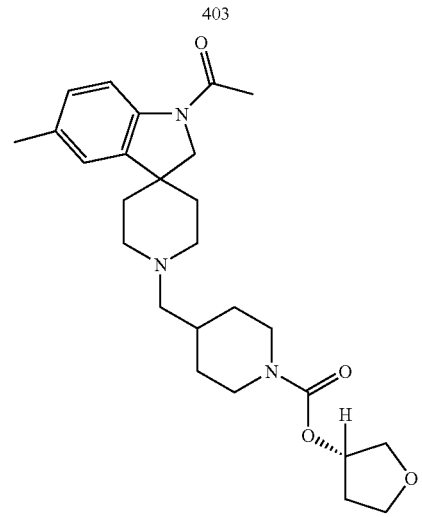
404
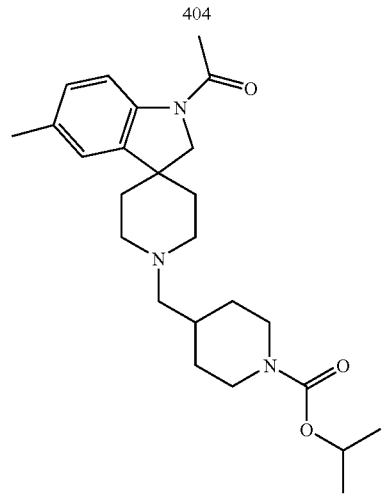
405
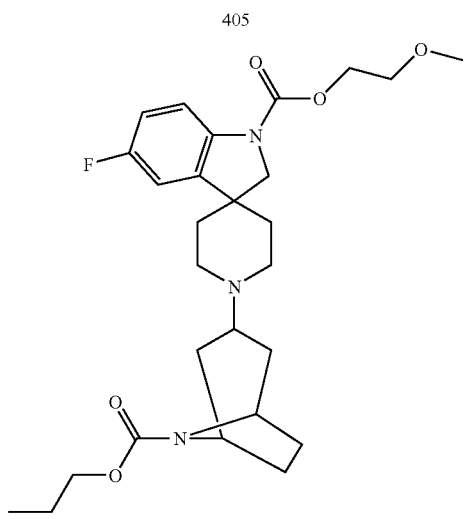
406
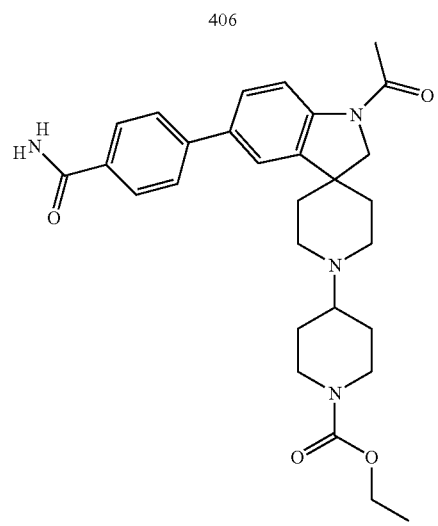
407
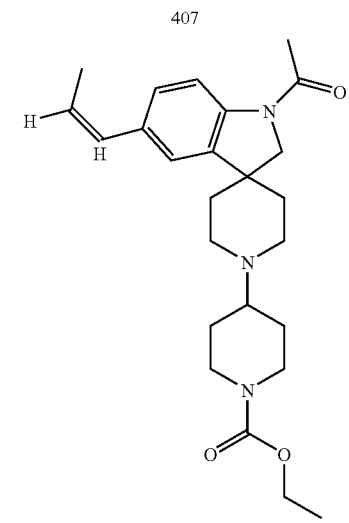
408
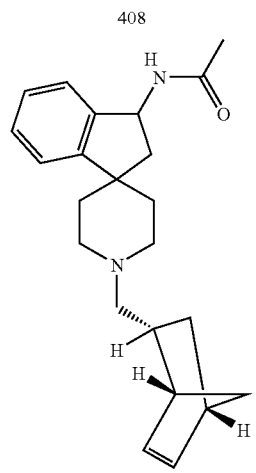

TABLE 1-continued
Exemplary compounds of formula I.
409
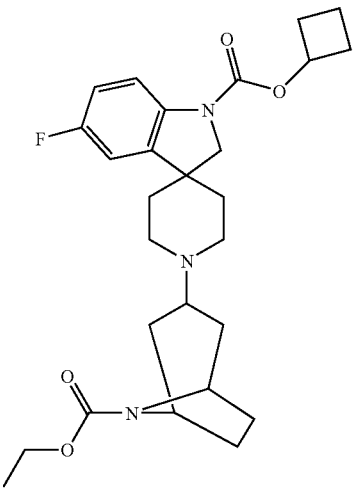 [SMILES: CCOC(=O)N1C2CCC1CC(N1CCC3(CC1)CN(C(=O)OC1CCC1)c1ccc(F)cc13)C2]
410
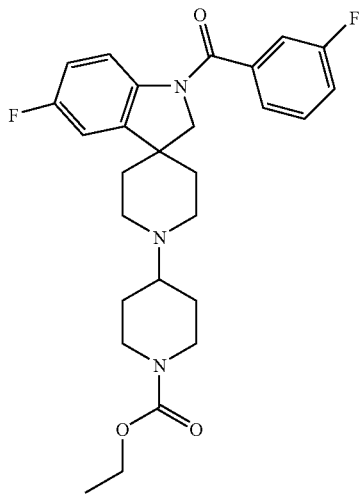 [SMILES: CCOC(=O)N1CCC(N2CCC3(CC2)CN(C(=O)c2cccc(F)c2)c2ccc(F)cc23)CC1]
411
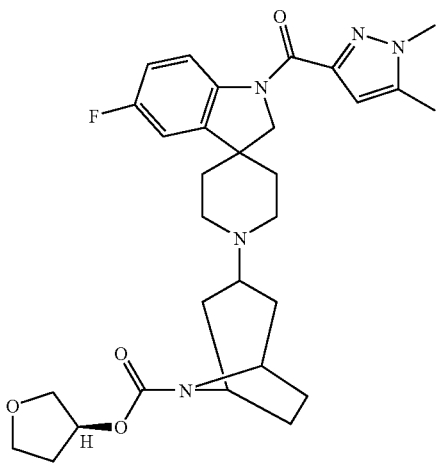
412
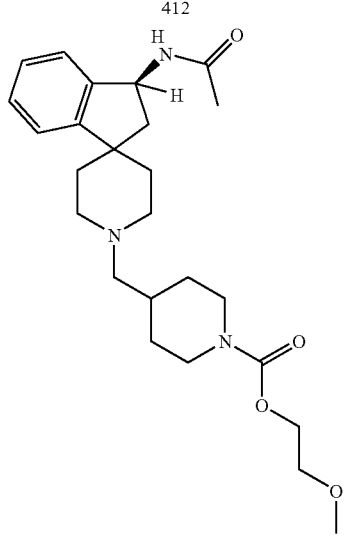
413
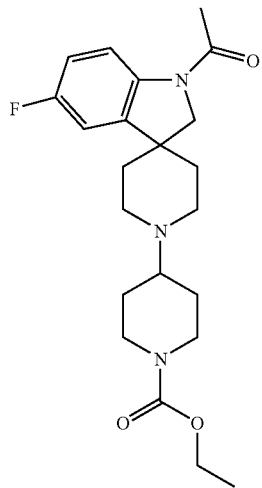 [SMILES: CCOC(=O)N1CCC(N2CCC3(CC2)CN(C(C)=O)c2ccc(F)cc23)CC1]
414
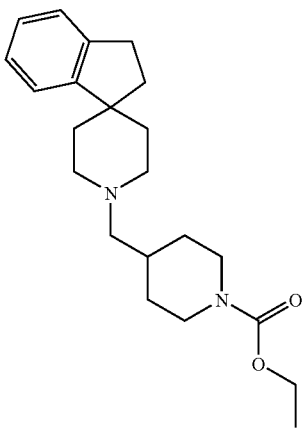 [SMILES: CCOC(=O)N1CCC(CN2CCC3(CCc4ccccc43)CC2)CC1]

TABLE 1-continued
Exemplary compounds of formula I.
415
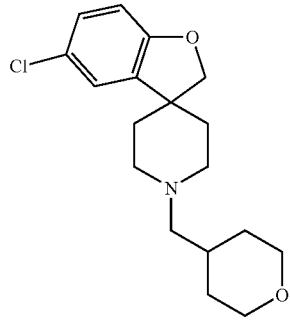 [SMILES: Clc1ccc2c(c1)C1(CCN(CC3CCOCC3)CC1)CO2]
416
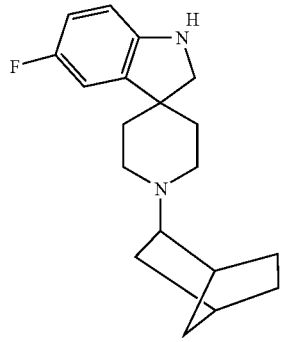
417
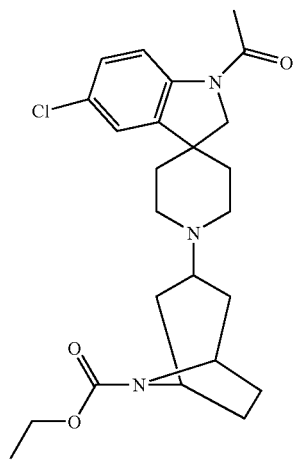 [SMILES: CCOC(=O)N1C2CCC1CC(N1CCC3(CC1)CN(C(C)=O)c1ccc(Cl)cc13)C2]
418
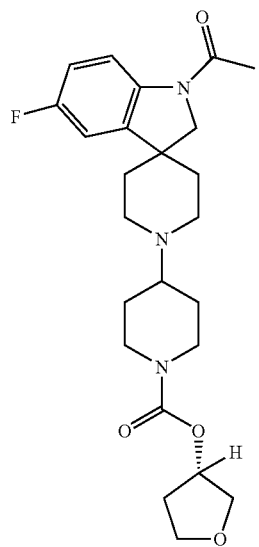 [SMILES: CC(=O)N1CC2(CCN(C3CCN(C(=O)O[C@H]4CCOC4)CC3)CC2)c2cc(F)ccc21]
419
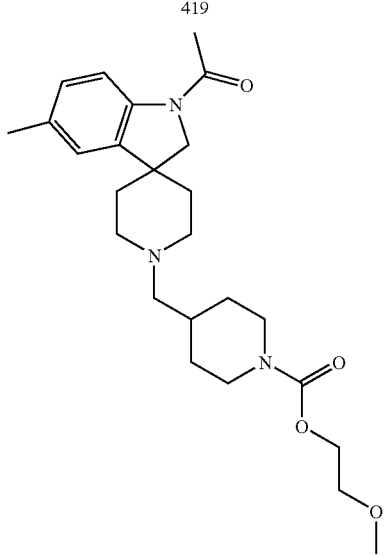
420
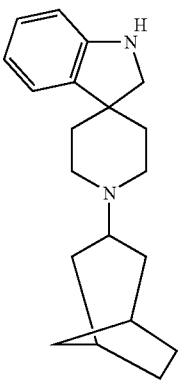

TABLE 1-continued
Exemplary compounds of formula I.
421
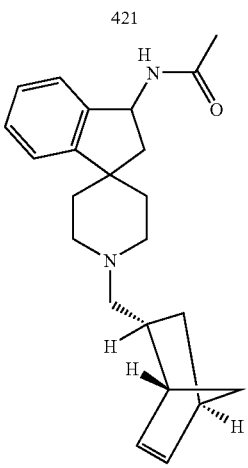
422
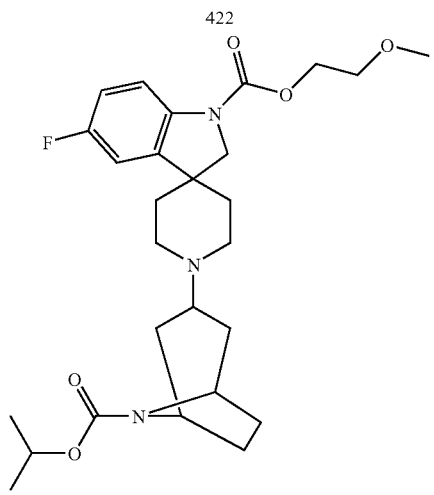
423
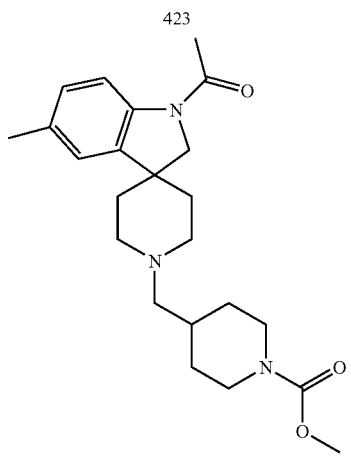
424
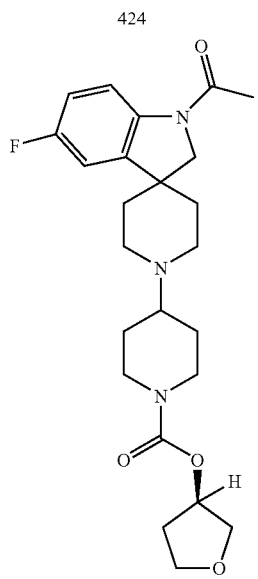
425
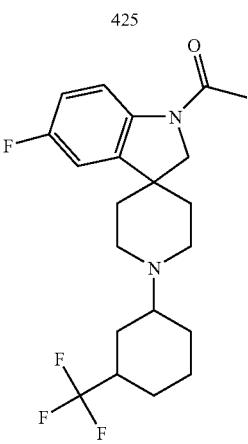
426
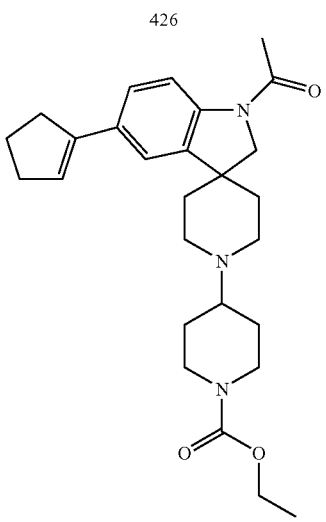

TABLE 1-continued
Exemplary compounds of formula I.
427
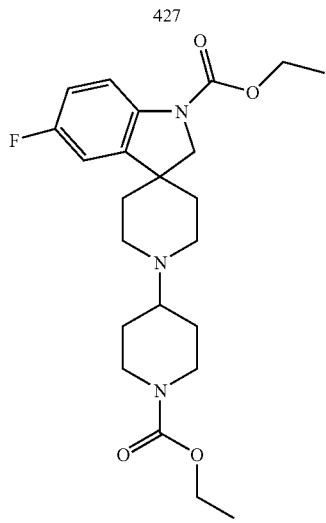
428
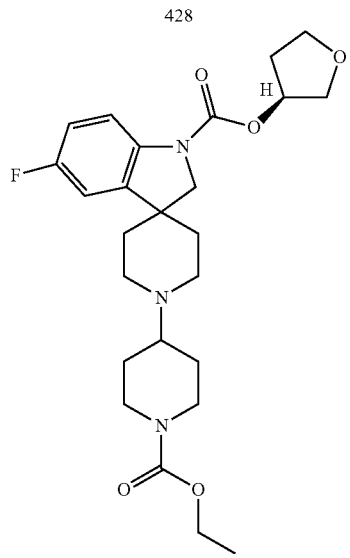
429
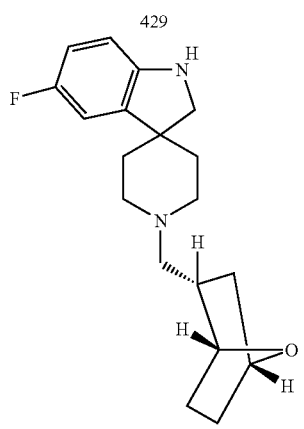
430
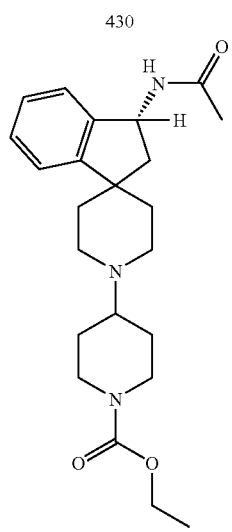
431
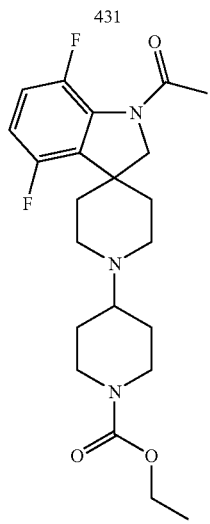
432
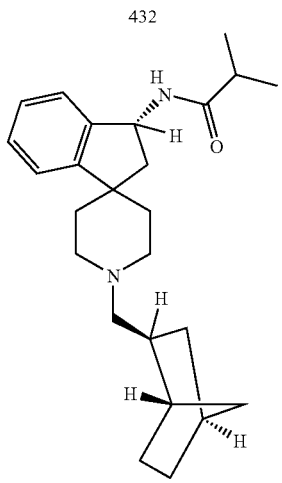

TABLE 1-continued
Exemplary compounds of formula I.
433
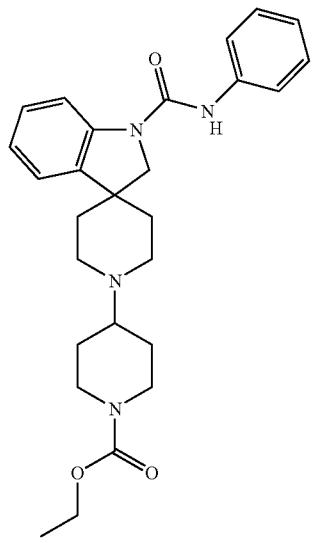
434
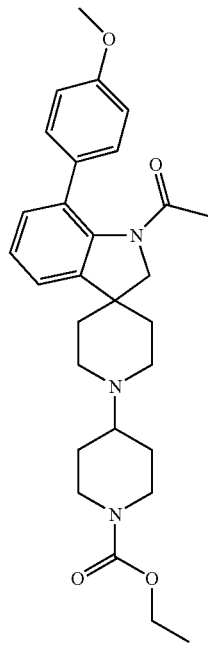 [SMILES: CCOC(=O)N1CCC(N2CCC3(CC2)CN(C(C)=O)c2c(-c4ccc(OC)cc4)cccc23)CC1]
435
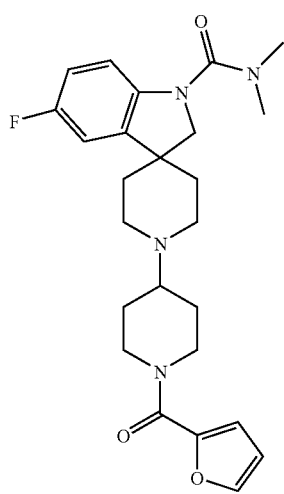 [SMILES: CN(C)C(=O)N1CC2(CCN(C3CCN(C(=O)c4ccco4)CC3)CC2)c2cc(F)ccc21]
436
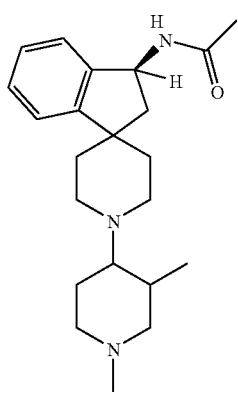

TABLE 1-continued
Exemplary compounds of formula I.
437
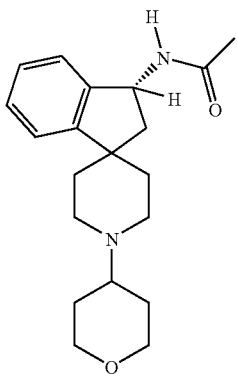 [SMILES: CC(=O)N[C@@H]1CC2(CCN(C3CCOCC3)CC2)c2ccccc21]
438
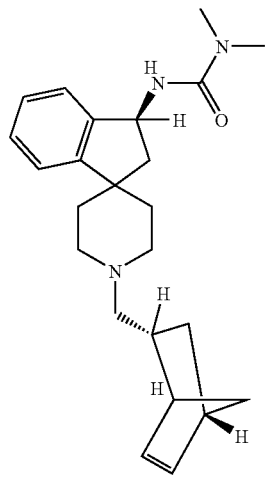
439
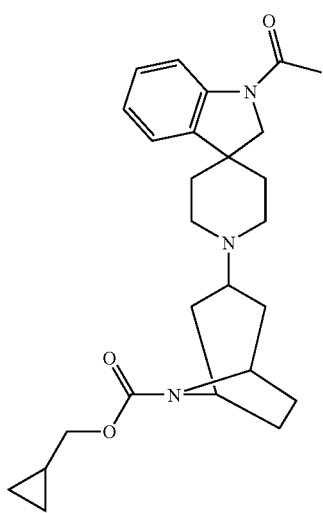 [SMILES: CC(=O)N1CC2(CCN(C3CC4CCC(C3)N4C(=O)OCC3CC3)CC2)c2ccccc21]
440
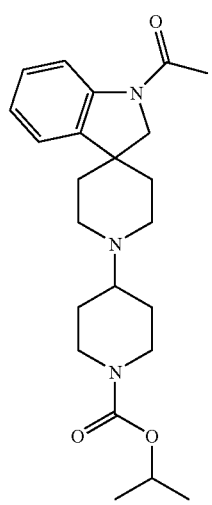 [SMILES: CC(=O)N1CC2(CCN(C3CCN(C(=O)OC(C)C)CC3)CC2)c2ccccc21]
441
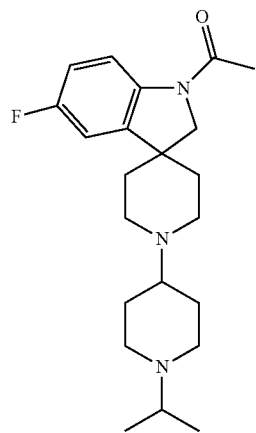 [SMILES: CC(=O)N1CC2(CCN(C3CCN(C(C)C)CC3)CC2)c2cc(F)ccc21]
442
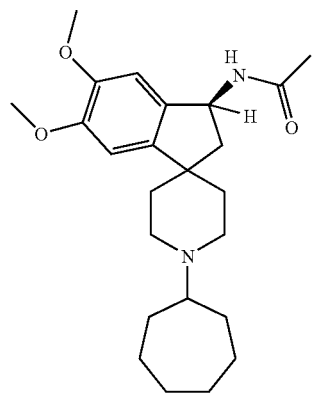

TABLE 1-continued
Exemplary compounds of formula I.
443
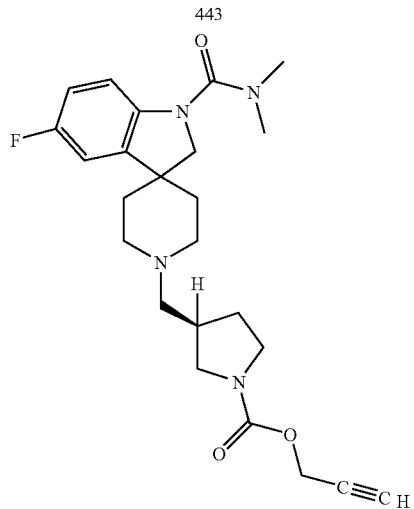
444
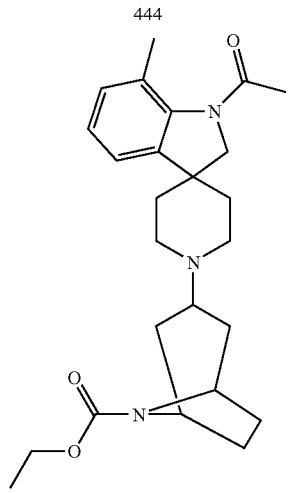
445
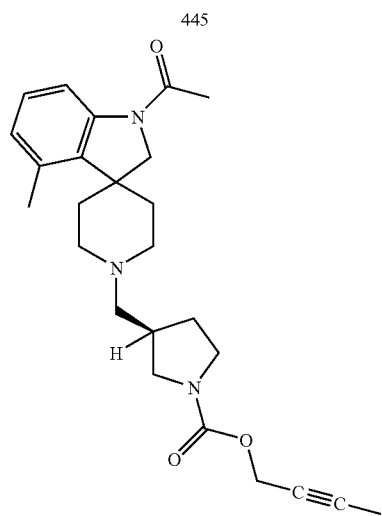
446
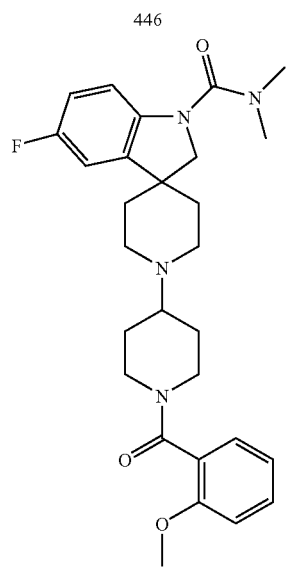
447
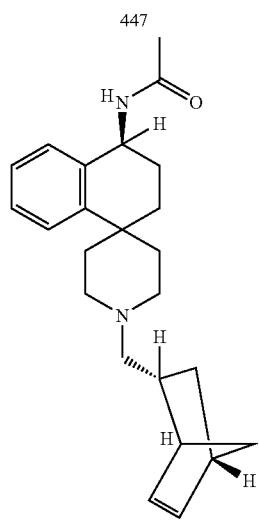
448
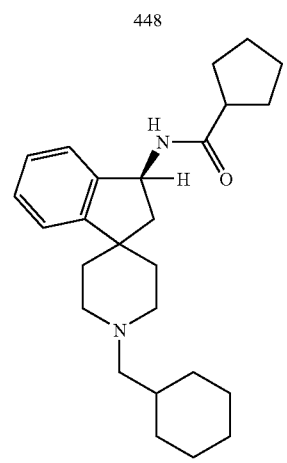

TABLE 1-continued
Exemplary compounds of formula I.
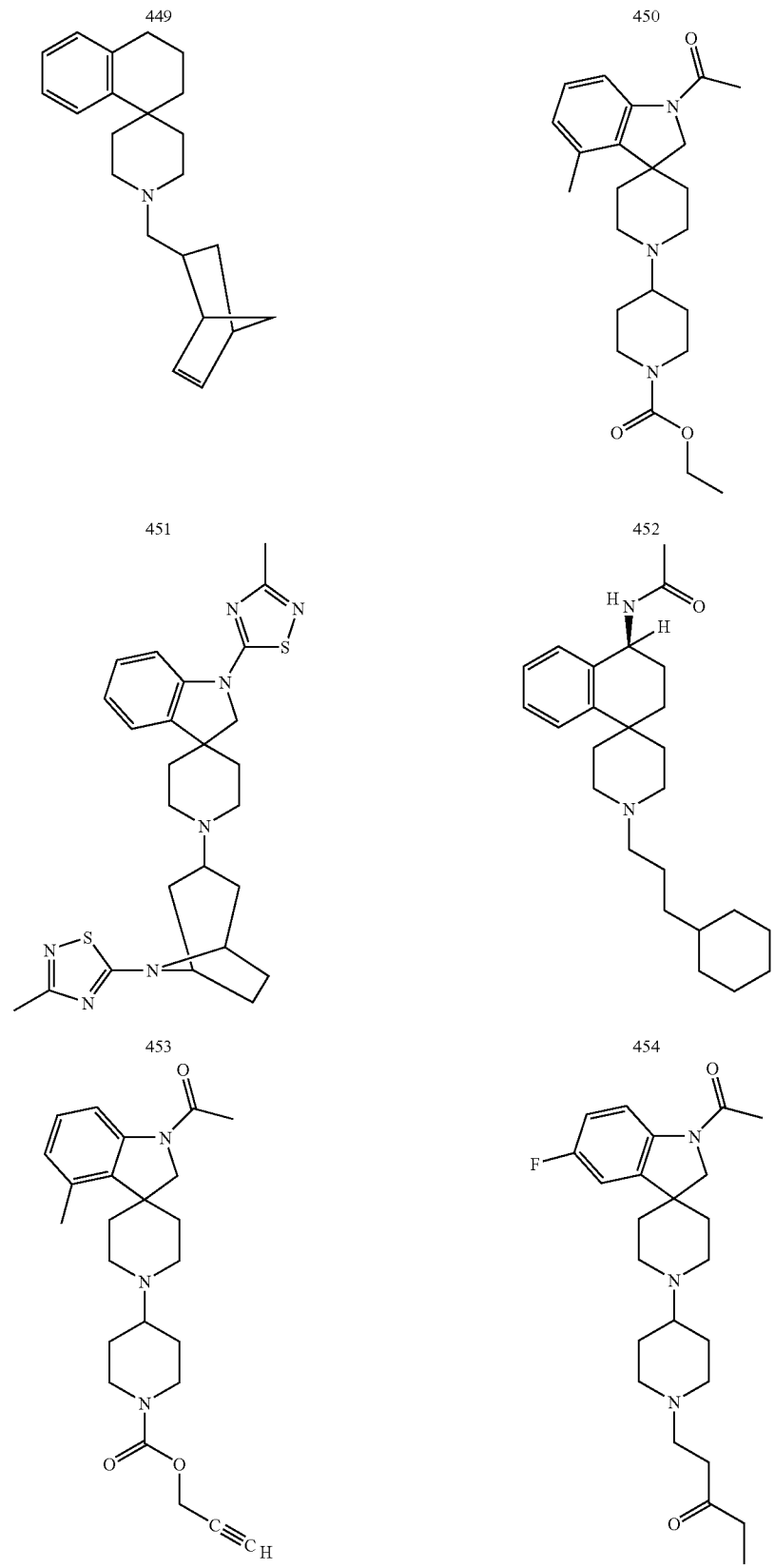

TABLE 1-continued
Exemplary compounds of formula I.
455
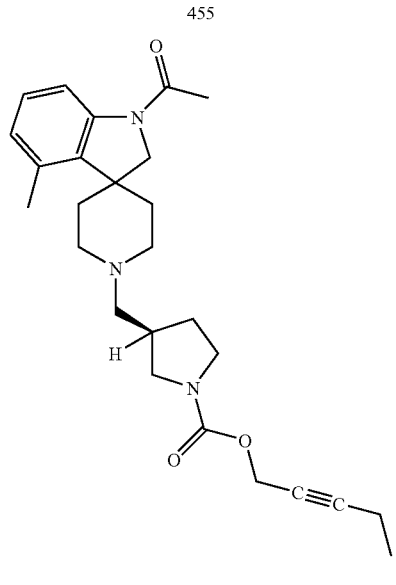
456
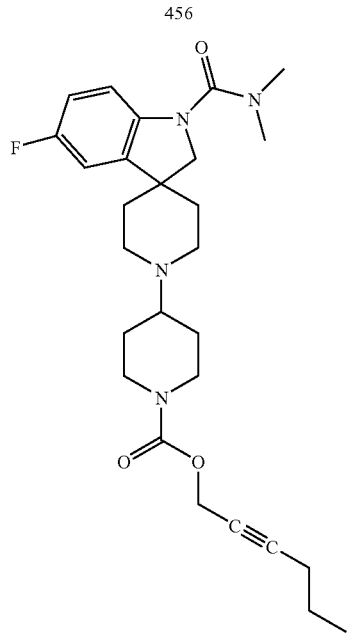
457
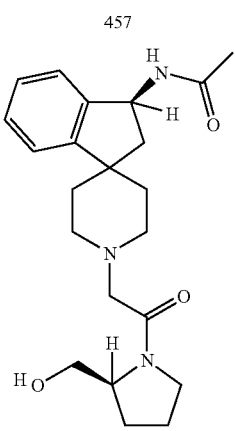
458
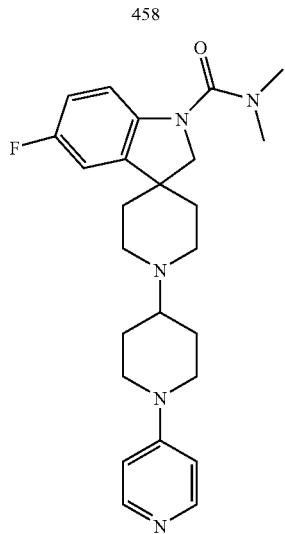

TABLE 1-continued
Exemplary compounds of formula I.
459
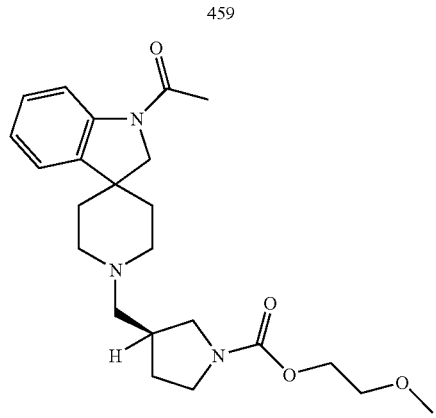
460
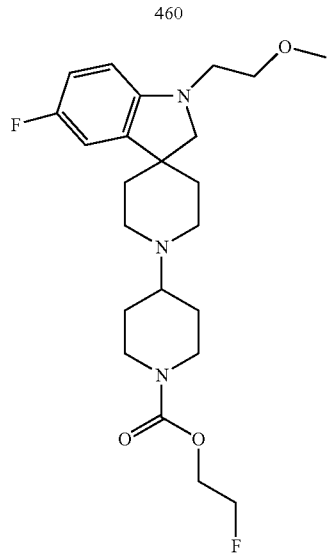
461
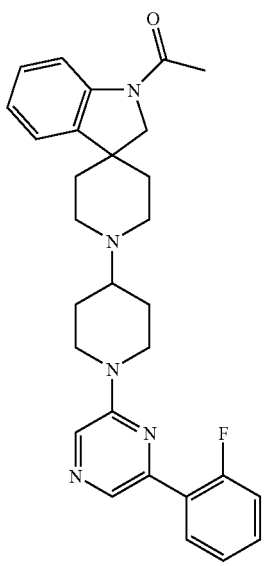 [SMILES: CC(=O)N1CC2(CCN(C3CCN(c4cncc(-c5ccccc5F)n4)CC3)CC2)c2ccccc21]
462
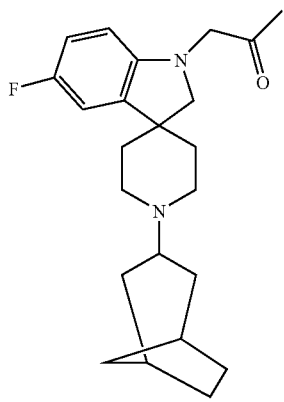 [SMILES: CC(=O)CN1CC2(CCN(C3CC4CCC(C4)C3)CC2)c2cc(F)ccc21]

TABLE 1-continued
Exemplary compounds of formula I.
463
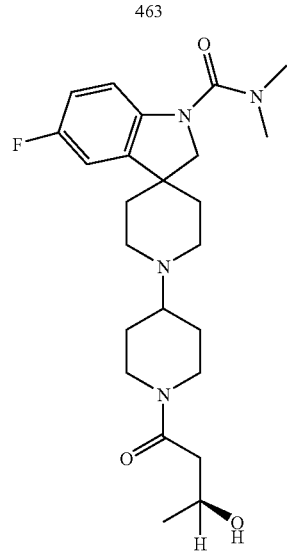
464
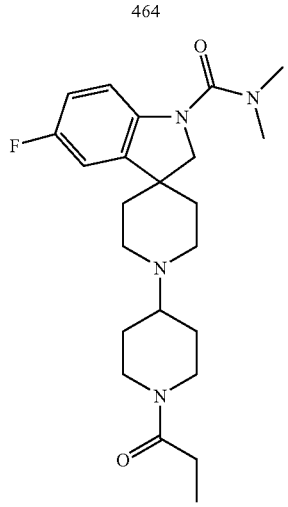
465
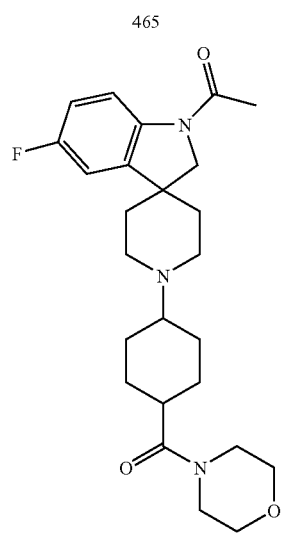
466
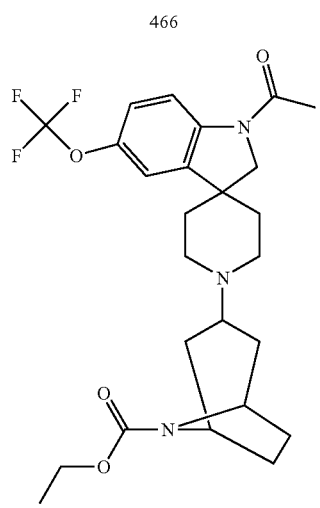

195 196
TABLE 1-continued
Exemplary compounds of formula I.
467
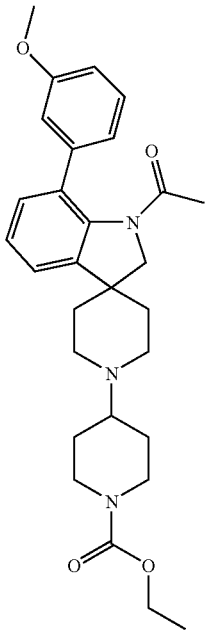 [SMILES: CCOC(=O)N1CCC(N2CCC3(CC2)CN(C(C)=O)c2c(-c4cccc(OC)c4)cccc23)CC1]
468
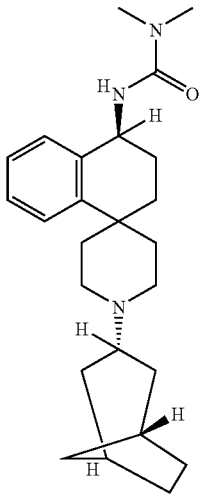
469
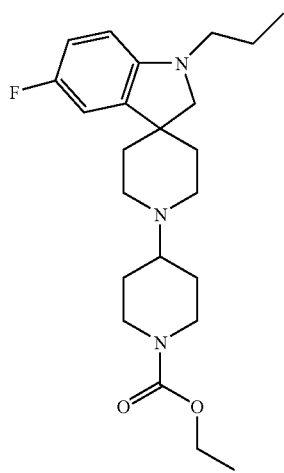 [SMILES: CCCN1CC2(CCN(C3CCN(C(=O)OCC)CC3)CC2)c2cc(F)ccc21]
470
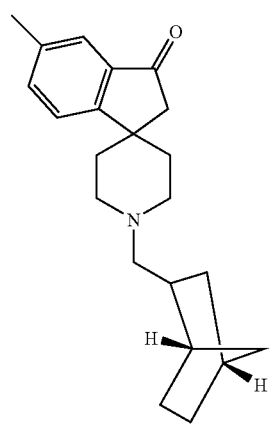 [SMILES: Cc1ccc2c(c1)C(=O)CC21CCN(CC2C[C@H]3CC[C@H]2C3)CC1]

TABLE 1-continued
Exemplary compounds of formula I.
471
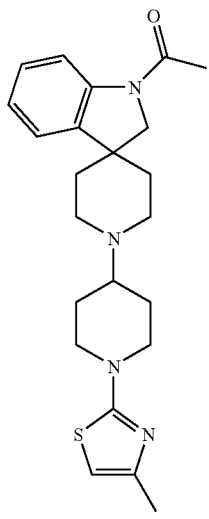 [SMILES: CC(=O)N1CC2(CCN(C3CCN(c4nc(C)cs4)CC3)CC2)c2ccccc21]
472
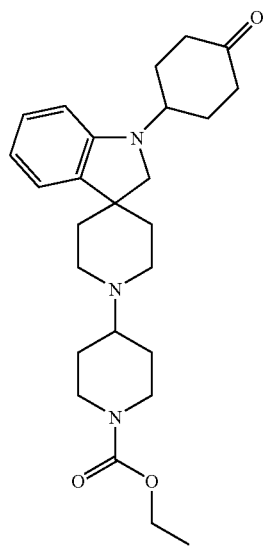 [SMILES: CCOC(=O)N1CCC(N2CCC3(CC2)CN(C2CCC(=O)CC2)c2ccccc23)CC1]
473
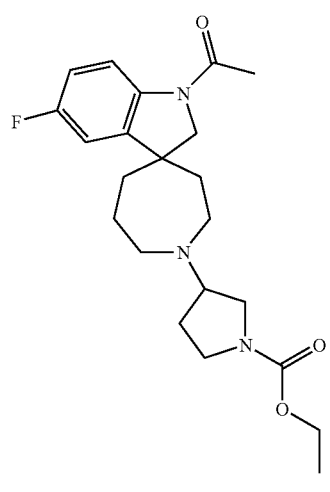 [SMILES: CCOC(=O)N1CCC(N2CCCC3(CC2)CN(C(C)=O)c2ccc(F)cc23)C1]
474
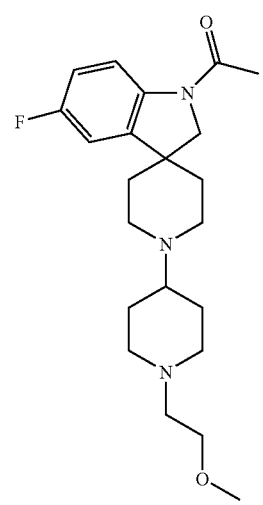 [SMILES: COCCN1CCC(N2CCC3(CC2)CN(C(C)=O)c2ccc(F)cc23)CC1]

TABLE 1-continued
Exemplary compounds of formula I.
475
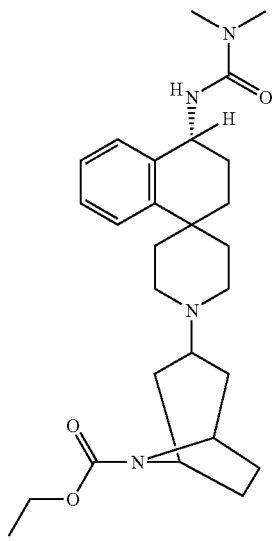
476
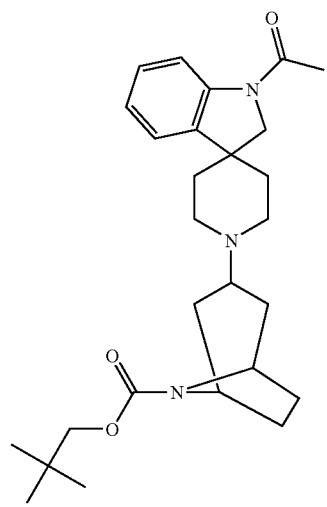 [SMILES: CC(=O)N1CC2(CCN(C3CC4CCC(C3)N4C(=O)OCC(C)(C)C)CC2)c2ccccc21]
477
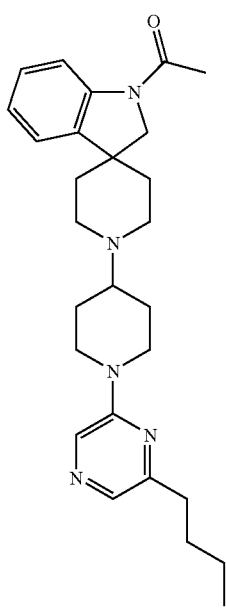 [SMILES: CCCCc1cncc(N2CCC(N3CCC4(CC3)CN(C(C)=O)c3ccccc34)CC2)n1]
478
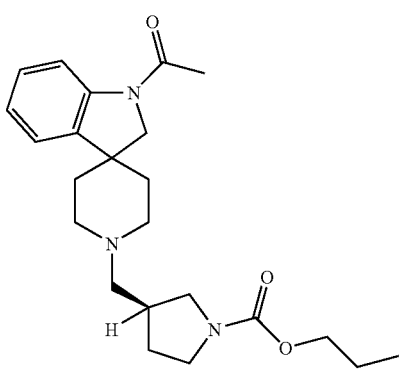 [SMILES: CCCOC(=O)N1CC[C@@H](CN2CCC3(CC2)CN(C(C)=O)c2ccccc23)C1]

TABLE 1-continued
Exemplary compounds of formula I.
479
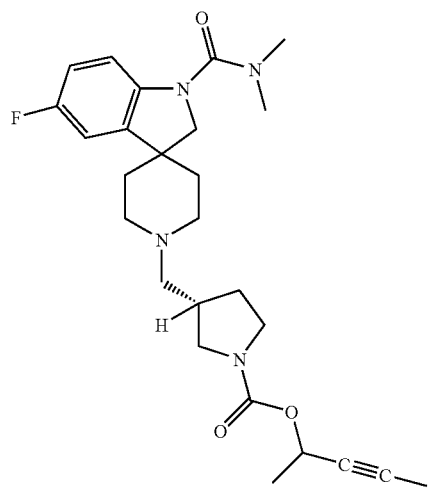 [SMILES: CC#CC(C)OC(=O)N1CC[C@@H](CN2CCC3(CC2)CN(C(=O)N(C)C)c2ccc(F)cc23)C1]
480
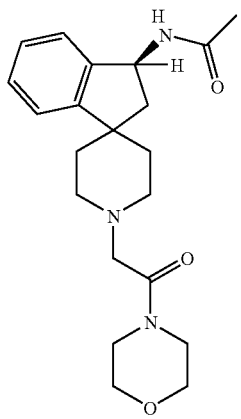
481
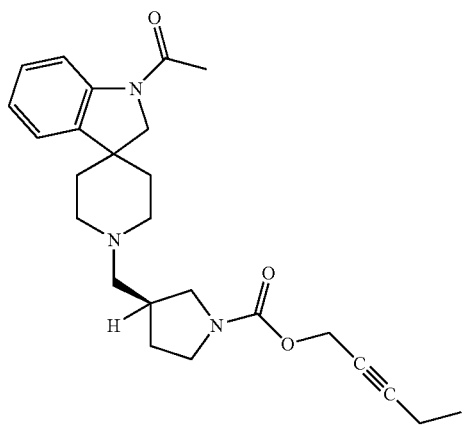 [SMILES: CCC#CCOC(=O)N1CC[C@@H](CN2CCC3(CC2)CN(C(C)=O)c2ccccc23)C1]
482
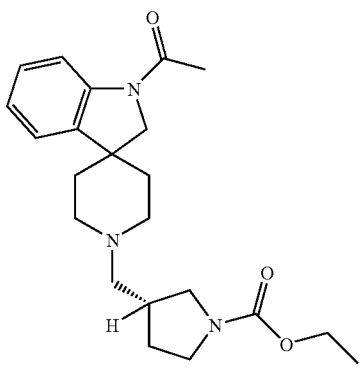 [SMILES: CCOC(=O)N1CC[C@H](CN2CCC3(CC2)CN(C(C)=O)c2ccccc23)C1]
483
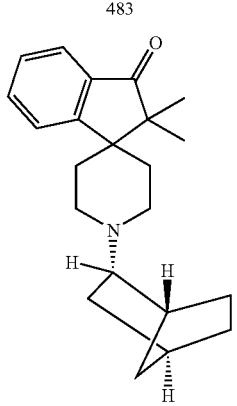
484
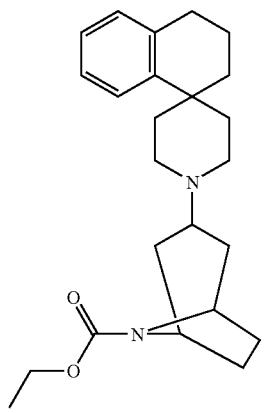 [SMILES: CCOC(=O)N1C2CCC1CC(N1CCC3(CCCc4ccccc43)CC1)C2]

TABLE 1-continued
Exemplary compounds of formula I.
485
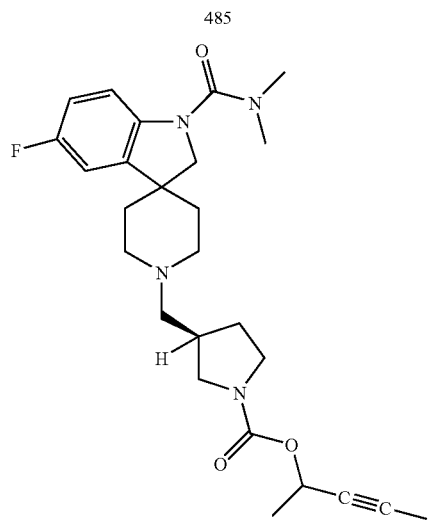
486
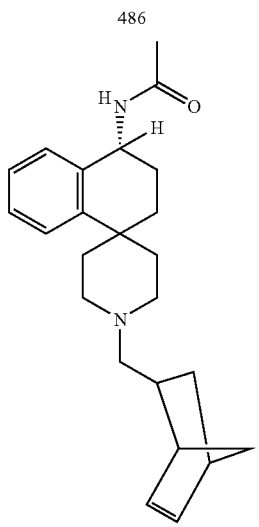
487
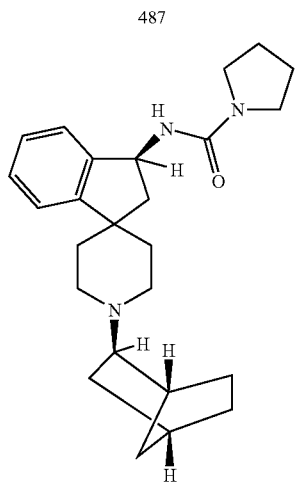
488
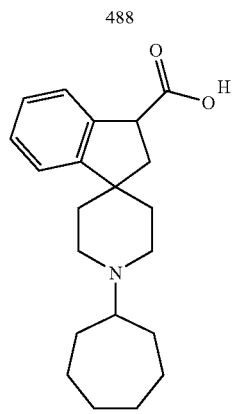
489
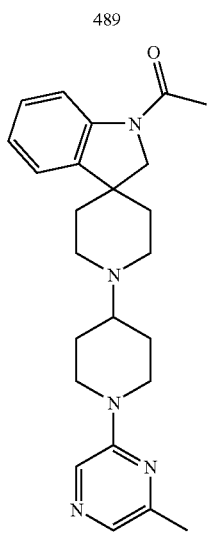
490
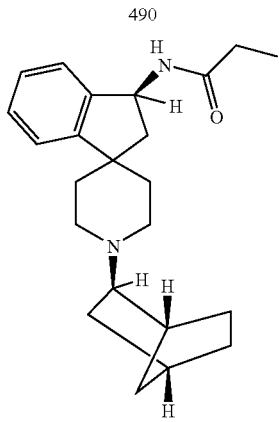

TABLE 1-continued
Exemplary compounds of formula I.
491
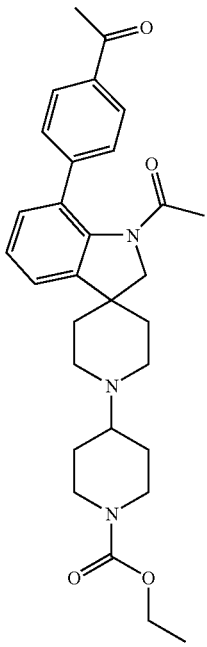 [SMILES: CCOC(=O)N1CCC(N2CCC3(CC2)CN(C(C)=O)c2c(-c4ccc(C(C)=O)cc4)cccc23)CC1]
492
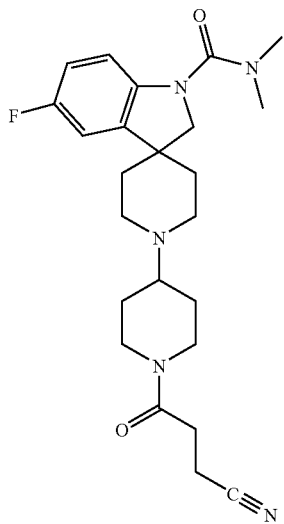 [SMILES: CN(C)C(=O)N1CC2(CCN(C3CCN(C(=O)CCC#N)CC3)CC2)c2cc(F)ccc21]
493
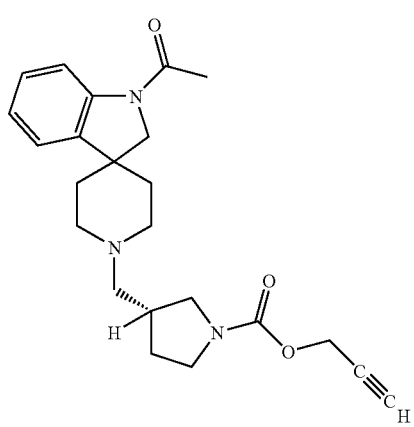
494
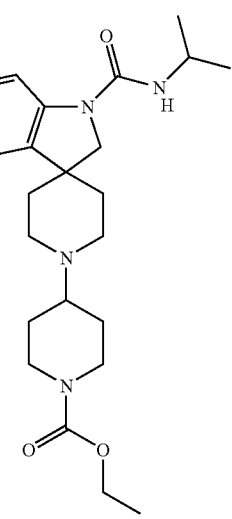

TABLE 1-continued
Exemplary compounds of formula I.
495
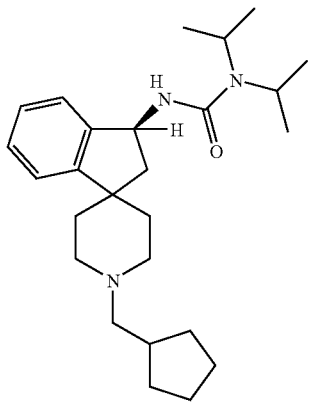
496
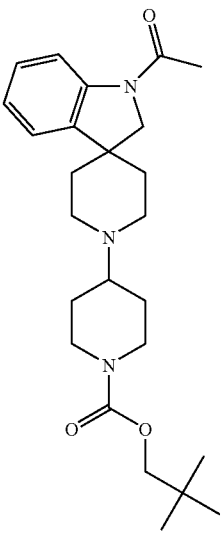 [SMILES: CC(=O)N1CC2(CCN(C3CCN(C(=O)OCC(C)(C)C)CC3)CC2)c2ccccc21]
497
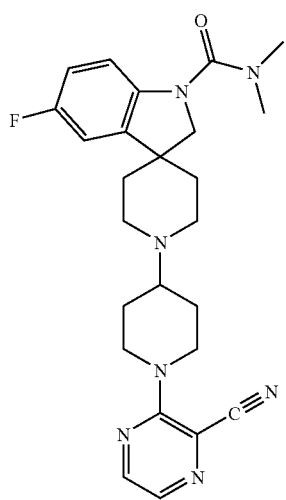 [SMILES: CN(C)C(=O)N1CC2(CCN(C3CCN(c4nccnc4C#N)CC3)CC2)c2cc(F)ccc21]
498
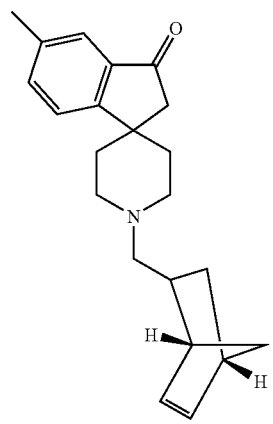 [SMILES: Cc1ccc2c(c1)C(=O)CC21CCN(CC2C[C@H]3C=C[C@H]2C3)CC1]

TABLE 1-continued
Exemplary compounds of formula I.
499
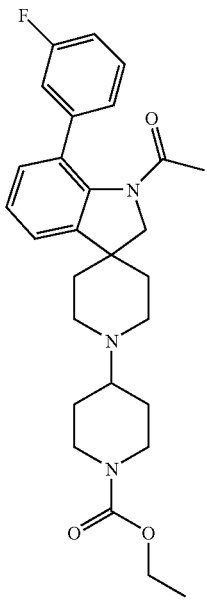 [SMILES: CCOC(=O)N1CCC(N2CCC3(CC2)CN(C(C)=O)c2c(-c4cccc(F)c4)cccc23)CC1]
500
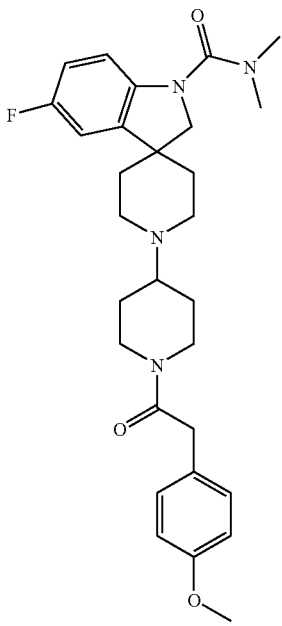 [SMILES: COc1ccc(CC(=O)N2CCC(N3CCC4(CC3)CN(C(=O)N(C)C)c3ccc(F)cc34)CC2)cc1]
501
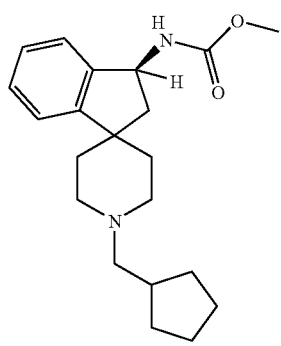
502
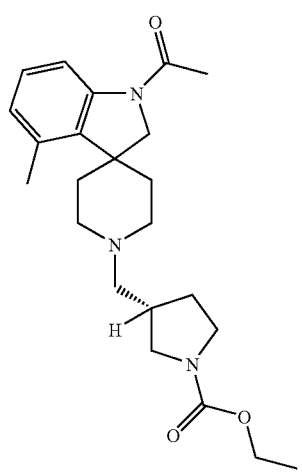 [SMILES: CCOC(=O)N1CC[C@@H](CN2CCC3(CC2)CN(C(C)=O)c2cccc(C)c23)C1]

TABLE 1-continued
Exemplary compounds of formula I.
503
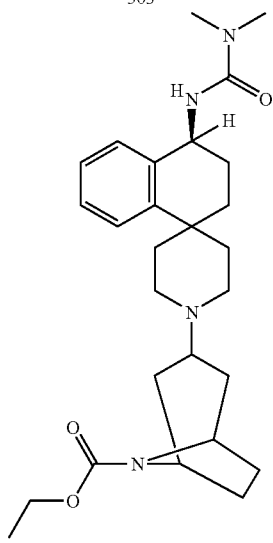
504
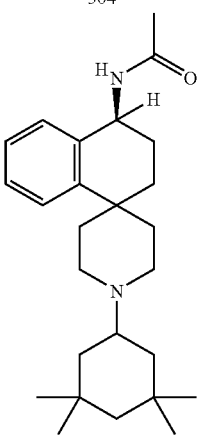
505
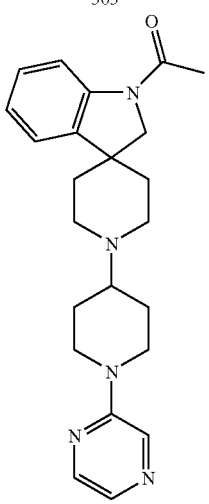
506
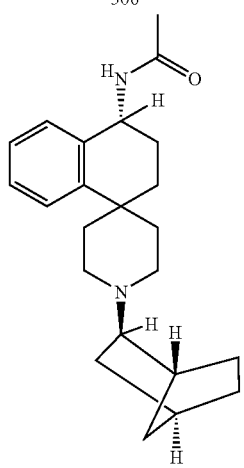
507
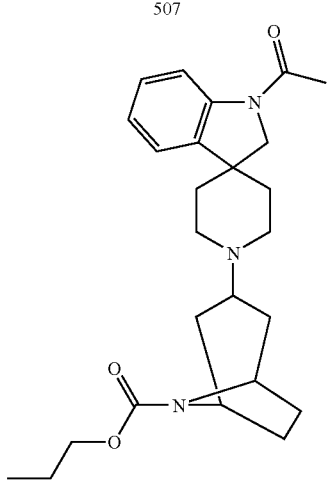
508
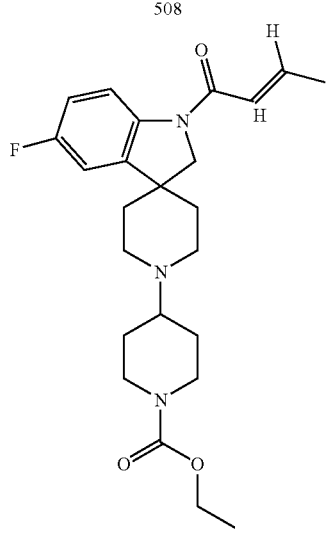

TABLE 1-continued
Exemplary compounds of formula I.
509
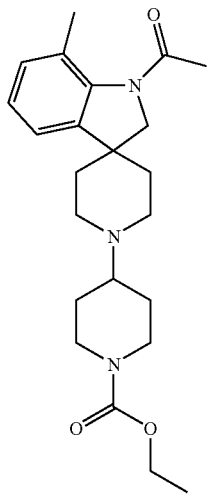 [SMILES: CCOC(=O)N1CCC(N2CCC3(CC2)CN(C(C)=O)c2c(C)cccc23)CC1]
510
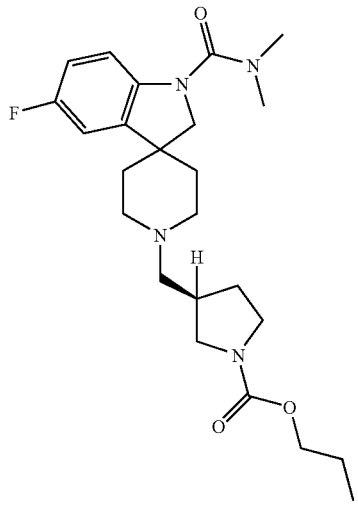 [SMILES: CCCOC(=O)N1CC[C@H](CN2CCC3(CC2)CN(C(=O)N(C)C)c2ccc(F)cc23)C1]
511
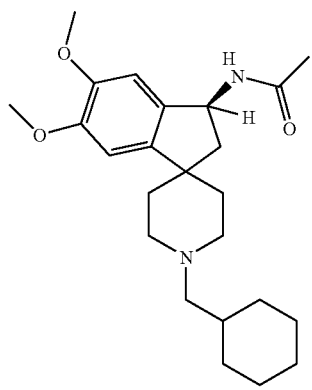
512
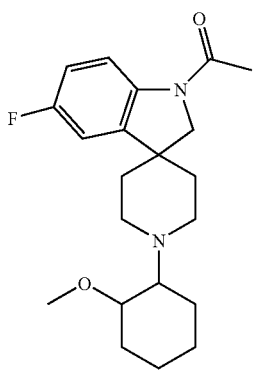 [SMILES: COC1CCCCC1N1CCC2(CC1)CN(C(C)=O)c1ccc(F)cc12]
513
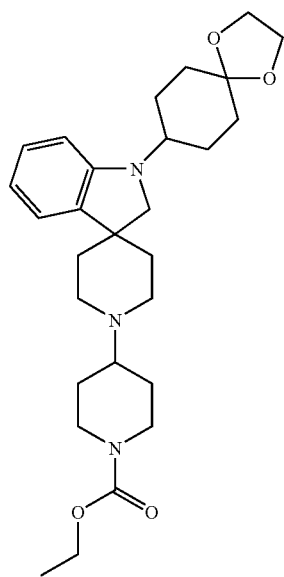 [SMILES: CCOC(=O)N1CCC(N2CCC3(CC2)CN(C2CCC4(CC2)OCCO4)c2ccccc23)CC1]
514
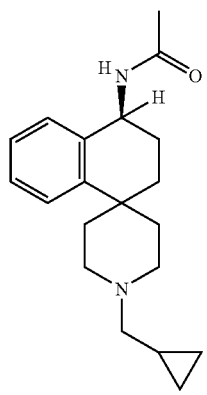

TABLE 1-continued
Exemplary compounds of formula I.
515
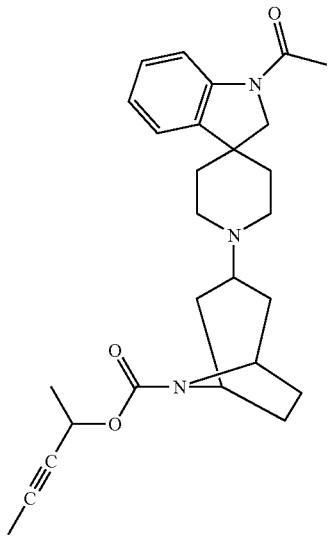 [SMILES: CC#CC(C)OC(=O)N1C2CCC1CC(N1CCC3(CC1)CN(C(C)=O)c1ccccc13)C2]
516
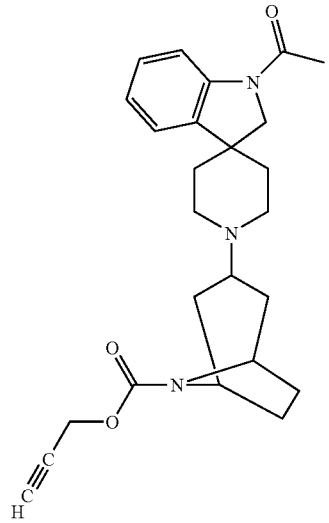
517
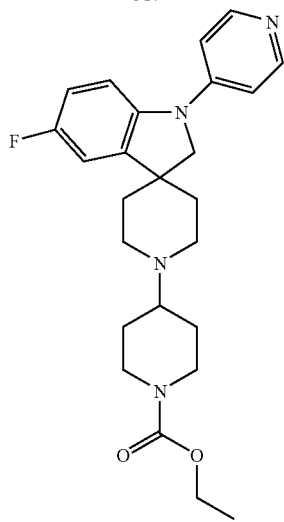 [SMILES: CCOC(=O)N1CCC(N2CCC3(CC2)CN(c2ccncc2)c2ccc(F)cc23)CC1]
518
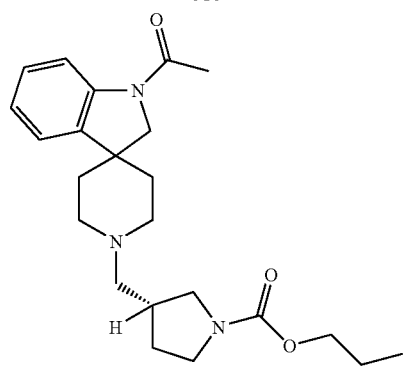 [SMILES: CCCOC(=O)N1CC[C@H](CN2CCC3(CC2)CN(C(C)=O)c2ccccc23)C1]
519
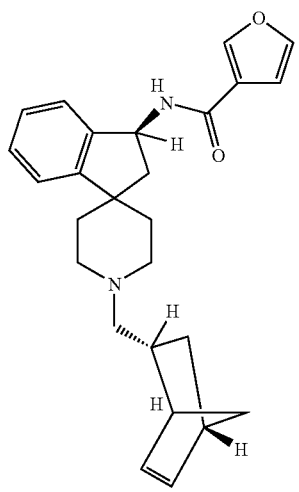
520
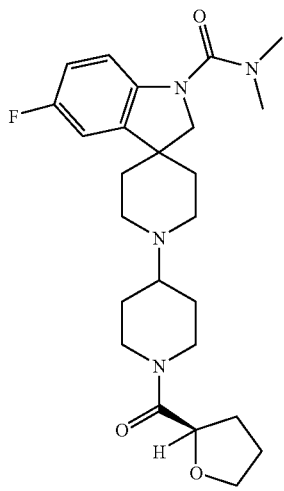 [SMILES: CN(C)C(=O)N1CC2(CCN(C3CCN(C(=O)[C@H]4CCCO4)CC3)CC2)c2cc(F)ccc21]

TABLE 1-continued
Exemplary compounds of formula I.
521
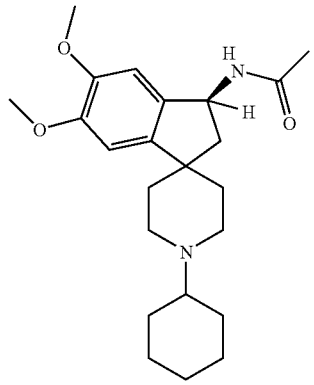
522
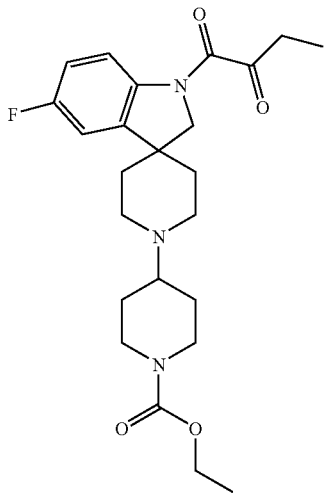 [SMILES: CCOC(=O)N1CCC(N2CCC3(CC2)CN(C(=O)C(=O)CC)c2ccc(F)cc23)CC1]
523
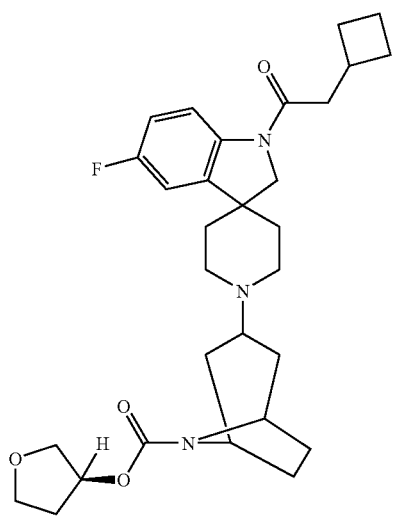
524
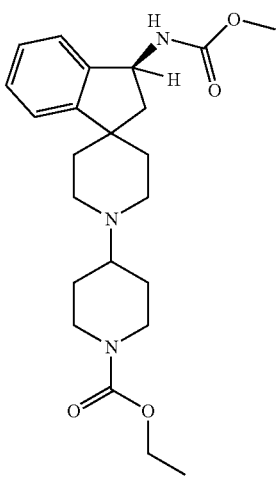

TABLE 1-continued
Exemplary compounds of formula I.
525
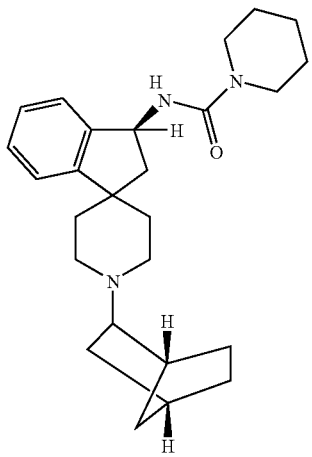
526
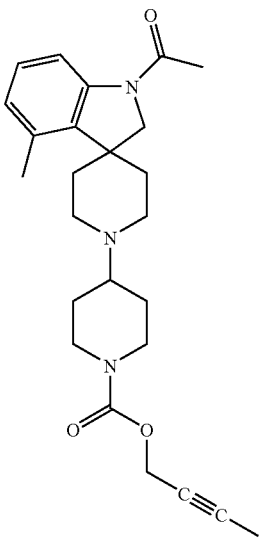 [SMILES: CC#CCOC(=O)N1CCC(N2CCC3(CC2)CN(C(C)=O)c2cccc(C)c23)CC1]
527
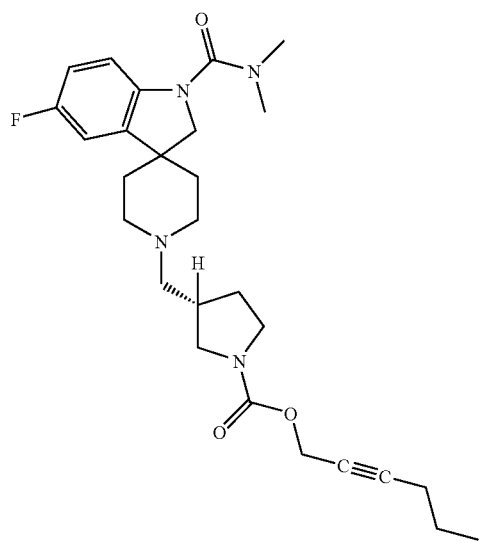 [SMILES: CCCC#CCOC(=O)N1CC[C@@H](CN2CCC3(CC2)CN(C(=O)N(C)C)c2ccc(F)cc23)C1]
528
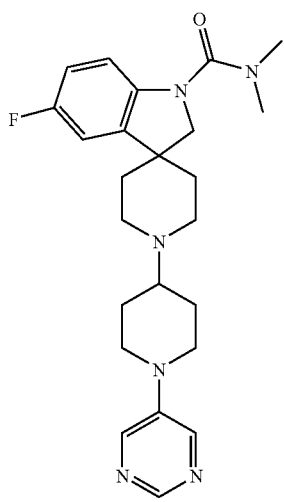 [SMILES: CN(C)C(=O)N1CC2(CCN(C3CCN(c4cncnc4)CC3)CC2)c2cc(F)ccc21]

TABLE 1-continued
Exemplary compounds of formula I.
529
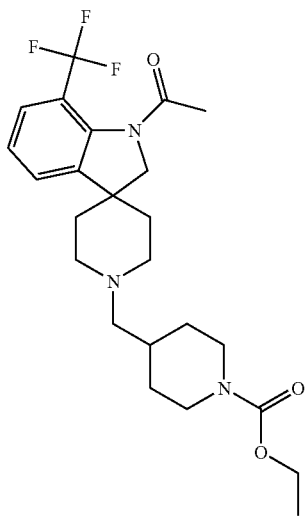 [SMILES: CCOC(=O)N1CCC(CN2CCC3(CC2)CN(C(C)=O)c2c(C(F)(F)F)cccc23)CC1]
530
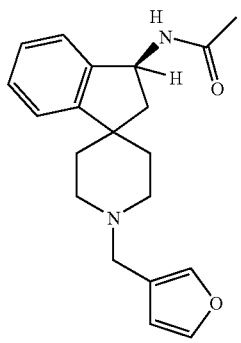
531
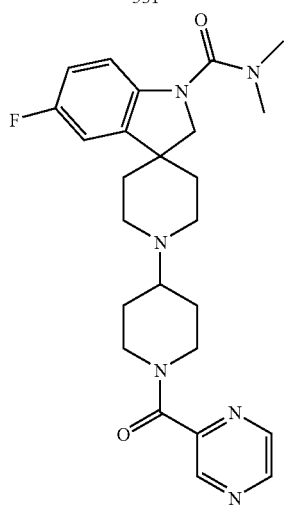
532
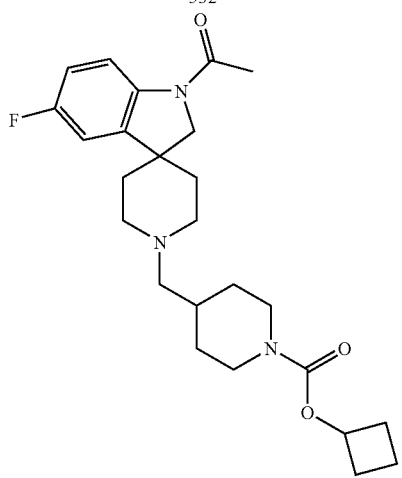
533
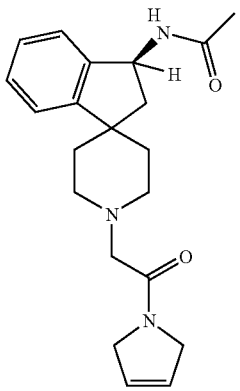
534
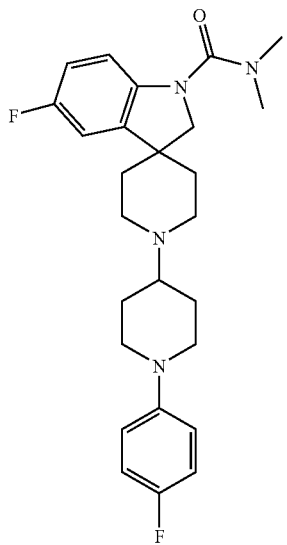 [SMILES: CN(C)C(=O)N1CC2(CCN(C3CCN(c4ccc(F)cc4)CC3)CC2)c2cc(F)ccc21]

TABLE 1-continued
Exemplary compounds of formula I.
535
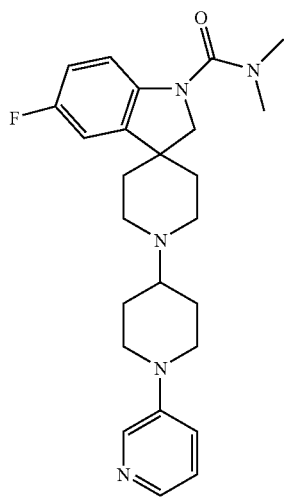 [SMILES: CN(C)C(=O)N1CC2(CCN(C3CCN(c4cccnc4)CC3)CC2)c2cc(F)ccc21]
536
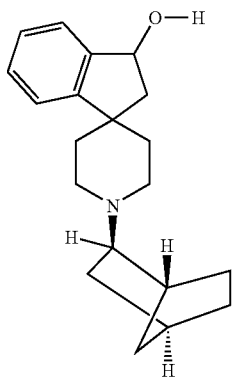 [SMILES: OC1CC2(CCN([C@@H]3C[C@H]4CC[C@@H]3C4)CC2)c2ccccc21]
537
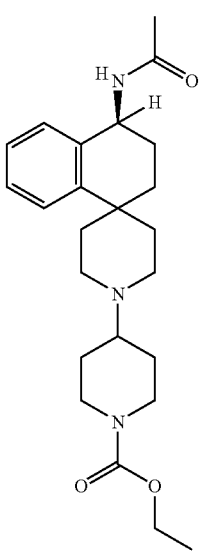
538
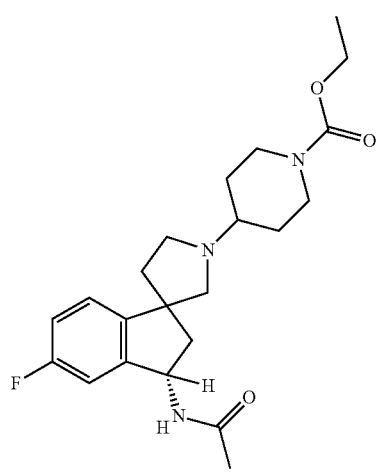

TABLE 1-continued
Exemplary compounds of formula I.
539
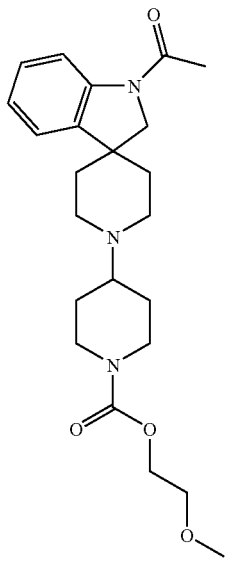 [SMILES: COCCOC(=O)N1CCC(N2CCC3(CC2)CN(C(C)=O)c2ccccc23)CC1]
540
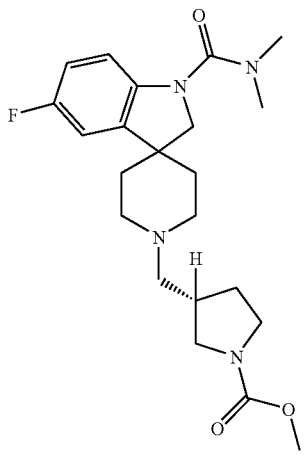 [SMILES: COC(=O)N1CC[C@@H](CN2CCC3(CC2)CN(C(=O)N(C)C)c2ccc(F)cc23)C1]
541
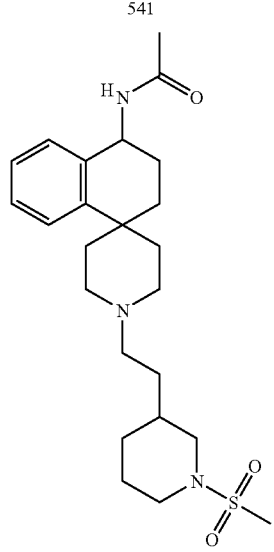
542
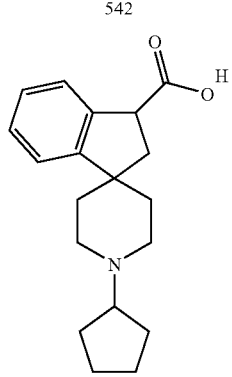

TABLE 1-continued
Exemplary compounds of formula I.
543
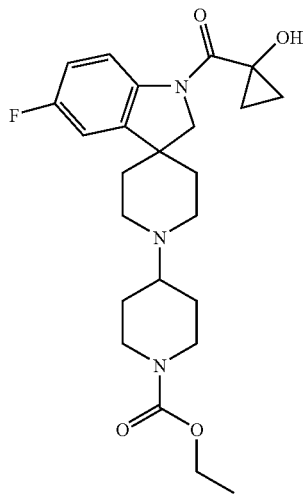 [SMILES: CCOC(=O)N1CCC(N2CCC3(CC2)CN(C(=O)C2(O)CC2)c2ccc(F)cc23)CC1]
544
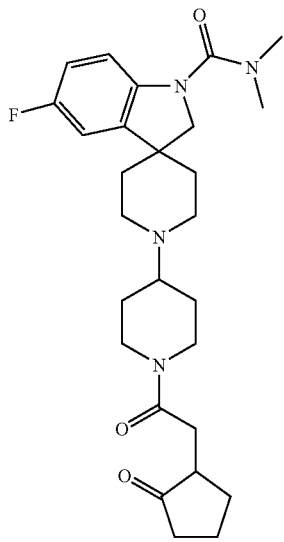 [SMILES: CN(C)C(=O)N1CC2(CCN(C3CCN(C(=O)CC4CCCC4=O)CC3)CC2)c2cc(F)ccc21]
545
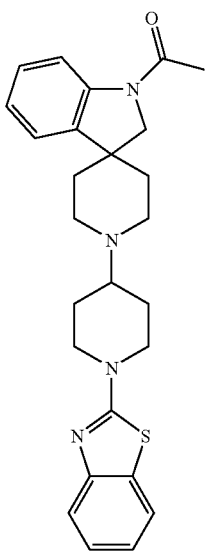 [SMILES: CC(=O)N1CC2(CCN(C3CCN(c4nc5ccccc5s4)CC3)CC2)c2ccccc21]
546
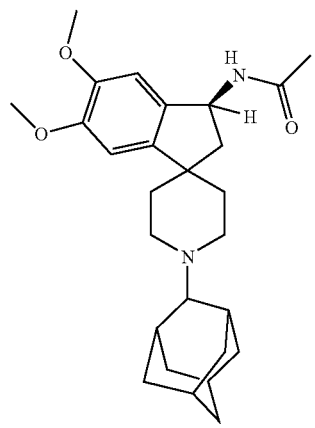
547
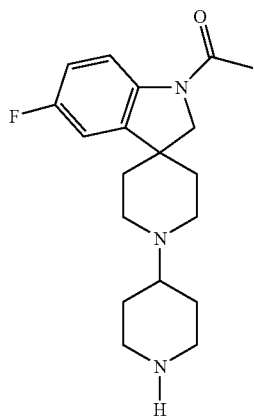 [SMILES: CC(=O)N1CC2(CCN(C3CCNCC3)CC2)c2cc(F)ccc21]
548
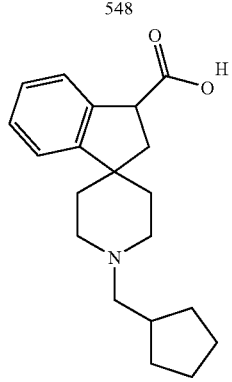

TABLE 1-continued
Exemplary compounds of formula I.
549
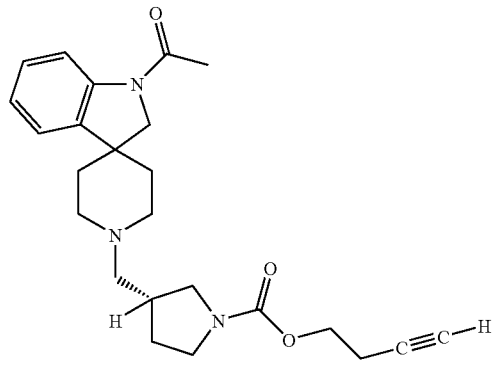 [SMILES: C#CCCOC(=O)N1CC[C@H](CN2CCC3(CC2)CN(C(C)=O)c2ccccc23)C1]
550
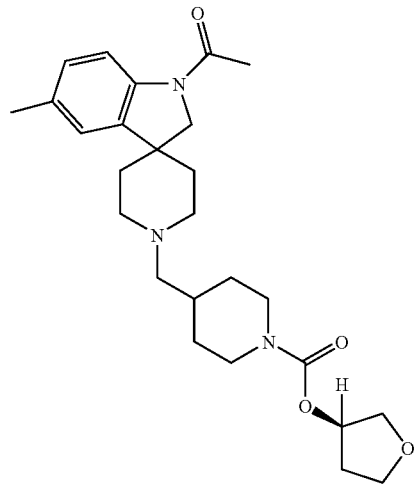 [SMILES: CC(=O)N1CC2(CCN(CC3CCN(C(=O)O[C@@H]4CCOC4)CC3)CC2)c2cc(C)ccc21]
551
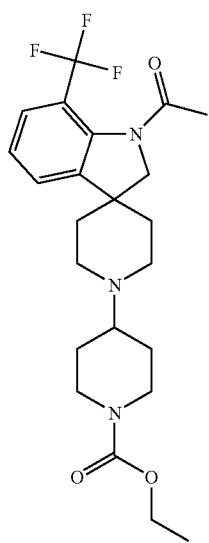 [SMILES: CCOC(=O)N1CCC(N2CCC3(CC2)CN(C(C)=O)c2c(C(F)(F)F)cccc23)CC1]
552
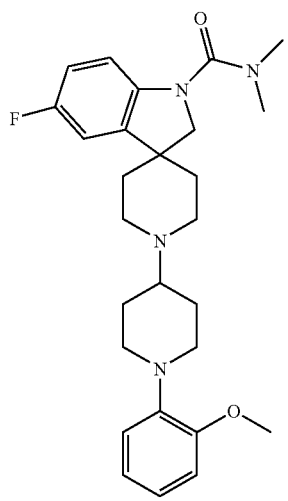

TABLE 1-continued
Exemplary compounds of formula I.
553
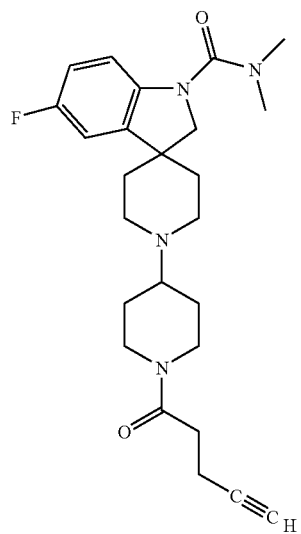
554
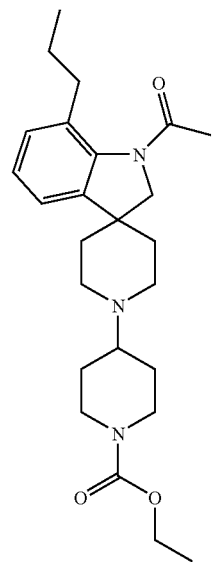 [SMILES: CCCc1cccc2c1N(C(C)=O)CC21CCN(C2CCN(C(=O)OCC)CC2)CC1]
555
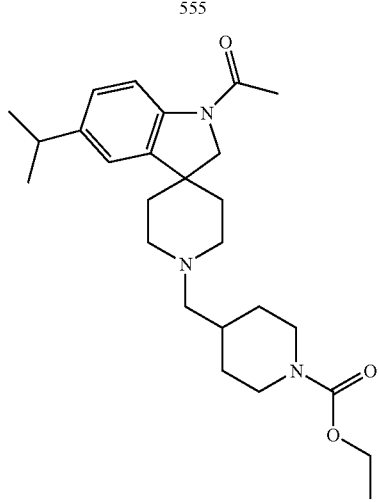
556
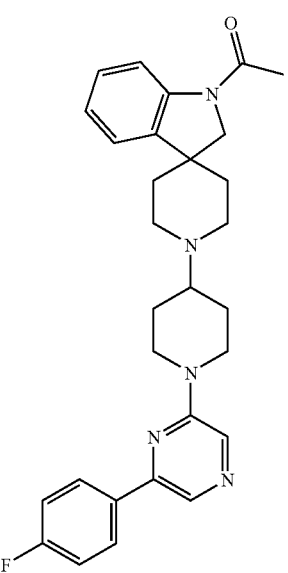 [SMILES: CC(=O)N1CC2(CCN(C3CCN(c4cncc(-c5ccc(F)cc5)n4)CC3)CC2)c2ccccc21]

US 8,367,691 B2
233                                                                                              234
TABLE 1-continued
Exemplary compounds of formula I.
557
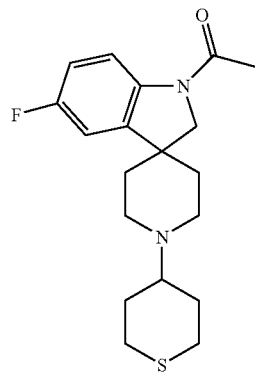 [SMILES: CC(=O)N1CC2(CCN(C3CCSCC3)CC2)c2cc(F)ccc21]
558
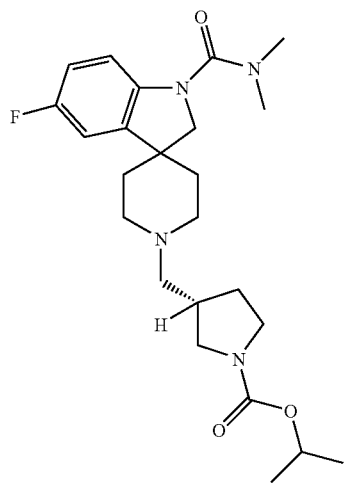 [SMILES: CC(C)OC(=O)N1CC[C@@H](CN2CCC3(CC2)CN(C(=O)N(C)C)c2ccc(F)cc23)C1]
559
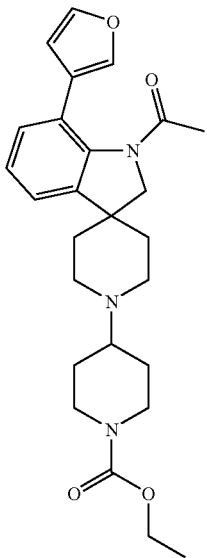 [SMILES: CCOC(=O)N1CCC(N2CCC3(CC2)CN(C(C)=O)c2c(-c4ccoc4)cccc23)CC1]
560
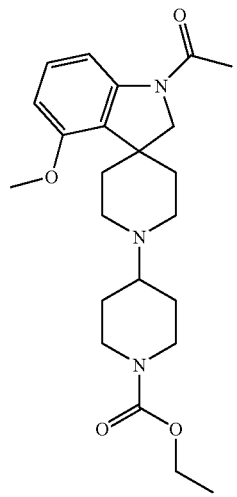 [SMILES: CCOC(=O)N1CCC(N2CCC3(CC2)CN(C(C)=O)c2cccc(OC)c23)CC1]
561
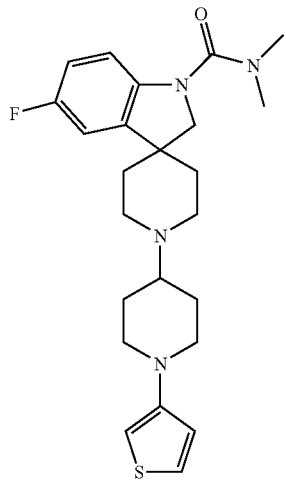 [SMILES: CN(C)C(=O)N1CC2(CCN(C3CCN(c4ccsc4)CC3)CC2)c2cc(F)ccc21]
562
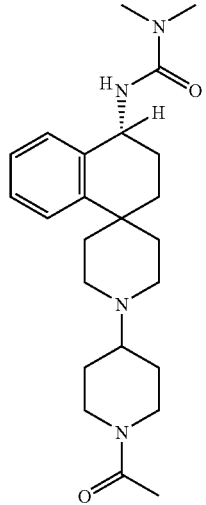

TABLE 1-continued
Exemplary compounds of formula I.
563
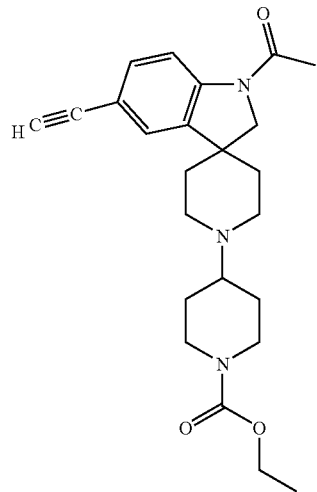
564
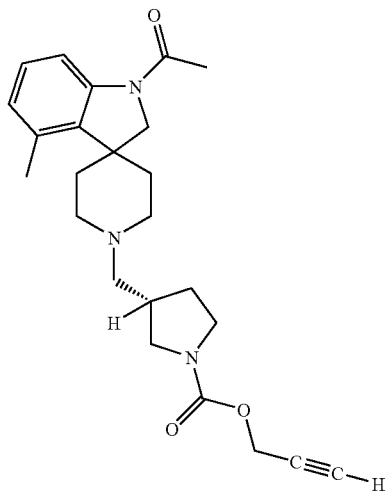 [SMILES: C#CCOC(=O)N1CC[C@@H](CN2CCC3(CC2)CN(C(C)=O)c2cccc(C)c23)C1]
565
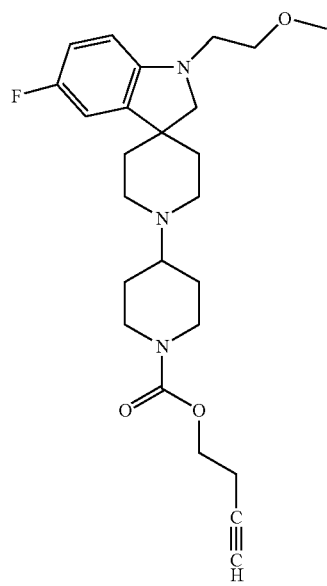 [SMILES: C#CCCOC(=O)N1CCC(N2CCC3(CC2)CN(CCOC)c2ccc(F)cc23)CC1]
566
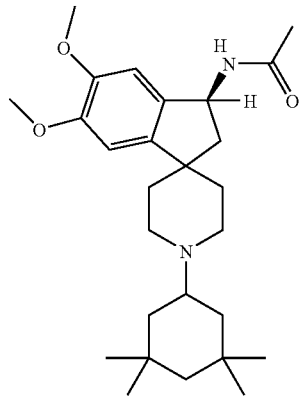

TABLE 1-continued
Exemplary compounds of formula I.
567
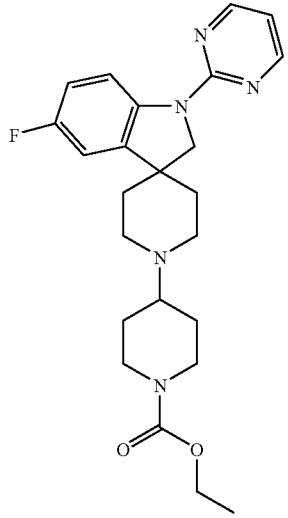 [SMILES: CCOC(=O)N1CCC(N2CCC3(CC2)CN(c2ncccn2)c2ccc(F)cc23)CC1]
568
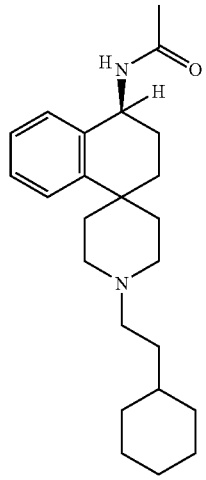
569
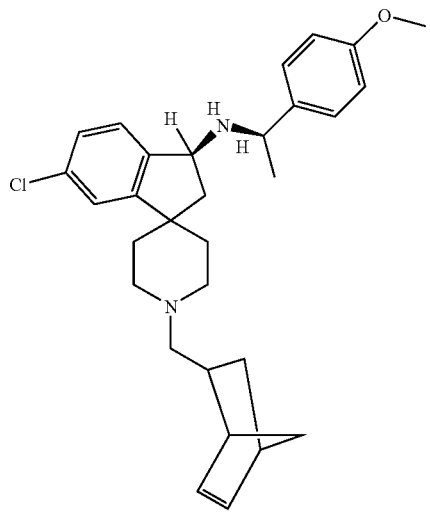
570
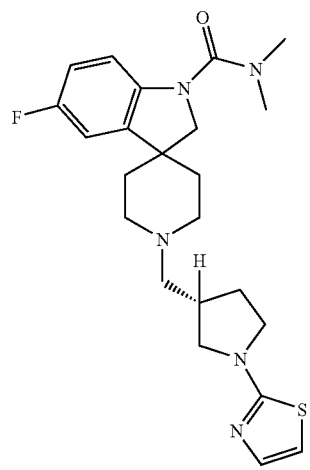 [SMILES: CN(C)C(=O)N1CC2(CCN(C[C@@H]3CCN(c4nccs4)C3)CC2)c2cc(F)ccc21]
571
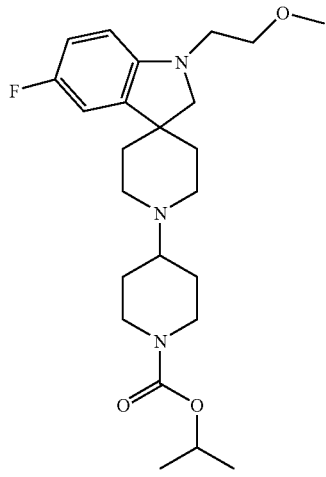 [SMILES: COCCN1CC2(CCN(C3CCN(C(=O)OC(C)C)CC3)CC2)c2cc(F)ccc21]
572
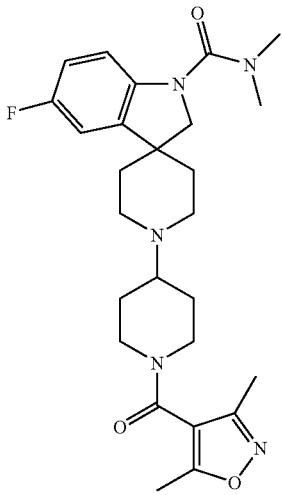 [SMILES: Cc1noc(C)c1C(=O)N1CCC(N2CCC3(CC2)CN(C(=O)N(C)C)c2ccc(F)cc23)CC1]

TABLE 1-continued
Exemplary compounds of formula I.
573
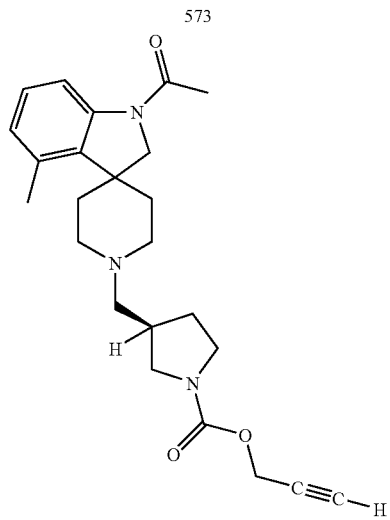
574
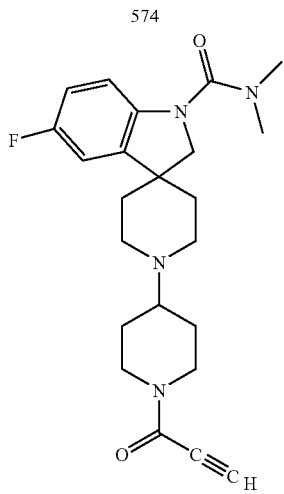
575
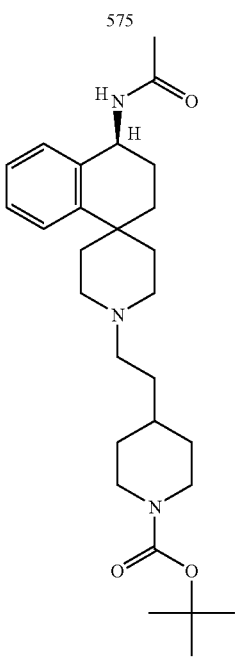
576
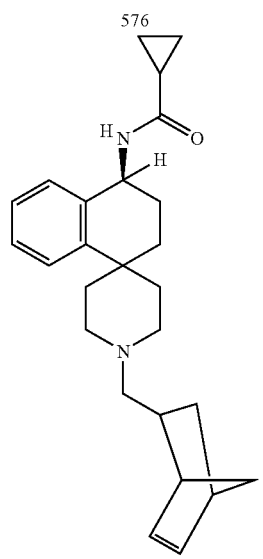
577
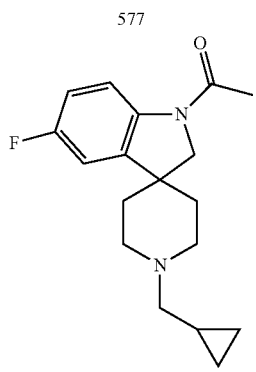
578
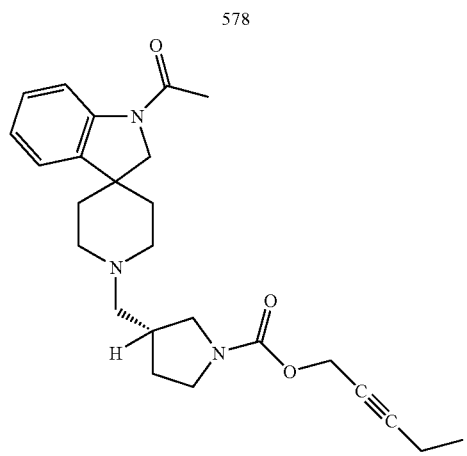

US 8,367,691 B2
TABLE 1-continued
Exemplary compounds of formula I.
579
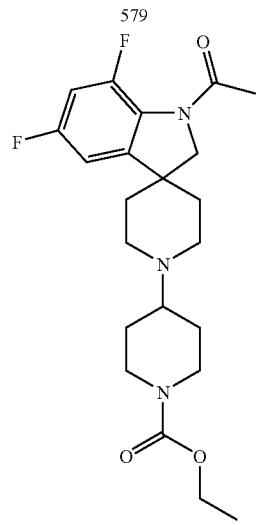
580
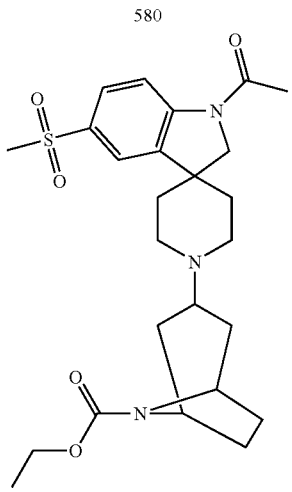
581
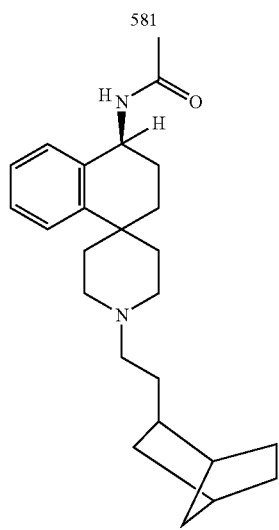
582
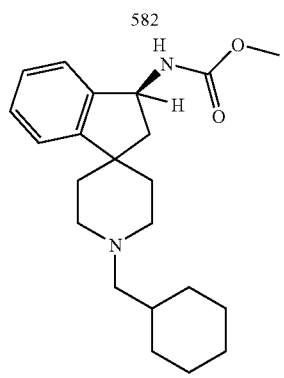
583
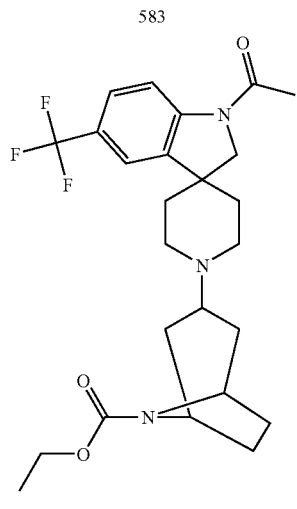
584
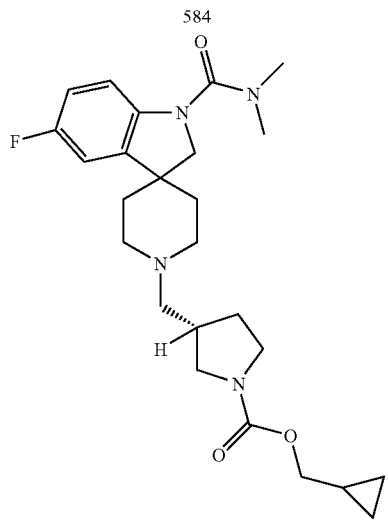

TABLE 1-continued
Exemplary compounds of formula I.
585
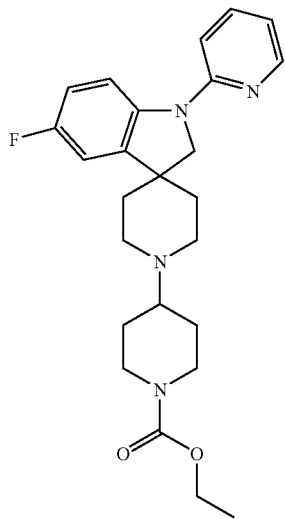 [SMILES: CCOC(=O)N1CCC(N2CCC3(CC2)CN(c2ccccn2)c2ccc(F)cc23)CC1]
586
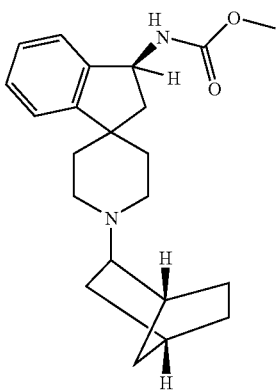
587
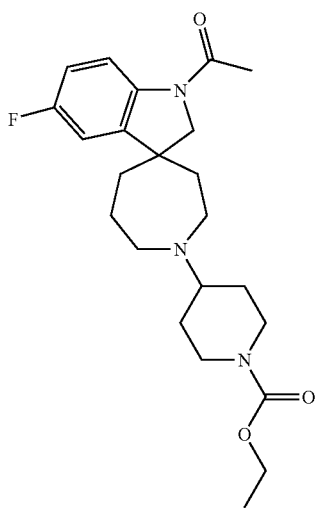 [SMILES: CCOC(=O)N1CCC(N2CCCC3(CC2)CN(C(C)=O)c2ccc(F)cc23)CC1]
588
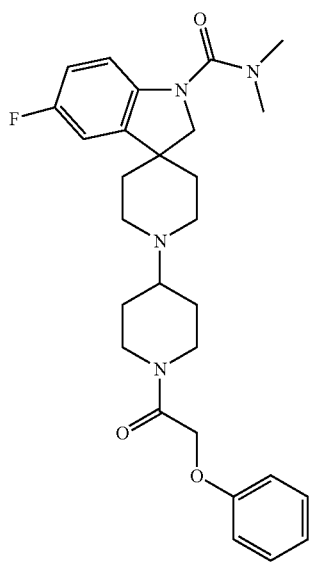 [SMILES: CN(C)C(=O)N1CC2(CCN(C3CCN(C(=O)COc4ccccc4)CC3)CC2)c2cc(F)ccc21]

TABLE 1-continued
Exemplary compounds of formula I.
589
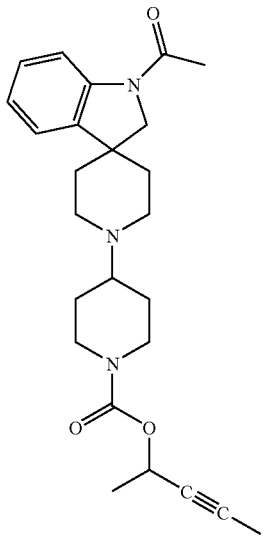 [SMILES: CC#CC(C)OC(=O)N1CCC(N2CCC3(CC2)CN(C(C)=O)c2ccccc23)CC1]
590
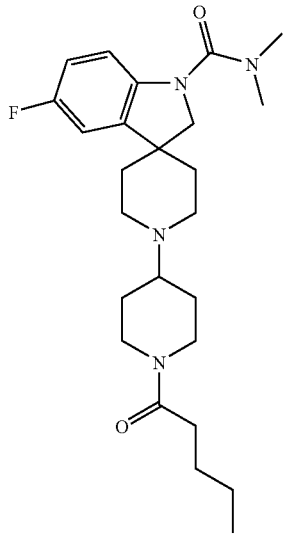 [SMILES: CCCCC(=O)N1CCC(N2CCC3(CC2)CN(C(=O)N(C)C)c2ccc(F)cc23)CC1]
591
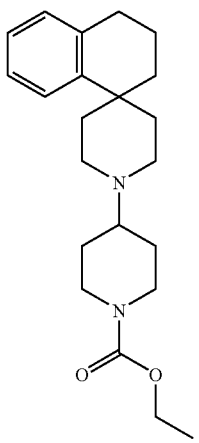 [SMILES: CCOC(=O)N1CCC(N2CCC3(CCCc4ccccc43)CC2)CC1]
592
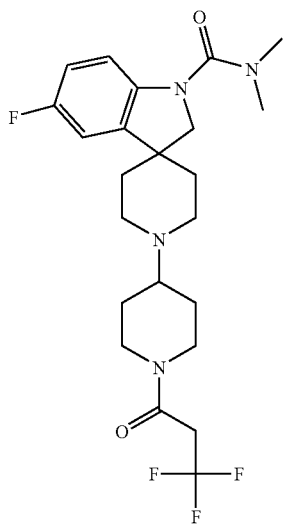 [SMILES: CN(C)C(=O)N1CC2(CCN(C3CCN(C(=O)CC(F)(F)F)CC3)CC2)c2cc(F)ccc21]

TABLE 1-continued
Exemplary compounds of formula I.
593
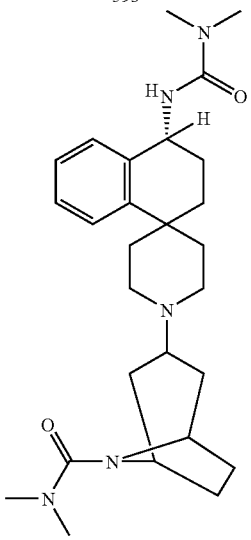
594
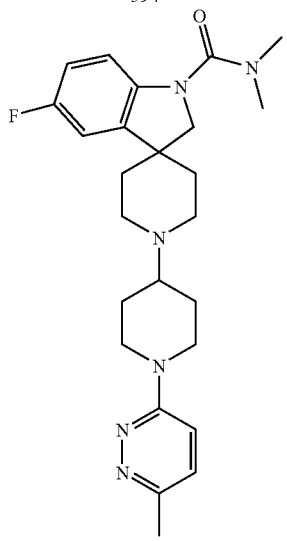
595
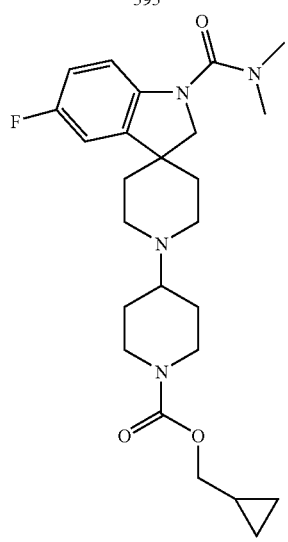
596
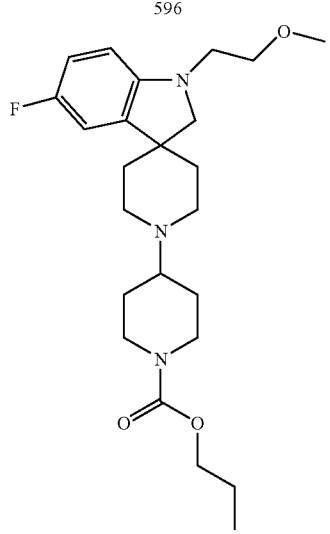
597
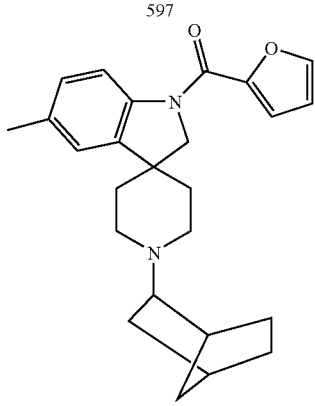
598
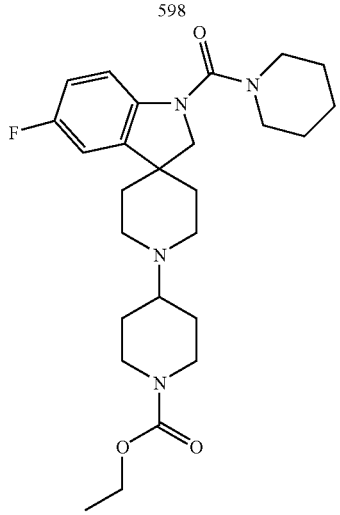

TABLE 1-continued
Exemplary compounds of formula I.
599
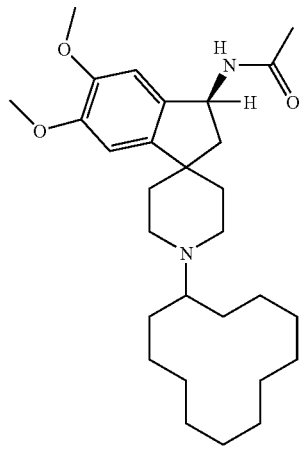
600
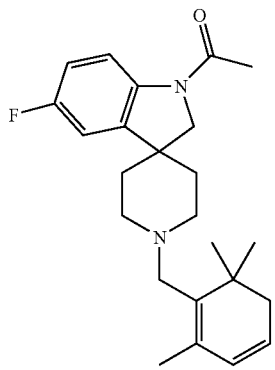 [SMILES: CC(=O)N1CC2(CCN(CC3=C(C)C=CCC3(C)C)CC2)c2cc(F)ccc21]
601
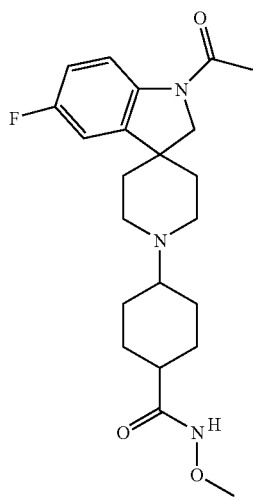
602
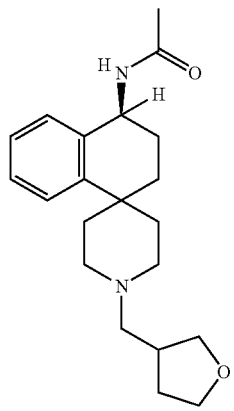
603
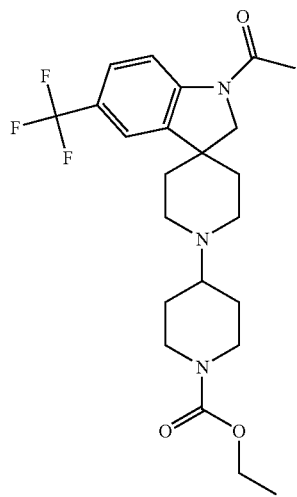 [SMILES: CCOC(=O)N1CCC(N2CCC3(CC2)CN(C(C)=O)c2ccc(C(F)(F)F)cc23)CC1]
604
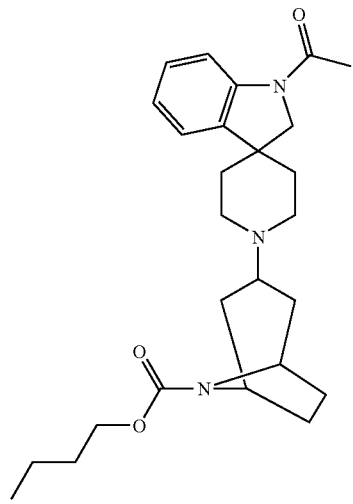 [SMILES: CCCCOC(=O)N1C2CCC1CC(N1CCC3(CC1)CN(C(C)=O)c1ccccc13)C2]

TABLE 1-continued
Exemplary compounds of formula I.
605
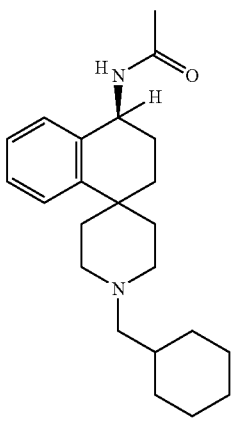
606
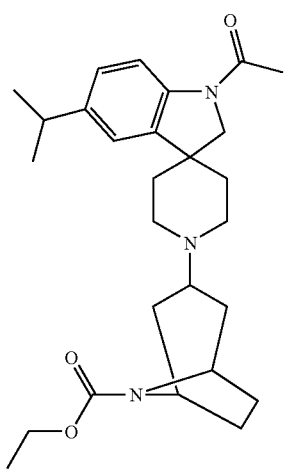 [SMILES: CCOC(=O)N1C2CCC1CC(N1CCC3(CC1)CN(C(C)=O)c1ccc(C(C)C)cc13)C2]
607
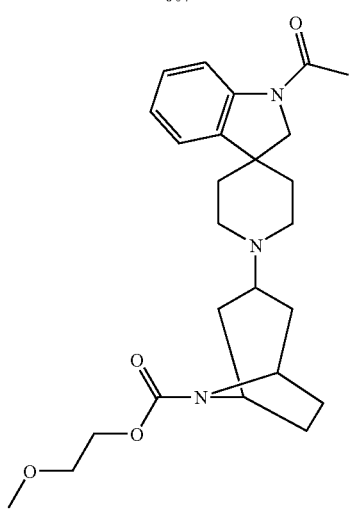
608
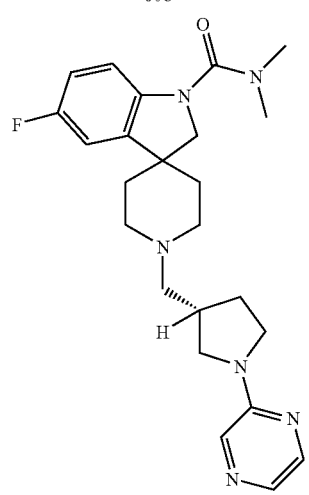
609
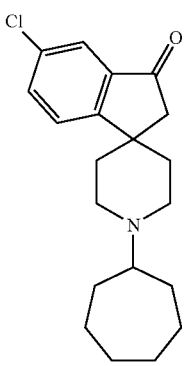 [SMILES: O=C1CC2(CCN(C3CCCCCC3)CC2)c2ccc(Cl)cc21]
610
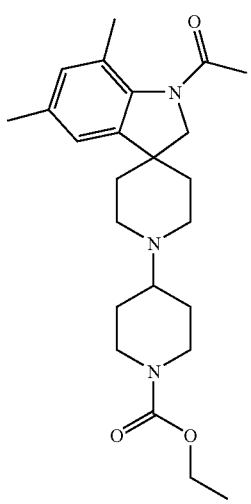 [SMILES: CCOC(=O)N1CCC(N2CCC3(CC2)CN(C(C)=O)c2c(C)cc(C)cc23)CC1]

TABLE 1-continued
Exemplary compounds of formula I.
611
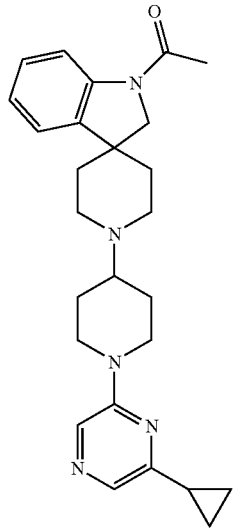 [SMILES: CC(=O)N1CC2(CCN(C3CCN(c4cncc(C5CC5)n4)CC3)CC2)c2ccccc21]
612
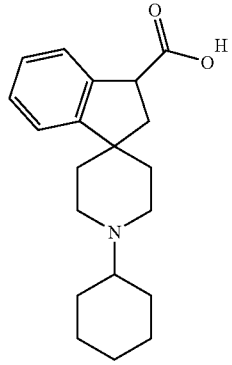
613
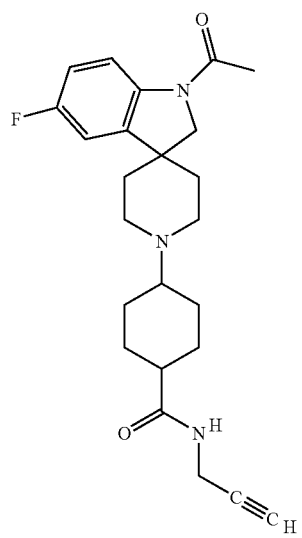
614
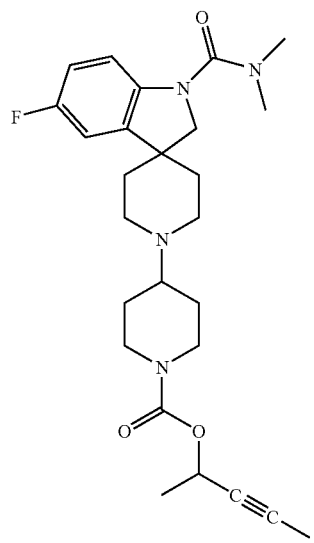 [SMILES: CC#CC(C)OC(=O)N1CCC(N2CCC3(CC2)CN(C(=O)N(C)C)c2ccc(F)cc23)CC1]

TABLE 1-continued
Exemplary compounds of formula I.
615
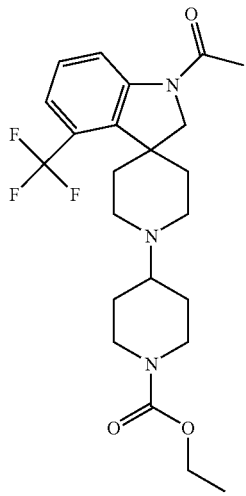 [SMILES: CCOC(=O)N1CCC(N2CCC3(CC2)CN(C(C)=O)c2cccc(C(F)(F)F)c23)CC1]
616
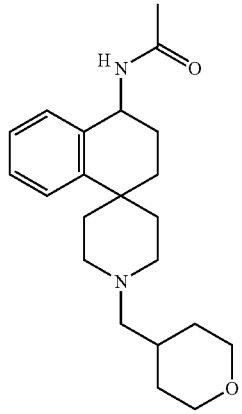
617
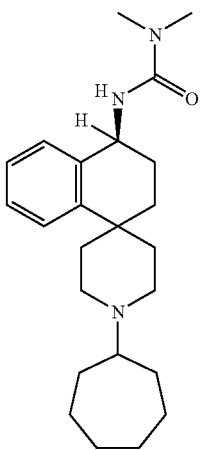
618
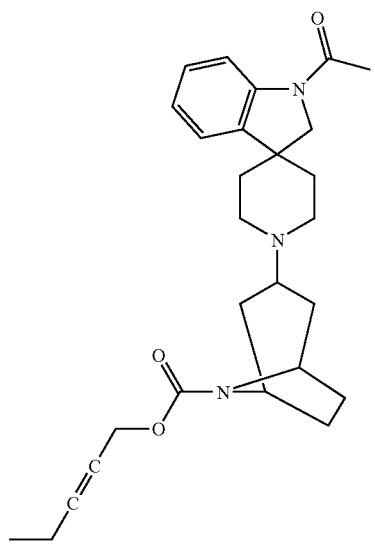 [SMILES: CCC=CCOC(=O)N1C2CCC1CC(N1CCC3(CC1)CN(C(C)=O)c1ccccc13)C2]

TABLE 1-continued
Exemplary compounds of formula I.
619
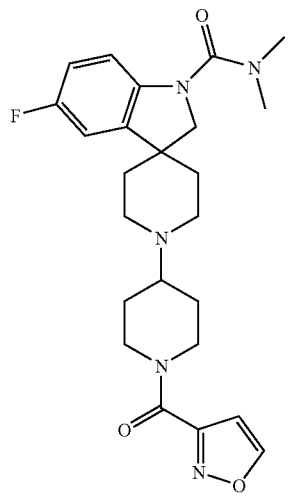 [SMILES: CN(C)C(=O)N1CC2(CCN(C3CCN(C(=O)c4ccon4)CC3)CC2)c2cc(F)ccc21]
620
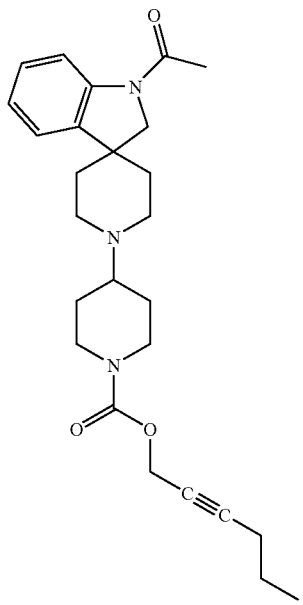 [SMILES: CCCC#CCOC(=O)N1CCC(N2CCC3(CC2)CN(C(C)=O)c2ccccc23)CC1]
621
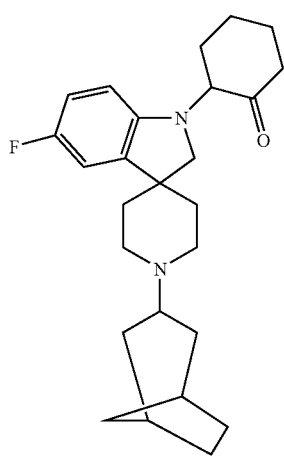 [SMILES: O=C1CCCCC1N1CC2(CCN(C3CC4CCC(C4)C3)CC2)c2cc(F)ccc21]
622
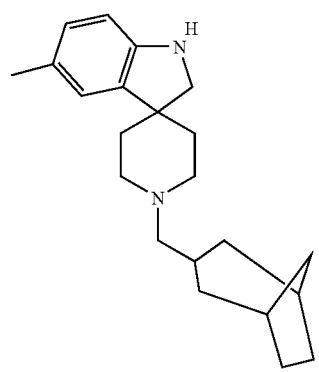

TABLE 1-continued
Exemplary compounds of formula I.
623
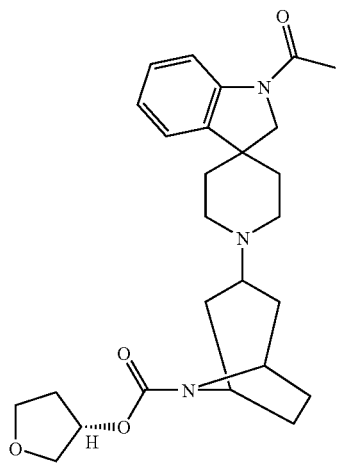
624
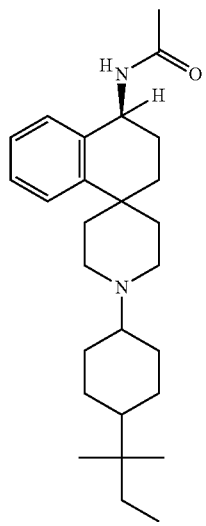
625
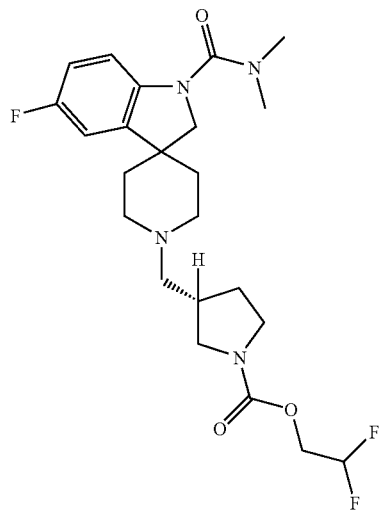 [SMILES: CN(C)C(=O)N1CC2(CCN(C[C@@H]3CCN(C(=O)OCC(F)F)C3)CC2)c2cc(F)ccc21]
626
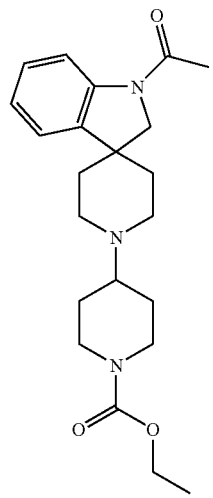 [SMILES: CCOC(=O)N1CCC(N2CCC3(CC2)CN(C(C)=O)c2ccccc23)CC1]
627
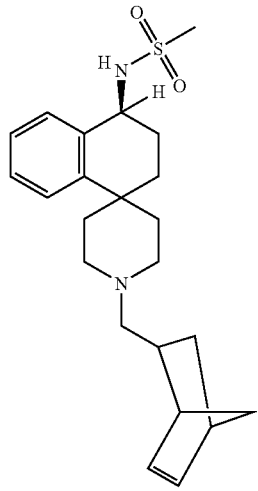
628
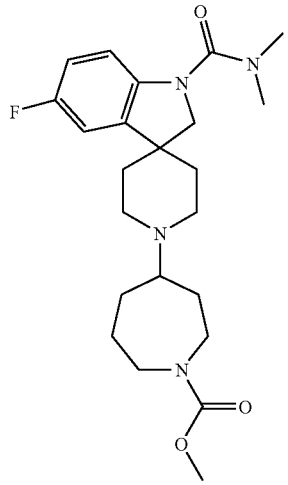 [SMILES: COC(=O)N1CCCC(N2CCC3(CC2)CN(C(=O)N(C)C)c2ccc(F)cc23)CC1]

TABLE 1-continued
Exemplary compounds of formula I.
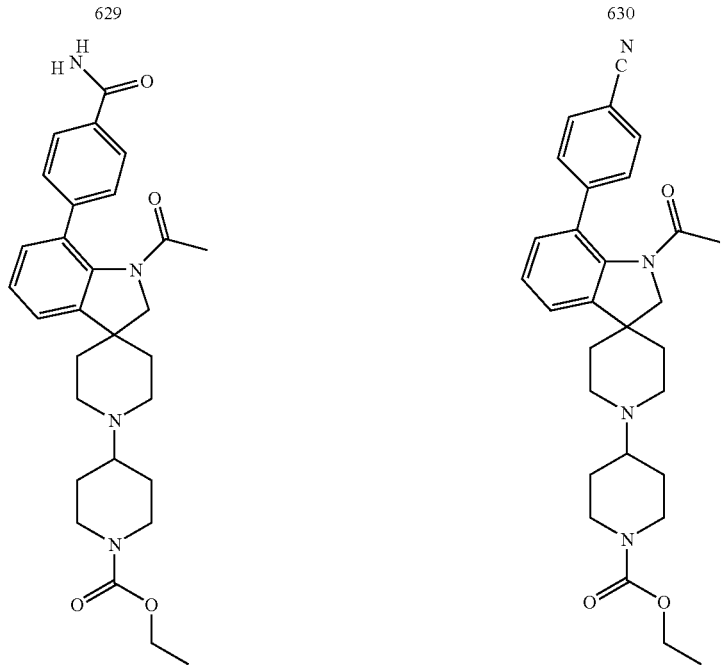
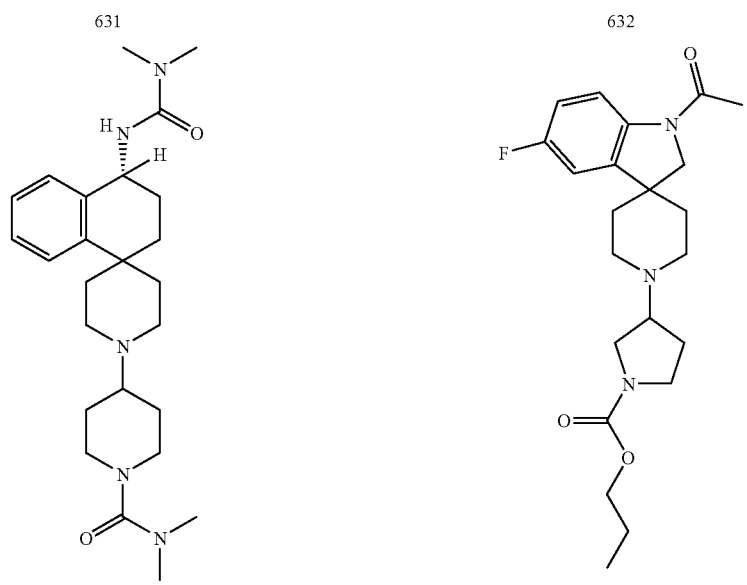

TABLE 1-continued
Exemplary compounds of formula I.
633
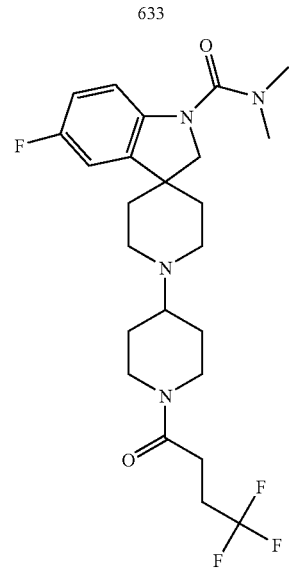
634
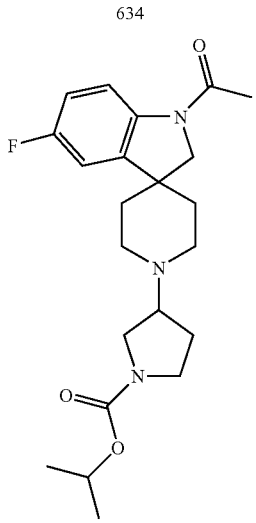
635
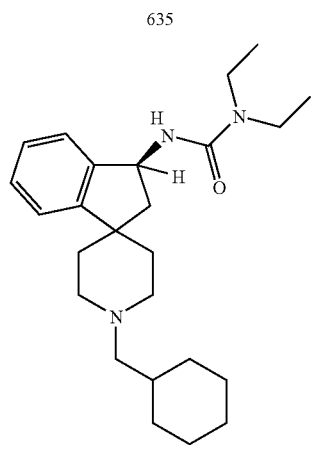
636
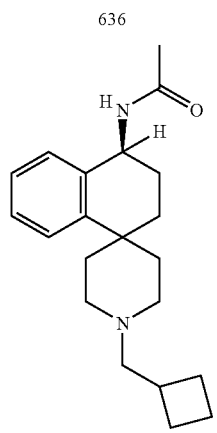
637
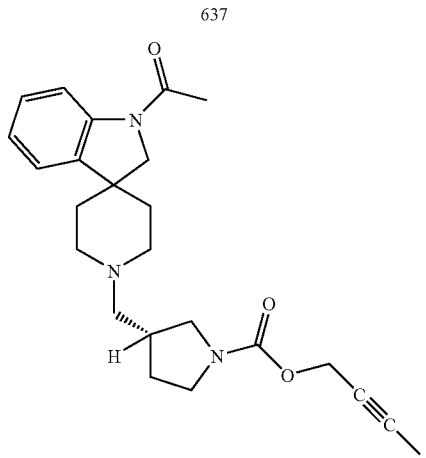
638
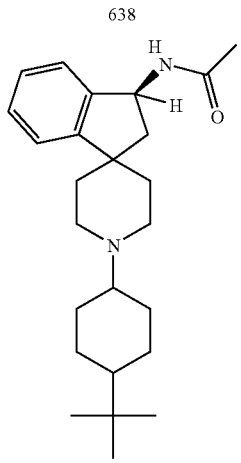

TABLE 1-continued
Exemplary compounds of formula I.
639
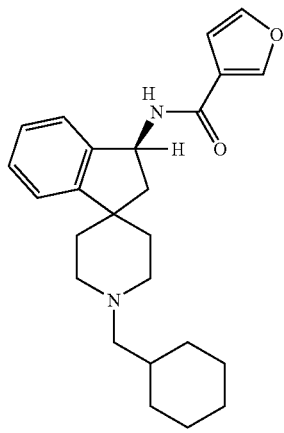
640
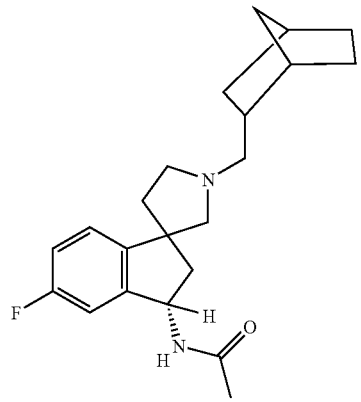
641
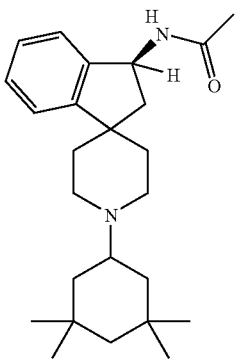
642
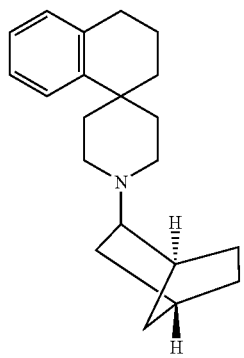 [SMILES: c1ccc2c(c1)CCCC21CCN(C2C[C@@H]3CC[C@H]2C3)CC1]
643
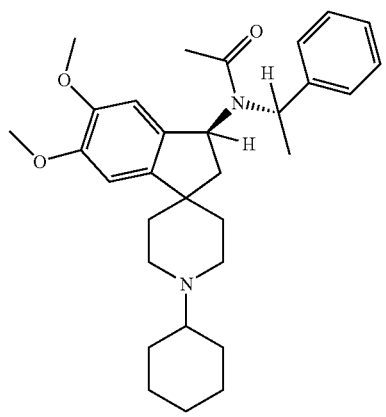 [SMILES: COc1cc2c(cc1OC)C1(CCN(C3CCCCC3)CC1)C[C@@H]2N(C(C)=O)[C@@H](C)c1ccccc1]
644
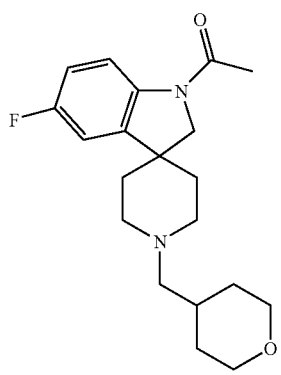 [SMILES: CC(=O)N1CC2(CCN(CC3CCOCC3)CC2)c2cc(F)ccc21]

TABLE 1-continued
Exemplary compounds of formula I.
645
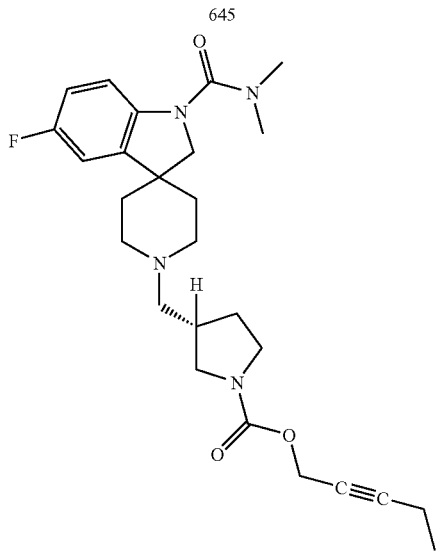
646
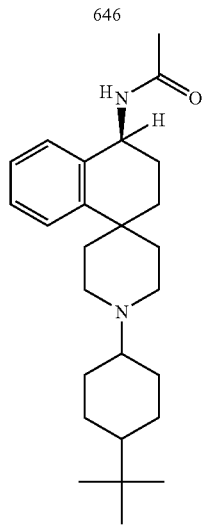
647
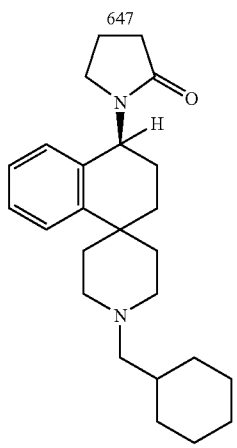
648
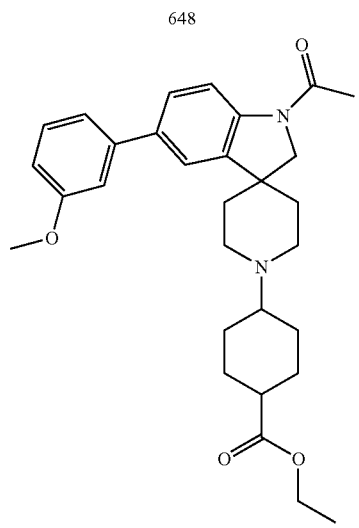
649
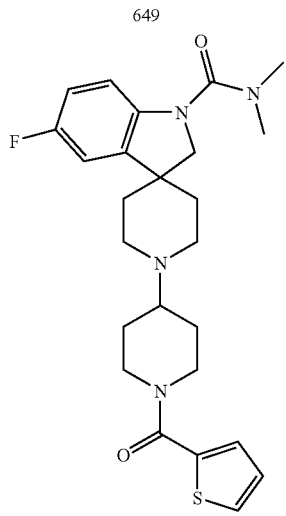
650
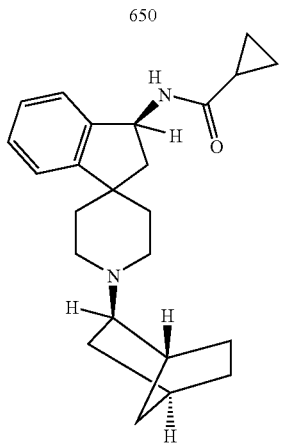

TABLE 1-continued
Exemplary compounds of formula I.
651
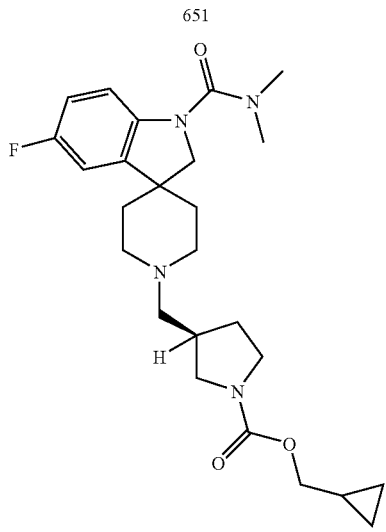
652
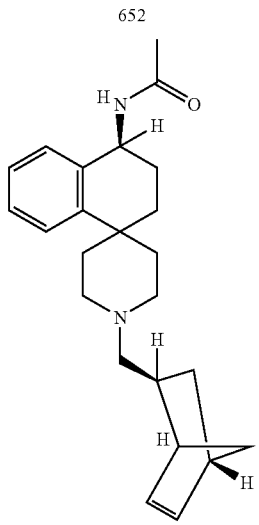
653
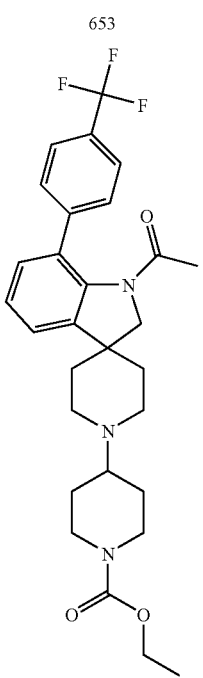
654
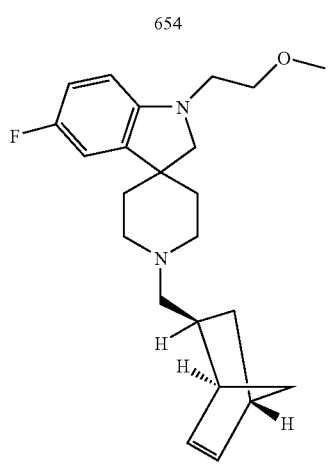

TABLE 1-continued
Exemplary compounds of formula I.
655
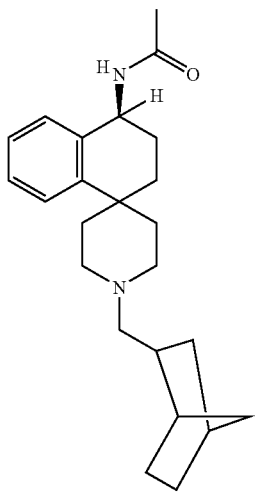
656
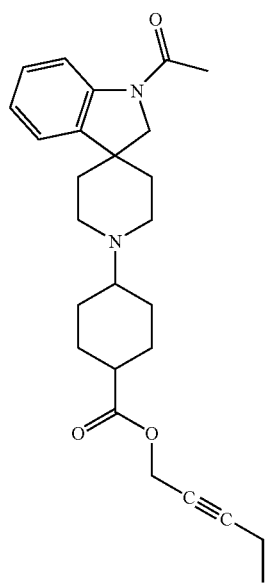 [SMILES: CCC#CCOC(=O)C1CCC(N2CCC3(CC2)CN(C(C)=O)c2ccccc23)CC1]
657
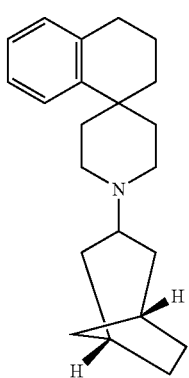 [SMILES: c1ccc2c(c1)CCCC21CCN(C2C[C@@H]3CC[C@@H](C2)C3)CC1]
658
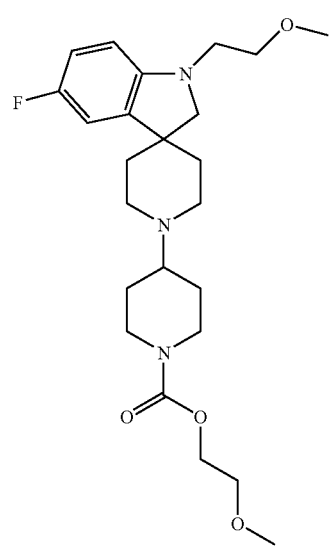 [SMILES: COCCOC(=O)N1CCC(N2CCC3(CC2)CN(CCOC)c2ccc(F)cc23)CC1]

TABLE 1-continued
Exemplary compounds of formula I.
659
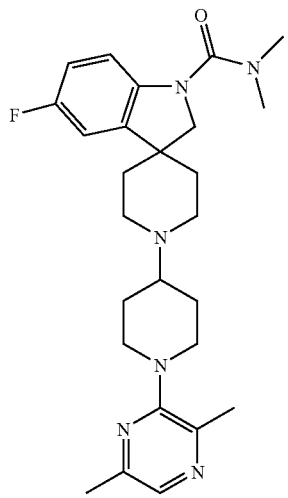 [SMILES: Cc1cnc(C)c(N2CCC(N3CCC4(CC3)CN(C(=O)N(C)C)c3ccc(F)cc34)CC2)n1]
660
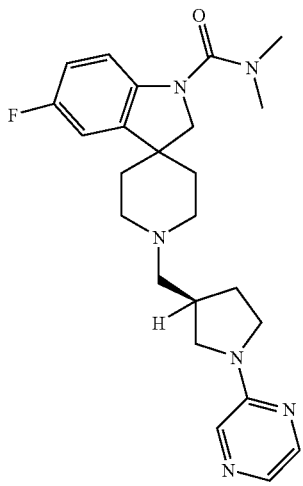 [SMILES: CN(C)C(=O)N1CC2(CCN(C[C@H]3CCN(c4cnccn4)C3)CC2)c2cc(F)ccc21]
661
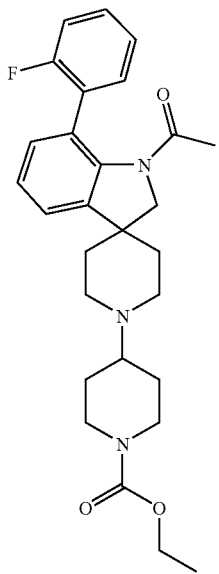 [SMILES: CCOC(=O)N1CCC(N2CCC3(CC2)CN(C(C)=O)c2c(-c4ccccc4F)cccc23)CC1]
662
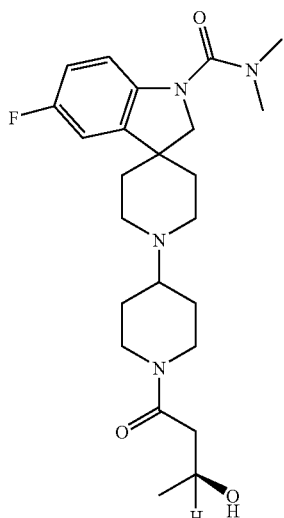

TABLE 1-continued
Exemplary compounds of formula I.
663 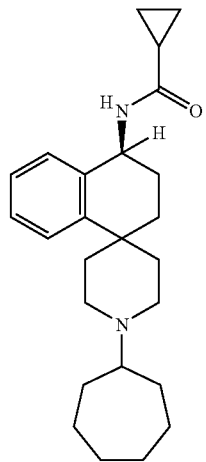
664 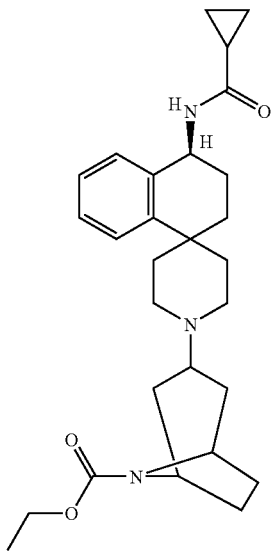
665 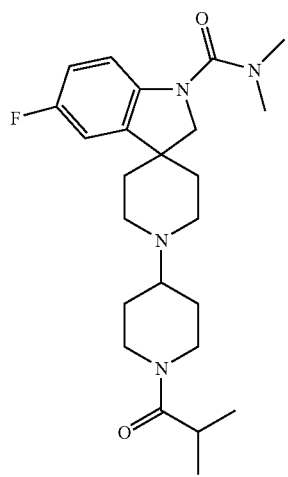 [SMILES: CC(C)C(=O)N1CCC(N2CCC3(CC2)CN(C(=O)N(C)C)c2ccc(F)cc23)CC1]
666 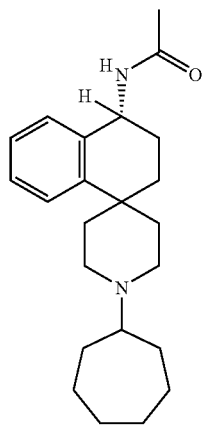
667 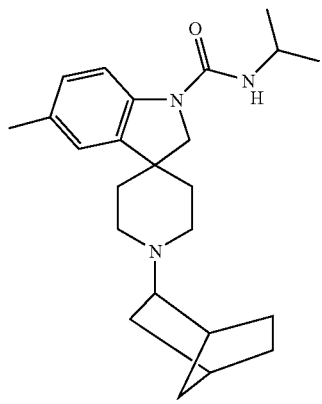
668 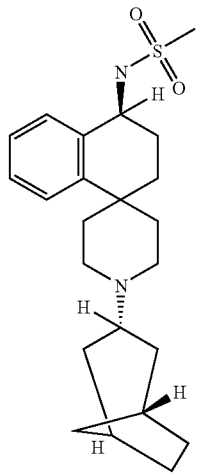

TABLE 1-continued
Exemplary compounds of formula I.
669
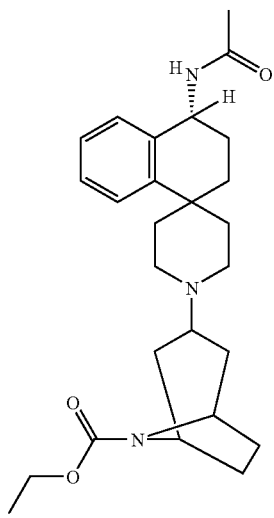
670
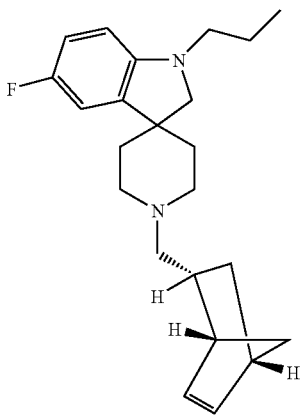 [SMILES: CCCN1CC2(CCN(C[C@@H]3C[C@H]4C=C[C@H]3C4)CC2)c2cc(F)ccc21]
671
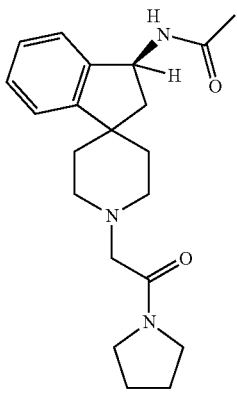
672
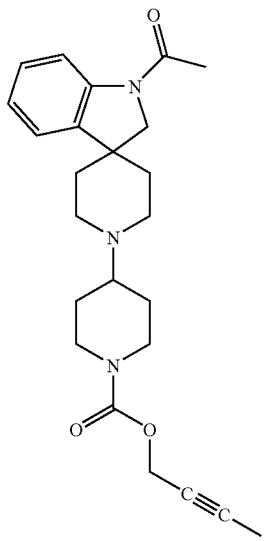 [SMILES: CC#CCOC(=O)N1CCC(N2CCC3(CC2)CN(C(C)=O)c2ccccc23)CC1]
673
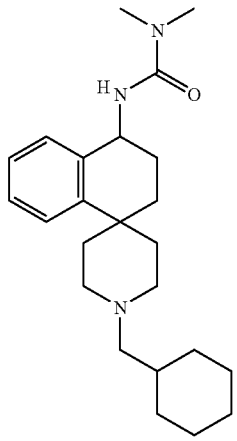
674
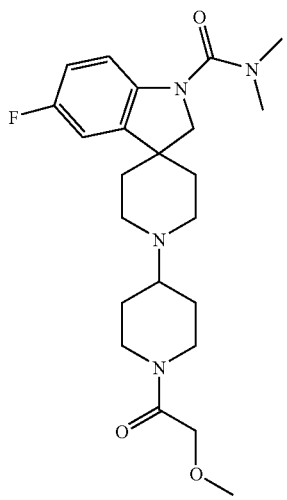 [SMILES: COCC(=O)N1CCC(N2CCC3(CC2)CN(C(=O)N(C)C)c2ccc(F)cc23)CC1]

TABLE 1-continued
Exemplary compounds of formula I.
675
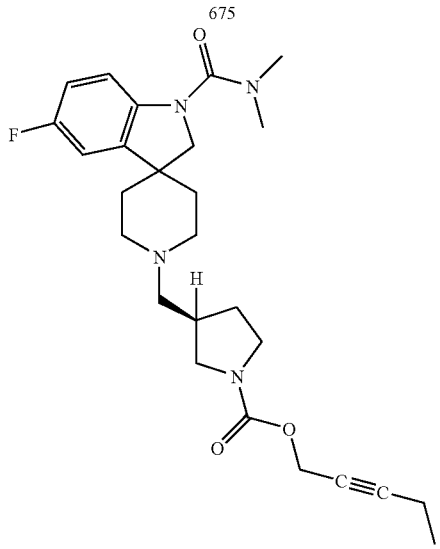
676
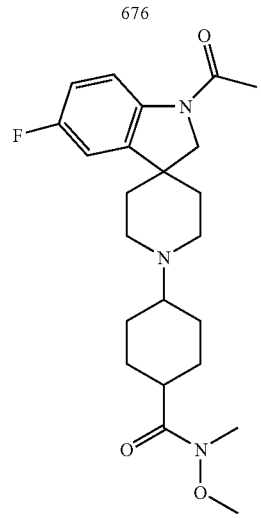
677
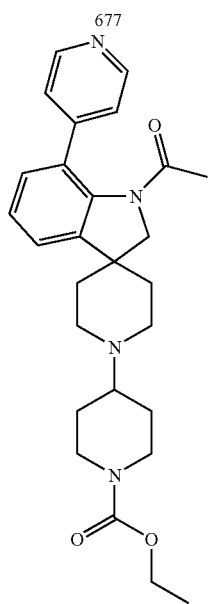
678
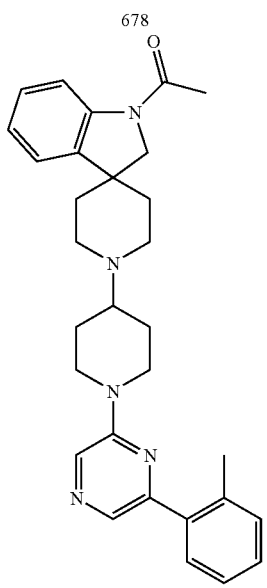
679
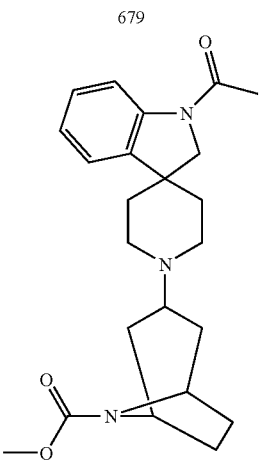
680
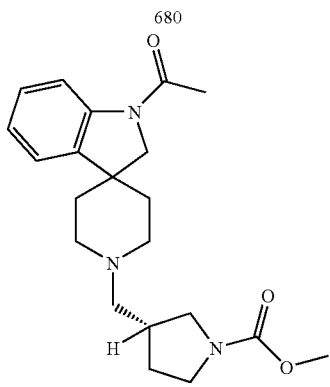

TABLE 1-continued
Exemplary compounds of formula I.
681
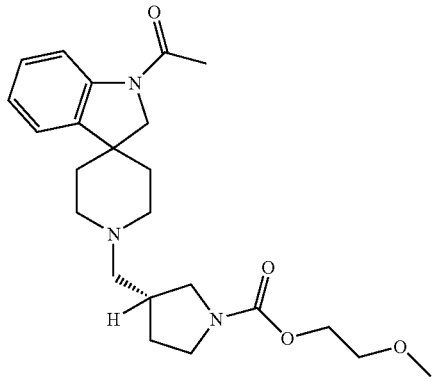 [SMILES: COCCOC(=O)N1CC[C@H](CN2CCC3(CC2)CN(C(C)=O)c2ccccc23)C1]
682
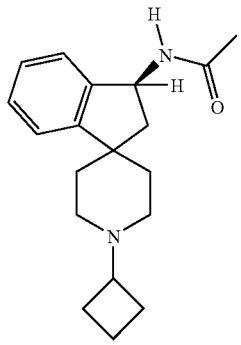 [SMILES: CC(=O)N[C@H]1CC2(CCN(C3CCC3)CC2)c2ccccc21]
683
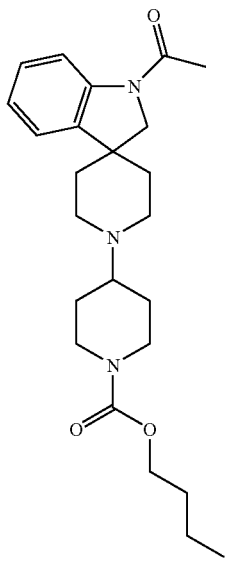
684
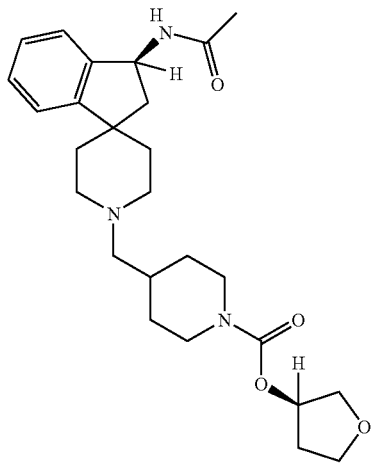
685
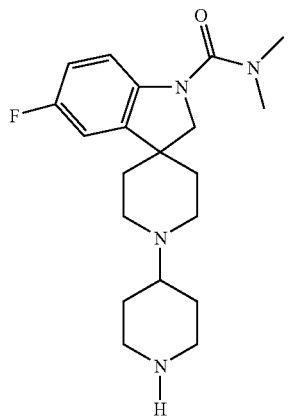 [SMILES: CN(C)C(=O)N1CC2(CCN(C3CCNCC3)CC2)c2cc(F)ccc21]
686
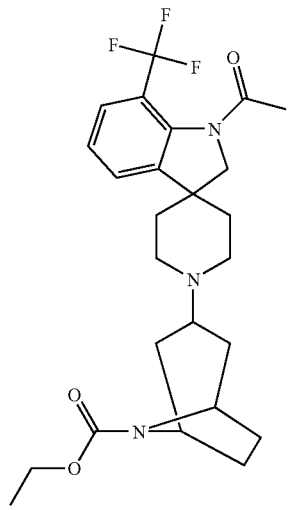 [SMILES: CCOC(=O)N1C2CCC1CC(N1CCC3(CC1)CN(C(C)=O)c1c(C(F)(F)F)cccc13)C2]

TABLE 1-continued
Exemplary compounds of formula I.
687
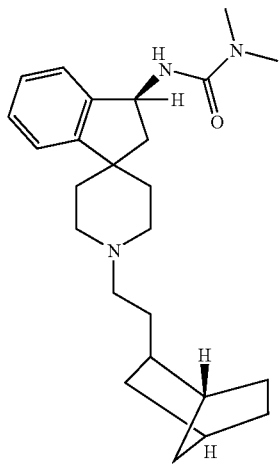
688
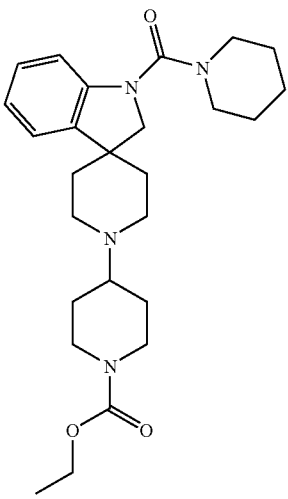 [SMILES: CCOC(=O)N1CCC(N2CCC3(CC2)CN(C(=O)N2CCCCC2)c2ccccc23)CC1]
689
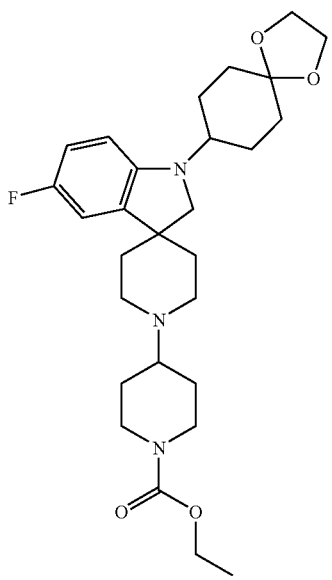 [SMILES: CCOC(=O)N1CCC(N2CCC3(CC2)CN(C2CCC4(CC2)OCCO4)c2ccc(F)cc23)CC1]
690
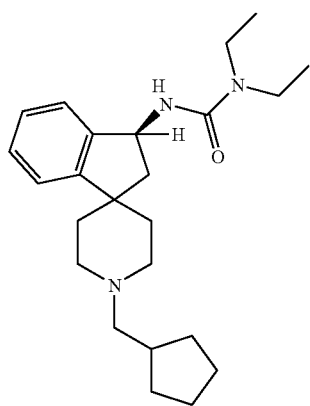
691
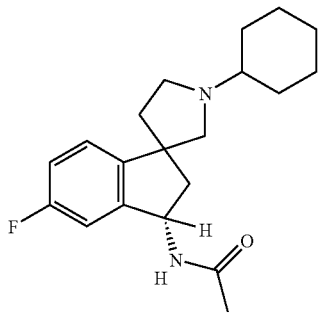
692
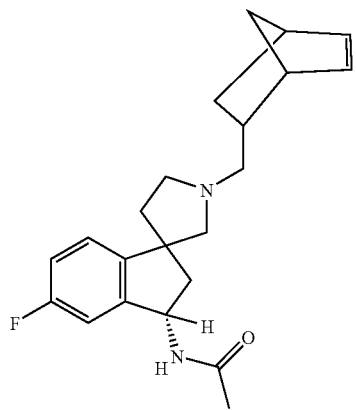

TABLE 1-continued
Exemplary compounds of formula I.
693
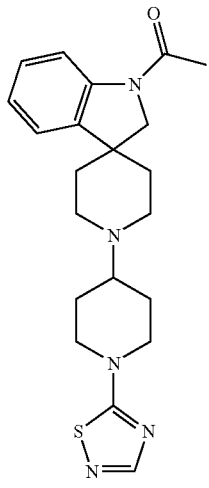
694
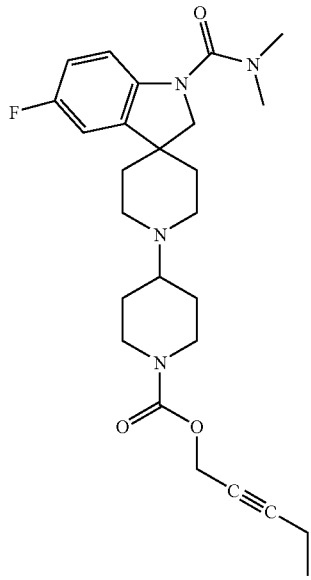 [SMILES: CCC#CCOC(=O)N1CCC(N2CCC3(CC2)CN(C(=O)N(C)C)c2ccc(F)cc23)CC1]
695
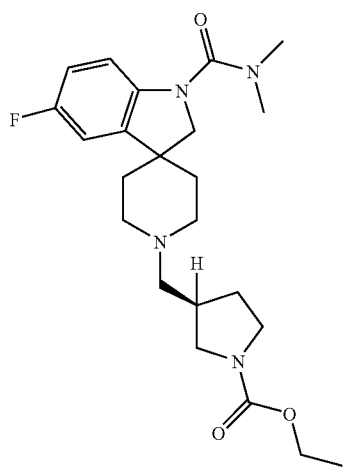 [SMILES: CCOC(=O)N1CC[C@H](CN2CCC3(CC2)CN(C(=O)N(C)C)c2ccc(F)cc23)C1]
696
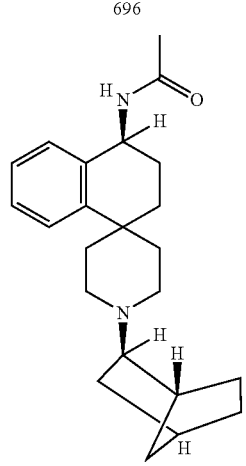

TABLE 1-continued
Exemplary compounds of formula I.
697
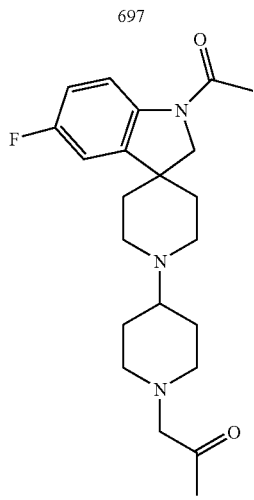
698
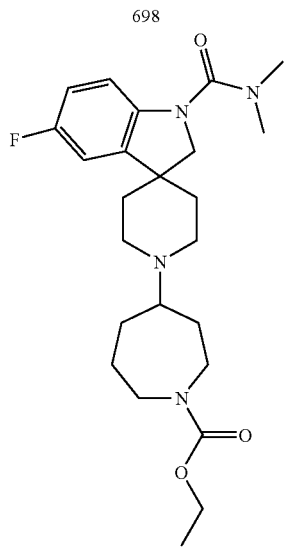
699
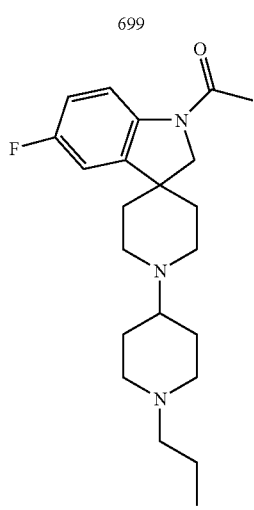
700
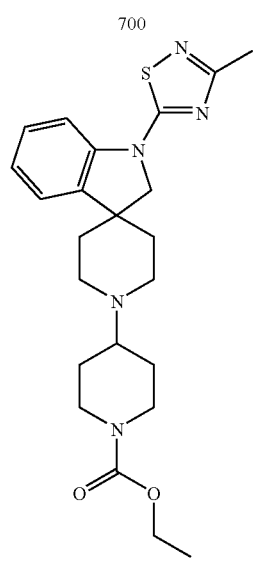
701
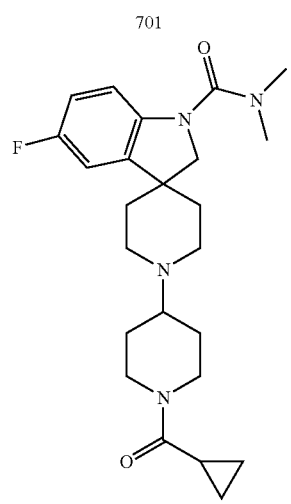
702
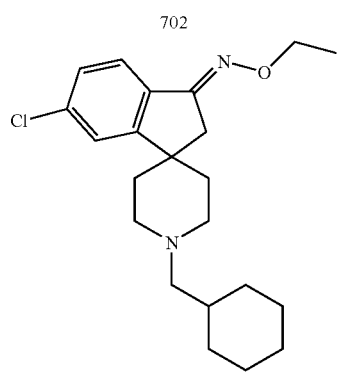

TABLE 1-continued
Exemplary compounds of formula I.
703
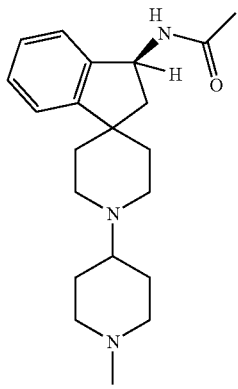
704
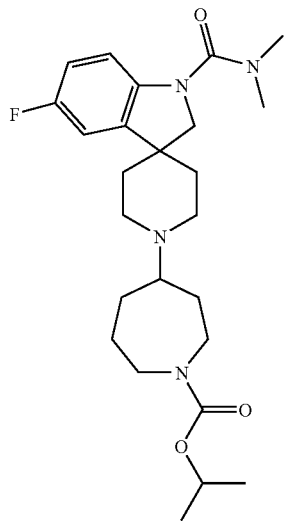 [SMILES: CC(C)OC(=O)N1CCCC(N2CCC3(CC2)CN(C(=O)N(C)C)c2ccc(F)cc23)CC1]
705
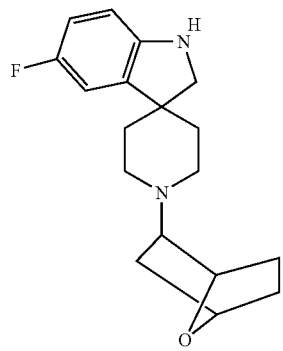
706
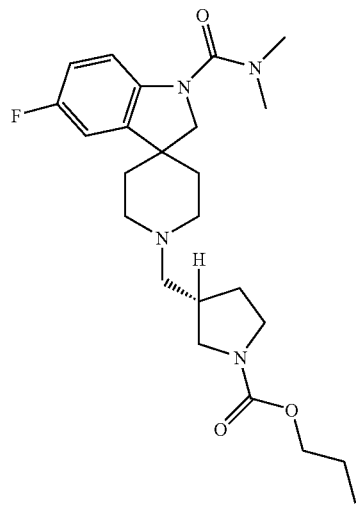 [SMILES: CCCOC(=O)N1CC[C@@H](CN2CCC3(CC2)CN(C(=O)N(C)C)c2ccc(F)cc23)C1]

TABLE 1-continued
Exemplary compounds of formula I.
707
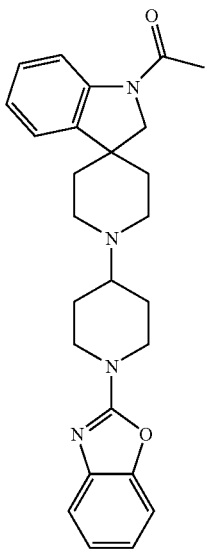 [SMILES: CC(=O)N1CC2(CCN(C3CCN(c4nc5ccccc5o4)CC3)CC2)c2ccccc21]
708
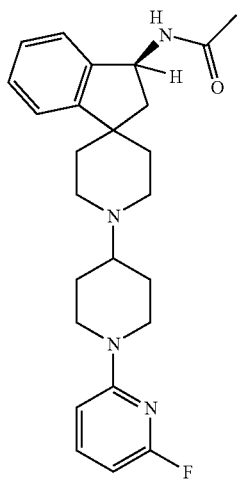
709
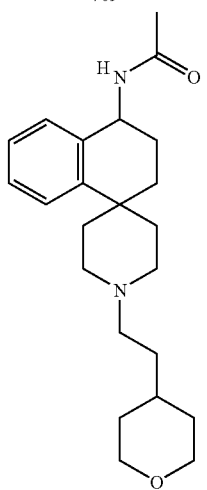
710
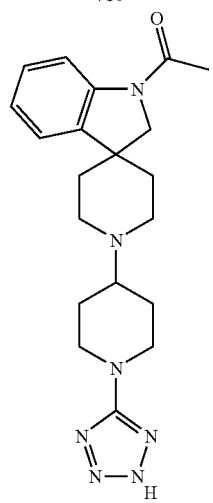
711
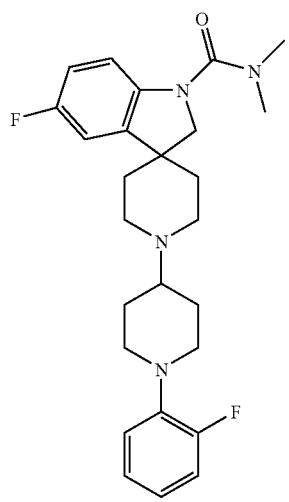 [SMILES: CN(C)C(=O)N1CC2(CCN(C3CCN(c4ccccc4F)CC3)CC2)c2cc(F)ccc21]
712
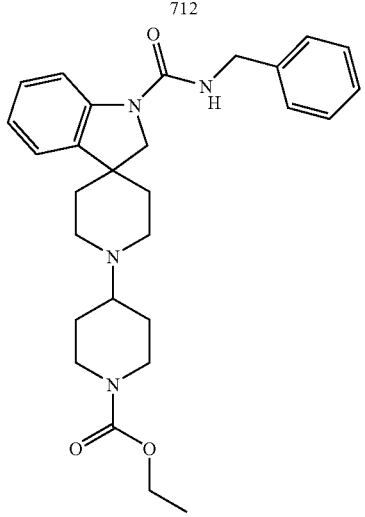

TABLE 1-continued
Exemplary compounds of formula I.
713
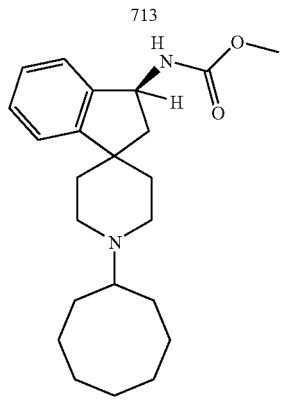
714
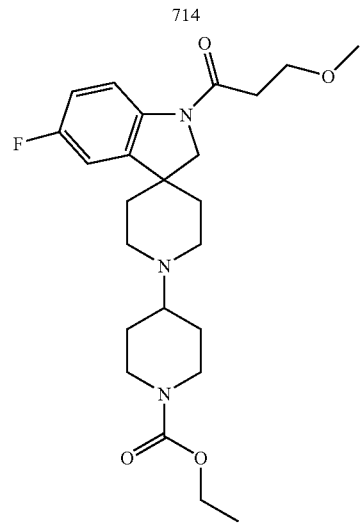
715
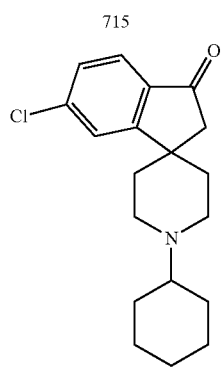
716
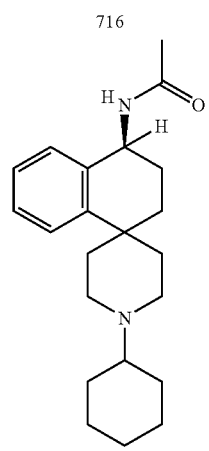
717
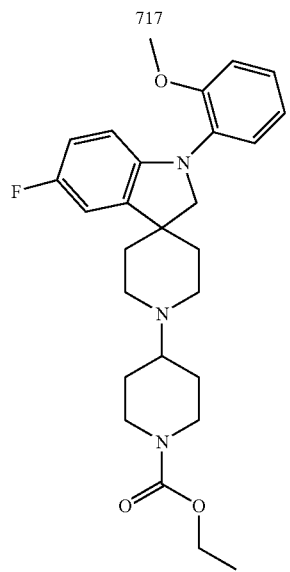
718
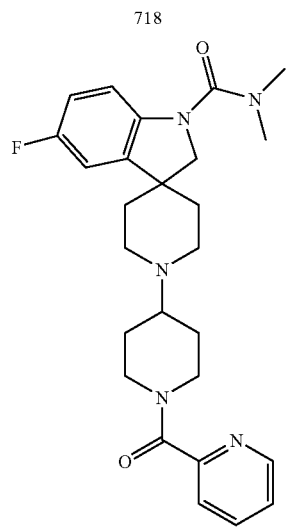

TABLE 1-continued
Exemplary compounds of formula I.
719
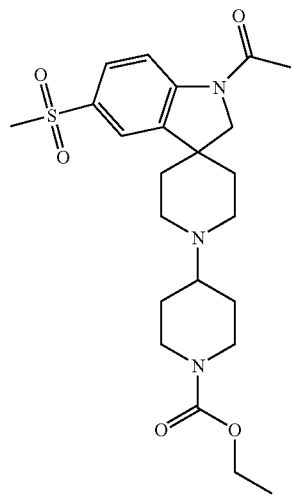 [SMILES: CCOC(=O)N1CCC(N2CCC3(CC2)CN(C(C)=O)c2ccc(S(C)(=O)=O)cc23)CC1]
720
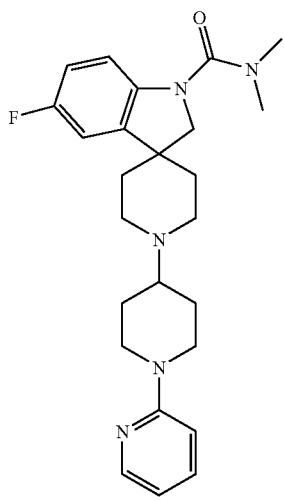 [SMILES: CN(C)C(=O)N1CC2(CCN(C3CCN(c4ccccn4)CC3)CC2)c2cc(F)ccc21]
721
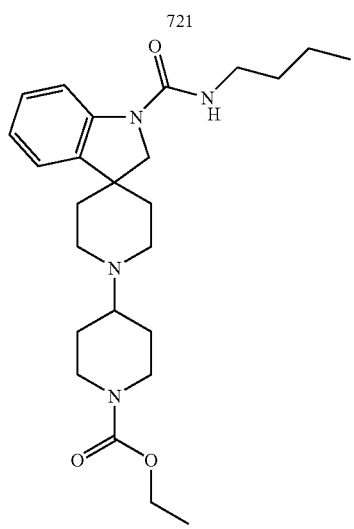
722
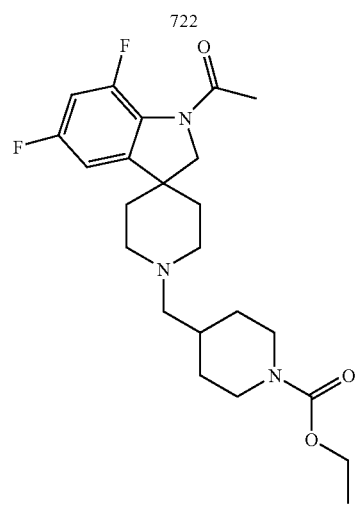
723
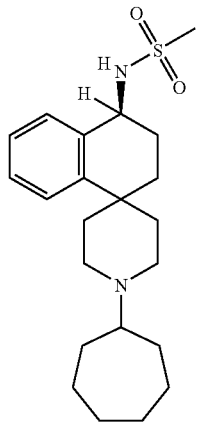
724
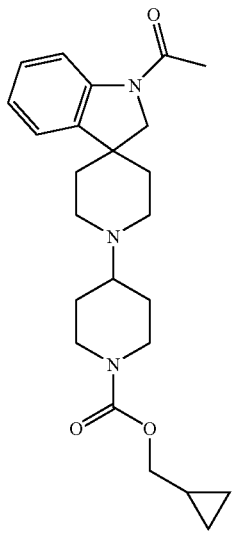 [SMILES: CC(=O)N1CC2(CCN(C3CCN(C(=O)OCC4CC4)CC3)CC2)c2ccccc21]

US 8,367,691 B2
297                                                                      298
TABLE 1-continued
Exemplary compounds of formula I.
725
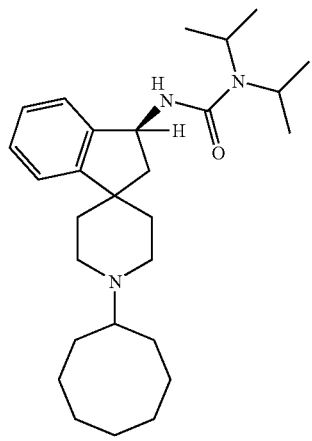
726
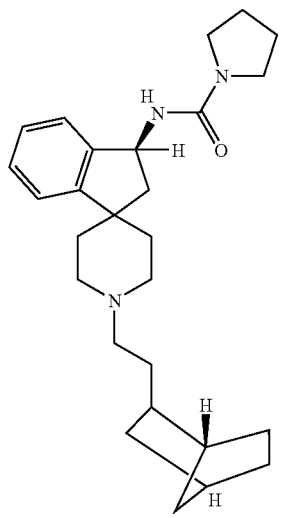
727
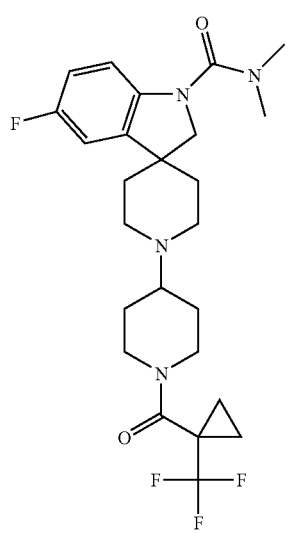 [SMILES: CN(C)C(=O)N1CC2(CCN(C3CCN(C(=O)C4(C(F)(F)F)CC4)CC3)CC2)c2cc(F)ccc21]
728
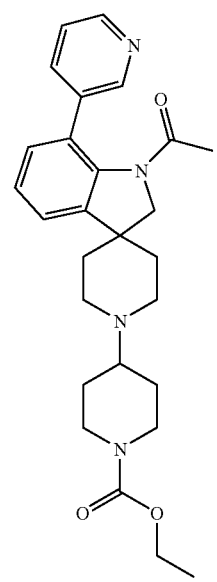 [SMILES: CCOC(=O)N1CCC(N2CCC3(CC2)CN(C(C)=O)c2c(-c4cccnc4)cccc23)CC1]

TABLE 1-continued
Exemplary compounds of formula I.
729
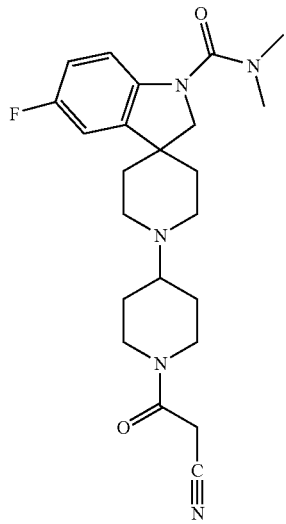 [SMILES: CN(C)C(=O)N1CC2(CCN(C3CCN(C(=O)CC#N)CC3)CC2)c2cc(F)ccc21]
730
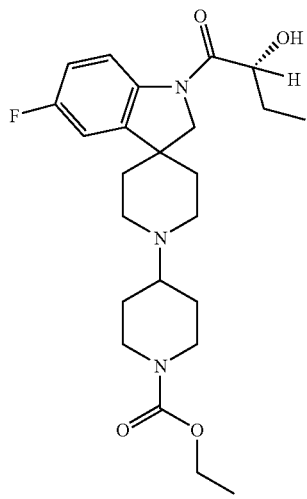 [SMILES: CCOC(=O)N1CCC(N2CCC3(CC2)CN(C(=O)[C@H](O)CC)c2ccc(F)cc23)CC1]
731
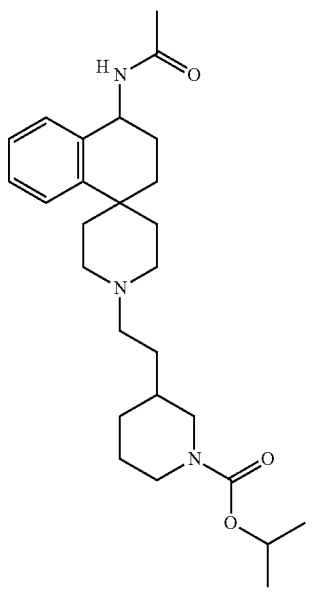
732
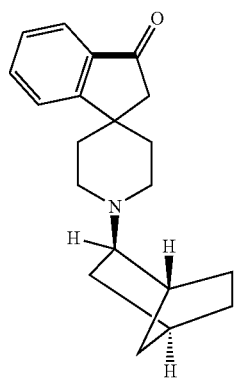

TABLE 1-continued
Exemplary compounds of formula I.
733
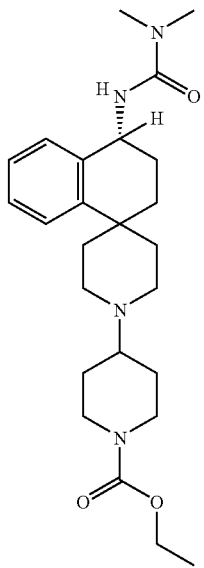
734
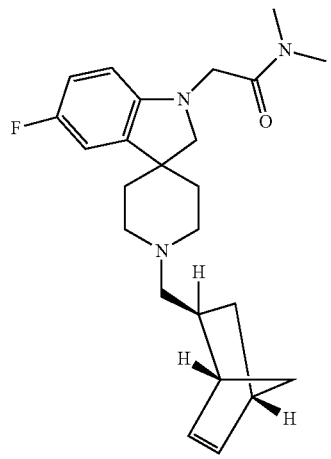 [SMILES: CN(C)C(=O)CN1CC2(CCN(C[C@H]3C[C@H]4C=C[C@H]3C4)CC2)c2cc(F)ccc21]
735
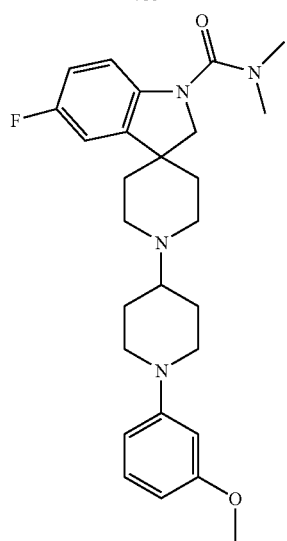 [SMILES: COc1cccc(N2CCC(N3CCC4(CC3)CN(C(=O)N(C)C)c3ccc(F)cc34)CC2)c1]
736
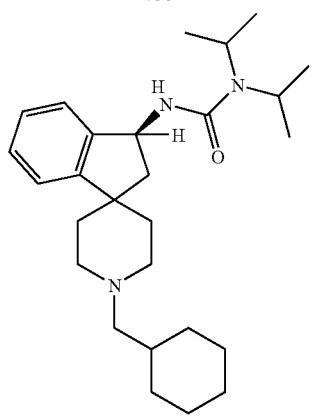
737
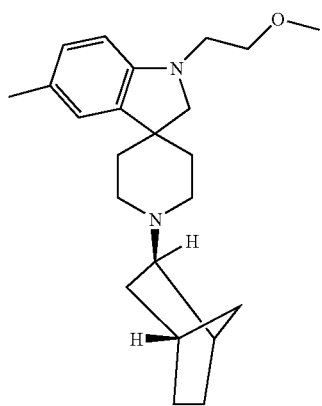
738
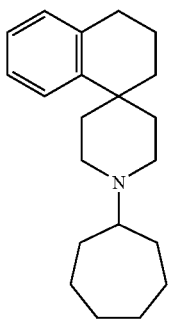 [SMILES: c1ccc2c(c1)CCCC21CCN(C2CCCCCC2)CC1]

TABLE 1-continued
Exemplary compounds of formula I.
739
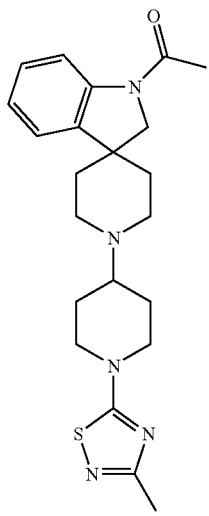 [SMILES: CC(=O)N1CC2(CCN(C3CCN(c4nc(C)ns4)CC3)CC2)c2ccccc21]
740
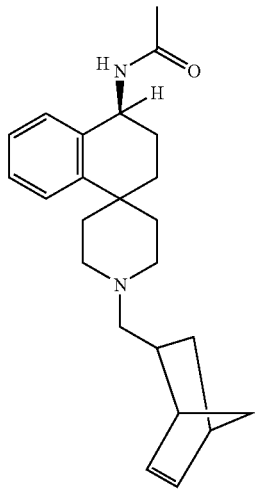
741
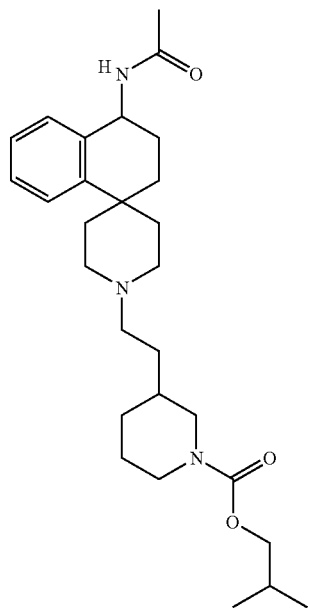
742
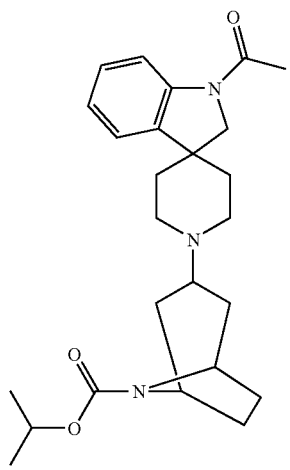 [SMILES: CC(=O)N1CC2(CCN(C3CC4CCC(C3)N4C(=O)OC(C)C)CC2)c2ccccc21]

TABLE 1-continued
Exemplary compounds of formula I.
743
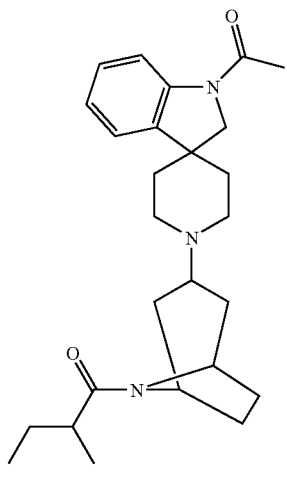 [SMILES: CCC(C)C(=O)N1C2CCC1CC(N1CCC3(CC1)CN(C(C)=O)c1ccccc13)C2]
744
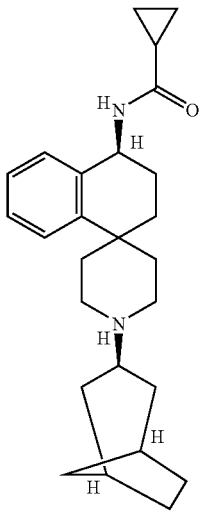
745
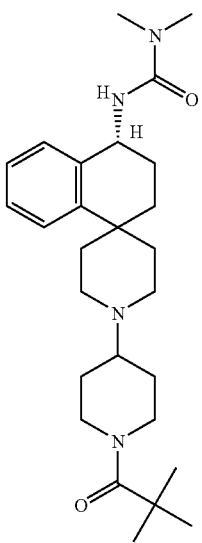
746
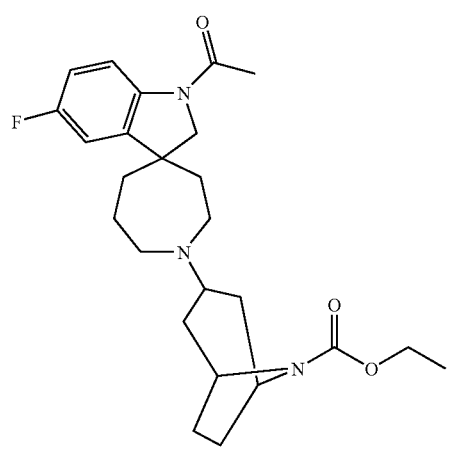 [SMILES: CCOC(=O)N1C2CCC1CC(N1CCCC3(CC1)CN(C(C)=O)c1ccc(F)cc13)C2]

TABLE 1-continued
Exemplary compounds of formula I.
747
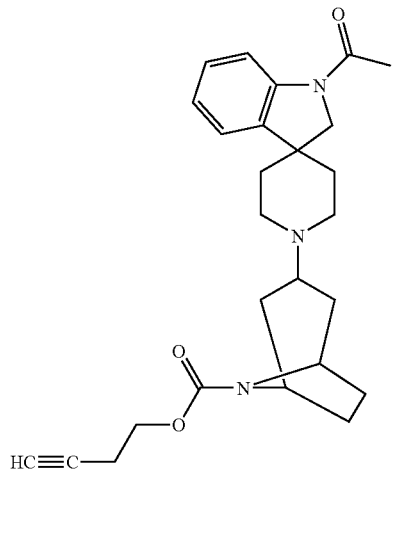 [SMILES: C#CCCOC(=O)N1C2CCC1CC(N1CCC3(CC1)CN(C(C)=O)c1ccccc13)C2]
748
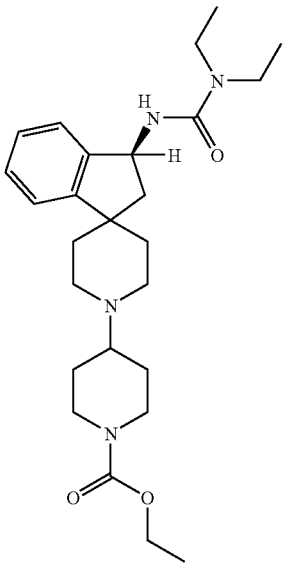
749
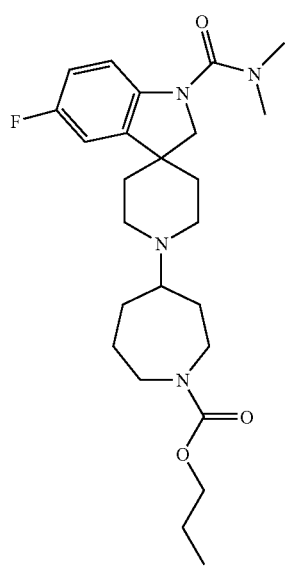 [SMILES: CCCOC(=O)N1CCCC(N2CCC3(CC2)CN(C(=O)N(C)C)c2ccc(F)cc23)CC1]
750
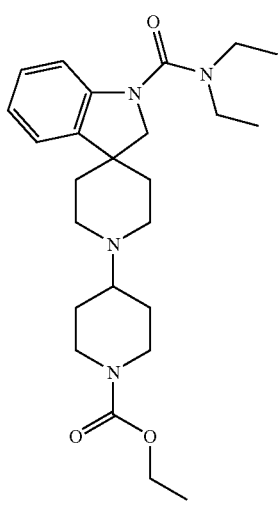 [SMILES: CCOC(=O)N1CCC(N2CCC3(CC2)CN(C(=O)N(CC)CC)c2ccccc23)CC1]

TABLE 1-continued
Exemplary compounds of formula I.
751
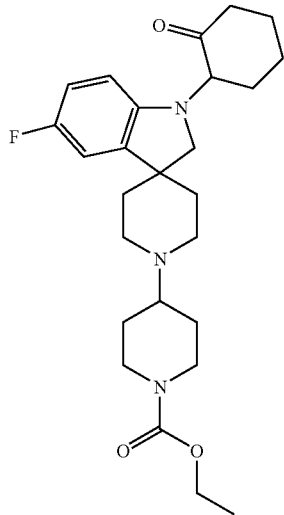 [SMILES: CCOC(=O)N1CCC(N2CCC3(CC2)CN(C2CCCCC2=O)c2ccc(F)cc23)CC1]
752
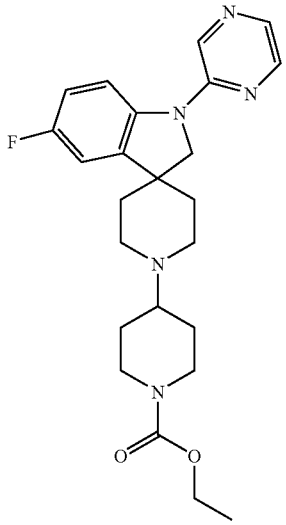 [SMILES: CCOC(=O)N1CCC(N2CCC3(CC2)CN(c2cnccn2)c2ccc(F)cc23)CC1]
753
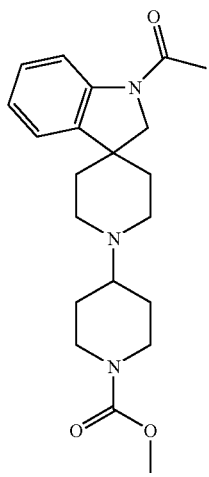 [SMILES: COC(=O)N1CCC(N2CCC3(CC2)CN(C(C)=O)c2ccccc23)CC1]
754
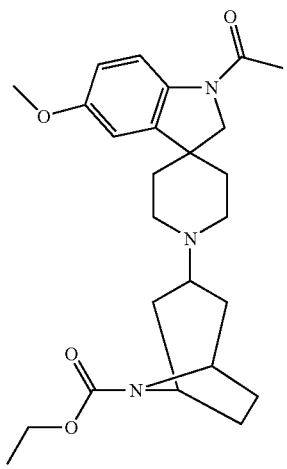
755
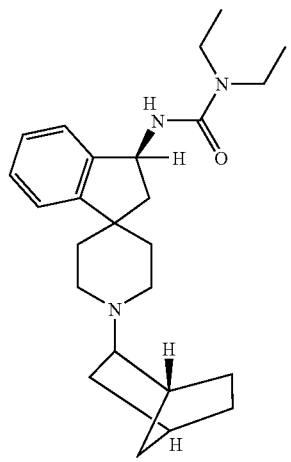
756
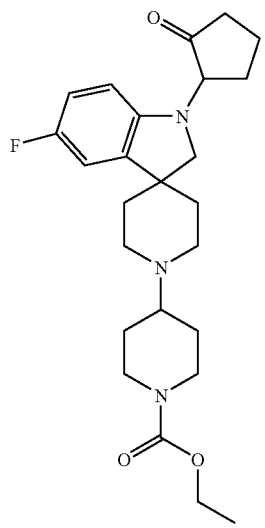 [SMILES: CCOC(=O)N1CCC(N2CCC3(CC2)CN(C2CCCC2=O)c2ccc(F)cc23)CC1]

TABLE 1-continued
Exemplary compounds of formula I.
757
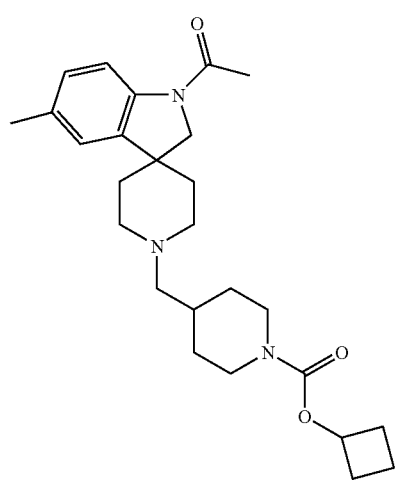 [SMILES: CC(=O)N1CC2(CCN(CC3CCN(C(=O)OC4CCC4)CC3)CC2)c2cc(C)ccc21]
758
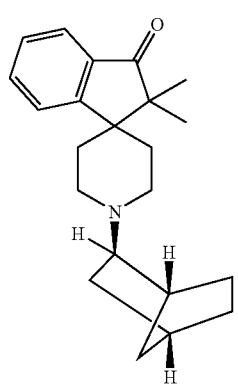 [SMILES: CC1(C)C(=O)c2ccccc2C12CCN([C@@H]1C[C@@H]3CC[C@@H]1C3)CC2]
759
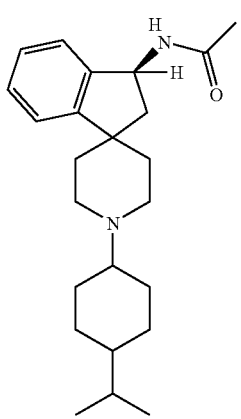
760
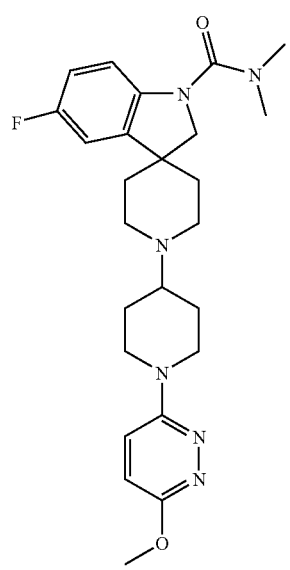 [SMILES: COc1ccc(N2CCC(N3CCC4(CC3)CN(C(=O)N(C)C)c3ccc(F)cc34)CC2)nn1]

TABLE 1-continued
Exemplary compounds of formula I.
761
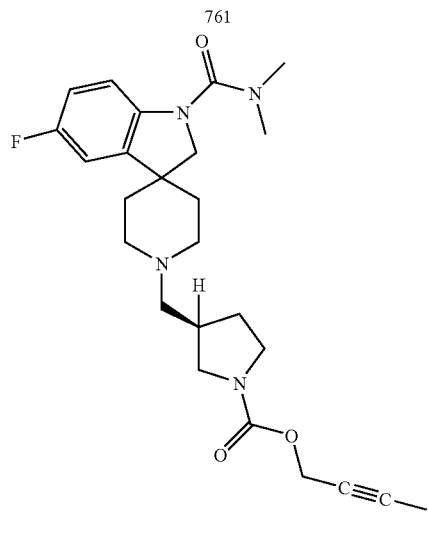
762
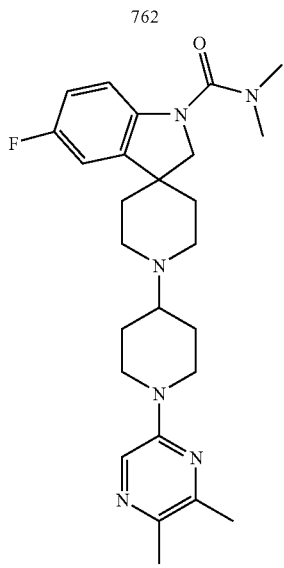
763
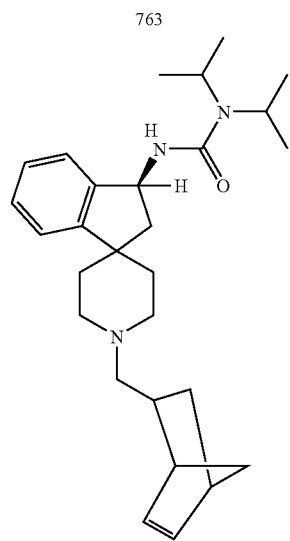
764
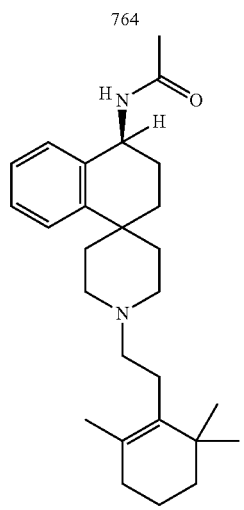
765
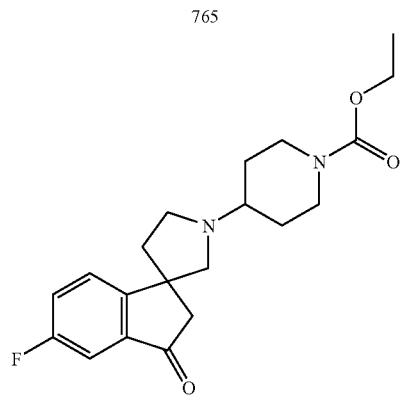
766
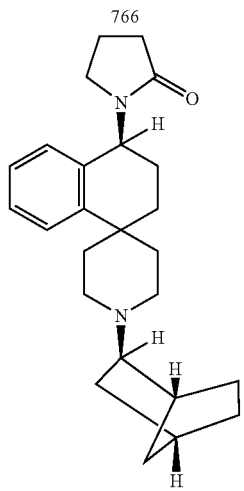

TABLE 1-continued
Exemplary compounds of formula I.
767
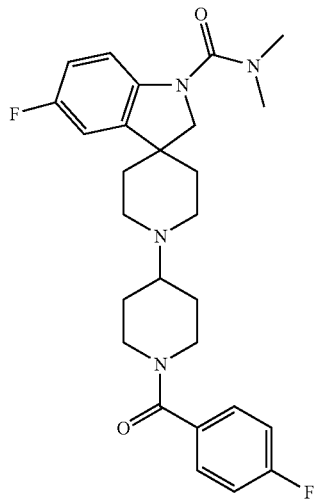 [SMILES: CN(C)C(=O)N1CC2(CCN(C3CCN(C(=O)c4ccc(F)cc4)CC3)CC2)c2cc(F)ccc21]
768
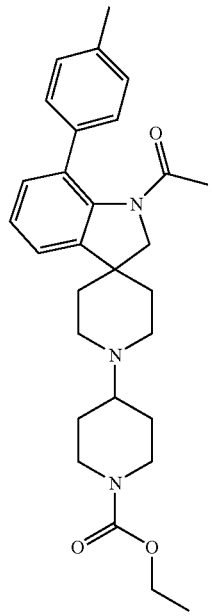 [SMILES: CCOC(=O)N1CCC(N2CCC3(CC2)CN(C(C)=O)c2c(-c4ccc(C)cc4)cccc23)CC1]
769
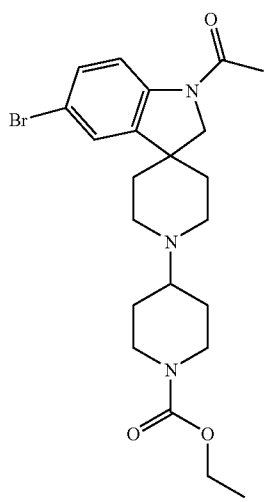 [SMILES: CCOC(=O)N1CCC(N2CCC3(CC2)CN(C(C)=O)c2ccc(Br)cc23)CC1]
770
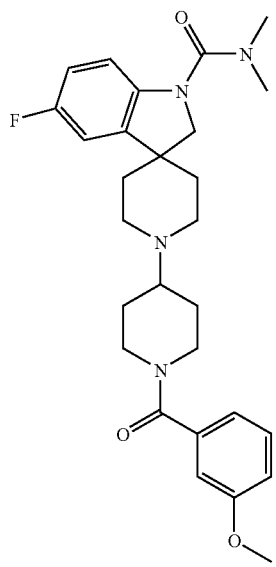 [SMILES: COc1cccc(C(=O)N2CCC(N3CCC4(CC3)CN(C(=O)N(C)C)c3ccc(F)cc34)CC2)c1]

TABLE 1-continued
Exemplary compounds of formula I.
771
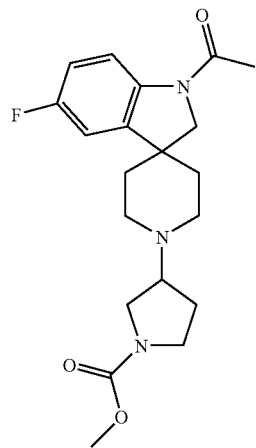 [SMILES: COC(=O)N1CCC(N2CCC3(CC2)CN(C(C)=O)c2ccc(F)cc23)C1]
772
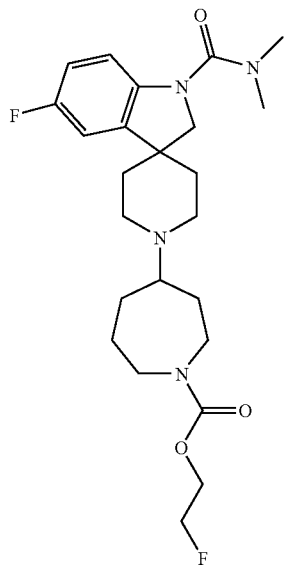
773
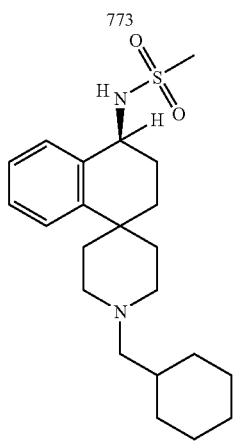
774
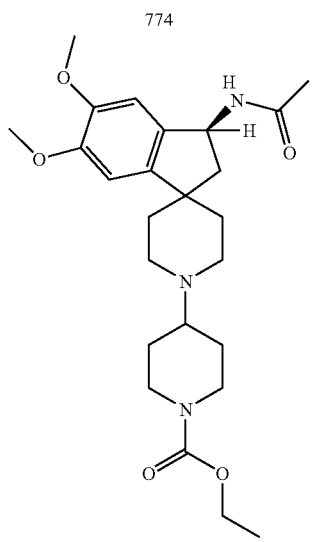
775
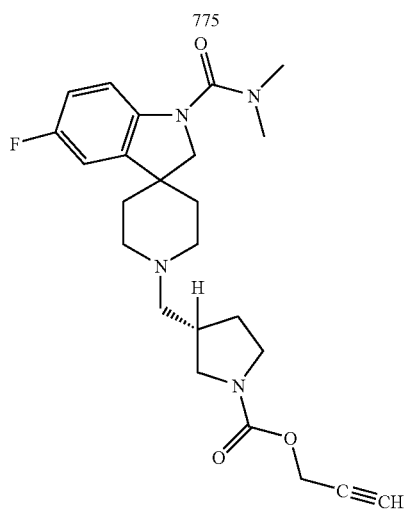
776
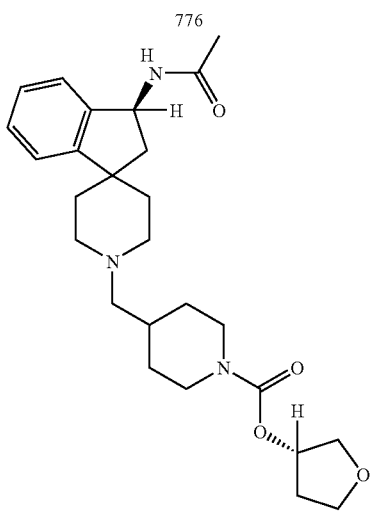

TABLE 1-continued
Exemplary compounds of formula I.
777
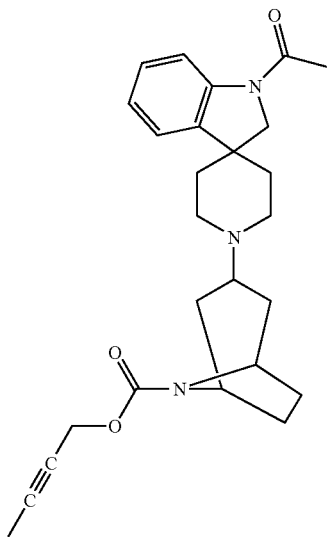 [SMILES: CC#CCOC(=O)N1C2CCC1CC(N1CCC3(CC1)CN(C(C)=O)c1ccccc13)C2]
778
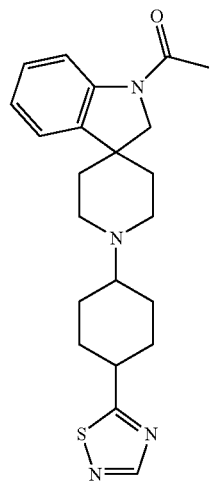 [SMILES: CC(=O)N1CC2(CCN(C3CCC(c4ncns4)CC3)CC2)c2ccccc21]
779
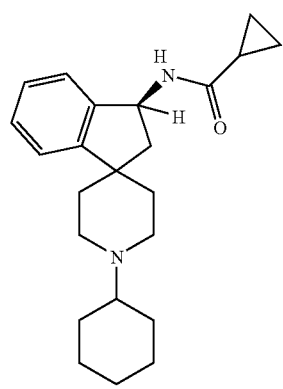
780
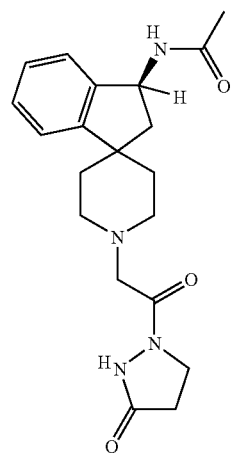

TABLE 1-continued
Exemplary compounds of formula I.
781
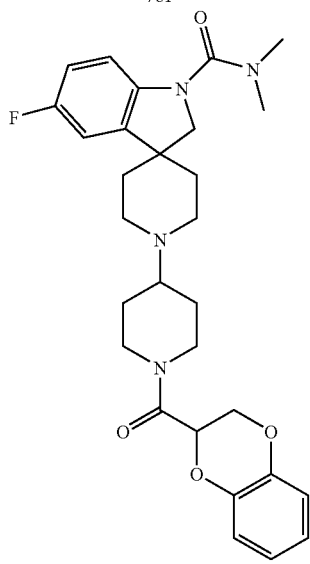
782
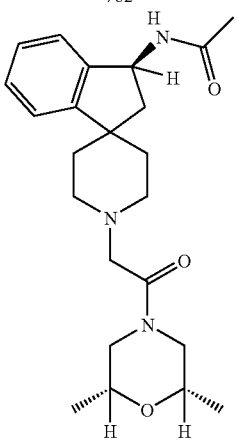
783
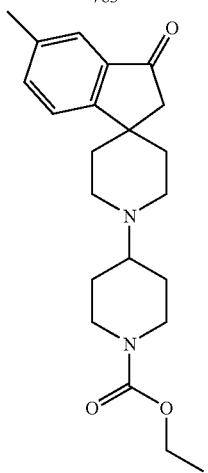
784
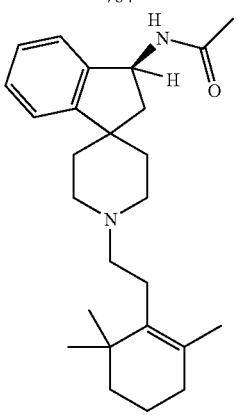
785
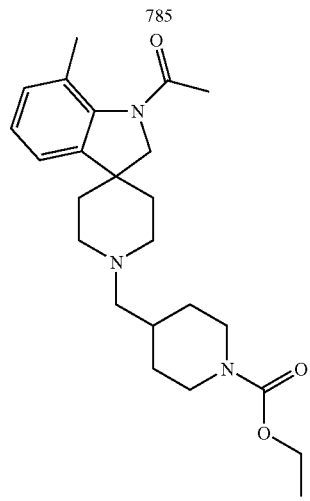
786
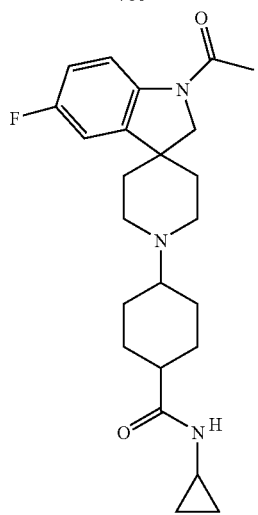

TABLE 1-continued
Exemplary compounds of formula I.
787
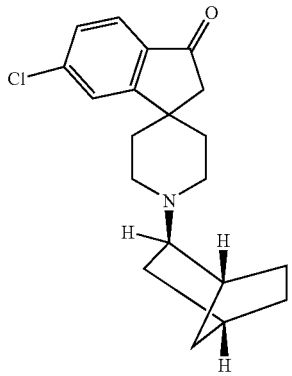 [SMILES: O=C1CC2(CCN([C@@H]3C[C@@H]4CC[C@@H]3C4)CC2)c2cc(Cl)ccc21]
788
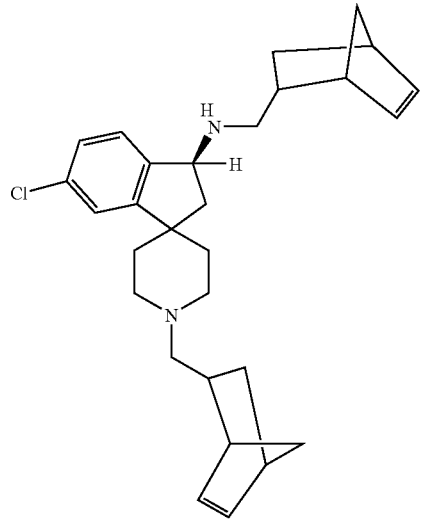
789
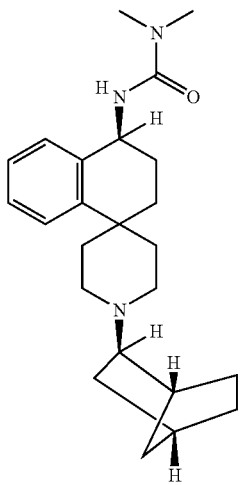
790
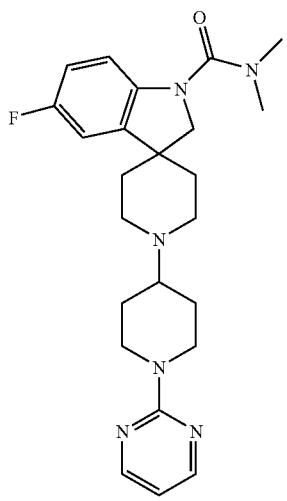
791
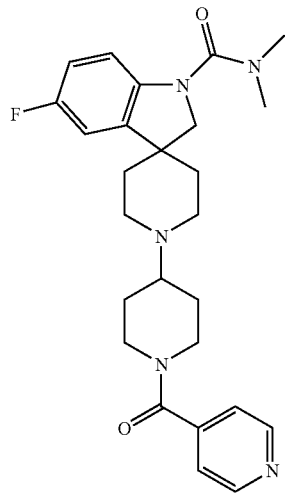
792
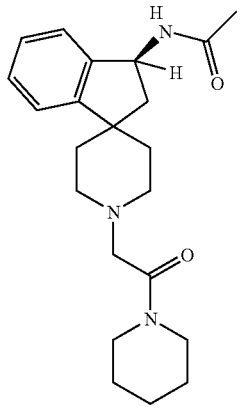

TABLE 1-continued
Exemplary compounds of formula I.
793
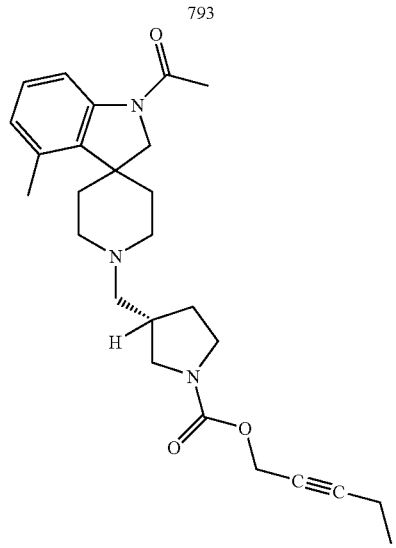
794
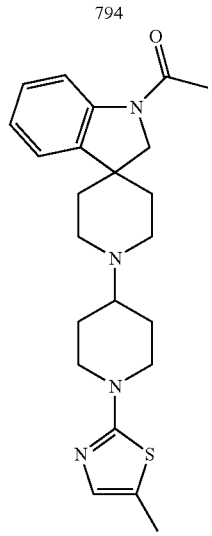
795
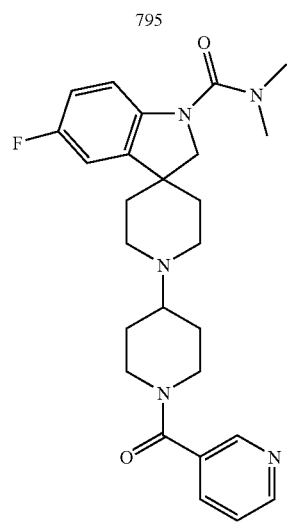
796
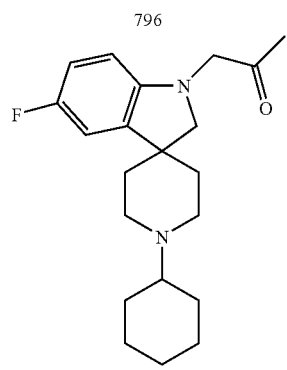
797
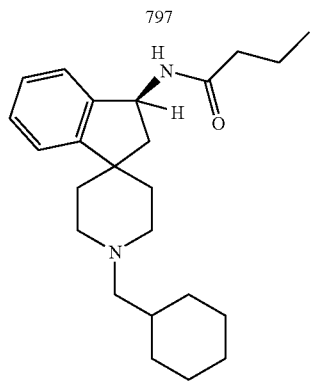
798
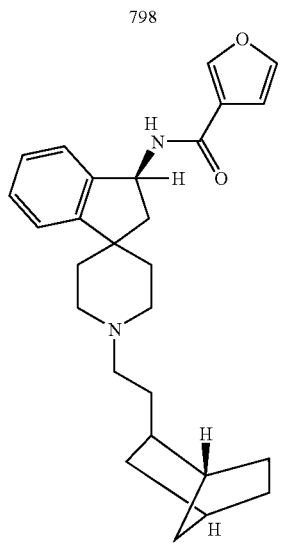

US 8,367,691 B2
TABLE 1-continued
Exemplary compounds of formula I.
799
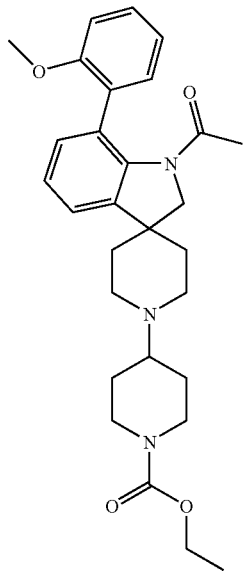 [SMILES: CCOC(=O)N1CCC(N2CCC3(CC2)CN(C(C)=O)c2c(-c4ccccc4OC)cccc23)CC1]
800
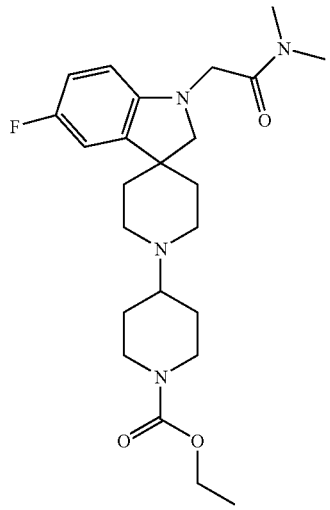 [SMILES: CCOC(=O)N1CCC(N2CCC3(CC2)CN(CC(=O)N(C)C)c2ccc(F)cc23)CC1]
801
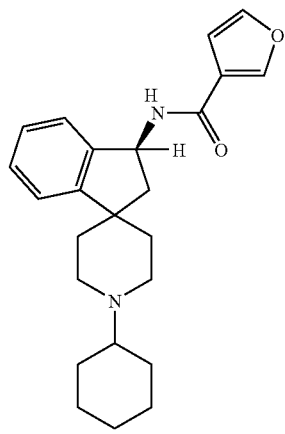
802
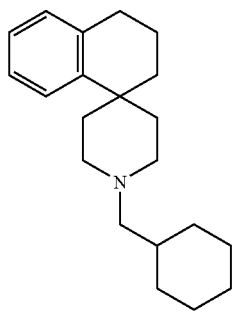 [SMILES: c1ccc2c(c1)CCCC21CCN(CC2CCCCC2)CC1]
803
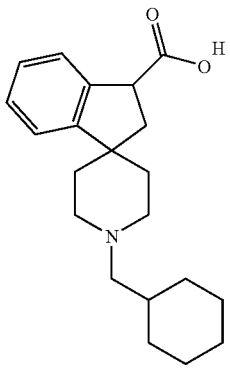
804
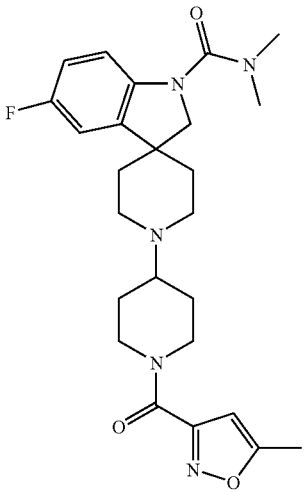 [SMILES: Cc1cc(C(=O)N2CCC(N3CCC4(CC3)CN(C(=O)N(C)C)c3ccc(F)cc34)CC2)no1]

TABLE 1-continued
Exemplary compounds of formula I.
805
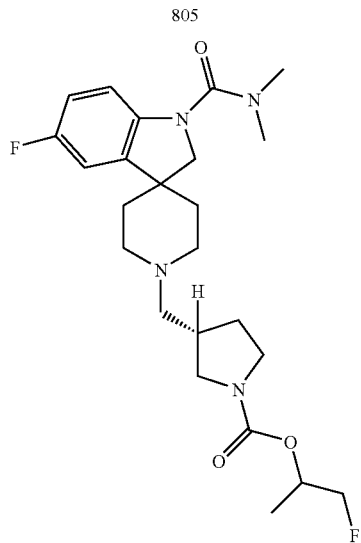
806
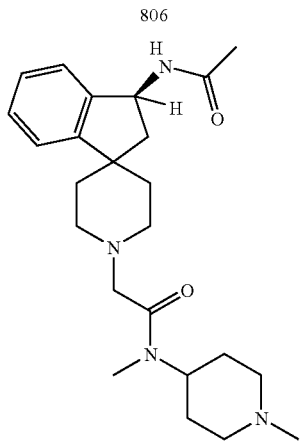
807
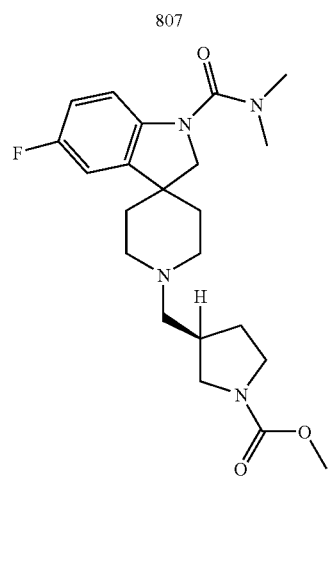
808

US 8,367,691 B2
331                                                              332
TABLE 1-continued
Exemplary compounds of formula I.
809
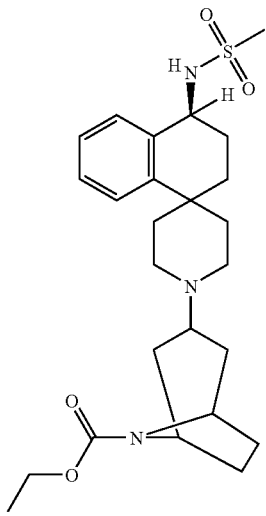
810
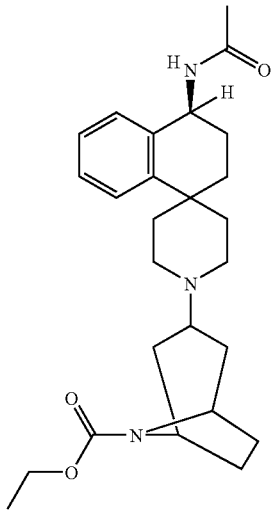
811
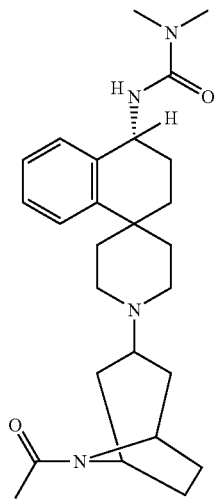
812
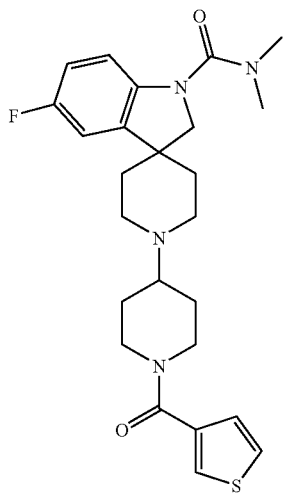
813
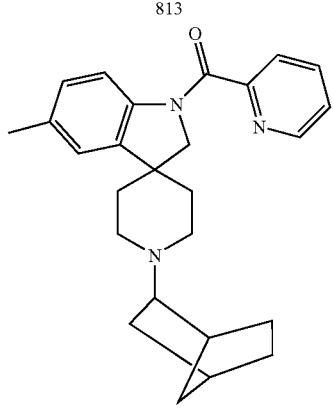
814
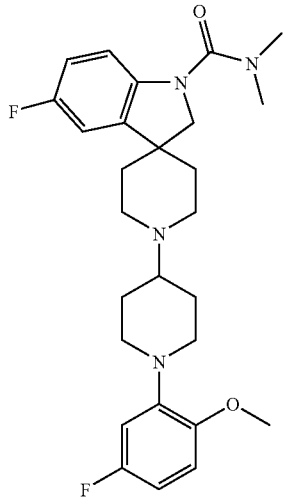 [SMILES: COc1ccc(F)cc1N1CCC(N2CCC3(CC2)CN(C(=O)N(C)C)c2ccc(F)cc23)CC1]

TABLE 1-continued
Exemplary compounds of formula I.
815
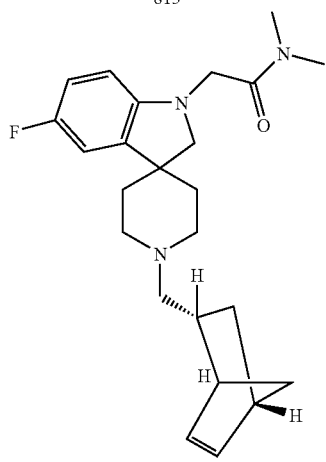
816
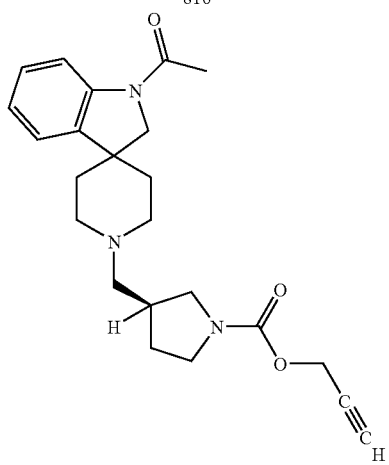
817
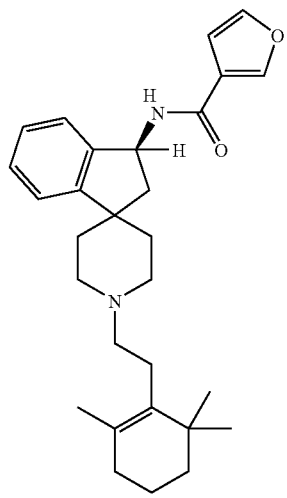
818
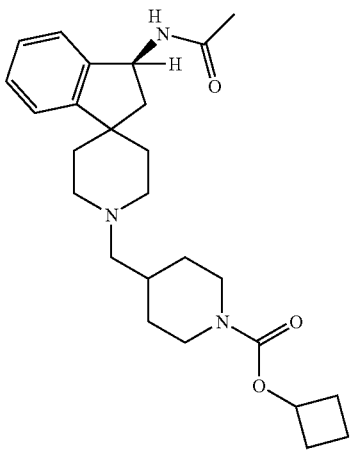
819
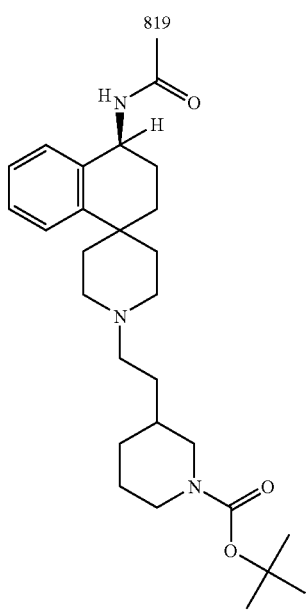
820
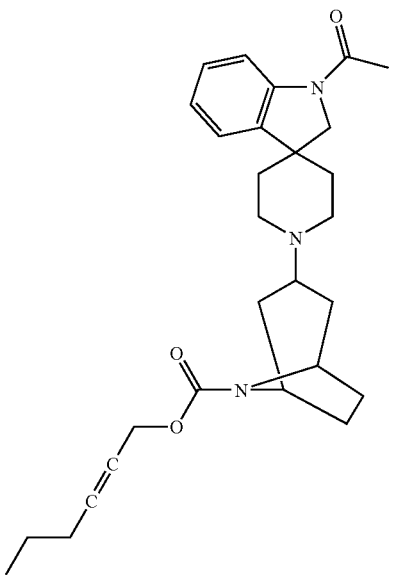 [SMILES: CCCC=CCOC(=O)N1C2CCC1CC(N1CCC3(CC1)CN(C(C)=O)c1ccccc13)C2]

TABLE 1-continued
Exemplary compounds of formula I.
821
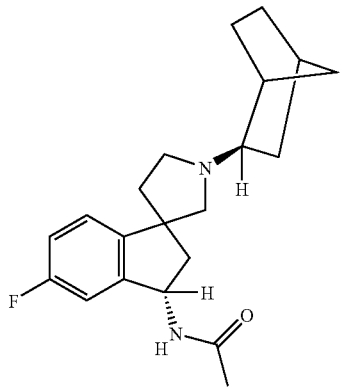
822
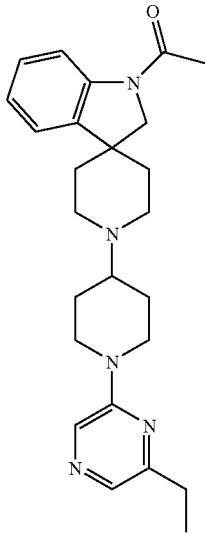 [SMILES: CCc1cncc(N2CCC(N3CCC4(CC3)CN(C(C)=O)c3ccccc34)CC2)n1]
823
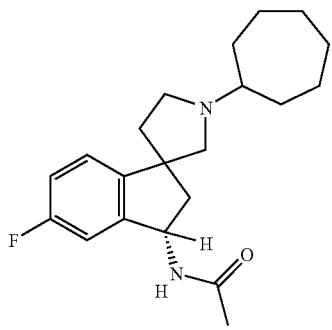
824
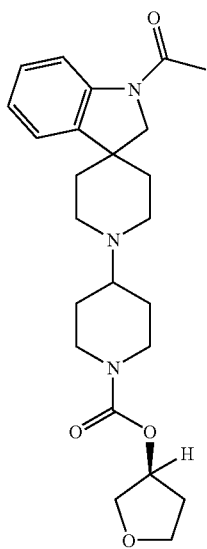 [SMILES: CC(=O)N1CC2(CCN(C3CCN(C(=O)O[C@H]4CCOC4)CC3)CC2)c2ccccc21]

TABLE 1-continued
Exemplary compounds of formula I.
825
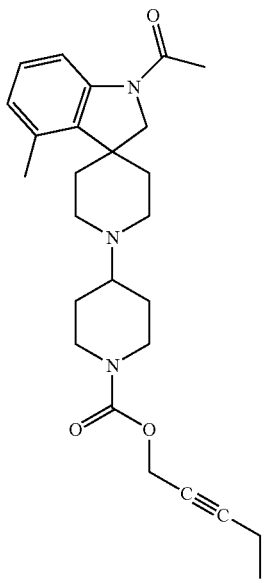 [SMILES: CCC#CCOC(=O)N1CCC(N2CCC3(CC2)CN(C(C)=O)c2cccc(C)c23)CC1]
826
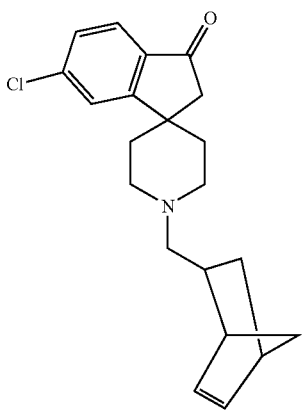 [SMILES: O=C1CC2(CCN(CC3CC4C=CC3C4)CC2)c2cc(Cl)ccc21]
827
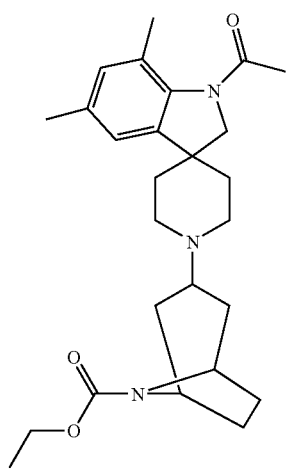 [SMILES: CCOC(=O)N1C2CCC1CC(N1CCC3(CC1)CN(C(C)=O)c1c(C)cc(C)cc13)C2]
828
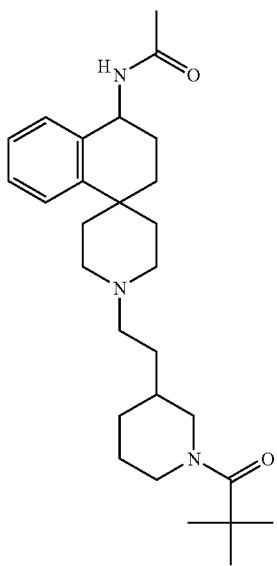

TABLE 1-continued
Exemplary compounds of formula I.
829
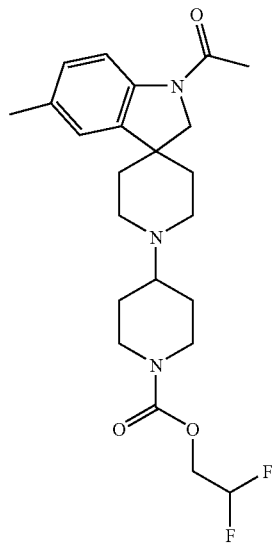 [SMILES: CC(=O)N1CC2(CCN(C3CCN(C(=O)OCC(F)F)CC3)CC2)c2cc(C)ccc21]
830
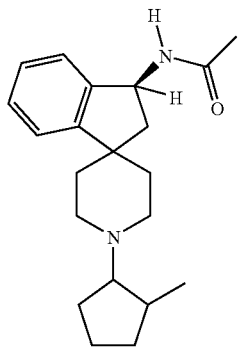 [SMILES: CC(=O)N[C@H]1CC2(CCN(C3CCCC3C)CC2)c2ccccc21]
831
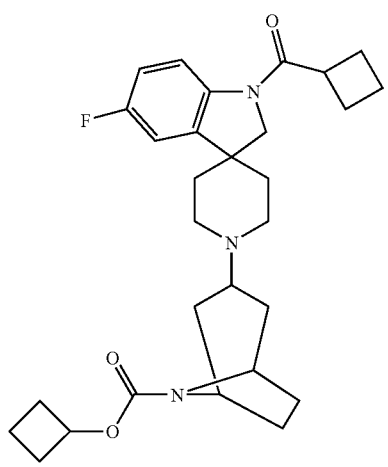 [SMILES: O=C(C1CCC1)N1CC2(CCN(C3CC4CCC(C3)N4C(=O)OC3CCC3)CC2)c2cc(F)ccc21]
832
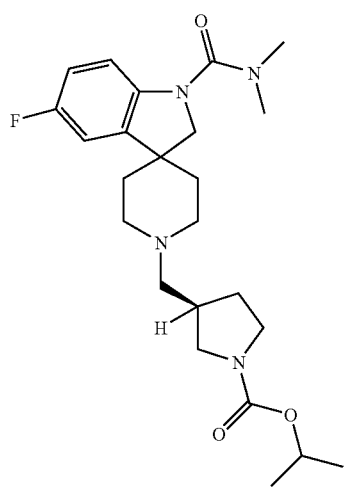 [SMILES: CC(C)OC(=O)N1CC[C@H](CN2CCC3(CC2)CN(C(=O)N(C)C)c2ccc(F)cc23)C1]

TABLE 1-continued
Exemplary compounds of formula I.
833
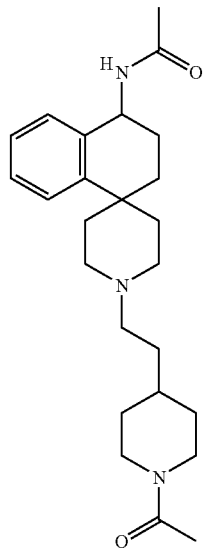
834
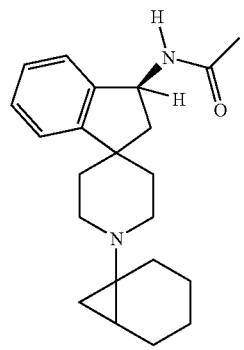 [SMILES: CC(=O)N[C@H]1CC2(CCN(C34CCCCC3C4)CC2)c2ccccc21]
835
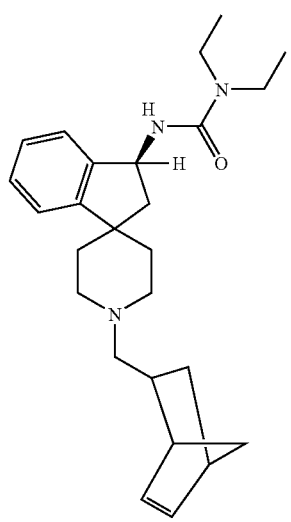
836
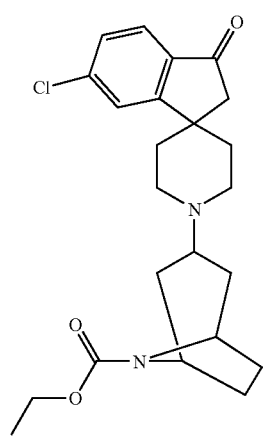 [SMILES: CCOC(=O)N1C2CCC1CC(N1CCC3(CC1)CC(=O)c1ccc(Cl)cc13)C2]

TABLE 1-continued
Exemplary compounds of formula I.
837
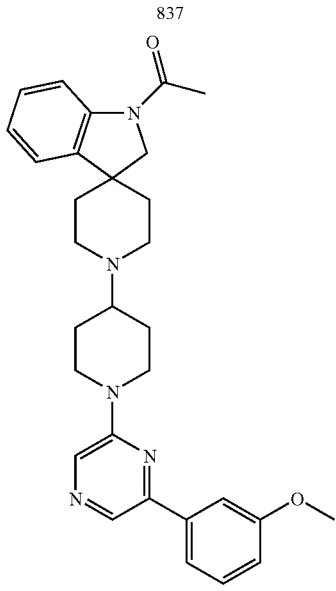
838
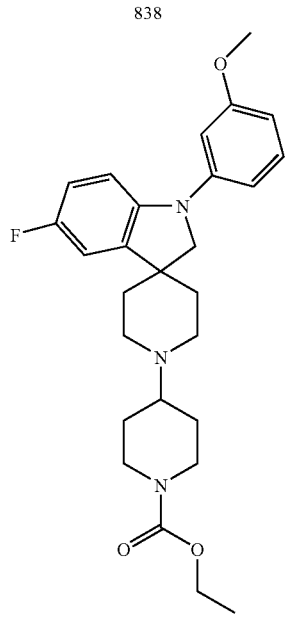
839
840
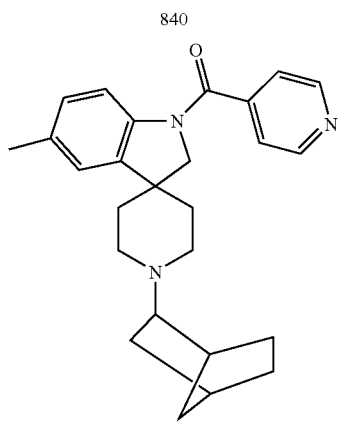

TABLE 1-continued
Exemplary compounds of formula I.
841
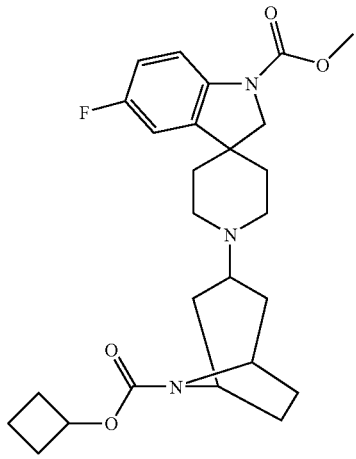 [SMILES: COC(=O)N1CC2(CCN(C3CC4CCC(C3)N4C(=O)OC3CCC3)CC2)c2cc(F)ccc21]
842
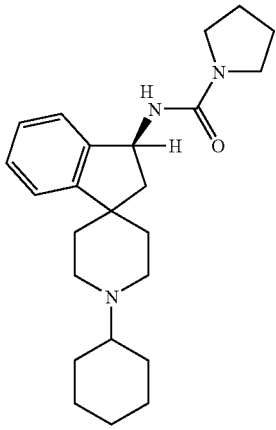
843
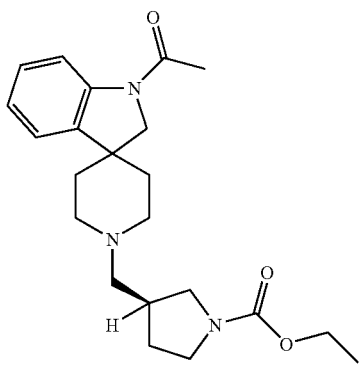 [SMILES: CCOC(=O)N1CC[C@@H](CN2CCC3(CC2)CN(C(C)=O)c2ccccc23)C1]
844
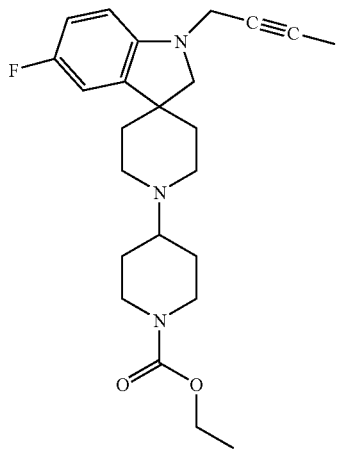 [SMILES: CC#CCN1CC2(CCN(C3CCN(C(=O)OCC)CC3)CC2)c2cc(F)ccc21]
845
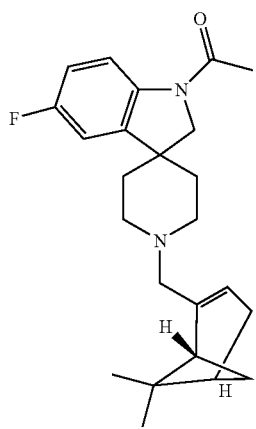
846
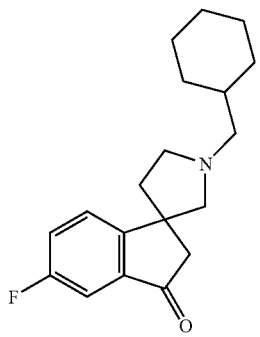 [SMILES: O=C1CC2(CCN(CC3CCCCC3)C2)c2ccc(F)cc21]

TABLE 1-continued
Exemplary compounds of formula I.
847
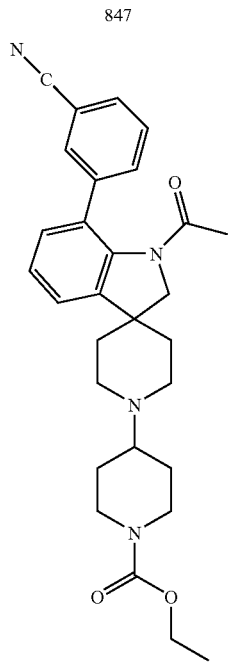
848
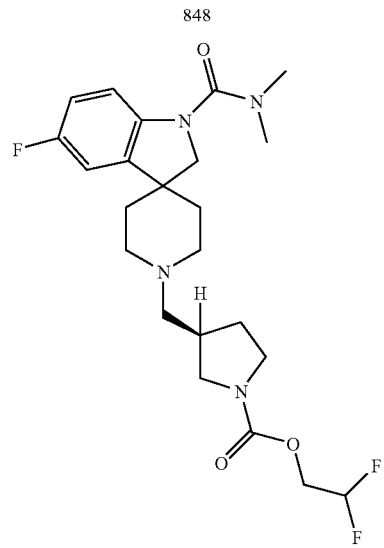
849
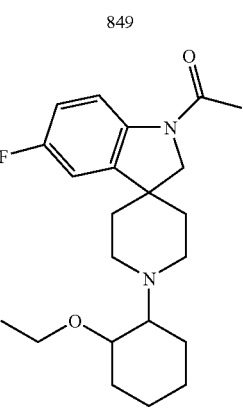
850
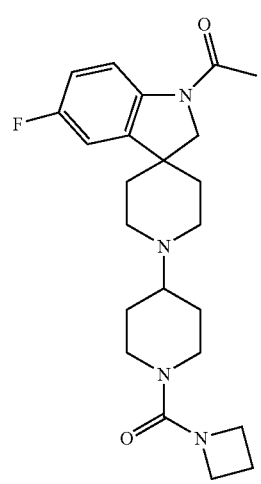 [SMILES: CC(=O)N1CC2(CCN(C3CCN(C(=O)N4CCC4)CC3)CC2)c2cc(F)ccc21]

TABLE 1-continued
Exemplary compounds of formula I.
851
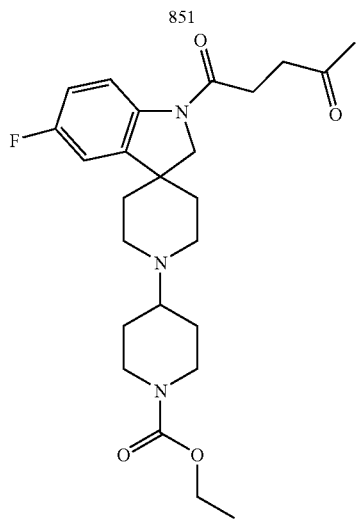
852
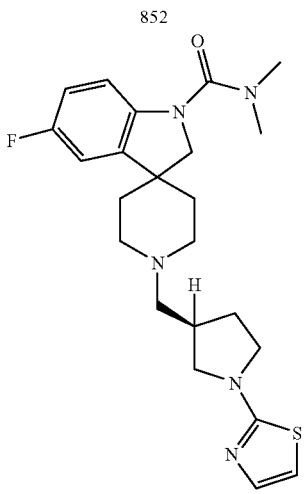
853
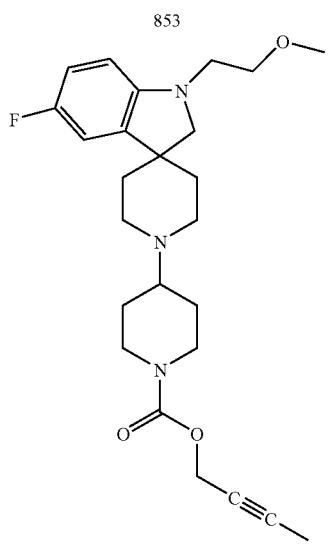
854
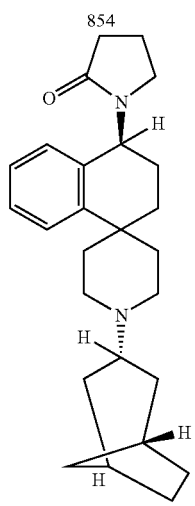
855
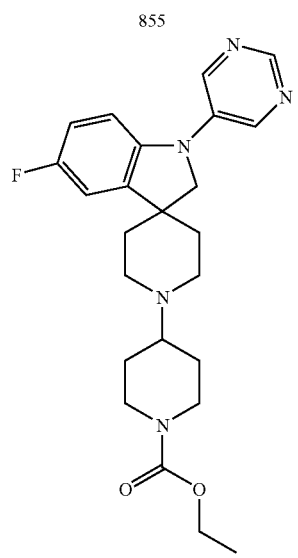
856
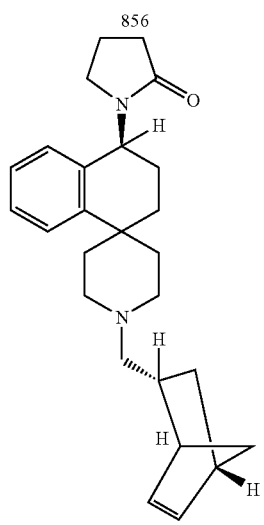

TABLE 1-continued
Exemplary compounds of formula I.
857
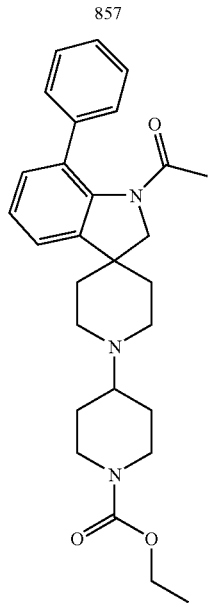
858
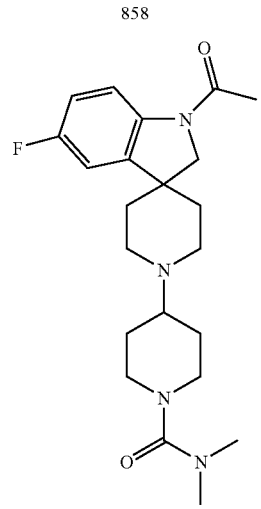
859
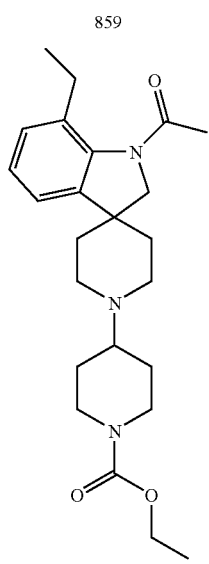
860
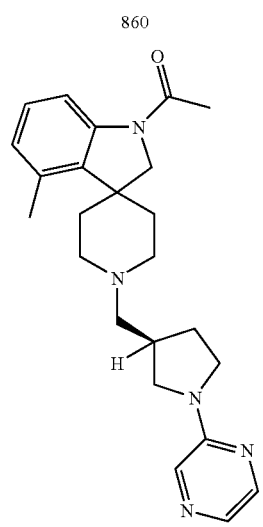

TABLE 1-continued
Exemplary compounds of formula I.
861
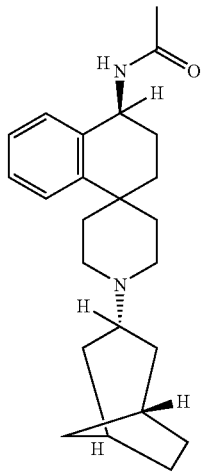
862
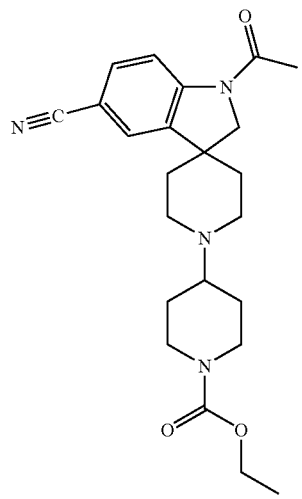 [SMILES: CCOC(=O)N1CCC(N2CCC3(CC2)CN(C(C)=O)c2ccc(C#N)cc23)CC1]
863
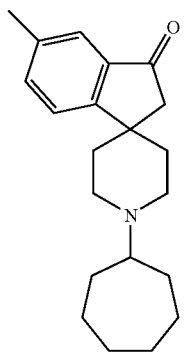 [SMILES: Cc1ccc2c(c1)C(=O)CC21CCN(C2CCCCCC2)CC1]
864
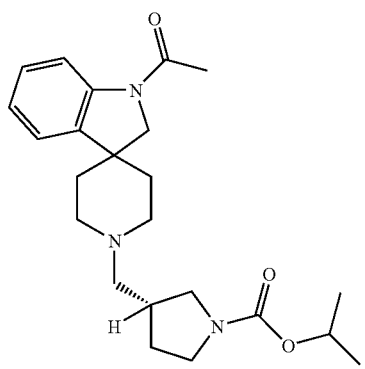 [SMILES: CC(=O)N1CC2(CCN(C[C@H]3CCN(C(=O)OC(C)C)C3)CC2)c2ccccc21]
865
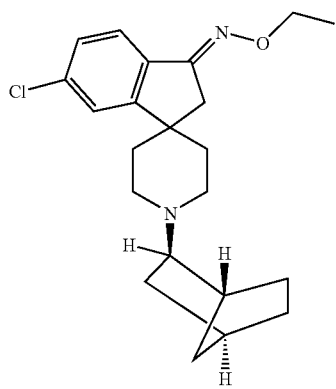 [SMILES: CCO/N=C1\CC2(CCN([C@@H]3C[C@H]4CC[C@@H]3C4)CC2)c2cc(Cl)ccc21]
866
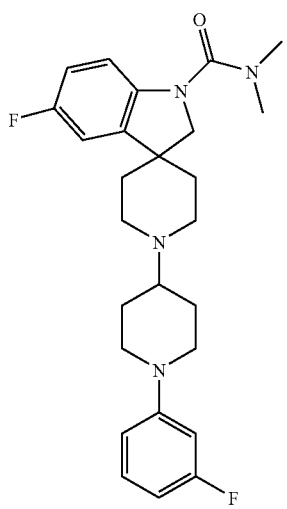 [SMILES: CN(C)C(=O)N1CC2(CCN(C3CCN(c4cccc(F)c4)CC3)CC2)c2cc(F)ccc21]

TABLE 1-continued
Exemplary compounds of formula I.
867
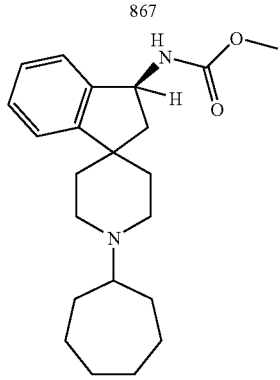
868
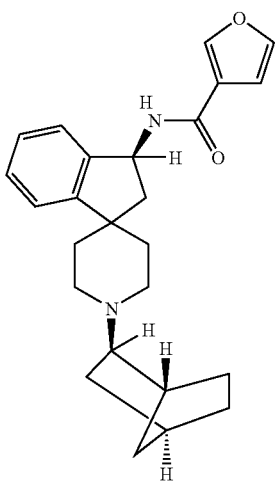
869
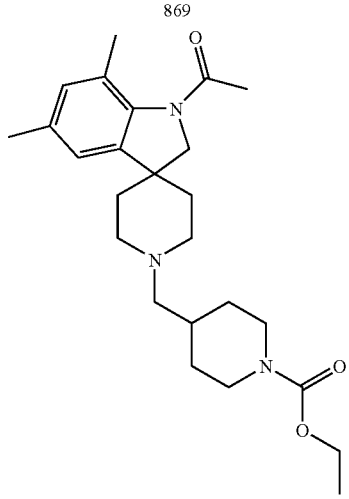
870
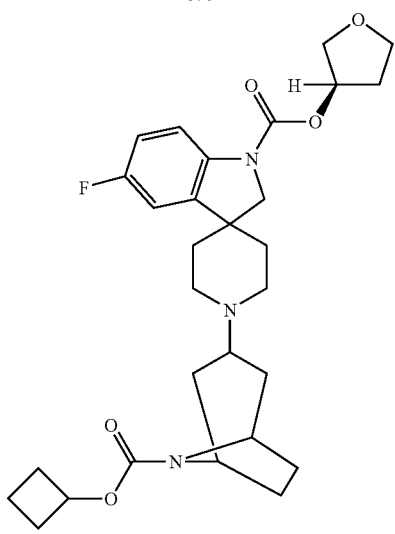 [SMILES: O=C(O[C@@H]1CCOC1)N1CC2(CCN(C3CC4CCC(C3)N4C(=O)OC3CCC3)CC2)c2cc(F)ccc21]
871
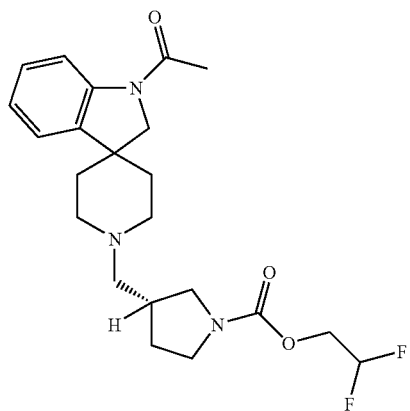 [SMILES: CC(=O)N1CC2(CCN(C[C@H]3CCN(C(=O)OCC(F)F)C3)CC2)c2ccccc21]
872
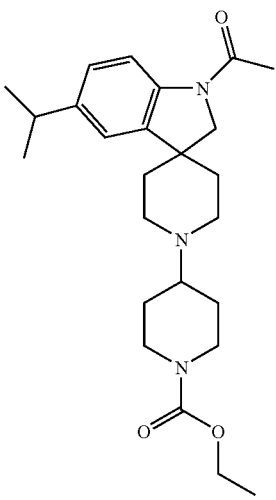 [SMILES: CCOC(=O)N1CCC(N2CCC3(CC2)CN(C(C)=O)c2ccc(C(C)C)cc23)CC1]

TABLE 1-continued
Exemplary compounds of formula I.
873
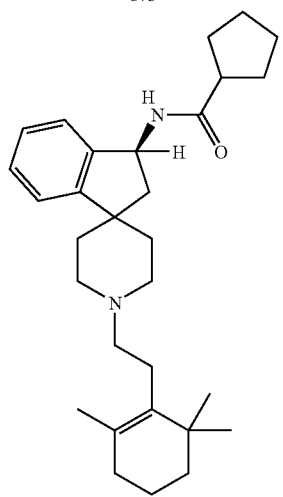
874
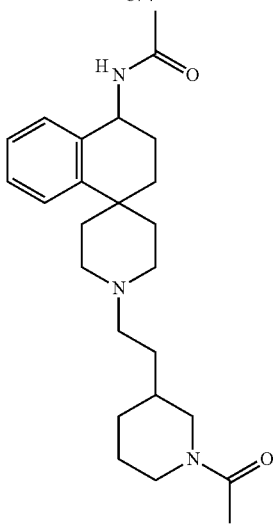
875
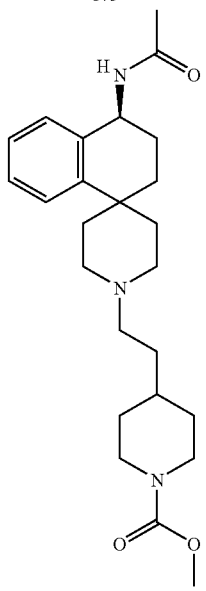
876
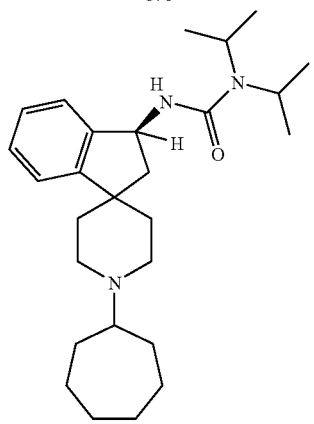
877
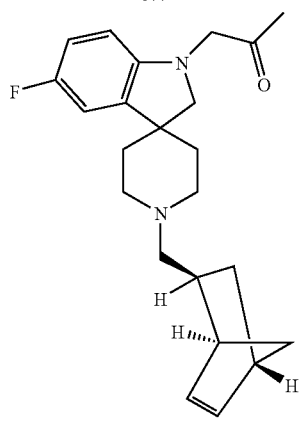
878
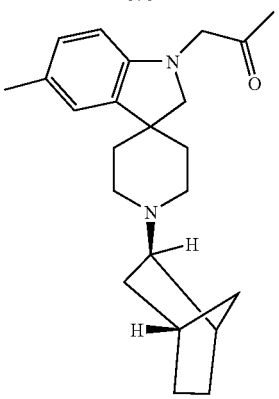

TABLE 1-continued
Exemplary compounds of formula I.
879
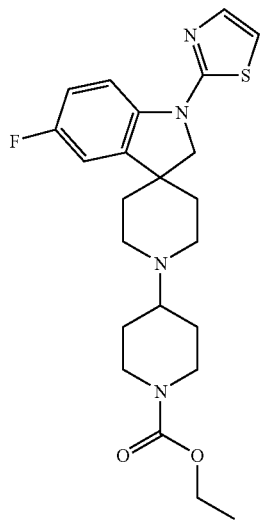 [SMILES: CCOC(=O)N1CCC(N2CCC3(CC2)CN(c2nccs2)c2ccc(F)cc23)CC1]
880
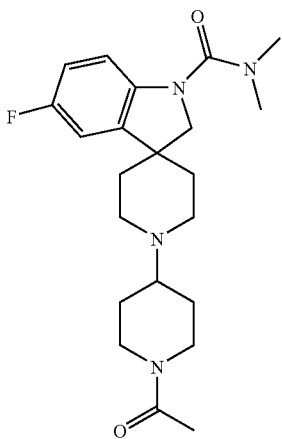
881
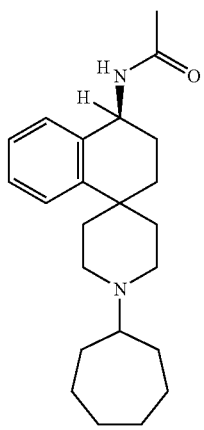
882
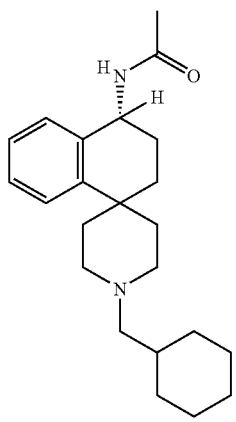
883
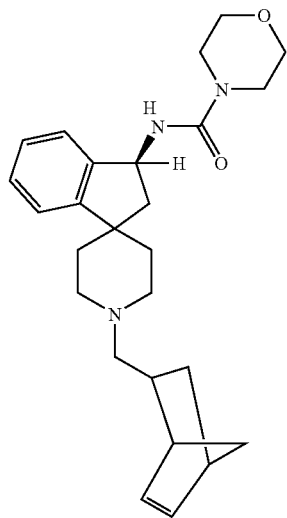
884
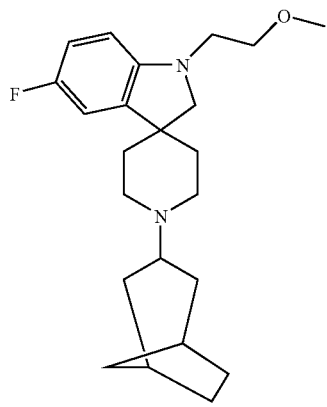 [SMILES: COCCN1CC2(CCN(C3CC4CCC(C4)C3)CC2)c2cc(F)ccc21]

TABLE 1-continued
Exemplary compounds of formula I.
885
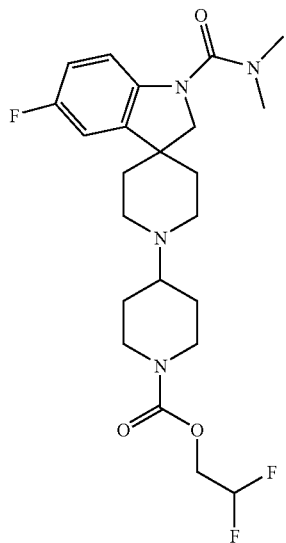 [SMILES: CN(C)C(=O)N1CC2(CCN(C3CCN(C(=O)OCC(F)F)CC3)CC2)c2cc(F)ccc21]
886
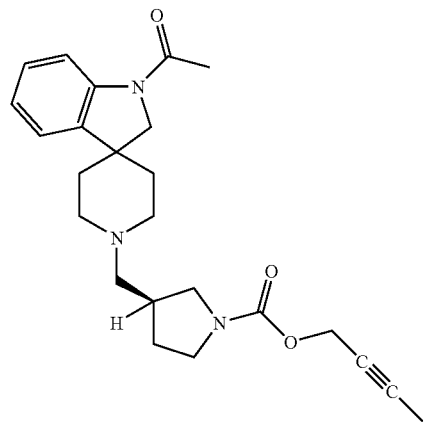 [SMILES: CC#CCOC(=O)N1CC[C@@H](CN2CCC3(CC2)CN(C(C)=O)c2ccccc23)C1]
887
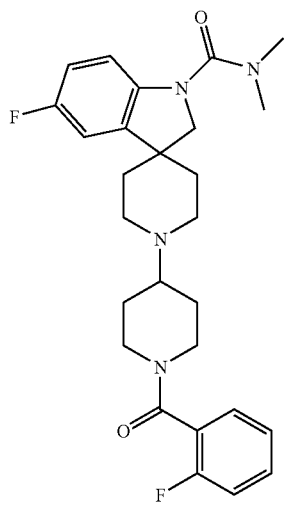 [SMILES: CN(C)C(=O)N1CC2(CCN(C3CCN(C(=O)c4ccccc4F)CC3)CC2)c2cc(F)ccc21]
888
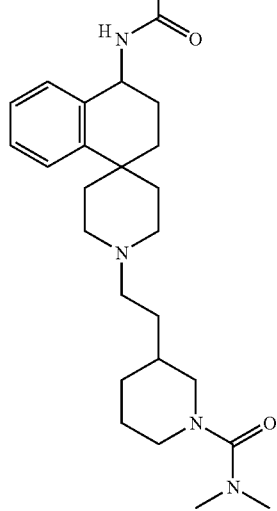

TABLE 1-continued
Exemplary compounds of formula I.
889
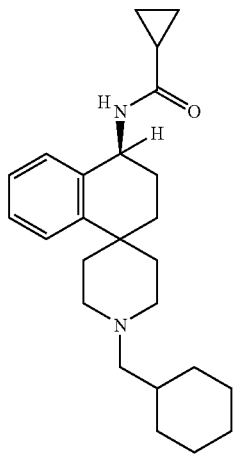
890
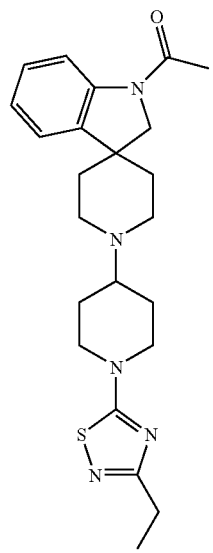 [SMILES: CCc1nsc(N2CCC(N3CCC4(CC3)CN(C(C)=O)c3ccccc34)CC2)n1]
891
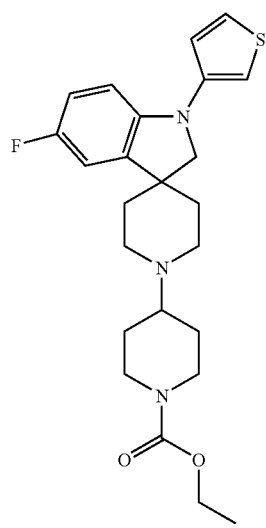
892
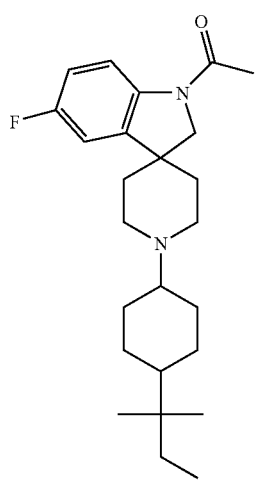 [SMILES: CCC(C)(C)C1CCC(N2CCC3(CC2)CN(C(C)=O)c2ccc(F)cc23)CC1]

TABLE 1-continued
Exemplary compounds of formula I.
893
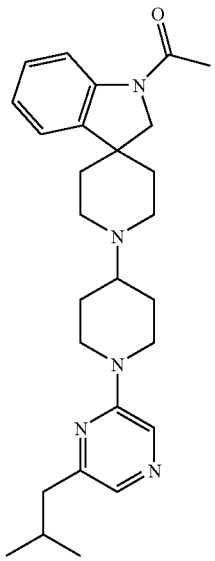 [SMILES: CC(=O)N1CC2(CCN(C3CCN(c4cncc(CC(C)C)n4)CC3)CC2)c2ccccc21]
894
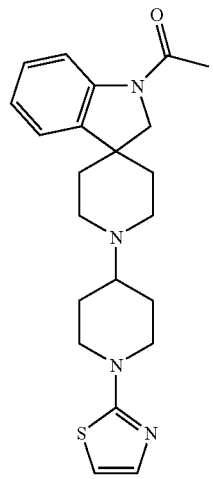 [SMILES: CC(=O)N1CC2(CCN(C3CCN(c4nccs4)CC3)CC2)c2ccccc21]
895
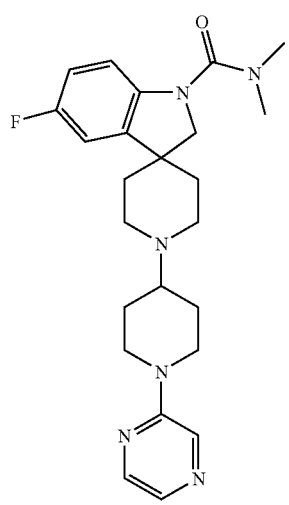 [SMILES: CN(C)C(=O)N1CC2(CCN(C3CCN(c4cnccn4)CC3)CC2)c2cc(F)ccc21]
896
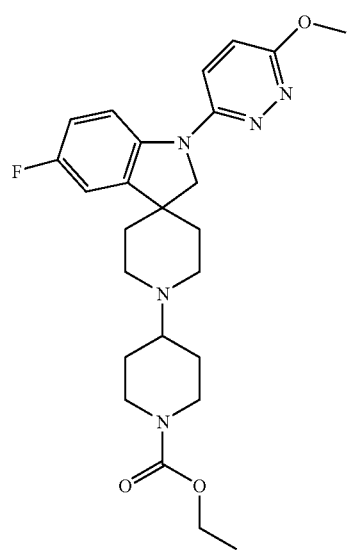 [SMILES: CCOC(=O)N1CCC(N2CCC3(CC2)CN(c2ccc(OC)nn2)c2ccc(F)cc23)CC1]

TABLE 1-continued
Exemplary compounds of formula I.
897
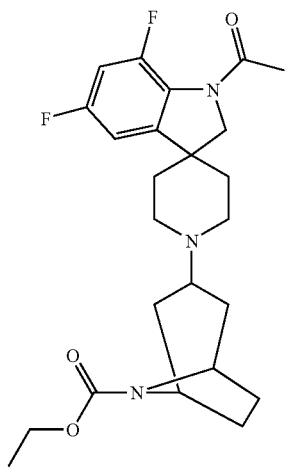 [SMILES: CCOC(=O)N1C2CCC1CC(N1CCC3(CC1)CN(C(C)=O)c1c(F)cc(F)cc13)C2]
898
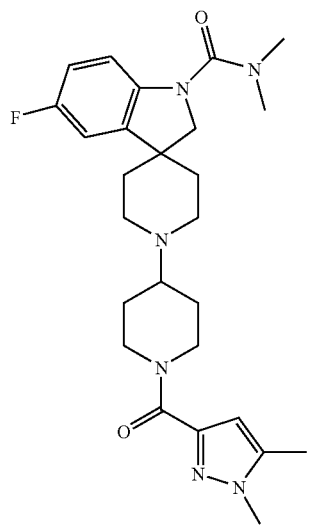 [SMILES: Cc1cc(C(=O)N2CCC(N3CCC4(CC3)CN(C(=O)N(C)C)c3ccc(F)cc34)CC2)nn1C]
899
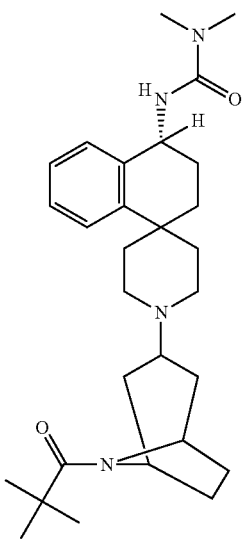
900
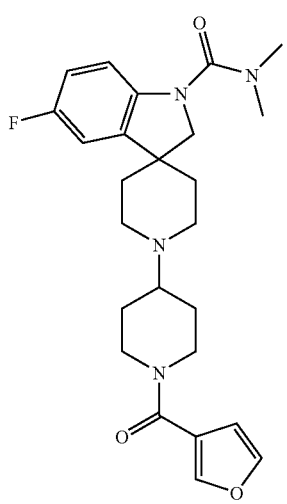 [SMILES: CN(C)C(=O)N1CC2(CCN(C3CCN(C(=O)c4ccoc4)CC3)CC2)c2cc(F)ccc21]
901
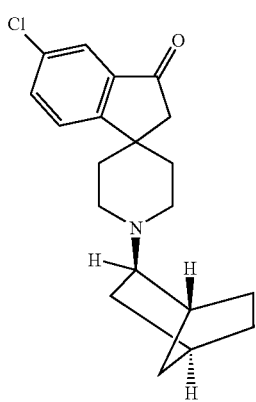 [SMILES: O=C1CC2(CCN([C@@H]3C[C@H]4CC[C@@H]3C4)CC2)c2ccc(Cl)cc21]
902
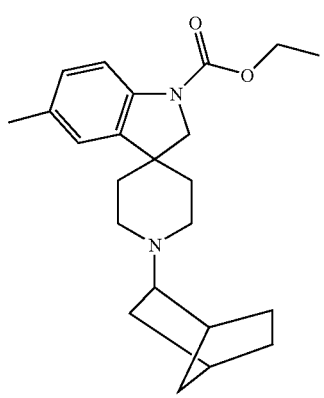 [SMILES: CCOC(=O)N1CC2(CCN(C3CC4CCC3C4)CC2)c2cc(C)ccc21]

TABLE 1-continued
Exemplary compounds of formula I.
903
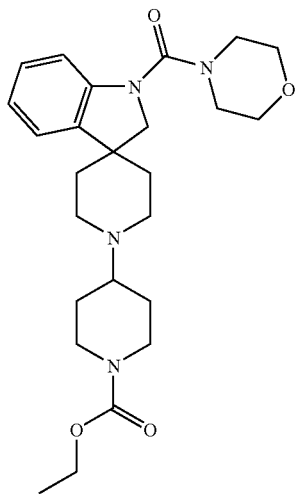 [SMILES: CCOC(=O)N1CCC(N2CCC3(CC2)CN(C(=O)N2CCOCC2)c2ccccc23)CC1]
904
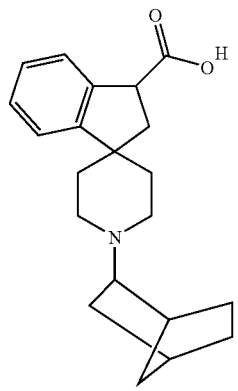
905
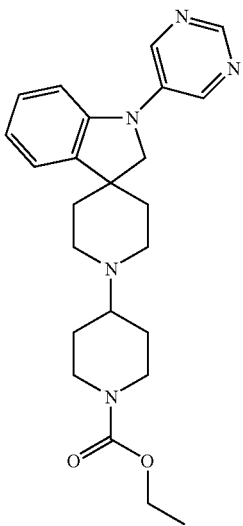 [SMILES: CCOC(=O)N1CCC(N2CCC3(CC2)CN(c2cncnc2)c2ccccc23)CC1]
906
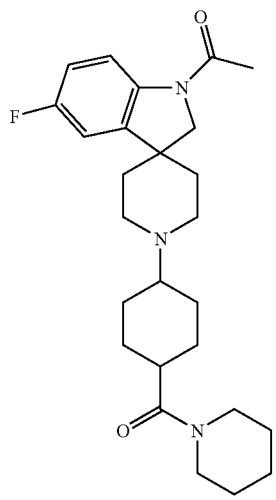 [SMILES: CC(=O)N1CC2(CCN(C3CCC(C(=O)N4CCCCC4)CC3)CC2)c2cc(F)ccc21]

TABLE 1-continued
Exemplary compounds of formula I.
907
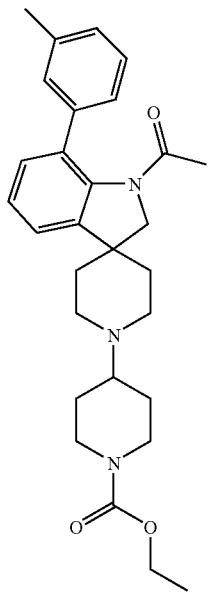 [SMILES: CCOC(=O)N1CCC(N2CCC3(CC2)CN(C(C)=O)c2c(-c4cccc(C)c4)cccc23)CC1]
908
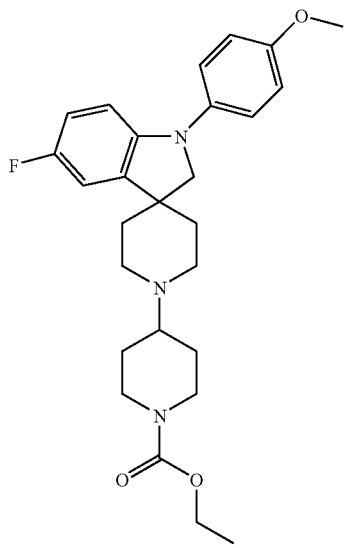 [SMILES: CCOC(=O)N1CCC(N2CCC3(CC2)CN(c2ccc(OC)cc2)c2ccc(F)cc23)CC1]
909
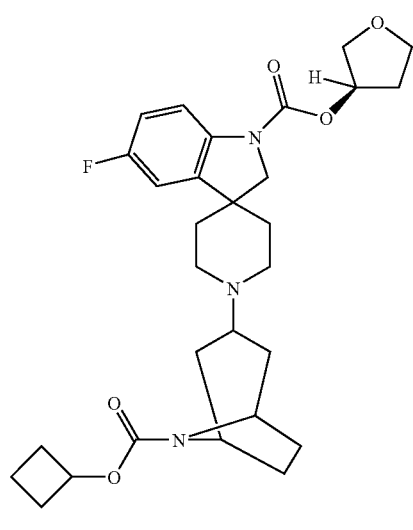 [SMILES: O=C(O[C@@H]1CCOC1)N1CC2(CCN(C3CC4CCC(C3)N4C(=O)OC3CCC3)CC2)c2cc(F)ccc21]
910
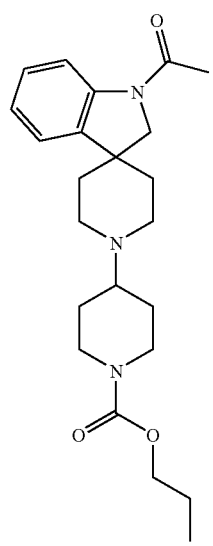 [SMILES: CCCOC(=O)N1CCC(N2CCC3(CC2)CN(C(C)=O)c2ccccc23)CC1]

TABLE 1-continued
Exemplary compounds of formula I.
911
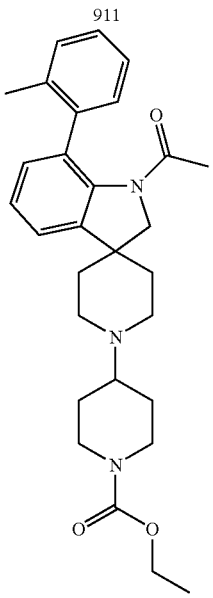
912
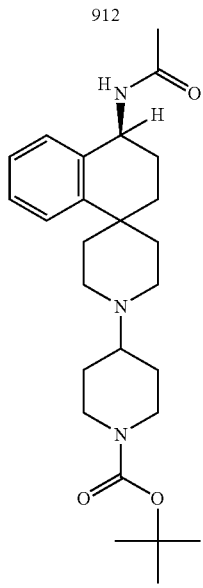
913
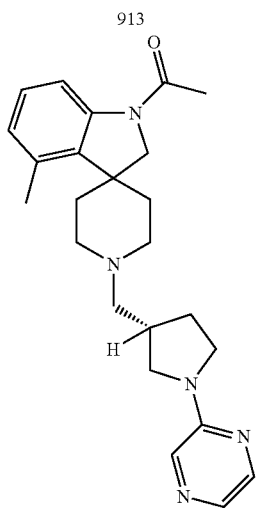
914
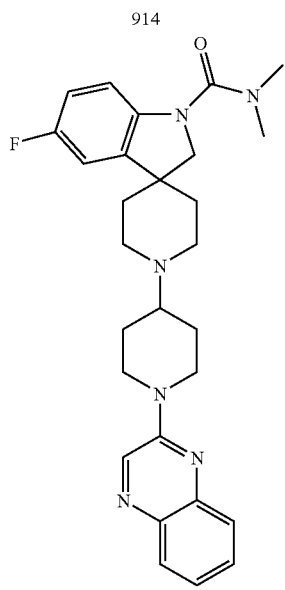
915
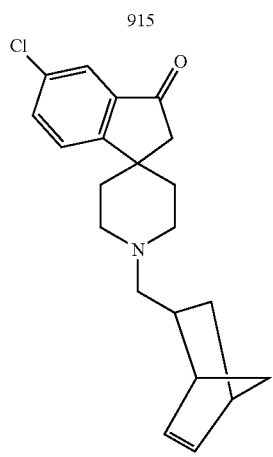
916
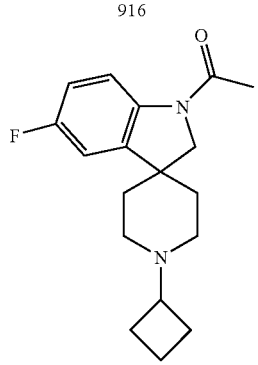

TABLE 1-continued
Exemplary compounds of formula I.
917
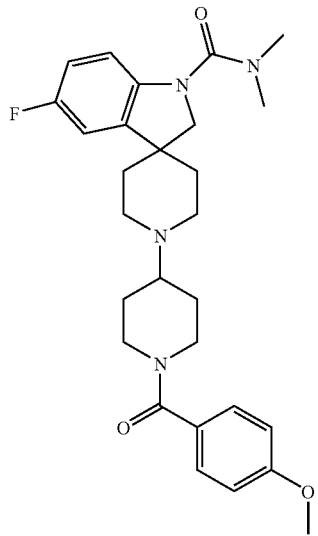 [SMILES: COc1ccc(C(=O)N2CCC(N3CCC4(CC3)CN(C(=O)N(C)C)c3ccc(F)cc34)CC2)cc1]
918
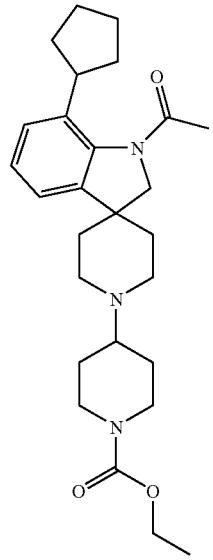 [SMILES: CCOC(=O)N1CCC(N2CCC3(CC2)CN(C(C)=O)c2c(C4CCCC4)cccc23)CC1]
919
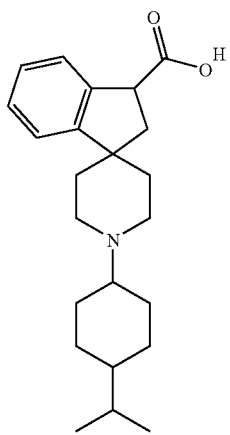
920
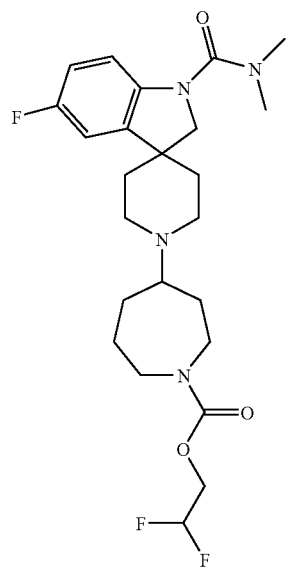 [SMILES: CN(C)C(=O)N1CC2(CCN(C3CCCN(C(=O)OCC(F)F)CC3)CC2)c2cc(F)ccc21]

TABLE 1-continued
Exemplary compounds of formula I.
921
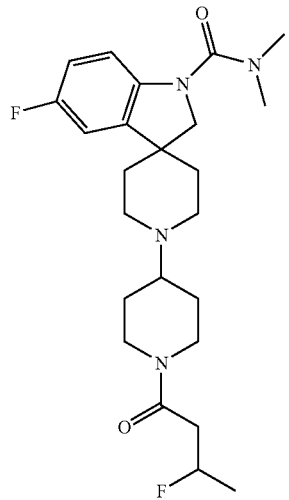 [SMILES: CC(F)CC(=O)N1CCC(N2CCC3(CC2)CN(C(=O)N(C)C)c2ccc(F)cc23)CC1]
922
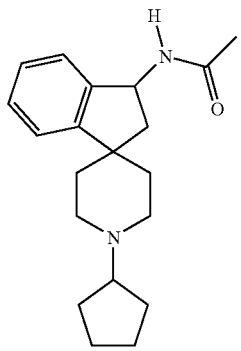 [SMILES: CC(=O)NC1CC2(CCN(C3CCCC3)CC2)c2ccccc21]
923
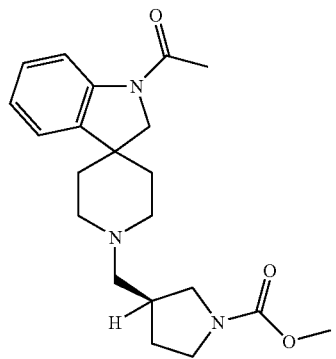 [SMILES: COC(=O)N1CC[C@@H](CN2CCC3(CC2)CN(C(C)=O)c2ccccc23)C1]
924
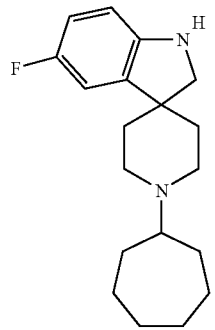
925
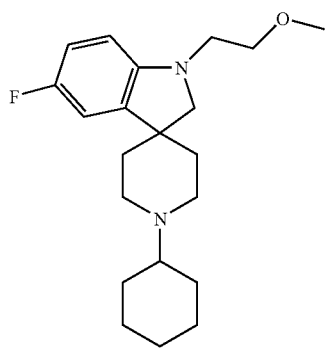 [SMILES: COCCN1CC2(CCN(C3CCCCC3)CC2)c2cc(F)ccc21]
926
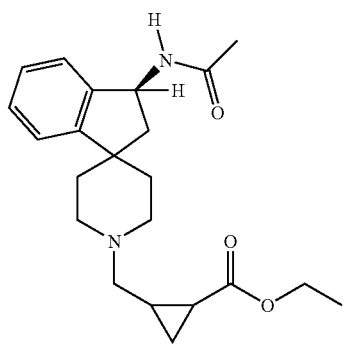 [SMILES: CCOC(=O)C1CC1CN1CCC2(CC1)C[C@H](NC(C)=O)c1ccccc12]

TABLE 1-continued
Exemplary compounds of formula I.
927
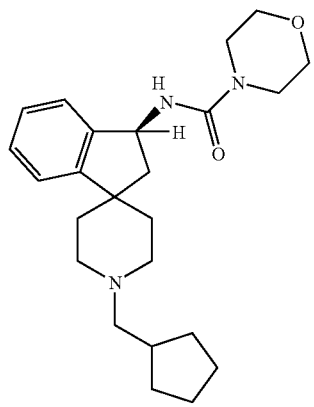
928
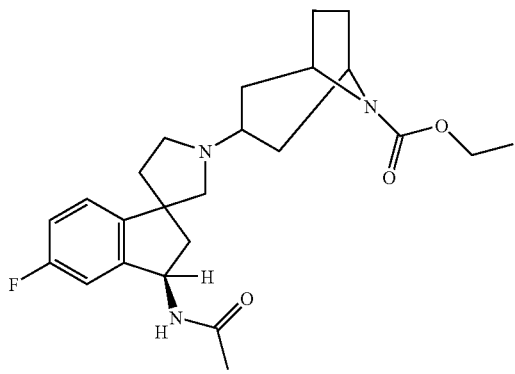
929
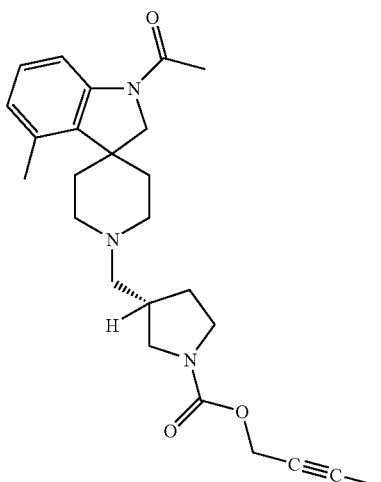
930
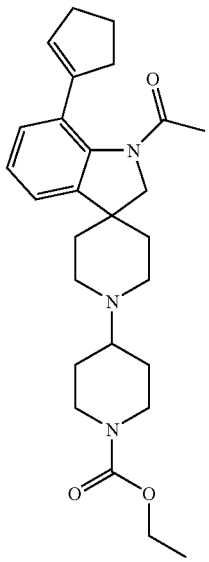 [SMILES: CCOC(=O)N1CCC(N2CCC3(CC2)CN(C(C)=O)c2c(C4=CCCC4)cccc23)CC1]
931
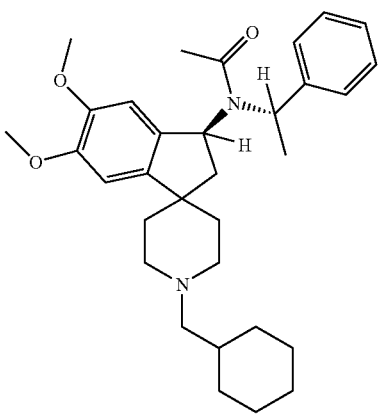 [SMILES: COc1cc2c(cc1OC)C1(CCN(CC3CCCCC3)CC1)C[C@@H]2N(C(C)=O)[C@@H](C)c1ccccc1]
932
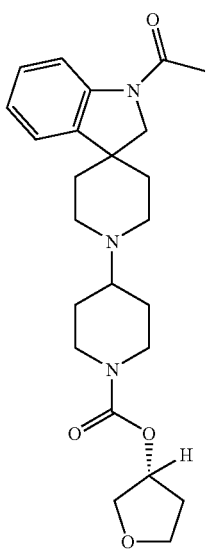 [SMILES: CC(=O)N1CC2(CCN(C3CCN(C(=O)O[C@@H]4CCOC4)CC3)CC2)c2ccccc21]

US 8,367,691 B2
381                                                                                                      382
TABLE 1-continued
Exemplary compounds of formula I.
933
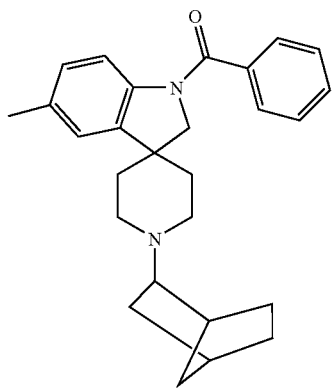
934
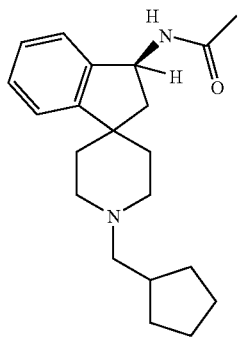
935
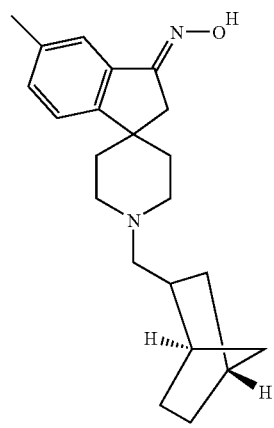
936
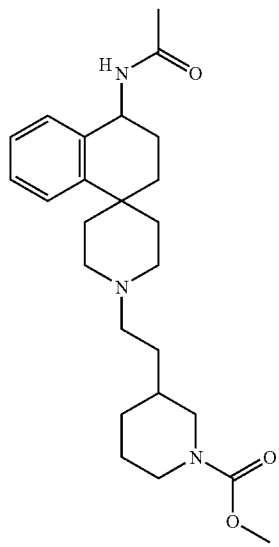
937
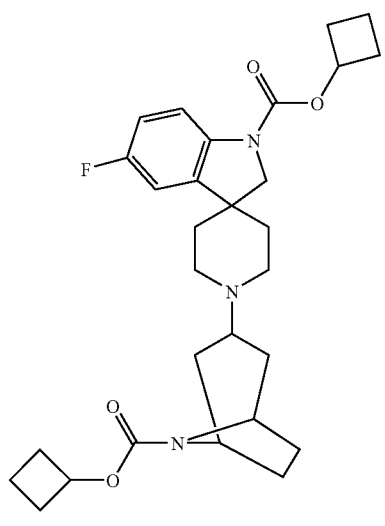 [SMILES: O=C(OC1CCC1)N1CC2(CCN(C3CC4CCC(C3)N4C(=O)OC3CCC3)CC2)c2cc(F)ccc21]
938
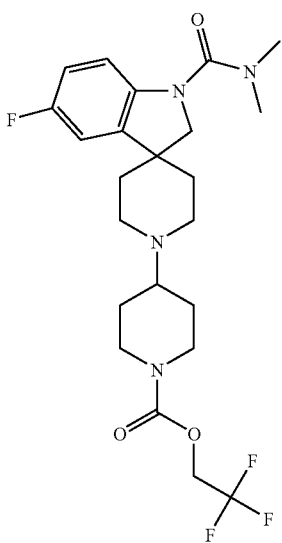 [SMILES: CN(C)C(=O)N1CC2(CCN(C3CCN(C(=O)OCC(F)(F)F)CC3)CC2)c2cc(F)ccc21]

TABLE 1-continued
Exemplary compounds of formula I.
939
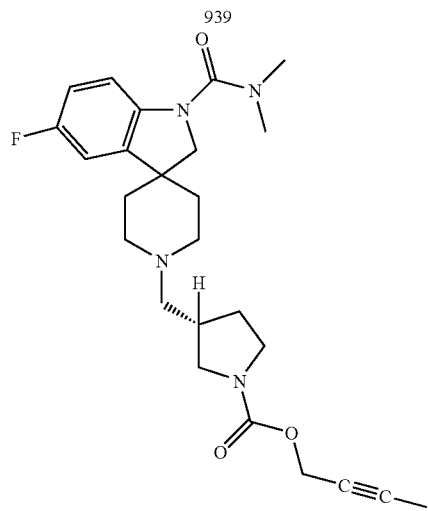
940
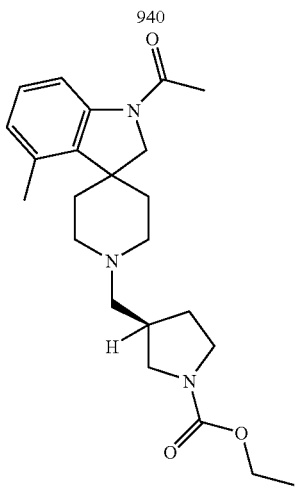
941
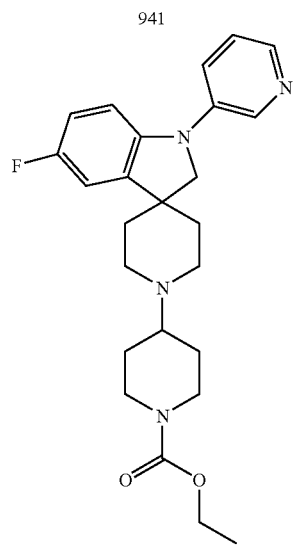
942
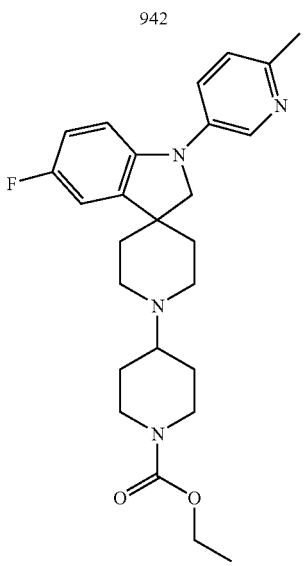
943
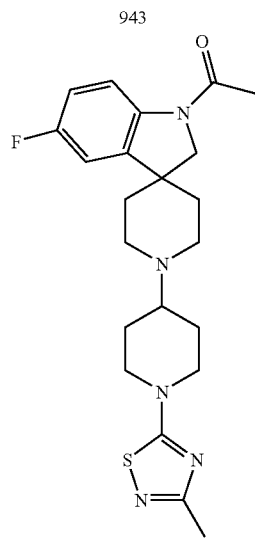
944
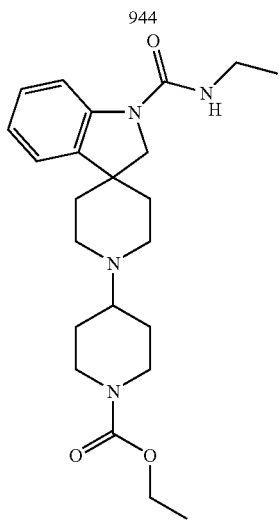

TABLE 1-continued
Exemplary compounds of formula I.
945
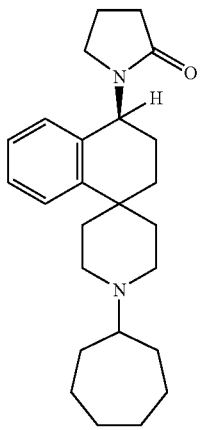 [SMILES: O=C1CCCN1[C@H]1CCC2(CCN(C3CCCCCC3)CC2)c2ccccc21]
946
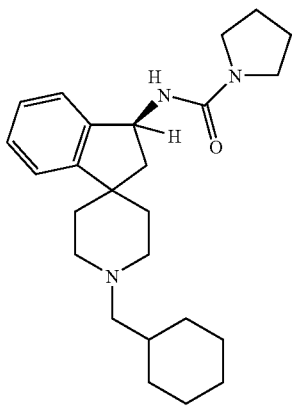
947
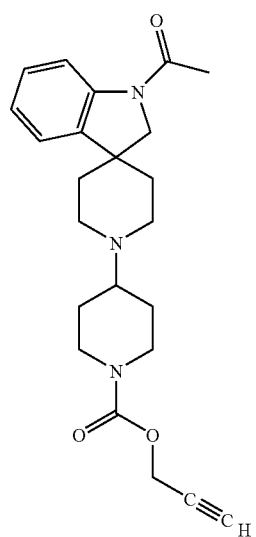
948
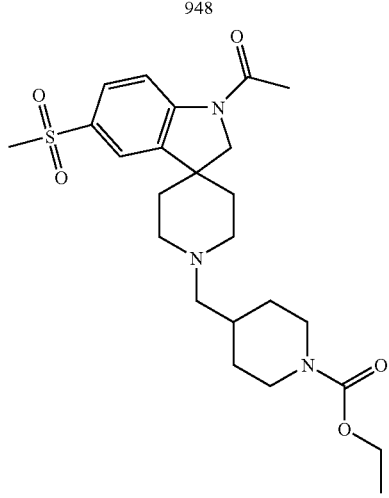
949
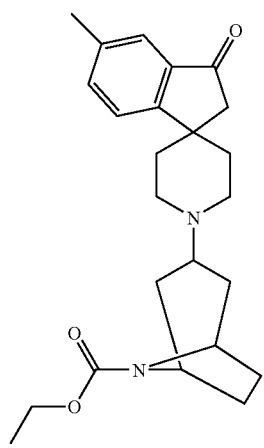 [SMILES: CCOC(=O)N1C2CCC1CC(N1CCC3(CC1)CC(=O)c1cc(C)ccc13)C2]
950
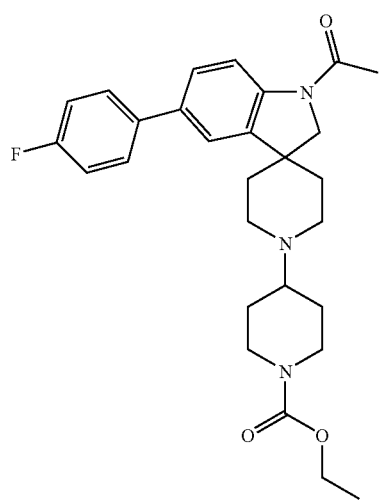 [SMILES: CCOC(=O)N1CCC(N2CCC3(CC2)CN(C(C)=O)c2ccc(-c4ccc(F)cc4)cc23)CC1]

TABLE 1-continued
Exemplary compounds of formula I.
951
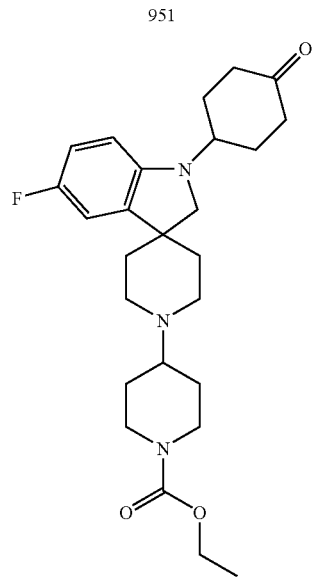
952
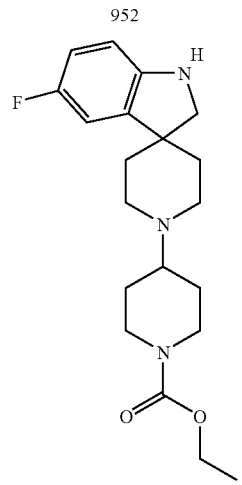
953
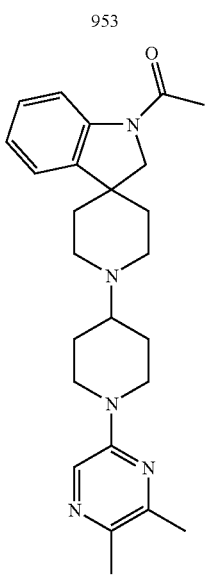
954
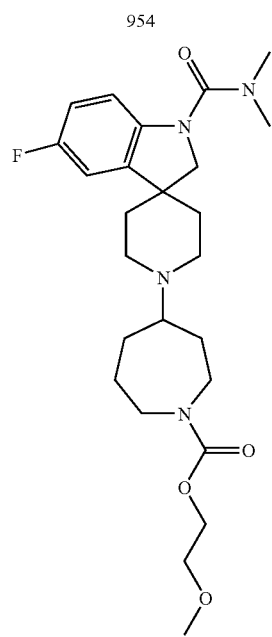

TABLE 1-continued
Exemplary compounds of formula I.
955
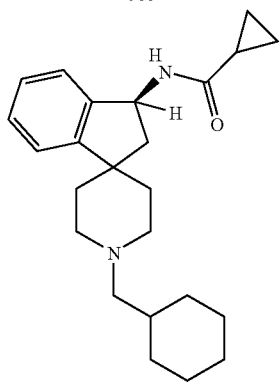
956
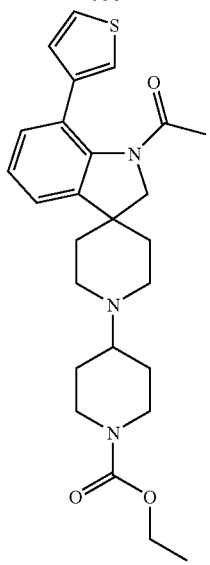
957
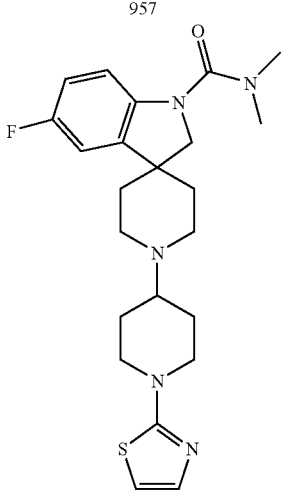
958
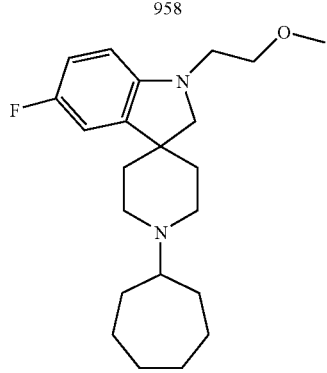
959
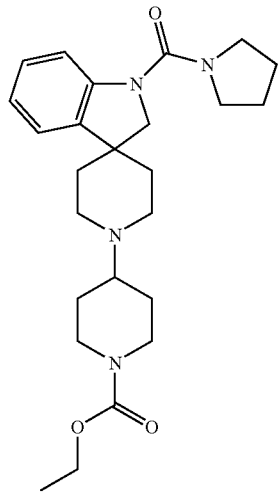 [SMILES: CCOC(=O)N1CCC(N2CCC3(CC2)CN(C(=O)N2CCCC2)c2ccccc23)CC1]
960
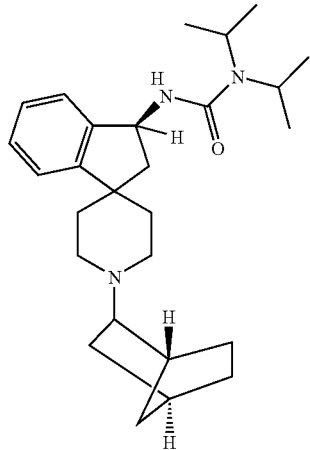

TABLE 1-continued
Exemplary compounds of formula I.
961
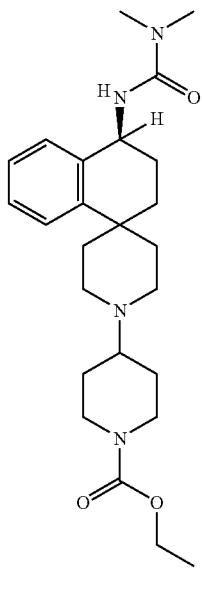
962
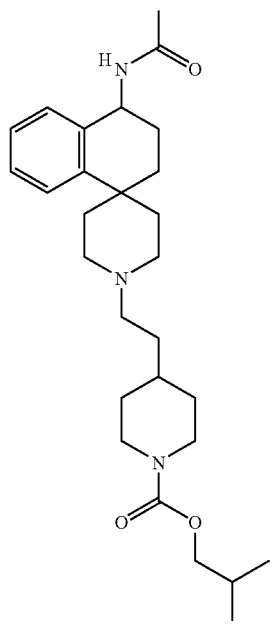
963
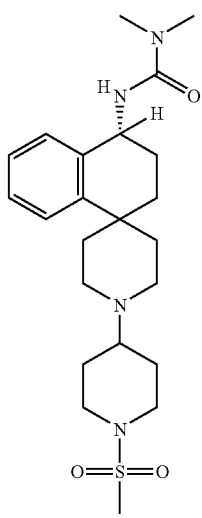
964
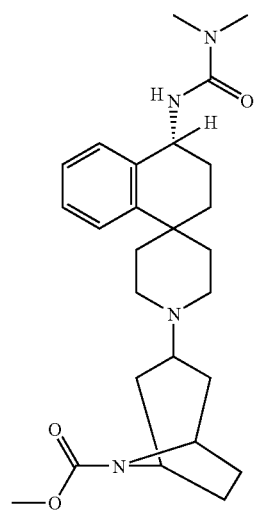

TABLE 1-continued
Exemplary compounds of formula I.
965
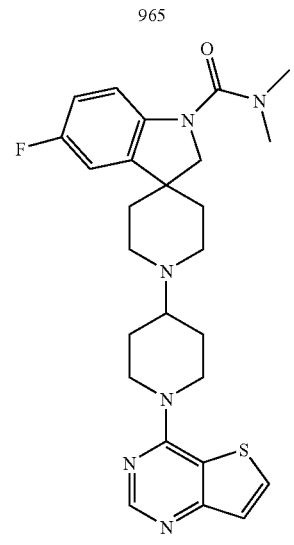
966
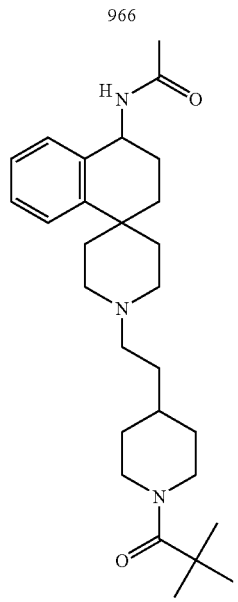
967
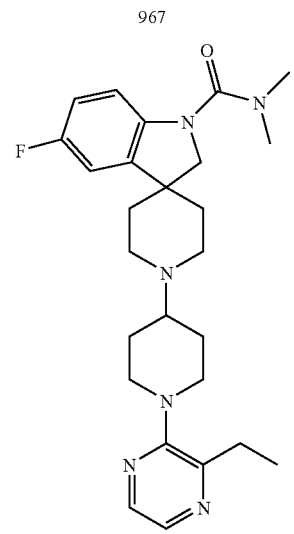
968
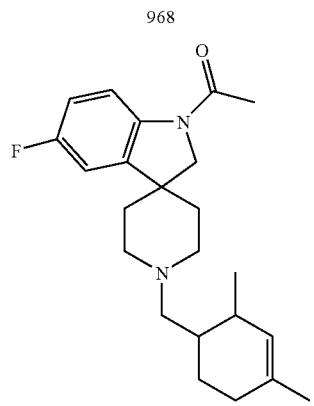

TABLE 1-continued
Exemplary compounds of formula I.
969
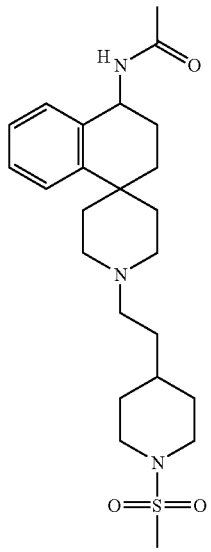
970
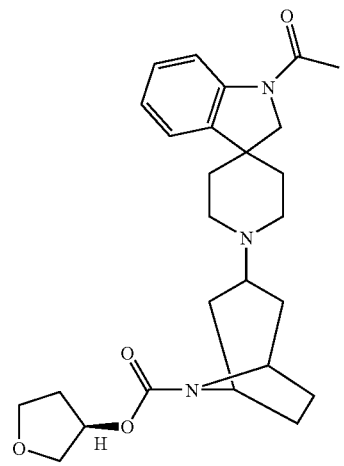
971
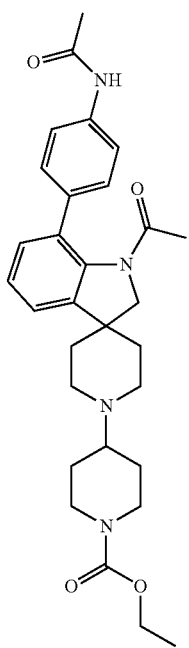 [SMILES: CCOC(=O)N1CCC(N2CCC3(CC2)CN(C(C)=O)c2c(-c4ccc(NC(C)=O)cc4)cccc23)CC1]
972
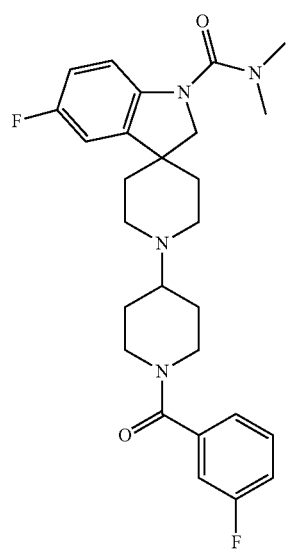 [SMILES: CN(C)C(=O)N1CC2(CCN(C3CCN(C(=O)c4cccc(F)c4)CC3)CC2)c2cc(F)ccc21]

TABLE 1-continued
Exemplary compounds of formula I.
973
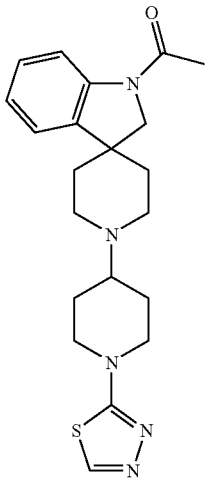 [SMILES: CC(=O)N1CC2(CCN(C3CCN(c4nncs4)CC3)CC2)c2ccccc21]
974
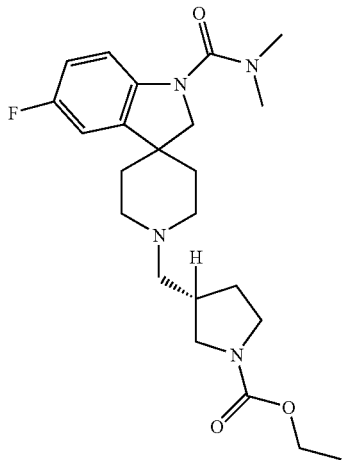 [SMILES: CCOC(=O)N1CC[C@@H](CN2CCC3(CC2)CN(C(=O)N(C)C)c2ccc(F)cc23)C1]
975
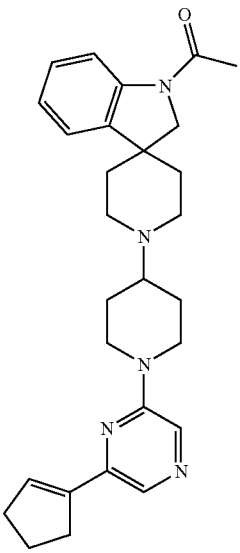 [SMILES: CC(=O)N1CC2(CCN(C3CCN(c4cncc(C5=CCCC5)n4)CC3)CC2)c2ccccc21]
976
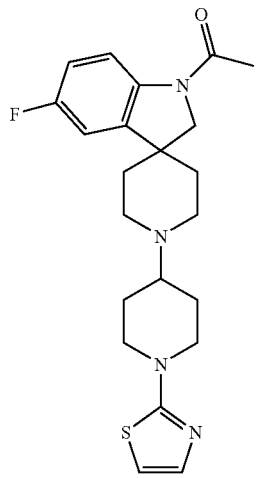 [SMILES: CC(=O)N1CC2(CCN(C3CCN(c4nccs4)CC3)CC2)c2cc(F)ccc21]
977
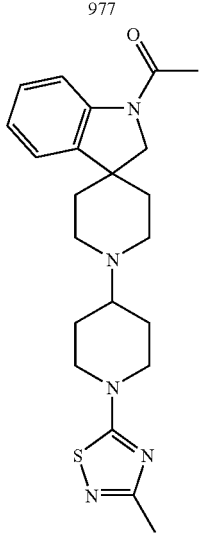
978
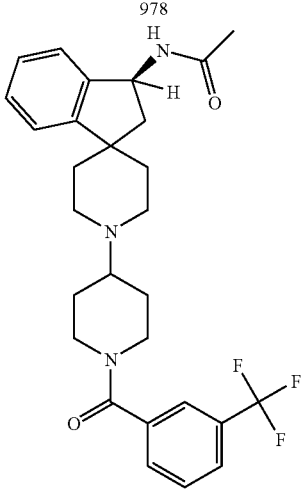

TABLE 1-continued
Exemplary compounds of formula I.
979
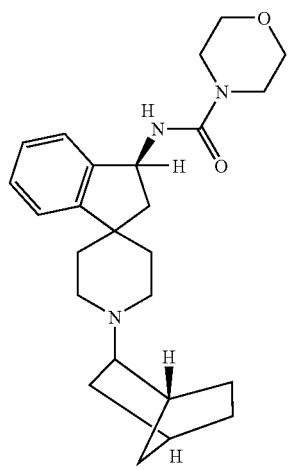
980
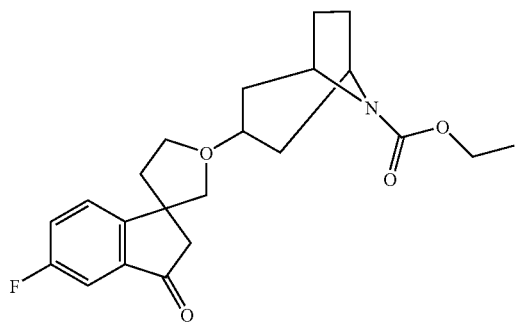
981
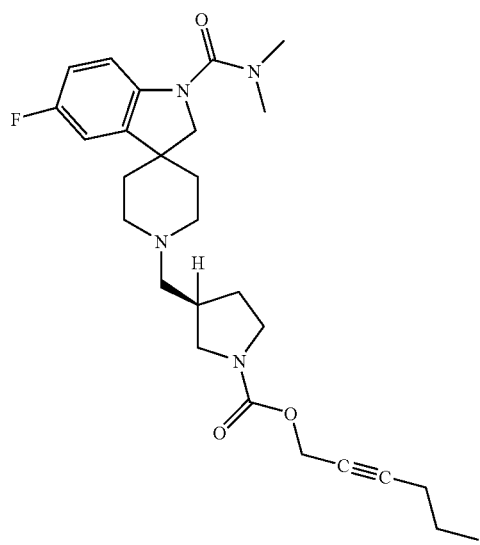 [SMILES: CCCC#CCOC(=O)N1CC[C@H](CN2CCC3(CC2)CN(C(=O)N(C)C)c2ccc(F)cc23)C1]
982
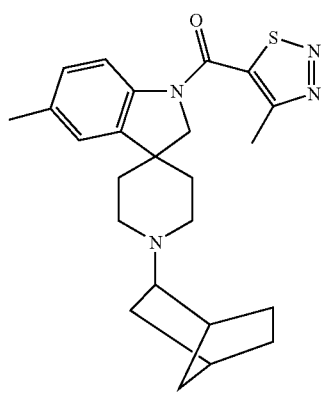 [SMILES: Cc1ccc2c(c1)C1(CCN(C3CC4CCC3C4)CC1)CN2C(=O)c1snnc1C]
983
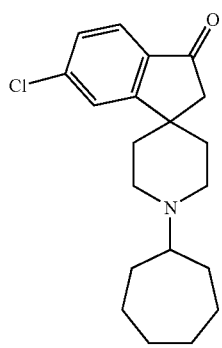 [SMILES: O=C1CC2(CCN(C3CCCCCC3)CC2)c2cc(Cl)ccc21]
984
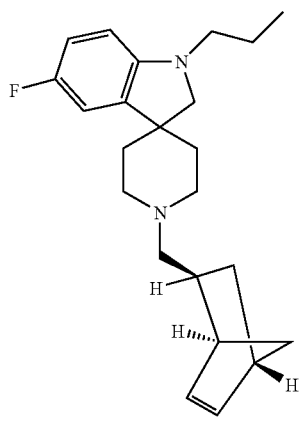 [SMILES: CCCN1CC2(CCN(C[C@H]3C[C@H]4C=C[C@@H]3C4)CC2)c2cc(F)ccc21]

TABLE 1-continued
Exemplary compounds of formula I.
985
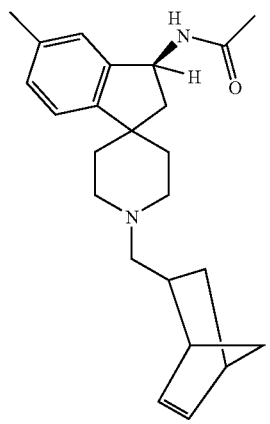
986
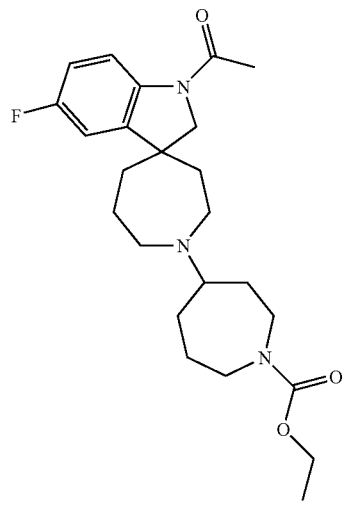 [SMILES: CCOC(=O)N1CCCC(N2CCCC3(CC2)CN(C(C)=O)c2ccc(F)cc23)CC1]
987
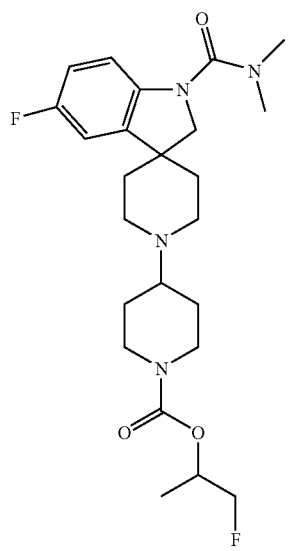 [SMILES: CC(CF)OC(=O)N1CCC(N2CCC3(CC2)CN(C(=O)N(C)C)c2ccc(F)cc23)CC1]
988
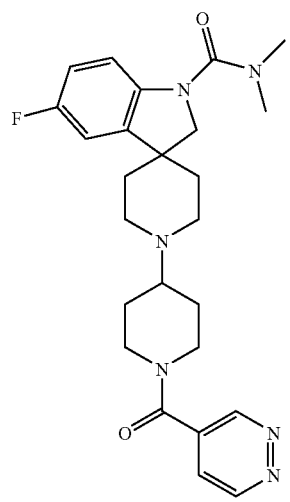 [SMILES: CN(C)C(=O)N1CC2(CCN(C3CCN(C(=O)c4ccnnc4)CC3)CC2)c2cc(F)ccc21]

TABLE 1-continued
Exemplary compounds of formula I.
989
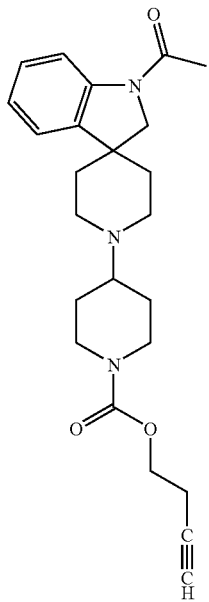 [SMILES: C#CCCOC(=O)N1CCC(N2CCC3(CC2)CN(C(C)=O)c2ccccc23)CC1]
990
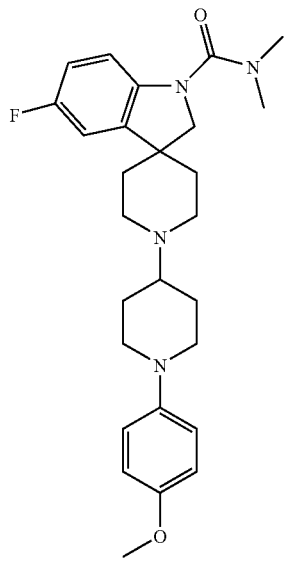 [SMILES: COc1ccc(N2CCC(N3CCC4(CC3)CN(C(=O)N(C)C)c3ccc(F)cc34)CC2)cc1]
991
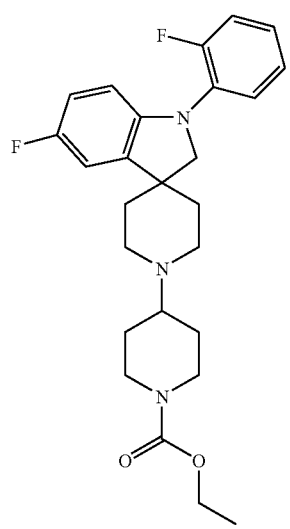 [SMILES: CCOC(=O)N1CCC(N2CCC3(CC2)CN(c2ccccc2F)c2ccc(F)cc23)CC1]
992
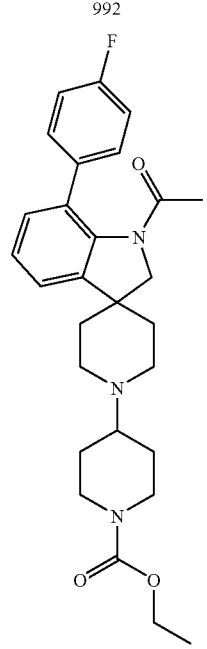

TABLE 1-continued
Exemplary compounds of formula I.
993
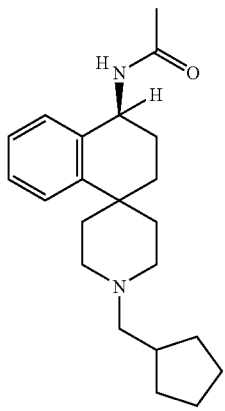
994
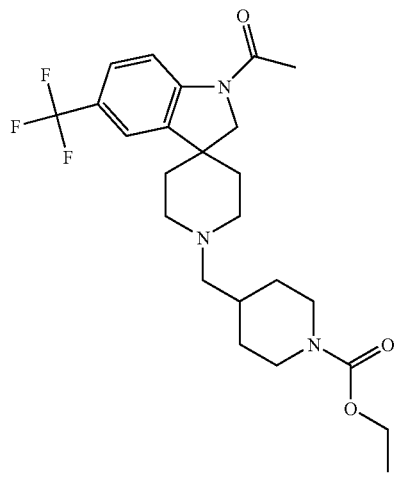 [SMILES: CCOC(=O)N1CCC(CN2CCC3(CC2)CN(C(C)=O)c2ccc(C(F)(F)F)cc23)CC1]
995
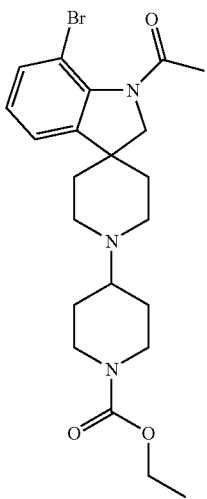 [SMILES: CCOC(=O)N1CCC(N2CCC3(CC2)CN(C(C)=O)c2c(Br)cccc23)CC1]
996
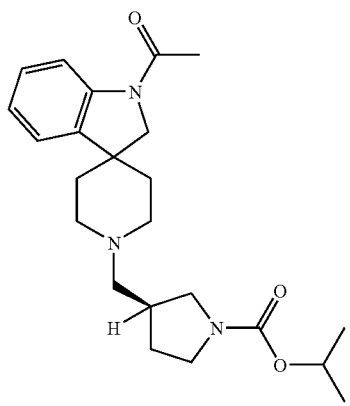 [SMILES: CC(=O)N1CC2(CCN(C[C@@H]3CCN(C(=O)OC(C)C)C3)CC2)c2ccccc21]
997
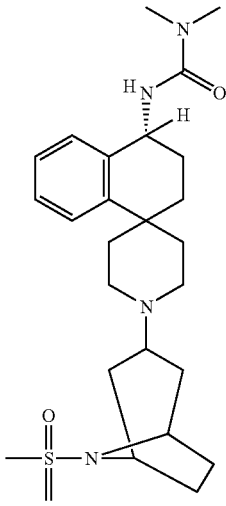
998
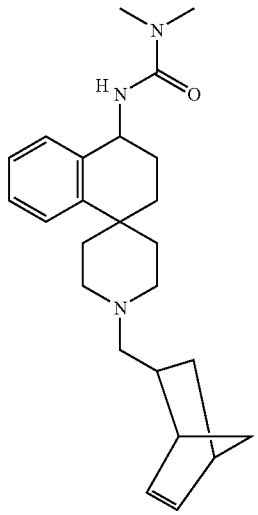

TABLE 1-continued
Exemplary compounds of formula I.
999
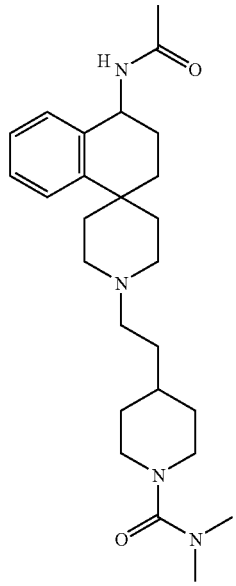
1000
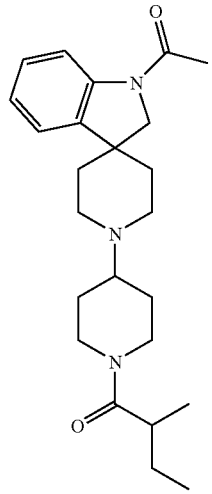 [SMILES: CCC(C)C(=O)N1CCC(N2CCC3(CC2)CN(C(C)=O)c2ccccc23)CC1]
1001
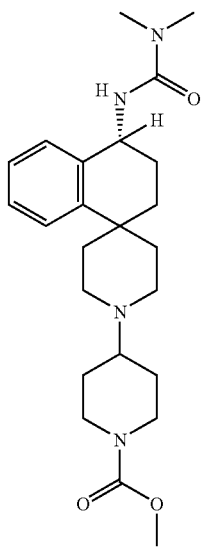
1002
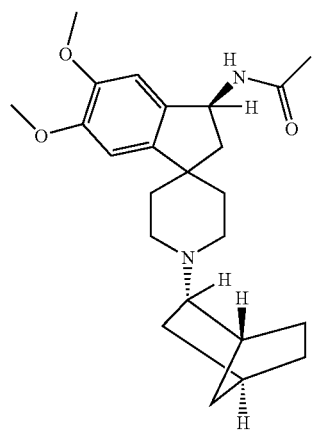

TABLE 1-continued
Exemplary compounds of formula I.
1003
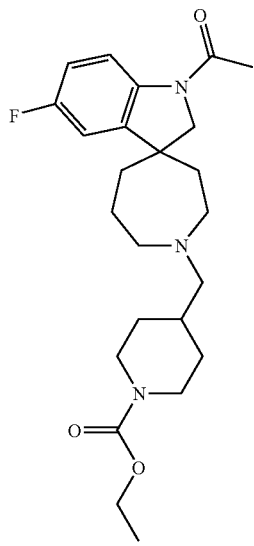 [SMILES: CCOC(=O)N1CCC(CN2CCCC3(CC2)CN(C(C)=O)c2ccc(F)cc23)CC1]
1004
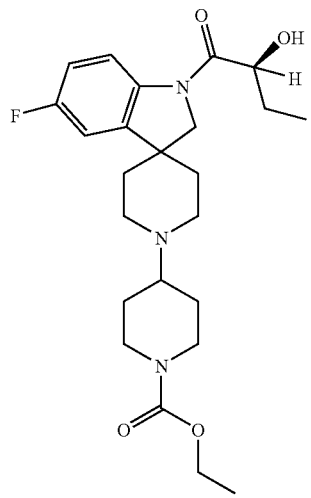 [SMILES: CCOC(=O)N1CCC(N2CCC3(CC2)CN(C(=O)[C@@H](O)CC)c2ccc(F)cc23)CC1]
1005
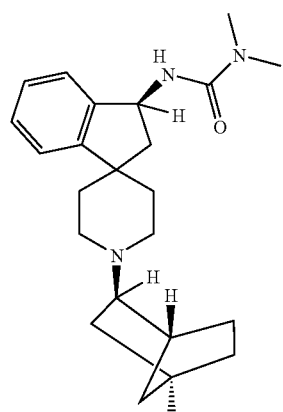
1006
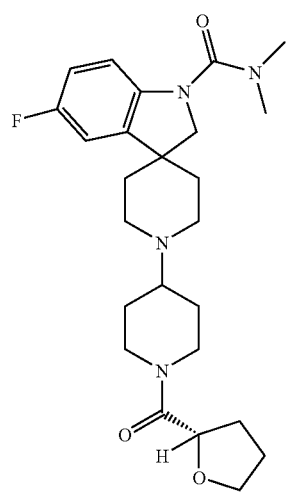 [SMILES: CN(C)C(=O)N1CC2(CCN(C3CCN(C(=O)[C@@H]4CCCO4)CC3)CC2)c2cc(F)ccc21]

TABLE 1-continued
Exemplary compounds of formula I.
1007
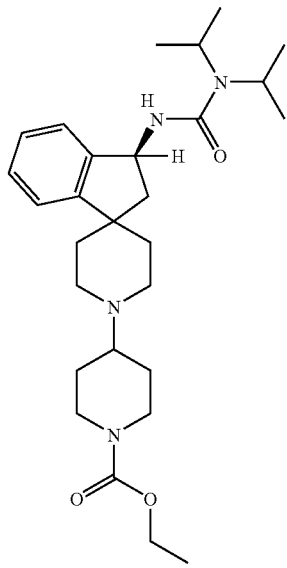
1008
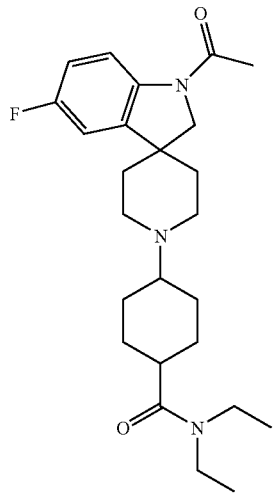 [SMILES: CCN(CC)C(=O)C1CCC(N2CCC3(CC2)CN(C(C)=O)c2ccc(F)cc23)CC1]
1009
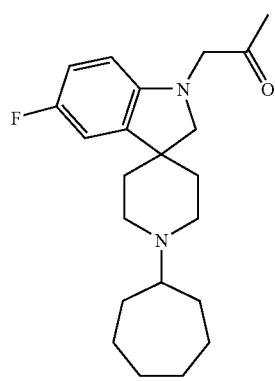 [SMILES: CC(=O)CN1CC2(CCN(C3CCCCCC3)CC2)c2cc(F)ccc21]
1010
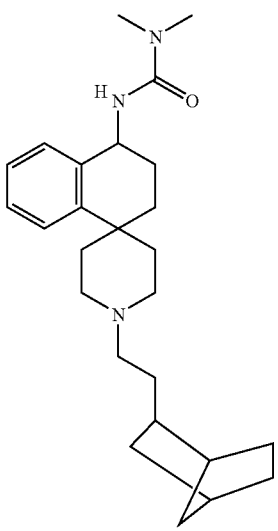

TABLE 1-continued
Exemplary compounds of formula I.
1011
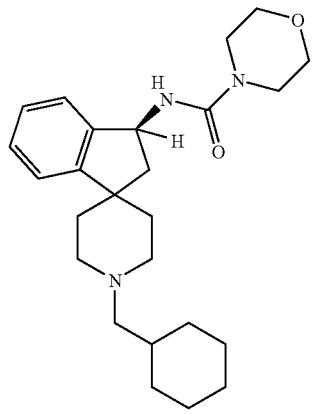
1012
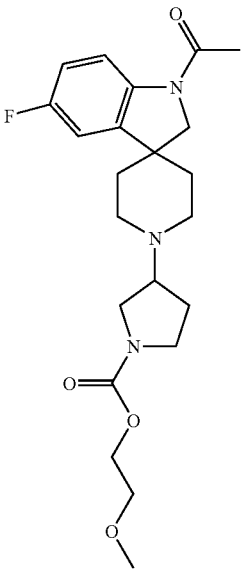 [SMILES: COCCOC(=O)N1CCC(N2CCC3(CC2)CN(C(C)=O)c2ccc(F)cc23)C1]
1013
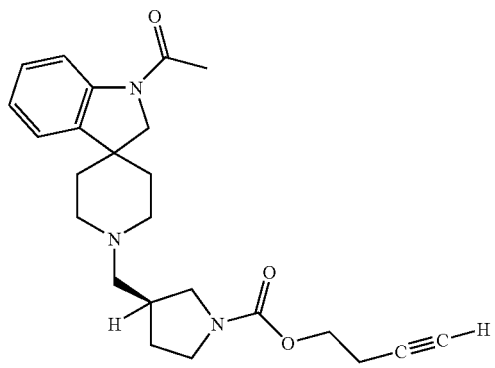 [SMILES: C#CCCOC(=O)N1CC[C@@H](CN2CCC3(CC2)CN(C(C)=O)c2ccccc23)C1]
1014
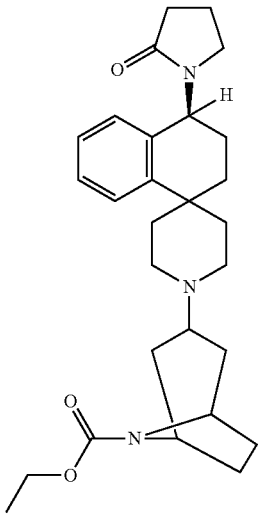 [SMILES: CCOC(=O)N1C2CCC1CC(N1CCC3(CC[C@H](N4CCCC4=O)c4ccccc43)CC1)C2]
1015
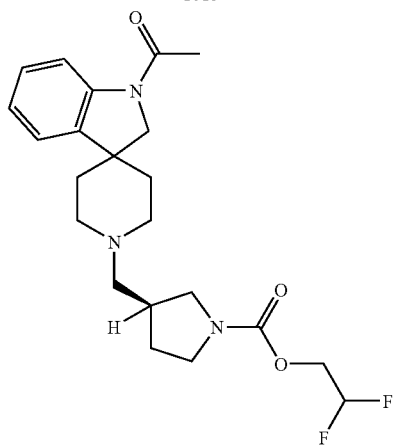 [SMILES: CC(=O)N1CC2(CCN(C[C@@H]3CCN(C(=O)OCC(F)F)C3)CC2)c2ccccc21]
1016
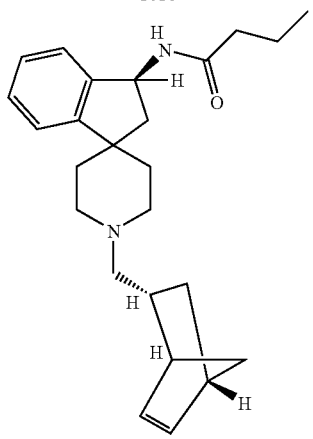

TABLE 1-continued
Exemplary compounds of formula I.
1017
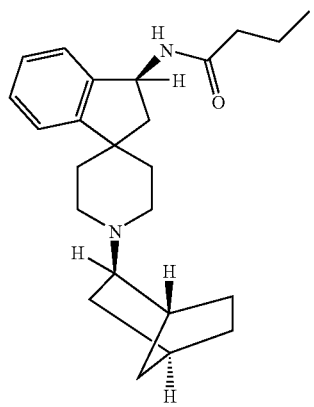
1018
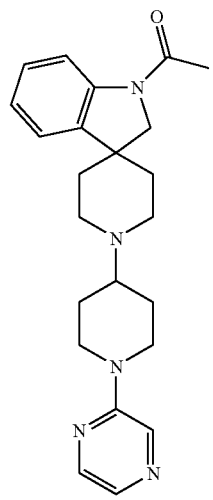 [SMILES: CC(=O)N1CC2(CCN(C3CCN(c4cnccn4)CC3)CC2)c2ccccc21]
1019
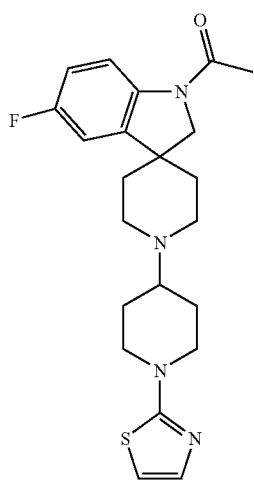 [SMILES: CC(=O)N1CC2(CCN(C3CCN(c4nccs4)CC3)CC2)c2cc(F)ccc21]
1020
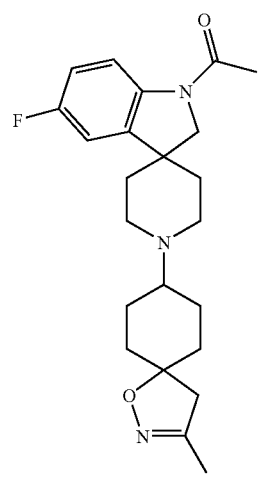 [SMILES: CC(=O)N1CC2(CCN(C3CCC4(CC3)CC(C)=NO4)CC2)c2cc(F)ccc21]
1021
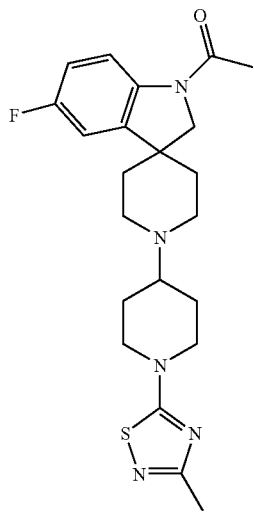 [SMILES: CC(=O)N1CC2(CCN(C3CCN(c4nc(C)ns4)CC3)CC2)c2cc(F)ccc21]
1022
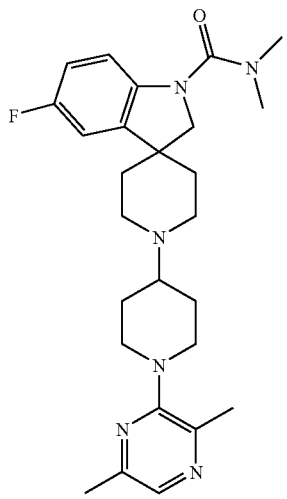 [SMILES: Cc1cnc(C)c(N2CCC(N3CCC4(CC3)CN(C(=O)N(C)C)c3ccc(F)cc34)CC2)n1]

TABLE 1-continued
Exemplary compounds of formula I.
1023
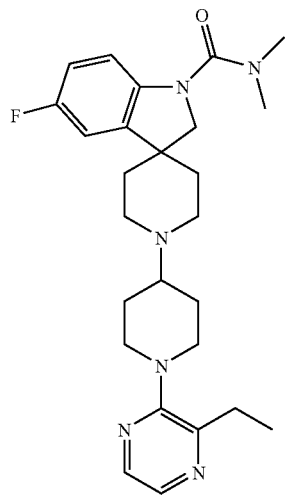 [SMILES: CCc1nccnc1N1CCC(N2CCC3(CC2)CN(C(=O)N(C)C)c2ccc(F)cc23)CC1]
1024
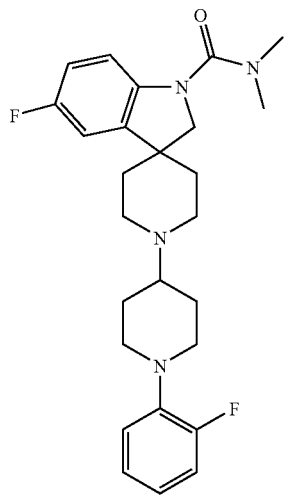 [SMILES: CN(C)C(=O)N1CC2(CCN(C3CCN(c4ccccc4F)CC3)CC2)c2cc(F)ccc21]
1025
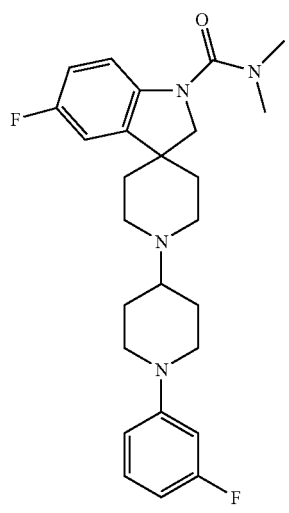 [SMILES: CN(C)C(=O)N1CC2(CCN(C3CCN(c4cccc(F)c4)CC3)CC2)c2cc(F)ccc21]
1026
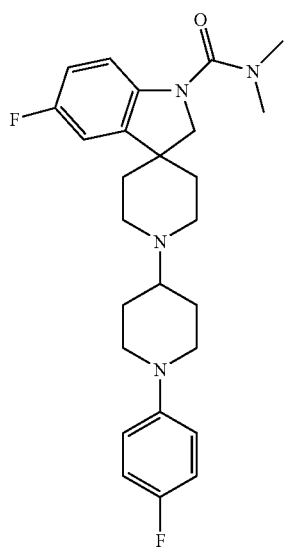 [SMILES: CN(C)C(=O)N1CC2(CCN(C3CCN(c4ccc(F)cc4)CC3)CC2)c2cc(F)ccc21]

TABLE 1-continued
Exemplary compounds of formula I.
1027
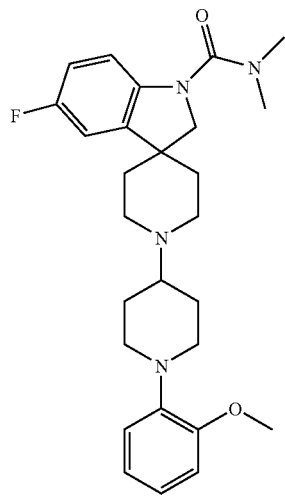 [SMILES: COc1ccccc1N1CCC(N2CCC3(CC2)CN(C(=O)N(C)C)c2ccc(F)cc23)CC1]
1028
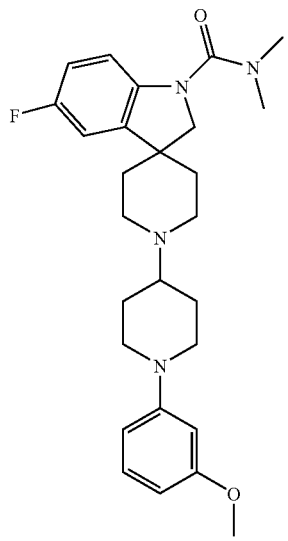 [SMILES: COc1cccc(N2CCC(N3CCC4(CC3)CN(C(=O)N(C)C)c3ccc(F)cc34)CC2)c1]
1029
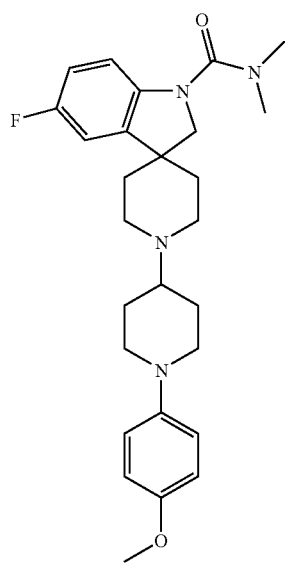 [SMILES: COc1ccc(N2CCC(N3CCC4(CC3)CN(C(=O)N(C)C)c3ccc(F)cc34)CC2)cc1]
1030
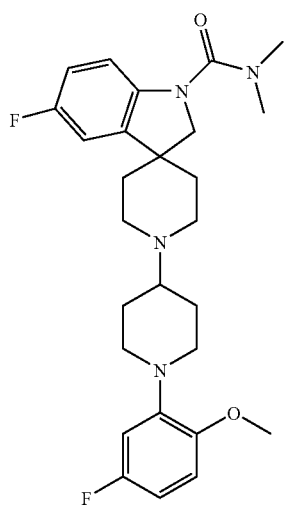 [SMILES: COc1ccc(F)cc1N1CCC(N2CCC3(CC2)CN(C(=O)N(C)C)c2ccc(F)cc23)CC1]

TABLE 1-continued
Exemplary compounds of formula I.
1031
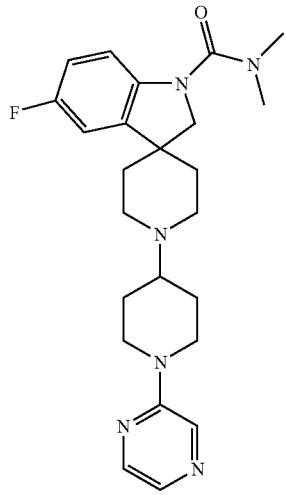 [SMILES: CN(C)C(=O)N1CC2(CCN(C3CCN(c4cnccn4)CC3)CC2)c2cc(F)ccc21]
1032
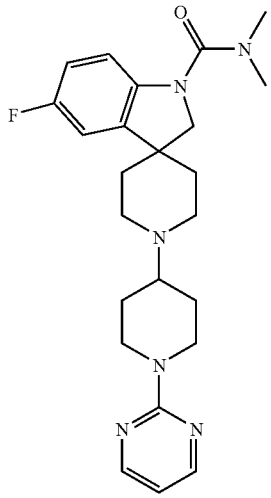
1033
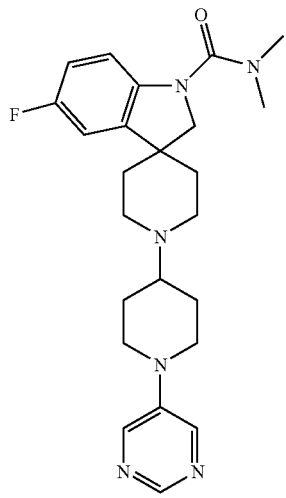
1034
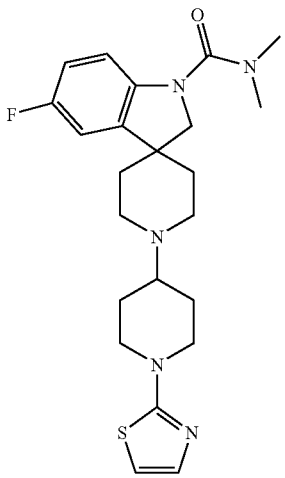 [SMILES: CN(C)C(=O)N1CC2(CCN(C3CCN(c4nccs4)CC3)CC2)c2cc(F)ccc21]
1035
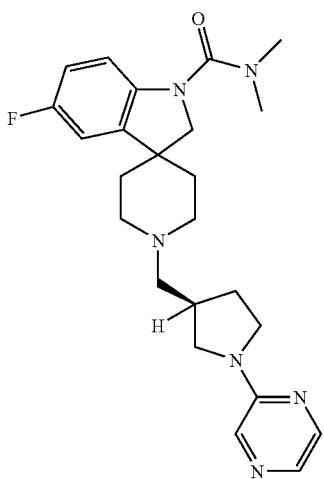 [SMILES: CN(C)C(=O)N1CC2(CCN(C[C@H]3CCN(c4cnccn4)C3)CC2)c2cc(F)ccc21]
1036
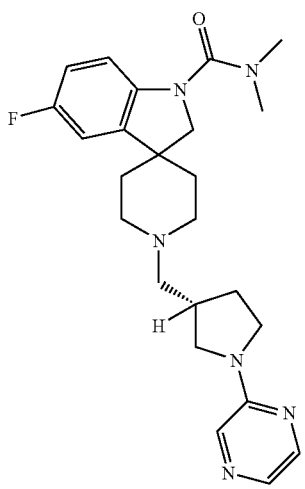 [SMILES: CN(C)C(=O)N1CC2(CCN(C[C@@H]3CCN(c4cnccn4)C3)CC2)c2cc(F)ccc21]

TABLE 1-continued
Exemplary compounds of formula I.
1037
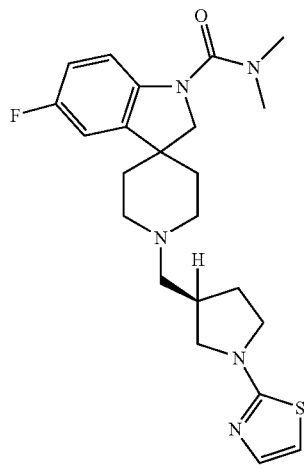 [SMILES: CN(C)C(=O)N1CC2(CCN(C[C@H]3CCN(c4nccs4)C3)CC2)c2cc(F)ccc21]
1038
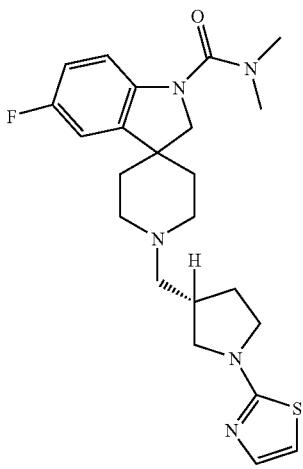 [SMILES: CN(C)C(=O)N1CC2(CCN(C[C@@H]3CCN(c4nccs4)C3)CC2)c2cc(F)ccc21]
1039
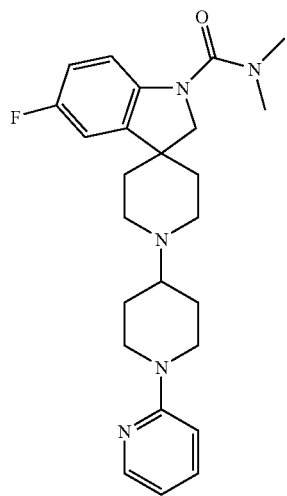
1040
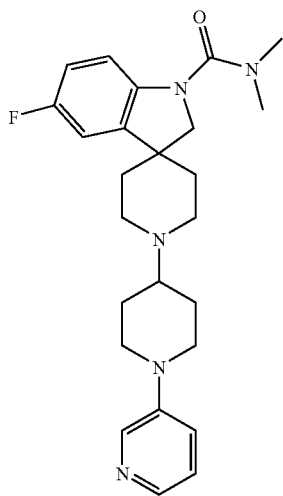
1041
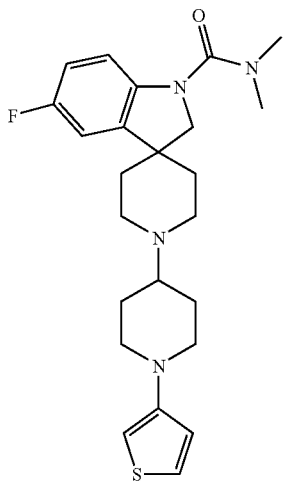 [SMILES: CN(C)C(=O)N1CC2(CCN(C3CCN(c4ccsc4)CC3)CC2)c2cc(F)ccc21]

IV. Synthetic Schemes

The compounds of formulae (I and II) may be readily synthesized from commercially available starting materials using methods known in the art. Exemplary synthetic routes to produce compounds of formulae (I and II), are provided below in Preparations A-F and Schemes 1-10. For simplicity of illustration, schemes 1-11 depict only a single $R_1$ substituent on the fused phenyl ring of formulae I and II, the compounds of this invention may include 1 to 4 $R_1$ substituents on the fused phenyl ring.

Scheme 1 below depicts general conditions for the synthesis of compounds of formula (I).

Scheme 1:

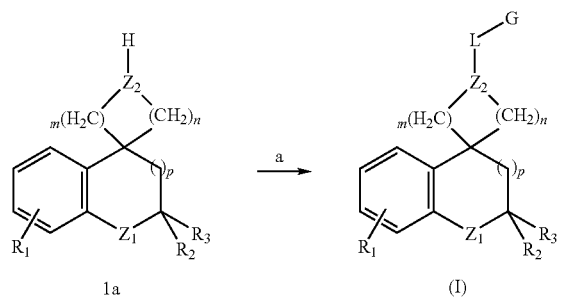

The reaction of amine 1a with an appropriate aldehyde or ketone under reductive amination conditions (step a), typically using $NaBH(OAc)_3$ in DCE/AcOH/TEA at room temperature, may be used to provide the desired compounds of formula I. For less reactive ketones, more forcing conditions may be used. For example, the treatment of the amine 1a and the ketone in a neat solution of $Ti(O^iPr)_4$, followed by treatment with $NaBH_4$ in MeOH, may be used to provide the desired compounds of formula I. See Abdel-Magid, A. F. et al., "Reductive Amination of Aldehydes and Ketones with Sodium Triacetoxyborohydride. Studies on Direct and Indirect Reductive Amination Procedures," *J. Org. Chem.*, 61, pp. 3849-3862 (1996) and the references sited therein.

Alternatively, the spiroamine of type I a may be alkylated with an alkyl halide in the presence of an appropriate base to provide the desired compounds of formula I. Typically, the amine 1a is reacted with an alkyl iodide, bromide, or chloride in the presence of an appropriate base to yield compounds of formula I. Bases may be organic such as triethylamine, or inorganic such as $Na_2CO_3$ or $Cs_2CO_3$. Typical reaction solvents include but are not limited to DMF, acetone, and acetonitrile.

Scheme 2 illustrates alternative conditions for the synthesis of compounds of formula I in which $Z_1$ is —C(H)$_2$— and $R_2$ and $R_3$ are hydrogen (Synthetic route A), or in which $Z_1$ is —C(O)— (Synthetic route B).

Scheme 2:

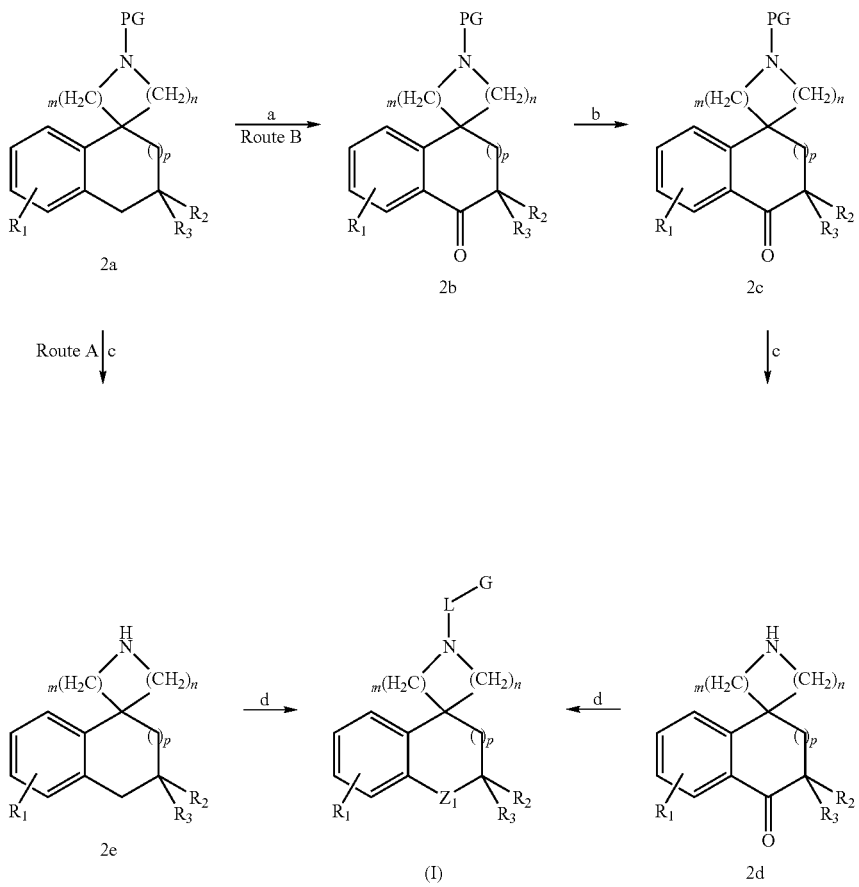

Compounds of type 2a in Scheme 2 may be prepared using procedures as described in Evans, B. E, et al., *J. Med. Chem.* 1992, 35, 3919 and M. S. Chambers *J. Med. Chem.* 1992, 35, 2033. Intermediate compounds may be produced from compound of type i using the following conditions: (a) KMnO$_4$ oxidation, TBAB, aqueous KOH (b) NaH, X—R$_2$ and/or X—R$_3$, THF (c) when PG is Cbz or Bz, ammonium formate, MeOH, Pd/C, room temperature or heat; or Pd/C, MeOH, H$_2$; or if PG=Boc, then TFA, CH$_2$Cl$_2$, −10° C.; (d) NaBH(OAc)$_3$, DCE, AcOH, TEA, appropriate ketone or aldehyde; or i. neat Ti(O$^i$Pr)$_4$, appropriate ketone; ii. NaBH$_4$, MeOH; or the appropriate alkyl halide, Cs$_2$CO$_3$, acetonitrile, heat.

Scheme 3 illustrates alternative conditions for the synthesis of compounds of formula I in which Z$_1$ is —O— and R$_2$ and R$_3$ are hydrogen.

Scheme 3:

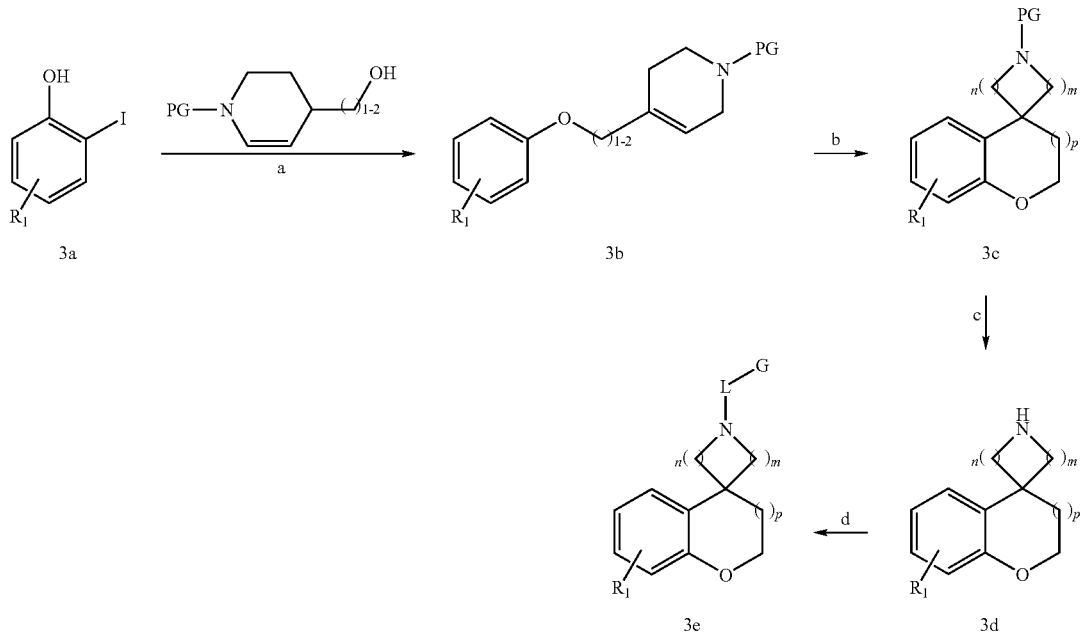

Amines of type 3e in Scheme 3 were prepared using procedures analogous to those found in the following references: WO 96/11934 "Tricyclic Spiro compounds process for their preparation" and US006013652A "Spiro-substituted azacyclics as neurokinin antagonists". Conditions: (a) Ph$_3$P/DEAD (b) Bu$_3$SnH, AIBN (c) ammonium formate, MeOH, Pd/C, room temperature or heat; or Pd/C, MeOH, H$_2$; or if PG=Boc, then TFA, CH$_2$Cl$_2$, −10° C.; (d) NaBH(OAc)$_3$, DCE, AcOH, TEA, appropriate ketone or aldehyde; or i. neat Ti(O$^i$Pr)$_4$, appropriate ketone; ii. NaBH$_4$, MeOH; or the appropriate alkyl halide, Cs$_2$CO$_3$, acetonitrile, heat.

Scheme 4 illustrates alternative conditions for the synthesis of compounds of formula I in which Z$_1$ is —N(Q1)- and R$_2$ and R$_3$ are hydrogen.

Scheme 4:

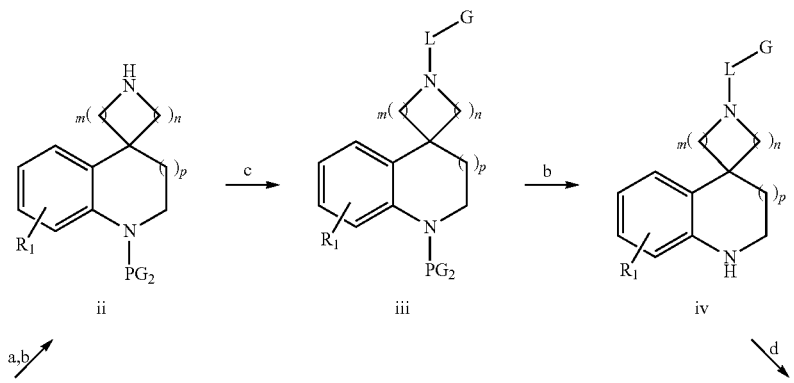

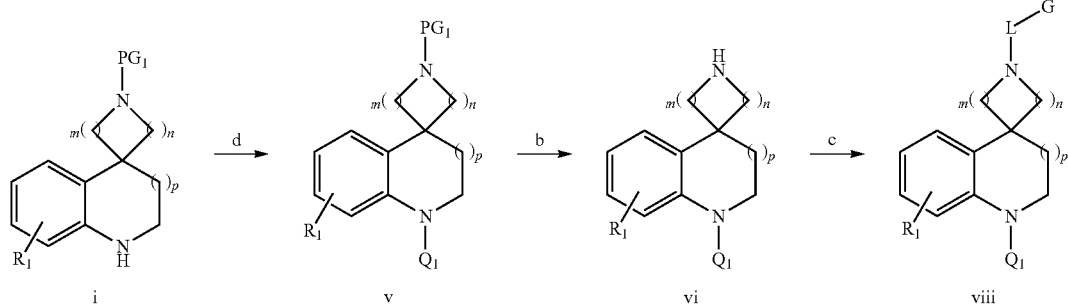

Amines of type i in Scheme 4 may be prepared from methods known in the art and by using procedures analogous to those found in the following references: WO 03/106457 "Spiroindolinepiperidine Derivatives"; Maligres, P. E., et al., *Tetrahedron*, 1997, 53, 10983-10992; Cheng, Y. and Chapman, K. T., *Tet. Lett.* 1997, 38, 1497-1500; US006013652A "Spiro-substituted azacyclics as neurokinin antagonists". Conditions: (a) amine protection orthoganol to $PG_1$; (b) amine deprotection of $PG_1$ (e.g. $PG_1$=Boc: TFA, $CH_2Cl_2$, −10° C.); (c) $NaBH(OAc)_3$, DCE, AcOH, TEA, appropriate ketone or aldehyde; or i. neat $Ti(OiPr)_4$, appropriate ketone; ii. $NaBH_4$, MeOH; or the appropriate alkyl halide, $Cs_2CO_3$, acetonitrile, heat; (d) $Q_2X$ ($Q_2$ may be, for example, H and aliphatic, X is halogen), $K_2CO_3$, DMF/THF, RT to 60° C.; or electrophile (e.g. $RSO_2Cl$, RCOCl, ROC($=$O)Cl, where R is H or $Q_2$, TEA, $CH_3CN$.

Scheme 5:

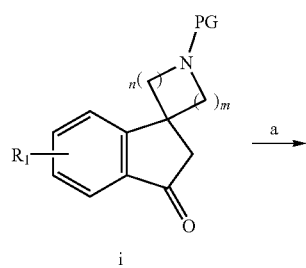

Reaction of i with intermediate under palladium cross coupling conditions (step a) $Pd(dppf)Cl2$ or $(Ph_3P)_4Pd$, 2M $K_2CO_3$, and acetonitrile under microwave irradiation at 150° C. for 10-20 minutes yields compound ii. Unsaturated compounds of type ii may be further elaborated (e.g. reduction; oxidation) to provide additional compounds of formula (I).

Scheme 6 illustrates alternative conditions for the synthesis of compounds of formula I in which $Z_1$ is $-N(Q_1)-$ or $-N(Q_2)-$, $R_2$ and $R_3$ together form oxo, and p=1.

Scheme 6:

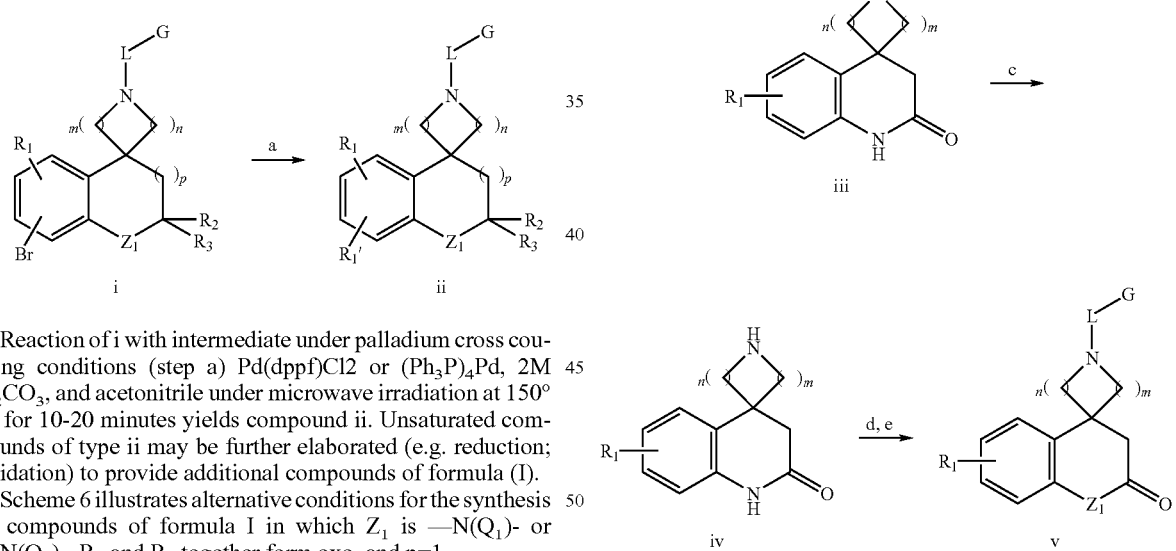

Compound i may be produced by methods disclosed above and by those known in the art. Intermediate compounds may be produced from compounds of type i using the following conditions: (a) $NH_2OH.HCl$; (b) 2,4,6-trichloro-1,3,5-triazine; (c) PG=Bn or Cbz; Ammonium formate, MeOH, Pd/C, room temperature; or Pd/C, MeOH, $H_2$; (d) $NaBH(OAc)_3$, DCE, AcOH, TEA, appropriate ketone or aldehyde; or i. neat $Ti(OiPr)_4$, appropriate ketone; ii. $NaBH_4$, MeOH; or the appropriate alkyl halide, $Cs_2CO_3$, acetonitrile, heat; (e) optional alkylation, NaH, THF, appropriate alkyl halide.

Scheme 7 illustrates alternative conditions for the synthesis of compounds of formula I in which $Z_1$ is $-CH(Q_1)-$ and $R_2$ and $R_3$ are hydrogen.

Scheme 7:

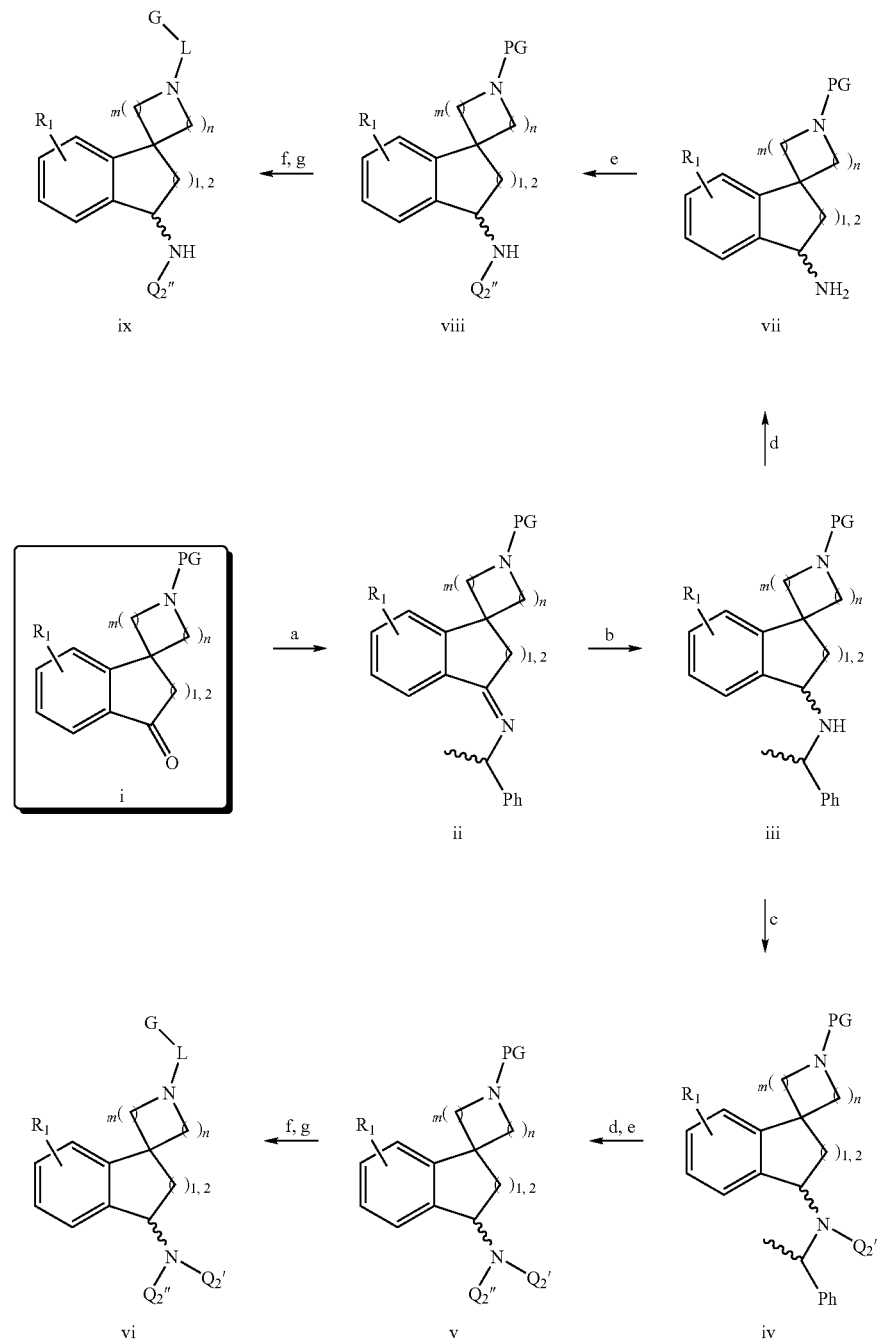

Compound i may be produced by methods disclosed above and by those known in the art. Compounds ii through ix may be produced from compound i using the following conditions: (a) ZnCl$_2$ or other Lewis acid, (R)- or (S)-1-phenylethanamine, PhCH$_3$ reflux, Dean-Stark; (b) NaBH$_4$, MeOH, −30° C.; (c) Q$_2$'X (Q$_2$' may be, for example, H and aliphatic, X is halogen), K$_2$CO$_3$, DMF/THF, RT to 60° C. (d) Ammonium formate, MeOH, Pd/C, room temperature; or Pd/C, MeOH, H$_2$; (e) electrophile (e.g. RSO$_2$Cl, RCOCl, ROC (=O)Cl, where R is H or alkyl, and Q$_2$" is RSO$_2$—, RC(O)—, ROC(O)—, TEA, CH$_3$CN; (f) PG=Boc: TFA, CH$_2$Cl$_2$, −10° C.; (g) NaBH(OAc)$_3$, DCE, AcOH, TEA, appropriate ketone or aldehyde; or i. neat Ti(OiPr)$_4$, appropriate ketone; ii. NaBH$_4$, MeOH; or the appropriate alkyl halide, Cs$_2$CO$_3$, acetonitrile, heat.

Scheme 8 illustrates alternative conditions as example for the synthesis of compounds of formula I in which Ring G contains or is substituted with a protected functionality which may be either be retained, deprotected and retained, or deprotected and further elaborated to produce additional compounds of formula I.

Scheme 8:

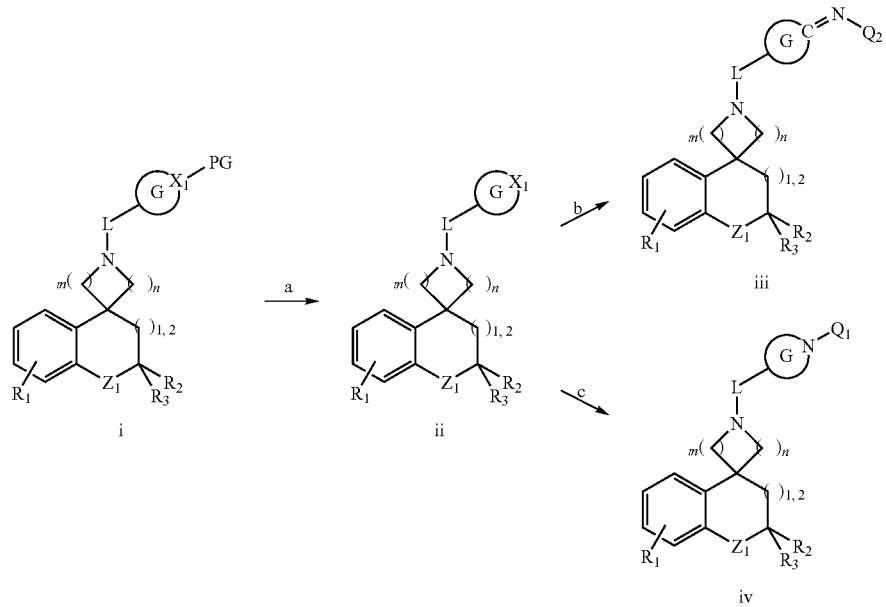

Compound i may be produced by methods disclosed above and by those known in the art. Compounds ii through iv may be produced from compound i using the following conditions: (a) e.g. PG=ketal: AcOH/H$_2$O, heat; PG=Boc: TFA, CH$_2$Cl$_2$; (b) e.g. if ring G is substituted by oxo, the compound of formula I may be further elaborated to the oxime: NH$_2$—O-Q$_2$, pyridine; (c) e.g. if ring G contains or is substituted by —NH— or —N(Q$_2$)-, it may be elaborated with an appropriate electrophile to produce iv.

Scheme 9 illustrates alternative conditions for the synthesis of compounds of formula I in which Z$_1$ is —N(Q$_1$)- or —N(Q$_2$)-, and R$_2$ and R$_3$ are oxo, and p=0.

Scheme 9:

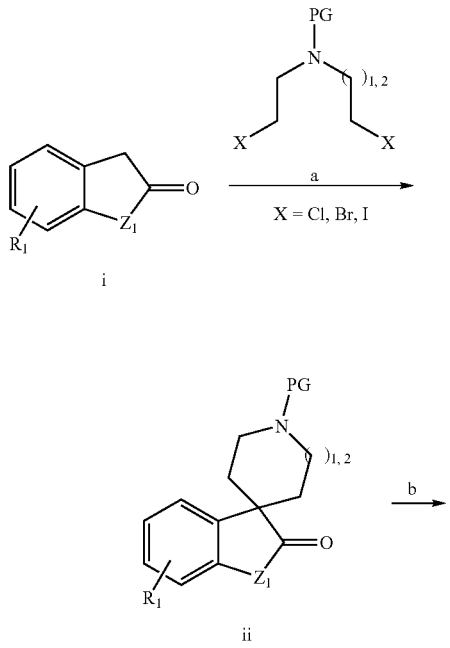

-continued

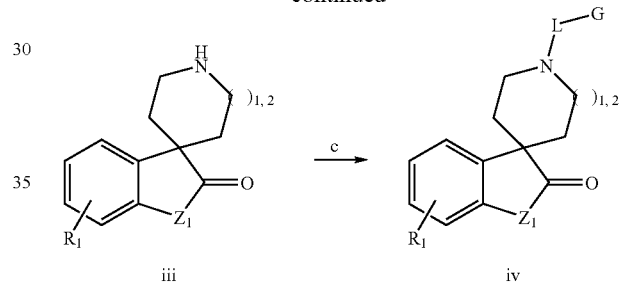

Compounds of type i may be purchased commercially or produced by methods known in the art. Conditions: (a) NaH/HMDS/THF; (b) e.g. PG=Bn: Pd(OH)$_2$; (c) NaBH(OAc)$_3$, DCE, AcOH, TEA, appropriate ketone or aldehyde; or i. neat Ti(OiPr)$_4$, appropriate ketone; ii. NaBH$_4$, MeOH; or the appropriate alkyl halide, Cs$_2$CO$_3$, acetonitrile, heat.

Scheme 10 outlines the general preparation of the appropriate aldehydes from the corresponding ketone.

Scheme 10:

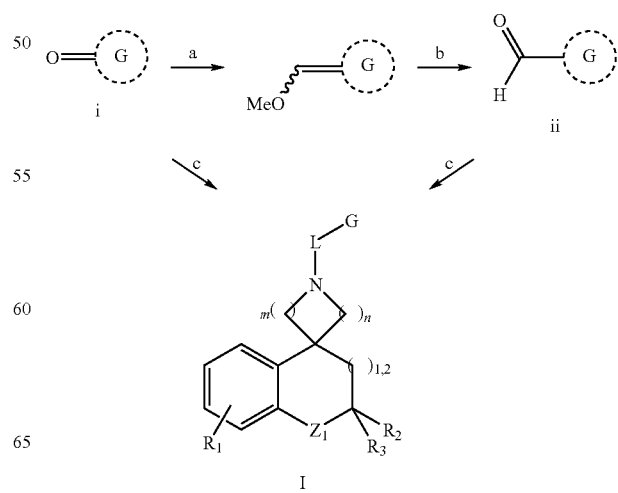

Ketone electrophiles of type i may be purchased commercially or produced by methods disclosed above and by those known in the art. Aldehydes of type ii may be purchased commercially or produced from compounds of type i using the following conditions: (a) $Ph_3P^+CH_2OMeCl^-$, NaN$(SiMe_3)_2$; (b) aqueous HCl, $CH_3CN$. The following conditions may be used for the synthesis of compounds of formula I using ketones of type i and aldehydes of type ii: (c) Spiroamine of type A (see Scheme 1), $NaBH(OAc)_3$, DCE, AcOH, TEA, appropriate ketone or aldehyde; or i. neat $Ti(OiPr)_4$, appropriate ketone; ii. $NaBH_4$, MeOH.

Scheme 11 illustrates conditions for the synthesis of compounds of formula I in which $Z_1$ is NH and $Q_2$ is aryl or heteroaryl.

Scheme 11:

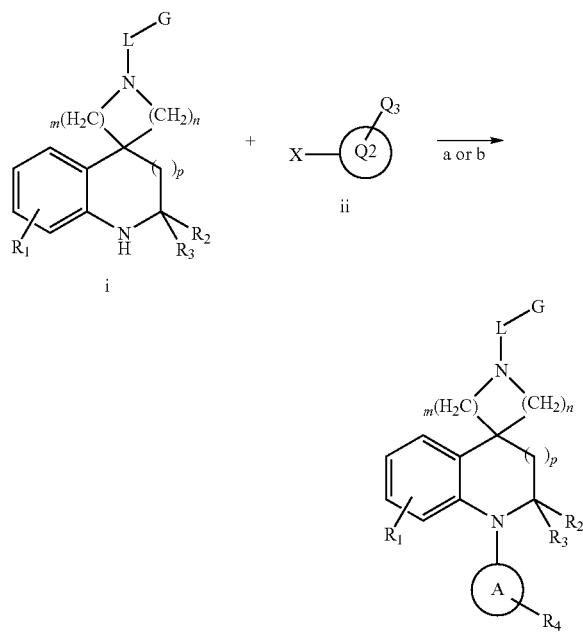

V. Formulations, Administrations, and Uses

The present invention includes within its scope pharmaceutically acceptable prodrugs of the compounds of the present invention. A "pharmaceutically acceptable prodrug" means any pharmaceutically acceptable salt, ester, salt of an ester, or other derivative of a compound of the present invention which, upon administration to a recipient, is capable of providing (directly or indirectly) a compound of this invention or an active metabolite or residue thereof. Preferred prodrugs are those that increase the bioavailability of the compounds of this invention when such compounds are administered to a mammal or which enhance delivery of the parent compound to a biological compartment relative to the parent species.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and $N^+(C_{1-4} alkyl)_4$ salts. This invention also envisions the quaternization of any basic nitrogen-containing groups of the compounds disclosed herein. Water or oil-soluble or dispersible products may be obtained by such quaternization.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

The amount of the compounds of the present invention that may be combined with the carrier materials to produce a composition in a single dosage form will vary depending upon the host treated, the particular mode of administration. Preferably, the compositions should be formulated so that a dosage of between 0.01-100 mg/kg body weight/day of the modulator can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Depending upon the particular condition, or disease, to be treated or prevented, additional therapeutic agents, which are normally administered to treat or prevent that condition, may also be present in the compositions of this invention. As used herein, additional therapeutic agents that are normally administered to treat or prevent a particular disease, or condition, are known as "appropriate for the disease, or condition, being treated."

According to a preferred embodiment, the compounds of formulae (I and II) are selective modulators of $M_1$, $M_2$ and $M_4$. More preferably, the compounds of formulae (I and II) are selective modulators of $M_1$ and/or $M_4$. Yet more preferably, certain compounds of formulae (I and II) are selective modulators of $M_1$. Or, preferably, certain compounds of formulae (I and II) are selective modulators of $M_4$.

Applicants believe that the ability of the compounds of the present invention to modulate the activity of muscarinic receptors is derived from the affinity of these compounds to the muscarinic receptors. Such affinity, applicants believe, activates a muscarinic receptor (i.e., an agonist) or inhibits the activity of a muscarinic receptor.

The term "selective" as used herein means a measurably greater ability to modulate one muscarinic receptor subtype when compared to the other muscarinic receptor subtypes. E.g., the term "selective $M_4$ agonist" means a compound that has a measurably greater ability to act as an $M_4$ agonist when compared to that compound's agonist activity with the other muscarinic receptor subtype(s).

According to an alternative embodiment, the present invention provides a method of treating a muscarinic receptor mediated disease in a mammal, such as a human, including the step of administering to said mammal a composition comprising a compound of formulae I and II, or an embodiment thereof as set forth herein.

According to another embodiment, the present invention provides a method of treating a disease mediated by a muscarinic receptor including the step of administering to said mammal a composition comprising a compound of formulae (I and II), or other embodiments thereof as set forth above. Preferably, said disease is mediated by $M_1$, or said disease is mediated by $M_4$.

According to yet another embodiment, the present invention provides a method of treating or reducing the severity of a disease in a patient, wherein said disease is selected from CNS derived pathologies including cognitive disorders, Attention Deficit Hyperactivity Disorder (ADHD), obesity, Alzheimer's disease, various dementias such as vascular dementia, psychosis including schizophrenia, mania, bipolar disorders, pain conditions including acute and chronic syndromes, Huntington's Chorea, Friederich's ataxia, Gilles de la Tourette's Syndrome, Downs Syndrome, Pick disease, clinical depression, sudden infant death syndrome, Parkinson's disease, peripheral disorders such as reduction of intra ocular pressure in Glaucoma and treatment of dry eyes and dry mouth including Sjögren's Syndrome, wherein said method comprises the step of contacting said patient with a compound according to the present invention.

According to an alternative embodiment, the present invention provides a method of treating or reducing the severity of a disease in a patient, wherein said disease is selected from pain, psychosis (including schizophrenia, hallucinations, and delusions), Alzheimer's disease, Parkinson's disease, glaucoma, bradhycardia, gastric acid secretion, asthma, or GI disturbances.

According to a preferred embodiment, the present invention is useful for treating or reducing the severity of psychosis, Alzheimer's disease, pain, or Parkinson's disease.

All references cited within this document are incorporated herein by reference.

VII. Preparation and Examples

In order that the invention described herein may be more fully understood, the following examples are set forth. It should be understood that these examples are for illustrative purposes only and are not to be construed as limiting this invention in any manner.

Preparation A: Synthesis of N-(ethoxycarbonyl)-8-aza-bicyclo[3.2.1]octane-3-carbaldehyde

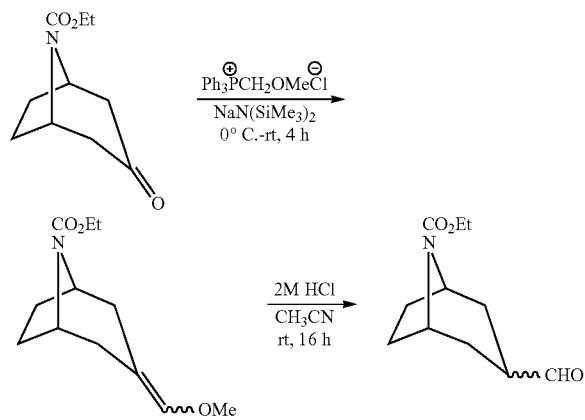

Sodium bis(trimethylsilyl)amide (6 mmol, 6 mL of 1 M solution in THF) was added to a suspension of 2.06 g (6.0 mmol) of methoxymethyltriphenylphosphonium chloride in 6 mL of THF at 0° C. under argon. After stirring at 0° C. for 15 min, the resulting dark red solution was added via syringe to a solution of 0.79 g (4.0 mmol) of N-(ethoxycarbonyl) tropinone (6) in 8 mL of THF at 0° C. and then stirred at room temperature for 4 h (an orange color persisted). The reaction mixture was quenched by adding sat. aq. NaCl (15 mL) and then extracted with ether (25 mL×3). The combined organic extracts were dried over $Na_2SO_4$. The solid residue obtained after solvent evaporation was loaded onto a short silica gel column (3.5 cm×4 cm) to remove the phosphorous impurities. The product was eluted with ether. After the solvent was evaporated, the product enol ether was obtained as a brown oil which was used in the next step without further purification.

The enol ether intermediate was dissolved in a solution of 12 mL of 2 N HCl and 20 mL of acetonitrile, and stirred at room temperature for 16 h. After removing the acetonitrile on a rotary evaporator, the aqueous solution was extracted with ether (25 mL×3). The combined organic extracts were washed with sat. aq. $NaHCO_3$ (15 mL×2), sat. aq. NaCl (15 mL) and then dried over $Na_2SO_4$. After the solution was evaporated to dryness, the residue was purified by chromatography ($SiO_2$, 10%-20% EtOAc in Hexane as eluent). N-(ethoxycarbonyl)-8-aza-bicyclo[3.2.1]octane-3-carbaldehyde was obtained as a colorless oil in an approximately 1:1 ratio of endo and exo isomers (77%). ESI-MS m/z 212.1 (MH$^+$); $^1$H NMR (300 MHz, CDCl$_3$) δ 9.53 (s, 1H), 4.54 (br s, 1H), 4.38 (br s, 1H), 4.16 (m, 2H), 2.72 (m, 2H), 2.38 (s, 1H), 2.32 (s, 1H), 2.10 (m, 3H), 1.69 (m, 2H), 1.29 (m, 3H).

Preparation B: Synthesis of bicyclo[3.2.1]octane-2-carbaldehyde

Bicyclo[3.2.1]octane-2-carbaldehyde was prepared using an analogous procedure as for Intermediate 1 from commercially available bicyclo[3.2.1]octan-2-one. The crude products were used in the next step without further purification.

Preparation C: Synthesis of 7-oxa-bicyclo[2.2.1]hept-5-ene-2-carbaldehyde

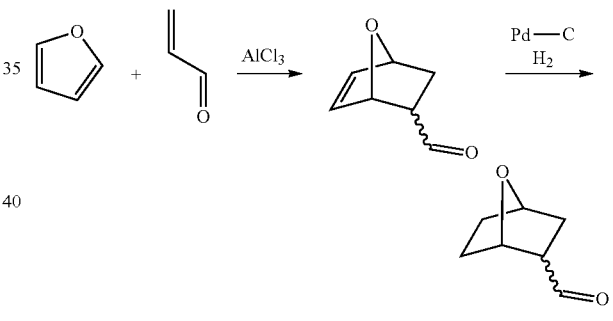

To a stirred solution of furan (9) (15 mL, 200 mmol) and acrolein (13) (6.7 mL, 100 mmol) in DCM (25 mL) was slowly added AlCl$_3$ (666 mg, 5 mmol) under argon at −43° C. (dry ice/isopropanol bath). The reaction mixture was stirred at −43° C. under argon for 30 min, and then quenched with sat. aq. $K_2CO_3$ (50 mL). After the reaction mixture was gradually warmed to room temperature, it was extracted with ether (200 mL×5). The combined ether extracts were washed with sat. aq. $K_2CO_3$ (200 mL×2) and sat. aq. NaCl (200 mL×2), dried over MgSO$_4$, filtered, and concentrated to give an oily crude product 7-oxa-bicyclo[2.2.1]hept-5-ene-2-carbaldehyde which was used in the next step without further purification. See references Laszlo, P.; Lucchetti, J. *Tetrahedron Lett.* 1984, 25, 4387-4388. Moore, J. A., Partain, E. M. III. *J. Org. Chem.* 1983, 48, 1105-1106. Dauben, W. G.; Krabbenhoft, H. O. *J. Am. Chem. Soc.* 1976, 98, 1992-1993. Nelson, W. L.; Allen, D. R.; Vincenzi, F. F. *J. Med. Chem.* 1971, 14, 698-702.

To a stirred solution of crude product 7-oxa-bicyclo[2.2.1] hept-5-ene-2-carbaldehyde (2.6 g. 20 mmol) in 95% EtOH (200 mL) was added 10% Pd—C (0.25 g) at room temperature under argon. The mixture was shaken on a Parr hydrogenation apparatus for 4 h at room temperature under 30 psi of hydrogen. After the Pd catalyst was removed by filtration through a Celite pad, the Celite was washed with MeOH (15 mL×2), the combined extracts were concentrated under vacuum to yield a crude 7-oxa-bicyclo[2.2.1]hept-5-ene-2-carbaldehyde as a pale yellow oil, which was used in the next step without further purification.

Preparation D: Synthesis of ethyl 4-formylpiperidine-1-carboxylate

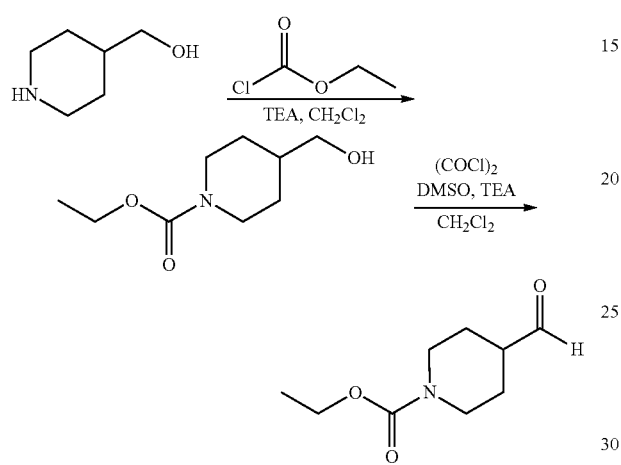

1.0 eq 4-piperidinemethanol (10.00 g, 86.8 mmol) was dissolved in dichloromethane (350 mL), cooled in an ice-$H_2O$ bath and treated dropwise with a solution of 1.05 eq ethyl chloroformate (9.89 g, 91.1 mmol) in dichloromethane (50 mL), followed by the dropwise addition of a solution of 1.0 eq triethylamine (8.78 g) in dichloromethane (50 mL). The reaction was stirred at –0° C. for 15 minutes, then at room temperature for 10 minutes. The reaction was diluted with dichloromethane (250 mL) and washed successively with (150 mL each) $H_2O$, 0.1 N HCl (aq) (×2), saturated brine, then dried ($Na_2SO_4$) and filtered. The filtrate was concentrated in vacuo to afford 15.60 g ethyl 4-(hydroxymethyl)-piperidine-1-carboxylate as a viscous, pale bluish-green oil. $^1$H-NMR (400 MHz, $CDCl_3$) δ 4.15 (br m, 2H), 4.09 (q,J=7.1 Hz, 2H), 3.46 (d, J=6.4 Hz, 2H), 2.72 (br t, J=12.4 Hz, 2H), 2.07 (s, 1H), 1.70 (m, 2H), 1.63 (m, 1H), 1.23 (t, J=7.2 Hz, 3H), 1.12 (m, 2H); $t_R$=1.56 min [10-99% $CH_3CN$ gradient over 5 mins with 0.1% TFA (aq)]; Theoretical $(M+H)^+$ m/z for $C_9H_{17}NO_3$=188.1; Found 188.0.

A solution of 1.2 eq oxalyl chloride (12.69 g, 0.10 mol) in dichloromethane (150 mL) was cooled to approximately –78° C. and treated dropwise, under nitrogen, with a solution of 2.4 eq anhydrous dimethylsulfoxide (15.63 g, 0.20 mol) in dichloromethane (50 mL). 15 minutes after the addition was complete, a solution of 1.0 eq ethyl 4-(hydroxymethyl)-piperidine-1-carboxylate (15.60 g, 83.3 mmol) in dichloromethane (50 mL) was added dropwise. 30 minutes after the addition was complete, a solution of 3.0 eq triethylamine (25.30 g, 0.25 mol) in dichloromethane (50 mL) was added dropwise and the reaction warmed to room temperature. The reaction was stirred at room temperature for 1 hour, then quenched with saturated sodium bicarbonate (500 mL). The layers were separated and the aqueous layer extracted once with dichloromethane (200 mL). The pooled organic layers were washed with $H_2O$ (3×100 mL), saturated sodium bicarbonate (1×100 mL) and saturated brine, then dried ($Na_2SO_4$) and filtered. The filtrate was concentrated in vacuo to afford 13.84 g ethyl 4-formylpiperidine-1-carboxylate as a viscous amber oil. $^1$H-NMR (400 MHz, $CDCl_3$) δ 9.64 (s, 1H), 4.10 (q, J=7.2 Hz, 2H), 4.00 (br m, 2H), 2.97 (m, 2H), 2.40 (m, 1H), 1.87 (br m, 2H), 1.54 (m, 2H), 1.23 (t, J=7.0 Hz, 3H).

Preparation E: Synthesis of ethyl 4-formyl-4-methylpiperidine-1-carboxylate

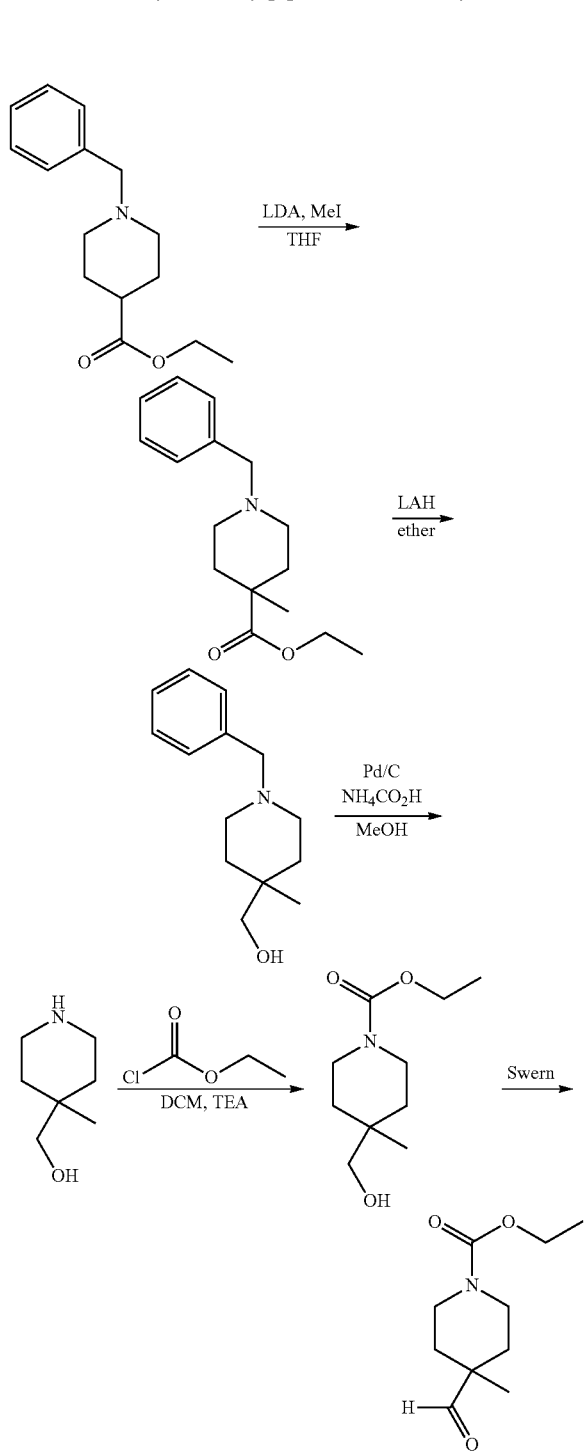

Diisopropylamine (3.14 mL; 22.23 mmol; 1.1 eq.) was dissolved in THF (60 mL) and cooled to –78° C. Butyl lithium (2.5 M in hexane; 8.89 mL; 22.23 mmol; 1.1 eq.) was then added and the solution was stirred for 30 minutes at −78° C. Ethyl 1-benzylpiperidine-4-carboxylate (5 g; 20.21 mmol; 1 eq.) was dissolved in THF (40 mL) and added to the LDA solution at −78° C. The solution was stirred at −78° C. for 30 minutes and iodomethane (1.32 mL; 21.22 mmol; 1.05 eq.) was added. The solution was slowly warmed to room temperature and stirred at room temperature for 1 hour. Water (100 mL) was then added to the reaction followed by EtOAc (50 mL). The layers were separated and the aqueous layer was extracted with EtOAc (2×50 mL). The combined organic layers were dried over $Na_2SO_4$, filtered, and concentrated under reduced pressure to afford the product as an oil. The product was analytically pure and used without further purification. LC/MS m/z (M+1) 262.0, Retention time 1.78 minutes; (10-99% $CH_3CN$—$H_2O$ gradient with 0.03% TFA, 5 min). $^1H$ NMR (400 MHz, $CDCl_3$) δ 7.24-7.14 (m, 5H), 4.08 (q, J=7.1 Hz, 2H), 3.40 (s, 2H), 2.60-2.57 (m, 2H), 2.08-2.02 (m, 4H), 1.47-1.40 (m, 2H), 1.17 (t, J=7.1 Hz, 3H), 1.10 (s, 3H).

1-Benzyl-4-methylpiperidine-4-carboxylate (5.0 g; 19.15 mmol) was dissolved in $Et_2O$ (50 mL) and cooled to 0° C. $LiAlH_4$ (1.0 g; 26.3 mmol) was slowly added portion-wise to the solution. After the addition was complete, the solution was slowly warmed to room temperature and stirred for 1 h. The solution was then cooled to 0° C. and slowly quenched with 1N NaOH (6 mL). The resultant white precipitates were filtered and washed with EtOAc (100 mL). The combined organic layers were concentrated under reduced pressure to provide the product as an oil that was used without further purification. LC/MS m/z M+1 220.0, retention time 0.64 minutes; (10-99% $CH_3CN$—$H_2O$ gradient with 0.03% TFA, 5 min). $^1H$ NMR (400 MHz, $CDCl_3$) δ 7.25-7.16 (m, 5H), 3.46 (s, 2H), 3.30 (d, J=3.9 Hz, 2H), 2.51-2.46 (m, 2H), 2.26-2.20 (m, 2H), 1.52-1.45 (m, 3H), 1.30-1.25 (m, 2H), 0.87 (s, 3H).

(1-benzyl-4-methylpiperidin-4-yl)methanol (3.9 g; 17.8 mmol) was dissolved in MeOH (50 mL) and $NH_4CO_2H$ (12.5 g; 178.0 mmol) was added. Pd/C (10% by weight, wet; 5.5 g) was then added and the system was flushed with nitrogen and then with hydrogen. The reaction was stirred at room temperature overnight (18 hours) and then filtered through a pad of Celite. The solvent was removed under high vacuum to provide a solid that was a mixture of the amino alcohol and $NH_4CO_2H$. The crude product (2.4 g as a mixture with $NH_4COOH$) was used in the next step without further purification. LC/MS m/z (M+1) 130.0, retention time 0.35 min; (10-99% $CH_3CN$—$H_2O$ gradient with 0.03% TFA, 5 min). $^1H$ NMR (400 MHz, $CDCl_3$) δ 3.17 (s, 2H), 3.03-2.98 (m, 2H), 2.95-2.88 (m, 2H), 1.64-1.57 (m, 2H), 1.36-1.31 (m, 2H), 0.89 (s, 3H).

(4-methylpiperidin-4-yl)methanol (2.4 g, a mixture of the amino alcohol and $NH_4CO_2H$) was suspended in DCM (70 mL). $Et_3N$ (5 mL; 37.2 mmol) was then added followed by the drop-wise addition of ethyl chloroformate (1.05 mL, 13 mmol, 1.4 eq.). After 1 hour at room temperature, 1N HCl (70 mL) was added and the layers were separated. The aqueous layer was extracted with DCM (70 mL) and the combined organic layers were dried over $Na_2SO_4$, filtered, and concentrated under high vacuum. The product is obtained as an analytically pure oil and used without further purification. LC/MS m/z (M+1) 202.2, retention time 1.89 minutes; (10-99% $CH_3CN$—$H_2O$ gradient with 0.03% TFA, 5 min). $^1H$ NMR (400 MHz, DMSO-$d_6$) δ 4.05 (q, J=7.1 Hz, 2H), 3.66 (dt, J=13.6, 4.7 Hz, 2H), 3.32 (s, 2H), 3.11 (t, J=5.2 Hz, 1H), 3.11 (dd, J=23.9, 3.5 Hz, 1H), 1.44-1.37 (m, 3H), 1.26-1.22 (m, 2H), 1.19 (t, J=7.1 Hz, 3H), 0.93 (s, 3H).

To a 100 mL round bottom flask was added DCM (30 mL) and oxalyl chloride (0.88 mL; 10.13 mmol). The solution was cooled to −78° C. and treated with DMSO (1.19 mL; 16.88 mmol). The solution was stirred at −78° C. for 20 minutes and then treated with ethyl 4-(hydroxymethyl)-4-methylpiperidine-1-carboxylate (1.7 g; 8.44 mmol, dissolved in 10 mL of DCM). The solution was stirred for 30 minutes at −78° C. and then treated with $Et_3N$ (3.53 mL; 25.32 mmol). The solution was stirred at −78° C. for 20 min and then slowly warmed to room temperature and stirred at room temperature for an additional 2 hours. The solution was then treated with saturated aqueous $NaHCO_3$ (50 mL), diluted with DCM (50 mL), and the layers were separated. The organic layer was washed with brine (50 mL), dried over $Na_2SO_4$, filtered, and concentrated under reduced pressure to afford the product as an oil that was used without further purification. LC/MS m/z (M+1) 200.0, retention time 2.23 minutes; (10-99% $CH_3CN$—$H_2O$ gradient with 0.03% TFA, 5 min). $^1H$ NMR (400 MHz, $CDCl_3$) δ 9.40 (s, 1H), 4.06 (q, J=7.1 Hz, 2H), 3.66 (dt, J=13.6, 4.7 Hz, 2H), 3.09 (dd, J=10.1, 3.5 Hz, 1H), 3.06 (dd, J=10.2, 3.4 Hz, 1H), 1.86 (dt, J=13.6, 4.4 Hz, 2H), 1.42-1.30 (m, 2H), 1.19 (t, J=7.1 Hz, 3H), 1.02 (s, 3H).

Preparation F: Synthesis of benzyl 4-oxotropane-N-carboxylate

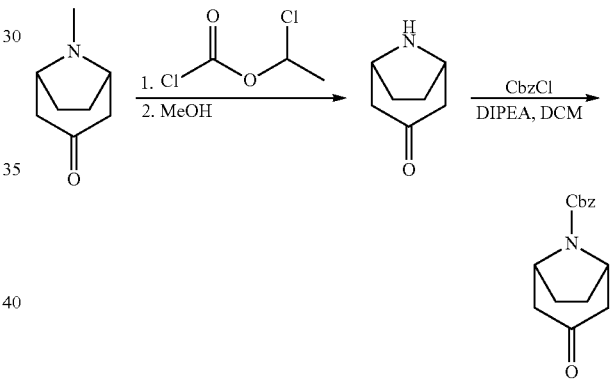

Tropinone (10.0 g; 71.84 mmol) was dissolved in DCE (60 mL) and treated drop-wise with 1-chloroethyl chloroformate ACE-Cl (14.5 mL; 19.11 g; 133.7 mmol). The reaction was allowed to stir at room temperature overnight and was then diluted with $Et_2O$ (400 mL) and filtered. The filtrate was concentrated under reduced pressure to provide the crude chloroethyl carbamate. This compound was taken in MeOH (200 mL) and stirred at room temperature for 1 h, then concentrated under reduced pressure (at 55° C.) to provide the crude des-methyltropinone as the HCl salt (tan solid). The crude material was recrystallized from acetonitrile to furnish the pure product as a white crystalline solid. $^1H$ NMR (400 MHz, DMSO-d6) δ 1.79 (dd, J=15.0, 6.9 Hz, 2H), 2.09 (m, 2H), 2.40 (d, J=16.7 Hz, 2H), 3.02 (dd, J=17.1, 4.3 Hz, 2H), 4.23 (s, 2H), 10.00 (br s, 2H)

Des-methyl tropinone (5.10 g; 31.55 mmol) was dissolved in $CH_2Cl_2$ (50 mL) and treated with benzyl chloroformate (4.29 mL; 5.11 g; 29.98 mmol) DIPEA (16.48 mL; 12.23 g; 94.66 mmol) was added drop-wise (exothermic reaction). The resulting clear solution was allowed to stir at room temperature for 30 min and was subsequently diluted with 100 mL $CH_2Cl_2$. The organic phase was washed with 1 N HCl (2×100 mL), dried on $Na_2SO_4$ and concentrated to provide the crude product. $^1$H NMR (400 MHz, CDCl$_3$) δ 1.71 (dd, J=15.0, 7.2 Hz, 2H), 2.12 (m, 2H), 2.38 (d, J=15.9 Hz, 2H), 2.67 (m, 2H), 4.62 (s, 2H), 5.22 (s, 2H), 7.38 (m, 5H).

Preparation G: Synthesis of
5-chloro-3-methyl-1,2,4-thiadiazole

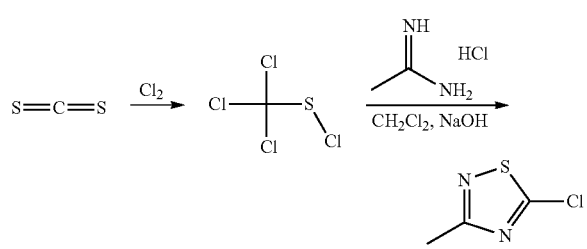

Dry chlorine gas was bubbled into CS$_2$ (1000 mL, containing about 1.0 g of iodine) at 5° C. for 48 hours. The excess CS$_2$ was evaporated and the residue was fractionally distilled to give perchloromethyl mercaptan (bp 144-145° C./1 atm, 300 g, 10%). $^{13}$C-NMR (300 MHz, CDCl$_3$) δ 96.69 (1 C).

To a mixture of perchloromethyl mercaptan (60 g, 323 mmol) and acetamidine hydrochloride (30.6 g, 323 mmol) in dichloromethane(200 mL) was added dropwise a solution of NaOH (64.8 g in water (200 mL) at −5° C. The resulting mixture was stirred at −5° C. for 30 min and then allowed to warm to room temperature. The organic layer was separated and the aqueous phase was extracted with dichloromethane (30 mL×3). The combined organic layers were washed with water (50 mL×2) and brine (100 mL), dried over Na$_2$SO$_4$, and the solvent was removed. The residue was distilled under reduced pressure to give 5-chloro-3-methyl-1,2,4-thiadiazole (bp 70° C./0.85 Mpa, 18 g, 41.8%). $^1$H-NMR (300 MHz, CDCl$_3$) δ 2.59 (s, 3H).

Preparation H: Synthesis of
1-(3-methyl-1,2,4-thiadiazol-5-yl)piperidin-4-one

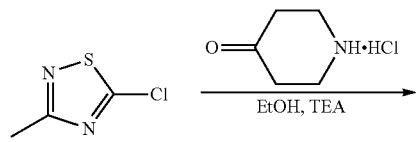

To a mixture of piperidin-4-one HCl salt (4.08 g, 30 mmol) and Et$_3$N (20 mL, 78.6 mmol) in EtOH (50 mL) was added 5-chloro-3-methyl-1,2,4-thiadiazole (4.05 g, 30 mmol). The mixture was heated to reflux for 1.5 hours and then concentrated to dryness. The residue was dissolved in EtOAc. The solution was washed with water (30 mL×3) and brine (30 mL), dried over Na$_2$SO$_4$, and concentrated to dryness. The residue was recrystalled from ether to give 1-(3-methyl-1,2, 4-thiadiazol-5-yl)piperidin-4-one (510 mg, 8.6%). $^1$H-NMR (300 MHz, CDCl$_3$) δ 3.86 (t, J=6.3 Hz, 4H), 2.62 (t, J=6.3, Hz, 4H), 2.44 (s, 3H).

Preparation I: Synthesis of
1-(3-ethyl-1,2,4-thiadiazol-5-yl)piperidin-4-one

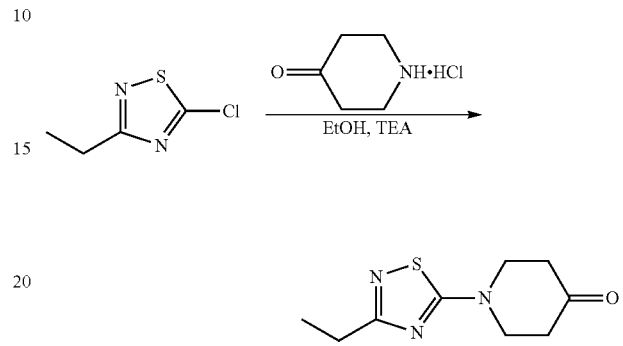

1-(3-ethyl-1,2,4-thiadiazol-5-yl)piperidin-4-one was made in a manner analogous to that found in Preparation B in 54% yield. $^1$H NMR (400 MHz, CDCl$_3$) δ 3.95 (t, J=6.4 Hz, 4H), 2.84 (q, J=7.6 Hz, 2H), 2.68 (t, J=6.4, Hz, 4H), 1.36 (t, J=7.6 Hz, 3H).

Preparation J: Synthesis of
5-chloro-1,2,4-thiadiazole

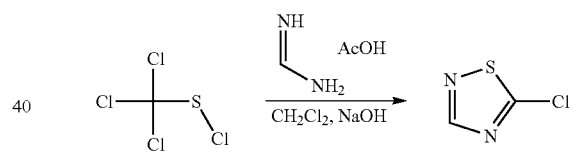

5-chloro-1,2,4-thiadiazole was made in a manner analogous to that found in Preparation A in 36% yield after distillation (bp 124° C./1 atm). $^1$H-NMR (300 MHz, CDCl$_3$) δ 8.45 (s, 1H).

Preparation K: Synthesis of
1-(1,2,4-thiadiazol-5-yl)piperidin-4-one

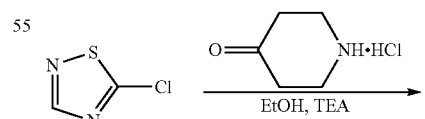

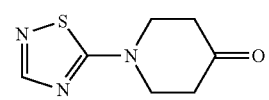

1-(1,2,4-thiadiazol-5-yl)piperidin-4-one was made in a manner analogous to that found in Preparation B in 9% yield. $^1$H-NMR (300 MHz, CDCl$_3$) δ 8.00 (s, 1H), 3.92 (t, J=4.5 Hz, 4H), 2.65 (t, J=4.8 Hz, 4H).

Preparation L: Synthesis of
5-chloro-2,3-dimethylpyrazine

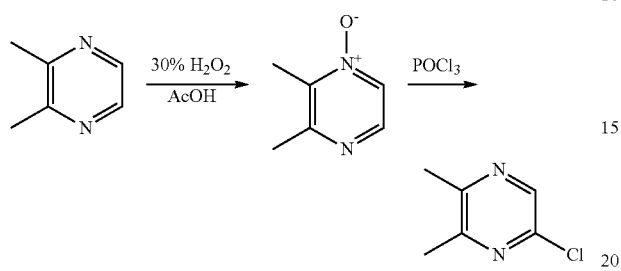

A mixture of 2,3-dimethylpyrazine (25 g, 0.23 mol) and 30% H$_2$O$_2$ (52.4 g, 0.46 mol) in acetic acid (74 mL) was stirred for two days at 35° C. The solvent was removed under vacuum. Water was added and the mixture evaporated again. The residue was basified with aqueous K$_2$CO$_3$ and extracted with EtOAc. The organic phases were dried over Na$_2$SO$_4$ and concentrated. The resulting solid combined from two batches was recrystallized from cyclohexane to give 2,3-dimethylpyrazine 1-oxide (27 g, 47%). $^1$HNMR (CDCl$_3$, 300 MHz) δ 8.18 (d, J=3.9 Hz, 1H), 8.02 (d, J=4.2 Hz, 1H), 2.58 (s, 3H), 2.48 (s, 3H).

2,3-Dimethyl-pyrazine 1-oxide (25 g, 0.2 mol) was dissolved in POCl$_3$ (200 mL) under cooling. The mixture was gradually heated to reflux and stirred for 2 hours. After cooling, the reaction mixture was poured onto ice, basified to pH 8 with a saturated KOH solution under cooling and extracted with EtOAc. The combined organics were dried over Na$_2$SO$_4$ and concentrated. The residue was purified by column (P.E./ EtOAc 100:1-60:1) to obtain 5-chloro-2,3-dimethylpyrazine. $^1$HNMR (CDCl$_3$, 300 MHz) δ 8.31 (s, 1H), 2.53 (s, 6H). MS (ESI) m/e (M+H$^+$) 143.2.

Preparation M: Synthesis of (S)-tert-butyl
3-formylpyrrolidine-1-carboxylate

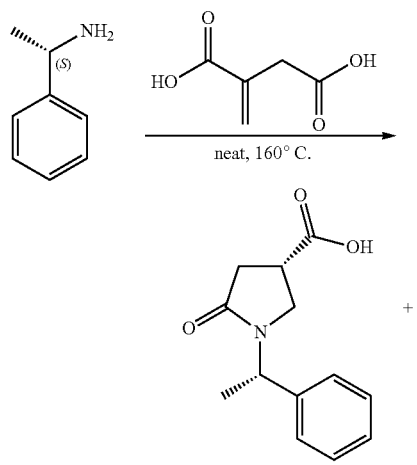

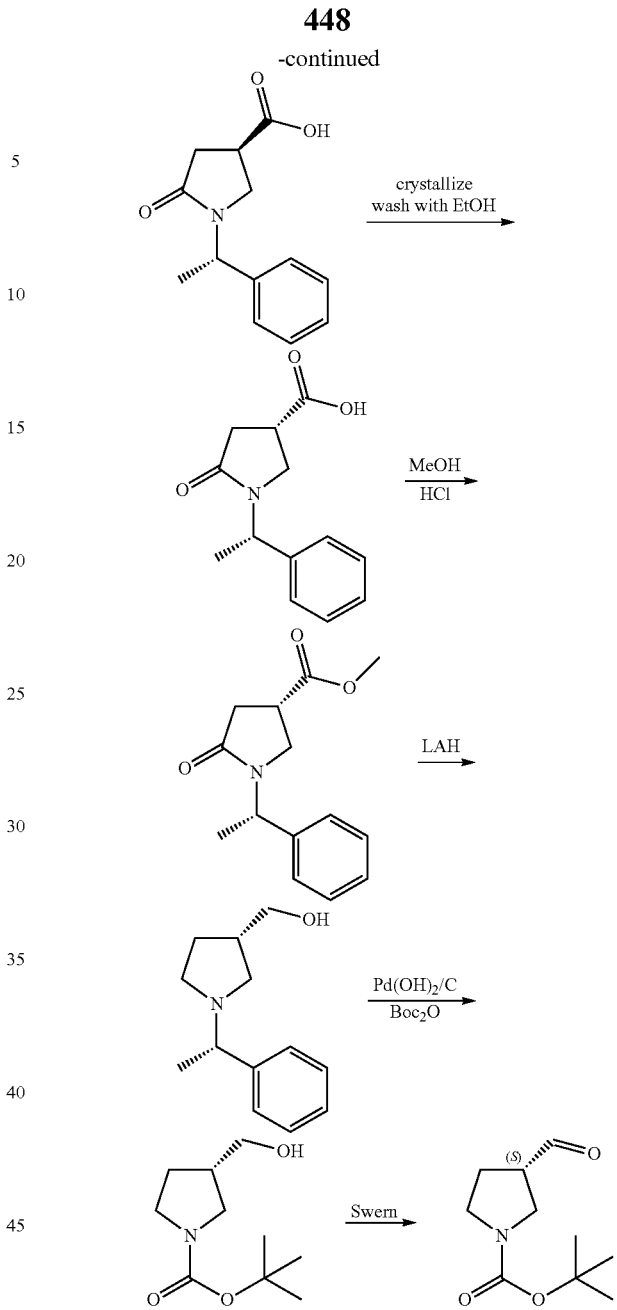

A mixture of itaconic acid (6.5 g, 50 mmol) and S-(-)-α-methylbenzylamine (6.05 g, 50 mmol) was heated at 160° C. (oil bath) for 4 hours. Upon cooling, methanol (25 mL) was added and the resulting solid was collected by filtration. The solid was treated with ethanol (75 mL) and warmed using a steam bath until ~40 mL solvent remained. After cooling to room temperature, the solid was collected and dried to afford (S)-5-oxo-1-((S)-1-phenylethyp)pyrrolidine-3-carboxylic acid as a white crystalline solid. $^1$H NMR (300 MHz, DMSO-d$_6$) δ 12.6 (br s, 1H), 7.23-7.36 (m, 5H), 5.21 (q, J=6.9 Hz, 1H), 3.43-3.48 (m, 1H), 3.11-3.19 (m, 2H), 2.41-2.58 (m, 2H), 1.43 (d, J=6.9 Hz, 3H).

(S)-5-oxo-1-((S)-1-phenylethyl)pyrrolidine-3-carboxylic acid (1.16 g, 5 mmol) was treated with CH$_3$OH/HCl (10 mL, 1 M) for 3 h. The excess CH$_3$OH/HCl was removed under reduced pressure. The residue was basified with saturated aqueous NaHCO$_3$ to pH 8. The aqueous phase was extracted with ethyl acetate (50 mL×3). The combined organics were washed with brine, dried over Na$_2$SO$_4$ and evaporated under reduced pressure to give (S)-methyl 5-oxo-1-((S)-1-phenylethyl)pyrrolidine-3-carboxylate, which was used directly in the next step. $^1$H NMR (300 MHz, CDCl$_3$) δ 7.24-7.37 (m, 5H), 5.48 (q, J=7.2 Hz, 1H), 3.72 (s, 3H), 3.51-3.56 (m, 1H), 3.03-3.21 (m, 2H), 2.62-2.79 (m, 2H), 1.53 (d, J=7.2 Hz, 3H).

To a suspension of LAH (20 g, 0.526 mol) in dried THF (400 mL) was added dropwise a solution of (S)-methyl 5-oxo-1-((S)-1-phenylethyl)pyrrolidine-3-carboxylate (50 g, 0.202 mol) in dried THF (50 mL) at 0° C. The mixture was heated to reflux overnight. The reaction mixture was cooled to 0° C. and treated with water (20 mL) and aqueous NaOH (10%, 20 mL). The slurry formed was filtered off and washed with THF. The combined filtrate was evaporated to give compound ((S)-1-((S)-1-phenylethyl)pyrrolidin-3-yl)methanol, which was used directly in the next step.

To a solution of ((S)-1-((S)-1-phenylethyl)pyrrolidin-3-yl)methanol (42.2 g, 0.194 mol) and (Boc)$_2$O (69.4 g, 0.292 mol) in methanol (300 mL) was added Pd(OH)$_2$/C (5 g). The resultant mixture was heated to 50° C. at 50 psi under H$_2$ and stirred overnight then cooled to room temperature. Pd(OH)$_2$/C was filtered and the filtrate was evaporated under reduced pressure to give a residue which was purified by column chromatography (P.E./EtOAc 5:1) to give (S)-tert-butyl 3-(hydroxymethyl)pyrrolidine-1-carboxylate. $^1$H NMR (300 MHz, CDCl$_3$) δ 3.60-3.63 (m, 2H), 3.29-3.52 (m, 3H), 3.07-3.13 (m, 1H), 2.37-2.42 (m, 1H), 1.94-1.98 (m, 1H), 1.62-1.70 (m, 1H), 1.45 (s, 9H).

To a solution of oxalyl chloride (22.17 g, 0.176 mol) in CH$_2$Cl$_2$ (200 mL) was added dropwise a solution of DMSO (20.59 g, 0.264 mol) in CH$_2$Cl$_2$ (50 mL) at -78° C. The mixture was stirred for 0.5 hours at this temperature. A solution of (S)-tert-butyl 3-(hydroxymethyl)pyrrolidine-1-carboxylate (11.8 g, 58.7 mmol) in CH$_2$Cl$_2$ (50 mL) was added dropwise to the reaction mixture at -78° C. The mixture was continued to stir for 1 hour at that temperature. Et$_3$N (29.7 g, 0.294 mol) was added at -78° C. The resultant mixture was warmed to room temperature and stirred for 3 hours. The mixture was poured into saturated aqueous NaHCO$_3$ and shaken. The organic layer was separated, washed twice with water, dried and evaporated to give a residue, which was purified by column chromatography (P.E./EtOAc 5:1) to give (S)-tert-butyl 3-formylpyrrolidine-1-carboxylate. $^1$H NMR (CDCl$_3$, 300 MHz): δ 9.68 (d, J=1.8 Hz, 1H), 3.67-3.68 (m, 1H), 3.51-3.55 (m, 1H), 3.35-3.40 (m, 2H), 2.99-3.04 (m, 1H), 2.04-2.18 (m, 2H), 1.46 (s, 9H).

Preparation N: Synthesis of (R)-tert-butyl 3-formylpyrrolidine-1-carboxylate (R)-tert-butyl 3-formylpyrrolidine-1-carboxylate was synthesized in a manner analogous to that of (S)-tert-butyl 3-formylpyrrolidine-1-carboxylate above by using the R-(+)-α-methyl benzylamine chiral auxillary. Intermediates are characterized below:

(R)-5-oxo-1-((R)-1-phenylethyl)pyrrolidine-3-carboxylic acid: $^1$H NMR (300 MHz, DMSO-d$_6$) δ 12.6 (br s, 1H), 7.25-7.36 (m, 5H), 5.21 (q, J=7.2 Hz, 1H), 3.43-3.51 (m, 1H), 3.08-3.19 (m, 2H), 2.48-2.58 (m, 2H), 1.43 (d, J=7.2 Hz, 3H).

(R)-methyl 5-oxo-1-((R)-1-phenylethyl)pyrrolidine-3-carboxylate: $^1$H NMR (300 MHz, CDCl$_3$) δ 7.23-7.35 (m, 5H), 5.47 (q, J=7.2 Hz, 1H), 3.70 (s, 3H), 3.50-3.55 (m, 1H), 3.02-3.20 (m, 2H), 2.60-2.78 (m, 2H), 1.51 (d, J=7.2 Hz, 3H).

Preparation O: Synthesis of 1-benzylazocan-5-one

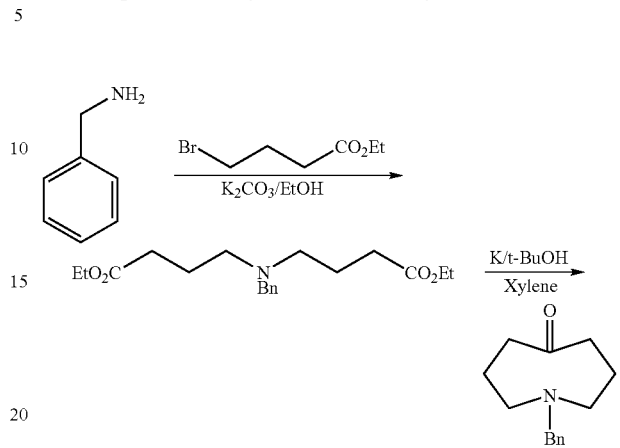

A mixture of benzylamine (83.7 g, 0.78 mol), 4-bromobutyric acid ethyl ester (304.6 g, 1.56 mol) and K$_2$CO$_3$ (215.8 g, 1.56 mol) in anhydrous EtOH (970 mL) was refluxed overnight. The mixture was filtered, and the filtrate was concentrated and dissolved into dichloromethane, which was washed with water, dried over Na$_2$SO$_4$ and concentrated. The residue was purified by column chromatoghraphy (P.E.) to provide diethyl 4,4'-(benzylazanediyl)dibutanoate (123 g, 47%). $^1$H NMR (CDCl$_3$, 400 MHz) δ 7.16-7.22 (m, 5H), 4.03 (q, J=7.2, 14.4 Hz, 4H), 3.47 (s, 2H), 2.36 (br s, 4H), 2.24 (t, J=7.6 Hz, 4H), 1.71 (br s, 4H), 1.17 (t, J=7.2 Hz, 6H).

To a stirred boiling slurry made from potassium (1.28 g, 32.8 mmol) and t-BuOH (2.43 g, 32.8 mmol) in xylene (182.5 mL) under N$_2$ was added diethyl 4,4'-(benzylazanediyl)dibutanoate (5 g, 14.9 mmol) over 5 hours in xylene (37.25 mL). The mixture was stirred and heated at reflux for 1 hour. After being cooled, the reaction mixture was neuturalized with 6N HCl (100 mL) and then was extracted with 6N HCl (3×50 mL). The combined acid solutions were filtered and the filtrate was heated under reflux for 1 hour. After cooling, the mixture was basified with concentrated KOH solution to pH 10 with cooling and extracted with dichloromethane. The combined organics were dried over Na$_2$SO$_4$ and concentrated to give a residue. Another 17 batches were done in parallel. The combined residue from 18 batches was purified together by column (P.E./EtOAc 5:1) to give 1-benzylazocan-5-one. $^1$H NMR (CDCl$_3$, 400 MHz) δ 7.30-7.33 (m, 2H), 7.21-7.25 (m, 3H), 3.56 (s, 2H), 2.55 (t, J=6.0, 4H), 2.24 (t, J=6.4 Hz, 4H), 1.86-1.91 (m, 4H).

Example 1

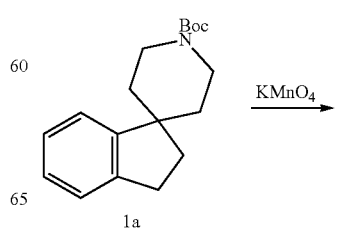

1a

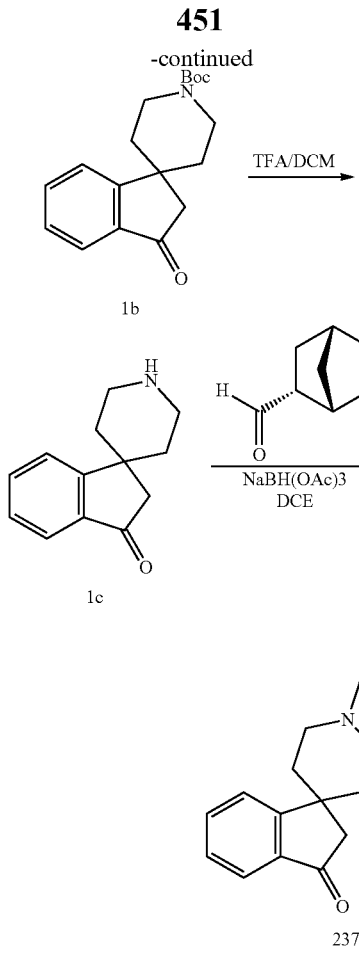

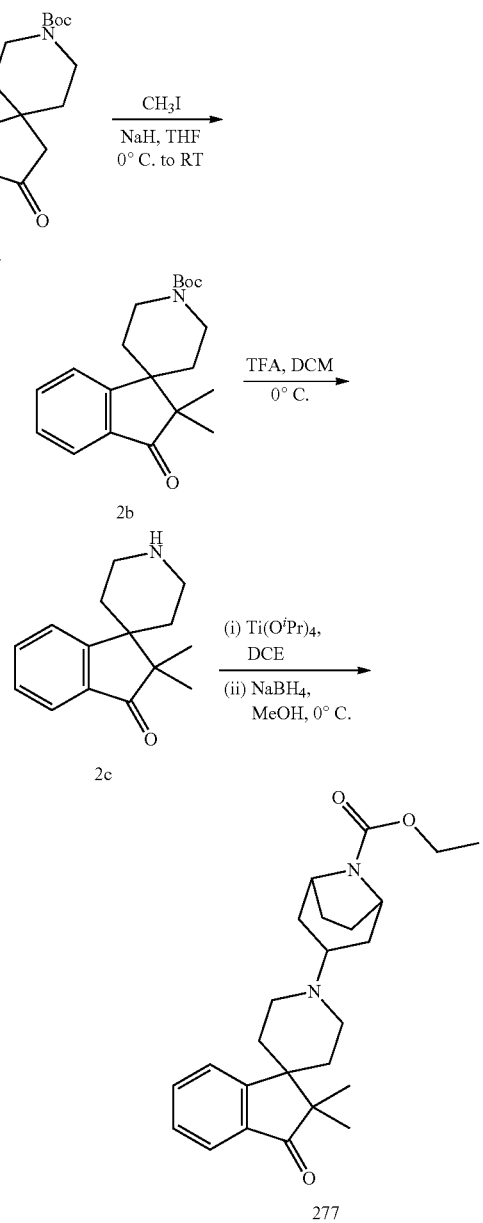

temperature for 1 h and was then quenched with MeOH (1 mL) and allowed to stir for another 30 min. The crude reaction mixture was purified by HPLC (10-99% CH₃CN gradient with 0.03% TFA, 15 min) to provide the purified compound no. 237. LC/MS m/z 308.2 [M+H]⁺, retention time 2.08 (10-99% CH₃CN—H₂O gradient with 0.03% TFA, 5 min). ¹H NMR (400 MHz, DMSO-d₆) δ 9.47 (br s, 1H), 7.81-7.77 (m, 1H), 7.66 (d, J=7.4 Hz, 1H), 7.59 (d, J=7.8 Hz, 7.53-7.49 (m, 1H), 6.27 (dd, J=5.7, 3.0 Hz, 1H), 6.05 (dd, J=5.7, 2.8 Hz, 1H), 3.60 (t, J=12.7 Hz, 3H), 3.11-2.90 (m, 4H), 2.85-2.74 (m, 4H), 2.29 (t, J=13.0 Hz, 2H), 2.05-1.99 (m, 1H), 1.76 (d, J=14.2 Hz, 2H), 1.39-1.35 (m, 1H), 1.29 (d, J=8.2 Hz, 1H), 0.71-0.66 (m, 1H).

Example 2

To a solution of compound N-Boc Spiroindane 1a (60.0 g, 0.21 mol) in CH₂Cl₂ (1000 mL) was added H₂O (500 mL), TBAB (6.9 g, 0.02 mol) and KOH (3.5 g, 0.06 mol) and followed by addition of KMnO₄ (70.0 g, 0.45 mol) in several portions. After stirring for two days at 35° C., another quantity of KMnO₄ (70.0 g, 0.45 mol) was added and the mixture was continued to stir for 2 days. After Na₂SO₃ (103.0 g, 1.0 mol) was added in portions at 5° C., the mixture was extracted with EtOAc. The combined organic layers were dried over anhydrous Na₂SO₄ and evaporated under vacuum. The residue was purified by column chromatography (PE/EtOAc: 5/1) to yield 1b. ¹H NMR (CDCl₃) δ: 7.74-7.72 (m, 1H), 7.66-7.64 (m, 1H), 7.62-7.61 (m, 1H), 7.49-7.38 (m, 1H), 4.22-4.20 (m, 2H), 2.89-2.82 (m, 2H), 2.63 (s, 2H), 2.02-1.94 (m, 2H), 1.56-1.52 (m, 2H), 1.49 (s, 9H). MS (ESI) m/z (M+⁺) 246.0/202.1.

Boc-protected starting material 1b (400.0 mg; 1.33 mmol) was dissolved in CH₂Cl₂ (1.5 mL) and treated with TFA (1.5 mL). The reaction was allowed to stir at room temperature for 1 h and was then quenched by adding H₂O (5 mL) and Et₂O (7 mL). The layers were separated, and the aqueous layer was brought to a basic pH by addition of solid KOH. The resulting emulsion was extracted with Et₂O (3×10 mL). The combined organic extracts were dried on Na₂SO₄ and concentrated to yield the desired product 1c as a colorless oil that solidifies upon standing. LC/MS m/z 202.2 [M+H]⁺, retention time 0.72 min (10-99% CH₃CN—H₂O gradient with 0.03% TFA, 5 min).

Intermediate 1c (40 mg; 0.2 mmol) was suspended in DCE (1 mL) and treated with (1R,2R,4R)-bicyclo[2.2.1]hept-5-ene-2-carbaldehyde (31 mg; 0.26 mmol; 1.300 eq.) in DCE (0.5 mL), followed by portion-wise addition of NaBH(OAc)₃ (127 mg; 0.6 mmol) The reaction was allowed to stir at room 1.0 eq of the Boc-protected spiroindanone 2a (2.06 g, 6.84 mmol) was dissolved in anhydrous tetrahydrofuran (5 mL) and added drop-wise, under nitrogen, to an ice-cold (~0° C.) suspension of 2.2 eq sodium hydride (600 mg, 60% dispersion in mineral oil, 15.0 mmol) in anhydrous tetrahydrofuran (10 mL). A solution of 10.0 eq iodomethane (9.71 g, 68.4 mmol) in anhydrous tetrahydrofuran (5 mL) was then added drop-wise over 20 min. The reaction was warmed to room temperature and stirred for 2 hours under nitrogen. The reaction mixture was concentrated under reduced pressure and slowly treated with $H_2O$ (25 mL). The product was extracted with ethyl acetate (2×50 mL) and the pooled extracts washed with saturated sodium bicarbonate and saturated brine, then dried ($Na_2SO_4$) and filtered. The filtrate was concentrated in vacuo to afford crude product 2b as a viscous, pale yellow oil. $^1$H-NMR (400 MHz, acetone-$d_6$) δ 7.90 (d, J=6.8 Hz, 1H), 7.71 (m, 2H), 7.49 (t, J=7.4 Hz, 1H), 3.75 (m, 2H), 3.56 (br m, 2H), 1.89 (m, 2H), 1.64 (br m, 2H), 1.48 (s, 9H), 1.12 (s, 6H); $t_R$=3.50 min [10-99% $CH_3CN$ gradient over 5 min with 0.1% TFA (aq)]; Theoretical (M+H)$^+$m/z for $C_{20}H_{27}NO_3$=330.2; Found 330.2.

The gem-dimethyl spiroindanone 2b (379 mg, 1.15 mmol) was dissolved in dichloromethane (2.5 mL), cooled in an ice-H20 bath and treated slowly with trifluoroacetic acid (2.5 mL). The reaction was stirred for 30 min at ~0° C., then concentrated under reduced pressure. The oil obtained was dissolved in acetonitrile and re-concentrated under reduced pressure. The crude TFA salt was treated with 1.0 N NaOH (5 mL) and extracted with ethyl acetate (2×30 mL). The pooled extracts were washed with H2O and saturated brine, then dried ($Na_2SO_4$) and filtered. The filtrate was concentrated in vacuo to afford 210 mg of the crude free base 2c as a colorless semi-solid. $t_R$=1.52 min [10-99% $CH_3CN$ gradient over 5 min with 0.1% TFA (aq)]; Theoretical (M+H)+ m/z for $C_{15}H_{19}NO$=230.2; Found 230.2

The crude free base 2c (53 mg, 0.23 mmol) was dissolved in anhydrous 1,2-dichloroethane (1.0 mL) and treated with N-(carbethoxy)-4-tropinone (55 mg, 0.28 mmol), followed by titanium tetraisopropoxide (202 μL, 196 mg, 0.69 mmol). The vial was flushed with nitrogen and stirred at room temperature for 2.5 days. The reaction was diluted with methanol (1.0 mL), cooled in an ice-$H_2O$ bath and treated with sodium borohydride (17 mg, 0.46 mmol). The reaction was warmed to room temperature and stirred thereafter for 30 min. The reaction was then quenched with 1.0 N NaOH (750 μL), diluted with methanol (1.5 mL) and stirred at room temperature for 10 min. The suspension obtained was centrifuged (3K rpm, 10 min) and the supernatant concentrated under reduced pressure. The residue obtained was dissolved in DMSO: methanol (1.5 mL, 1:1 v/v), filtered, and purified by reverse-phase HPLC (2-40% $CH_3CN$ gradient over 10 min with 0.1% TFA (aq), 35 mL/min, 1.0 mL injected) to produce the compound no. 277 as a TFA salt. $t_R$=2.12 min [10-99% $CH_3CN$ gradient over 5 min with 0.1% TFA (aq)]; Theoretical (M+H)$^+$ m/z for $C_{25}H_{34}N_2O_3$=411.3; Found 411.2.

Example 3

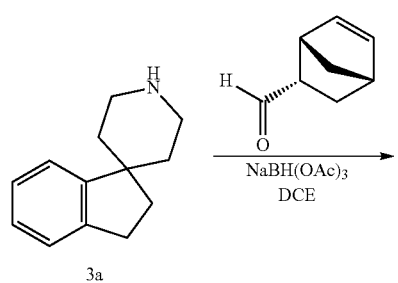

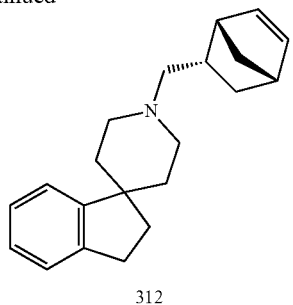

312

The starting Spiroindane 3a (45 mg, 0.2 mmol) was suspended in DCE (1 mL) and treated with (1S,2S,4S)-bicyclo[2.2.1]hept-5-ene-2-carbaldehyde (25 mg, 0.2 mmol) in DCE, followed by the addition of NaBH(OAc)$_3$ (63 mg, 0.3 mmol). The reaction was allowed to stir at room temperature for 1 h and was then quenched with MeOH (0.5 mL) and allowed to stir for another 30 min (until gas evolution stopped). The crude reaction mixture was filtered, then purified by HPLC (10-99% $CH_3CN$/0.05% TFA gradient) to yield compound no. 312. LC/MS m/z 294.4 [M+H]$^+$, retention time 2.33 min (RP-$C_{18}$, 10-99% $CH_3CN$/0.05% TFA); $^1$H NMR (400 MHz, DMSO-$d_6$) δ 9.33 (br s, 1H), 7.25-7.17 (m, 3H), 7.13 (d, J=6.9 Hz, 1H), 6.27-6.26 (m, 1H), 6.06-6.04 (m, 1H), 3.56-3.40 (m, 3H), 3.11-3.03 (m, 2H), 2.98-2.78 (m, 6H), 2.09-1.98 (m, 5H), 1.67 (d, J=13.9 Hz, 2H), 1.36 (t, J=8.0 Hz, 1H), 1.29 (d, J=8.2 Hz, 1H), 0.70-0.66 (m, 1H).

Example 4

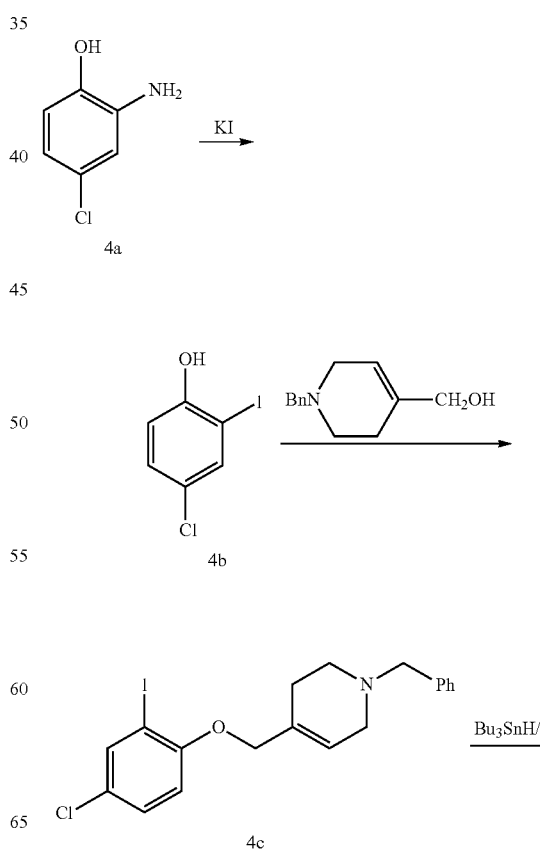

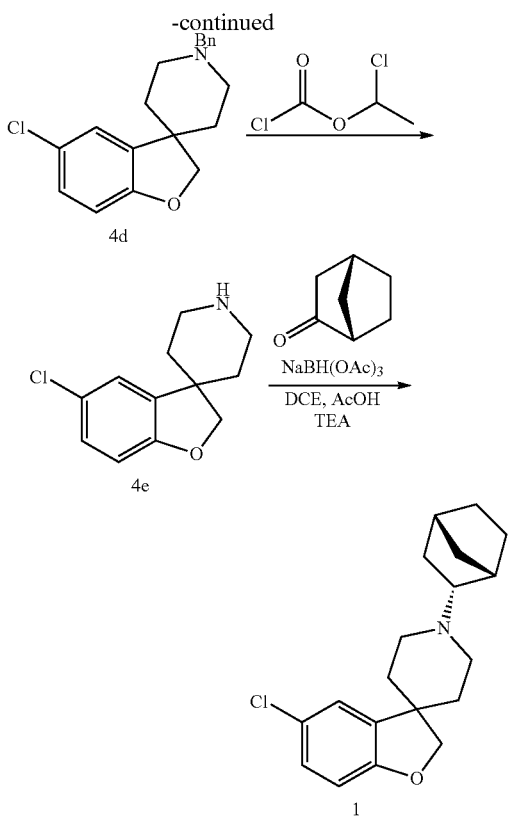

To a solution of 2-amino-4-chloro-phenol 4a (50 g, 0.35 mol) in HCl (2.5 mol, 500 mL) was added drop-wise a solution of sodium nitrite (25.25 g, 0.35 mol) in water (50 mL) at 0° C. The mixture was stirred at this temperature for 30 min. Then a cooled solution of KI (70 g, 0.42 mol) in $H_2O$ (100 mL) was slowly added at 0° C. After addition, the mixture was allowed to warm to room temperature and stirred overnight. The reaction mixture was diluted with ethyl acetate (200 mL) and the separated aqueous phase was extracted with ethyl acetate (100 mL×3). The combined organic fraction was washed with $Na_2S_2O_3$ (10%, 100 mL), water (100 mL×2) and brine (200 mL), dried over $Na_2SO_4$ and concentrated to dryness. The residue was purified by column on silica gel to afford 4-chloro-2-iodo-phenol 4b as a yellow solid. $^1$H NMR (400 MHz, $CDCl_3$): δ 7.67 (d, J=2.4 Hz, 1H), 7.21 (dd, J=2.4, 8.4, Hz, 1H), 6.91 (d, J=8.4 Hz, 1H), 5.33 (s, 1H).

To a solution of 4-chloro-2-iodo-phenol 4b (20.32 g, 0.08 mol), (1-benzyl-1,2,3,6-tetrahydro-pyridin-4-yl)-methanol (20.5 g, 0.08 mol) and triphenylphosphine (23.58 g, 0.09 mol) in dry THF (150 mL) was added DEAD (17.4 g, 0.09 mol) at 0° C. under nitrogen atmosphere. After addition, the mixture was stirred at room temperature overnight. The mixture was concentrated to dryness and the residue was basified by $Na_2CO_3$ solution (10% 100 mL) and extracted with ethyl acetate (100 mL×3). The combined organic layers were washed with water (100 mL×2) and brine (200 mL), dried over $Na_2SO_4$, concentrated to dryness. The residue was purified by column on silica gel to afford 1-benzyl-4-(4-chloro-2-iodo-phenoxymethyl)-1,2,3,6-tetrahydro-pyridine 4c. $^1$H NMR (400 MHz, $CDCl_3$): δ 7.73 (d, J=2.4 Hz, 1H), 7.22-7.38 (m, 6H), 6.70 (d, J=8.8 Hz, 1H), 5.82 (s, 1H), 4.43 (s, 2H), 3.63 (s, 2H), 3.05 (s, 2H), 2.67 (t, J=5.6 Hz, 2H), 2.28 (s, 2H).

To a refluxing solution of 1-benzyl-4-(4-chloro-2-iodo-phenoxymethyl)-1,2,3,6-tetrahydro-pyridine 4c (26.7 g, 0.06 mol) and AIBN (0.05 g, 0.003 mol) in dry benzene was added a solution of $Bu_3SnH$ (40 g, 0.137 mol) in benzene (100 mL) over 1 h under nitrogen atmosphere. After addition, the mixture was refluxed for 3 hr and additional AIBN (0.5 g, 0.003 mol) and $Bu_3SnH$ (20 g, 0.68 mol) were added. After refluxing for 4 hr, the mixture was concentrated to dryness, and EtOAc (100 mL) and HCl (10%, 40 mL) were added. The precipitate was filtered and washed with petroleum ether to give 2,3-dihydro-1'-benzyl-5-chlorospiro(benzofuran-3,4'-piperidine) as its HCl salt, which was basified by $NaHCO_3$ solution to give 2,3-dihydro-1'-benzyl-5-chlorospiro(benzofuran-3,4'-piperidine) 4d (13 g, 68%).

To a solution of 2,3-dihydro-1'-benzyl-5-chlorospiro(benzofuran-3,4'-piperidine) 4d (13 g, 0.04 mol) in $CH_2Cl_2$ (130 mL) was added drop-wise 1-chloroethyl chloroformate (7.2 g, 0.05 mol). The mixture was stirred for 3 hr at room temperature and then concentrated to dryness. The residue was dissolved in $CH_3OH$ (30 mL) and the solution was heated to reflux for 30 min. After removing of the solvent, ether was added. The resulted solid was filtered and washed with ether to the debenzylated product 4e as the HCl salt (5.5 g, yield 48%). $^1$H NMR (400 MHz, DMSO-$d_6$): δ 9.08 (br s, 1H), 7.16-7.19 (m, 2H), 6.82 (d, J=8.4 Hz, 1H), 4.50 (s, 2H), 3.25-9.29 (m, 2H), 2.98-2.92 (m, 2H), 2.12-2.05 (m, 2H), 1.83-1.8 (m, 2H).

The chloro-dihydrobenzofuran spiro amine 4e (3.18 mmol) was dissolved in anhydrous DCE (15 mL) and treated with triethylamine (322 mg, 3.18 mmol), followed by (+)-2-norcamphor (421 mg, 3.82 mmol), acetic acid (382 mg, 6.36 mmol) and $NaBH(OAc)_3$ (1.35 g, 6.37 mmol). The reaction was stirred vigorously under nitrogen at room temperature for ~36 hours. The reaction was quenched with methanol (15 mL) and stirred vigorously for 10 min at room temperature. The reaction mixture was then concentrated under reduced pressure and the residue obtained dissolved in a mixture of DMSO:$CH_3OH$ (20 mL, 1:3 v/v). The solution was filtered and purified by reverse-phase HPLC (2-99% $CH_3CN$/0.05% TFA, 35 mL/min). The combined pure fractions were concentrated under reduced pressure until ~25 mL of solvent remained. The suspension was treated with 1 N NaOH (25 mL) and extracted with $CH_2Cl_2$ (3×50 mL). The combined organic extracts were washed with $H_2O$, saturated brine, dried over $Na_2SO_4$ and filtered. The filtrate was concentrated under reduced pressure to afford 522 mg pure free base (1.64 mmol) as a crystalline white solid. The free base was readily dissolved in anhydrous diethyl ether (10 mL) and treated with 1.0 eq 1 N ethereal HCl (1.7 mL). The thick, gelatinous suspension obtained was cooled in an ice/$H_2O$ bath for 1 hour, filtered, rinsed with $Et_2O$ (3×10 mL), and dried overnight under reduced pressure to yield compound no. 1 as a fine white powder. $^1$H-NMR (400 MHz, DMSO-$d_6$) δ 10.1 (br s, 1H), 7.77 (d, J=2.2 Hz, 0.2H), 7.21 (dd, J=2.3 Hz, 8.5 Hz, 1H), 7.08 (d, J=2.3 Hz, 0.8H), 6.85 (d, J=8.5 Hz, 0.8H), 6.84 (d, J=8.5 Hz, 0.2H), 4.52 (s, 1.6H), 4.45 (s, 0.4H), 3.41 (m, 1.8H), 3.24 (m, 0.8H), 3.01 (br m, 1.6H), 2.63 (br m, 2H), 2.44 (m, 0.9H), 2.27 (br s, 1.1H), 1.86 (br m, 4H), 1.51 (br m, 3.3H), 1.39 (br m, 2.7H), 1.24 (br m, 0.7H); LC/MS m/z 318.0 $[M+H]^+$, retention time 2.14 min (RP-$C_{18}$ 10-99% $CH_3CN$/ 0.05% TFA).

Example 5

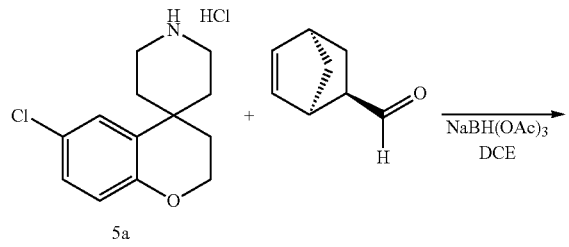

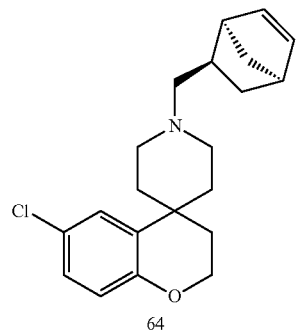

The starting material 5a (54 mg, 0.2 mmol, 1.0 eq) was suspended in DCE (1 mL) and treated with (1R,2R,4R)-bicyclo[2.2.1]hept-5-ene-2-carbaldehyde (31 mg, 0.26 mmol, 1.3 eq) in DCE (0.5 mL), followed by portion-wise addition of NaBH(OAc)$_3$ (127 mg, 0.6 mmol). The reaction was allowed to stir at room temperature for 3 h and was then quenched with MeOH (2 mL) and allowed to stir for another hour (until gas evolution stopped). The reaction mixture was then diluted with H$_2$O (5 mL) and extracted with Et$_2$O (10 mL). The organic layer was treated with 1 N HCl (5 mL) and formation of an insoluble precipitate was observed. The biphasic emulsion was filtered, and the white precipitate was washed with Et$_2$O (3×5 mL) and hexanes (2×10 mL) and dried under vacuum to provide the pure HCl salt of compound no. 64 as white shiny platelets. LC/MS m/z 344.0 [M+H]$^+$, retention time 2.56 min (RP-C$_{18}$ 10-99% CH$_3$CN/0.05% TFA). $^1$H NMR (400 MHz, DMSO-d$_6$) δ 10.11 (s, 1H), 7.37 (d, J=2.4 Hz, 1H), 7.10 (d, J=2.5 Hz, 1H), 6.74 (d, J=8.7 Hz, 1H), 6.18 (q, J=2.8 Hz, 1H), 6.02 (q, J=2.7 Hz, 1H), 4.05-4.03 (m, 2H), 3.37-3.32 (m, 2H), 3.08-2.97 (m, 3H), 2.85-2.77 (m, 2H), 2.72-2.65 (m, 1H), 2.49-2.45 (m, 3H), 1.98-1.90 (m, 3H), 1.72-1.70 (m, 2H), 1.26 (dd, J=33.4, 7.3 Hz, 2H), 0.63 (d, J=10.5 Hz, 1H).

Example 6

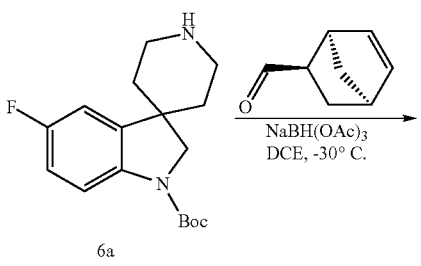

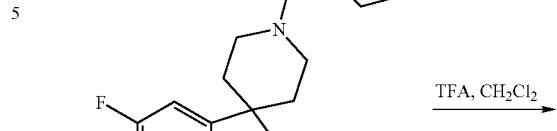

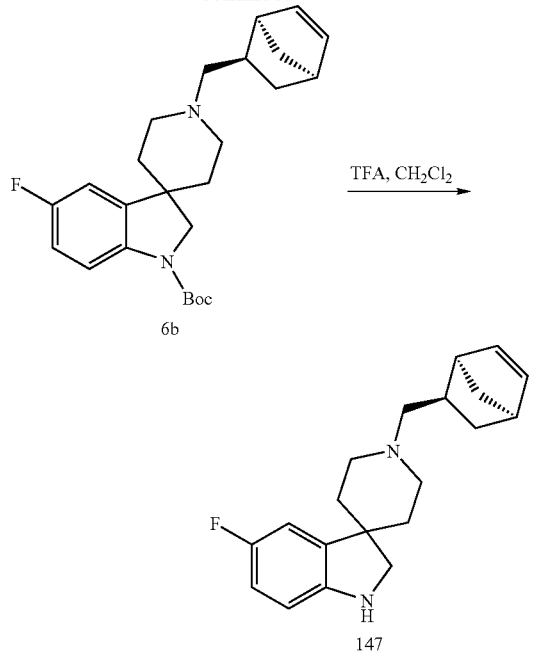

The fluoroindoline 6a (1.22 g; 4.0 mmol) was suspended in DCE (10 mL) and cooled to −30° C. A solution of (1R,2R,4R)-bicyclo[2.2.1]hept-5-ene-2-carbaldehyde (635 mg; 5.2 mmol) in dry DCE (2 mL) was added, followed by portion-wise addition of NaBH(OAc)$_3$ (1.18 g; 5.6 mmol). The reaction was stirred at −30° C. under nitrogen for 90 min then at room temperature until complete consumption of starting material was observed by LC/MS (30 h). The reaction was quenched with MeOH (10 mL) and allowed to stir vigorously for 30 min (until gas evolution stopped). The reaction was diluted with 1N HCl (80 mL) and Et$_2$O (50 mL). Formation of a white precipitate can be observed as the HCl salt of the desired product is insoluble in both phases. The biphasic mixture was filtered, and the precipitate was washed with Et$_2$O (2×20 mL) and hexanes (2×30 mL) and dried under high vacuum to provide the product 6b as the corresponding HCl salt (white powder).

The HCl salt 6b (1.4 g; 3.1 mmol) was dissolved in CH$_2$Cl$_2$ (10 mL) and TFA (10 mL) was added. The reaction mixture was allowed to stir at room temperature for 1 h. The reaction was quenched with water (100 mL) and diluted with hexanes (40 mL) and Et$_2$O (50 mL). The layers were separated, and the organic layer was extracted with H$_2$O (2×100 mL). The combined aqueous layers were washed with Et$_2$O (50 mL) then neutralized with solid KOH (under dry-ice bath cooling) until formation of an oily suspension was observed. The suspension was extracted with EtOAc (3×100 mL) and CH$_2$Cl$_2$ (100 mL), and the combined organic extracts were dried over Na$_2$SO$_4$ and concentrated to provide the crude product as a light brown oil. The amine was dissolved in 15 mL Et$_2$O and treated with 2 N HCl in ether (1.5 mL, 3.0 mmol, 0.96 eq). After 20 min of stirring the resulting precipitate was vacuum filtered under a nitrogen atmosphere, washed with 50 mL Et$_2$O, 30 mL Et$_2$O:CH$_3$CN (5:1) and 40 mL hexanes and dried under high vacuum to provide the HCl salt of compound no. 147 as an off-white powder. LC/MS m/z 313.30 [M+H]$^+$, retention time 1.73 min (RP-C$_{18}$ 10-99% CH$_3$CN/0.05% TFA). $^1$H NMR (400 MHz, MeOD) δ 0.83 (ddd, J=5.8, 2.6 Hz, 1H), 1.41 (d, J=8.4 Hz, 1H), 1.54 (m, 1H), 2.01 (s, 1H), 2.05 (d, J=3.9 Hz, 1H), 2.15 (ddd, J=6.1, 3.1 Hz, 1H), 2.23 (m, 2H), 2.60 (m, 1H), 2.86 (dd, J=13.0, 7.4 Hz, 1H), 2.93 (s, 1H), 3.11 (m, 4H), 3.66 (m, 4H), 6.09 (d, J=2.8 Hz, 1H), 6.33 (d, J=3.0 Hz, 1H), 6.90 (m, 3H).

Example 7

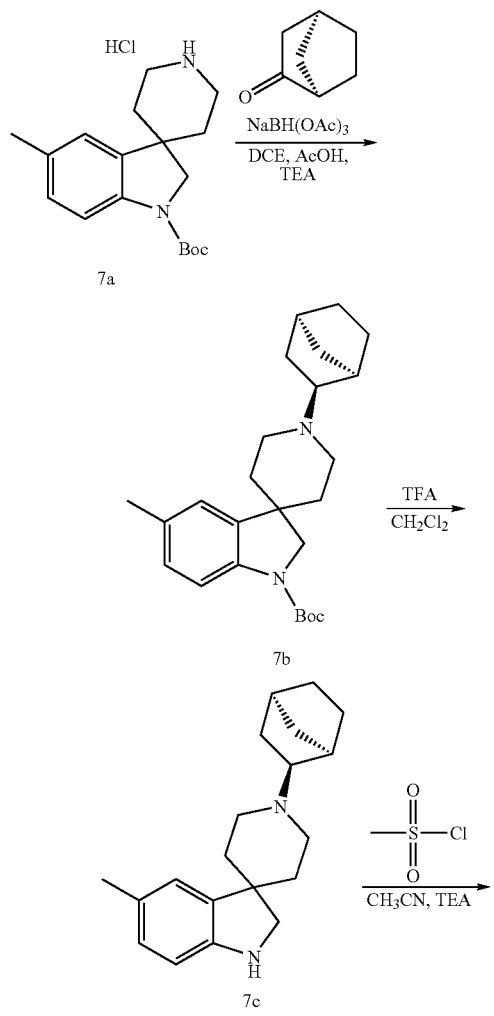

Starting material 7a hydrochloride (2.17 g, 6.40 mmol) was suspended in anhydrous DCE (30 mL) and treated with triethylamine (648 mg, 6.40 mmol), followed by (−)-2-norcamphor (706 mg, 6.40 mmol), acetic acid (770 mg, 12.8 mmol) and $NaBH(OAc)_3$ (2.72 g, 12.8 mmol). The reaction was stirred vigorously under nitrogen at room temperature for ~72 hours (~77% conversion by LC/MS at 220 nm). The reaction was quenched with methanol (10 mL) and stirred vigorously for 10 min at room temperature. The reaction mixture was then concentrated under reduced pressure and the residue obtained dissolved in a 1:1 mixture of $DMSO:CH_3OH$ (30 mL). The mixture was centrifuged (3,000 rpm, 10 min) and the supernatant filtered and purified by reverse-phase HPLC (10-99% $CH_3CN$/0.05% TFA, 50 mL/min). The combined pure fractions were concentrated under reduced pressure to afford 2.25 g of the N-Boc intermediate 7b (isolated as the TFA salt) as an off-white solid. LC/MS (RP-$C_{18}$, 10-99% $CH_3CN$/0.05% TFA gradient over 5 min) m/z 397.4 $[M+H]^+$, retention time 2.70 min.

The N-Boc intermediate 7b (2.25 g, 4.41 mmol) was dissolved in dichloromethane (25 mL) and slowly treated with trifluoroacetic acid (15 mL). The reaction was stirred at room temperature for 30 min, and then concentrated under reduced pressure. The oil obtained was slowly treated with 1 N NaOH (100 mL) and extracted with $CH_2Cl_2$ (2×75 mL). The combined extracts were washed with $H_2O$, saturated brine, dried over $Na_2SO_4$ and filtered. The filtrate was concentrated under reduced pressure to afford a free base as a yellow oil. The free base was dissolved in a minimal volume of anhydrous diethyl ether and treated with 0.95 eq 1 N ethereal HCl. The suspension was cooled in an ice/$H_2O$ bath for 1 hour, filtered, rinsed with $Et_2O$, and dried overnight under reduced pressure to yield the desired product 7c as a fine, off-white to very pale yellow powder. LC/MS (RP-$C_{18}$, 10-99% $CH_3CN$/0.05% TFA gradient over 5 min) m/z 297.2 $[M+H]^+$, retention time 1.72 min.

The deprotected amine HCl salt 7c (33 mg, 0.10 mmol) was suspended in anhydrous $CH_3CN$ (1.0 mL) and treated with triethylamine (20 mg, 0.20 mmol), followed by methanesulfonyl chloride (14 mg, 0.12 mmol). The reaction was stirred at room temperature for 10 min, then quenched with $DMSO:CH_3OH$ (1.0 mL, 1:1 v/v) and centrifuged (4000 rpm, 7 min). The supernatant was filtered and purified by reverse-phase HPLC (2-99% $CH_3CN$, 50 mUmin, 2.0 mL injected) to yield the desired compound no. 231 as the TFA salt. LC/MS (RP-$C_{18}$, 10-99% $CH_3CN$/0.05% TFA gradient over 5 min) m/z 375.0 $[M+H]^+$, retention time 2.08 min.

Example 8

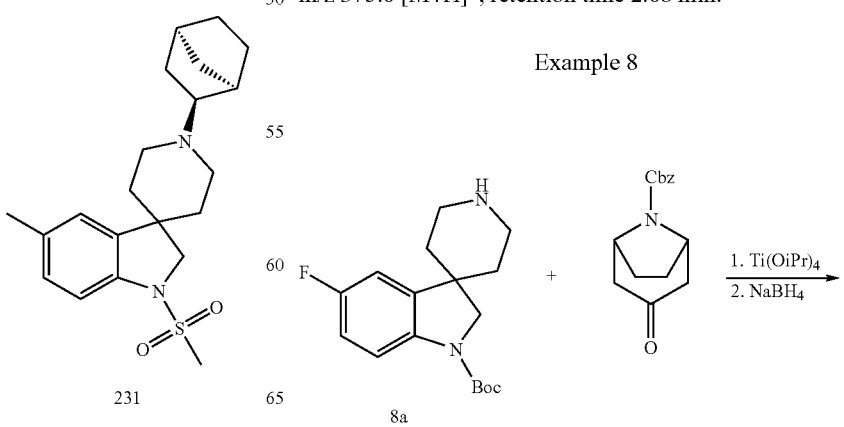

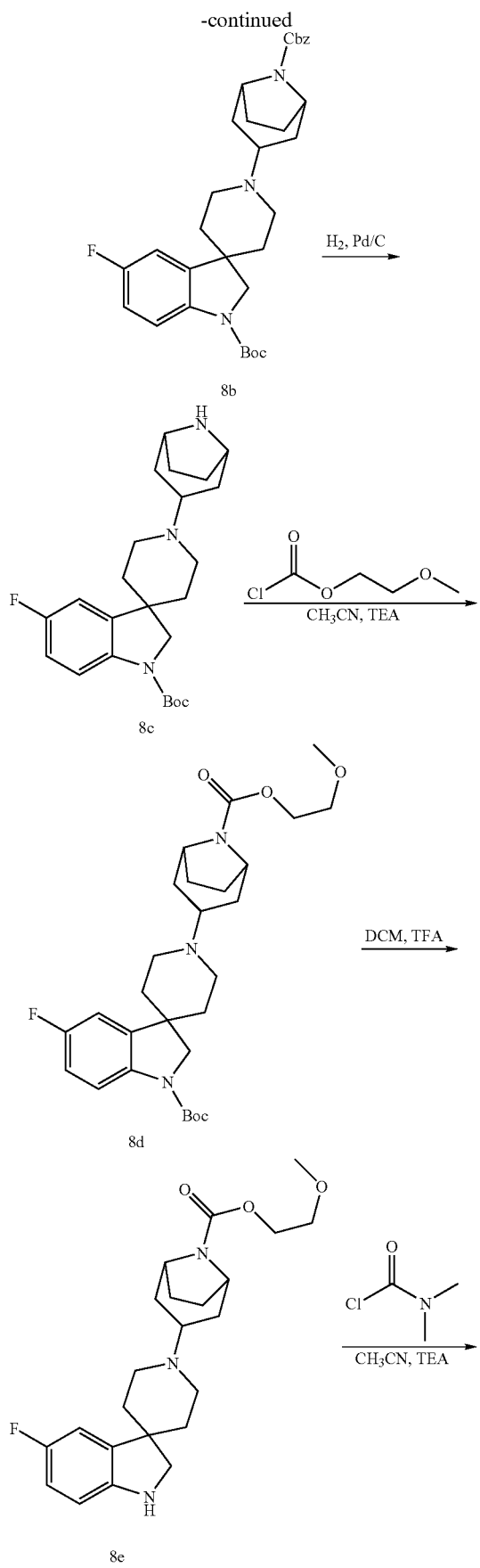

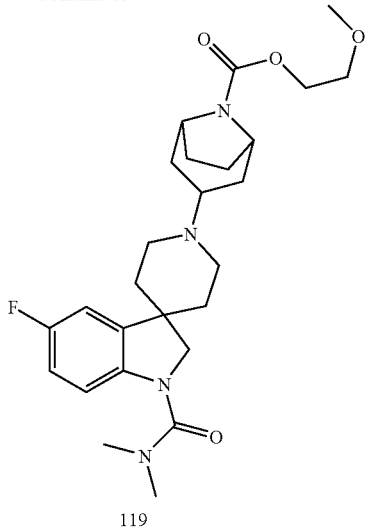

Boc-protected fluoroindoline 8a (1.41 g; 4.11 mmol) and benzyl 4-oxotropane-N-carboxylate (1.07 g; 4.11 mmol) were dissolved in a mixture of DCE (5 mL) and DME (5 mL) and placed under a nitrogen atmosphere. TEA (0.57 mL; 0.42 g; 4.11 mmol) was added, followed by Ti(OiPr)$_4$ (1.21 mL; 1.17 g; 4.11 mmol) and the reaction was allowed to stir at room temperature for 60 hours. The reaction mixture was diluted with 30 mL MeOH and cooled to −40° C. to −50° C. NaBH$_4$ (0.6 g; 13.45 mmol) was added portion-wise over 30 min and the reaction was allowed to stir at −40° C. to −20° C. until bubbling subsided (3 hours), then warmed slowly to room temperature and was stirred for 2 hours. The sticky suspension was filtered through a pad of Celite, and the filter cake was washed with MeOH (2×30 mL) and Et$_2$O (3×50 mL). The filtrate was separated into the corresponding layers, and the aqueous layer was extracted with Et$_2$O (2×50 mL). The combined organic extracts were dried over Na$_2$SO$_4$ and concentrated to provide the crude product as a white foam. This material was dissolved in Et$_2$O (400 mL) and treated with 1 N aq. HCl (500 mL) and the mixture was vigorously stirred for 20 min. The resulting biphasic suspension was filtered, the precipitate was washed with HCl 1N (2×30 mL), H$_2$O (2×30 mL) and Et$_2$O (3×30 mL) and dried. To remove the unreacted starting material by conversion to the corresponding ethyl carbamate, the crude HCl salt was suspended in acetonitrile (10 mL) and treated sequentially with ethyl chloroformate (1 mL) and triethylamine (2 mL). After 10 min, the mixture was diluted with Et$_2$O (300 mL) and poured onto 1 N aq HCl (300 mL). The biphasic suspension was filtered, and the precipitate was washed with HCl 1N (2×30 mL), H$_2$O (2×30 mL) and Et$_2$O (3×30 mL) and dried to provide the desired product 8b hydrochloride salt. LC/MS m/z [M+H]$^+$ 550.4 retention time 2.93 min (10-99% CH$_3$CN—H$_2$O gradient with 0.03% TFA, 5 min).

Cbz-protected starting material 8b (1.140 g; 1.945 mmol) was dissolved in methanol (20 mL) and treated with 10% wet Pd/C (1.14 g) and NH$_4$COOH (2.45 g; 38.9 mmol). The mixture was allowed to stir vigorously overnight under an empty balloon (for venting). LC/MS analysis showed complete conversion to the desired product. The reaction mixture was filtered through a pad of Celite under a nitrogen atmosphere, and the filter cake was rinsed with methanol (4×30 mL). The filtrate was concentrated to provide the crude product, which was taken up in a mixture of EtOAc (100 mL) and NaHCO$_3$ sat. (100 mL). The layers were separated, the aqueous layer was extracted with EtOAc (2×100 mL), Et$_2$O (100 mL), and CH$_2$Cl$_2$ (2×100 mL). The combined organic layers were dried over Na$_2$SO$_4$ and concentrated to provide the crude product 8c as a white foam (707 mg, 87% yield).

LC/MS m/z 416.4 [M₊H]⁺, retention time 2.26 (10-99% CH₃CN—H₂O gradient with 0.03% TFA, 5 min)

Compound 8c (250.0 mg; 0.60 mmol) was dissolved in DCM (15 mL) and treated sequentially with methoxyethyl chloroformate (138.4 uL; 166.1 mg; 1.203 mmol) and TEA (401.7 uL; 291.7 mg; 2.89 mmol). After 10 min, the reaction mixture was diluted with DCM (30 mL) and washed with saturated NaHCO₃ solution (30 mL). The aqueous layer was extracted with DCM (30 mL) and the combined organic extracts were dried on Na₂SO₄ and concentrated to provide the desired product 8d which was taken to the next step without further purification. LC/MS m/z 518.0 [M+H]⁺, retention time 2.43 min (10-99% CH₃CN—H₂O gradient with 0.03% TFA, 5 min).

Intermediate 8d was dissolved in a mixture of DCM (15 mL) and TFA (20 mL) and allowed to stir at room temperature for 2 h. The reaction mixture was concentrated, dissolved in water (20 mL) and the pH was adjusted to basic by portionwise addition of solid KOH. The resulting suspension was extracted with DCM (3×30 mL) and Et₂O (30 mL) and the organic extracts were dried over Na₂SO₄, and then concentrated to provide the free base of the desired product. The material was dissolved in Et₂O (20 mL) and treated with excess 1N HCl in ether (2 mL). The resulting suspension was filtered under nitrogen and the filtrate was washed with Et₂O (3×10 mL) and dried under vacuum to provide the desired product 8e as an off white solid (232 mg, 85% yield over 2 steps). LC/MS m/z 418.2 [M+H]⁺, retention time 1.16 min (10-99% CH₃CN—H₂O gradient with 0.03% TFA, 5 min).

Intermediate 8e (230.0 mg; 0.51 mmol) was suspended in DCM (15 mL) and treated sequentially with dimethyl carbamoyl chloride (931.3 uL; 1089.7 mg; 10.13 mmol) and TEA (704.8 uL; 511.70 mg; 5.07 mmol). The reaction was allowed to stir overnight at room temperature, and then the mixture was diluted with DCM (30 mL) and washed with saturated NaHCO₃ solution (30 mL). The aqueous layer was extracted with DCM (30 mL) and the combined organic extracts were dried over Na₂SO₄ and concentrated to provide the free base of the desired product. This material was dissolved in Et₂O (20 mL) and treated with excess 1N HCl in ether (3 mL). The resulting suspension was filtered under nitrogen and the filtrate was washed with Et₂O (3×10 mL) and dried under vacuum to provide the desired compound no. 119 as an off-white solid. LC/MS m/z 489.4 [M+H]⁺, retention time 2.20 min (10-99% CH₃CN—H₂O gradient with 0.03% TFA, 5 min). ¹H NMR (400 MHz, DMSO-d₆) δ 1.66 (d, J=7.0 Hz, 2H), 1.82 (s, 4H), 1.86 (s, 2H), 1.92 (s, 2H), 2.07 (s, 2H), 2.22 (t, J=12.1 Hz, 2H), 2.87 (s, 6H), 3.05 (q, J=11.1 Hz, 2H), 3.28 (s, 3H), 3.53 (m, 4H), 3.73 (m, 1H), 4.15 (d, J=4.4 Hz, 2H), 4.27 (s, 2H), 6.90 (dd, J=8.3, 2.4 Hz, 1H), 7.00 (m, 2H), 10.41 (s, 1H).

Example 9

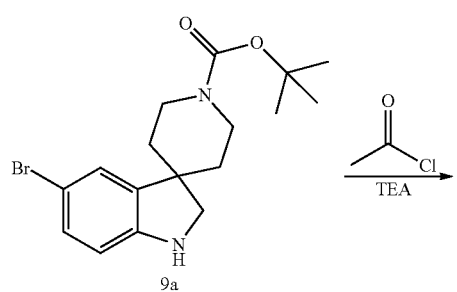

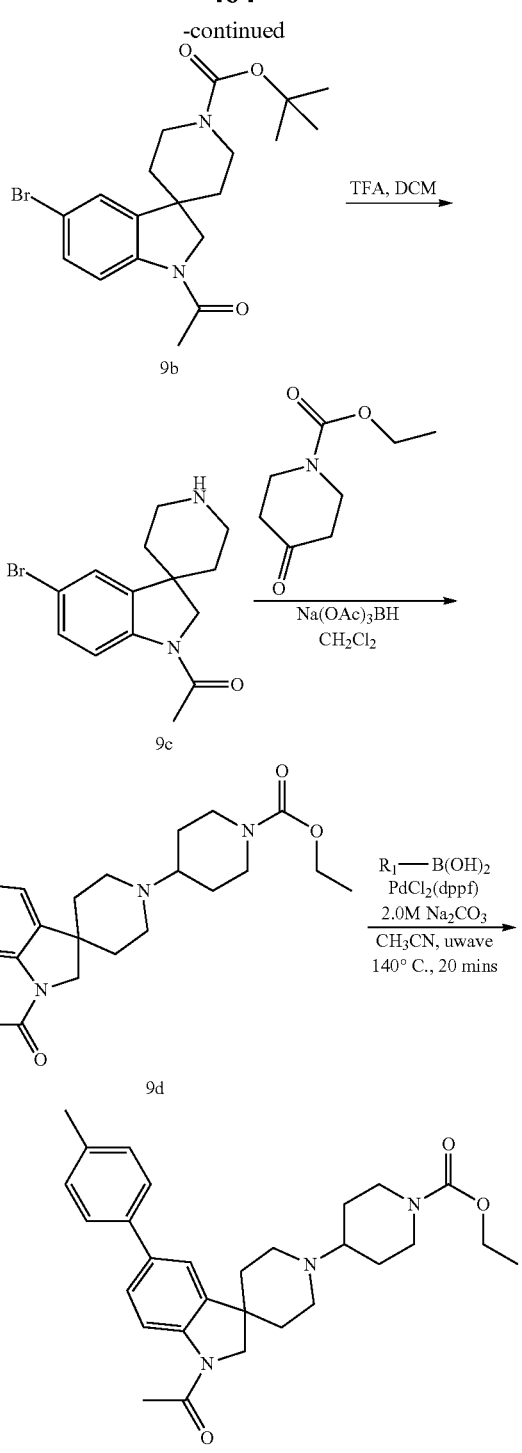

Example 9: Bromo-spiroindoline 9a (1.5 g, 4.08 mmol) was dissolved in anhydrous dichloromethane (20 mL) and cooled to 0° C. To the rapidly stirring solution was added acetyl chloride (0.481 g, 6.13 mmol) followed by triethylamine (0.853 mL, 6.13 mmol). The reaction mixture was stirred at room temperature for 1 h. Then mixture was concentrated under reduced pressure to afford desired product 9b as viscous pale yellow oil and carried to the next step without further purification. LC/MS (RP-C₁₈, 10-99% CH₃CN/0.05% TFA gradient over 5 min) m/z 411.0 [M+H]⁺, retention time 3.39 min.

The intermediate 9b was dissolved in 10 mL of dichloromethane and treated with trifluoroacetic acid (10 mL). The reaction was stirred at room temperature for 30 min, and then concentrated under reduced pressure. The oil obtained was re-dissolved in acetonitrile, re-concentrated under reduced pressure, treated with 2 N NaOH (25 mL) and extracted with dichloromethane (2×50 mL). The combined extracts were washed with saturated NaHCO$_3$, saturated brine, dried over Na$_2$SO$_4$ and filtered. The filtrate was concentrated under reduced pressure to afford crude free base 9c as a pale yellow oil. LC/MS (RP-C$_{18}$, 10-99% CH$_3$CN/0.05% TFA gradient over 5 min) m/z 309.7 [M+H]$^+$, retention time 2.07 min.

Intermediate 9c (1.260 g, 4.08 mmol) was dissolved in anhydrous 1,2-dichloroethane (10 mL) and treated with 2 eq of 1-carbethoxy-4-piperidone (1.393 g, 8.16 mmol), followed by glacial acetic acid (0.490 g, 8.16 mmol) and sodium triacetoxyborohydride (1.721 g, 8.16 mmol). The reaction was stirred at room temperature under nitrogen for 48 h. The reaction was diluted with dichloromethane (50 mL), quenched with 1.0 N NaOH (20 mL) and stirred vigorously at room temperature for 30 min. The layers were separated and the aqueous layer extracted with DCM (2×20 mL). The pooled organic layers were washed with H$_2$O (20 mL), brine (20 mL), then dried over Na$_2$SO$_4$ and filtered. The filtrate was concentrated under reduced pressure to afford 1.8 g crude product 9d as pale yellow oil (~95% yield). An analytical sample was subjected to reverse-phase HPLC purification (2-50% CH$_3$CN gradient over 13 min with 0.1% TFA (aq), 35 mL/min, 1.0 mL injected). The remainder of the material was taken to the next step without purification. $^1$H NMR (400 MHz, DMSO-d$_6$) δ 9.94 (s, 1H), 8.00 (d, J=8.6 Hz, 1H), 7.41 (d, J=8.6 Hz, 1H), 7.27 (d, J=2.0 Hz, 1H), 4.13 (m, 4H), 4.06 (q, J=7.1 Hz, 2H), 3.54-3.46 (m, 3H), 3.16 (q, J=11.0 Hz, 2H), 2.83 (bs, 2H), 2.21 (s, 3H), 2.17-2.07 (m, 4H), 1.93 (d, J=15.6 Hz, 2H), 1.66-1.55 (m, 2H), 1.20 (t, J=7.0 Hz, 3H). LC/MS (RP-C$_{18}$, 10-99% CH$_3$CN/0.05% TFA gradient over 5 min) m/z 467.2 [M+H]$^+$, retention time 1.97 min.

Product 9d (46.4 mg, 0.1 mmol) was mixed with 4-methylphenyl boronic acid (14 mg, 0.1 mmol) in 1 mL of CH$_3$CN and 1 mL of 2 M aq. Na$_2$CO$_3$. The microwave tube was purged with N$_2$ and 7 mg (10 mol %) of PdCl$_2$(dppf) was added and tube was again purged with N$_2$, then sealed and microwaved for 20 min at 150° C. After reaction was complete, organic layer was separated, filtered through silica gel plug, concentrated and was subjected to reverse-phase HPLC purification (RP-C$_{18}$, 2-50% CH$_3$CN/0.1% aq. TFA gradient over 13 min, 35 mL/min) to yield compound no. 58. $^1$H NMR (400 MHz, DMSO-d6) δ 9.79 (s, 1H), 8.11 (d, J=8.4 Hz, 1H), 7.53 (d, J=1.9 Hz, 1H), 7.52 (d, J=8.1 Hz, 2H), 7.39 (d, J=1.5 Hz, 1H), 7.26 (d, J=8.0 Hz, 2H), 4.14 (s, 4H), 4.06 (q, J=7.1 Hz, 2H), 3.58 (m, 3H), 3.19 (q, J=11.1 Hz, 2H), 2.85 (bs, 2H), 2.34 (s, 3H), 2.29-2.23 (m, 5H), 2.09 (d, J=12.9 Hz, 2H), 1.96 (d, J=13.9 Hz, 2H), 1.67-1.57 (m, 2H), 1.20 (t, J=7.1 Hz, 3H).

LC/MS (RP-C$_{18}$, 10-99% CH$_3$CN/0.05% TFA gradient over 5 min): m/z 476.2 [M+H]$^+$, retention time 2.36 min.

Example 10

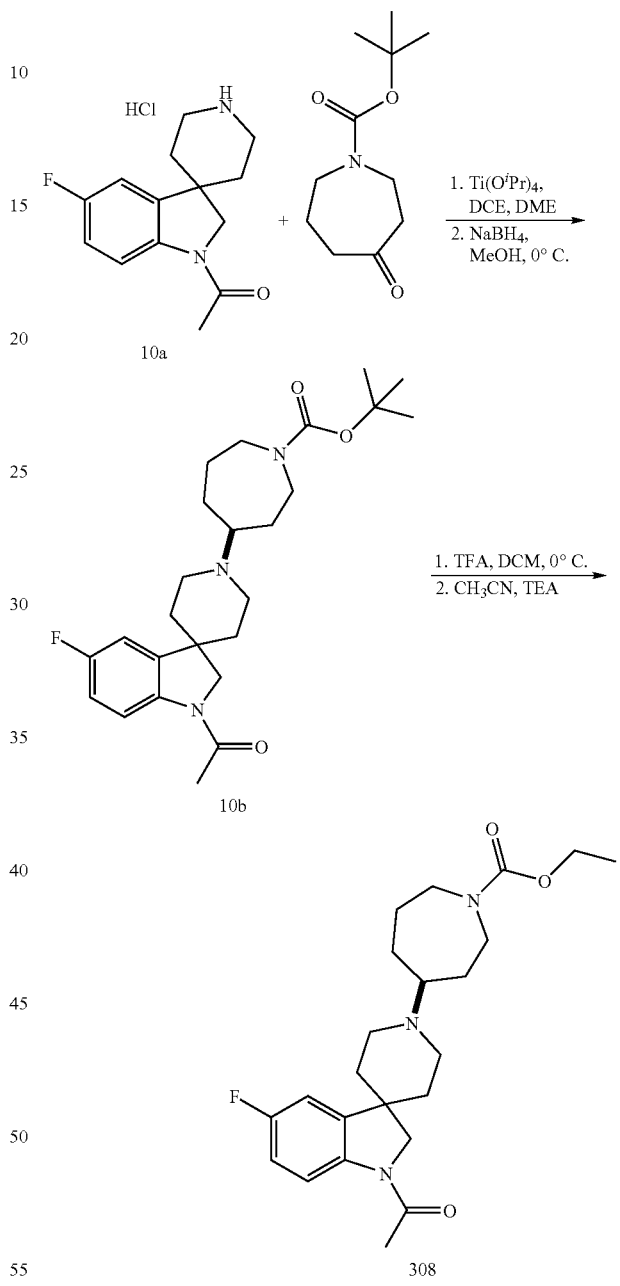

1.0 eq of the amine hydrochloride 10a (416 mg, 1.46 mmol) was suspended in anhydrous 1,2-dichloroethane:1,2-dimethoxyethane (6.0 mL, 1:1 v/v) and treated with 1.0 eq triethylamine (148 mg), followed by 1.5 eq tert-butyl 4-oxoazepane-1-carboxylate (467 mg, 2.19 mmol) and 3.0 eq titanium tetraisopropoxide (1.3 mL, 1.26 g, 4.4 mmol). The reaction vial was flushed with nitrogen and stirred at room temperature for 3 days. The reaction was diluted with methanol (6.0 mL), cooled in an ice-H$_2$O bath and treated with sodium borohydride (110 mg, 2.92 mmol). The reaction was slowly warmed to room temperature and stirred thereafter for 90 min. The reaction was then further diluted with methanol (10 mL), quenched with 1.0 N NaOH (5.0 mL) and stirred vigorously at room temperature for 10 min. The suspension obtained was centrifuged (3K rpm, 10 min) and the supernatant concentrated under reduced pressure. The residue obtained was dissolved in dichloromethane (75 mL) and washed successively with $H_2O$, saturated sodium bicarbonate, and saturated brine, then dried over $Na_2SO_4$ and filtered. The filtrate was concentrated in vacuo to afford 704 mg crude product 10b as a viscous, pale yellow oil. The crude product was used in the next step without further purification. $t_R$=2.14 min [10-99% $CH_3CN$ gradient over 5 mins with 0.1% TFA (aq)]; Theoretical $(M+H)^+$ m/z for $C_{25}H_{36}FN_3O_3$=446.3; Found 446.4.

The Boc-protected amine 10b (573 mg) was dissolved in dichloromethane (5 mL), cooled in an ice-$H_2O$ bath and treated slowly with ice-cold trifluoroacetic acid (5 mL). The reaction was stirred at –0° C. for 1 h, then concentrated under reduced pressure. The oil obtained was dissolved in acetonitrile and re-concentrated under reduced pressure. The crude TFA salt was dissolved in methanol (6.0 mL) and purified by reverse-phase HPLC (2-25% $CH_3CN$/0.1% TFA gradient over 10 min, 6×1.0 mL injected, 35 mL/min). The combined pure fractions were concentrated in vacuo to afford 291 mg amine 10c as the di-TFA salt, as a viscous, colorless oil. Yield (over 2 steps)=35%. $^1$H-NMR (400 MHz, DMSO-$d_6$) δ 9.83 (br s, 1H), 8.74 (br s, 2H), 8.06 (dd, J=8.8 Hz, 5.0 Hz, 1H), 7.06 (br m, 1H), 6.97 (br m, 1H), 4.12 (s, 2H), 3.59 (br s, 1H), 3.13 (br m, 6H), 2.36 (m, 1H), 2.20 (s, 3H), 2.13 (m, 5H), 1.89 (m, 5H), 1.71 (m, 1H); $t_R$=1.06 min [10-99% $CH_3CN$ gradient over 5 min with 0.1% TFA (aq)]; Theoretical $(M+H)^+$ m/z for $C_{20}H_{28}FN_3O$=346.2; Found 346.0.

Deprotected amine 10c (46 mg, 0.080 mmol, di-TFA salt) was dissolved in anhydrous acetonitrile (750 μL) and treated with 3.0 eq triethylamine (24 mg, 0.24 mmol). The mixture was then treated with ethyl chloroformate (9 μl, 10 mg, 0.096 mmol) and stirred at room temperature for 30 min. The reaction was quenched with methanol (500 μL) and purified by reverse-phase HPLC to provide compound no. 308 (2-40% $CH_3CN$/0.1% TFA gradient over 10 min, 1.0 mL injected, 35 mL/min). $t_R$=1.90 min [10-99% $CH_3CN$ gradient over 5 min with 0.1% TFA (aq)]; Theoretical $(M+H)^+$ m/z for $C_{23}H_{32}FN_3O_3$=418.2; Found 418.4.

Example 11

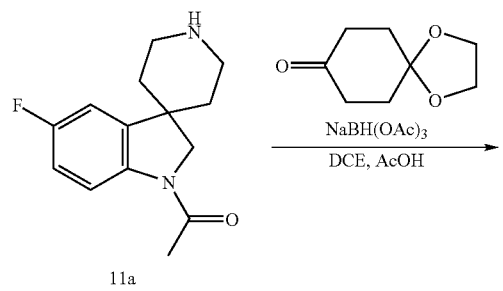

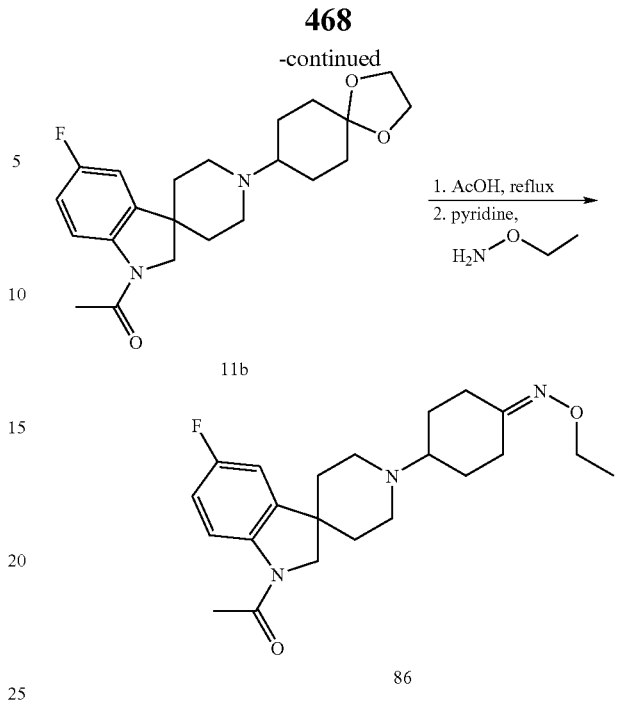

Spiroindoline 11a (300.0 mg; 1.21 mmol) and 4-oxocyclohexane spirodioxolane (283.1 mg; 1.81 mmol) were dissolved in DCE (5 mL). After 10 min, $NaBH(OAc)_3$ (512.1 mg; 2.42 mmol) was added, followed by AcOH (69.7 uL; 72.5 mg; 1.208 mmol) and the mixture was allowed to stir at room temperature for 75 h. The reaction was quenched by adding MeOH (10 mL) and was allowed to stir for 24 h. The resulting suspension was diluted with DCM (30 mL) and NaOH 1 N (5 mL) was added. The layers were separated, and the aqueous layer was extracted with DCM (3×30 mL). The combined organic extracts were dried on $Na_2SO_4$ and concentrated. The white solid residue was suspended in ether, the ethereal suspension was filtered and the precipitate was washed with ether (3×20 mL) and dried to provide the acetate salt of the desired product 11b (400 mg, 74% yield). The material was used for the next step without further purification. LC/MS m/z 389.2 $[M+H]^+$, retention time 1.73 min (10-99% $CH_3CN$—$H_2O$ gradient with 0.03% TFA, 5 min). $^1$HNMR (400 MHz, DMSO-$d_6$) δ 1.49 (m, 4H), 1.60 (d, J=13.0 Hz, 2H), 1.72 (d, J=9.4 Hz, 4H), 1.81 (td, J=13.4, 2.5 Hz, 2H), 2.19 (s, 3H), 2.28 (t, J=11.5 Hz, 2H), 2.37 (m, 1H), 2.80 (d, J=11.5 Hz, 2H), 3.85 (t, J=2.3 Hz, 4H), 3.95 (s, 2H), 6.97 (td, J=8.3, 1.8 Hz, 1H), 7.18 (dd, J=8.8, 2.7 Hz, 1H), 8.02 (dd, J=8.8, 5.0 Hz, 1H)

The ketal 11b (350.0 mg; 0.82 mmol) was dissolved in 80% aq. acetic acid (20 mL) and the solution was refluxed overnight. LC/MS analysis shows complete deprotection of the ketal, along with some deacetylation of the indoline nitrogen. The reaction mixture was diluted with water (20 mL), cooled on an ice bath and neutralized by addition of solid KOH. The resulting suspension was filtered and the precipitate was washed with water (3×10 mL) and dried to provide the crude product as a tan powder. This material was dissolved in DCM (10 mL) and treated with excess AcCl (1 mL) and triethylamine (1 mL). After stirring at room temperature for 3 h, the mixture was diluted with DCM (30 mL) and washed with saturated $NaHCO_3$. The organic layer was dried on $Na_2SO_4$ and concentrated to provide the product 11c as a yellow oil (253 mg, 89% yield), which was used for the next step without further purification. LC/MS m/z 345.0 $[M+H]^+$, retention time 1.43 min (10-99% $CH_3CN$—$H_2O$ gradient with 0.03%

TFA, 5 min); $^1$H NMR (400 MHz, CDCl$_3$) δ 1.68 (d, J=13.3 Hz, 2H), 1.82 (m, 2H), 1.91 (m, 2H), 2.07 (m, 2H), 2.18 (s, 3H), 2.29 (m, 6H), 2.45 (m, 2H), 2.78 (t, J=9.5 Hz, 1H), 2.97 (d, J=11.6 Hz, 2H), 3.81 (s, 2H) 6.88 (m, 2H), 8.16 (dd, J=8.5, 4.8 Hz, 1H).

The crude ketone 11c (100.0 mg; 0.29 mmol) was dissolved in pyridine (1 mL) and treated with O-ethyl hydroxylamine hydrochloride (21.3 mg; 0.35 mmol). The vial was sealed and heated to 60° C. for 1 h. The solvent was evaporated under reduced pressure and the residue was dissolved in DMSO (2 mL) and the product oxime compound no. 86 purified by reverse phase HPLC (2-99% CH$_3$CN—H$_2$O gradient with 0.03% TFA, 15 min. run). LC/MS m/z 388.4 [M+H]$^+$, retention time 1.87 min (10-99% CH$_3$CN—H$_2$O gradient with 0.03% TFA, 5 min); $^1$H NMR (free base, 400 MHz, CDCl$_3$) δ 1.25 (t, J=7.0 Hz, 3H), 1.55 (m, 2H), 1.71 (d, J=13.1 Hz, 2H), 1.94 (m, 5H), 2.14 (m, 1H), 2.25 (s, 3H), 2.30 (td, J=11.9, 5.6 Hz, 2H), 2.50 (d, J=14.3 Hz, 1H), 2.62 (t, J=9.6 Hz, 1H), 2.94 (d, J=11.8 Hz, 2H), 3.25 (d, J=14.7 Hz, 1H), 3.86 (s, 2H), 4.07 (q, J=7.0 Hz, 2H), 6.88 (m, 2H), 8.16 (dd, J=8.5, 4.8 Hz, 1H).

Example 12

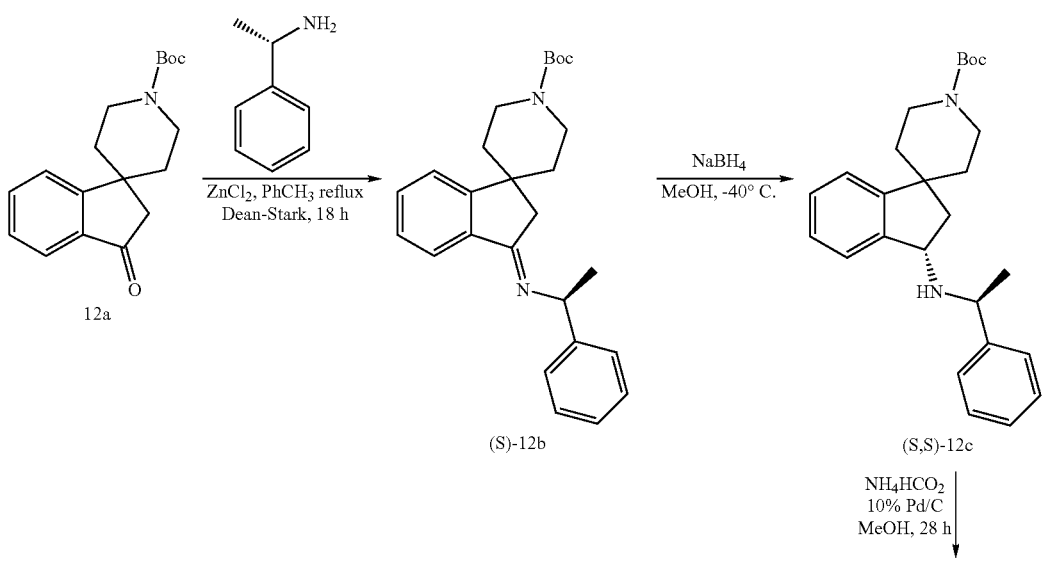

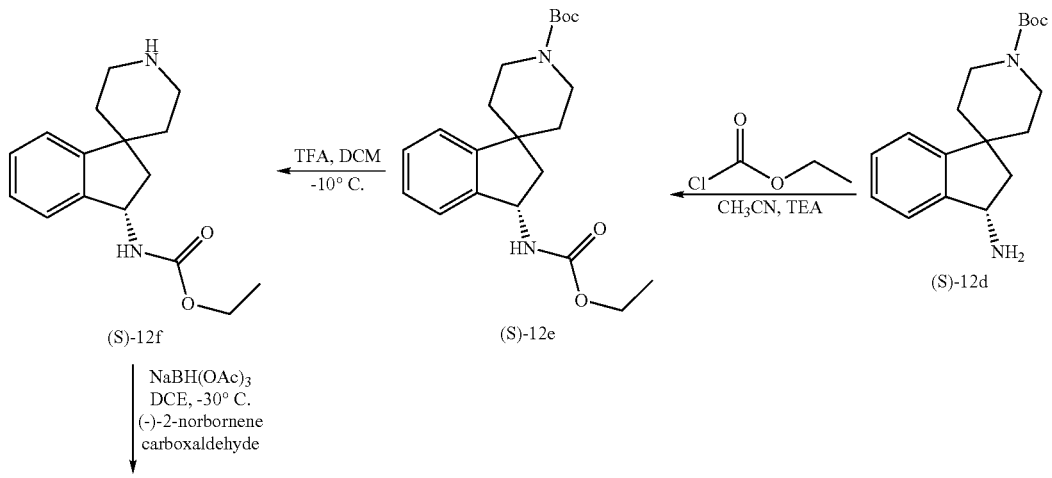

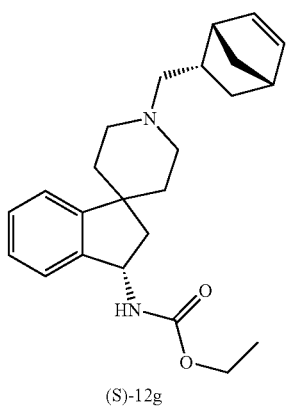

(S)-12g

10% Pd/C
CH₃CN/H₂O
0.05% TFA
→

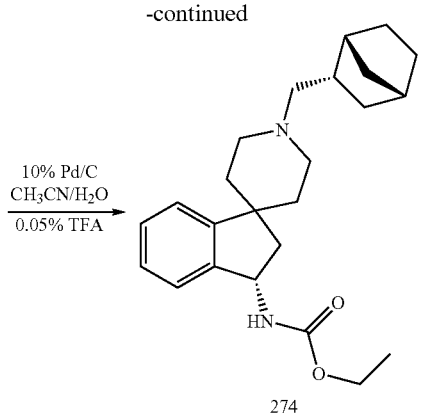

274

The N-Boc protected indanone 12a (6.5 g, 21.6 mmol), (S)-1-phenylethanamine (2.875 g, 23.72 mmol, 1.1 eq), and anhydrous $ZnCl_2$ (88 mg, 0.647 mmol, 0.03 eq) were brought up in 35 mL dry toluene in a 100-mL flask under $N_2$ atmosphere. The flask was fitted with a Dean-Stark trap and reflux condenser for the removal of water. The reaction mixture was heated at reflux for 18 h. The reaction mixture was cooled, diluted with EtOAc (200 mL), and washed with 0.1 N NaOH (2×30 mL), 20% saturated $NH_4Cl$ (1×100 mL), and brine (1×100 mL). The organic layer was then dried over $Na_2SO_4$, filtered, and dried down to afford imine (S)-12b as a light orange solid. LC/MS analysis of the crude product indicated complete conversion to the desired product. LC/MS (10-99%) m/z 405.2 [M+H]$^+$, retention time 2.76 min.

The crude imine (S)-12b (21.6 mmol) was dissolved in anhydrous MeOH (30 mL) and cooled to −40° C. under $N_2$ atmosphere. $NaBH_4$ (816 mg, 21.6 mmol, 1.0 eq) was added in one portion. The reaction mixture was allowed to warm to −20° C. over 2 h, then warmed to −5° C. for 3 h. The reaction mixture was then diluted with EtOAc (200 mL), then washed with 50% saturated $NaHCO_3$ (100 mL), water (2×100 mL), and brine (100 mL). The organic layer was dried over $Na_2SO_4$, filtered, and dried down to yield (S,S)-12c as a colorless oil. The oil was brought up in anhydrous diethyl ether, and 1 eq of ethereal HCl was added to precipitate the product as a fine white solid. The solid was filtered, washed with ether (100 mL), and dried under vacuum to obtain 7.2 of (S,S)-12c HCl salt as a white powder (75% yield). $^1$H NMR (400 MHz, DMSO-$d_6$) δ 10.08 (m, 1H), 9.49 (m, 1H), 8.01 (d, J=7.5 Hz, 1H), 7.77 (d, J=7.1 Hz, 2H), 7.29-7.47 (m, 6H), 4.91 (m, 1H), 4.62 (m, 1H), 3.94 (m, 2H), 2.87 (bs, 2H), 2.62 (dd, J=13.5, 8.0 Hz, 1H), 1.99 (dd, J=13.5, 7.5 Hz, 1H), 1.92 (dt, J=12.9, 4.4 Hz, 1H), 1.76 (d, J=6.7 Hz, 3H), 1.58 (d, J=12.9 Hz, 1H), 1.42 (s+obscured m, 11H); LC/MS (10-99%) m/z 407.4 [M+H]$^+$, retention time 2.70 min.

(S,S)-12c (3.0 g, 6.8 mmol), ammonium formate (8.5 g, 135.4 mmol, 20 eq), and 800 mg 10% Pd/C (wet, 50% by weight) were brought up in MeOH (30 mL) in a 100-mL flask fixed with a $N_2$ balloon. The mixture was stirred at room temperature for 28 h. The reaction mixture filtered through packed Celite and concentrated in vacuo to ~10 mL. The concentrate was diluted with 50% saturated $NaHCO_3$ (200 mL), and the product extracted into EtOAc (3×100 mL). The combined extracts were washed with brine (50 mL), dried over $Na_2SO_4$, and concentrated in vacuo to obtain (S)-12d as a colorless oil (2.0 g, 98% yield). $^1$H NMR (400 MHz, DMSO-$d_6$) δ 7.34 (m, 1H), 7.02-7.21 (m, 3H), 4.23 (t, J=7.7 Hz, 1H), 3.99 (m, 2H), 2.90 (br s, 2H), 2.57 (dd, J=12.7, 7.3 Hz, 1H), 2.00 (bs, 2H), 1.92 (dt, J=12.9, 4.5 Hz 1H), 1.42 (s+obscured m, 13H); LC/MS (10-99%) m/z 303.2 [M+H]$^+$, 286.2 [m/z−NH$_3$]$^+$, retention time 2.31 min.

(S)-12d (300 mg, 0.99 mmol) was dissolved in 1.5 mL anhydrous $CH_3CN$ and cooled to 0° C., followed by ethyl chloroformate (118 mg, 1.09 mmol, 1.1 eq) and triethylamine (200 μL). White precipitate formed upon addition of the triethylamine. The reaction was allowed to warm to room temperature and then stirred for 1 h. The reaction mixture was diluted with EtOAc (30 mL) and washed with 50% saturated $NaHCO_3$ (20 mL), water (20 mL), and brine (20 mL). The solution was dried over $Na_2SO_4$, filtered, and dried in vacuo to obtain product (S)-12e as a light yellow oil (>90% pure). LC/MS (10-99%) m/z 375.2 [M+H]$^+$, retention time 3.43 min.

The crude (S)-12e was dissolved 5 mL $CH_2Cl_2$ and cooled to 0° C., followed by the addition of 5 mL TFA. The reaction mixture was stirred at 0° C. for 1 h, diluted with $CH_3CN$ (20 mL), and dried in vacuo to obtain the (S)-12f TFA salt. The oil was dissolved in $CH_2Cl_2$ (30 mL), washed with 0.1 N NaOH (2×10 mL), brine (10 mL), dried over $Na_2SO_4$, filtered, and dried in vacuo to obtain the product (S)-12f as a light yellow oil (269 mg, 98% yield over 2 steps). LC/MS (10-99%) m/z 275.2 [M+H]$^+$, retention time 1.42 min.

(S)-12f (269 mg, 0.98 mmol) was dissolved in cold DCE (1.5 mL) and treated with (1S,2S,4S)-bicyclo[2.2.1]hept-5-ene-2-carbaldehyde (119 mg, 0.98 mmol, 1.0 eq), followed by portion-wise addition of $NaBH(OAc)_3$ (300 mg, 1.4 mmol, 1.4 eq). The reaction was allowed to stir at room temperature for 1 h and was then quenched with MeOH (1 mL) and allowed to stir for another 30 min (until gas evolution stopped). The crude reaction mixture was purified by HPLC (10-99 $CH_3CN$ gradient, 0.05% TFA) to provide the desired product (S)-12 g as the TFA salt. LC/MS (10-99%) m/z 381.2 [M+H]$^+$, retention time 2.28 min.

The combined HPLC fractions (~10 mL) were treated with 10% Pd/C (50 mg, wet, 50% by weight) under $H_2$ atmosphere with to cleanly provide (S)-12 g after 2 h of rapid stirring at room temperature. The solution was filtered through a 0.2 micron nylon filter and concentrated to provide 114 mg of compound no. 274 TFA salt (23% over 2 steps). LC/MS (10-99%) m/z 383.2 [M+H]$^+$, retention time 2.28 min; $^1$H-NMR (HCl salt, 400 MHz, DMSO-$d_6$) δ 10.39 (br s, 1H), 7.55 (d, J=8.4 Hz, 1H), 7.25 (m, 4H), 5.11 (m, 1H), 4.06 (q, J=7.0 Hz, 2H), 3.45 (m, 2H), 3.09 (m, 4H), 2.64 (m, 2H), 2.33 (br s, 2H), 2.15 (m, 2H), 1.84 (m, 1H), 1.67 (m, 3H), 1.48 (m, 2H), 1.34 (m, 3H), 1.20 (t, J=7.1 Hz, 3H), 1.14 (m, 1H), 0.88 (m, 1H).

Spiroindane (R)-compound no. 274 was produced utilizing an analogous synthetic route with the substitution of (R)-1-phenylethanamine for (S)-1-phenylethanamine in the synthesis of intermediate imine 12b (step 1).

Example 13

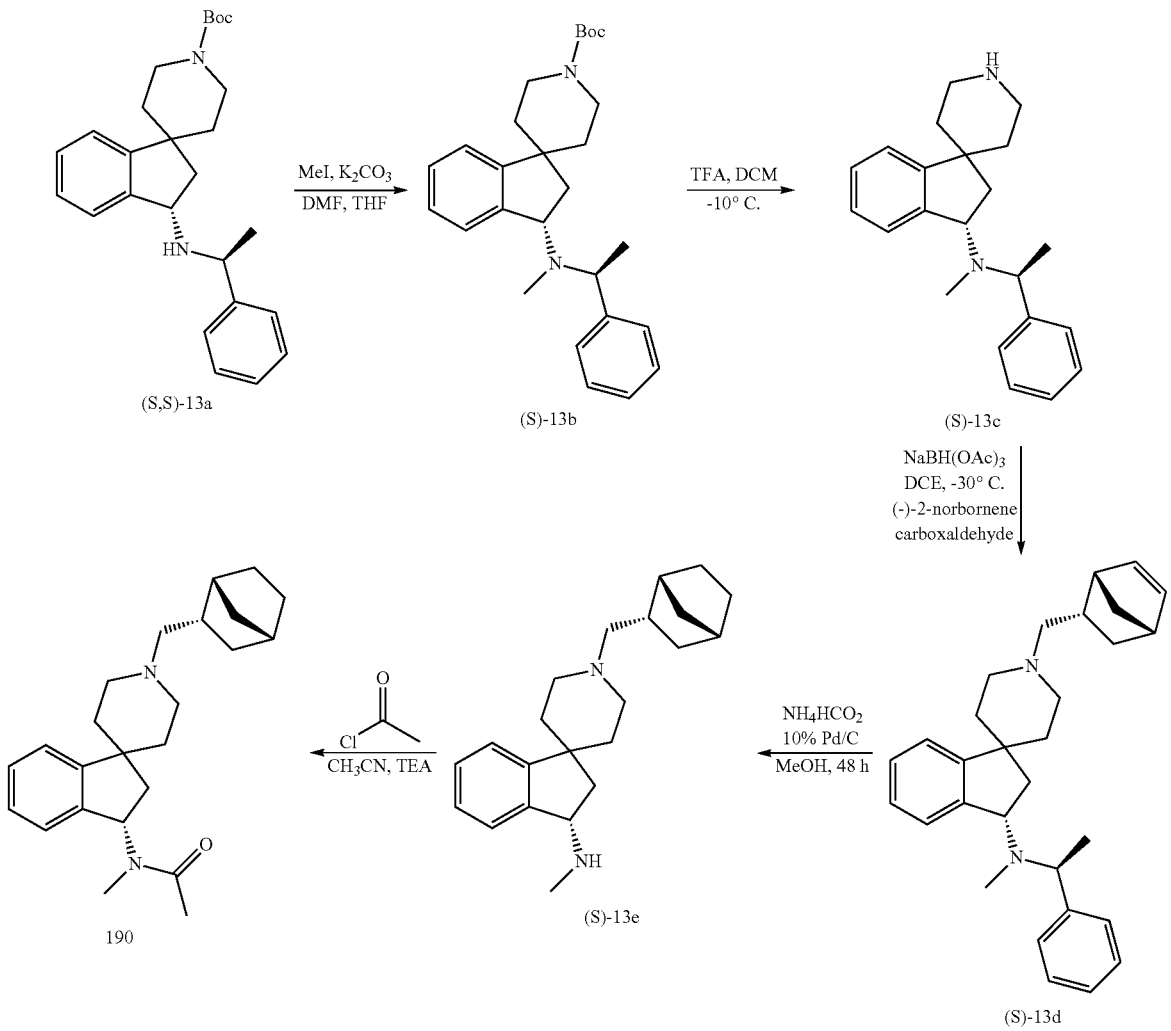

To a flask containing (S,S)-13a (See Example 12, 1.5 g, 3.39 mmol) and $K_2CO_3$ (1.87 g, 13.54 mmol, 4 eq) was added 2 mL anhydrous DMF followed by 8 mL anhydrous THF. The mixture was treated with MeI (2.40 g, 16.93 mmol, 5 eq) and heated to 45° C. for 6 h, followed by stirring at room temperature for 16 h. The reaction mixture was diluted with EtOAc (200 mL) and washed with 20% saturated $NH_4Cl$ (50 mL), 50% saturated $NaHCO_3$ (50 mL), brine (50 mL). The solution was dried over $Na_2SO_4$, filtered, and dried in vacuo to yield a reddish oil. The oil was dissolved in diethyl ether and filtered to remove insoluble material, followed by treatment with 1 eq of ethereal HCl. The resulting solution was dried down in vacuo to yield crude (S)-13b as a light orange solid. LC/MS (10-99%) m/z 421.0 $[M+H]^+$, retention time 2.77 min.

Crude (S)-13b was dissolved in $CH_2Cl_2$ (50 mL) and cooled to −10° C., followed by the addition of 10 mL TFA. The reaction mixture was stirred at −10° C. for 1 h, diluted with $CH_3CN$ (20 mL), and dried in vacuo to obtain the (S)-13c TFA salt. The oil was dissolved in $CH_2Cl_2$ (30 mL), washed with 50% saturated $NaHCO_3$ (2×10 mL), brine (10 mL), dried over $Na_2SO_4$, filtered, and dried in vacuo to obtain the product (S)-13c as a colorless oil (673 mg, 67% yield over 2 steps). $^1$H NMR (400 MHz, DMSO-$d_6$) δ 7.46 (d, J=7.2 Hz, 2H), 7.34 (t, J=7.4 Hz, 2H), 7.16-7.25 (m, 5H), 4.66 (t, J=8.0 Hz, 1H), 3.79 (q, J=6.7 Hz, 1H), 2.99 (app t, J=12.0 Hz, 2H), 2.79 (dt, J=12.4, 2.5 Hz, 1H), 2.69 (dt, J=12.7, 2.3 Hz, 1H), 2.07 (q, J=8.0 Hz, 1H), 1.97 (dt, J=13.3, 4.2 Hz, 1H), 1.85 (s, 3H), 1.73 (m, 1H), 1.52 (dt, J=12.7, 4.2 Hz, 1H), 1.42 (d, J=6.6 Hz, 3H), 1.36 (app t, J=12.9 Hz, 3H); LC/MS (10-99%) m/z 321.2 $[M+H]^+$, retention time 1.60 min.

(S)-13c (650 mg, 2.03 mmol) and (1S,2S,4S)-bicyclo[2.2.1]hept-5-ene-2-carbaldehyde (262 mg, 2.15 mmol) were dissolved in DCE (13 mL) and the mixture cooled to −30° C., followed by portion-wise addition of $NaBH(OAc)_3$ (646 mg, 3.05 mmol). The reaction was stirred at −30° C. for 2 h and was the allowed to come to room temperature and stirred for 16 h. The reaction was quenched with MeOH (5 mL) and diluted with EtOAc (200 mL). The crude reaction was washed with 50% saturated $NaHCO_3$ (50 mL), water (50 mL), and brine (50 mL). The organic layer was dried over $Na_2SO4$, filtered and dried in vacuo to yield the product (S)-13d as a colorless oil (802 mg, 93% yield).

(S)-13d (800 mg, 6.8 mmol), ammonium formate (2.36 g, 37.5 mmol), and 800 mg 10% Pd/C (wet, 50% by weight) were brought up in MeOH (8 mL) in a 25-mL flask fixed with a $N_2$ balloon. The mixture was stirred at room temperature for 24 h. 1.18 g of ammonium formate were added and the mixture stirred for an additional 24 h. The reaction mixture was filtered through packed Celite, diluted with 50% saturated $NaHCO_3$ (200 mL), and the product (S)-13e extracted into EtOAc (5×75 mL). The combined extracts were washed with brine (50 mL), dried over $Na_2SO_4$, and concentrated in vacuo to obtain (S)-13e as a colorless oil (493 mg, 81% yield). LC/MS (10-99%) m/z 325.4 [M+H]$^+$, retention time 1.52 min.

(S)-13e (123 mg, 0.38 mmol) was dissolved in 1.5 mL anhydrous $CH_3CN$ and cooled to 0° C., followed by the additional of acetyl chloride (33 mg, 0.42 mmol) and triethylamine (200 μL). White precipitate formed upon addition of the triethylamine. The reaction was allowed to warm to room temperature and then stirred for 1 h. The crude reaction mixture was purified by HPLC (10-99 $CH_3CN$ gradient, 0.05% TFA) to provide the desired compound no. 190 as the TFA salt (65 mg, 47% yield). LC/MS (10-99%) m/z 367.2 [M+H]$^+$, retention time 1.99 min.

Spiroindane (R) form of compound no. 190 was produced utilizing an analogous synthetic route with the substitution of (R)-1-phenylethanamine for (S)-1-phenylethanamine in the synthesis of intermediate 13a (See Example 12).

Example 14

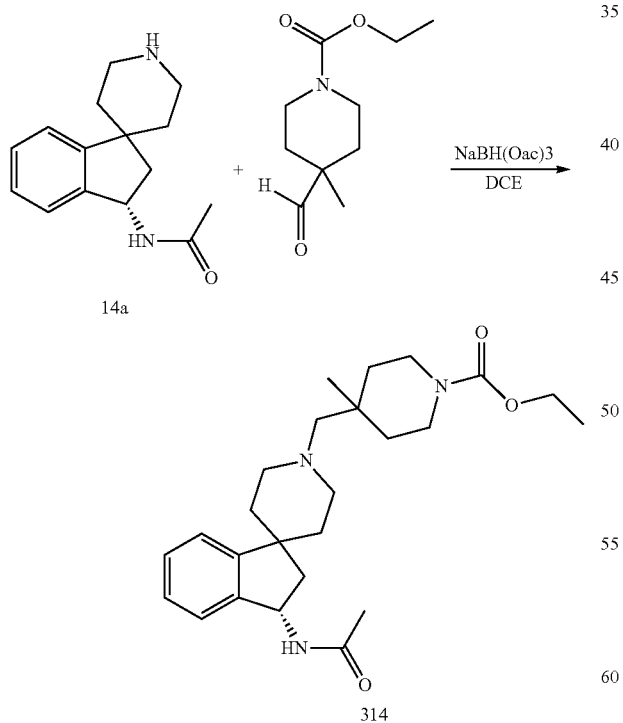

Intermediate 14a (49 mg; 0.2 mmol) and 4-formyl-4-methylpiperidine-1-carboxylate (40 mg; 0.2 mmol) were dissolved in DCE (2 mL) and NaBH(OAc)$_3$ (85 mg; 0.4 mmol) was added. The reaction was stirred at room temperature for 20 hours. The reaction was diluted with DCM (10 mL) and 1N HCl (20 mL), the layers were separated, and the organic layer was discarded. The aqueous layer was washed with DCM (10 mL) and then was basified with NaOH. The aqueous layer was then washed with EtOAc (3×20 mL) and the combined organic layers were dried over $Na_2SO_4$, filtered, and concentrated under high vacuum. The crude product compound no. 314 was purified using reversed-phase chromatography (2-99% $CH_3CN/H_2O$ gradient with 0.05% TFA). LC/MS m/z [M+H]$^+$ 428.2, retention time 1.85 min (10-99% $CH_3CN$—$H_2O$ gradient with 0.03% TFA, 5 min); $^1$H-NMR (400 MHz, DMSO-$d_6$) δ 8.50 (br s, 1H), 8.26 (d, J=8.2 Hz, 1H), 7.27 (m, 4H), 5.35 (m, 1H), 4.04 (q, J=7.1 Hz, 2H), 3.69 (m, 2H), 3.53 (m, 2H), 3.31 (m, 2H), 3.18 (m, 5H), 2.69 (m, 1H), 2.07 (m, 1H), 1.89 (s, 3H), 1.66 (m, 3H), 1.50 (m, 4H), 1.19 (overlapping q and s, 6H).

Example 15

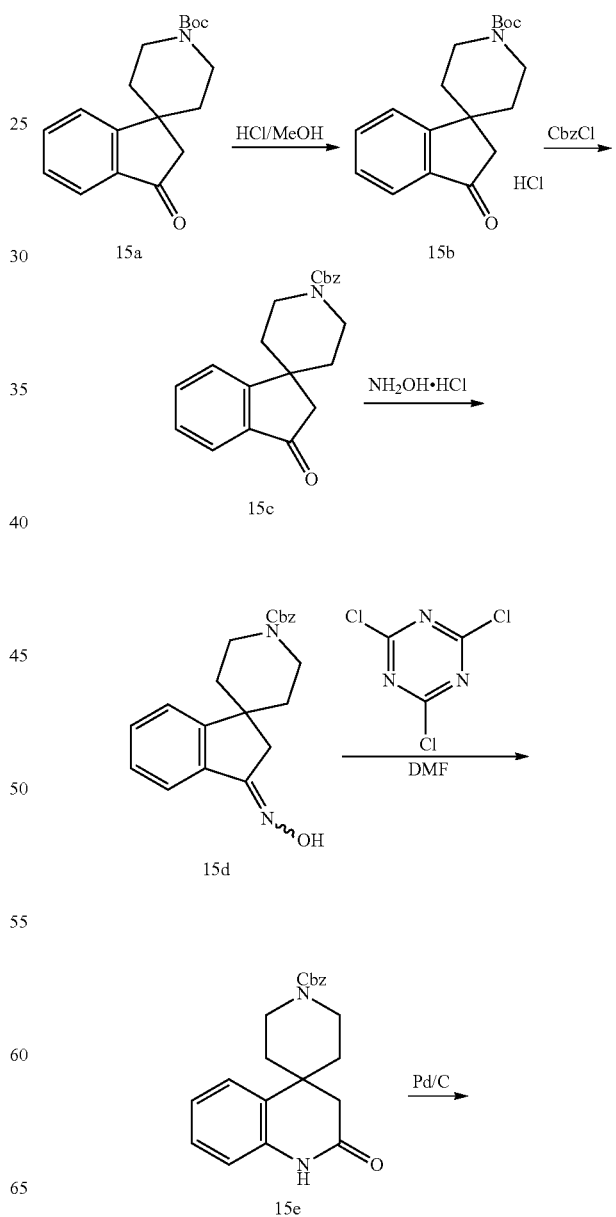

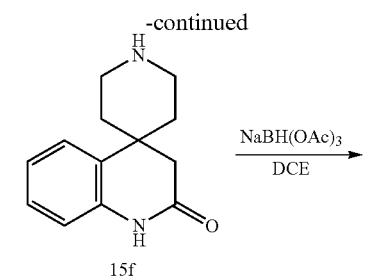

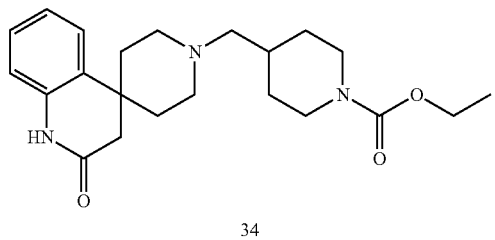

The mixture of N-Boc protected spiroindanone 15a (20 g, 66.4 mmol) and MeOH/HCl (2.5 mol/L, 100 mL) were stirred overnight. After evaporation the residue was washed by petroleum ether to gave the corresponding amine hydrochloride 15b (15.4 g, 97.6%).

To a solution of compound 15b (5.0 g, 24.84 mmol) and Et$_3$N (7.54 g, 74.53 mol) in CH$_2$Cl$_2$ (50 mL) was added drop-wise Cbz-Cl (4.66 g, 27.33 mmol) at 0° C. The reaction was allowed to warm to room temperature and stirred overnight. The precipitate was filtered, washed with Et$_2$O and dried to furnish compound 15c (6.1 g, yield 99%).

A solution of compound 15c (3 g, 10.3 mmol) in EtOH (30 mL) containing NH$_2$OH.HCl (1.43 g, 20.6 mmol) and NaOAc (1.52 g, 18.53 mmol) was heated under reflux for 1.5 hours. The solvent was removed by evaporation and the residue was partitioned between CH$_2$Cl$_2$ and water. The organic phase was washed with brine, dried over Na$_2$SO$_4$, and concentrated to give compound 15d (3.14 g, yield 99%), which could be used directly in the next step.

2,4,6-trichloro-[1,3,5]-triazine (1.32 g, 7.16 mmol) was added to DMF (9.6 mL) maintained at 25° C. The reaction was monitored by TLC until TCT was consumed. Then compound 15d (1.6 g, 4.77 mmol) in DMF (17 mL) was added. After the addition, the mixture was stirred at room temperature overnight. Water was added. The mixture was extracted with EtOAc. The combined organic layers were washed with saturated Na$_2$CO$_3$, followed by 1N HCl and brine, dried over Na$_2$SO$_4$ and concentrated. The residue was purified by prep HPLC to obtain compound 15e (260 mg, yield 16%).

The mixture of compound 15e (1.2 g, 3.4 mmol) and Pd/C (200 mg) in MeOH (20 mL) was hydrogenated under atmosphere pressure at room temperature for 3 hours. The catalyst was filtered and the filtrate was concentrated under reduced pressure. The residue was purified by preparative HPLC twice to give 15f (110 mg, 11%) as a TFA salt. $^1$H NMR (CDCl$_3$) δ 7.65 (d, J=7.5 Hz, 1H), 7.29-7.45 (m, 3H), 3.45 (d, J=12.3 Hz, 2H), 3.20 (t, J=12.3 Hz, 2H), 2.96 (s, 2H), 2.10-2.21 (m, 2H), 1.70 (d, J=14.1 Hz, 2H). MS (ESI) m/z 217.06 [M+H]$^+$.

Amine 15f (22 mg, 0.1 mmol) and ethyl 4-formylpiperidine-1-carboxylate (28 mg, 0.15 mmol) were dissolved in DCE (1 mL) and NaBH(OAc)$_3$ (42 mg; 0.2 mmol) was added. The reaction was stirred at room temperature for 16 hours. The reaction was diluted methanol (0.5 mL), filtered, and compound no. 34 was purified using reversed-phase chromatography (10-99% CH$_3$CN/H$_2$O gradient with 0.05% TFA). LC/MS m/z 386.2 [M$_+$H]$^+$, retention time 2.05 min (10-99% CH$_3$CN—H$_2$O gradient with 0.03% TFA, 5 min); $^1$H NMR (free base, 400 MHz, DMSO-d$_6$) δ 7.71 (d, J=3.9 Hz, 2H), 7.61 (d, J=7.6 Hz, 1H), 7.47-7.41 (m, 1H), 4.05-3.96 (m, 4H), 2.86-2.67 (m, 4H), 2.56 (d, J=9.7 Hz, 2H), 2.18 (s, 2H), 2.01 (d, J=7.7 Hz, 4H), 1.73 (d, J=11.1 Hz, 4H), 1.45 (d, J=8.7 Hz, 2H), 1.18 (t, J=7.1 Hz, 3H), 1.03-0.96 (m, 2H).

Example 16

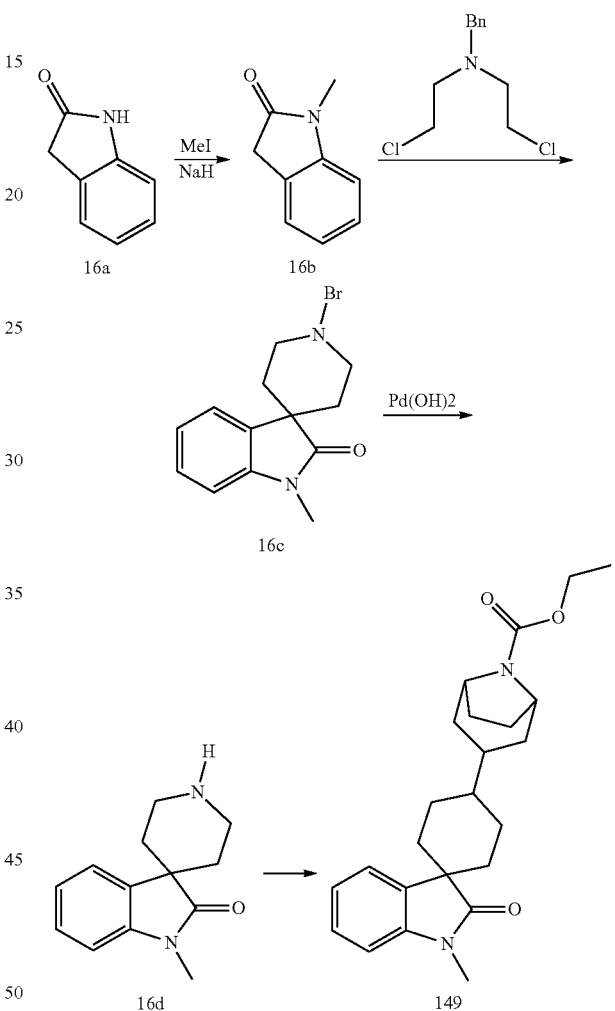

A stirred mixture of sodium hydride (60%, 31 g, 0.79 mol) in dry xylene (500 mL), under a nitrogen atmosphere, was heated to reflux for 30 min. 1,3-Dihydro-indol-2-one 16a (100 g, 0.75 mol) was then slowly added via an addition funnel and stirred at reflux for 1.5 hours. Dimethyl sulfate (104 g, 0.83 mol) was added drop-wise, whereupon the resulting homogeneous solution was refluxed for an additional 2 hours. After cooling to room temperature, the reaction mixture was washed with water, dried over Na$_2$SO$_4$, and concentrated under reduced pressure to afford 1-methyl-1,3-dihydro-indol-2-one 16b (74 g, 67.3%). $^1$H NMR (300 MHz, CDCl$_3$) δ 7.23-7.31 (m, 2H), 7.04 (t, J=7.5 Hz, 1H), 6.82 (d, J=7.8 Hz, 1H), 3.52 (s, 2H), 3.21 (s, 3H).

A suspension of NaH (60%, 70 g, 0.48 mol) in THF (300 mL) was stirred for 10 min at 0° C. Then a solution of 1-methyl-1,3-dihydro-indol-2-one 16b (70 g, 2.88 mol) in THF (200 mL) was added at 0° C., and the mixture was stirred for 1 hour at room temperature. Benzyl-bis-(2-chloro-ethyl)-amine (129 g, 0.48 mol) was added in portions at 0° C. The mixture was stirred overnight at room temperature, and then was poured into ice-water, extracted with EtOAc. The combined organic layers were dried over $Na_2SO_4$, and concentrated under reduced pressure. The residue was purified by column on silica gel (P.E./E.A. 2:1) to give compound 16c (24 g, 16.3%). $^1$H NMR (300 MHz, CDCl$_3$) δ 7.25-7.42 (m, 7H), 7.02-7.07 (m, 1H), 6.83 (d, J=7.5, 1H), 3.68 (s, 2H), 3.19 (s, 3H), 2.74-2.99 (m, 2H), 2.66-2.72 (m, 2H), 1.93-2.01 (m, 2H), 1.79-1.85 (m, 2H).

To a solution of compound 16c (12 g, 39.2 mmol) in MeOH (100 mL) was added Pd(OH)$_2$/C (1.5 g, 20%) under $N_2$. The suspension was hydrogenated under $H_2$ (50 psi) at room temperature for 4.5 hours. The catalyst was filtered off, and the filtrate was concentrated under reduced pressure to give the deprotected spiroindolone product 16d (8 g, 94.5%). $^1$H NMR (400 MHz, DMSO-d$_6$) δ 7.46 (d, J=7.2, 1H), 7.23-7.27 (m, 1H), 6.96-7.03 (m, 2H), 3.04-3.14 (m, 5H), 2.83-2.89 (m, 2H), 1.61-1.67 (m, 2H), 1.45-1.51 (m, 2H). MS (ESI) m/z 217.1 [M+H]$^+$.

1.0 eq of deprotected spiroindolone 16d (22 mg, 0.10 mmol) was dissolved in anhydrous 1,2-dichloroethane:1,2-dimethoxyethane (1.0 mL, 1:1 v/v) and treated with 1.5 N-Carbethoxy-4-tropinone (30 mg, 0.15 mmol), followed by titanium tetraisopropoxide (88 µL, 85 mg, 0.30 mmol). The vial was flushed with nitrogen and stirred at room temperature ~70 hours. The reaction was then diluted with methanol (1.0 mL), cooled in an ice-H$_2$O bath and treated with sodium borohydride (8 mg, 0.20 mmol). After warming to room temperature and stirring for 90 min, the reaction was further diluted with methanol (2.0 mL), quenched with 1.0 N NaOH (500 µL) and stirred vigorously at room temperature for 10 min. The suspension obtained was centrifuged (3K rpm, 10 min) and the supernatant concentrated under reduced pressure. The residue obtained was dissolved in MeOH:acetonitrile (1250 µL, 1:1 v/v), filtered, and purified by reverse-phase HPLC (2-40% CH$_3$CN/0.1% TFA gradient over 10 min) to yield product compound no. 149. LC/MS (10-99%) m/z [M$_+$H]$^+$398.2, retention time 1.93 min.

Example 17

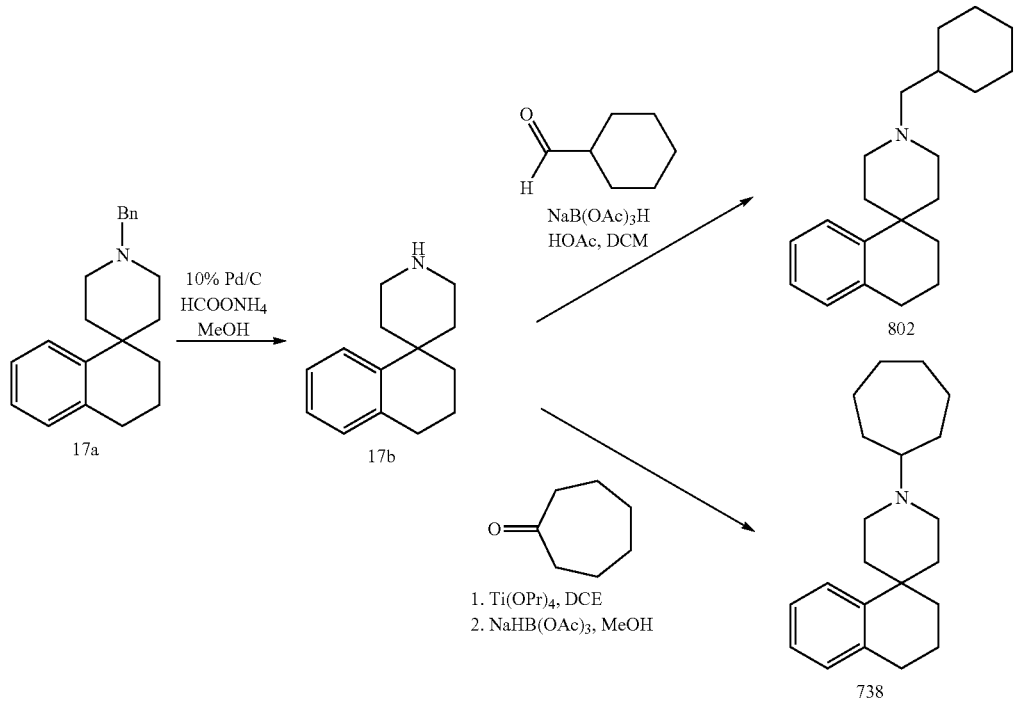 [SMILES: c1ccc(CN2CCC3(CCCc4ccccc43)CC2)cc1 ; c1ccc2c(c1)CCCC21CCNCC1 ; O=C1CCCCCC1 ; O=CC1CCCCC1 ; c1ccc2c(c1)CCCC21CCN(CC2CCCCC2)CC1 ; c1ccc2c(c1)CCCC21CCN(C2CCCCCC2)CC1]

A suspension of 1'-benzyl-3,4-dihydro-2H-spiro[naphthalene-1,4'-piperidine] 17a (1.7 g, 5.8 mmol), 10% Pd/C (1 g), and ammonium formate (4.8 g, 76 mmol) in MeOH (50 ml) was stirred under $N_2$ for 24 hours. The mixture was filtered through Celite, and the filtrate was concentrated. The filtrate was dissolved in CH$_2$Cl$_2$, washed with diluted NaOH, and the aqueous phase was re-extracted with CH$_2$Cl$_2$. The combined organic phase was dried (Na$_2$SO$_4$) and concentrated to give 3,4-dihydro-2H-spiro[naphthalene-1,4'-piperidine] 17b. LC-MS: m/e=202.1 (M+H). R$_t$=1.61 min. $^1$H-NMR (500 MHz, CDCl$_3$): 9.74 (s, 2H), 7.58 (d, J=7.9, 1H), 7.22 (t, J=7.8, 1H), 7.14 (t, J=7.9, 1H), 7.08 (d, J=8.0, 1H), 3.47 (d, J=12.4, 2H), 3.22-3.18 (m, 2H), 2.88 (t, J=4.9, 2H), 2.81 (t, J=6.2, H), 2.60 (td, 2H), 1.93-1.89 (m, 2H), 1.83-1.77 (m, 2H).

A solution of cyclohexanecarbaldehyde (40 mg, 0.35 mmol) and 3,4-dihydro-2H-spiro[naphthalene-1,4'-piperidine] 17b (33 mg, 0.16 mmol) in 1,2-dichloroethane (2 mL) was stirred at 50° C. for 1 hour. The reaction mixture was cooled to room temperature and treated with sodium triacetoxyborohydride (44 mg, 0.2 mL), followed by acetic acid (1 drop) and methanol (1 mL). The reaction mixture was stirred for another 5 hours and concentrated under a stream of N$_2$. The residue was dissolved in methanol (1 mL) and purified by reverse phase HPLC to give compound no. 802 as a TFA salt. LC-MS: m/e=298.0 (M+H). R$_t$=2.09 min. $^1$H-NMR (500 MHz, DMSO-d$_6$): 8.70 (s, 1H), 7.39 (d, 1H), 7.22 (t, 1H), 7.14 (t, 1H), 7.06 (d, 1H), 3.40 (d, 2H), 3.14 (dd, 2H), 3.00 (t, 2H), 2.72 (t, 2H), 2.28 (td, 2H), 1.89-1.87 (m, 2H), 1.83-1.66 (m, 10H), 1.28 (q, 2H), 1.21-1.13 (m, 1H), 1.03-0.96 (m, 2H).

A solution of 3,4-dihydro-2H-spiro[naphthalene-1,4'-piperidine] 18a (33 mg, 0.16 mmol) and cycloheptanone (86 mg, 0.76 mmol) in dichloromethane (2 ml) was stirred in a sealed vial for 90 min and treated with titanium(IV)propoxide (60 ul, 0.21 mmol) for 24 hours. Sodium borohydride (10 mg, 0.27 mmol) was added to the reaction mixture and the resulting mixture was stirred for 5 hours then treated with methanol (1 mL) and acetic acid (1 drop) for 1 hour. The solvents were evaporated and the residue was dissolved in methanol (1 ml) and acidified with TFA and purified by HPLC to give compound no. 738. LC-MS: m/z=298.3 (M+H). $R_t$=2.05 min. $^1$H-NMR (500 MHz, DMSO-$d_6$): 9.01 (s, H), 7.38 (d, 1H), 7.21 (t, 1H), 7.14 (t, 1H), 7.05 (d, 1H), 3.40 (m, 1H), 3.27-3.17 (m, 4H), 2.72 (t, 2H), 2.26 (td, 2H), 2.12-2.05 (m, 2H), 1.88-1.86 (m, 2H), 1.76-1.67 (m, 8H), 1.57-1.46 (m, 6H).

Example 18

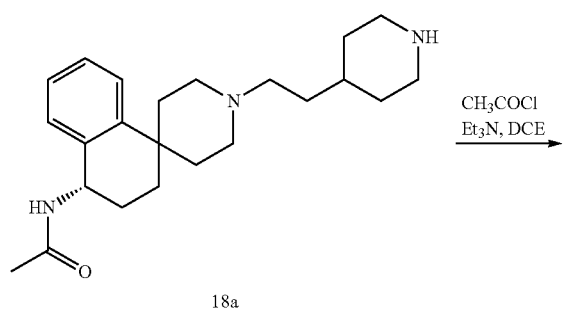

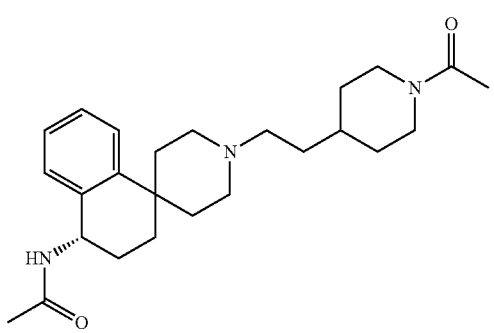

A solution of (S)—N-(1'-(2-(piperidin-4-yl)ethyl)-3,4-dihydro-2H-spiro [naphthalene-1,4'-piperidine]-4-ylacetamide 18a (18 mg, 0.048 mmol), Et$_3$N (0.2 ml) in 1,2-dichloroethane (2 ml was treated acetyl chloride (2 drops, ca. 0.05 ml) for 2 hours. The solvent was evaporated. The residue was dissolved in MeOH (1 ml), acidified with CF$_3$COOH and purified with HPLC to give compound no. 832 as a TFA salt. LC-MS: m/z=412.20 (M+H). $R_t$=1.48 min. $^1$H-NMR (500 MHz, DMSO-$d_6$): 9.03 (s, 1H), 8.17 (d, 1H), 7.34 (t, 1H), 7.30 (d, 1H), 7.20 (t, 1H), 7.17 (d, 1H), 4.92 (q, 1H), 4.35 (d, 1H), 3.80 (m, 2H), 3.43 (m, 2H), 3.16 (t, 4H), 3.00 (t, 1H), 2.22-2.14 (m, 2H), 2.06 (ddd, 1H), 1.98 (s, 3H), 1.87 (s, 3H), 1.82 (m, 3H), 1.75-1.53 (m, 7H), 1.13 (m, 1H), 1.00 (m, 1H).

Example 19

Compound no. 364 was synthesized using known methods and those described above.
$^1$H NMR (400 MHz, CDCl$_3$) δ 1.27 (t, J=6.3 Hz, 3H), 1.56 (d, J=11.5 Hz, 2H), 1.67 (q, J=7.0 Hz, 4H), 1.82 (m, 2H), 1.97 (m, 6H), 2.29 (t, J=11.5 Hz, 2H), 2.82 (m, 1H), 2.89 (dd, J=13.7, 6.5 Hz, 2H), 4.13 (q, J=7.1 Hz, 2H), 4.35 (d, J=24.4 Hz, 2H), 7.17 (m, 4H).

Example 20

Compound no. 413 was synthesized using known methods and those described above.
$^1$H NMR (free base, 400 MHz, DMSO-d6) δ 7.20-7.10 (m, 4H), 4.02 (q, J=7.1 Hz, 2H), 3.99-3.96 (m, 2H), 2.84 (t, J=7.3 Hz, 2H), 2.81-2.77 (m, 4H), 2.16 (d, J=4.9 Hz, 2H), 2.06 (t, J=12.2 Hz, 2H), 1.94 (t, J=7.3 Hz, 2H), 1.80 (t, J=11.3 Hz, 2H), 1.74-1.70 (m, 3H), 1.43 (d, J=12.5 Hz, 2H), 1.18 (t, J=7.1 Hz, 3H), 1.02-0.93 (m, 2H).

Example 21

Compound no. 375 was synthesized using known methods and those described above.
$^1$H NMR (400 MHz, DMSO-$d_6$) δ 10.18 (s, 1H), 6.99 (dt, J=12.8, 4.5 Hz, 1H), 6.91 (dd, J=8.0, 2.7 Hz, 1H), 6.82 (dd, J=8.7, 4.1 Hz, 1H), 6.25 (q, J=2.9 Hz, 1H), 6.07 (q, J=2.7 Hz, 1H), 4.50 (s, 2H), 3.51 (t, J=13.2 Hz, 2H), 3.04-2.96 (m, 3H), 2.91-2.84 (m, 2H), 2.74-2.68 (m, 1H), 2.40-2.30 (m, 2H), 2.03-1.97 (m, 2H), 1.88 (d, J=14.2 Hz, 2H), 1.32 (dd, J=33.8, 7.1 Hz, 2H), 0.69 (d, J=11.4 Hz, 1H).

Example 22

Compound no. 181 was synthesized using known methods and those described above.
$^1$H-NMR (400 MHz, DMSO-$d_6$) δ 10.03 (br s, 1H), 7.21 (dd, J=8.5, 2.3 Hz, 1H), 7.08 (d, J=2.3 Hz, 1H), 6.85 (d, J=8.5 Hz, 1H), 4.52 (s, 2H), 3.41 (m, 2H), 3.25 (m, 1H), 3.01 (m, 2H), 2.63 (m, 2H), 2.44 (m, 1H), 2.27 (m, 1H), 1.86 (m, 4H), 1.51 (m, 3H), 1.39 (m, 2H), 1.24 (m, 1H).

Example 23

Compound no. 23 was synthesized using known methods and those described above.
$^1$H-NMR (400 MHz, DMSO-$d_6$) δ 10.27 (br s, 1H), 8.53 (br s, 1H), 6.93 (d, J=7.9 Hz, 1H), 6.88 (s, 1H), 6.72 (d, J=7.9 Hz, 1H), 3.48 (s, 2H), 3.40 (m, 3H), 3.04 (m, 2H), 2.64 (m, 1H), 2.57 (br s, 1H), 2.38 (m, 1H), 2.26 (m, 1H), 2.24 (s, 3H), 1.94 (m, 2H), 1.78 (m, 2H), 1.55 (m, 3H), 1.39 (m, 3H).

Example 24

Compound no. 367 was synthesized using known methods and those described above.
$^1$H-NMR (300 MHz, CDCl$_3$): δ 7.08 (m, 1H), 6.95 (m, 2H), 4.28 (br s, 2H), 4.09 (q, J=7.2 Hz, 2H), 3.80 (s, 2H), 3.62 (m, 2H), 3.00 (m, 2H), 2.91 (m, 2H), 2.49 (m, 3H), 1.95-2.02 (m, 6H), 1.69 (m, 2H), 1.48 (m, 2H), 1.25 (t, J=7.2 Hz, 3H).

Example 25

Compound no. 370 was synthesized using known methods and those described above.
$^1$H-NMR (400 MHz, DMSO-$d_6$) δ 10.65 (br s, 1H), 8.05 (dd, J=8.9, 4.9 Hz, 1H), 7.06 (td, J=9.0, 2.7 Hz, 1H), 6.92 (dd, J=8.3, 2.7 Hz, 1H), 4.27 (br s, 2H), 4.08 (m, 4H), 3.74 (m, 1H), 3.55 (br s, 2H), 3.06 (m, 2H), 2.30 (m, 2H), 2.20 (s, 3H), 2.07 (m, 2H), 1.86 (m, 6H), 1.67 (m, 2H), 1.22 (t, J=7.1 Hz, 3H).

Example 26

Compound no. 422 was synthesized using known methods and those described above.
$^1$H-NMR (400 MHz, DMSO-$d_6$) δ 10.61 (br s, 1H), 7.93 (d, J=8.1 Hz, 1H), 7.02 (d, J=8.2 Hz, 1H), 6.96 (s, 1H), 4.06 (s, 2H), 3.96 (m, 3H), 3.59 (s, 3H), 3.51 (m, 2H), 3.11 (m, 2H), 3.00 (t, J=6.0 Hz, 2H), 2.83 (br s, 2H), 2.47 (m, 1H), 2.28 (s, 3H), 2.18 (s, 3H), 2.11 (m, 1H), 1.88 (m, 2H), 1.77 (m, 2H), 1.13 (m, 2H).

Example 27

Compound no. 92 was synthesized using known methods and those described above.
$^1$H-NMR (400 MHz, DMSO-$d_6$) δ 10.97 (br s, 1H), 7.93 (d, J=8.1 Hz, 1H), 7.02 (d, J=8.2 Hz, 1H), 6.95 (s, 1H), 4.13 (m, 2H), 4.06 (m, 4H), 3.45 (m, 3H), 3.12 (m, 2H), 2.83 (br s, 2H), 2.43 (m, 2H), 2.28 (s, 3H), 2.19 (s, 3H), 2.17 (m, 2H), 1.82 (m, 2H), 1.64 (m, 2H), 1.20 (t, J=7.1 Hz, 3H).

Example 28

Compound no. 412 was synthesized using known methods and those described above.
$^1$HNMR (400 MHz, DMSO-$d_6$) δ 11.06 (s, 1H), 8.05 (q, J=4.6 Hz, 1H), 7.06 (dt, J=12.9, 4.5 Hz, 1H), 6.94 (dd, J=8.3, 2.6 Hz, 1H), 4.13-4.09 (m, 4H), 4.05 (q, J=7.1 Hz, 2H), 3.50-3.39 (m, 3H), 3.13 (q, J=11.4 Hz, 2H), 2.83 (bs, 2H), 2.46 (t, J=13.5 Hz, 2H), 2.20 (s, 3H), 2.16 (d, J=11.6 Hz, 2H), 1.88 (d, J=13.8 Hz, 2H), 1.67-1.59 (m, 2H), 1.20 (t, J=7.1 Hz, 3H).

Example 29

Compound no. 361 was synthesized using known methods and those described above.
$^1$H NMR (400 MHz, DMSO-$d_6$) δ 1.22 (t, J=7.2 Hz, 3H), 1.66 (d, J=6.5 Hz, 2H), 1.87 (m, 6H), 2.05 (s, 2H), 2.21 (t, J=12.3 Hz, 2H), 2.87 (s, 6H), 3.05 (m, 2H), 3.52 (d, J=11.6 Hz, 2H), 3.73 (m, 1H), 3.84 (s, 2H), 4.08 (q, J=7.1 Hz, 2H), 4.26 (s, 2H), 6.90 (dd, J=8.3, 2.4 Hz, 1H), 7.00 (m, 2H), 10.38 (br s, 1H).

Example 30

Compound no. 39 was synthesized using known methods and those described above.
$^1$H NMR (400 MHz, CD$_3$CN) δ 1.25 (t, J=7.1 Hz, 3H), 1.66 (qd, J=12.3, 4.5 Hz, 2H), 1.98 (s, 2H), 2.10 (d, J=11.8 Hz, 2H), 2.28 (td, J=14.2, 3.7 Hz, 2H), 2.81 (t, J=15.9 Hz, 2H), 2.92 (s, 6H), 3.08 (q, J=11.3 Hz, 2H), 3.38 (dd, J=13.4, 10.5 Hz, 1H), 3.52 (d, J=12.3 Hz, 2H), 3.87 (s, 2H), 4.11 (q, J=7.1 Hz, 2H), 4.26 (d, J=12.1 Hz, 2H), 6.97 (m, 3H).

Example 31

Compound no. 91 was synthesized using known methods and those described above.
$^1$H NMR (400 MHz, CD$_3$CN) δ 0.96 (t, J=7.4 Hz, 3H), 1.66 (m, 4H), 1.98 (s, 2H), 2.10 (d, J=11.3 Hz, 2H), 2.28 (dt, J=19.9, 7.2 Hz, 2H), 2.87 (br s, 2H), 2.92 (s, 6H), 3.08 (q, J=11.2 Hz, 2H), 3.38 (t, J=12.2 Hz, 1H), 3.52 (d, J=11.9 Hz, 2H), 3.87 (s, 2H), 4.02 (t, J=6.6 Hz, 2H), 4.27 (d, J=12.8 Hz, 2H), 6.97 (m, 3H).

Example 32

Compound no. 54 was synthesized using known methods and those described above.
$^1$H NMR (400 MHz, CD$_3$CN) δ 1.24 (d, J=6.2 Hz, 6H), 1.65 (dq, J=12.3, 4.5 Hz, 2H), 1.99 (s, 2H), 2.09 (d, J=11.9 Hz, 2H), 2.25 (td, J=14.2, 3.7 Hz, 2H), 2.81 (t, J=11.4 Hz, 2H), 2.93 (s, 6H), 3.09 (q, J=11.3 Hz, 2H), 3.39 (m, 1H), 3.52 (d, J=12.3 Hz, 2H), 3.87 (s, 2H), 4.26 (d, J=12.8 Hz, 2H), 4.86 (heptet, J=6.2 Hz, 1H), 6.98 (m, 3H).

Example 33

Compound no. 208 was synthesized using known methods and those described above.
$^1$H NMR (400 MHz, CD$_3$CN) δ 1.67 (dq, J=12.2, 4.2 Hz, 2H), 2.15 (m, 4H), 2.27 (t, J=14.2 Hz, 2H), 2.87 (br s, 2H), 2.92 (s, 6H), 3.09 (q, J=11.3 Hz, 2H), 3.39 (t, J=12.0 Hz, 1H), 3.52 (d, J=12.0 Hz, 2H), 3.82 (m, 6H), 3.87 (s, 2H), 4.25 (d, J=11.2 Hz, 2H), 5.19 (s, 1H), 6.96 (m, 3H).

Example 34

Compound no. 120 was synthesized using known methods and those described above.
$^1$H NMR (400 MHz, CD$_3$CN) δ 1.67 (dq, J=12.2, 4.2 Hz, 2H), 2.15 (m, 4H), 2.27 (t, J=14.2 Hz, 2H), 2.87 (br s, 2H), 2.92 (s, 6H), 3.09 (q, J=11.3 Hz, 2H), 3.39 (t, J=12.0 Hz, 1H), 3.52 (d, J=12.0 Hz, 2H), 3.82 (m, 6H), 3.87 (s, 2H), 4.25 (d, J=11.2 Hz, 2H), 5.19 (s, 1H), 6.96 (m, 3H).

Example 35

Compound no. 48 was synthesized using known methods and those described above.
$^1$H NMR (400 MHz, CD$_3$CN) δ 1.69 (dq, J=12.3, 4.1 Hz, 2H), 1.99 (s, 2H), 2.12 (d, J=11.5 Hz, 2H), 2.28 (t, J=14.1 Hz, 2H), 2.87 (brs, 2H), 2.92 (s, 6H), 3.09 (q, J=11.3 Hz, 2H), 3.40 (t, J=11.9 Hz, 1H), 3.52 (d, J=12.3 Hz, 2H), 3.87 (s, 2H), 4.27 (m, 3H), 4.34 (m, 1H), 4.56 (t, J=3.9 Hz, 1H), 4.68 (t, J=3.9 Hz, 1H), 6.97 (m, 3H).

Example 36

Compound no. 352 was synthesized using known methods and those described above.
$^1$H NMR (400 MHz, CD$_3$CN) δ 1.68 (qd, J=12.3, 4.5 Hz, 2H), 1.85 (t, J=2.3 Hz, 3H), 1.98 (s, 2H), 2.12 (d, J=12.1 Hz, 2H), 2.30 (td, J=14.1, 3.7 Hz, 2H), 2.87 (br s, 2H), 2.92 (s, 6H), 3.08 (q, J=11.0 Hz, 2H), 3.39 (t, J=12.1 Hz, 1H), 3.51 (d, J=11.8 Hz, 2H), 3.87 (s, 2H), 4.25 (br s, 2H), 4.65 (d, J=2.1 Hz, 2H), 6.98 (m, 3H).

Example 37

Compound no. 127 was synthesized using known methods and those described above.
$^1$H NMR (400 MHz, CD$_3$CN) δ 1.68 (qd, J=12.3, 4.4 Hz, 2H), 1.99 (s, 2H), 2.11 (d, J=12.3 Hz, 2H), 2.27 (m, 2H), 2.55 (td, J=6.6, 2.7 Hz, 2H), 2.85 (br s, 2H), 2.92 (s, 6H), 3.08 (q, J=11.1 Hz, 2H), 3.39 (t, J=11.9 Hz, 1H), 3.51 (d, J=12.4 Hz, 2H), 3.87 (s, 2H), 4.15 (t, J=6.6 Hz, 2H), 4.26 (d, J=13.2 Hz, 2H), 6.97 (m, 3H).

Example 38

Compound no. 264 was synthesized using known methods and those described above.

¹H NMR (400 MHz, CD₃CN) δ 1.67 (qd, J=12.3, 4.3 Hz, 2H), 1.99 (s, 2H), 2.11 (d, J=10.6 Hz, 2H), 2.29 (t, J=14.1 Hz, 2H), 2.87 (br s, 2H), 2.92 (s, 6H), 3.08 (q, J=10.9 Hz, 2H), 3.34 (s, 3H), 3.40 (t, J=6.6 Hz, 1H), 3.52 (d, J=6.3 Hz, 2H), 3.57 (t, J=4.6 Hz, 2H), 3.86 (s, 2H), 4.18 (dd, J=5.1, 4.0 Hz, 2H), 4.26 (d, J=12.7 Hz, 2H), 6.96 (m, 3H).

Example 39

Compound no. 172 was synthesized using known methods and those described above.

¹H NMR (400 MHz, CD₃CN) δ 1.71 (qd, J=12.3, 4.4 Hz, 2H), 1.99 (s, 2H), 2.14 (d, J=14.4 Hz, 2H), 2.22 (s, 3H), 2.35 (td, J=14.2, 3.4 Hz, 2H), 2.89 (br s, 2H), 3.10 (q, J=10.6 Hz, 2H), 3.41 (t, J=11.4 Hz, 1H), 3.53 (d, J=12.6 Hz, 2H), 4.06 (s, 2H), 4.28 (m, 2H), 4.35 (t, J=4.0 Hz, 1H), 4.57 (t, J=4.0 Hz, 1H), 4.69 (t, J=4.0 Hz, 1H), 7.01 (m, 2H), 8.14 (dd, J=8.8, 4.9 Hz, 1H).

Example 40

Compound no. 102 was synthesized using known methods and those described above.

¹H NMR (400 MHz, CD₃CN) δ 1.71 (qd, J=12.3, 4.4 Hz, 2H), 1.85 (t, J=2.4 Hz, 3H), 1.99 (s, 2H), 2.13 (d, J=12.2 Hz, 2H), 2.22 (s, 3H), 2.35 (td, J=14.1, 3.6 Hz, 2H), 2.88 (br s, 2H), 3.09 (q, J=11.2 Hz, 2H), 3.40 (t, J=12.0 Hz, 1H), 3.53 (d, J=12.7 Hz, 2H), 4.06 (s, 2H), 4.26 (br s, 2H), 4.66 (d, J=2.2 Hz, 2H), 6.99 (td, J=9.0, 2.7 Hz, 1H), 7.05 (dd, J=8.6, 2.6 Hz, 1H), 8.14 (dd, 8.7, 4.8, 1H).

Example 41

Compound no. 62 was synthesized using known methods and those described above.

¹H NMR (400 MHz, CD₃CN) δ 1.70 (qd, J=12.2, 4.3 Hz, 2H), 1.99 (s, 2H), 2.13 (d, J=11.1 Hz, 2H), 2.22 (s, 3H), 2.27 (t, J=2.6 Hz, 1H), 2.36 (td, J=14.0, 3.5 Hz, 2H), 2.55 (td, J=6.6, 2.7 Hz, 2H), 2.87 (br s, 2H), 3.09 (q, J=10.4 Hz, 2H), 3.40 (t, J=12.1 Hz, 1H), 3.53 (d, J=12.3 Hz, 2H), 4.06 (s, 2H), 4.16 (t, J=6.6 Hz, 2H), 4.28 (d, J=12.6 Hz, 2H), 6.99 (td, J=9.0, 2.6 Hz, 1H), 7.05 (dd, J=8.6, 2.6 Hz, 1H), 8.13 (dd, J=8.8, 4.9 Hz, 1H).

Example 42

Compound no. 32 was synthesized using known methods and those described above.

¹H NMR (400 MHz, CD₃CN) δ 1.72 (d, J=7.3 Hz, 2H), 1.91 (d, J=2.5 Hz, 2H), 1.99 (s, 2H), 2.10 (m, 2H), 2.31 (td, J=14.0, 3.7 Hz, 2H), 2.91 (s, 6H), 2.96 (m, 2H), 3.36 (m, 2H), 3.57 (d, J=12.4 Hz, 2H), 3.63 (br s, 1H), 3.84 (s, 2H), 4.29 (t, J=4.0 Hz, 1H), 4.37 (m, 3H), 4.58 (t, J=3.9 Hz, 1H), 4.70 (t, J=3.9 Hz, 1H), 6.96 (m, 3H).

Example 43

Compound no. 200 was synthesized using known methods and those described above.

¹NMR (400 MHz, CD₃CN) δ 1.72 (d, J=7.2 Hz, 2H), 1.85 (t, J=2.4 Hz, 3H), 1.98 (m, 4H), 2.11 (m, 2H), 2.30 (td, J=14.0, 3.6 Hz, 2H), 2.91 (s, 6H), 2.96 (br s, 2H), 3.08-3.72 (m, 5H), 3.84 (s, 2H), 4.37 (s, 2H), 4.67 (d, J=16.6 Hz, 2H), 6.96 (m, 3H).

Example 44

Compound no. 229 was synthesized using known methods and those described above.

¹H NMR (400 MHz, CD₃CN) δ 1.66 (br s, 2H), 1.84 (br s, 2H), 1.92 (br s, 2H), 1.98 (br s, 2H), 2.23 (m, 3H), 2.50 (dd, J=6.4, 2.5 Hz, 2H), 2.84 (s, 6H), 2.93 (m, 2H), 3.08 (m, 2H), 3.50 (d, J=10.9 Hz, 2H), 3.65 (br s, 1H), 3.77 (s, 2H), 4.11 (s, 2H), 4.30 (s, 2H), 6.90 (m, 3H).

Example 45

Compound no. 165 was synthesized using known methods and those described above.

¹H NMR (400 MHz, DMSO-d₆) d 9.73 (s, 1H), 8.08 (d, J=8.4 Hz, 1H), 7.74 (q, J=1.3 Hz, 1H), 7.65 (q, J=2.6 Hz, 1H), 7.60 (dd, J=8.4, 1.7 Hz, 1H), 7.49 (dd, J=5.0, 1.2 Hz, 1H), 7.45 (d, J=1.5 Hz, 1H), 4.16-4.10 (m, 4H), 4.06 (q, J=7.1 Hz, 2H), 3.56-3.49 (m, 3H), 3.19 (q, J=11.3 Hz, 2H), 2.85 (br s, 2H), 2.28-2.23 (m, 5H), 2.10 (d, J=12.9 Hz, 2H), 1.96 (d, J=13.9 Hz, 2H), 1.66-1.57 (m, 2H), 1.20 (t, J=7.1 Hz, 3H).

Example 46

Compound no. 406 was synthesized using known methods and those described above.

¹H NMR (400 MHz, DMSO-d₆) δ 9.62 (s, 1H), 8.03 (d, J=8.3 Hz, 1H), 7.18 (d, J=8.4 Hz, 1H), 7.10 (s, 1H), 6.39 (d, J=10.3 Hz, 1H), 5.78-5.69 (m, 1H), 4.15-4.10 (m, 4H), 4.06 (q, J=7.1 Hz, 2H), 3.58-3.49 (m, 3H), 3.16 (q, J=10.8 Hz, 2H), 2.84 (br s, 2H), 2.21 (s, 3H), 2.16-2.07 (m, 4H), 1.93 (d, J=13.9 Hz, 2H), 1.87 (d, J=7.2 Hz, 3H), 1.63-1.55 (m, 2H), 1.20 (t, J=7.1 Hz, 3H

Example 47

Compound no. 158 was synthesized using known methods and those described above.

¹H-NMR (400 MHz, DMSO-d₆) δ 10.40 (br s, 1H), 8.31 (d, J=8.2 Hz, 1H), 7.27 (m, 4H), 5.34 (m, 1H), 3.40 (m, 3H), 3.13 (m, 1H), 2.97 (m, 2H), 2.65 (m, 1H), 2.57 (br s, 1H), 2.30 (m, 2H), 1.97 (m, 2H), 1.88 (s, 3H), 1.65 (m, 4H), 1.46 (m, 5H).

Example 48

Compound no. 182 was synthesized using known methods and those described above.

¹H-NMR (400 MHz, DMSO-d₆) δ 10.43 (br s, 1H), 8.31 (d, J=8.2 Hz, 1H), 7.28 (m, 4H), 5.34 (m, 1H), 3.96 (br m, 2H), 3.59 (s, 3H), 3.50 (m, 2H), 3.07 (m, 4H), 2.72 (m, 4H), 2.28 (m, 1H), 2.08 (m, 1H), 1.88 (s, 3H), 1.85 (m, 2H), 1.66 (m, 3H), 1.12 (m, 2H).

Example 49

Compound no. 358 was synthesized using known methods and those described above.

¹H NMR (400 MHz, DMSO-d₆) δ 10.65 (s, 1H), 8.30 (d, J=8.1 Hz, 1H), 7.34-7.31 (m, 1H), 7.27 (dt, J=10.1, 3.7 Hz, 1H), 7.22 (d, J=7.3 Hz, 1H), 7.17 (d, J=7.3 Hz, 1H), 5.33 (q, J=7.8 Hz, 1H), 4.26 (m, 2H), 4.08 (q, J=7.0 Hz, 2H), 3.77-3.70 (m, 1H), 3.52 (t, J=13.0 Hz, 2H), 3.06 (q, J=11.5 Hz, 1H), 2.97 (q, J=11.8 Hz, 1H), 2.61 (dd, J=13.2, 8.0 Hz, 1H), 2.54-2.47 (m, 1H), 2.15-2.04 (m, 3H), 1.91-1.81 (m, 7H), 1.71-1.66 (m, 5H), 1.22 (t, J=7.1 Hz, 3H).

Example 50

Compound no. 191 was synthesized using known methods and those described above.

$^1$H NMR (free base, 400 MHz, DMSO-$d_6$) δ 10.34 (s, 1H), 7.43 (d, J=7.3 Hz, 1H), 7.18 (dt, J=10.6, 3.8 Hz, 1H), 6.94 (dt, J=10.4, 3.8 Hz, 1H), 6.84 (d, J=7.6 Hz, 1H), 4.03 (q, J=7.1 Hz, 4H), 2.94-2.88 (m, 2H), 2.79 (s, 2H), 2.72-2.66 (m, 2H), 2.58-2.51 (m, 1H), 1.82-1.75 (m, 4H), 1.64-1.59 (m, 2H), 1.43-1.33 (m, 2H), 1.18 (t, J=7.1 Hz, 3H).

Example 51

Compound no. 199 was synthesized using known methods and those described above.

$^1$H NMR ((free base, 400 MHz, DMSO-$d_6$) δ 10.35 (s, 1H), 7.42 (d, J=7.4 Hz, 1H), 7.17 (dt, J=10.5, 3.8 Hz, 1H), 6.94 (t, J=7.1 Hz, 1H), 6.83 (d, J=7.4 Hz, 1H), 4.18 (m, 2H), 4.05 (q, J=6.5 Hz, 2H), 2.94-2.84 (m, 3H), 2.63 (t, J=8.1 Hz, 2H), 1.97-1.83 (m, 3H), 1.78-1.70 (m, 5H), 1.62-1.58 (m, 4H), 1.19 (t, J=7.1 Hz, 3H).

Example 52

Compound no. 318 was synthesized using known methods and those described above. Compound was prepared using reductive amination conditions described above. $^1$H NMR ((free base, 400 MHz, DMSO-$d_6$) δ 10.35 (s, 1H), 7.46 (d, J=7.4 Hz, 1H), 7.18 (dt, J=10.6, 3.8 Hz, 1H), 6.94 (dt, J=10.4, 3.8 Hz, 1H), 6.85 (d, J=7.6 Hz, 1H), 4.02 (q, J=7.1 Hz, 2H), 3.97 (m, 2H), 2.82-2.77 (m, 4H), 2.56-2.52 (m, 1H), 2.27 (d, J=6.8 Hz, 2H), 1.84-1.72 (m, 5H), 1.63-1.59 (m, 2H), 1.18 (t, J=7.1 Hz, 3H), 1.04-0.94 (m, 2H).

Example 53

Compound no. 104 was synthesized using known methods and those described above.

$^1$H NMR (free base, 400 MHz, DMSO-d6) δ 7.74-7.68 (m, 2H), 7.61 (d, J=7.6 Hz, 1H), 7.46-7.42 (m, 1H), 6.17-6.15 (m, 1H), 5.97-5.95 (m, 1H), 2.95-2.76 (m, 4H), 2.55 (s, 2H), 2.36-2.28 (m, 1H), 2.09-1.99 (m, 6H), 1.87-1.81 (m, 1H), 1.45 (d, J=3.9 Hz, 2H), 1.34-1.20 (m, 2H), 0.55-0.51 (m, 1H)

Example 54

Compound no. 186 was synthesized using known methods and those described above.

$^1$H NMR (400 MHz, DMSO-$d_6$) δ 9.44 (br s, 1H), 7.07-6.95 (m, 2H), 6.85-6.82 (m, 1H), (tt, J=28.8, 18.1 Hz, 1H), 4.51 (s, 2H), 4.40-4.31 (m, 4H), 3.74 (q, J=5.5 Hz, 1H), 3.59-3.40 (m, 4H), 2.98 (q, J=10.8 Hz, 2H), 2.07-1.93 (m, 8H), 1.68 (d, J=5.5 Hz, 4H).

Example 55

Compound no. 275 was synthesized using known methods and those described above.

$^1$H NMR (400 MHz, DMSO-$d_6$) δ 9.25 (br s, 1H), 7.32 (d, J=2.6 Hz, 1H), 7.16 (dd, J=8.7, 2.5 Hz, 1H), 6.82 (d, J=8.7 Hz, 1H), 4.11 (t, J=5.1 Hz, 2H), 3.38-3.34 (m, 2H), 3.25-3.13 (m, 3H), 2.31-2.23 (m, 2H), 2.08-2.04 (m, 4H), 1.85 (d, J=13.7 Hz, 4H), 1.63 (d, J=12.6 Hz, 1H), 1.49-1.39 (m, 2H), 1.34-1.29 (m, 2H), 1.21 (m, 1H)

Example 56

Compound no. 258 was synthesized using known methods and those described above.

$^1$H NMR (400 MHz, DMSO-$d_6$) δ 10.60 (s, 1H), 9.20 (bs, 1H), 7.30-7.15 (m, 2H), 7.07-6.87 (m, 2H), 3.65-3.35 (m, 5H), 2.66-2.64 (m, 1H), 2.40-2.30 (m, 3H), 2.07-1.98 (m, 1H), 1.92 (d, J=14.7 Hz, 1H), 1.79 (d, J=14.3 Hz, 1H), 1.68-1.51 (m, 3H), 1.47-1.38 (m, 3H), 1.27-1.20 (m, 1H).

Example 57

Compound no. 152 was synthesized using known methods and those described above.

$^1$H NMR (400 MHz, DMSO-$d_6$) δ 9.41 (br s, 1H), 7.04-6.93 (m, 2H), 6.84-6.80 (m, 1H), 4.53 (s, 2H), 3.47 (d, J=12.1 Hz, 1H), 3.40-3.38 (m, 1H), 3.24-3.17 (m, 1H), 3.06 (q, J=11.3 Hz, 2H), 2.19-2.11 (m, 2H), 2.05 (d, J=10.2 Hz, 2H), 1.94 (d, J=14.1 Hz, 2H), 1.84 (d, J=12.9 Hz, 2H), 1.63 (d, J=12.5 Hz, 1H), 1.46-1.23 (m, 4H), 1.17-1.07 (m, 1H).

Example 58

Compound no. 288 was synthesized using known methods and those described above.

$^1$H NMR (400 MHz, DMSO-$d_6$) δ 9.33 (br s, 1H), 7.05-6.92 (m, 2H), 6.85-6.80 (m, 1H), 6.34-6.31 (m, 1H), 4.50 (s, 2H), 4.33 (d, J=13.4 Hz, 2H), 3.83-3.74 (m, 1H), 3.67-3.51 (m, 3H), 2.95 (q, J=11.0 Hz, 2H), 2.07-1.85 (m, 8H), 1.74-1.58 (m, 4H), 1.08 (d, J=6.6 Hz, 6H).

Example 59

Compound no. 211 was synthesized using known methods and those described above.

$^1$H NMR (400 MHz, DMSO-$d_6$) δ 7.65 (br s, 1H), 7.06-6.95 (m, 2H), 6.85-6.80 (m, 1H), 5.18 (s, 1H), 4.51 (s, 2H), 4.25 (s, 2H), 3.81-3.71 (m, 5H), 3.58 (d, J=12.1 Hz, 2H), 2.98-2.93 (m, 2H), 2.13-1.94 (m, 10H), 1.65 (d, J=7.4 Hz, 4H).

Example 60

Compound no. 156 was synthesized using known methods and those described above.

$^1$H NMR (400 MHz, DMSO-$d_6$) δ 9.56 (br s, 1H), 7.06-6.95 (m, 2H), 6.86-6.80 (m, 1H), 4.51 (s, 2H), 4.26 (s, 2H), 3.57-3.44 (m, 6H), 2.97 (q, J=11.1 Hz, 2H), 2.08-2.02 (m, 4H), 1.94 (d, J=13.5 Hz, 4H), 1.70-1.65 (m, 4H).

Example 61

Compound no. 181 was synthesized using known methods and those described above.

$^1$H NMR (400 MHz, DMSO-$d_6$) δ 10.06 (br s, 1H), 7.21 (dd, J=8.5, 2.2 Hz, 1H), 7.08 (d, J=2.2 Hz, 1H), 6.85 (d, J=8.5 Hz, 1H), 4.52 (s, 2H), 3.47-3.21 (m, 3H), 3.10-2.94 (m, 2H), 2.66-2.40 (m, 3H), 2.27 (s, 1H), 1.96-1.83 (m, 4H), 1.56-1.53 (m, 3H), 1.42-1.33 (m, 3H).

Example 62

Compound no. 178 was synthesized using known methods and those described above.

$^1$H NMR (400 MHz, DMSO-$d_6$) δ 9.42 (br s, 1H), 7.30 (d, J=2.6 Hz, 1H), 7.18-7.16 (m, 1H), 6.84-6.81 (m, 1H), 4.14-3.99 (m, 2H), 3.46 (d, J=12.1 Hz, 4H), 3.36-3.31 (m, 2H), 3.20-3.11 (m, 3H), 2.28-2.20 (m, 2H), 2.07-2.00 (m, 4H), 1.88 (d, J=14.4 Hz, 2H), 1.75-1.64 (m, 2H).

Example 63

Physical Characteristics of Compounds of Formulae (I and II)

Additional compounds having the structures shown in Table 2 were synthesized using known methods and those described above.

TABLE 2

Physical Characteristics of Compounds in Table 1.

| Cmd No. | LCMS Plus | LCMS RT | NMR |
|---|---|---|---|
| 2 | 327.3 | 2.8 | |
| 3 | 309 | 1.88 | |
| 4 | 379.2 | 1.99 | |
| 5 | 306.2 | 2.32 | |
| 6 | 476.2 | 2.34 | |
| 7 | 309.4 | 1.93 | |
| 8 | 353.3 | 2.16 | |
| 9 | 426.2 | 1.94 | |
| 10 | 519.4 | 1.92 | |
| 11 | 412.2 | 1.98 | |
| 12 | 397.5 | 2.48 | |
| 13 | 328.2 | 2.05 | |
| 14 | 460.5 | 2.13 | |
| 15 | 369.2 | 2.19 | |
| 16 | 508.5 | 2.2 | |
| 17 | 458.4 | 2.35 | |
| 18 | 286 | 2.13 | |
| 19 | 378.2 | 1.94 | |
| 20 | 336.4 | 2.23 | |
| 21 | 484.2 | 2.2 | |
| 22 | 459.4 | 2.04 | |
| 23 | 297.4 | 1.26 | |
| 24 | 524.5 | 2.44 | |
| 25 | 496.5 | 2.35 | |
| 26 | 448.5 | 2.18 | |
| 27 | 359.2 | 2.09 | |
| 28 | 502.2 | 2.15 | |
| 29 | 367.2 | 2.31 | |
| 30 | 462.4 | 2.53 | |
| 31 | 372.2 | 1.83 | |
| 32 | 477.2 | 2.2 | |
| 33 | 476.5 | 2.29 | |
| 35 | 357.2 | 1.99 | |
| 36 | 428.2 | 2.08 | |
| 37 | 307.2 | 1.01 | |
| 38 | 464.2 | 2.1 | |
| 39 | 433.2 | 2.14 | |
| 40 | 546.4 | 2.53 | |
| 41 | 496.4 | 2.28 | |
| 42 | 389.2 | 2.22 | |
| 43 | 411.4 | 2.31 | |
| 44 | 496.5 | 2.31 | |
| 45 | 496.4 | 2.29 | |
| 46 | 414.5 | 2.26 | |
| 47 | 472.3 | 2.08 | |
| 48 | 451.2 | 2.1 | |
| 49 | 476.2 | 2.08 | |
| 50 | 510.5 | 2.12 | |
| 51 | 365.2 | 2.11 | |
| 52 | 345.2 | 1.91 | |
| 53 | 480.2 | 2.35 | |
| 54 | 447.2 | 2.22 | |
| 55 | 381.2 | 2.21 | |
| 56 | 398.2 | 2.07 | |
| 57 | 498.5 | 2.28 | |
| 59 | 514.4 | 2.2 | |
| 60 | 418.3 | 2.22 | |
| 61 | 400.5 | 1.89 | |
| 62 | 428.2 | 2.12 | |
| 63 | 476.4 | 2.63 | |

TABLE 2-continued

Physical Characteristics of Compounds in Table 1.

| Cmd No. | LCMS Plus | LCMS RT | NMR |
|---|---|---|---|
| 65 | 448.2 | 1.77 | |
| 66 | 550.4 | 2.6 | |
| 67 | 472.3 | 2.06 | |
| 68 | 395 | 2.6 | |
| 69 | 512.5 | 2.41 | |
| 70 | 387.2 | 2.02 | |
| 71 | 414.2 | 1.98 | |
| 72 | 325.5 | 1.94 | |
| 73 | 510.3 | 2.4 | |
| 74 | 428.2 | 2.19 | |
| 75 | 347 | 1.57 | |
| 76 | 460.5 | 2.11 | |
| 77 | 484.2 | 2.3 | |
| 78 | 476 | 2.34 | |
| 79 | 418.3 | 2.24 | |
| 80 | 532.5 | 2.33 | |
| 81 | 410.3 | 2.27 | |
| 82 | 460.5 | 2.12 | |
| 83 | 526.6 | 2.09 | |
| 84 | 480.2 | 2.28 | |
| 85 | 331.3 | 1.98 | |
| 87 | 498.5 | 2.29 | |
| 88 | 483.3 | 2.15 | |
| 89 | 547.4 | 2.49 | |
| 90 | 490.4 | 2.16 | |
| 91 | 447.2 | 2.23 | |
| 92 | 400.3 | 2.16 | |
| 93 | 544.5 | 2.29 | |
| 94 | 444.5 | 2.29 | |
| 95 | 399.2 | 2.31 | |
| 96 | 488.7 | 2.25 | |
| 97 | 460.5 | 2.95 | |
| 98 | 432.5 | 2.33 | |
| 99 | 405.2 | 2.36 | |
| 100 | 467.4 | 2.41 | |
| 101 | 351.2 | 2.11 | |
| 102 | 428.2 | 2.18 | |
| 103 | 466.4 | 2.09 | |
| 104 | 308.2 | 2.08 | |
| 105 | 463.4 | 1.45 | |
| 106 | 516.5 | 2.61 | |
| 107 | 377.4 | 2.29 | |
| 108 | 473.4 | 2.35 | |
| 109 | 384.3 | 1.72 | |
| 110 | 297.5 | 1.7 | |
| 111 | 315.3 | 1.65 | |
| 112 | 544.5 | 2.3 | |
| 113 | 390.2 | 1.76 | |
| 114 | 448.4 | 2.37 | |
| 115 | 516.5 | 2.51 | |
| 116 | 397.3 | 2.59 | |
| 117 | 520.5 | 2.33 | |
| 118 | 353.4 | 2.62 | |
| 120 | 475.2 | 2.05 | |
| 122 | 492.5 | 2.53 | |
| 123 | 415.2 | 2.29 | |
| 124 | 443 | 2.33 | |
| 125 | 528.3 | 2.6 | |
| 126 | 462.4 | 2.23 | |
| 127 | 457.4 | 2.19 | |
| 128 | 452.2 | 2.06 | |
| 129 | 404.5 | 2.09 | |
| 130 | 501.3 | 2.21 | |
| 131 | 373.2 | 2.31 | |
| 132 | 404.4 | 1.76 | |
| 133 | 429 | 2.39 | |
| 134 | 399.2 | 2.02 | |
| 135 | 333.2 | 1.47 | |
| 136 | 430.2 | 2.07 | |
| 137 | 414.4 | 1.99 | |
| 138 | 339.3 | 1.97 | |
| 139 | 398.2 | 2.21 | |
| 140 | 430.5 | 2.29 | |
| 141 | 420.2 | 1.95 | |
| 142 | 432.4 | 2.08 | |

TABLE 2-continued

Physical Characteristics of Compounds in Table 1.

| Cmd No. | LCMS Plus | LCMS RT | NMR |
|---|---|---|---|
| 143 | 341.2 | 1.78 | |
| 144 | 467.4 | 1.78 | |
| 145 | 448.2 | 2.36 | |
| 146 | 480.2 | 2.24 | |
| 148 | 494.5 | 2.56 | |
| 150 | 492.4 | 2.25 | |
| 151 | 426.3 | 2.32 | |
| 152 | 290 | 2.16 | |
| 153 | 370.3 | 1.6 | |
| 154 | 419.2 | 2.03 | |
| 155 | 305.2 | 1.88 | |
| 156 | 375 | 1.92 | |
| 157 | 319.2 | 2 | |
| 158 | 339.3 | 1.92 | |
| 159 | 341.3 | 2.96 | |
| 160 | 417.5 | 2.35 | |
| 161 | 353.3 | 2.25 | |
| 162 | 532.5 | 2.33 | |
| 163 | 343 | 2.03 | |
| 164 | 344 | 2.56 | |
| 165 | 468.2 | 1.16 | |
| 166 | 500.5 | 2.78 | |
| 167 | 446.4 | 2.12 | |
| 168 | 436.2 | 1.84 | |
| 169 | 495.4 | 2.27 | |
| 170 | 480.3 | 2.93 | |
| 171 | 339.3 | 1.92 | |
| 172 | 422.2 | 2 | |
| 173 | 420.2 | 2.07 | |
| 174 | 456.5 | 2.4 | |
| 175 | 302.3 | 2.16 | |
| 176 | 393.2 | 2.42 | |
| 177 | 540.5 | 2 | |
| 178 | 322.4 | 2.17 | |
| 179 | 470.5 | 2.51 | |
| 180 | 351.3 | 2.22 | |
| 181 | 318 | 2.38 | |
| 182 | 400.2 | 1.86 | |
| 183 | 313 | 1.46 | |
| 184 | 341.2 | 1.87 | |
| 185 | 351.4 | 1.86 | |
| 186 | 425 | 2.15 | |
| 187 | 331 | 1.89 | |
| 188 | 501.3 | 2.19 | |
| 189 | 552.6 | 2.52 | |
| 191 | 358 | 1.68 | |
| 192 | 488.3 | 2.25 | |
| 193 | 492.4 | 2.25 | |
| 194 | 460.4 | 2.49 | |
| 195 | 516.5 | 2.56 | |
| 196 | 327.2 | 1.62 | |
| 197 | 525.6 | 2.44 | |
| 198 | 544.5 | 2.3 | |
| 199 | 384.2 | 2.06 | |
| 200 | 483.4 | 2.35 | |
| 202 | 432.5 | 2.31 | |
| 203 | 388.2 | 2.12 | |
| 204 | 302.3 | 2.14 | |
| 205 | 412 | 1.86 | |
| 206 | 329.5 | 0.92 | |
| 207 | 316.2 | 2.45 | |
| 208 | 406.4 | 2.29 | |
| 209 | 475.2 | 2.04 | |
| 210 | 345.2 | 1.94 | |
| 211 | 419.4 | 2.12 | |
| 212 | 431.4 | 1.96 | |
| 213 | 351.2 | 2.11 | |
| 214 | 456.5 | 2.38 | |
| 215 | 491.2 | 2.25 | |
| 216 | 532.5 | 2.33 | |
| 217 | 410.2 | 2.26 | |
| 218 | 351.2 | 2.11 | |
| 219 | 388.2 | 2.04 | |
| 220 | 462.4 | 2.54 | |
| 221 | 504.4 | 2.14 | |
| 222 | 510.4 | 2.35 | |
| 223 | 461.4 | 2.24 | |
| 224 | 317 | 1.8 | |
| 225 | 470.5 | 2.43 | |
| 226 | 373 | 2.23 | |
| 227 | 389.2 | 2.28 | |
| 228 | 403.2 | 1.93 | |
| 229 | 446.2 | 2.21 | |
| 230 | 483.4 | 2.3 | |
| 232 | 375 | 2.08 | |
| 233 | 552.5 | 2.25 | |
| 234 | 463.2 | 1.49 | |
| 235 | 432.5 | 2.24 | |
| 236 | 399.2 | 2.03 | |
| 238 | 308.2 | 2.09 | |
| 239 | 303.3 | 1.73 | |
| 240 | 345.2 | 2.28 | |
| 241 | NA | NA | |
| 242 | 313.2 | 1.88 | |
| 243 | 544.5 | 2.31 | |
| 244 | 297.5 | 1.59 | |
| 245 | 426.2 | 2.05 | |
| 246 | 395.2 | 2.28 | |
| 247 | 431.5 | 2.46 | |
| 248 | 359.2 | 2.08 | |
| 249 | 418.4 | 1.98 | |
| 250 | 414.4 | 1.91 | |
| 251 | 357.2 | 1.99 | |
| 252 | 414.5 | 2.35 | |
| 253 | 487.4 | 2.18 | |
| 254 | 444.4 | 2.23 | |
| 255 | 459.4 | 2.02 | |
| 256 | 434.4 | 2.05 | |
| 257 | 308.2 | 2.09 | |
| 258 | 409.2 | 2.68 | |
| 259 | 297.2 | 1.78 | |
| 260 | 467.4 | 1.74 | |
| 261 | 355.4 | 1.94 | |
| 262 | 496.4 | 2.25 | |
| 263 | 294.4 | 2.33 | |
| 264 | 297.4 | 1.24 | |
| 265 | 463.2 | 2.04 | |
| 266 | 432.4 | 2.04 | |
| 267 | 484.2 | 2.27 | |
| 268 | 333.5 | 1.84 | |
| 269 | 418.3 | 2.23 | |
| 270 | 446.4 | 2.29 | |
| 271 | 424.2 | 2.38 | |
| 272 | 283.3 | 1.34 | |
| 273 | 403.4 | 2.17 | |
| 275 | 383 | 2.47 | |
| 276 | 320.2 | 2.37 | |
| 278 | 411.2 | 2.12 | |
| 279 | 442.5 | 2.08 | |
| 280 | 341.2 | 1.85 | |
| 281 | 472.4 | 2.44 | |
| 282 | 446.4 | 2.24 | |
| 283 | 403.5 | 2.21 | |
| 284 | 434.5 | 2.05 | |
| 285 | 383.2 | 2.53 | |
| 286 | 417.5 | 2.36 | |
| 287 | 474.3 | 2.58 | |
| 288 | 336.4 | 2.17 | |
| 289 | 402.4 | 2.16 | |
| 290 | 475.2 | 1.89 | |
| 291 | 339.5 | 0.51 | |
| 292 | 392.2 | 2.13 | |
| 293 | 430.5 | 2.14 | |
| 294 | 480.5 | 2.48 | |
| 295 | 530.2 | 2.55 | |
| 296 | 473.4 | 2.11 | |
| 297 | 516.5 | 2.65 | |
| 298 | 526.6 | 2.57 | |
| 299 | 291 | 0.45 | |
| 300 | 316.2 | 1.44 | |

TABLE 2-continued

Physical Characteristics of Compounds in Table 1.

| Cmd No. | LCMS Plus | LCMS RT | NMR |
|---|---|---|---|
| 301 | 426.2 | 1.98 | |
| 302 | 484.5 | 2.61 | |
| 303 | 432.5 | 2.13 | |
| 304 | 532.3 | 2.31 | |
| 305 | 351.3 | 2.22 | |
| 306 | 428.5 | 2.38 | |
| 307 | 418.4 | 1.84 | |
| 309 | 418.4 | 1.9 | |
| 310 | 388.5 | 1.66 | |
| 311 | 486.5 | 2.3 | |
| 313 | 294 | 2.33 | |
| 315 | 428 | 1.85 | |
| 316 | 428.2 | 1.95 | |
| 317 | 418.6 | 1.97 | |
| 318 | 426.3 | 2.1 | |
| 319 | 372.2 | 1.79 | |
| 320 | 403.2 | 2.23 | |
| 321 | 457.2 | 2.07 | |
| 322 | 430.2 | 1.94 | |
| 323 | 339.1 | 1.92 | |
| 324 | 432.4 | 2.14 | |
| 325 | 289.2 | 0.77 | |
| 326 | 383.2 | 2.3 | |
| 327 | 386 | 1.92 | |
| 328 | 331.2 | 2.11 | |
| 329 | 500.3 | 2.86 | |
| 330 | 480.2 | 2.38 | |
| 331 | 467.4 | 2.01 | |
| 332 | 397.27 | 1.79 | |
| 333 | 319.2 | 1.86 | |
| 334 | 313 | 2.01 | |
| 335 | 484.2 | 2.34 | |
| 336 | 426 | 1.96 | |
| 337 | 353.2 | 1.84 | |
| 338 | 431.4 | 1.97 | |
| 339 | 367.3 | 2.3 | |
| 340 | 416.2 | 1.76 | |
| 341 | 347 | 2.41 | |
| 342 | 285.3 | 1.65 | |
| 343 | 316.8 | 1.64 | |
| 344 | 502.4 | 2.17 | |
| 345 | 470.5 | 2.48 | |
| 346 | 458.4 | 2.35 | |
| 347 | 397.2 | 2.47 | |
| 348 | 331.3 | 1.96 | |
| 349 | 494.3 | 2.3 | |
| 350 | 297.3 | 1.04 | |
| 351 | 404.5 | 1.9 | |
| 352 | 344 | 0.7 | |
| 353 | 457.4 | 2.22 | |
| 354 | 437.2 | 2.48 | |
| 355 | 411.4 | 2.31 | |
| 356 | 417.4 | 1.94 | |
| 357 | 403 | 2.19 | |
| 358 | 341.2 | 1.77 | |
| 359 | 426 | 1.79 | |
| 360 | 473.4 | 2.35 | |
| 361 | 516.5 | 2.5 | |
| 362 | 459.2 | 1.96 | |
| 363 | 445.3 | 2.08 | |
| 364 | 424 | 1.8 | |
| 365 | 369.2 | 2.41 | |
| 366 | 369.2 | 2.14 | |
| 367 | 355.2 | 2.02 | |
| 368 | 401.25 | 1.75 | |
| 369 | 332.2 | 2.4 | |
| 370 | 452.2 | 2.19 | |
| 371 | 430.2 | 1.94 | |
| 372 | 313.1 | 1.55 | |
| 373 | 487.4 | 2.19 | |
| 374 | 390.3 | 1.98 | |
| 375 | 271.2 | 0.59 | |
| 376 | 314 | 2.39 | |
| 377 | 315.3 | 1.66 | |
| 378 | 419.2 | 1.97 | |
| 379 | 482.5 | 2.55 | |
| 380 | 414.5 | 2.28 | |
| 381 | 404.4 | 1.75 | |
| 382 | 411.4 | 2.75 | |
| 383 | 452.3 | 2.17 | |
| 384 | 466.4 | 2.23 | |
| 385 | 369 | 2.19 | |
| 386 | 460.5 | 2.51 | |
| 387 | 331 | 1.78 | |
| 388 | 508.5 | 2.21 | |
| 389 | 470.5 | 2.5 | |
| 390 | 458.5 | 2.12 | |
| 391 | 420.3 | 2.08 | |
| 392 | 351.2 | 2.11 | |
| 393 | 345.2 | 2.03 | |
| 394 | 408.2 | 1.72 | |
| 395 | 432.4 | 2.01 | |
| 396 | 502.2 | 2.34 | |
| 397 | 311.3 | 1.72 | |
| 398 | 442.5 | 2.08 | |
| 399 | 428.2 | 2.06 | |
| 400 | 368 | 1.97 | |
| 401 | 510.4 | 2.27 | |
| 402 | 516.5 | 2.51 | |
| 403 | 456.5 | 2.17 | |
| 404 | 428.3 | 2.36 | |
| 405 | 504.5 | 2.53 | |
| 406 | 505.4 | 1.81 | |
| 407 | 426 | 2.1 | |
| 408 | 351.2 | 2.11 | |
| 409 | 486.5 | 2.7 | |
| 410 | 484.2 | 2.3 | |
| 411 | 552.5 | 2.25 | |
| 412 | 444.4 | 1.81 | |
| 413 | 404.5 | 2.11 | |
| 414 | 357.2 | 2.39 | |
| 415 | 322.4 | 2.15 | |
| 416 | 301.2 | 1.23 | |
| 417 | 446.2 | 2.04 | |
| 418 | 446.3 | 2.02 | |
| 419 | 444.5 | 2.18 | |
| 420 | 297.5 | 1.61 | |
| 421 | 351.2 | 2.11 | |
| 422 | 504.5 | 2.51 | |
| 423 | 400.5 | 2.16 | |
| 424 | 446.3 | 2.01 | |
| 425 | 399.2 | 2.31 | |
| 426 | 452.4 | 2.28 | |
| 427 | 434.4 | 2.21 | |
| 428 | 476.2 | 2.09 | |
| 429 | 316.2 | 1.4 | |
| 430 | 400.3 | 1.88 | |
| 431 | 422.2 | 1.78 | |
| 432 | 381.2 | 2.38 | |
| 433 | 463.2 | 2.19 | |
| 434 | 492 | 2.2 | |
| 435 | 455.2 | 1.78 | |
| 436 | 356.3 | 1.6 | |
| 437 | 329.5 | 0.88 | H NMR (500 MHz, DMSO) 8.97 (s, 1H), 7.32-7.15 (m, 4H), 6.52 (d, J = 8.5 Hz, 1H), 6.27 (dd, J = 3.0, 5.5 Hz, 1H), 6.05 (dd, J = 2.6, 5.5 Hz, 1H), 5.26 (dd, J = 8.0, 16.4 Hz, 2H), 3.54 (d, J = 11.6 Hz, 2H), 3.25-2.58 (m, 13H), 2.40-2.36 (m, 1H), 2.04-2.01 (m, 1H), 1.85-1.68 (m, 4H), 1.40-1.23 (m, 2H), 0.72-0.67 (m, 1H), |
| 438 | 379.3 | 1.9 | |
| 439 | 438.2 | 1.97 | |
| 440 | 400.2 | 1.8 | |

TABLE 2-continued

Physical Characteristics of Compounds in Table 1.

| Cmd No. | LCMS Plus | LCMS RT | NMR |
|---|---|---|---|
| 441 | 374.2 | 1.02 | CD3OD: 6.85 (s, 1H), 6.77 (s, 1H), 5.36 (t, 1H), 4.30 (m, 2H), 4.13 (q, 2H), 3.83 (s, 3H), 3.81 (s, 3H), 3.45 (m, 3H), 3.20 (m, 1H), 2.72 (dd, 1H), 2.35 (m, 1H), 2.10 (m, 2H), 2.00 (s, 3H), 1.59-1.90 (m, 14H) |
| 442 | 401.6 | 1.85 | |
| 443 | 443.4 | 1.9 | |
| 444 | 426.2 | 1.93 | |
| 445 | 424.2 | 2.31 | |
| 446 | 495.2 | 1.91 | NMR (500 MHz, DMSO-d6) 8.98 (br. s, 1H), 8.18 (d, 1 H), 7.40 (d, 1H), 7.32 (t, 1H), 7.22 (t, 1H), 7.19 (d, 1H), 6.27 (dd, 1H), 6.17-6.15 (m, 1H), 6.05 (q, 1H), 4.94-4.92 (m, 1H), 3.45 (m, 2H), 3.20-3.13 (m, 2H), 2.98 (br.s, 1H), 2.95 (m, 1H), 2.86 (br.s, 1H), 2.85-2.79 (m, 1H), 2.28-2.22 (m, 2H), 2.07-1.99 (m, 2H), 1.87 (s, 3H), 1.83-1.78 (m, 3H), 1.73 (d, 1H), 1.65-1.61 (m, 1H), 1.39-1.29 (m, 3H), 0.70 (dt, 1H). |
| 447 | 365.32 | 1.63 | : |
| 448 | 395.5 | 2.69 | 1H NMR (500 MHz, DMSO (d6)): 8.98 (s, 1H), 7.37 (d, 1H), 7.22 (t, H), 7.10 (t, 1H), 7.07 (d, 1H), 6.27 (q, 0.7 H), 6.18-6.14 (m, 0.6H), 6.05 (q, 0.7H), 3.43 (m, 2H), 3.30-3.21 (m, 1H), 3.22-3.10 (m, 2H), 2.98 (s, 1H), 2.95-2.90 (m, 1H), 2.85 (s, 1H), 2.85-2.80 (m, 1H), 2.73 (t, 2H), 2.28-2.22 (m, 2H), 2.00 (ddd, 1H), 1.89-1.87 (m, 1H), 1.78-1.67 (m, 4H), 1.39-1.29 (m, 2H), 0.72-0.67 (m, 1H). |
| 449 | 308.6 | 2.01 | |
| 450 | 400.1 | 1.81 | |
| 451 | 494.4 | 1.97 | DMSO (d6): 9.53 (br. s), 8.18 (d, 1H), 7.40 (d, 1H), 7.30 (t, 1H), 7.19 (t, 1H), 7.16 (d, 1H), 4.92 (q, 1H), 3.40 (m, 2H), 3.14 (t, 2H), 3.07 (m, 2H), 2.27 (m, 2H), 2.05 (dd, 1H), 1.87 (s, 3H), 1.81 (m, 3H), 1.74-1.59 (m, 9H), 1.27-1.12 (m, 6H), 0.89 (m, 2H). |
| 452 | 383.44 | 1.96 | |
| 453 | 410.2 | 2.19 | |
| 454 | 416.6 | 1.3 | |
| 455 | 438.4 | 2.44 | |
| 456 | 485.4 | 2.22 | |
| 457 | 386.3 | 1.2 | |
| 458 | 438.4 | 1.39 | |
| 459 | 416.4 | 1.62 | |
| 460 | 438.4 | 1.95 | |
| 461 | 486.2 | 2.2 | |
| 462 | 371.2 | 2.12 | |
| 463 | 447.2 | 1.6 | |
| 464 | 417.4 | 1.66 | |
| 465 | 444.4 | 1.98 | |
| 466 | 496.5 | 2.57 | |
| 467 | 492.4 | 2.24 | |
| 468 | 396.2 | 1.95 | |
| 469 | 404.4 | 2.26 | |
| 470 | 324.2 | 2.08 | |
| 471 | 411.2 | 2 | |
| 472 | 440.4 | 1.99 | |
| 473 | 404.4 | 1.97 | |
| 474 | 390.4 | 1.03 | |
| 475 | 469.3 | 1.78 | |
| 476 | 454.2 | 2.23 | |
| 477 | 448.4 | 2.13 | |
| 478 | 400.2 | 1.84 | |
| 479 | 471.4 | 2.13 | |
| 480 | 372.3 | 1.2 | |
| 481 | 424.4 | 1.98 | |
| 482 | 386.2 | 1.73 | |
| 483 | 324.2 | 2.05 | |
| 484 | 383.2 | 1.94 | |
| 485 | 471.4 | 2.16 | DMSO (d6): 9.06 (br. s, 1H), 8.18 (d, 1H), 7.39 (d, 1H), 7.30 (t, 1H), 7.20 (t, 1H), 7.17 (d, 1H), 6.27 (dd, 1H), 6.05 (m, 1H), 4.92 (q, 1H), 3.47 (m, 3H), 3.15 (m, 2H), 2.98 (s, 1H), 2.93 (dd, 1H), 2.85 (s, 1H), 2.80 (ddd, 1H), 2.25 (m, 2H), 2.20 (m, 2H), 1.87 (s, 3H), 1.81 (m, 3H), 1.71 (d, 1H), 1.62 (m, 1H), 1.35 (t, 1H), 1.30 (d, 1H), 0.68 (dq, 1H). |
| 486 | 365.3 | 1.61 | |
| 487 | 394.5 | 2 | |
| 488 | 328.2 | 1.7 | |
| 489 | 406.4 | 1.65 | |
| 490 | 353.3 | 1.8 | |
| 491 | 504 | 2.28 | |
| 492 | 442.4 | 1.66 | |
| 493 | 396 | 1.71 | |
| 494 | 428.6 | 1.89 | |
| 495 | 412.3 | 2.3 | |
| 496 | 428.2 | 2.11 | |
| 497 | 464.4 | 1.92 | (CDCl3, ppm) 11.89 (br s, 1H), 7.47 (m, 3H), 6.22 (s, 2H) 5.98 (s, 1H), 3.75 (br s, 2H), 3.00 (s, 2H), 2.86 (s, 1H), 2.58 (m, 5H), 2.57 (m, 3H), 2.38 (s, 3H), 2.06 (m, 1H), 1.65 (m, 2H), 1.48 (m, 1H), 1.27 (m, 1H), 0.72 (d, J = 11 Hz, 1H). |
| 498 | 321.9 | 1.76 | |
| 499 | 480 | 2.43 | |
| 500 | 509.4 | 2 | |
| 501 | 343.2 | 1.9 | |
| 502 | 400.2 | 1.84 | DMSO (d6): 9.03 (s, 1H), 7.31 (d, 1H), 7.27 (t, 1H), 7.24 (d, 1H), 7.18 (t, 1H), 6.47 (d, 1H), 4.81 (m, 1H), 4.39 (m, 1H), 4.34 (m, 1H), 4.26 (m, 1H), 4.10 (q, 2H), 3.45 (m, 2H), 3.21-3.08 (m, 2H), 2.82 (s, 6H), 32.68-2.61 (m, H), 2.23 (m, 1H), 2.03-1.92 (m, 5H), 1.79 (m, 1H), 1.73-1.62 (m, 5H), 1.57 (d, 1H), 1.51 (t, 1H), 1.19 (t, 3H). |
| 503 | 469.3 | 1.87 | DMSO (d6): 9.17 (br.s, 1H), 8.18 (d, 1H), 7.40 (d, 1H), 7.30 (t, 1H), 7.20 (t, 1H), 7.16 (d, 1H), 4.93 (m, 1H), 3.55 (td, 1H), 3.43 (d, 1H), 3.19 (m, 2H), 2.29 (td, 1H), 2.24 (td, 1H), 2.06 (dd, 1H), 1.87 (s, 3H), 1.83 (m, 6H), 1.63 (m, 1H), 1.27 (t, 3H), 1.08 (d, 1H), 1.04 (s, 6H), 0.97 (s, 6H). |
| 504 | 397.4 | 1.94 | |
| 505 | 392.2 | 1.62 | |
| 506 | 353.3 | 1.5 | |
| 507 | 426.2 | 1.91 | |
| 508 | 430.2 | 2.12 | |
| 509 | 400.2 | 1.83 | |
| 510 | 447.4 | 2 | CD3OD: 6.85 (s, 1H), 6.78 (s, 1H), 5.36 (t, 1H), 3.83 (s, 3H), 3.81 (s, 3H), 3.60 (m, 2H), 3.10-3.20 (m, 2H), 3.02 (d, 2H), 2.72 (dd, 1H), 2.25 (m1H), 2.03 (m, 1H), 2.00 (s, 3H), 1.65-1.95 (m, 8H), 1.38 (m, 2H), 1.26 (m, 1H), 1.07 (m, 2H) |
| 511 | 401.5 | 1.8 | |
| 512 | 361.4 | 2.2 | |
| 513 | 484.4 | 2.17 | DMSO (d6): 9.25 (m, 1H), 8.19 (d, 1H), 7.39 (d, 1H), 7.31 (t, 1H), 7.20 (t, 1H), 7.17 (d, 1H), 4.93 (ddd, 1H), 3.49 (t, 2H), 3.18 (m, 2H), 3.05 (t, t, 2H), 2.25 (ddd, 2H), 2.06 (dd, 1H), 1.87 (s, 3H), 1.83 (m, 3H), 1.75 (d, 1H), 1.63 (m, 1H), 1.10 (m, 1H), 0.68 (m, 2H), 0.39 (m, 2H). |

TABLE 2-continued

Physical Characteristics of Compounds in Table 1.

| Cmd No. | LCMS Plus | LCMS RT | NMR |
|---|---|---|---|
| 514 | 313.2 | 1.27 | |
| 515 | 450 | 2.04 | |
| 516 | 422.2 | 1.79 | |
| 517 | 439.4 | 1.44 | |
| 518 | 400.2 | 1.88 | |
| 519 | 403.5 | 2.1 | |
| 520 | 459.2 | 1.67 | CD3OD: 6.86 (s, 1H), 6.77 (s, 1H), 5.36 (t, 1H), 4.30 (m, 2H), 4.13 (q, 2H), 3.83 (s, 3H), 3.81 (s, 3H), 3.54 (m, 2H),, 3.15 (m, 3H), 2.70 (m, 1H), 2.30 (m, 1H), 2.15 (m, 2H), 2.00 (s, 3H), 1.70-2.009 m, 7H0, 1.25-1.60 (m, 5H) |
| 521 | 387 | 1.46 | |
| 522 | 446.3 | 2.41 | |
| 523 | 528.3 | 2.6 | |
| 524 | 416.2 | 1.8 | |
| 525 | 408.21 | 1.89 | |
| 526 | 424.2 | 2.29 | |
| 527 | 485.4 | 2.32 | |
| 528 | 439.4 | 1.66 | |
| 529 | 468.2 | 2.1 | |
| 530 | 325.2 | 1.3 | |
| 531 | 467.4 | 1.61 | |
| 532 | 444.5 | 2.37 | |
| 533 | 354.3 | 1.3 | |
| 534 | 455 | 2.02 | |
| 535 | 438.4 | 1.46 | 500 mHz, MeOH-d4; 7.36 (d, 1H), 7.30-7.22 (m, 3H), 5.20-5.17 (m, 1H), 3.01 (br s, 2H), 2.52-2.48 (m, 1H), 2.39 (s, 2H), 2.25-2.0 (m, 4H), 1.95-1.49 (m, 6H), 1.45-1.29 (m, 5H), 0.99-0.97 (m, 1H) |
| 536 | | | DMSO (d6): 9.50 (br.s, 1H), 8.18 (d, 1H), 7.39 (d, 1H), 7.29 (t, 1H), 7.19 (t, 1H), 7.16 (d, 1H), 4.92 (m, 1H), 4.12 (d, 2H), 4.05 (q, 2H), 3.40 (m, 3H), 3.19 (m, 2H), 2.82 (m, 2H), 2.25 (m, 2H), 2.09 (d, 2H), 2.03 (td, 1H), 1.86 (s, 3H), 1.82 (m, 4H), 1.61 (m, 3H), 1.19 (t, 3H). |
| 537 | 414.3 | 1.46 | DMSO-d6: 9.95-9.58 (m, 1H), 8.30-8.26 (m, 1H), 7.53-7.40 (m, 1H), 7.21-7.18 (m, 1H), 7.03-6.98 (m, 1H), 5.36-5.28 (m, 1H), 4.08-4.05 (m, 4H), 3.78 (s, 1H), 3.68-3.65 (m, 2H), 2.80 (br s, 2H), 2.72 (s, 1H), 2.69-2.63 (m, 1H), 2.58 (s, 2H), 2.20-2.07 (m, 1H), 2.03 (s, 2H), 1.97-1.90 (m, 3H), 1.82-1.77 (m, 1H), 1.51-1.47 (m, 2H), 1.21-1.18 (m, 3H) |
| 538 | 404.5 | 1.65 | |
| 539 | 416.4 | 1.57 | |
| 540 | 419.4 | 1.75 | |
| 541 | 448.2 | 1.65 | |
| 542 | 300.2 | 1.46 | |
| 543 | 446.3 | 2.13 | |
| 544 | 485.4 | 1.78 | |
| 545 | 447.2 | 2.4 | CD3OD: 6.86 (s, 1H), 6.79 (s, 1H), 5.37 (m, 1H), 3.84 (s, 3H), 3.82 (m, 3H), 3.40 (m, 2H), 3.55 (m, 3H), 3.00-3.20 (m, 2H), 2.70 (m, 1H), 2.48 (m, 2H), 1.77-2.10 (m, 19H including 3H singlet at 2.00) |
| 546 | 439.6 | 1.9 | |
| 547 | 332.2 | 0.75 | |
| 548 | 314.2 | 1.64 | |
| 549 | 410.2 | 1.81 | |
| 550 | 456.5 | 2.17 | |
| 551 | 454.2 | 2.03 | |
| 552 | 467.4 | 1.76 | |
| 553 | 441.4 | 1.76 | |
| 554 | 428.4 | 2.4 | |
| 555 | 442.4 | 2.24 | |
| 556 | 486.8 | 2.23 | |
| 557 | 349.2 | 2.03 | |
| 558 | 447.4 | 1.99 | |
| 559 | 451.8 | 2.24 | |
| 560 | 416.4 | 1.82 | |
| 561 | 443.2 | 1.93 | |
| 562 | 413.2 | 1.48 | |
| 563 | 410.4 | 1.91 | |
| 564 | 410.2 | 2.2 | |
| 565 | 444.4 | 2.08 | CD3OD: 6.86 (s, 1H), 6.78 (s, 1H), 5.36 (m, 1H), 3.83 (s, 3H), 3.82 (m, 3H), 3.55 (m, 3H), 3.15-3.25 (m, 2H), 2.25 (m, 1H), 2.35 (m, 1H), 2.00 (s, 3H), 1.80-1.90 (m, 5H), 1.36 (m, 2H), 1.12 (s, 6H), 1.04 (s, 6H) |
| 566 | 442.3 | 2.1 | |
| 567 | 440.4 | 2.17 | DMSO (d6): 9.40 (br. s), 8.18 (d, 1H), 7.38 (d, 1H), 7.30 (t, 1H), 7.20 (t, 1H), 7.16 (d, 1H), 4.92 (q, 1H), 3.41 (m, 2H), 3.13 (m, 4H), 2.24 (m, 2H), 2.05 (dd, 1H), 1.87 (s, 3H), 1.84-1.76 (m, 3H), 1.74-1.65 (m, 5H), 1.64-1.56 (m, 4H), 1.33-1.12 (m, 4H), 0.96 (m, 2H). |
| 568 | 369.43 | 1.82 | DMSO-d6: 7.69 (d, 1H), 7.52 (d, 2H), 7.43 (t, 2H), 7.25 (d, 2H), 7.01 (d, 1H), 6.26 (m, 1H), 6.06 (d, 1H), 4.95 (m, 1H), 4.49 (m, 1H), 3.77 (s, 3H), 3.55 (m, 2H), 2.42 (m, 1H), 2.79-3.15 (m, 7H), 1.94-2.11 (m, 3H), 1.71 (d, 3H), 0.68-0.70 (m, 2H) |
| 569 | 477 | 1.58 | |
| 570 | 444.4 | 1.5 | |
| 571 | 434 | 2.14 | |
| 572 | 484.2 | 1.76 | |
| 573 | 410.2 | 2.21 | |
| 574 | 413 | 1.68 | DMSO (d6): 9.25 (br. s), 8.17 (d, 1H), 7.37 (d, 1H), 7.30 (t, 1H), 7.20 (t, 1H), 7.16 (d, 1H), 4.92 (q, 1H), 3.93 (d, 2H), 3.42 (m, 3H), 3.15 (m, 4H), 2.71 (m, 1H), 2.20 (m, 2H), 2.04 (dd, 1H), 11.87 (s, 3H), .82 (m, 3H), 1.72 (d, 1H), 1.63 (m, 5H), 1.49 (m, 1H), 1.39 (s, 9H), 1.04 (ddd, 1H). |
| 575 | 470.4 | 1.82 | DMSO (d6): 8.92 (br.s, 1H), 8.39 (d, 1H), 7.39 (d, 1H), 7.32 (t, 1H), 7.21 (t, 1H), 7.16 (d, 1H), 6.27 (dd, 1H), 6.05 (m, 1H), 4.95 (q, 1H), 3.45 (m, 3H), 3.28-3.10 (m, 3H), 2.98 (s, 1H), 2.94 (ddd, 1H), 2.85 (s, 1H), 2.81 (ddd, 1H), 2.25 (m, 2H), 2.03 (ddd, 2H), 1.82 (m, 3H), 1.71 (d, 1H), 1.65 (m, 1H), 1.58 (m, 1H), 1.38 (dd, 1H), 1.29 (d, 1H), 0.78-0.63 (m, 4H). |
| 576 | 391.38 | 1.83 | |
| 577 | 303.2 | 1.93 | |
| 578 | 424.2 | 1.99 | |
| 579 | 422.2 | 1.79 | |
| 580 | 490.2 | 1.79 | DMSO (d6): 9.14 (br. s), 8.17 (d, 1H), 7.36 (d, 1H), 7.30 (t, 1H), 7.20 (t, 1H), 7.16 (d, 1H), 4.92 (q, 1H), 3.4 (m, 2H), 3.18-3.01 (m, 4H), 2.21 (m, 3H), 2.04 (dd, 1H), 2.00 (s, 1H), 1.87 (s, 3H), 1.82 (m, 3H), 1.72 (d, 1H), 1.64 (m, 3H), 1.47 (m, 4H), 1.35 (m, 2H), 1.17-1.02 (m, 4H). |
| 581 | 381.4 | 1.89 | |
| 582 | 357.2 | 2.1 | |
| 583 | 480.2 | 2.2 | |
| 584 | 459.4 | 2.08 | |
| 585 | 439.2 | 1.95 | |
| 586 | 355.23 | 1.59 | |
| 587 | 418.4 | 1.9 | |
| 588 | 495.4 | 2.01 | |
| 589 | 424.2 | 1.95 | |

TABLE 2-continued

Physical Characteristics of Compounds in Table 1.

| Cmd No. | LCMS Plus | LCMS RT | NMR |
|---|---|---|---|
| 590 | 445.6 | 1.88 | H NMR (500 MHz, DMSO (d6)): 9.14 (s, H), 7.36 (d, 1H), 7.22 (t, 1H), 7.09 (t, 1H), 7.07 (d, 1H), 4.10 (d, 2H), 4.05 (q, 2H), 3.48-3.39 (m, 4H), 3.19 (q, 2H), 2.83 (m, 2H), 2.71 (t, 2H), 2.27 (td, 2H), 2.09 (d, 2H), 1.87 (m, 2H), 1.77 (d, 2H), 1.72-1.68 (m, 2H), 1.58 (qd, 2H), 1.22 (t, 3H). |
| 591 | 357.4 | 1.87 | |
| 592 | 471.4 | 1.83 | |
| 593 | 468.3 | 1.61 | |
| 594 | 453.4 | 1.4 | |
| 595 | 459.4 | 2.01 | |
| 596 | 434 | 2.14 | |
| 597 | 391.2 | 2.16 | |
| 598 | 473.4 | 2.28 | CD3OD: 6.86 (s, 1H), 6.77 (s, 1H), 5.35 (m, 1H), 3.83 (s, 3H), 3.82 (m, 3H), 3.15-3.25 (m, 3H), 2.25 (m, 1H), 2.35 (m, 1H), 2.00 (s, 3H), 1.40-1.90 (m, 26H) |
| 599 | 471.6 | 2.3 | |
| 600 | 383.4 | 2.28 | |
| 601 | 404.4 | 1.86 | DMSO (d6): 9.09 (m, 1H), 8.18 (d, 1H), 7.38 (d, 1H), 7.30 (t, 1H), 7.20 (t, 1H), 7.16 (d, 1H), 4.92 (ddd, 1H), 3.86 (t, 1H), 3.78 (ddd, 1H), 3.67 (q, 2H, 3H), 3.43 (m, 3H), 3.19 (m, 4H), 3.66 (m, 1H), 2.25 (m, 2H), 2.12 (m, 1H), 2.05 (dd, 1H), 1.87 (s, 3H), 1.82 (m, 3H), 1.73 (d, 1H), 1.63 (m, 2H). |
| 602 | 343.1 | 0.97 | |
| 603 | 454.2 | 2.13 | |
| 604 | 440.4 | 2.08 | DMSO (d6): 8.85 (br.s, 1H), 8.18 (d, 1H), 7.41 (d, 1H), 7.30 (t, 1H), 7.19 (t, 1H), 7.16 (d, 1H), 4.92 (m, 1H), 3.42 (m, 2H), 3.14 (m, 2H), 3.00 (t, 2H), 2.29 (m, 2H), 2.05 (m, 1H), 1.86 (s, 3H), 1.85-1.58 (m, 11H), 1.26 (m, 2H), 1.17 (m, 1H), 0.99 (m, 2H). |
| 605 | 355.3 | 1.71 | |
| 606 | 454.2 | 2.24 | |
| 607 | 442.4 | 1.69 | |
| 608 | 439.4 | 1.73 | CD3OD: 7.73 (dd, 1H), 7.67 (d, 1H), 7.63 (d, 1H), 3.50 (, .2H), 3.26 (m, 2H), 2.83 (s, 2H), 2.37 (m, 2H), 2.13 (m, 2H), 1.60-1.90 (m, 12H) |
| 609 | 332 | 1.84 | |
| 610 | 414.4 | 1.96 | |
| 611 | 432.4 | 1.86 | |
| 612 | 314.2 | 1.59 | |
| 613 | 412.2 | 2.01 | |
| 614 | 471.4 | 2 | |
| 615 | 454.2 | 1.98 | DMSO (d6): 8.76 (s, 1H), 8.17 (d, 1H), 7.39 (t, 1H), 7.31 (d, 1H), 7.20 (t, 1H), 7.17 (d, 1H), 4.92 (q, 1H), 3.88 (dd, 2H), 3.44 (m, 2H), 3.34 (t, 2H), 3.17 (m, 2H), 3.06 (t, 2H), 2.31-2.14 (m, 2H), 2.11-2.02 (m, 2H), 1.86 (s, 3H), 1.81 (m, 3H), 1.71 (d, 1H), 1.64 (m, 3H), 1.27 (ddd, 2H). |
| 616 | 357.2 | 1.48 | |
| 617 | 384.2 | 1.91 | |
| 618 | 450.4 | 2.08 | |
| 619 | 456.2 | 1.72 | |
| 620 | 438.2 | 2.12 | |
| 621 | 411.2 | 2.38 | |
| 622 | 324.3 | 2.07 | |
| 623 | 454.2 | 1.69 | DMSO (d6): 8.29 (s, 1H), 8.17 (d, 1H), 7.45 (d, 1H), 7.31 (t, 1H), 7.20 (t, 1H), 7.17 (d, 1H), 4.93 (m, 1H), 3.38 (m, 2H), 3.20-3.09 (m, 3H), 2.34 (qd, 2H), 2.25-2.13 (m, 2H), 2.08-2.03 (m, 1H), 1.87 (s, 3H), 1.83 (m, 4H), 1.74-1.60 (m, 4H), 1.55 (d, 2H), 1.33-1.22 (m, 4H), 0.82 (s, 6H), 0.79 (t, 3H). |
| 624 | 411.3 | 2.34 | |
| 625 | 469.2 | 2.32 | |
| 626 | 386.2 | 1.72 | DMSO (d6): 9.06 (br.s, 1H), 7.47 (d, 1H), 7.45 (d, 1H), 7.32 (t, 1H), 7.24 (t, 1H), 6.26 (dd, 1H), 6.04 (dd, 1H), 4.45 (q, 1H), 3.38 (m, 2H), 3.15 (m, 2H), 3.05 (s, 3H), 2.98 (s, 1H), 2.93 (ddd, 1H), 2.85 (s, 1H), 2.80 (ddd, 1H), 2.23 (m, 2H), 2.07 (m, 1H), 2.01 (ddd, 1H), 1.94 (m, 1H), 1.86 (dd, 1H), 1.78 (m, 2H), 1.69 (d, 1H), 1.38 (d, 1H), 1.35 (d, 1H), 1.29 (d, 1H), 0.68 (dq, 1H). |
| 627 | 401.35 | 1.79 | |
| 628 | 433.4 | 1.78 | |
| 629 | 505.4 | 2.03 | |
| 630 | 487 | 2.31 | |
| 631 | 442.3 | 1.52 | |
| 632 | 404.4 | 1.9 | |
| 633 | 485.4 | 1.94 | |
| 634 | 404.4 | 1.88 | |
| 635 | 398.3 | 2.2 | DMSO (d6): 9.16 (br. s, 1H), 8.18 (d, 1H), 7.36 (d, 1H), 7.30 (t, 1H), 7.19 (t, 1H), 7.16 (d, 1H), 4.91 (q, 1H), 3.31 (m, 2H), 3.20 (t, 2H), 3.13 (t, 2H), 2.74 (m, 1H), 2.25-2.09 (m, 4H), 2.04 (dd, 1H), 1.91 (m, 1H), 1.87 (s, 3H), 1.82 (m, 6H), 1.71 (d, 1H), 1.62 (m, 1H). |
| 636 | 327.3 | 1.42 | |
| 637 | 410.2 | 1.86 | |
| 638 | 383.4 | 2.28 | |
| 639 | 393.5 | 2.1 | CD3CN: 7.50-7.35 (m, 1H), 7.12-7.05 (m, 1H), 7.02-6.99 (m, 1H), 6.86-6.77 (m, 1H), 5.42-5.35 (m, 1H), 3.88-3.84 (m, 2H), 3.36-3.13 (m, 4H), 2.72 (dd, J = 7.5, 12.7 Hz, 1H), 2.63-2.54 (m, 1H), 2.32 (s, 1H), 2.29 (s, 1H), 2.23-2.18 (m, 4H), 2.12-1.93 (m, 1H), 1.89-1.79 (m, 1H), 1.57-1.34 (m, 5H), 1.27-1.21 (m, 2H), 0.87-0.75 (m, 1H) |
| 640 | 357.1 | 1.71 | |
| 641 | 383.4 | 2.24 | 1H NMR (500 MHz, DMSO (d6)): 8.50 (br. s, 1H), 7.41 (d, 1H), 7.22 (t, 1H), 7.13 (t, 1H), 7.06 (d, 1H), 3.50 (m, 2H), 3.38 (m, 1H), 3.30 (m, 1H), 3.22-3.10 (m, 2H), 2.72 (t, 2H), 2.37-2.25 (m, 4H), 2.01 (t, 1H), 1.90-1.87 (m, 2H), 1.75-1.59 (m, 8H), 1.52-1.37 (m, 2H), 1.30-1.15 (m, 2H). |
| 642 | 296.3 | 1.9 | CD3OD: 7.38-7.63 (m, 5H), 6.66 (s, 1H), 6.45 (m, 1H), 5.70 (s, 1H), 5.40 (m, 1H), 3.73 (s, 3H), 3.54 (m, 2H), 3.47 (s, 3H), 2.33 (s, 3H), 2.16 (m, 4H), 1.96 (m, 4H), 1.20-1.75 (m, 13H) |
| 643 | 491.6 | 2.2 | |
| 644 | 347.4 | 1.91 | |
| 645 | 471.4 | 2.17 | DMSO (d6): 8.35 (s, 1H), 8.18 (d, 1H), 7.45 (d, 1H), 7.31 (t, 1H), 7.21 (t, 1H), 7.17 (d, 1H), 4.93 (m, 1H), 3.55 (m, 2H), 3.37 (m, 1H), 3.20-3.09 (m, 2H), 2.34 (qd, 2H), 2.24-2.13 (m, 2H), 2.06 (m, 1H), 1.87 (s, 3H), 1.90-1.81 (m, 3H), 1.74-1.58 (m, 5H), 1.30 (q, 2H), 1.15 (m, 2H), 0.88 (s, 9H). |
| 646 | 397.2 | 2.2 | DMSO-d6: 9.12 (s, 1H), 7.49 (d, 1H), 7.30 (t, 1H), 7.20 (t, 1H), 6.93 (d, 1H), 5.14 (dd, 1H), 3.39 (dd, 2H), 3.24-3.07 (m, 3H), 2.98 (t, 2H), 2.88 (ddd, 1H), 2.59 (td, 1H), 2.41-2.29 (m, 3H), 2.19 (td, 1H), 1.95-1.59 (m, 13H), 1.27 (m, 2H), 1.17 (tt, 1H), 0.99 (m, 2H). |
| 647 | 381.4 | 1.78 | |
| 648 | 492.4 | 2.22 | |

TABLE 2-continued

Physical Characteristics of Compounds in Table 1.

| Cmd No. | LCMS Plus | LCMS RT | NMR |
|---|---|---|---|
| 649 | 471.4 | 1.85 | H NMR (500 MHz, DMSO) 8.60 (br s, 1H, from TFA), 8.44 (d, J = 8.0 Hz, 1H), 7.32 (dt, J = 25.2, 8.1 Hz, 2H), 7.21 (dd, J = 7.3, 18.5 Hz, 2H), 5.39 (q, 1H), 4.07-2.97 (m, 4H, partially obscured by solvent), 2.70-2.60 (m, 2H), 2.45-2.31 (m, 2H), 2.07-1.91 (m, 2H), 1.72-1.55 (m, 8H), 1.46-1.41 (m, 3H), 1.25-1.17 (m, 1H), 0.77-0.66 (m, 4H) |
| 650 | 365.3 | 1.9 | |
| 651 | 459.4 | 2.06 | NMR (500 MHz, DMSO-d6) 8.98 (br. s, 1H), 8.18 (d, 1 H), 7.40 (d, 1H), 7.32 (t, 1H), 7.22 (t, 1H), 7.19 (d, 1H), 6.27 (dd, 1H), 6.17-6.15 (m, 1 H), 6.05 (q, 1 H), 4.94-4.92 (m, 1H), 3.45 (m, 2H), 3.20-3.13 (m, 2H), 2.98 (br.s, 1H), 2.95 (m, 1H), 2.86 (br.s, 1H), 2.85-2.79 (m, 1H), 2.28-2.22 (m, 2H), 2.07-1.99 (m, 2H), 1.87 (s, 3H), 1.83-1.78 (m, 3H), 1.73 (d, 1H), 1.65-1.61 (m, 1H), 1.39-1.29 (m, 3H), 0.70 (dt, 1H). |
| 652 | 365.32 | 1.63 | |
| 653 | 530 | 2.65 | |
| 654 | 371.1 | 2.75 | DMSO (d6): 9.28 (br.s, 1H), 8.19 (d, 1H), 7.39 (d, 1H), 7.30 (t, 1H), 7.19 (t, 1H), 7.16 (d, 1H), 4.92 (m, 1H), 3.42 (m, 2H), 3.25-3.08 (m, 4H), 2.34-2.14 (m, 5H), 2.05 (t, 1H), 1.87 (s, 3H), 1.81 (m, 4H), 1.70 (d, 1H), 1.63 (m, 1H), 1.49 (m, 2H), 1.37 (m, 2H), 1.30 (d, 1H), 1.14 (m, 2H) 0.81 (m, 1H). |
| 655 | 367.4 | 1.71 | |
| 656 | 424.2 | 1.98 | 1H NMR (500 MHz, DMSO (d6)): 8.82 (s, 1H), 7.33 (d, 1H), 7.22 (t, 1H), 7.14 (t, 1H), 7.06 (d, 1H), 3.43-3.35 (m, 3H), 3.14-3.03 (m, 2H), 2.72 (t, 2H), 2.45-2.39 (m, 2H), 2.32 (m, 2H), 2.18 (td, 2H), 1.87-1.84 (m, 2H), 1.76-1.67 (m, 4H), 1.60 (t, 2H), 1.56-1.46 (m, 1H), 1.42 (d, 2H), 1.30 (t, 2H), 1.02 (dt, 1H). |
| 657 | 310.3 | 2.05 | |
| 658 | 450 | 1.93 | |
| 659 | 467.4 | 1.87 | |
| 660 | 439.2 | 1.74 | |
| 661 | 480.2 | 2.4 | |
| 662 | 447.4 | 1.57 | DMSO (d6): 9.16 (br.s, 1H), 8.39 (d, 1H), 7.43 (d, 1H), 7.31 (t, 1H), 7.21 (t, 1H), 7.15 (d, 1H), 4.95 (q, 1H), 3.27 (m, 3H), 2.31 (m, 2H), 2.07 (m, 3H), 1.85-1.26 (m, 18H), 0.78-0.63 (m, 4H). |
| 663 | 381.44 | 1.79 | |
| 664 | 466.43 | 1.72 | |
| 665 | 431.4 | 1.78 | |
| 666 | 355.4 | 1.57 | |
| 667 | 382.4 | 2.11 | DMSO (d6): 8.93 (br.s, 1H), 7.46 (d, 1H), 7.44 (d, 1H), 7.35 (d, 1H), 7.32 (t, 1H), 7.21 (t, 1H), 4.45 (q, 1H), 3.11 (m, 2H), 3.04 (s, 3H), 2.35 (m, 2H), 2.15 (m, 2H), 2.05 (dd, 1H), 1.97 (m, 2H), 1.86-1.62 (m, 6H), 1.56-1.26 (m, 7H), 1.15 (t, 1H). |
| 668 | 403.34 | 1.79 | |
| 669 | 440.3 | 1.57 | |
| 670 | 355 | 2.51 | |
| 671 | 356.3 | 1.3 | |
| 672 | 410.2 | 1.82 | DMSO (d6): 8.68 (s, 1H), 7.38 (d, 1H), 7.27 (t, 1H), 7.24 (t, 1H), 7.18 (t, 1H), 6.48 (d, 1H), 4.82 (q, 1H), 3.42 (d, 2H), 3.15 (m, 2H), 3.00 (t, 2H), 2.82 (s, 6H), 2.41 (td, 1H), 2.22 (dd, 1H), 2.15 (td, 1H), 1.89 (d, 1H), 1.82-1.63 (m, 10H), 1.28 (q, 2H), 1.17 (m, 1H), 0.99 (q, 2H). |
| 673 | 384.3 | 2 | |
| 674 | 433.2 | 1.6 | |
| 675 | 471.4 | 2.17 | |
| 676 | 418.2 | 2.07 | |
| 677 | 463.2 | 0.96 | |
| 678 | 482.4 | 2.24 | |
| 679 | 398.2 | 1.64 | |
| 680 | 372.2 | 1.56 | |
| 681 | 416.4 | 1.62 | |
| 682 | 299.1 | 1.8 | |
| 683 | 414.4 | 1.99 | |
| 684 | 456.4 | 1.81 | |
| 685 | 361.2 | 1.32 | |
| 686 | 480.2 | 2.08 | |
| 687 | 396.5 | 2.1 | |
| 688 | 455.4 | 2.09 | |
| 689 | 502.2 | 2.27 | |
| 690 | 384.3 | 2.1 | DMSO-d6: 10.16-9.77 (m, 1H), 8.28 (m, 1H), 7.54-7.42 (m, 1H), 7.19 (m, 1H), 7.03-6.97 (m, 1H), 5.37-5.28 (m, 1H), 3.79-3.74 (m, 1H), 3.69-3.47 (m, 1H), 3.30-3.16 (m, 1H), 2.74-2.62 (m, 1H), 2.58 (s, 3H), 2.19-2.04 (m, 3H), 1.89 (m, 3H), 1.82-1.77 (m, 3H), 1.63 (m, 1H), 1.40-1.35 (m, 2H), 1.28-1.23 (m, 2H), 1.10 (td, J = 12.7, 9.5 Hz, 1H) |
| 691 | 331.4 | 1.71 | DMSO-d6: 9.65-9.45 (m, 1H), 8.27 (d, J = 7.5 Hz, 1H), 7.54-7.45 (m, 1H), 7.50 (s, 1H), 7.22-7.15 (m, 1H), 7.04-6.99 (m, 1H), 6.25 (dd, J = 3.1, 6.9 Hz, 1H), 6.06-6.04 (m, 1H), 5.34-5.28 (m, 1H), 3.86 (d, J = 4.1 Hz, 1H), 3.77-3.69 (m, 2H), 3.31-3.21 (m, 2H), 3.03-3.01 (m, 1H), 2.98-2.94 (m, 2H), 2.90 (s, 1H), 2.58 (s, 2H), 2.36 (t, J = 1.8 Hz, 1H), 2.18-2.12 (m, 1H), 2.02-1.94 (m, 1H), 1.83 (s, 3H), 1.38-1.28 (m, 2H) |
| 692 | 355.4 | 1.87 | |
| 693 | | | |
| 694 | 471.4 | 2.06 | |
| 695 | 433.2 | 1.87 | DMSO (d6): 8.64 (m, 1H), 8.18 (t, 1H), 7.43 (d, 1H), 7.31 (t, 1H), 7.20 (t, 1H), 7.17 (d, 1H), 4.92 (m, 1H), 3.49 (m, 1H), 3.41 (t, 1H), 3.33 (t, 1H), 3.17 (m, 2H), 2.61 (s, 1H), 2.31 (m, 3H), 2.02 (m, 2H), 1.86 (s, 3H), 1.85-1.60 (m, 8H), 1.40 (m, 3H), 1.20 (dd, 1H). |
| 696 | 353.3 | 1.54 | |
| 697 | 388.2 | 0.95 | |
| 698 | 447.4 | 1.89 | |
| 699 | 374.2 | 0.92 | |
| 700 | 442.2 | 2.36 | |
| 701 | 429.4 | 1.71 | CD3OD: 7.63 (d, 1H), 7.39 (d, 1H), 7.35 (d, 1H), 4.21 (q, 2H), 3.63 (m, 2H), 3.30 (m, 2H), 3.17 (d, 2H), 2.98 (s, 2H), 12.24 (m, 2H), .75-1.90 (m, 8H), 1.29-1.39 (m, 5H), 1.09 (m, 2H) |
| 702 | 375 | 2.18 | |
| 703 | 342.2 | 1.7 | |
| 704 | 461.4 | 2.01 | 1H-NMR (300 MHz, DMSO-d6): ? 6.87 (d, J = 8.7 Hz, 1H), 6.69 (t, J = 7.5 Hz, 1H), 6.40 (dd, J = 8.7 Hz, J = 4.5 Hz, 1H), 4.42 (m, 2H), 3.28 (s, 2H), 2.78 (d, J = 11.1 Hz, 1H), 2.58 (m, J = 11.7 Hz, 1H), 3.38 (m, 1H), 11.85-2.05 (m, 4H), .70-1.85 (m, 3H), 1.40-1.60 (m, 4H), 1.09 (dd, J = 11.7 Hz, J = 4.8 Hz, 1H). |
| 705 | 302.2 | 1.33 | |
| 706 | 447.4 | 2.01 | |
| 707 | 431.2 | 2.41 | |

TABLE 2-continued

Physical Characteristics of Compounds in Table 1.

| Cmd No. | LCMS Plus | LCMS RT | NMR |
|---|---|---|---|
| 708 | 423.4 | 1.6 | DMSO (d6): 9.00 (s, 1H), 8.17 (d, 1H), 7.34 (t, 1H), 7.30 (d, 1H), 7.20 (t, 1H), 7.17 (d, 1H), 4.92 (q, 1H), 3.85 (dd, 2H), 3.4 (m, 2H), 3.29 (t, 2H), 3.15 (m, 4H), 2.22-2.14 (m, 2H), 2.04 (dd, 1H), 1.87 (s, 3H), 1.81 (m, 3H), 1.73 (d, 1H), 1.65-1.55 (m, 6H), 1.21 (ddd, 2H). |
| 709 | 371.2 | 1.52 | |
| 710 | 382.4 | 1.4 | |
| 711 | 455.2 | 2.15 | |
| 712 | 477.4 | 2.15 | |
| 713 | 371.2 | 2.1 | |
| 714 | 448.3 | 2.18 | CD3OD: 7.71 (d, 1H), 7.62 (d, 1H), 7.52 (dd, 1H), 3.68 (m, 2H), 3.48 (m, 1H), 3.30 (m, 2H), 2.80 (s, 2H), 2.40 (m, 2H), 12.15 (m, 1H), .88 (m, 2H), 1.56-1.91 (m, 4H), 1.30 (m, 1H) |
| 715 | 318 | 1.71 | DMSO (d6): 9.20 (m, 1H), 8.19 (d, 1H), 7.41 (d, 1H), 7.29 (t, 1H), 7.19 (t, 1H), 7.16 (d, 1H), 4.92 (m, 1H), 3.38 (m, 2H), 3.20 (m, 2H), 2.26 (m, 2H), 2.10 (m, 1H), 2.03 (dd, 1H), 1.87 (s, 3H), 1.85-1.68 (m, 6H), 1.63 (m, 3H), 1.44 (q, 2H), 1.29 (q, 2H), 1.12 (m, 2H). |
| 716 | 341.2 | 1.46 | |
| 717 | 468.4 | 2.48 | |
| 718 | 466 | 1.67 | |
| 719 | 464.2 | 1.66 | |
| 720 | 438.2 | 1.44 | |
| 721 | 443.4 | 2.03 | |
| 722 | 436.2 | 1.91 | DMSO (d6): 9.07 (br.s, 1H), 7.46 (d, 1H), 7.44 (d, 1H), 7.41 (d, 1H), 7.32 (t, 1H), 7.23 (t, 1H), 4.45 (q, 1H), 3.04 (s, 3H), 2.26 (m, 2H), 2.06 (m, 3H), 1.93 (m, 3H), 1.87-1.67 (m, 8H), 1.59-1.38 (m, 8H), 1.30 (m, 1H). |
| 723 | 391.36 | 1.76 | |
| 724 | 412 | 1.88 | |
| 725 | 440.3 | 2.5 | |
| 726 | 422.5 | 2.3 | |
| 727 | 497.4 | 1.92 | |
| 728 | 463.2 | 1.04 | |
| 729 | 428 | 1.63 | |
| 730 | 448.3 | 2.18 | |
| 731 | 456.3 | 1.95 | H NMR (500 MHz, MeOD) 7.72-7.64 (m, 3H), 7.45-7.41 (dt, 1H), 3.05 (t, 2H), 2.62 (s, 2H), 2.42-2.38 (m, 2H), 2.27-2.15 (m, 3H), 2.12-2.0 (m, 2H), 1.85-1.77 (m, 2H), 1.60-1.32 (m, 7H), 1.00-0.97 (m, 1H), |
| 732 | 296.2 | 1.46 | |
| 733 | 443.2 | 1.69 | |
| 734 | 398.2 | 2.19 | |
| 735 | 467 | 2.05 | |
| 736 | 426.3 | 2.4 | |
| 737 | 355.4 | 2.38 | 1H NMR (500 MHz, DMSO (d6)): 9.01 (s, H), 7.38 (d, 1H), 7.21 (t, 1H), 7.14 (t, 1H), 7.05 (d, 1H), 3.40 (m, 1H), 3.27-3.17 (m, 4H), 2.72 (t, 2H), 2.26 (td, 2H), 2.12-2.05 (m, 2H), 1.88-1.86 (m, 2H), 1.76-1.67 (m, 8H), 1.57-1.46 (m, 6H). |
| 739 | | | DMSO (d6): 9.12 (br.s, 1H), 8.18 (d, 1H), 7.39 (d, 1H), 7.30 (t, 1H), 7.20 (t, 1H), 7.17 (d, 1H), 6.27 (m, 1H), 6.04 (m, 1H), 4.92 (m, 1H), 3.44 (m, 2H), 3.14 (m, 2H), 2.98 (s, 1H), 2.94 (m, 1H), 2.84 (s, 1H), 2.80 (m, 1H), 2.26 (m, 2H), 2.03 (m, 2H), 1.86 (s, 3H), 1.81 (m, 3H), 1.70 (d, 1H), 1.62 (m, 1H), 1.37 (t, 1H), 1.29 (d, 1H), 0.68 (m, 1H). |
| 740 | 365.3 | 1.67 | DMSO (d6): 9.04 (s, 1H), 8.17 (d, 1H), 7.34 (t, 1H), 7.30 (d, 1H), 7.20 (t, 1H), 7.17 (d, 1H), 4.92 (q, 1H), 3.79 (m, 1H), 3.42 (m, 3H), 3.16 (m, 7H), 2.89 (m, 1H), 2.22-2.14 (m, 2H), 2.05 (m, 1H), 1.87 (s, 3H), 1.83 (m, 5H), 1.74 (d, 1H), 1.63 (m, 3H), 1.46 (m, 1H), 1.35 (m, 1H), 1.17 (q, 1H), 0.90 (d, 6H). |
| 741 | 470.3 | 2.13 | |
| 742 | 426.2 | 1.93 | |
| 743 | 424.2 | 1.8 | DMSO (d6): 9.05 (br.s, 1H), 8.39 (d, 1H), 7.38 (d, 1H), 7.30 (t, 1H), 7.21 (t, 1H), 7.15 (d, 1H), 4.95 (q, 1H), 3.11 (m, 2H), 2.35 (m, 2H), 2.25-2.12 (m, 3H), 2.07-1.96 (m, 2H), 1.82 (m, 3H), 1.72 (m, 2H), 1.65 (m, 2H), 1.60-1.25 (m, 9H), 1.16 (t, 1H), 0.78-0.63 (m, 4H). |
| 744 | 393.4 | 1.83 | |
| 745 | 455.3 | 1.74 | |
| 746 | 444.6 | 1.99 | |
| 747 | 436.4 | 1.89 | |
| 748 | 457.2 | 2 | |
| 749 | 461.4 | 2.01 | |
| 750 | 443.2 | 2.08 | |
| 751 | 458.6 | 2.31 | |
| 752 | 440.4 | 2.13 | |
| 753 | 372.2 | 1.53 | |
| 754 | 442.5 | 2.23 | |
| 755 | 396.62 | 1.7 | |
| 756 | 444.6 | 2.19 | |
| 757 | 440.5 | 2.41 | |
| 758 | 324.2 | 2.04 | |
| 759 | 369.2 | 2.15 | |
| 760 | 469.4 | 1.5 | |
| 761 | 457.2 | 1.96 | |
| 762 | 467.4 | 2.21 | |
| 763 | 436.3 | 2.4 | DMSO (d6): 9.38 (m, 1H), 8.19 (d, 1H), 7.37 (d, 1H), 7.31 (t, 1H), 7.20 (t, 1H), 7.17 (d, 1H), 4.92 (m, 1H), 3.53 (m, 2H), 3.22 (m, 2H), 3.04 (m, 2H), 2.42 (m, 2H), 2.21 (qd, 2H), 2.10 (dd, 1H), 1.91 (t, 2H), 1.87 (s, 3H), 1.84 (m, 3H), 1.74 (d, 1H), 1.64 (s, 3H), 1.63 (m, 1H), 1.54 (m, 2H), 1.41 (m, 2H), 1.01 (s, 6H). |
| 764 | 409.4 | 2.09 | CDCl3 (ppm): 7.93 (1H, br s), 7.43 (1H, m), 7.36 (1H, m), 4.35 (2H, br s), 4.12 (2H, m), 3.98 (1H, br s), 3.21 (1H, br s), 3.08 (2H, br s), 2.76 (4H, m), 2.05 (3H, m), 1.62 (1H, br s), 1.28 (6H, m). |
| 765 | 360.9 | 1.68 | DMSO-d6: 9.16 (s, 1H), 7.55 (d, 1H), 7.31 (t, 1H), 7.20 (t, 1H), 6.93 (d, 1H), 5.15 (dd, 1H), 3.47 (m, 1H), 3.34 (t, 2H), 3.24-3.11 (m, 3H), 2.88 (q, 1H), 2.60 (t, 2H), 2.41-2.26 (m, 5H), 2.08-1.33 (m, 13H), 1.28-1.14 (m, 2H). |
| 766 | 379.35 | 1.63 | |
| 767 | 483.4 | 1.93 | |
| 768 | 476 | 2.5 | |
| 769 | 464.5 | 1.67 | |
| 770 | 495.4 | 1.95 | |
| 771 | 376.2 | 1.59 | |
| 772 | 465.2 | 1.86 | DMSO (d6): 8.74 (br.s, 1H), 7.47 (d, 1H), 7.45 (d, 1H), 7.32 (t, 1H), 7.23 (t, 1H), 4.45 (q, 1H), 3.43 (m, 2H), 3.15 (q, 2H), 3.05 (s, 3H), 3.00 (t, 2H), 2.28 (m, 2H), 2.07 (dd, 1H), 1.95 (m, 1H), 1.88-1.63 (m, 10H), 1.28 (q, 2H), 1.18 (tt, 1H), 0.99 (q, 2H). |
| 773 | 391.38 | 1.79 | CD3OD: 6.86 (s, 1H), 6.77 (s, 1H), 5.36 (t, 1H), 4.30 (t, 2H), 4.13 (q, 2H), 3.83 (s, 3H), 3.81 (s, 3H), 3.60 (m, 2H), 3.45 (m, 1H), 3.15 (m, 2H), 2.85 (brm, 4H), 2.70 (m, 2H), 2.40 (m, 2H), 2.20 (m, 2H), 2.00 (s, 3H), 1.60-1.90 (m, 5H), 1.26 (t, 3H) |

TABLE 2-continued

Physical Characteristics of Compounds in Table 1.

| Cmd No. | LCMS Plus | LCMS RT | NMR |
|---|---|---|---|
| 774 | 460.1 | 1.45 | |
| 775 | 443.4 | 1.9 | |
| 776 | 456.4 | 1.81 | |
| 777 | 436.2 | 1.93 | |
| 778 | | | |
| 779 | 353.2 | 1.8 | |
| 780 | 371.3 | 0.9 | |
| 781 | 523.6 | 2.08 | |
| 782 | 400.3 | 1.4 | |
| 783 | 371.2 | 1.82 | in DMSO-d6 |
| 784 | 395.6 | 2.39 | |
| 785 | 414.2 | 1.92 | |
| 786 | 414.2 | 1.98 | CD3OD: 7.70 (d, 1H), 7.66 (d, 1H), 7.52 (dd, 1H), 3.62 (m, 2H), 3.23 (m, 3H), 2.81 (s, 2H), 2.33 (m, 2H), 2.18 (m, 2H), 1.90-1.99 (m, 4H), 1.75 (s, 1H), 1.56 (m, 2H), 1.44 (m, 2H), 1.25 (m, 1H) |
| 787 | 330 | 1.74 | CD3OD: 7.61 (d, 1H), 7.45 (m, 1H), 7.37 (s, 1H), 6.29 (m, 2H), 6.05 (m, 2H), 4.93 (m, 1H), 3.65 (m, 2H), 2.90-3.10 (m, 10H), 2.40-2.60 (m, 3H), 1.70-2.10 (m, 7H), 1.55 (m, 2H), 1.40 (m, 2H), 0.65-0.80 (m, 2H) |
| 788 | 449 | 1.38 | DMSO (d6): 8.51 (s, 1H), 7.40 (d, 1H), 7.28 (t, 1H), 7.24 (d, 1H), 7.19 (t, 1H), 6.48 (d, 1H), 4.82 (q, 1H), 3.50 (m, 1H), 3.42 (d, 1H), 3.33 (d, 1H), 3.16 (m, 2H), 2.82 (s, 6H), 2.61 (m, 1H), 2.41 (dd, 1H), 2.31 (m, 1H), 2.22 (dd, 1H), 2.19 (td, 1H), 2.01 (m, 1H), 1.89 (d, 1H), 1.80 (m, 1H), 1.71-1.56 (m, 6H), 1.41 (m, 3H), 1.17 (dd, 1H). |
| 789 | 382.1 | 1.87 | |
| 790 | 439.4 | 1.75 | |
| 791 | 466.4 | 1.46 | |
| 792 | 370.3 | 1.98 | |
| 793 | 438.4 | 2.44 | |
| 794 | 411.2 | 2.04 | |
| 795 | 466.4 | 1.57 | |
| 796 | 345.2 | 1.95 | H NMR (500 MHz, DMSO) 8.79 (s, 1H), 8.16 (d, J = 8.2 Hz, 1H), 7.34-7.16 (m, 4H), 5.37 (q, J = 7.9 Hz, 2H), 3.53-3.47 (m, 2H), 3.07-2.98 (m, 4H), 2.69-2.63 (m, 1H), 2.40-2.34 (m, 1H), 2.11 (dt, 2H), 1.90-1.54 (m, 12H), 1.31-1.13 (m, 3H), 1.02-0.96 (m, 2H), 0.89 (t, J = 7.4 Hz, 3H), |
| 797 | 369.5 | 2.1 | |
| 798 | 419.5 | 2.1 | |
| 799 | 492.2 | 2.36 | |
| 800 | 447.3 | 1.98 | |
| 801 | 379.5 | 2 | 1H NMR (500 MHz,DMSO (d6)): 8.70 (s, 1H), 7.39 (d, 1H), 7.22 (t, 1H), 7.14 (t, 1H), 7.06 (d, 1H), 3.40 (d, 2H), 3.14 (dd, 2H), 3.00 (t, 2H), 2.72 (t, 2H), 2.28 (td, 2H), 1.89-1.87 (m, 2H), 1.83-1.66 (m, 10H), 1.28 (q, 2H), 1.21-1.13 (m, 1H), 1.03-0.96 (m, 2H). |
| 803 | 328.2 | 1.7 | |
| 804 | 470.2 | 1.81 | |
| 805 | 465 | 1.98 | |
| 806 | 413.3 | 0.5 | |
| 807 | 419.2 | 1.75 | |
| 808 | 456.2 | 2.56 | DMSO (d6): 9.09 (br.s, 1H), 7.46 (d, 1H), 7.45 (t, 1H), 7.31 (d, 2H), 7.23 (m, 1H), 7.21 (t, 1H), 4.45 (q, 1H), 4.26 (br.s, 2H), 4.08 (m, 4H), 3.89 (m, 1H), 3.76 (m, 1H), 3.10 (q, 2H), 3.05 (s, 3H), 2.11 (m, 3H), 1.93 (m, 2H), 1.87-1.59 (dd, 7H), 1.34 (m, 1H), 1.21 (t, 3H), 1.16 (q, 2H). |
| 809 | 476.35 | 1.68 | DMSO (d6): 9.51 (m, 0.62H), 9.29 (m, 0.38H), 8.18 (d, 1H), 7.36 (d, 0.64H), 7.33 (d, 0.36H), 7.28 (t, 1H), 7.19 (t, 1H), 7.16 (d, 1H), 4.92 (m, 1H), 4.33-4.26 (m, 2H), 4.06 (q, 2H), 4.05 (m, 1H), 3.45 (m, 2H), 3.13 (m, 2H), 2.66 (m, 1H), 2.26-1.98 (m, 4H), 1.92 (m, 2H), 1.86 (s, 3H), 1.85-1.58 (m, 9H), 1.54 (t, 1H), 1.24 (t, 3H), 1.20 (m, 1H). |
| 810 | 440.3 | 1.57 | |
| 811 | 439.2 | 1.52 | |
| 812 | 471.4 | 1.81 | |
| 813 | 402.2 | 2.04 | |
| 814 | 485.4 | 2.12 | |
| 815 | 398.2 | 2.19 | |
| 816 | 396.2 | 1.73 | |
| 817 | 447.5 | 2.5 | |
| 818 | 440 | 2.1 | DMSO (d6): 9.15 (br. s), 8.17 (d, 1H), 7.36 (d, 1H), 7.30 (t, 1H), 7.20 (t, 1H), 7.17 (d, 1H), 4.92 (q, 1H), 3.76 (m, 2H), 3.42 (m, 3H), 3.18 (m, 4H), 2.80 (t, 1H), 2.20 (m, 2H), 2.05 (dd, 1H), 1.87 (s, 3H), 1.81 (m, 4H), 1.73 (d, 1H), 1.67-1.52 (m, 4H), 1.45-1.29 (m, 2H), 1.40 (s, 9H), 1.15 (m, 1H). |
| 819 | 470.43 | 1.85 | |
| 820 | 464.2 | 2.24 | DMSO-d6: 9.48-9.05 (m, 1H), 8.28-8.25 (m, 1H), 7.58-7.40 (m, 1H), 7.22-7.19 (m, 1H), 7.05-7.00 (m, 1H), 5.32-5.29 (m, 1H), 3.90-3.88 (m, 1H), 3.73 (d, J = 9.6 Hz, 1H), 3.69-3.63 (m, 2H), 2.63 (t, J = 1.8 Hz, 1H), 2.51 (s, 4H), 2.28 (t, J = 5.1 Hz, 1H), 2.19-2.10 (m, 1H), 2.02-1.98 (m, 1H), 1.95-1.89 (m, 3H), 1.61-1.52 (m, 3H), 1.38 (d, J = 9.7 Hz, 3H), 1.12 (t, J = 12.7 Hz, 1H) |
| 821 | 343.4 | 1.71 | |
| 822 | 420.2 | 1.81 | DMSO-d6: 10.17-9.82 (m, 1H), 8.31-8.23 (m, 1H), 7.55-7.50 (m, 1H), 7.21-7.16 (m, 1H), 7.03-6.99 (m, 1H), 5.35-5.29 (m, 1H), 4.92-4.85 (m, 1H), 3.76-3.66 (m, 1H), 3.53-3.30 (m, 3H), 2.75-2.61 (m, 1H), 2.58 (s, 2H), 2.31-2.20 (m, 1H), 2.18-2.00 (m, 3H), 1.86-1.77 (m, 3H), 1.74-1.60 (m, 4H), 1.53-1.40 (m, 5H) |
| 823 | 345.4 | 1.86 | |
| 824 | 428.2 | 1.57 | |
| 825 | 438.4 | 2.42 | |
| 826 | 342.2 | 1.91 | |
| 827 | 440.4 | 2.07 | DMSO (d6): 9.04 (s, 1H), 8.17 (d, 1H), 7.34 (t, 1H), 7.30 (d, 1H), 7.20 (t, 1H), 7.17 (d, 1H), 4.93 (q, 1H), 4.10 (m, 2H), 3.43 (m, 3H), 3.18 (m, 4H), 2.92 (m, 1H), 2.20 (m, 2H), 2.06 (m, 1H), 1.87 (s, 3H), 1.83 (m, 4H), 1.74 (m, 1H), 1.66 (m, 3H), 1.55 (m, 1H), 1.44 (m, 1H), 1.35 (m, 1H), 1.24 (m, 1H), 1.20 (s, 9H). |
| 828 | 454.3 | 1.91 | |
| 829 | 436.4 | 1.87 | |
| 830 | 327.1 | 2.1 | |
| 831 | 496.5 | 2.68 | |
| 833 | 412.2 | 1.48 | in DMSO-d6 |
| 834 | 339.22 | 2.7 | |
| 835 | 408.3 | 2.2 | CD3OD: 7.70 (d, 1H), 7.65 (s, 1H), 7.52 (d, 1H), 4.45 (m, 2H), 4.17 (m, 3H), 3.76 (m, 2H), 3.13 (m, 2H), 2.79 (s, 2H), 1.60-2.30 (m, 13H), 1.27 (m, 3H), |
| 836 | 417 | 1.76 | |
| 837 | 498.4 | 2.18 | |
| 838 | 468.2 | 2.56 | |
| 839 | 540 | 2.16 | |
| 840 | 402.2 | 1.81 | |
| 841 | 472.3 | 2.56 | |
| 842 | 382.5 | 2 | |
| 843 | 386.2 | 1.71 | |
| 844 | 414.2 | 2.2 | |

TABLE 2-continued

Physical Characteristics of Compounds in Table 1.

| Cmd No. | LCMS Plus | LCMS RT | NMR |
|---|---|---|---|
| 845 | 383.2 | 2.33 | MeOD: 7.86 (m, 1H), 7.55 (d, J = 2.4 Hz, 1H), 7.40 (d, J = 7.3 Hz, 1H), 4.02 (m, 1H), 3.89 (m, 1H), 3.25-3.15 (m, 2H), 3.58 (m, 1H), 3.47 (m, 1H), 3.05 (m, 1H), 2.84 (d, J = 6.9 Hz, 1H), 2.65 (br m, 1H), 2.32 (m, 1H), 1.89 (m, 1H), 1.82-1.79 (m, 4H), 1.73-1.71 (m, 1H), 1.34-1.23 (m, 3H), 1.10-1.04 (m, 2H) |
| 846 | 302.4 | 2.04 | |
| 847 | 487.2 | 2.33 | |
| 848 | 469.4 | 2.44 | |
| 849 | 375.4 | 2.4 | |
| 850 | 414.2 | 1.98 | |
| 851 | 460.4 | 2.4 | |
| 852 | 444.4 | 1.5 | |
| 853 | 444.4 | 2.14 | DMSO-d6: 9.58 (s, 1H), 7.46 (d, 1H), 7.29 (t, 1H), 7.20 (t, 1H), 6.93 (d, 1H), 5.14 (dd, 1H), 3.47-3.36 (m, 3H), 3.21 (q, 2H), 3.01 (m, 2H), 2.88 (ddd, 1H), 2.44-2.29 (m, 6H), 2.11 (td, 1H), 2.00-1.87 (m, 5H), 1.84-1.69 (m, 2H), 1.66-1.52 (m, 5H), 1.48-1.34 (m, 3H). |
| 854 | 393.36 | 1.74 | |
| 855 | 440.4 | 1.85 | DMSO-d6: 9.46 (s, 1H), 7.48 (d, 1H), 7.31 (t, 1H), 7.20 (t, 1H), 6.93 (d, 1H), 6.26 (dd, 1H), 6.06 (dd, 1H), 5.14 (dd, 1H), 3.43 (m, 2H), 3.21 (q, 2H), 3.13 (m, 2H), 3.00 (s, 1H), 2.95-2.74 (m, 3H), 2.84 (s, 1H), 2.57 (m, 1H), 2.41-2.29 (m, 3H), 2.16 (m, 1H), 2.00 (m, 1H), 1.91 (m, 3H), 1.80 (t, 1H), 1.74 (m, 1H), 1.62 (t, 2H), 1.37 (d, 1H), 1.29 (d, 1H), 0.69 (m, 1H). |
| 856 | 391.38 | 1.74 | |
| 857 | 462 | 2.42 | |
| 858 | 402.4 | 1.98 | |
| 859 | 414 | 2.26 | |
| 860 | 406.4 | 1.99 | DMSO (d6): 9.05 (m, 1H), 8.18 (d, 1H), 7.35 (d, 1H), 7.29 (t, 1H), 7.19 (t, 1H), 7.16 (d, 1H), 4.92 (m, 1H), 3.42 (m, 3H), 3.06 (m, 2H), 2.42 (m, 2H), 2.34 (m, 2H), 2.18 (m, 2H), 2.01 (m, 1H), 1.86 (s, 3H), 1.81 (m, 3H), 1.72 ({m, 3H), 1.63 (m, 1H), 1.54 (d, 1H), 1.41 (m, 2H), 1.32 (t, 2H), 1.01 (dt, 1H). |
| 861 | 367.4 | 1.65 | |
| 862 | 411.2 | 1.81 | (DMSO-d6, ppm) 9.03 (br s, 1H), 7.59 (d, J = 8 Hz, 1H), 7.45 (m, 2H), 3.43 (m, 2H), 3.16 (q, J = 10 Hz, 23 Hz, 2H), 2.77 (s, 2H), 2.39 (s, 3H), 2.03 (m, 3H), 1.72 (m, 6H), 1.53 (m, 8H). |
| 863 | 311.2 | 1.99 | |
| 864 | 400.2 | 1.84 | CD3OD: 7.64 (d, 1H), 7.35-7.39 ((m, 2H), 4.21 (q, 2H), 3.64 (m, 2H), 3.46 (m, 1H), 3.30 (m, 2H), 3.17 (d, 2H), 2.98 (s, 2H), 2.10-2.30 (m, 3H), 1.49-1.80 (m, 10H), 1.29-1.35 (m, 4H) |
| 865 | 373 | 2.06 | |
| 866 | 455.2 | 2.19 | |
| 867 | 357.2 | 2 | |
| 868 | 390.2 | 2.1 | |
| 869 | 428 | 2.02 | |
| 870 | 528.3 | 2.56 | |
| 871 | 422 | 1.79 | |
| 872 | 428.2 | 2.14 | : |
| 873 | 449.5 | 2.69 | DMSO (d6): 9.02 (s, 1H), 8.17 (d, 1H), 7.34 (t, 1H), 7.30 (d, 1H), 7.20 (t, 1H), 7.17 (d, 1H), 4.92 (q, 1H), 4.14 (m, 1H), 3.66 (m, 2H), 3.43 (m, 3H), 3.18 (m, 4H), 3.07 (t, 1H), 2.18 (m, 2H), 2.05 (m, 1H), 2.00 (s, 3H), 1.87 (s, 3H), 1.82 (m, 4H), 1.74 (d, 1H), 1.69-1.50 (m, 4H), 1.41 (m, 1H), 1.22 (m, 1H). |
| 874 | 412.2 | 1.52 | DMSO (d6): 9.04 (s, 1H), 8.17 (d, 1H), 7.34 (t, 1H), 7.30 (d, 1H), 7.20 (t, 1H), 7.17 (d, 1H), 4.92 (q, 1H), 3.96 (d, 2H), 3.58 (s, 3H), 3.42 (m, 2H), 3.16 (m, 4H), 2.79 (m, 2H), 2.22-2.14 (m, 2H), 2.04 (dd, 1H), 1.87 (s, 3H), 1.83 (m, 1H), 1.74 (d, 1H), 1.68-1.60 (m, 5H), 1.51 (m, 1H), 1.07 (ddd, 2H). |
| 875 | 428.2 | 1.69 | |
| 876 | 426.3 | 2.4 | |
| 877 | 369 | 2.15 | |
| 878 | 353 | 2.3 | |
| 879 | 445.2 | 2.2 | |
| 880 | 403.4 | 1.62 | DMSO (d6): 9.35 (m, 1H), 8.19 (d, 1H), 7.42 (d, 1H), 7.29 (t, 1H), 7.19 (t, 1H), 7.15 (d, 1H), 4.91 (m, 1H), 3.39 (m, 1H), 3.32-3.15 (m, 4H), 2.28 (m, 2H), 2.06 (m, 3H), 1.87 (s, 3H), 1.82 (m, 3H), 1.71 (m, 5H), 1.62 (m, 1H), 1.51 (m, 5H). |
| 881 | 355.4 | 1.57 | DMSO (d6): 8.89 (br. s, 1H), 8.18 (d, 1H), 7.41 (d, 1H), 7.30 (t, 1H), 7.19 (t, 1H), 7.16 (d, 1H), 4.92 (q, 1H), 3.42 (t, 2H), 3.15 (t, 2H), 2.99 (t, 2H), 2.36-2.25 (m, 2H), 2.04 (dd, 1H), 1.87 (s, 3H), 1.85-1.57 (m, 11H), 1.27 (q, 2H), 1.18 (t, 1H), 1.00 (q, 2H). |
| 882 | 355.4 | 1.65 | |
| 883 | 422.3 | 1.9 | |
| 884 | 373.2 | 2.29 | |
| 885 | 469.2 | 1.89 | |
| 886 | 410.2 | 1.83 | |
| 887 | 483.2 | 1.9 | DMSO (d6): 9.04 (s, 1H), 8.17 (d, 1H), 7.34 (t, 1H), 7.30 (d, 1H), 7.20 (t, 1H), 7.17 (d, 1H), 4.92 (q, 1H), 3.44 (m, 5H), 3.18 (m, 4H), 2.89 (m, 1H), 2.72 (s, 6H), 2.18 (m, 2H), 2.05 (dd, 1H), 1.87 (s, 3H), 1.82 (m, 4H), 1.73 (d, 1H), 1.66-1.48 (m, 5H), 1.42 (m, 1H), 1.13 (m, 1H). |
| 888 | 441.3 | 1.69 | DMSO (d6): 8.74 (br.s, 1H), 8.39 (d, 1H), 7.41 (d, 1H), 7.31 (t, 1H), 7.21 (t, 1H), 7.16 (d, 1H), 4.95 (q, 1H), 3.41 (t, 2H), 3.16 (t, 2H), 3.16 (t, 2H), 2.29 (ddd, 2H), 2.06 (dd, 1H), 1.86-1.61 (m, 11H), 1.88 (ddd, 1H), 1.28 (q, 2H), 1.18 (tt, 1H), 1.00 (q, 2H), 0.78-0.63 (m, 4H). |
| 889 | 381.4 | 1.83 | |
| 890 | | | |
| 891 | 444.4 | 2.47 | |
| 892 | 401 | 2.51 | |
| 893 | 448.4 | 2.11 | |
| 894 | 397 | 1.99 | |
| 895 | 439.4 | 1.76 | |
| 896 | 470.4 | 2 | |
| 897 | 448 | 1.93 | |
| 898 | 483.4 | 1.78 | |
| 899 | 481.3 | 1.78 | |
| 900 | 455.2 | 1.78 | CD3OD: 7.74 (dd, 1H), 7.68 (d, 1H), 7.61 (d, 1H), 3.69 (m, 2H), 3.48 (m, 1H), 3.30 (m, 2H), 2.81 (s, 2H), 2.46 (m, 3H), 2.15 (m, 1H), 1.88 (m, 2H), 1.49-1.75 (m, 7H), 1.30 (m, 1H) |
| 901 | 330 | 1.75 | |
| 902 | 369 | 2.28 | |
| 903 | 457.2 | 1.75 | 1H NMR-MeOD: 7.46 (d, J = 7.3 Hz, 1H), 7.30 (dd, J = 7.2, 15.1 Hz, 2H), 7.21 (d, J = 7.2 Hz, 1H), 4.18-4.15 (m, 1H), 3.62 (m, 2H), 3.50 (m, 1H), 3.22-3.18 (m, 2H), 2.71 (m, 1H), |

TABLE 2-continued

Physical Characteristics of Compounds in Table 1.

| Cmd No. | LCMS Plus | LCMS RT | NMR |
|---|---|---|---|
| | | | 2.49-2.41 (m, 3H), 2.4-2.1 (m, 3H), 1.99 (m, 1H), 1.80-1.65 (m, 3H), 1.58-1.5 (m, 4H), 1.22 (d, 1H) |
| 904 | 326.2 | 1.6 | |
| 905 | 422.2 | 1.81 | |
| 906 | 442.6 | 2.23 | |
| 907 | 476.2 | 2.53 | |
| 908 | 468.2 | 2.51 | |
| 909 | 528.3 | 2.56 | |
| 910 | 400.2 | 1.84 | |
| 911 | 476 | 2.46 | DMSO (d6): 8.15 (d, 1H), 7.41 (d, 1H), 7.21 (ddd, 1H), 7.12 (m, 2H), 4.81 (m, 1H), 3.95 (d, 2H), 2.61 (m, 4H), 2.42 (m, 3H), 1.94 (m, 3H), 1.86 (s, 3H), 1.76 (m, 3H), 1.67 (t, 1H), 1.61 (d, 1H), 1.47 (d, 1H), 1.39 (s, 9H), 1.30 (ddd, 2H). |
| 912 | 442.4 | 1.68 | |
| 913 | 406.4 | 2.01 | |
| 914 | 489.2 | 2.03 | |
| 915 | 342.2 | 1.91 | |
| 916 | 303.2 | 1.56 | |
| 917 | 495.4 | 1.93 | |
| 918 | 454.4 | 2.52 | |
| 919 | 356.3 | 1.94 | |
| 920 | 483.2 | 1.99 | |
| 921 | 449.2 | 1.77 | |
| 922 | 313.4 | 1.5 | |
| 923 | 372.2 | 1.56 | |
| 924 | 303.2 | 1.21 | |
| 925 | 347 | 2.11 | in DMSO-d6 |
| 926 | 371.4 | 1.6 | |
| 927 | 398.2 | 1.8 | DMSO-d6: 9.93-9.62 (m, 1H), 8.30-8.24 (m, 1H), 7.53-7.32 (m, 1H), 7.22-7.17 (m, 1H), 7.04-6.96 (m, 1H), 5.35-5.27 (m, 1H), 4.39 (br s, 3H), 4.32 (s, 2H), 4.13-4.03 (m, 2H), 3.96 (m, 1H), 3.75-3.73 (m, 1H), 3.68-3.63 (m, 1H), 2.62-2.58 (m, 3H), 2.30-2.20 (m, 2H), 2.08 (s, 1H), 2.00 (s, 2H), 1.95-1.88 (m, 2H), 1.69-1.63 (m, 3H), 1.57 (d, J = 7.9 Hz, 1H), 1.24-1.15 (m, 3H) |
| 928 | 430.5 | 1.74 | |
| 929 | 424.2 | 2.23 | |
| 930 | 452 | 2.44 | CD3OD: 7.30-7.63 (m, 5H), 6.61 (s, 1H), 6.35 (m, 1H), 5.65 (s, 1H), 5.43 (m, 1H), 3.73 (s, 3H), 3.56 (m, 2H), 3.47 (s, 3H), 3.20 (m, 1H), 3.03 (m, 2H), 2.33 (s, 3H), 1.10-1.95 (brm, 21H) |
| 931 | 505.6 | 2.3 | |
| 932 | 428.2 | 1.57 | |
| 933 | 401 | 2.27 | in DMSO-d6 |
| 934 | 327.4 | 1.7 | |
| 935 | 339.2 | 2.08 | DMSO (d6): 9.01 (s, 1H), 8.17 (d, 1H), 7.34 (t, 1H), 7.30 (d, 1H), 7.20 (t, 1H), 7.17 (d, 1H), 4.92 (q, 1H), 3.85 (d, 2H), 3.59 (s, 3H), 3.42 (m, 3H), 3.17 (m, 4H), 2.87 (m, 1H), 2.18 (m, 2H), 2.05 (dd, 1H), 1.87 (s, 3H), 1.83 (m, 4H), 1.74 (d, 1H), 1.63 (m, 3H), 1.55 (m, 1H), 1.46 (m, 1H), 1.35 (q, 1H), 1.16 (q, 1H). |
| 936 | 428.2 | 1.74 | |
| 937 | 512.5 | 2.81 | |
| 938 | 487.4 | 2.04 | |
| 939 | 457.4 | 2 | |
| 940 | 400.2 | 2.19 | |
| 941 | 439.4 | 1.55 | |
| 942 | 454.2 | 1.54 | |
| 943 | 430 | 1.71 | |
| 944 | 415.2 | 1.74 | DMSO-d6: 9.24 (s, 1H), 7.48 (d, 1H), 7.31 (t, 1H), 7.20 (t, 1H), 6.93 (d, 1H), 5.14 (dd, 1H), 3.47 (m, 2H), 3.31-3.12 (m, 5H), 2.88 (m, 1H), 2.53 (m, 1H), 2.40-2.30 (m, 4H), 2.17-2.04 (m, 2H), 1.91 (m, 3H), 1.84-1.59 (m, 7H), 1.57-1.42 (m, 5H). |
| 945 | 381.36 | 1.71 | |
| 946 | 396.5 | 2.1 | |
| 947 | 396.2 | 1.68 | |
| 948 | 478.2 | 1.77 | |
| 949 | 397.2 | 1.91 | |
| 950 | 480.2 | 2.23 | |
| 951 | 458.4 | 2.07 | |
| 952 | 362.4 | 1 | |
| 953 | 420.2 | 2.09 | |
| 954 | 477.4 | 1.8 | |
| 955 | 367.3 | 2 | |
| 956 | 468 | 1.04 | |
| 957 | 444.4 | 1.53 | |
| 958 | 361.2 | 2.24 | |
| 959 | 441.2 | 1.93 | |
| 960 | 424.27 | 2.04 | DMSO (d6): 9.12 (s, 1H), 7.35 (d, 1H), 7.27 (t, 1H), 7.24 (d, 1H), 7.18 (t, 1H), 6.48 (d, 1H), 4.82 (q, 1H), 4.12 (d, 2H), 4.05 (q, 2H), 3.43 (m, 4H), 3.20 (m, 2H), 2.82 (s, 6H), 2.38-2.31 (m, 2H), 2.20 (dd, 1H), 2.13-2.06 (m, 2H), 1.95 (d, 1H), 1.83-1.78 (m, 1H), 1.73-1.65 (m, 3H), 1.63-1.53 (m, 2H), 1.19 (t, 3H). |
| 961 | 443.2 | 1.74 | DMSO (d6): 9.04 (s, 1H), 8.17 (d, 1H), 7.34 (t, 1H), 7.29 (d, 1H), 7.20 (t, 1H), 7.17 (d, 1H), 4.92 (q, 1H), 3.98 (d, 2H), 3.77 (d, 2H), 3.42 (m, 2H), 3.16 (m, 4H), 2.79 (m, 2H), 2.22-2.14 (m, 2H), 2.05 (dd, 1H), 1.87 (s, 3H), 1.82 (m, 3H), 1.75-1.52 (m, 10H), 1.07 (m, 2H), 0.89 (d, 6H). |
| 962 | 470.3 | 2.08 | |
| 963 | 449.2 | 1.56 | |
| 964 | 455.2 | 1.65 | |
| 965 | 495.4 | 1.51 | DMSO (d6): 9.04 (s, 1H), 8.17 (d, 1H), 7.34 (t, 1H), 7.30 (d, 1H), 7.20 (t, 1H), 7.17 (d, 1H), 4.92 (q, 1H), 4.26 (d, 2H), 3.42 (m, 2H), 3.16 (m, 4H), 2.77 (t, 2H), 2.22-2.14 (m, 2H), 2.04 (m, 1H), 1.87 (s, 3H), 1.83 (m, 3H), 1.72 (t, 3H), 1.65-1.59 (m, 4H), 1.19 (s, 9H), 1.05 (q, 2H). |
| 966 | 454.3 | 1.82 | |
| 967 | 467.4 | 1.96 | |
| 968 | 371.2 | 2.24 | |
| 969 | 448.2 | 1.65 | |
| 970 | 454.2 | 1.69 | |
| 971 | 519 | 2.15 | |
| 972 | 483.2 | 1.95 | |
| 973 | 398.2 | 2.1 | |
| 974 | 433.4 | 1.88 | |
| 975 | 458.4 | 2.17 | |
| 976 | 415 | 1.43 | |
| 977 | | | |
| 978 | 500.3 | 1.7 | |
| 979 | 410.19 | 1.6 | MeOD: 7.86 (m, 1H), 7.55 (d, J = 2.5 Hz, 1H), 7.40 (dd, J = 2.4, 7.5 Hz, 1H), 4.17 (q, J = 7 Hz, 2H), 4.10 (br s, 2H), 3.89 (br s, 2H), 3.81 (br s, 2H), 3.02 (s, 2H), 2.94 (s, 1H), 2.79 (s, 1H), 2.50 (m, 1H), 2.37 (br s, 1H), 2.32 (br d, J = 13.0 Hz, 5H), 2.14 (d, J = 9.0 Hz, 2H), 1.27 (t, J = 7 Hz, 3H) |
| 980 | 387.5 | 1.91 | |
| 981 | 485.2 | 2.31 | |

TABLE 2-continued

Physical Characteristics of Compounds in Table 1.

| Cmd No. | LCMS Plus | LCMS RT | NMR |
|---|---|---|---|
| 982 | 423 | 2.2 | CD3OD: 7.70 (d, 1H), 7.67 (d, 1H), 7.52 (dd, 1H), 3.53 (m, 2H), 3.48 (m, 1H), 3.28 (m, 2H), 2.81 (s, 2H), 2.34 (m, 2H), 2.12 (m, 4H), 1.58-1.95 (m, 10H) |
| 983 | 332 | 1.8 | |
| 984 | 355 | 2.5 | |
| 985 | 365.2 | 2 | |
| 986 | 432.4 | 2.08 | |
| 987 | 465.2 | 1.86 | |
| 988 | 467.4 | 1.58 | |
| 989 | 410.2 | 1.78 | |
| 990 | 467.4 | 1.73 | |
| 991 | 456.4 | 2.51 | |
| 992 | 480.2 | 2.24 | DMSO (d6): 8.80 (m, 1H), 8.18 (d, 1H), 7.40 (d, 1H), 7.31 (t, 1H), 7.20 (t, 1H), 7.16 (d, 1H), 4.93 (ddd, 1H), 3.46 (m, 2H), 3.14 (m, 4H), 2.27 (m, 3H), 2.04 (dd, 1H), 1.87 (s, 3H), 1.82 (m, 5H), 1.71 (d, 1H), 1.68-1.51 (m, 5H), 1.24 (m, 2H). |
| 993 | 341.2 | 1.56 | |
| 994 | 468.2 | 2.28 | |
| 995 | 464 | 1.95 | |
| 996 | 400.2 | 1.84 | |
| 997 | 475.2 | 1.61 | DMSO (d6): 8.85 (s, 1H), 7.36 (d, 1H), 7.28 (t, 1H), 7.24 (d, 1H), 7.18 (t, 1H), 6.48 (d, 1H), 6.27 (dd, 0.8H), 6.16 (m, 0.6H), 6.04 (dd, 0.8H), 4.82 (q, 1H), 3.45 (m, 2H), 3.19-3.09 (m, 2H), 2.98 (br.s, 1H), 2.97-2.90 (m, 1H), 2.85 (s, 1H), 2.82 (s, 6H), 2.79 (m, 1H), 2.36 (m, 1H), 2.22 (dd, 1H), 2.11 (m, 1H), 2.02 (td, 1H), 1.90 (d, 1H), 1.81-1.64 (m, 4H), 1.37 (dd, 2H), 1.30 (d, 1H), 0.68 (d, 1H). |
| 998 | 394.3 | 1.95 | DMSO (d6): 9.03 (s, 1H), 8.17 (d, 1H), 7.34 (t, 1H), 7.30 (d, 1H), 7.20 (t, 1H), 7.17 (d, 1H), 4.92 (q, 1H), 3.54 (d, 2H), 3.42 (m, 2H), 3.16 (m, 4H), 2.71 (s, 6H), 2.67 (m, 2H), 2.22-2.14 (m, 2H), 2.04 (m, 1H), 1.87 (s, 3H), 1.82 (m, 3H), 1.73 (d, 1H), 1.64 (m, 5H), 1.48 (m, 1H), 1.13 (q, 2H). |
| 999 | 441.3 | 1.61 | |
| 1000 | 398.4 | 1.68 | |
| 1001 | 429.2 | 1.56 | CD3OD: 6.86 (s, 1H), 6.75 (s, 1H), 5.35 (t, 1H), 3.83 (s, 3H), 3.81 (s, 3H), 3.60 (m, 2H), 3.45 (m, 1H), 3.10 (m, 2H), 2.71 (m, 2H), 2.45 (m, 2H), 2.00 (s, 1H), 1.50-2.20 (brm, 11H0, 1.25 (m, 1H), |
| 1002 | 399.6 | 1.78 | |
| 1003 | 432.4 | 1.98 | |
| 1004 | 448.2 | 1.91 | in DMSO-d6 |
| 1005 | 368.5 | 1.9 | |
| 1006 | 459.4 | 1.66 | |
| 1007 | 485.3 | 2.2 | |
| 1008 | 430.4 | 2.2 | |
| 1009 | 359 | 2.09 | DMSO (d6): 9.01 (s, 1H), 7.32 (d, 1H), 77.27 (t, 1H), .24 (d, 1H), 7.18 (t, 1H), 6.48 (d, 1H), 4.82 (q, 1H), 3.42 (d, 2H), 3.18-3.02 (m, 4H), 2.82 (s, 6H), 2.30 (t, 1H), 2.21 (m, 2H), 2.01 (m, 2H), 1.92 (d, 1H), 1.80 (m, 1H), 1.73-1.63 (m, 4H), 1.52-1.43 (m, 4H), 1.39-1.32 (m, 2H), 1.17-1.03 (m, 4H). |
| 1010 | 410.3 | 2.21 | |
| 1011 | 412.3 | 1.9 | |
| 1012 | 420.2 | 1.66 | |
| 1013 | 410.2 | 1.78 | DMSO-d6: 9.78 (s, 1H), 7.43 (d, 1H), 7.29 (t, 1H), 7.20 (t, 1H), 6.93 (d, 1H), 5.14 (dd, 1H), 4.05 (m, 2H), 3.74 (m, 1H), 3.45 (dd, 2H), 3.21 (q, 1H), 3.08 (m, 2H), 2.88 (ddd, 1H), 2.42-2.29 (m, 3H), 2.09 (m, 4H), 1.97-1.60 (m, 16H), 1.15 (t, 3H). |
| 1014 | 466.37 | 1.67 | |
| 1015 | 422.2 | 1.78 | |
| 1016 | 379.5 | 2 | |
| 1017 | 367.5 | 1.9 | |
| 682 | 422.2 | 1.78 | |
| 683 | 381.2 | 2.38 | |
| 684 | 463.2 | 2.19 | |
| 685 | 492 | 2.2 | |
| 686 | 455.2 | 1.78 | |
| 687 | 356.3 | 1.6 | |
| 688 | 329.5 | 0.88 | H NMR (500 MHz, DMSO) 8.97 (s, 1H), 7.32-7.15 (m, 4H), 6.52 (d, J = 8.5 Hz, 1H), 6.27 (dd, J = 3.0, 5.5 Hz, 1H), 6.05 (dd, J = 2.6, 5.5 Hz, 1H), 5.26 (dd, J = 8.0, 16.4 Hz, 2H), 3.54 (d, J = 11.6 Hz, 2H), 3.25-2.58 (m, 13H), 2.40-2.36 (m, 1H), 2.04-2.01 (m, 1H), 1.85-1.68 (m, 4H), 1.40-1.23 (m, 2H), 0.72-0.67 (m, 1H), |
| 689 | 379.3 | 1.9 | |
| 690 | 438.2 | 1.97 | |
| 691 | 400.2 | 1.8 | |
| 692 | 374.2 | 1.02 | CD3OD: 6.85 (s, 1H), 6.77 (s, 1H), 5.36 (t, 1H), 4.30 (m, 2H), 4.13 (q, 2H), 3.83 (s, 3H), 3.81 (s, 3H), 3.45 (m, 3H), 3.20 (m, 1H), 2.72 (dd, 1H), 2.35 (m, 1H), 2.10 (m, 2H), 2.00 (s, 3H), 1.59-1.90 (m, 14H) |
| 693 | 401.6 | 1.85 | |
| 694 | 443.4 | 1.9 | |
| 695 | 426.2 | 1.93 | |
| 696 | 424.2 | 2.31 | |
| 697 | 495.2 | 1.91 | NMR (500 MHz, DMSO-d6) 8.98 (br. s, 1H), 8.18 (d, 1 H), 7.40 (d, 1H), 7.32 (t, 1H), 7.22 (t, 1H), 7.19 (d, 1H), 6.27 (dd, 1H), 6.17-6.15 (m, 1 H), 6.05 (q, 1H), 4.94-4.92 (m, 1H), 3.45 (m, 2H), 3.20-3.13 (m, 2H), 2.98 (br.s, 1H), 2.95 (m, 1H), 2.86 (br.s, 1H), 2.85-2.79 (m, 1H), 2.28-2.22 (m, 2H), 2.07-1.99 (m, 2H), 1.87 (s, 3H), 1.83-1.78 (m, 3H), 1.73 (d, 1H), 1.65-1.61 (m, 1H), 1.39-1.29 (m, 3H), 0.70 (dt, 1H). |
| 698 | 365.32 | 1.63 | : |
| 699 | 395.5 | 2.69 | 1H NMR (500 MHz, DMSO (d6)): 8.98 (s, 1H), 7.37 (d, 1H), 7.22 (t, H), 7.10 (t, 1H), 7.07 (d, 1H), 6.27 (q, 0.7 H), 6.18-6.14 (m, 0.6H), 6.05 (q, 0.7H), 3.43 (m, 2H), 3.30-3.21 (m, 1H), 3.22-3.10 (m, 2H), 2.98 (s, 1H), 2.95-2.90 (m, 1H), 2.85 (s, 1H), 2.85-2.80 (m, 1H), 2.73 (t, 2H), 2.28-2.22 (m, 2H), 2.00 (ddd, 1H), 1.89-1.87 (m, 2H), 1.78-1.67 (m, 4H), 1.39-1.29 (m, 2H), 0.72-0.67 (m, 1H). |
| 700 | 308.6 | 2.01 | |
| 701 | 400.1 | 1.81 | |
| 702 | 494.4 | 1.97 | DMSO (d6): 9.53 (br. s), 8.18 (d, 1H), 7.40 (d, 1H), 7.30 (t, 1H), 7.19 (t, 1H), 7.16 (d, 1H), 4.92 (q, 1H), 3.40 (m, 2H), 3.14 (t, 2H), 3.07 (m, 2H), 2.27 (m, 2H), 2.05 (dd, 1H), 1.87 (s, 3H), 1.81 (m, 3H), 1.74-1.59 (m, 9H), 1.27-1.12 (m, 6H), 0.89 (m, 2H). |
| 703 | 383.44 | 1.96 | |
| 704 | 410.2 | 2.19 | |
| 705 | 416.6 | 1.3 | |
| 706 | 438.4 | 2.44 | |
| 707 | 485.4 | 2.22 | |
| 708 | 386.3 | 1.2 | |
| 709 | 438.4 | 1.39 | |

TABLE 2-continued

Physical Characteristics of Compounds in Table 1.

| Cmd No. | LCMS Plus | LCMS RT | NMR |
|---|---|---|---|
| 710 | 416.4 | 1.62 | |
| 711 | 438.4 | 1.95 | |
| 712 | 486.2 | 2.2 | |
| 713 | 371.2 | 2.12 | |
| 714 | 447.2 | 1.6 | |
| 715 | 417.4 | 1.66 | |
| 716 | 444.4 | 1.98 | |
| 717 | 496.5 | 2.57 | |
| 718 | 492.4 | 2.24 | |
| 719 | 396.2 | 1.95 | |
| 720 | 404.4 | 2.26 | |
| 721 | 324.2 | 2.08 | |
| 722 | 411.2 | 2 | |
| 723 | 440.4 | 1.99 | |
| 724 | 404.4 | 1.97 | |
| 725 | 390.4 | 1.03 | |
| 726 | 469.3 | 1.78 | |
| 727 | 454.2 | 2.23 | |
| 728 | 448.4 | 2.13 | |
| 729 | 400.2 | 1.84 | |
| 730 | 471.4 | 2.13 | |
| 731 | 372.3 | 1.2 | |
| 732 | 424.4 | 1.98 | |
| 733 | 386.2 | 1.73 | |
| 734 | 324.2 | 2.05 | |
| 735 | 383.2 | 1.94 | |
| 736 | 471.4 | 2.16 | DMSO (d6): 9.06 (br. s, 1H), 8.18 (d, 1H), 7.39 (d, 1H), 7.30 (t, 1H), 7.20 (t, 1H), 7.17 (d, 1H), 6.27 (dd, 1H), 6.05 (m, 1H), 4.92 (q, 1H), 3.47 (m, 3H), 3.15 (m, 2H), 2.98 (s, 1H), 2.93 (dd, 1H), 2.85 (s, 1H), 2.80 (ddd, 1H), 2.25 (m, 2H), 2.20 (m, 2H), 1.87 (s, 3H), 1.81 (m, 3H), 1.71 (t, 1H), 1.62 (m, 1H), 1.35 (t, 1H), 1.30 (d, 1H), 0.68 (dq, 1H). |
| 737 | 365.3 | 1.61 | |
| 738 | 394.5 | 2 | |
| 739 | 328.2 | 1.7 | |
| 740 | 406.4 | 1.65 | |
| 741 | 353.3 | 1.8 | |
| 742 | 504 | 2.28 | |
| 743 | 442.4 | 1.66 | |
| 744 | 396 | 1.71 | |
| 745 | 428.6 | 1.89 | |
| 746 | 412.3 | 2.3 | |
| 747 | 428.2 | 2.11 | |
| 748 | 464.4 | 1.92 | (CDCl3, ppm) 11.89 (br s, 1H), 7.47 (m, 3H), 6.22 (s, 2H) 5.98 (s, 1H), 3.75 (br s, 2H), 3.00 (s, 2H), 2.86 (s, 1H), 2.58 (m, 5H), 2.57 (m, 3H), 2.38 (s, 3H), 2.06 (m, 1H), 1.65 (m, 2H), 1.48 (m, 1H), 1.27 (m, 1H), 0.72 (d, J = 11 Hz, 1H). |
| 749 | 321.9 | 1.76 | |
| 750 | 480 | 2.43 | |
| 751 | 509.4 | 2 | |
| 752 | 343.2 | 1.9 | |
| 753 | 400.2 | 1.84 | DMSO (d6): 9.03 (s, 1H), 7.31 (d, 1H), 7.27 (t, 1H), 7.24 (d, 1H), 7.18 (t, 1H), 6.47 (d, 1H), 4.81 (m, 1H), 4.39 (m, 1H), 4.34 (m, 1H), 4.26 (m, 1H), 4.10 (q, 2H), 3.45 (m, 2H), 3.21-3.08 (m, 2H), 2.82 (s, 6H), 2.68-2.61 (m, 3H), 2.23 (m, 1H), 2.03-1.92 (m, 5H), 1.79 (m, 1H), 1.73-1.62 (m, 5H), 1.57 (d, 1H), 1.51 (t, 1H), 1.19 (t, 3H). |
| 754 | 469.3 | 1.87 | DMSO (d6): 9.17 (br.s, 1H), 8.18 (d, 1H), 7.40 (d, 1H), 7.30 (t, 1H), 7.20 (t, 1H), 7.16 (d, 1H), 4.93 (m, 1H), 3.55 (td, 1H), 3.43 (d, 2H), 3.19 (m, 2H), 2.29 (td, 1H), 2.24 (td, 1H), 2.06 (dd, 1H), 1.87 (s, 3H), 1.83 (m, 6H), 1.63 (m, 1H), 1.27 (t, 3H), 1.08 (d, 1H), 1.04 (s, 6H), 0.97 (s, 6H). |
| 755 | 397.4 | 1.94 | |
| 756 | 392.2 | 1.62 | |
| 757 | 353.3 | 1.5 | |
| 758 | 426.2 | 1.91 | |
| 759 | 430.2 | 2.12 | |
| 760 | 400.2 | 1.83 | |
| 761 | 447.4 | 2 | CD3OD: 6.85 (s, 1H), 6.78 (s, 1H), 5.36 (t, 1H), 3.83 (s, 3H), 3.81 (s, 3H), 3.60 (m, 2H), 3.10-3.20 (m, 2H), 23.02 (d, 2H), .72 (dd, 1H), 2.25 (m 1 H), 2.03 (m, 1H), 2.00 (s, 3H), 1.65-1.95 (m, 8H), 1.38 (m, 2H), 1.26 (m, 1H), 1.07 (m, 2H) |
| 762 | 401.5 | 1.8 | |
| 763 | 361.4 | 2.2 | |
| 764 | 484.4 | 2.17 | DMSO (d6): 9.25 (m, 1H), 8.19 (d, 1H), 7.39 (d, 1H), 7.31 (t, 1H), 7.20 (t, 1H), 7.17 (d, 1H), 4.93 (ddd, 1H), 3.49 (t, 2H), 3.18 (m, 2H), 3.05 (t, t, 2H), 2.25 (ddd, 2H), 2.06 (dd, 1H), 1.87 (s, 3H), 1.83 (m, 3H), 1.75 (d, 1H), 1.63 (m, 1H), 1.10 (m, 1H), 0.68 (m, 2H), 0.39 (m, 2H). |
| 765 | 313.2 | 1.27 | |
| 766 | 450 | 2.04 | |
| 767 | 422.2 | 1.79 | |
| 768 | 439.4 | 1.44 | |
| 769 | 400.2 | 1.88 | |
| 770 | 403.5 | 2.1 | |
| 771 | 459.2 | 1.67 | CD3OD: 6.86 (s, 1H), 6.77 (s, 1H), 5.36 (t, 1H), 4.30 (m, 2H), 4.13 (q, 2H), 3.83 (s, 3H), 3.81 (s, 3H), 3.54 (m, 2H),, 3.15 (m, 3H), 2.70 (m, 1H), 2.30 (m, 1H), 2.15 (m, 2H), 2.00 (s, 3H),1.70-2.009m, 7H0, 1.25-1.60 (m, 5H) |
| 772 | 387 | 1.46 | |
| 773 | 446.3 | 2.41 | |
| 774 | 528.3 | 2.6 | |
| 775 | 416.2 | 1.8 | |
| 776 | 408.21 | 1.89 | |
| 777 | 424.2 | 2.29 | |
| 778 | 485.4 | 2.32 | |
| 779 | 439.4 | 1.66 | |
| 780 | 468.2 | 2.1 | |
| 781 | 325.2 | 1.3 | |
| 782 | 467.4 | 1.61 | |
| 783 | 444.5 | 2.37 | |
| 784 | 354.3 | 1.3 | |
| 785 | 455 | 2.02 | |
| 786 | 438.4 | 1.46 | 500 mHz, MeOH-d4; 7.36 (d, 1H), 7.30-7.22 (m, 3H), 5.20-5.17 (m, 1H), 3.01 (br s, 2H), 2.52-2.48 (m, 1H), 2.39 (s, 2H), 2.25-2.0 (m, 4H), 1.95-1.49 (m, 6H), 1.45-1.29 (m, 5H), 0.99-0.97 (m, 1H) |
| 787 | | | DMSO (d6): 9.50 (br.s, 1H), 8.18 (d, 1H), 7.39 (d, 1H), 7.29 (t, 1H), 7.19 (t, 1H), 7.16 (d, 1H), 4.92 (m, 1H), 4.12 (d, 2H), 4.05 (q, 2H), 3.40 (m, 3H), 3.19 (m, 2H), 2.82 (m, 2H), 2.25 (m, 2H), 2.09 (d, 2H), 2.03 (td, 1H), 1.86 (s, 3H), 1.82 (m, 4H), 1.61 (m, 3H), 1.19 (t, 3H). |
| 788 | 414.3 | 1.46 | DMSO-d6: 9.95-9.58 (m, 1H), 8.30-8.26 (m, 1H), 7.53-7.40 (m, 1H), 7.21-7.18 (m, 1H), 7.03-6.98 (m, 1H), 5.36-5.28 (m, 1H), 4.08-4.05 (m, 4H), 3.78 (s, 1H), 3.68-3.65 (m, 2H), 2.80 (br s, 2H), 2.72 (s, 1H), 2.69-2.63 (m, 1H), 2.58 (s, 2H), 2.20-2.07 (m, 1H), 2.03 (s, 2H), 1.97-1.90 (m, 3H), 1.82-1.77 (m, 1H), 1.51-1.47 (m, 2H), 1.21-1.18 (m, 3H) |
| 789 | 404.5 | 1.65 | |
| 790 | 416.4 | 1.57 | |

TABLE 2-continued

Physical Characteristics of Compounds in Table 1.

| Cmd No. | LCMS Plus | LCMS RT | NMR |
|---|---|---|---|
| 791 | 419.4 | 1.75 | |
| 792 | 448.2 | 1.65 | |
| 793 | 300.2 | 1.46 | |
| 794 | 446.3 | 2.13 | |
| 795 | 485.4 | 1.78 | |
| 796 | 447.2 | 2.4 | CD3OD: 6.86 (s, 1H), 6.79 (s, 1H), 5.37 (m, 1H), 3.84 (s, 3H), 3.82 (m, 3H), 3.40 (m, 2H), 3.55 (m, 3H), 3.00-3.20 (m, 2H), 2.70 (m, 1H), 2.48 (m, 2H), 1.77-2.10 (m, 19H including 3H singlet at 2.00) |
| 797 | 439.6 | 1.9 | |
| 798 | 332.2 | 0.75 | |
| 799 | 314.2 | 1.64 | |
| 800 | 410.2 | 1.81 | |
| 801 | 456.5 | 2.17 | |
| 802 | 454.2 | 2.03 | |
| 803 | 467.4 | 1.76 | |
| 804 | 441.4 | 1.76 | |
| 805 | 428.4 | 2.4 | |
| 806 | 442.4 | 2.24 | |
| 807 | 486.8 | 2.23 | |
| 808 | 349.2 | 2.03 | |
| 809 | 447.4 | 1.99 | |
| 810 | 451.8 | 2.24 | |
| 811 | 416.4 | 1.82 | |
| 812 | 443.2 | 1.93 | |
| 813 | 413.2 | 1.48 | |
| 814 | 410.4 | 1.91 | |
| 815 | 410.2 | 2.2 | |
| 816 | 444.4 | 2.08 | CD3OD: 6.86 (s, 1H), 6.78 (s, 1H), 5.36 (m, 1H), 3.83 (s, 3H), 3.82 (m, 3H), 3.55 (m, 3H), 3.15-3.25 (m, 2H), 2.25 (m, 1H), 2.35 (m, 1H), 2.00 (s, 3H), 1.80-1.90 (m, 5H), 1.36 (m, 2H), 1.12 (s, 6H), 1.04 (s, 6H) |
| 817 | 442.3 | 2.1 | |
| 818 | 440.4 | 2.17 | DMSO (d6): 9.40 (br. s), 8.18 (d, 1H), 7.38 (d, 1H), 7.30 (t, 1H), 7.20 (t, 1H), 7.16 (d, 1H), 4.92 (q, 1H), 3.41 (m, 2H), 3.13 (m, 4H), 2.24 (m, 2H), 2.05 (dd, 1H), 1.87 (s, 3H), 1.84-1.76 (m, 3H), 1.74-1.65 (m, 5H), 1.64-1.56 (m, 4H), 1.33-1.12 (m, 4H), 0.96 (m, 2H). |
| 819 | 369.43 | 1.82 | DMSO-d6: 7.69 (d, 1H), 7.52 (d, 2H), 7.43 (d, 2H), 7.25 (m, 2H), 7.01 (d, 2H), 6.26 (m, 1H), 6.06 (d, 1H), 4.95 (m, 1H), 4.49 (m, 1H), 3.77 (s, 3H), 3.55 (m, 2H), 2.42 (m, 1H), 2.79-3.15 (m, 7H), 1.94-2.11 (m, 3H), 1.71 (d, 3H), 0.68-0.70 (m, 2H) |
| 820 | 477 | 1.58 | |
| 821 | 444.4 | 1.5 | |
| 822 | 434 | 2.14 | |
| 823 | 484.2 | 1.76 | |
| 824 | 410.2 | 2.21 | |
| 825 | 413 | 1.68 | DMSO (d6): 9.25 (br. s), 8.17 (d, 1H), 7.37 (d, 1H), 7.30 (t, 1H), 7.20 (t, 1H), 7.16 (d, 1H), 4.92 (q, 1H), 3.93 (d, 2H), 3.42 (m, 3H), 3.15 (m, 4H), 2.71 (m, 1H), 2.20 (m, 2H), 2.04 (dd, 1H), 1.87 (s, 3H), 1.82 (m, 3H), 1.72 (d, 1H), 1.63 (m, 5H), 1.49 (m, 1H), 1.39 (s, 9H), 1.04 (ddd, 1H). |
| 826 | 470.4 | 1.82 | DMSO (d6): 8.92 (br.s, 1H), 8.39 (d, 1H), 7.39 (d, 1H), 7.32 (t, 1H), 7.21 (t, 1H), 7.16 (d, 1H), 6.27 (dd, 1H), 6.05 (m, 1H), 4.95 (q, 1H), 3.45 (m, 3H), 3.28-3.10 (m, 3H), 2.98 (s, 1H), 2.94 (ddd, 1H), 2.85 (s, 1H), 2.81 (ddd, 1H), 2.25 (m, 2H), 2.03 (ddd, 2H), 1.82 (m, 3H), 1.71 (d, 1H), 1.65 (m, 1H), 1.58 (m, 1H), 1.38 (dd, 1H), 1.29 (d, 1H), 0.78-0.63 (m, 4H). |
| 827 | 391.38 | 1.83 | |
| 828 | 303.2 | 1.93 | |
| 829 | 424.2 | 1.99 | |
| 830 | 422.2 | 1.79 | |
| 831 | 490.2 | 1.79 | DMSO (d6): 9.14 (br. s), 8.17 (d, 1H), 7.36 (d, 1H), 7.30 (t, 1H), 7.20 (t, 1H), 7.16 (d, 1H), 4.92 (q, 1H), 3.4 (m, 2H), 3.18-3.01 (m, 4H), 2.21 (m, 3H), 2.04 (dd, 1H), 2.00 (s, 1H), 1.87 (s, 3H), 1.82 (m, 3H), 1.72 (d, 1H), 1.64 (m, 2H), 1.47 (m, 4H), 1.35 (m, 2H), 1.17-1.02 (m, 4H). |
| 832 | 381.4 | 1.89 | |
| 833 | 357.2 | 2.1 | |
| 834 | 480.2 | 2.2 | |
| 835 | 459.4 | 2.08 | |
| 836 | 439.2 | 1.95 | |
| 837 | 355.23 | 1.59 | |
| 838 | 418.4 | 1.9 | |
| 839 | 495.4 | 2.01 | |
| 840 | 424.2 | 1.95 | |
| 841 | 445.6 | 1.88 | H NMR (500 MHz, DMSO (d6)): 9.14 (s, H), 7.36 (d, 1H), 7.22 (t, 1H), 7.09 (t, 1H), 7.07 (d, 1H), 4.10 (d, 2H), 4.05 (q, 2H), 3.48-3.39 (m, 4H), 3.19 (q, 2H), 2.83 (m, 2H), 2.71 (t, 2H), 2.27 (td, 2H), 2.09 (d, 2H), 1.87 (m, 2H), 1.77 (d, 2H), 1.72-1.68 (m, 2H), 1.58 (qd, 2H), 1.22 (t, 3H). |
| 842 | 357.4 | 1.87 | |
| 843 | 471.4 | 1.83 | |
| 844 | 468.3 | 1.61 | |
| 845 | 453.4 | 1.4 | |
| 846 | 459.4 | 2.01 | |
| 847 | 434 | 2.14 | |
| 848 | 391.2 | 2.16 | |
| 849 | 473.4 | 2.28 | CD3OD: 6.86 (s, 1H), 6.77 (s, 1H), 5.35 (m, 1H), 3.83 (s, 3H), 3.82 (m, 3H), 3.15-3.25 (m, 3H), 2.25 (m, 1H), 2.35 (m, 1H), 2.00 (s, 3H), 1.40-1.90 (m, 26H) |
| 850 | 471.6 | 2.3 | |
| 851 | 383.4 | 2.28 | |
| 852 | 404.4 | 1.86 | DMSO (d6): 9.09 (m, 1H), 8.18 (d, 1H), 7.38 (d, 1H), 7.30 (t, 1H), 7.20 (t, 1H), 7.16 (d, 1H), 4.92 (ddd, 1H), 3.86 (t, 1H), 3.78 (ddd, 1H), 3.67 (q, 1H), 3.43 (m, 3H), 3.19 (m, 4H), 3.66 (m, 1H), 2.25 (m, 2H), 2.12 (m, 1H), 2.05 (dd, 1H), 1.87 (s, 3H), 1.82 (m, 3H), 1.73 (d, 1H), 1.63 (m, 2H). |
| 853 | 343.1 | 0.97 | |
| 854 | 454.2 | 2.13 | |
| 855 | 440.4 | 2.08 | DMSO (d6): 8.85 (br.s, 1H), 8.18 (d, 1H), 7.41 (d, 1H), 7.30 (t, 1H), 7.19 (t, 1H), 7.16 (d, 1H), 4.92 (m, 1H), 3.42 (m, 3H), 3.14 (m, 2H), 3.00 (t, 2H), 2.29 (m, 2H), 2.05 (m, 2H), 1.86 (s, 3H), 1.85-1.58 (m, 11H), 1.26 (m, 2H), 1.17 (m, 1H), 0.99 (m, 2H). |
| 856 | 355.3 | 1.71 | |
| 857 | 454.2 | 2.24 | |
| 858 | 442.4 | 1.69 | |
| 859 | 439.4 | 1.73 | CD3OD: 7.73 (dd, 1H), 7.67 (d, 1H), 7.63 (d, 1H), 3.50 (, .2H), 3.26 (m, 2H), 2.83 (s, 2H), 2.37 (m, 2H), 2.13 (m, 2H), 1.60-1.90 (m, 12H) |
| 860 | 332 | 1.84 | |
| 861 | 414.4 | 1.96 | |
| 862 | 432.4 | 1.86 | |
| 863 | 314.2 | 1.59 | |
| 864 | 412.2 | 2.01 | |
| 865 | 471.4 | 2 | |

TABLE 2-continued

Physical Characteristics of Compounds in Table 1.

| Cmd No. | LCMS Plus | LCMS RT | NMR |
|---|---|---|---|
| 866 | 454.2 | 1.98 | DMSO (d6): 8.76 (s, 1H), 8.17 (d, 1H), 7.39 (t, 1H), 7.31 (d, 1H), 7.20 (t, 1H), 7.17 (d, 1H), 4.92 (q, 1H), 3.88 (dd, 2H), 3.44 (m, 2H), 3.34 (t, 2H), 3.17 (m, 2H), 3.06 (t, 2H), 2.31-2.14 (m, 2H), 2.11-2.02 (m, 2H), 1.86 (s, 3H), 1.81 (m, 3H), 1.71 (d, 1H), 1.64 (m, 3H), 1.27 (ddd, 2H). |
| 867 | 357.2 | 1.48 | |
| 868 | 384.2 | 1.91 | |
| 869 | 450.4 | 2.08 | |
| 870 | 456.2 | 1.72 | |
| 871 | 438.2 | 2.12 | |
| 872 | 411.2 | 2.38 | |
| 873 | 324.3 | 2.07 | |
| 874 | 454.2 | 1.69 | DMSO (d6): 8.29 (s, 1H), 8.17 (d, 1H), 7.45 (d, 1H), 7.31 (t, 1H), 7.20 (t, 1H), 7.17 (d, 1H), 4.93 (m, 1H), 3.38 (m, 2H), 3.20-3.09 (m, 3H), 2.34 (qd, 2H), 2.25-2.13 (m, 2H), 2.08-2.03 (m, 1H), 1.87 (s, 3H), 1.83 (m, 4H), 1.74-1.60 (m, 4H), 1.55 (d, 2H), 1.33-1.22 (m, 4H), 0.82 (s, 6H), 0.79 (t, 3H). |
| 875 | 411.3 | 2.34 | |
| 876 | 469.2 | 2.32 | |
| 877 | 386.2 | 1.72 | DMSO (d6): 9.06 (br.s, 1H), 7.47 (d, 1H), 7.45 (d, 1H), 7.32 (t, 1H), 7.24 (t, 1H), 6.26 (dd, 1H), 6.04 (dd, 1H), 4.45 (q, 1H), 3.38 (m, 2H), 3.15 (m, 2H), 3.05 (s, 3H), 2.98 (s, 1H), 2.93 (ddd, 1H), 2.85 (s, 1H), 2.80 (ddd, 1H), 2.23 (m, 2H), 2.07 (m, 1H), 2.01 (ddd, 1H), 1.94 (m, 1H), 1.86 (m, 1H), 1.78 (m, 2H), 1.69 (d, 1H), 1.38 (d, 1H), 1.35 (d, 1H), 1.29 (d, 1H), 0.68 (dq, 1H). |
| 878 | 401.35 | 1.79 | |
| 879 | 433.4 | 1.78 | |
| 880 | 505.4 | 2.03 | |
| 881 | 487 | 2.31 | |
| 882 | 442.3 | 1.52 | |
| 883 | 404.4 | 1.9 | |
| 884 | 485.4 | 1.94 | |
| 885 | 404.4 | 1.88 | |
| 886 | 398.3 | 2.2 | DMSO (d6): 9.16 (br. s, 1H), 8.18 (d, 1H), 7.36 (d, 1H), 7.30 (t, 1H), 7.19 (t, 1H), 7.16 (d, 1H), 4.91 (q, 1H), 3.31 (m, 2H), 3.20 (t, 2H), 3.13 (t, 2H), 2.74 (m, 1H), 2.25-2.09 (m, 4H), 2.04 (dd, 1H), 1.91 (m, 1H), 1.87 (s, 3H), 1.82 (m, 6H), 1.71 (d, 1H), 1.62 (m, 1H). |
| 887 | 327.3 | 1.42 | |
| 888 | 410.2 | 1.86 | |
| 889 | 383.4 | 2.28 | |
| 890 | 393.5 | 2.1 | CD3CN: 7.50-7.35 (m, 1H), 7.12-7.05 (m, 1H), 7.02-6.99 (m, 1H), 6.86-6.77 (m, 1H), 5.42-5.35 (m, 1H), 3.88-3.84 (m, 2H), 3.36-3.13 (m, 4H), 2.72 (dd, J = 7.5, 12.7 Hz, 1H), 2.63-2.54 (m, 1H), 2.32 (s, 1H), 2.29 (s, 1H), 2.23-2.18 (m, 4H), 2.12-1.93 (m, 1H), 1.89-1.79 (m, 1H), 1.57-1.34 (m, 5H), 1.27-1.21 (m, 2H), 0.87-0.75 (m, 1H) |
| 891 | 357.1 | 1.71 | |
| 892 | 383.4 | 2.24 | 1H NMR (500 MHz, DMSO (d6)): 8.50 (br. s, 1H), 7.41 (d, 1H), 7.22 (t, 1H), 7.13 (t, 1H), 7.06 (d, 1H), 3.50 (m, 2H), 3.38 (m, 1H), 3.30 (m, 1H), 3.22-3.10 (m, 2H), 2.72 (t, 2H), 2.37-2.25 (m, 4H), 2.01 (t, 1H), 1.90-1.87 (m, 2H), 1.75-1.59 (m, 8H), 1.52-1.37 (m, 2H), 1.30-1.15 (m, 2H). |
| 893 | 296.3 | 1.9 | CD3OD: 7.38-7.63 (m, 5H), 6.66 (s, 1H), 6.45 (m, 1H), 5.70 (s, 1H), 5.40 (m, 1H), 3.73 (s, 3H), 3.54 (m, 2H), 3.47 (s, 3H), 2.33 (s, 3H), 2.16 (m, 4H), 1.96 (m, 4H), 1.20-1.75 (m, 13H) |
| 894 | 491.6 | 2.2 | |
| 895 | 347.4 | 1.91 | |
| 896 | 471.4 | 2.17 | DMSO (d6): 8.35 (s, 1H), 8.18 (d, 1H), 7.45 (d, 1H), 7.31 (t, 1H), 7.21 (t, 1H), 7.17 (d, 1H), 4.93 (m, 1H), 3.55 (m, 2H), 3.37 (m, 1H), 3.20-3.09 (m, 3H), 2.34 (qd, 2H), 2.24-2.13 (m, 2H), 2.06 (m, 1H), 1.87 (s, 3H), 1.90-1.81 (m, 3H), 1.74-1.58 (m, 5H), 1.30 (q, 2H), 1.15 (m, 2H), 0.88 (s, 9H). |
| 897 | 397.2 | 2.2 | DMSO-d6: 9.12 (s, 1H), 7.49 (d, 1H), 7.30 (t, 1H), 7.20 (t, 1H), 6.93 (d, 1H), 5.14 (dd, 1H), 3.39 (dd, 2H), 3.24-3.07 (m, 3H), 2.98 (t, 2H), 2.88 (ddd, 1H), 2.59 (td, 1H), 2.41-2.29 (m, 3H), 12.19 (td, 1H), .95-1.59 (m, 13H), 1.27 (m, 2H), 1.17 (tt, 1H), 0.99 (m, 2H). |
| 898 | 381.4 | 1.78 | |
| 899 | 492.4 | 2.22 | |
| 900 | 471.4 | 1.85 | H NMR (500 MHz, DMSO) 8.60 (br s, 81H, from TFA), .44 (d, J = 8.0 Hz, 1H), 7.32 (dt, J = 25.2, 8.1 Hz, 2H), 7.21 (dd, J = 7.3, 18.5 Hz, 2H), 5.39 (q, 1H), 4.07-2.97 (m, 4H, partially obscured by solvent), 2.70-2.60 (m, 2H), 2.45-2.31 (m, 2H), 2.07-1.91 (m, 2H), 1.72-1.55 (m, 8H), 1.46-1.41 (m, 3H), 1.25-1.17 (m, 1H), 0.77-0.66 (m, 4H) |
| 901 | 365.3 | 1.9 | |
| 902 | 459.4 | 2.06 | NMR (500 MHz, DMSO-d6) 8.98 (br. s, 1H), 8.18 (d, 1H), 7.40 (d, 1H), 7.32 (t, 1H), 7.22 (t, 1H), 7.19 (d, 1H), 6.27 (dd, 1H), 6.17-6.15 (m, 1 H), 6.05 (q, 1H), 4.94-4.92 (m, 1H), 3.45 (m, 2H), 3.20-3.13 (m, 2H), 2.98 (br.s, 1H), 2.95 (m, 1H), 2.86 (br.s, 1H), 2.85-2.79 (m, 1H), 2.28-2.22 (m, 2H), 2.07-1.99 (m, 2H), 1.87 (s, 3H), 1.83-1.78 (m, 3H), 1.73 (d, 1H), 1.65-1.61 (m, 1H), 1.39-1.29 (m, 3H), 0.70 (dt, 1H). |
| 903 | 365.32 | 1.63 | |
| 904 | 530 | 2.65 | |
| 905 | 371.1 | 2.75 | DMSO (d6): 9.28 (br.s, 1H), 8.19 (d, 1H), 7.39 (d, 1H), 7.30 (t, 1H), 7.19 (t, 1H), 7.16 (d, 1H), 4.92 (m, 1H), 3.42 (m, 2H), 3.25-3.08 (m, 4H), 2.34-2.14 (m, 5H), 2.05 (t, 1H), 1.87 (s, 3H), 1.81 (m, 4H), 1.70 (d, 1H), 1.63 (m, 1H), 1.49 (m, 2H), 1.37 (m, 2H), 1.30 (d, 1H), 1.14 (m, 2H) 0.81 (m, 1H). |
| 906 | 367.4 | 1.71 | |
| 907 | 424.2 | 1.98 | 1H NMR (500 MHz, DMSO (d6)): 8.82 (s, 1H), 7.33 (d, 1H), 7.22 (t, 1H), 7.14 (t, 1H), 7.06 (d, 1H), 3.43-3.35 (m, 3H), 3.14-3.03 (m, 2H), 2.72 (t, 2H), 2.45-2.39 (m, 2H), 2.32 (m, 2H), 2.18 (td, 2H), 1.87-1.84 (m, 2H), 1.76-1.67 (m, 4H), 1.60 (t, 2H), 1.56-1.46 (m, 1H), 1.42 (d, 2H), 1.30 (t, 2H), 1.02 (dt, 1H). |
| 908 | 310.3 | 2.05 | |
| 909 | 450 | 1.93 | |
| 910 | 467.4 | 1.87 | |
| 911 | 439.2 | 1.74 | |
| 912 | 480.2 | 2.4 | |
| 913 | 447.4 | 1.57 | DMSO (d6): 9.16 (br.s, 1H), 8.39 (d, 1H), 7.43 (d, 1H), 7.31 (t, 1H), 7.21 (t, 1H), 7.15 (d, 1H), 4.95 (q, 1H), 3.27 (m, 3H), 2.31 (m, 2H), 2.07 (m, 3H), 1.85-1.26 (m, 18H), 0.78-0.63 (m, 4H). |
| 914 | 381.44 | 1.79 | |
| 915 | 466.43 | 1.72 | |
| 916 | 431.4 | 1.78 | |

TABLE 2-continued

Physical Characteristics of Compounds in Table 1.

| Cmd No. | LCMS Plus | LCMS RT | NMR |
|---|---|---|---|
| 917 | 355.4 | 1.57 | |
| 918 | 382.4 | 2.11 | DMSO (d6): 8.93 (br.s, 1H), 7.46 (d, 1H), 7.44 (d, 1H), 7.35 (d, 1H), 7.32 (t, 1H), 7.21 (t, 1H), 4.45 (q, 1H), 33.11 (m, 2H), 3.04 (s, H), 2.35 (m, 2H), 2.15 (m, 2H), 2.05 (dd, 1H), 1.97 (m, 2H), 1.86-1.62 (m, 6H), 1.56-1.26 (m, 7H), 1.15 (t, 1H). |
| 919 | 403.34 | 1.79 | |
| 920 | 440.3 | 1.57 | |
| 921 | 355 | 2.51 | |
| 922 | 356.3 | 1.3 | |
| 923 | 410.2 | 1.82 | DMSO (d6): 8.68 (s, 1H), 7.38 (d, 1H), 7.27 (t, 1H), 7.24 (d, 1H), 7.18 (t, 1H), 6.48 (d, 1H), 4.82 (q, 1H), 3.42 (d, 2H), 3.15 (m, 2H), 3.00 (t, 2H), 2.82 (s, 6H), 2.41 (td, 1H), 2.22 (dd, 1H), 2.15 (td, 1H), 1.89 (d, 1H), 1.82-1.63 (m, 10H), 1.28 (q, 2H), 1.17 (m, 1H), 0.99 (q, 2H). |
| 924 | 384.3 | 2 | |
| 925 | 433.2 | 1.6 | |
| 926 | 471.4 | 2.17 | |
| 927 | 418.2 | 2.07 | |
| 928 | 463.2 | 0.96 | |
| 929 | 482.4 | 2.24 | |
| 930 | 398.2 | 1.64 | |
| 931 | 372.2 | 1.56 | |
| 932 | 416.4 | 1.62 | |
| 933 | 299.1 | 1.8 | |
| 934 | 414.4 | 1.99 | |
| 935 | 456.4 | 1.81 | |
| 936 | 361.2 | 1.32 | |
| 937 | 480.2 | 2.08 | |
| 938 | 396.5 | 2.1 | |
| 939 | 455.4 | 2.09 | |
| 940 | 502.2 | 2.27 | |
| 941 | 384.3 | 2.1 | DMSO-d6: 10.16-9.77 (m, 1H), 8.28 (m, 1H), 7.54-7.42 (m, 1H), 7.19 (m, 1H), 7.03-6.97 (m, 1H), 5.37-5.28 (m, 1H), 3.79-3.74 (m, 1H), 3.69-3.47 (m, 1H), 3.30-3.16 (m, 1H), 2.74-2.62 (m, 1H), 2.58 (s, 3H), 2.19-2.04 (m, 3H), 1.89 (m, 3H), 1.82-1.77 (m, 3H), 1.63 (m, 1H), 1.40-1.35 (m, 2H), 1.28-1.23 (m, 2H), 1.10 (td, J = 12.7, 9.5 Hz, 1H) |
| 942 | 331.4 | 1.71 | DMSO-d6: 9.65-9.45 (m, 1H), 8.27 (d, J = 7.5 Hz, 1H), 7.54-7.45 (m, 1H), 7.50 (s, 1H), 7.22-7.15 (m, 1H), 7.04-6.99 (m, 1H), 6.25 (dd, J = 3.1, 6.9 Hz, 1H), 6.06-6.04 (m, 1H), 5.34-5.28 (m, 1H), 3.86 (d, J = 4.1 Hz, 1H), 3.77-3.69 (m, 2H), 3.31-3.21 (m, 2H), 3.03-3.01 (m, 1H), 2.98-2.94 (m, 2H), 2.90 (s, 1H), 2.58 (s, 2H), 2.36 (t, J = 1.8 Hz, 1H), 2.18-2.12 (m, 1H), 2.02-1.94 (m, 1H), 1.83 (s, 3H), 1.38-1.28 (m, 2H) |
| 943 | 355.4 | 1.87 | |
| 944 | | | |
| 945 | 471.4 | 2.06 | |
| 946 | 433.2 | 1.87 | DMSO (d6): 8.64 (m, 1H), 8.18 (t, 1H), 7.43 (d, 1H), 7.31 (t, 1H), 7.20 (t, 1H), 7.17 (d, 1H), 4.92 (m, 1H), 3.49 (m, 1H), 3.41 (t, 1H), 3.33 (t, 1H), 3.17 (m, 2H), 2.61 (s, 1H), 2.31 (m, 3H), 2.02 (m, 2H), 11.86 (s, 3H), .85-1.60 (m, 8H), 1.40 (m, 3H), 1.20 (dd, 1H). |
| 947 | 353.3 | 1.54 | |
| 948 | 388.2 | 0.95 | |
| 949 | 447.4 | 1.89 | |
| 950 | 374.2 | 0.92 | |
| 951 | 442.2 | 2.36 | |
| 952 | 429.4 | 1.71 | CD3OD: 7.63 (d, 1H), 7.39 (d, 1H), 7.35 (d, 1H), 4.21 (q, 2H), 3.63 (m, 2H), 3.30 (m, 2H), 3.17 (m, 2H), 2.98 (s, 2H), 2.24 (m, 2H), 1.75-1.90 (m, 8H), 1.29-1.39 (m, 5H), 1.09 (m, 2H) |
| 953 | 375 | 2.18 | |
| 954 | 342.2 | 1.7 | |
| 955 | 461.4 | 2.01 | 1H-NMR (300 MHz, DMSO-d6): ? 6.87 (d, J = 8.7 Hz, 1H), 6.69 (t, J = 7.5 Hz, 1H), 6.40 (dd, J = 8.7 Hz, J = 4.5 Hz, 1H), 4.42 (m, 2H), 3.28 (s, 2H), 2.78 (d, J = 11.1 Hz, 1H), 2.58 (d, J = 11.7 Hz, 1H), 3.38 (m, 1H), 1.85-2.05 (m, 4H), 1.70-1.85 (m, 3H), 1.40-1.60 (m, 4H), 1.09 (dd, J = 11.7 Hz, J = 4.8 Hz, 1H). |
| 956 | 302.2 | 1.33 | |
| 957 | 447.4 | 2.01 | |
| 958 | 431.2 | 2.41 | |
| 959 | 423.4 | 1.6 | DMSO (d6): 9.00 (s, 1H), 8.17 (d, 1H), 7.34 (t, 1H), 7.30 (d, 1H), 7.20 (t, 1H), 7.17 (d, 1H), 4.92 (q, 1H), 3.85 (dd, 2H), 3.4 (m, 2H), 3.29 (t, 2H), 3.15 (m, 4H), 2.22-2.14 (m, 2H), 2.04 (dd, 1H), 1.87 (s, 3H), 1.81 (m, 3H), 1.73 (d, 1H), 1.65-1.55 (m, 6H), 1.21 (ddd, 2H). |
| 960 | 371.2 | 1.52 | |
| 961 | 382.4 | 1.4 | |
| 962 | 455.2 | 2.15 | |
| 963 | 477.4 | 2.15 | |
| 964 | 371.2 | 2.1 | |
| 965 | 448.3 | 2.18 | CD3OD: 7.71 (d, 1H), 7.62 (d, 1H), 7.52 (dd, 1H), 3.68 (m, 2H), 3.48 (m, 1H), 3.30 (m, 2H), 2.80 (s, 2H), 2.40 (m, 2H), 2.15 (m, 1H), 1.88 (m, 2H), 1.56-1.91 (m, 4H), 1.30 (m, 1H) |
| 966 | 318 | 1.71 | DMSO (d6): 9.20 (m, 1H), 8.19 (d, 1H), 7.41 (d, 1H), 7.29 (t, 1H), 7.19 (t, 1H), 7.16 (d, 1H), 4.92 (m, 1H), 3.38 (m, 2H), 3.20 (m, 2H), 2.26 (m, 2H), 2.10 (m, 1H), 2.03 (dd, 1H), 1.87 (s, 3H), 1.85-1.68 (m, 6H), 1.63 (m, 3H), 1.44 (q, 2H), 1.29 (q, 2H), 1.12 (m, 2H). |
| 967 | 341.2 | 1.46 | |
| 968 | 468.4 | 2.48 | |
| 969 | 466 | 1.67 | |
| 970 | 464.2 | 1.66 | |
| 971 | 438.2 | 1.44 | |
| 972 | 443.4 | 2.03 | |
| 973 | 436.2 | 1.91 | DMSO (d6): 9.07 (br.s, 1H), 7.46 (d, 1H), 7.44 (d, 1H), 7.41 (d, 1H), 7.32 (t, 1H), 7.23 (t, 1H), 4.45 (q, 1H), 3.04 (s, 3H), 2.26 (m, 2H), 2.06 (m, 3H), 1.93 (m, 3H), 1.87-1.67 (m, 8H), 1.59-1.38 (m, 8H), 1.30 (m, 1H). |
| 974 | 391.36 | 1.76 | |
| 975 | 412 | 1.88 | |
| 976 | 440.3 | 2.5 | |
| 977 | 422.5 | 2.3 | |
| 978 | 497.4 | 1.92 | |
| 979 | 463.2 | 1.04 | |
| 980 | 428 | 1.63 | |
| 981 | 448.3 | 2.18 | |
| 982 | 456.3 | 1.95 | H NMR (500 MHz, MeOD) 7.72-7.64 (m, 3H), 7.45-7.41 (dt, 1H), 3.05 (t, 2H), 2.62 (s, 2H), 2.42-2.38 (m, 2H), 2.27-2.15 (m, 3H), 2.12-2.0 (m, 2H), 1.85-1.77 (m, 2H), 1.60-1.32 (m, 7H), 1.00-0.97 (m, 1H), |
| 983 | 296.2 | 1.46 | |
| 984 | 443.2 | 1.69 | |
| 985 | 398.2 | 2.19 | |
| 986 | 467 | 2.05 | |
| 987 | 426.3 | 2.4 | |

TABLE 2-continued

Physical Characteristics of Compounds in Table 1.

| Cmd No. | LCMS Plus | LCMS RT | NMR |
|---|---|---|---|
| 988 | 355.4 | 2.38 | 1H NMR (500 MHz, DMSO (d6)): 9.01 (s, H), 7.38 (d, 1H), 7.21 (t, 1H), 7.14 (t, 1H), 7.05 (d, 1H), 3.40 (m, 1H), 3.27-3.17 (m, 4H), 2.72 (t, 2 H), 2.26 (td, 2H), 2.12-2.05 (m, 2H), 1.88-1.86 (m, 2H), 1.76-1.67 (m, 8H), 1.57-1.46 (m, 6H). |
| 989 | 298.3 | 2.05 | |
| 990 | | | DMSO (d6): 9.12 (br.s, 1H), 8.18 (d, 71H), 7.39 (d, 1H), .30 (t, 1H), 7.20 (t, 1H), 7.17 (d, 1H), 6.27 (m, 1H), 6.04 (m, 1H), 4.92 (m, 1H), 3.44 (m, 2H), 3.14 (m, 2H), 2.98 (s, 1H), 2.94 (m, 1H), 2.84 (s, 1H), 2.80 (m, 1H), 2.26 (m, 2H), 2.03 (m, 2H), 1.86 (s, 3H), 1.81 (m, 3H), 1.70 (d, 1H), 1.62 (m, 1H), 1.37 (t, 1H), 1.29 (d, 1H), 0.68 (m, 1H). |
| 991 | 365.3 | 1.67 | DMSO (d6): 9.04 (s, 1H), 8.17 (d, 1H), 7.34 (t, 1H), 7.30 (d, 1H), 7.20 (t, 1H), 7.17 (d, 1H), 4.92 (q, 1H), 3.79 (m, 1H), 3.42 (m, 3H), 3.16 (m, 7H), 2.89 (m, 1H), 2.22-2.14 (m, 2H), 2.05 (m, 1H), 1.87 (s, 3H), 1.83 (m, 5H), 1.74 (d, 1H), 1.63 (m, 3H), 1.46 (m, 1H), 1.35 (m, 1H), 1.17 (q, 1H), 0.90 (d, 6H). |
| 992 | 470.3 | 2.13 | |
| 993 | 426.2 | 1.93 | |
| 994 | 424.2 | 1.8 | DMSO (d6): 9.05 (br.s, 1H), 8.39 (d, 1H), 7.38 (d, 1H), 7.30 (t, 1H), 7.21 (t, 1H), 7.15 (d, 1H), 4.95 (q, 1H), 3.11 (m, 2H), 2.35 (m, 2H), 2.25-2.12 (m, 3H), 2.07-1.96 (m, 2H), 1.82 (m, 3H), 1.72 (m, 2H), 1.65 (m, 2H), 1.60-1.25 (m, 9H), 1.16 (t, 1H), 0.78-0.63 (m, 4H). |
| 995 | 393.4 | 1.83 | |
| 996 | 455.3 | 1.74 | |
| 997 | 444.6 | 1.99 | |
| 998 | 436.4 | 1.89 | |
| 999 | 457.2 | 2 | |
| 1000 | 461.4 | 2.01 | |
| 1001 | 443.2 | 2.08 | |
| 1002 | 458.6 | 2.31 | |
| 1003 | 440.4 | 2.13 | |
| 1004 | 372.2 | 1.53 | |
| 1005 | 442.5 | 2.23 | |
| 1006 | 396.62 | 1.7 | |
| 1007 | 444.6 | 2.19 | |
| 1008 | 440.5 | 2.41 | |
| 1009 | 324.2 | 2.04 | |
| 1010 | 369.2 | 2.15 | |
| 1011 | 469.4 | 1.5 | |
| 1012 | 457.2 | 1.96 | |
| 1013 | 467.4 | 2.21 | |
| 1014 | 436.3 | 2.4 | DMSO (d6): 9.38 (m, 1H), 8.19 (d, 1H), 7.37 (d, 1H), 7.31 (t, 1H), 7.20 (t, 1H), 7.17 (d, 1H), 4.92 (m, 1H), 3.53 (m, 2H), 3.22 (m, 2H), 3.04 (m, 2H), 2.42 (m, 2H), 2.21 (qd, 2H), 2.10 (dd, 1H), 1.91 (t, 2H), 1.87 (s, 3H), 1.84 (m, 3H), 1.74 (d, 1H), 1.64 (s, 3H), 1.63 (m, 1H), 1.54 (m, 2H), 1.41 (m, 2H), 1.01 (s, 6H). |
| 1015 | 409.4 | 2.09 | CDCl3 (ppm): 7.93 (1H, br s), 7.43 (1H, m), 7.36 (1H, m), 4.35 (2H, br s), 4.12 (2H, m), 3.98 (1H, br s), 3.21 (1H, br s), 3.08 (2H, br s), 2.76 (4H, m), 2.05 (3H, m), 1.62 (1H, br s), 1.28 (6H, m). |
| 1016 | 360.9 | 1.68 | DMSO-d6: 9.16 (s, 1H), 7.55 (d, 1H), 7.31 (t, 1H), 7.20 (t, 1H), 6.93 (d, 1H), 5.15 (dd, 1H), 3.47 (m, 1H), 3.34 (t, 2H), 3.24-3.11 (m, 3H), 2.88 (q, 1H), 2.60 (t, 2H), 2.41-2.26 (m, 5H), 2.08-1.33 (m, 13H), 1.28-1.14 (m, 2H). |
| 1017 | 379.35 | 1.63 | |
| 1018 | 392.2 | 1.62 | |
| 1019 | 415 | 1.43 | |
| 1020 | 400 | 1.7 | |
| 1021 | 430 | 1.71 | |
| 1022 | 467.4 | 1.87 | |
| 1023 | 467.4 | 1.96 | |
| 1024 | 455.2 | 2.15 | |
| 1025 | 455.2 | 2.19 | |
| 1026 | 455 | 2.02 | |
| 1027 | 467.4 | 1.76 | |
| 1028 | 467 | 2.05 | |
| 1029 | 467.4 | 1.73 | |
| 1030 | 485.4 | 2.12 | |
| 1031 | 439.4 | 1.76 | |
| 1032 | 439.4 | 1.75 | |
| 1033 | 439.4 | 1.66 | |
| 1034 | 444.4 | 1.53 | |
| 1035 | 439.2 | 1.74 | |
| 1036 | 439.4 | 1.73 | |
| 1037 | 444.4 | 1.5 | |
| 1038 | 444.4 | 1.5 | |
| 1039 | 438.2 | 1.44 | |
| 1040 | 438.4 | 1.46 | |
| 1041 | 443.2 | 1.93 | |

Example 62

Assays

Functional Mobilization of Intracellular Calcium to Determine Muscarinic Receptor Activity:

CHO cells expressing muscarinic receptors ($M_1$ to $M_5$) are grown as monolayers in tissue culture flasks at 37° C. in a humidified atmosphere containing 5% $CO_2$ and passaged every 3-5 days. The growth media is Dulbecco's modified eagles medium (DMEM, Gibco Cat #12430-054), containing 25 mM Hepes and supplemented with Fetal Bovine Serum (Hyclone, cat #SH30071.03), 0.1 mM of MEM non-essential amino acids (GIBCO, Cat #11140-050), 1 mM MEM Sodium Pyruvate (GIBCO Cat #11360-070) and 100 units/ml of Penicillin G and 100 µg/ml of Streptomycin (GIBCO Cat #15140-122). The recombinant muscarinic receptor cell lines are grown under antibiotic pressure with media containing 25 µg/ml zeocin and 500 µg/ml G418 (M1-CHO), 4 µg/ml puromycin, 50 µg/ml zeocin and 2.5 µg/ml blasticidin (M2 and M4-CHO) or 50 µg/ml zeocin and 4 µg/ml puromycin (M3 and M5-CHO).

Cells are harvested at 80-90% confluence using Versene (GIBCO Cat #15040-066), collected by centrifugation and seeded 18-24 hrs prior to running the calcium assay at a density of 5,000-10,000 cells/well in back-walled, clear-bottomed 384-well plates (BD Biocoat, poly-D-lysine, Cat #356663). The day of the experiment, the cells are washed with a plate washer (Bioteck Instruments, ELX 405) using bath 1 buffer (140-mM NaCl, 4.5-mM KCl, 2-mM $CaCl_2$, 1-mM $MgCl_2$, 10-mM Hepes-Na, 10-mM Glucose, pH 7.4, with NaOH) containing 1 mM Probenecid. Next, the calcium dye Fluo-3 (25 µl/well of Fluo-3 AM at 4 µM, Molecular Probes F-1241, in Bath 1 buffer containing 1 mM Probenecid) is added to the 25 µl of Bath 1 remaining in each well after the plate wash and the dye is loaded at 37° C. in the tissue culture incubator for 60-90 min. The fluorescent dye is removed using the plate washer with Bath 1 containing 1 mM Probenecid, leaving 25 μl/well of this solution after the wash. Alternatively, cells can be loaded with the calcium indicator from Molecular Devices (Calcium 3 Assay Reagents, Cat #R7181) adding 5 μl of a 5× solution dye in Bath 1 containing 1 mM Probenecid (10 ml per dye flask cat #R7182 to generate a solution 20×) to 20 μl of the same buffer. After loading for 60 min, the experiment can be run without having to remove the dye.

Compounds are prepared at a 2× fold concentration in a 96-well plate (round bottom, Costar Corning cat #3656), by reconstituting the pre-spotted compounds in bath 1 containing 1 mM probenecid. The final concentration DMSO is 0.5% and the amount of DMSO is normalized across the assay plate. To determine an agonist action of the compounds on muscarinic receptors, the reconstituted compounds are added (25 μl compound/well) to the cell assay plate (containing 25 μl/well) using the multi-channel robotic system of the FLIPR 3 Instrument (Molecular Devices, Sunnyvale, Calif.). To determine a functional inhibitory action of the compounds on muscarinic receptors, the reconstituted compounds are added (25 μl compound/well) to the assay plate and pre-incubated for 15 min prior to adding 25 μl of Carbachol at 3× the EC80 for each muscarinic subtype. Alternatively, the compounds can be co-applied simultaneously with the agonist. In both assay modes, the fluorescence is recorded for 60 sec (excitation wavelength is 488 nM and emission wavelength 540 nm) using the FLIPR 3 instrument.

The potency, efficacy and selectivity of the muscarinic compounds were evaluated by screening the compound activity across the whole family ($M_1$ to $M_5$ cells). Compounds were also screened for activity on other proteins such as other GPCRs and ion channels to determine selectivity on M4 receptors.

The compounds of the present invention were found to modulate the $M_1$ and/or $M_4$ muscarinic receptors selectively over the other receptor types.

Examples of activities and efficacies of the muscarinic compounds of formulae (I and II) on modulating $M_1$ and $M_4$ receptors are shown below in Table 2. The compound activity for the $M_1$ and $M_4$ receptor is illustrated with "xxx" if activity was measured to be less than 0.1 μM, "xx" if activity was measured to be between 0.1 μM and 1.0 μM, and "x" if activity was measured to be greater than 1.0 μM. The efficacy for $M_1$ and $M_4$ modulation is illustrated with "xxx" if efficacy was calculated to be greater than 85%, "xx" if efficacy was calculated to be between 85% and 65%, and "x" if efficacy was calculated to be less than 65%.

Table 2. Compound activities and efficacies for modulating $M_1$ and $M_4$ receptors

TABLE 3

Compound activities and efficacies for modulating $M_1$ and $M_4$ receptors.

| Cmd No. | $M_1$ Activity | $M_4$ Activity | $M_1$ Efficacy | $M_4$ Efficacy |
| --- | --- | --- | --- | --- |
| 1 | xx | xx | xx | xxx |
| 2 | x | x | x | x |
| 3 | xxx | xx | xx | xx |
| 4 | xxx | x | x | x |
| 5 | xxx | xxx | xx | xxx |
| 6 | xxx | xx | xx | xx |
| 7 | xxx | xx | xx | xxx |
| 8 | xx | xx | x | xx |
| 9 | xxx | x | xx | xx |
| 10 | xx | xx | xx | xx |
| 11 | x | x | x | x |
| 12 | xxx | xx | x | x |
| 13 | xx | x | xx | x |
| 14 | xxx | xxx | xx | xxx |
| 15 | xxx | xx | xx | xxx |
| 16 | xxx | xxx | xx | xx |
| 17 | xx | xx | x | xx |
| 18 | xxx | xx | x | xxx |
| 19 | xxx | xx | xx | xx |
| 20 | x | xx | x | x |
| 21 | xx | x | x | x |
| 22 | xxx | x | xx | x |
| 23 | xx | x | x | x |
| 24 | xx | x | x | x |
| 25 | xxx | xxx | xx | xxx |
| 26 | xxx | xx | xx | x |
| 27 | xxx | xxx | xx | xx |
| 28 | xxx | xx | xxx | xx |
| 29 | xxx | xxx | xxx | xxx |
| 30 | xxx | xxx | xxx | xxx |
| 31 | xxx | xxx | xxx | xx |
| 32 | xxx | xxx | xxx | xx |
| 33 | xxx | xxx | xxx | xxx |
| 34 | xxx | xx | xx | xxx |
| 35 | xxx | xx | xxx | xxx |
| 36 | xxx | xx | xx | xxx |
| 37 | xxx | xx | xx | xxx |
| 38 | xxx | xxx | xxx | xxx |
| 39 | xxx | xx | xx | xxx |
| 40 | xxx | xx | xx | xxx |
| 41 | xxx | xxx | xxx | xxx |
| 42 | xxx | xx | xxx | xxx |
| 43 | xxx | x | xxx | xxx |
| 44 | xxx | xx | xx | xxx |
| 45 | xxx | xxx | xxx | xx |
| 46 | xxx | xxx | xxx | xx |
| 47 | xxx | xx | xx | xx |
| 48 | xxx | xx | xxx | xx |
| 49 | xxx | xxx | xxx | xx |
| 50 | xxx | xx | xxx | xxx |
| 51 | xxx | xx | xx | xx |
| 52 | xxx | xxx | xxx | xx |
| 53 | xx | xx | x | xx |
| 54 | xxx | xx | xxx | xx |
| 55 | xxx | xxx | xxx | xx |
| 56 | xxx | xxx | xx | xx |
| 57 | xxx | xxx | xx | xx |
| 58 | xxx | xx | xx | xx |
| 59 | xxx | xx | x | xx |
| 60 | xx | x | xx | xx |
| 61 | xxx | xx | xx | xx |
| 62 | xxx | xx | x | xx |
| 63 | xxx | x | x | x |
| 64 | xxx | xx | x | x |
| 65 | xx | x | xx | x |
| 66 | xxx | xxx | xxx | xxx |
| 67 | xxx | xx | x | x |
| 68 | xx | x | x | x |
| 69 | xx | xx | x | x |
| 70 | xx | x | xx | xx |
| 71 | xxx | xx | x | x |
| 72 | xxx | xx | xx | xx |
| 73 | xxx | xx | xx | xx |
| 74 | xxx | xx | xx | xx |
| 75 | xxx | xx | x | xx |
| 76 | xxx | xx | xx | xx |
| 77 | xxx | xx | xx | x |
| 78 | xxx | xx | xx | x |
| 79 | xx | x | x | x |
| 80 | xx | xx | x | x |
| 81 | xx | x | x | x |
| 82 | xxx | xx | xx | xx |
| 83 | xxx | x | x | x |
| 84 | xxx | xx | xx | xx |
| 85 | xxx | xx | xx | xx |
| 86 | xxx | x | xx | x |
| 87 | xxx | x | xx | x |

TABLE 3-continued

Compound activities and efficacies for modulating $M_1$ and $M_4$ receptors.

| Cmd No. | $M_1$ Activity | $M_4$ Activity | $M_1$ Efficacy | $M_4$ Efficacy |
|---|---|---|---|---|
| 88 | xxx | xx | xx | x |
| 89 | xxx | xx | xx | x |
| 90 | xx | x | xx | x |
| 91 | xxx | xx | xx | x |
| 92 | xxx | xx | xx | x |
| 93 | xx | xx | x | x |
| 94 | xxx | xx | x | x |
| 95 | xxx | xx | xx | x |
| 96 | xx | x | xx | x |
| 97 | xxx | x | xx | x |
| 98 | xxx | xx | xx | x |
| 99 | xxx | x | x | x |
| 100 | xxx | xx | xx | xx |
| 101 | xxx | xx | xx | xx |
| 102 | xxx | xx | xx | xx |
| 103 | xxx | xx | xx | x |
| 104 | xxx | x | xx | x |
| 105 | xx | x | x | x |
| 106 | xxx | xx | xx | x |
| 107 | xxx | x | xx | x |
| 108 | xxx | xx | xx | x |
| 109 | xxx | xx | xx | x |
| 110 | xxx | xx | x | x |
| 111 | xxx | xx | xx | x |
| 112 | xxx | xx | xx | x |
| 113 | xxx | x | xx | x |
| 114 | xx | x | xx | x |
| 115 | xxx | xx | xx | x |
| 116 | xxx | xx | xx | x |
| 117 | xxx | xx | xx | x |
| 118 | xxx | x | xx | x |
| 119 | xxx | x | x | x |
| 120 | xx | x | x | x |
| 122 | xxx | xx | xx | x |
| 123 | xx | x | x | x |
| 124 | xxx | xx | x | x |
| 125 | xxx | xx | xx | x |
| 126 | xxx | x | x | x |
| 127 | xxx | xx | xx | x |
| 128 | xxx | xx | x | x |
| 129 | xxx | x | xx | x |
| 130 | xxx | xx | x | x |
| 131 | xxx | xx | xx | xxx |
| 132 | xxx | xxx | xxx | xxx |
| 133 | xxx | xx | xxx | xx |
| 134 | xxx | xx | xxx | x |
| 135 | xxx | xx | xxx | xxx |
| 136 | xxx | xxx | xxx | xxx |
| 137 | xxx | x | xxx | xxx |
| 138 | xxx | x | xx | xx |
| 139 | xxx | xxx | xxx | xxx |
| 140 | xxx | xxx | xxx | xxx |
| 141 | xxx | xx | xxx | xxx |
| 142 | xxx | x | xx | xxx |
| 143 | xxx | xxx | xx | xxx |
| 144 | xxx | xxx | xxx | xxx |
| 145 | xxx | x | xxx | xxx |
| 146 | xxx | xxx | xxx | xxx |
| 147 | xxx | xx | xx | xxx |
| 148 | xxx | xx | xx | xxx |
| 149 | xxx | x | xxx | xxx |
| 150 | xxx | x | xx | xxx |
| 151 | xxx | xxx | xxx | xxx |
| 152 | xx | x | xx | xxx |
| 153 | xxx | xxx | xxx | xxx |
| 154 | xxx | xxx | xx | xxx |
| 155 | xxx | x | xxx | xxx |
| 156 | xxx | xxx | xx | xxx |
| 157 | xxx | x | xx | xxx |
| 158 | xxx | x | xxx | xxx |
| 159 | xx | x | xxx | xxx |
| 160 | xxx | xx | xxx | xxx |
| 161 | xx | x | xxx | xxx |
| 162 | xxx | x | xx | xxx |
| 163 | xxx | xx | xx | xxx |
| 164 | xx | x | xxx | xxx |
| 165 | x | x | xx | xxx |
| 166 | xxx | x | xxx | xxx |
| 167 | xxx | xx | xx | xxx |
| 168 | xx | xx | | xxx |
| 169 | xxx | x | xx | xxx |
| 170 | xx | x | xx | xxx |
| 171 | xx | x | xxx | xx |
| 172 | x | x | xxx | xx |
| 173 | xxx | xx | xx | xxx |
| 174 | xxx | x | xxx | xx |
| 175 | xxx | xx | xx | xx |
| 176 | xx | xx | xxx | xx |
| 177 | xxx | xx | xx | xx |
| 178 | xx | x | xxx | xx |
| 179 | xx | x | xxx | xx |
| 180 | xxx | xxx | xx | xx |
| 181 | xx | x | xx | xx |
| 182 | x | x | xx | xx |
| 183 | xx | x | xx | xx |
| 184 | xx | x | xxx | xx |
| 185 | x | x | xx | xx |
| 186 | xxx | x | xxx | xx |
| 187 | xx | x | xx | xx |
| 188 | x | x | x | xx |
| 189 | xxx | x | xx | xx |
| 190 | x | x | xxx | xx |
| 191 | xxx | x | xx | xx |
| 192 | xxx | x | xx | xx |
| 193 | x | x | x | x |
| 194 | xxx | x | xxx | xx |
| 195 | xx | x | x | x |
| 196 | xxx | x | xx | x |
| 197 | xx | x | x | x |
| 198 | xx | x | xx | x |
| 199 | xx | x | xx | x |
| 200 | xx | x | xx | x |
| 202 | xx | x | xx | x |
| 203 | xxx | xx | xx | x |
| 204 | xxx | x | xx | x |
| 205 | x | x | x | x |
| 206 | xxx | x | xx | x |
| 207 | xx | x | xx | x |
| 208 | xx | x | x | x |
| 209 | xx | x | xxx | x |
| 210 | xx | x | xx | x |
| 211 | x | x | xx | x |
| 212 | x | x | x | x |
| 213 | xx | x | xx | x |
| 214 | x | x | x | x |
| 215 | xx | x | x | x |
| 216 | xxx | x | xxx | x |
| 217 | xx | x | x | x |
| 218 | xx | x | x | x |
| 219 | x | x | xx | x |
| 220 | x | x | xx | x |
| 221 | xx | x | xx | x |
| 222 | x | x | x | x |
| 223 | x | x | x | x |
| 224 | x | x | xx | x |
| 225 | x | x | x | x |
| 226 | x | x | x | x |
| 227 | xxx | xxx | xxx | xxx |
| 228 | x | x | x | x |
| 229 | xx | xxx | x | xxx |
| 230 | x | xx | x | xxx |
| 231 | x | x | xx | xxx |
| 232 | xx | xxx | x | xxx |
| 233 | xxx | xxx | xx | xxx |
| 234 | xxx | xxx | xx | xx |
| 235 | xx | x | xx | xx |
| 236 | xxx | xx | xx | xx |
| 237 | xxx | xx | x | x |
| 238 | x | x | x | x |
| 239 | x | x | xx | xx |

TABLE 3-continued

Compound activities and efficacies for modulating $M_1$ and $M_4$ receptors.

| Cmd No. | $M_1$ Activity | $M_4$ Activity | $M_1$ Efficacy | $M_4$ Efficacy |
|---|---|---|---|---|
| 240 | xx | x | xx | xxx |
| 241 | xx | x | x | xxx |
| 242 | xxx | xx | xx | xxx |
| 243 | xxx | x | xx | xx |
| 244 | xx | x | xx | xx |
| 245 | xx | xx | x | xxx |
| 246 | xx | xx | x | xxx |
| 247 | xx | x | xx | xxx |
| 248 | xx | x | xx | x |
| 249 | x | x | xx | xx |
| 250 | xx | x | xx | xx |
| 251 | xx | x | xx | xx |
| 252 | x | x | x | xx |
| 253 | xx | x | xx | xx |
| 254 | x | x | xx | xx |
| 255 | x | x | x | x |
| 256 | xx | xx | x | x |
| 257 | x | x | xxx | x |
| 258 | x | x | xx | x |
| 259 | x | x | xx | x |
| 260 | xxx | x | xx | x |
| 261 | xx | x | x | x |
| 262 | x | x | x | x |
| 263 | xxx | xxx | x | x |
| 264 | x | x | x | x |
| 265 | xx | xx | x | x |
| 266 | x | x | x | x |
| 267 | x | x | x | x |
| 268 | x | x | x | x |
| 269 | xxx | xxx | xx | xxx |
| 270 | xxx | xxx | xx | xxx |
| 271 | xxx | xxx | xx | x |
| 272 | xxx | xxx | xx | xxx |
| 273 | xxx | xx | xxx | xxx |
| 274 | xxx | x | xx | xxx |
| 275 | xxx | xx | xx | xxx |
| 276 | xxx | x | xx | xx |
| 277 | xxx | x | xx | x |
| 278 | xx | xx | xx | xx |
| 279 | xx | xx | x | x |
| 280 | x | x | xx | xx |
| 281 | xx | xx | x | xx |
| 282 | xxx | xx | x | xx |
| 283 | xx | x | xx | xx |
| 284 | xx | xx | x | x |
| 285 | xx | x | x | x |
| 286 | xx | x | x | x |
| 287 | xx | x | x | x |
| 288 | x | x | x | x |
| 289 | xxx | x | x | x |
| 290 | xxx | x | x | x |
| 291 | xx | x | xx | xx |
| 292 | xx | x | xx | xx |
| 293 | xx | xxx | xxx | xxx |
| 294 | xx | xx | xxx | xx |
| 295 | xxx | xxx | xx | xx |
| 296 | x | x | xx | xx |
| 297 | x | x | xx | xx |
| 298 | x | x | x | xx |
| 299 | x | x | xx | xx |
| 300 | xx | x | xx | x |
| 301 | x | x | x | x |
| 302 | x | x | x | x |
| 303 | xx | x | xxx | x |
| 304 | xxx | x | xx | x |
| 305 | x | x | x | x |
| 306 | x | x | x | x |
| 307 | xx | x | xx | x |
| 308 | xxx | x | xxx | x |
| 309 | xx | x | xxx | x |
| 310 | xx | x | x | x |
| 311 | xxx | x | xx | xx |
| 312 | x | x | x | x |
| 313 | x | x | x | x |
| 314 | xx | x | x | x |
| 315 | x | x | x | x |
| 316 | x | x | x | x |
| 317 | x | x | x | x |
| 318 | xxx | xxx | xx | xxx |
| 319 | xx | x | x | x |
| 320 | xx | x | xx | x |
| 321 | xx | x | xx | xx |
| 322 | xx | xxx | x | xxx |
| 323 | xx | x | xx | xx |
| 324 | xx | x | xx | xx |
| 325 | x | x | xx | x |
| 326 | x | x | x | x |
| 327 | x | x | x | x |
| 328 | xx | x | x | xx |
| 329 | xxx | x | xx | x |
| 330 | x | x | x | x |
| 331 | xx | x | x | x |
| 332 | x | x | x | x |
| 333 | x | x | x | x |
| 334 | x | x | x | x |
| 335 | x | x | x | x |
| 336 | x | x | x | x |
| 337 | x | x | x | x |
| 338 | x | x | x | x |
| 339 | x | x | x | x |
| 340 | xx | x | x | x |
| 341 | x | x | x | x |
| 342 | xxx | xx | xx | xx |
| 343 | xxx | xxx | xx | x |
| 344 | xxx | xx | xx | x |
| 345 | xxx | xx | x | x |
| 346 | xxx | x | x | x |
| 347 | xxx | xx | xx | xxx |
| 348 | xxx | xx | xxx | xxx |
| 349 | xx | xx | xxx | xxx |
| 350 | xxx | xxx | xxx | xxx |
| 351 | xxx | xx | xx | xxx |
| 352 | xxx | x | xxx | xxx |
| 353 | xxx | x | xxx | xx |
| 354 | x | x | xx | xx |
| 355 | xx | xx | xx | xx |
| 356 | xxx | x | xxx | xx |
| 357 | xx | x | x | x |
| 358 | xxx | xx | xx | xx |
| 359 | xx | xx | x | x |
| 360 | xx | x | xx | x |
| 361 | xx | x | x | x |
| 362 | xx | x | xx | x |
| 363 | xx | x | x | x |
| 364 | xxx | x | xxx | x |
| 365 | xxx | x | xx | x |
| 366 | xx | x | x | x |
| 367 | x | x | x | x |
| 368 | xxx | xx | x | x |
| 369 | xxx | xx | xxx | xxx |
| 370 | xxx | xx | xx | xxx |
| 371 | xxx | x | xx | xxx |
| 372 | xxx | xx | xx | xxx |
| 373 | xxx | xx | xx | xxx |
| 374 | xx | x | xx | xx |
| 375 | xxx | xxx | xxx | xx |
| 376 | xxx | x | xx | xx |
| 377 | xxx | xx | xx | xx |
| 378 | xx | x | xx | xx |
| 379 | xxx | xx | xx | xx |
| 380 | xxx | xx | xx | xx |
| 381 | xxx | x | xx | x |
| 382 | xxx | x | xx | xx |
| 383 | xxx | xx | xx | x |
| 384 | xx | x | x | x |
| 385 | xx | x | xx | x |
| 386 | xx | xx | x | x |
| 387 | xxx | xx | xx | x |
| 388 | xxx | x | xx | x |
| 389 | xx | x | xx | x |

TABLE 3-continued

Compound activities and efficacies for modulating $M_1$ and $M_4$ receptors.

| Cmd No. | $M_1$ Activity | $M_4$ Activity | $M_1$ Efficacy | $M_4$ Efficacy |
|---|---|---|---|---|
| 390 | xxx | x | xx | x |
| 391 | xx | x | x | x |
| 392 | xxx | x | xx | x |
| 393 | xxx | x | xx | x |
| 394 | xxx | xx | x | x |
| 395 | xxx | x | x | x |
| 396 | xx | x | x | x |
| 397 | xx | x | xx | x |
| 398 | xx | x | x | x |
| 399 | xx | xx | xx | x |
| 400 | x | x | x | x |
| 401 | xxx | x | xx | x |
| 402 | xx | x | xx | x |
| 403 | xxx | x | xx | x |
| 404 | xx | x | x | x |
| 405 | xx | x | x | x |
| 406 | xx | x | x | x |
| 407 | xx | x | x | x |
| 408 | xxx | xxx | xx | xx |
| 409 | xxx | xxx | xxx | xxx |
| 410 | xx | xx | x | x |
| 411 | xxx | xx | x | x |
| 412 | xx | x | x | x |
| 413 | xxx | xx | x | x |
| 414 | x | x | x | x |
| 415 | x | x | x | x |
| 416 | x | x | x | x |
| 417 | xx | x | x | x |
| 418 | x | x | x | x |
| 419 | x | x | x | x |
| 420 | xx | x | x | x |
| 421 | x | x | x | x |
| 422 | xxx | x | x | x |
| 423 | xx | x | x | x |
| 424 | x | x | x | x |
| 425 | x | x | x | x |
| 426 | x | x | x | x |
| 427 | xx | x | x | x |
| 428 | xx | x | x | x |
| 429 | xx | x | x | x |
| 430 | xx | x | x | x |

Additional examples of activities and efficacies of the muscarinic compounds of formulae (I and II) on modulating $M_1$ and $M_4$ receptors are shown below in Table 4. The compound activity for the $M_1$ and $M_4$ receptor is illustrated with "xxx" if activity was measured to be less than 2.0 µM, "xx" if activity was measured to be between 2.0 µM and 5.0 µM, and "x" if activity was measured to be greater than 5.0 µM. The efficacy for $M_1$ and $M_4$ modulation is illustrated with "xxx" if efficacy was calculated to be greater than 100%, "xx" if efficacy was calculated to be between 100% and 25%, "x" if efficacy was calculated to be less than 25%, and "-" if no data was available. It should be noted that 100% efficacy is the maximum response obtained with the Carbachol control.

TABLE 4

Additional exemplary compounds of formulae (I and II).

| Cmd No. | $M_1$ Activity | $M_4$ Activity | $M_1$ Efficacy | $M_4$ Efficacy |
|---|---|---|---|---|
| 431 | xx | xx | xx | xx |
| 432 | x | x | x | x |
| 433 | xxx | xxx | xxx | xx |
| 434 | x | xxx | xx | xx |
| 435 | xxx | xxx | xx | xx |
| 436 | x | x | x | x |
| 437 | x | x | x | x |
| 438 | xxx | xxx | xx | x |
| 439 | xxx | xxx | xx | xx |
| 440 | xxx | xxx | xx | xx |
| 441 | x | x | x | x |
| 442 | x | x | x | x |
| 443 | xxx | xxx | xxx | xxx |
| 444 | xx | xx | xx | xx |
| 445 | xxx | xxx | xx | xx |
| 446 | x | x | xx | x |
| 447 | xxx | xxx | xx | xx |
| 448 | x | xxx | x | x |
| 449 | xx | xxx | xx | xx |
| 450 | xxx | x | xx | x |
| 451 | xxx | xxx | xx | xx |
| 452 | xxx | x | xx | x |
| 453 | xxx | x | xx | x |
| 454 | x | x | x | x |
| 455 | xxx | xxx | xx | xx |
| 456 | xxx | xxx | xx | xx |
| 457 | x | x | x | x |
| 458 | x | x | x | x |
| 459 | x | xx | xx | x |
| 460 | xxx | xxx | xx | xx |
| 461 | xx | x | xx | x |
| 462 | xxx | xxx | xx | xx |
| 463 | x | x | xx | x |
| 464 | xx | xx | xx | xx |
| 465 | — | — | — | — |
| 466 | xxx | xxx | xx | xx |
| 467 | xx | xx | xx | xx |
| 468 | xx | xxx | xx | xx |
| 469 | xxx | xxx | xx | xx |
| 470 | xx | xx | xx | xx |
| 471 | xx | xx | xx | xx |
| 472 | xxx | xxx | xxx | xx |
| 473 | x | x | xx | x |
| 474 | x | x | x | x |
| 475 | — | — | — | — |
| 476 | x | x | x | x |
| 477 | x | x | x | x |
| 478 | x | x | x | x |
| 479 | xxx | xxx | xx | x |
| 480 | x | x | x | x |
| 481 | xxx | xxx | xx | xx |
| 482 | xxx | xxx | xx | xx |
| 483 | x | x | x | x |
| 484 | xxx | xxx | xx | xx |
| 485 | xx | xxx | xx | x |
| 486 | x | xxx | x | xx |
| 487 | x | xxx | x | xx |
| 488 | x | x | xx | xx |
| 489 | xxx | xxx | xx | xx |
| 490 | x | xxx | xx | xxx |
| 491 | xx | xx | xx | x |
| 492 | x | x | xx | x |
| 493 | xxx | xxx | xxx | xxx |
| 494 | xx | xxx | xx | xx |
| 495 | — | — | — | — |
| 496 | x | x | x | x |
| 497 | xx | xx | xx | xx |
| 498 | xxx | xxx | xx | xx |
| 499 | x | x | xx | x |
| 500 | x | x | x | x |
| 501 | — | — | — | — |
| 502 | xxx | xx | xx | xx |
| 503 | xxx | xxx | xx | xx |
| 504 | x | x | x | x |
| 505 | xxx | xxx | xx | xx |
| 506 | x | xx | x | xx |
| 507 | xxx | xxx | xx | xx |
| 508 | xxx | xxx | xx | xx |
| 509 | xx | x | xx | xx |
| 510 | xxx | xxx | xx | xx |
| 511 | x | x | x | x |
| 512 | x | x | x | x |

TABLE 4-continued

Additional exemplary compounds of formulae (I and II).

| Cmd No. | M₁ Activity | M₄ Activity | M₁ Efficacy | M₄ Efficacy |
|---|---|---|---|---|
| 513 | xxx | xxx | xx | xx |
| 514 | xx | x | xx | xx |
| 515 | xxx | xxx | xx | xx |
| 516 | xxx | xxx | xx | xx |
| 517 | xxx | xxx | xx | xx |
| 518 | x | x | x | x |
| 519 | xxx | x | xx | x |
| 520 | x | x | xx | x |
| 521 | x | x | x | x |
| 522 | xxx | xxx | xxx | xx |
| 523 | — | — | — | — |
| 524 | — | — | — | — |
| 525 | x | xxx | x | xx |
| 526 | xxx | x | xx | x |
| 527 | xxx | xxx | xx | xx |
| 528 | xx | xxx | xx | xx |
| 529 | x | xx | xx | xx |
| 530 | x | x | x | x |
| 531 | x | x | x | x |
| 532 | x | x | x | x |
| 533 | x | x | x | x |
| 534 | xx | xxx | xx | x |
| 535 | xxx | xxx | xx | xx |
| 536 | xxx | xxx | xx | xx |
| 537 | xxx | xxx | xx | xx |
| 538 | xx | x | xx | x |
| 539 | xx | xx | xx | xx |
| 540 | xxx | xxx | xx | xx |
| 541 | xxx | x | xx | x |
| 542 | x | x | x | x |
| 543 | xxx | xxx | xxx | xx |
| 544 | xx | xx | xx | x |
| 545 | x | x | x | x |
| 546 | x | x | xx | xx |
| 547 | xx | x | xx | xx |
| 548 | x | x | x | x |
| 549 | x | x | x | x |
| 550 | x | x | x | x |
| 551 | x | x | x | xx |
| 552 | x | x | xx | xx |
| 553 | xxx | xxx | xx | x |
| 554 | — | — | — | — |
| 555 | xxx | xx | xx | xx |
| 556 | x | x | xx | x |
| 557 | — | — | — | — |
| 558 | xxx | xxx | xx | xx |
| 559 | xxx | x | xx | xx |
| 560 | xxx | x | xx | x |
| 561 | x | xx | xx | xx |
| 562 | — | — | — | — |
| 563 | xxx | xxx | xxx | xx |
| 564 | xxx | xxx | xx | xx |
| 565 | xxx | xxx | xx | xx |
| 566 | x | x | x | x |
| 567 | xxx | xxx | xx | xx |
| 568 | xxx | xxx | xx | x |
| 569 | xx | xx | xx | xx |
| 570 | xx | xxx | xx | xx |
| 571 | xxx | xxx | xx | xx |
| 572 | xx | x | xx | x |
| 573 | xxx | xxx | xx | xx |
| 574 | xx | xxx | xx | xx |
| 575 | x | x | x | x |
| 576 | xxx | xxx | xx | xx |
| 577 | x | x | x | x |
| 578 | xxx | xxx | xx | xx |
| 579 | xxx | xxx | xx | xx |
| 580 | xxx | x | xx | xx |
| 581 | xxx | xxx | xx | x |
| 582 | — | — | — | — |
| 583 | xxx | xxx | xx | xx |
| 584 | xxx | xxx | xx | xx |
| 585 | xxx | xxx | xx | xx |
| 586 | xxx | xxx | xx | xx |
| 587 | xxx | xxx | xx | xx |
| 588 | x | x | x | x |
| 589 | x | x | x | x |
| 590 | xx | xx | xx | x |
| 591 | xxx | xxx | xxx | xx |
| 592 | xx | x | xx | x |
| 593 | — | — | — | — |
| 594 | x | xx | xx | x |
| 595 | xxx | xxx | xx | xx |
| 596 | xxx | xxx | xx | xx |
| 597 | x | x | xx | x |
| 598 | xxx | xxx | xx | xx |
| 599 | x | x | xx | xx |
| 600 | x | x | x | x |
| 601 | — | — | — | — |
| 602 | xxx | xx | xx | xx |
| 603 | xxx | xxx | xx | xx |
| 604 | x | xxx | x | xx |
| 605 | xxx | xxx | xx | xx |
| 606 | xxx | xxx | xx | xx |
| 607 | xxx | xxx | xx | xx |
| 608 | xxx | xxx | xx | xx |
| 609 | xx | xxx | xx | xx |
| 610 | xxx | xxx | xx | xx |
| 611 | xxx | x | xx | x |
| 612 | x | x | x | xx |
| 613 | — | — | — | — |
| 614 | xxx | xxx | xx | xx |
| 615 | xxx | xx | xx | x |
| 616 | xxx | x | xxx | xx |
| 617 | xx | xxx | xx | xxx |
| 618 | xxx | xxx | xx | xx |
| 619 | xx | xxx | xx | xx |
| 620 | x | x | xx | x |
| 621 | xx | xxx | xx | xx |
| 622 | x | x | x | x |
| 623 | xxx | xxx | xx | xx |
| 624 | xxx | x | xx | x |
| 625 | xxx | xxx | xx | xxx |
| 626 | xxx | xxx | xx | xx |
| 627 | xxx | xxx | xx | xx |
| 628 | xxx | xxx | xx | xx |
| 629 | xx | xx | xx | xx |
| 630 | x | xxx | xx | xx |
| 631 | — | — | — | — |
| 632 | x | x | x | x |
| 633 | xx | x | xx | x |
| 634 | x | x | x | x |
| 635 | — | — | — | — |
| 636 | xxx | xxx | xx | xx |
| 637 | xxx | xxx | xxx | xx |
| 638 | x | x | x | x |
| 639 | x | x | xx | x |
| 640 | xxx | xxx | xx | xx |
| 641 | x | x | x | x |
| 642 | x | xxx | xx | xxx |
| 643 | x | x | x | x |
| 644 | x | x | x | x |
| 645 | xxx | xxx | xx | xx |
| 646 | xxx | x | xx | x |
| 647 | xxx | xxx | xx | xx |
| 648 | xx | x | xx | x |
| 649 | xxx | xxx | xx | x |
| 650 | xxx | xxx | xx | xx |
| 651 | xxx | xxx | xx | xx |
| 652 | xxx | xxx | xx | xx |
| 653 | x | x | xx | xx |
| 654 | — | — | — | — |
| 655 | xxx | xxx | xx | xx |
| 656 | xxx | xxx | xx | xx |
| 657 | xx | xxx | xx | xx |
| 658 | xxx | xxx | xx | xx |
| 659 | xxx | xxx | xx | xx |
| 660 | xxx | xxx | xxx | xxx |
| 661 | x | x | xx | x |
| 662 | x | xx | xx | xx |

TABLE 4-continued

Additional exemplary compounds of formulae (I and II).

| Cmd No. | M₁ Activity | M₄ Activity | M₁ Efficacy | M₄ Efficacy |
|---|---|---|---|---|
| 663 | xxx | xxx | xx | xx |
| 664 | xxx | xxx | xx | xx |
| 665 | x | x | xx | x |
| 666 | x | xxx | x | xx |
| 667 | x | x | x | xx |
| 668 | xxx | xxx | xx | xx |
| 669 | xxx | xxx | xx | xx |
| 670 | x | xx | xx | xx |
| 671 | x | x | x | x |
| 672 | xxx | xxx | xx | xx |
| 673 | x | xx | x | xx |
| 674 | x | x | xx | xx |
| 675 | xxx | xxx | xx | xx |
| 676 | — | — | — | — |
| 677 | x | x | xx | x |
| 678 | xxx | x | xx | x |
| 679 | xxx | xxx | xx | xx |
| 680 | xx | xxx | xx | xx |
| 681 | x | x | xx | x |
| 682 | x | x | x | x |
| 683 | xx | x | xx | x |
| 684 | x | x | x | x |
| 685 | x | xxx | x | xx |
| 686 | x | x | x | x |
| 687 | x | x | x | x |
| 688 | xxx | xxx | xx | xx |
| 689 | xxx | xxx | xxx | xx |
| 690 | — | — | — | — |
| 691 | x | x | xx | x |
| 692 | xxx | xxx | xx | xx |
| 693 | x | x | xx | x |
| 694 | xxx | xxx | xx | xx |
| 695 | xxx | xxx | xx | xx |
| 696 | xx | xxx | xx | xx |
| 697 | x | x | xx | x |
| 698 | xxx | xxx | xxx | xxx |
| 699 | x | x | x | x |
| 700 | xxx | xxx | xxx | xxx |
| 701 | xxx | xxx | xx | xx |
| 702 | x | x | xx | xx |
| 703 | x | x | x | x |
| 704 | xxx | xxx | xx | xx |
| 705 | x | x | x | x |
| 706 | xxx | xxx | xx | xx |
| 707 | — | — | — | — |
| 708 | xxx | xxx | xx | xx |
| 709 | xxx | xxx | xx | x |
| 710 | x | x | xx | xx |
| 711 | xx | x | xx | x |
| 712 | xxx | xxx | xx | xx |
| 713 | — | — | — | — |
| 714 | xxx | xxx | xxx | xx |
| 715 | xxx | xxx | xx | xx |
| 716 | xxx | xxx | xx | xx |
| 717 | xxx | xxx | xx | xx |
| 718 | x | x | x | x |
| 719 | xxx | x | xx | x |
| 720 | xx | xxx | xx | xx |
| 721 | xxx | xxx | xx | xx |
| 722 | xxx | xxx | xx | xx |
| 723 | xxx | xxx | xx | xx |
| 724 | xx | x | xx | x |
| 725 | — | — | — | — |
| 726 | x | x | x | x |
| 727 | x | xxx | xx | xx |
| 728 | xx | x | xx | x |
| 729 | x | x | x | x |
| 730 | xxx | xxx | xx | xx |
| 731 | xxx | x | x | x |
| 732 | x | xx | xx | xx |
| 733 | — | — | — | — |
| 734 | xxx | xxx | xx | xx |
| 735 | xx | xxx | xx | xx |
| 736 | — | — | — | — |
| 737 | xx | xxx | xx | xx |
| 738 | xx | xxx | xx | xx |
| 739 | x | xx | xx | x |
| 740 | xxx | xxx | xx | xx |
| 741 | x | x | x | x |
| 742 | xxx | xxx | xx | xx |
| 743 | x | x | x | x |
| 744 | xxx | xxx | xx | xx |
| 745 | — | — | — | — |
| 746 | xxx | xxx | xx | xx |
| 747 | xxx | xxx | xx | xx |
| 748 | — | — | — | — |
| 749 | xxx | xxx | xx | xx |
| 750 | xxx | xxx | xx | xx |
| 751 | xxx | xxx | xx | xx |
| 752 | xxx | xxx | xx | xx |
| 753 | xx | xx | xx | xx |
| 754 | xxx | xxx | xx | xx |
| 755 | x | xxx | x | xx |
| 756 | xxx | xxx | xx | xx |
| 757 | x | x | x | x |
| 758 | x | x | x | x |
| 759 | x | x | x | x |
| 760 | x | xxx | xx | xx |
| 761 | xxx | xxx | xx | xx |
| 762 | xxx | xxx | xx | xx |
| 763 | — | — | — | — |
| 764 | xxx | xxx | xx | x |
| 765 | x | x | xx | x |
| 766 | xxx | xxx | xx | xx |
| 767 | x | x | xx | x |
| 768 | x | x | xx | x |
| 769 | xxx | xxx | xx | xx |
| 770 | xxx | xx | xx | x |
| 771 | x | x | x | x |
| 772 | xxx | xxx | xx | xx |
| 773 | xxx | xxx | xx | xx |
| 774 | x | x | xx | xx |
| 775 | xxx | xxx | xx | xx |
| 776 | x | x | x | x |
| 777 | xxx | xxx | xx | xx |
| 778 | x | x | x | x |
| 779 | xx | xxx | xx | x |
| 780 | x | x | x | x |
| 781 | x | x | xx | x |
| 782 | x | x | x | x |
| 783 | xxx | xx | xx | xx |
| 784 | x | x | x | x |
| 785 | xx | xxx | xx | xx |
| 786 | — | — | — | — |
| 787 | xxx | xxx | xx | xx |
| 788 | xx | xx | xx | xx |
| 789 | x | x | xx | xx |
| 790 | xx | xxx | xx | Efficacy |
| 791 | xx | x | xx | x |
| 792 | x | x | xx | xx |
| 793 | xxx | xxx | xx | xx |
| 794 | x | x | x | x |
| 795 | xx | x | x | x |
| 796 | xxx | xxx | xx | xx |
| 797 | x | xxx | xx | xx |
| 798 | x | x | x | x |
| 799 | x | x | x | x |
| 800 | xxx | xxx | xx | xx |
| 801 | x | x | x | x |
| 802 | x | xxx | xx | xx |
| 803 | x | x | x | x |
| 804 | x | x | x | x |
| 805 | xxx | xxx | xx | xx |
| 806 | x | x | x | x |
| 807 | xxx | xxx | xx | xx |
| 808 | xxx | xxx | xx | xx |
| 809 | xxx | xxx | xx | xx |
| 810 | xxx | xxx | xx | xx |
| 811 | — | — | — | — |
| 812 | xx | x | xx | x |

TABLE 4-continued

Additional exemplary compounds of formulae (I and II).

| Cmd No. | $M_1$ Activity | $M_4$ Activity | $M_1$ Efficacy | $M_4$ Efficacy |
|---|---|---|---|---|
| 813 | x | x | xx | x |
| 814 | x | xx | xx | xx |
| 815 | xx | xxx | xx | xx |
| 816 | xxx | xxx | xxx | xxx |
| 817 | x | x | x | x |
| 818 | x | x | x | x |
| 819 | xxx | x | xx | x |
| 820 | xxx | xxx | xx | xx |
| 821 | x | x | xx | x |
| 822 | xxx | xxx | xx | xx |
| 823 | xx | xx | xx | xx |
| 824 | x | x | xx | x |
| 825 | xxx | x | xx | x |
| 826 | xxx | xxx | xx | xx |
| 827 | xxx | xxx | xx | xx |
| 828 | xxx | x | xx | x |
| 829 | xxx | xxx | xx | xx |
| 830 | x | xx | xx | xx |
| 831 | — | — | — | — |
| 832 | xxx | xxx | xx | xx |
| 833 | xxx | xxx | xx | xx |
| 834 | xxx | xxx | xx | xx |
| 835 | — | — | — | — |
| 836 | xxx | xxx | xx | xx |
| 837 | x | x | x | x |
| 838 | xxx | xxx | xx | xx |
| 839 | xx | x | x | x |
| 840 | x | x | x | x |
| 841 | — | — | — | — |
| 842 | x | xxx | x | x |
| 843 | xxx | xxx | xx | xx |
| 844 | xxx | xxx | xx | xx |
| 845 | x | x | x | x |
| 846 | xx | xx | x | x |
| 847 | xxx | x | xx | x |
| 848 | xxx | xxx | xx | xxx |
| 849 | x | x | x | x |
| 850 | — | — | — | — |
| 851 | xxx | xxx | xx | xx |
| 852 | xx | xxx | xx | xx |
| 853 | xxx | xxx | xx | xx |
| 854 | xxx | xxx | xx | xx |
| 855 | xxx | xxx | xx | xx |
| 856 | xxx | xxx | xx | xx |
| 857 | x | x | xx | x |
| 858 | — | — | — | — |
| 859 | x | x | xx | xx |
| 860 | xxx | xxx | xx | xx |
| 861 | xxx | xxx | xx | xx |
| 862 | xxx | xxx | xx | xx |
| 863 | x | xx | xx | xx |
| 864 | x | x | x | x |
| 865 | xx | xxx | xx | xx |
| 866 | xx | xxx | xx | xx |
| 867 | — | — | — | — |
| 868 | x | xxx | x | xx |
| 869 | xx | xxx | xx | xx |
| 870 | — | — | — | — |
| 871 | x | xx | xx | xx |
| 872 | xxx | xxx | xx | xx |
| 873 | x | x | x | x |
| 874 | xx | x | xx | x |
| 875 | xxx | x | xx | x |
| 876 | — | — | — | — |
| 877 | xxx | xxx | xx | xx |
| 878 | xxx | xxx | xx | xx |
| 879 | xxx | xxx | xx | xx |
| 880 | x | x | x | x |
| 881 | xxx | xxx | xx | xx |
| 882 | x | x | x | x |
| 883 | — | — | — | — |
| 884 | xxx | xxx | xx | xx |
| 885 | xxx | xxx | xx | xx |
| 886 | xxx | xxx | xx | xx |
| 887 | xx | x | xx | x |
| 888 | xxx | x | xx | x |
| 889 | xxx | xxx | xx | xx |
| 890 | xxx | xxx | xx | xx |
| 891 | xxx | xxx | xx | xx |
| 892 | x | x | x | x |
| 893 | x | x | x | x |
| 894 | x | x | xx | x |
| 895 | xxx | xxx | xx | xx |
| 896 | xxx | xxx | xx | xx |
| 897 | xxx | xxx | xx | xx |
| 898 | x | x | x | x |
| 899 | — | — | — | — |
| 900 | xx | x | x | x |
| 901 | xx | xx | xx | xx |
| 902 | x | x | xx | x |
| 903 | xx | xxx | xx | xx |
| 904 | x | x | x | x |
| 905 | xxx | xxx | xx | xx |
| 906 | — | — | — | — |
| 907 | x | x | xx | x |
| 908 | xxx | xxx | xx | xx |
| 909 | — | — | — | — |
| 910 | xxx | xx | xx | x |
| 911 | x | x | x | x |
| 912 | xxx | x | xx | x |
| 913 | x | x | xx | x |
| 914 | xxx | xxx | xx | xx |
| 915 | x | x | xx | xx |
| 916 | x | x | x | x |
| 917 | x | x | x | x |
| 918 | x | x | xx | x |
| 919 | x | x | x | x |
| 920 | xxx | xxx | xx | xx |
| 921 | x | x | xx | x |
| 922 | x | x | xx | xx |
| 923 | xx | xxx | xx | xx |
| 924 | — | — | — | — |
| 925 | xxx | xxx | xx | xx |
| 926 | x | x | xx | x |
| 927 | — | — | — | — |
| 928 | xxx | xxx | xx | xx |
| 929 | xxx | xxx | xx | xx |
| 930 | x | x | x | x |
| 931 | x | x | x | x |
| 932 | x | x | xx | x |
| 933 | x | x | x | x |
| 934 | xx | xxx | xx | xx |
| 935 | x | xxx | xx | xx |
| 936 | xxx | x | xx | x |
| 937 | — | — | — | — |
| 938 | xxx | xxx | xx | xx |
| 939 | xxx | xxx | xx | xx |
| 940 | xxx | xxx | xx | xx |
| 941 | xxx | xxx | xx | xx |
| 942 | xxx | xxx | xxx | xx |
| 943 | xxx | xxx | xx | xx |
| 944 | xxx | xxx | xx | xx |
| 945 | xxx | xxx | xx | xx |
| 946 | x | xxx | x | x |
| 947 | xxx | xxx | xxx | xx |
| 948 | x | x | x | x |
| 949 | xxx | xxx | xx | xx |
| 950 | xx | xx | xx | xx |
| 951 | xxx | xxx | xx | xx |
| 952 | xxx | xxx | xx | xx |
| 953 | xx | xxx | xx | xx |
| 954 | xxx | xxx | xx | xx |
| 955 | xxx | xxx | xx | xx |
| 956 | x | x | xx | x |
| 957 | xxx | xxx | xx | xx |
| 958 | xxx | xxx | xx | xx |
| 959 | xx | xxx | xx | xx |
| 960 | x | xx | x | xx |
| 961 | xxx | xxx | xx | xx |
| 962 | x | x | x | x |

TABLE 4-continued

Additional exemplary compounds of formulae (I and II).

| Cmd No. | M₁ Activity | M₄ Activity | M₁ Efficacy | M₄ Efficacy |
|---|---|---|---|---|
| 963 | — | — | — | — |
| 964 | — | — | — | — |
| 965 | x | xxx | xx | xx |
| 966 | xxx | x | xx | x |
| 967 | xx | xx | xx | xx |
| 968 | x | x | x | x |
| 969 | xxx | x | xx | x |
| 970 | xxx | xxx | xx | xx |
| 971 | xx | xx | xx | xx |
| 972 | xx | x | xx | x |
| 973 | x | x | xx | x |
| 974 | xxx | xxx | xx | xx |
| 975 | x | x | x | x |
| 976 | xxx | xxx | xx | xx |
| 977 | xxx | xxx | xx | xx |
| 978 | x | x | x | x |
| 979 | x | xxx | xx | xx |
| 980 | xxx | xxx | xxx | xx |
| 981 | xxx | xxx | xx | xx |
| 982 | x | x | x | x |
| 983 | xxx | xxx | xx | xx |
| 984 | xx | xxx | xx | xx |
| 985 | x | xx | xx | xx |
| 986 | xxx | xxx | xx | xx |
| 987 | xxx | xxx | xx | xx |
| 988 | xxx | xxx | xx | xx |
| 989 | xxx | x | xx | x |
| 990 | xx | x | xx | xx |
| 991 | xxx | xxx | xx | xx |
| 992 | x | x | xx | xx |
| 993 | xxx | xxx | xx | xx |
| 994 | xxx | xxx | xx | xx |
| 995 | x | xx | xx | xx |
| 996 | x | x | x | x |
| 997 | — | — | — | — |
| 998 | x | xxx | x | xx |
| 999 | xxx | x | xx | x |
| 1000 | x | x | xx | xx |
| 1001 | — | — | — | — |
| 1002 | x | x | x | x |
| 1003 | xxx | xxx | xx | xx |
| 1004 | xxx | xxx | xx | xx |
| 1005 | x | xxx | x | xx |
| 1006 | x | x | xx | x |
| 1007 | — | — | — | — |
| 1008 | — | — | — | — |
| 1009 | xxx | xxx | xx | xx |
| 1010 | x | x | x | x |
| 1011 | — | — | — | — |
| 1012 | x | x | x | x |
| 1013 | x | x | x | x |
| 1014 | xxx | xxx | xx | xx |
| 1015 | xx | xxx | xx | x |
| 1016 | xxx | xxx | xx | xx |
| 1017 | x | xxx | xx | xx |

Additional examples of activities and efficacies of the muscarinic compounds of formulae (I and II) on modulating $M_1$ and $M_4$ receptors are shown below in Table 5. The compound activity for the $M_1$ and $M_4$ receptor is illustrated with "xxx" if activity was measured to be less than 2.0 µM, "xx" if activity was measured to be between 2.0 µM and 10 µM, and "x" if activity was measured to be greater than 10 µM. The efficacy for $M_1$ and $M_4$ modulation is illustrated with "xxx" if efficacy was calculated to be greater than 100%, "xx" if efficacy was calculated to be between 100% and 25%, "x" if efficacy was calculated to be less than 25%, and "-" if no data was available. It should be noted that 100% efficacy is the maximum response obtained with the Carbachol control.

TABLE 5

Additional compound activities and efficacies for modulating $M_1$ and $M_4$ receptors.

| Cmd No. | M₁ Activity | M₄ Activity | M₁ Efficacy | M₄ Efficacy |
|---|---|---|---|---|
| 1018 | — | — | — | — |
| 1019 | xxx | xxx | xx | xx |
| 1020 | xx | xx | xx | x |
| 1021 | — | — | — | — |
| 1022 | — | — | — | — |
| 1023 | — | — | — | — |
| 1024 | xx | xx | xx | x |
| 1025 | xx | xxx | xx | xx |
| 1026 | xx | xxx | xx | x |
| 1027 | xx | xx | xx | xx |
| 1028 | xx | xxx | xx | xx |
| 1029 | xx | xx | xx | xx |
| 1030 | xx | xx | xx | xx |
| 1031 | xxx | xxx | xx | xx |
| 1032 | xx | xxx | xx | xx |
| 1033 | xx | xxx | xx | xx |
| 1034 | xxx | xxx | xx | xx |
| 1035 | xxx | xxx | xxx | xx |
| 1036 | xxx | xxx | xx | xx |
| 1037 | xx | xxx | xx | xx |
| 1038 | xx | xxx | xx | xx |
| 1039 | xx | xxx | xx | xx |
| 1040 | xxx | xxx | xx | xx |
| 1041 | xx | xx | xx | xx |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A compound selected from:

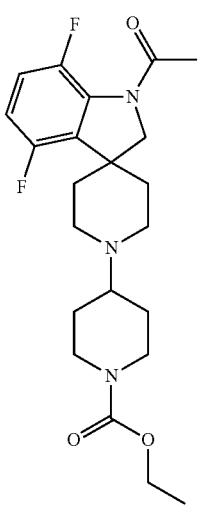

431

433
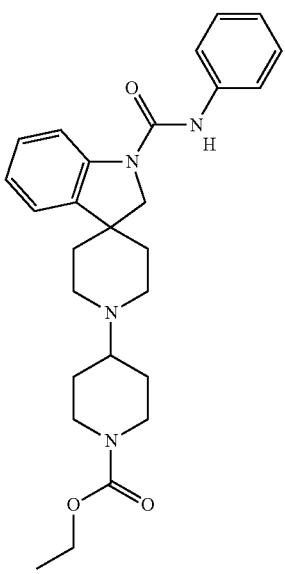
434
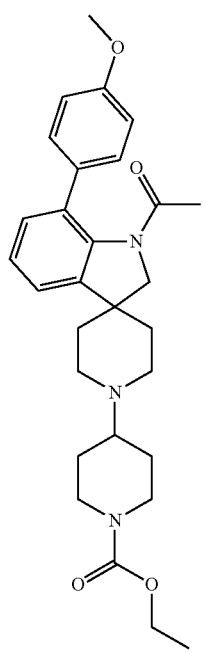
435
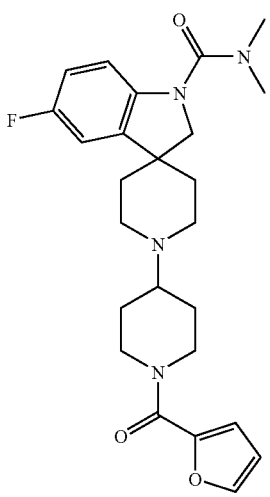
440
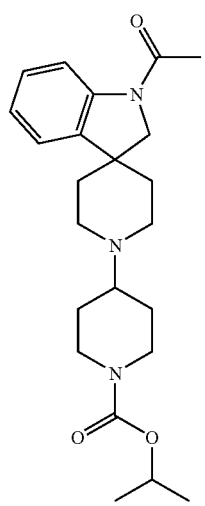
441
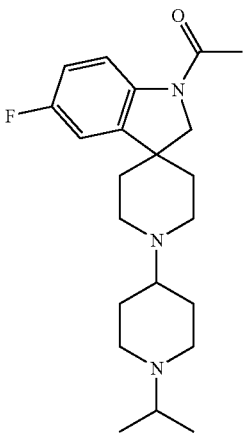

541
446
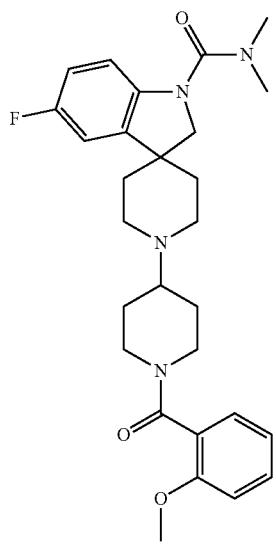
450
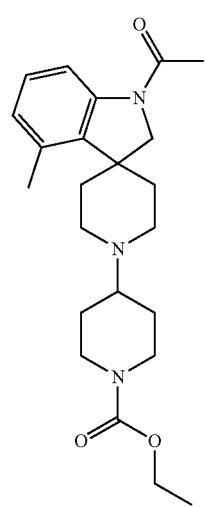
453
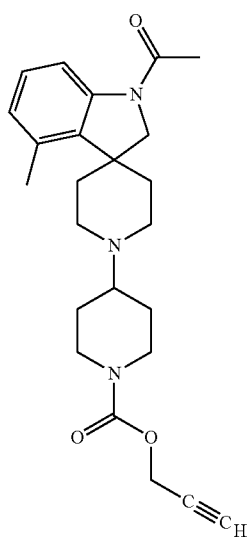
542
454
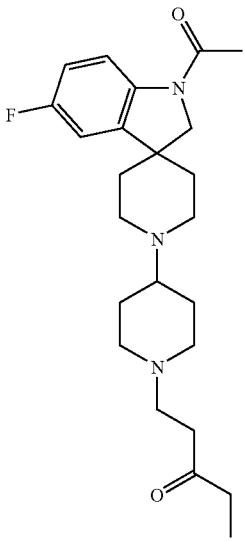
456
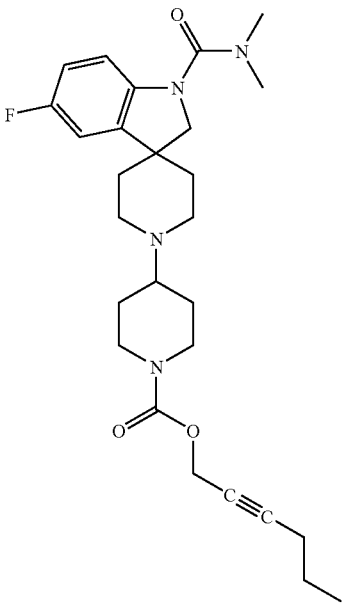
458
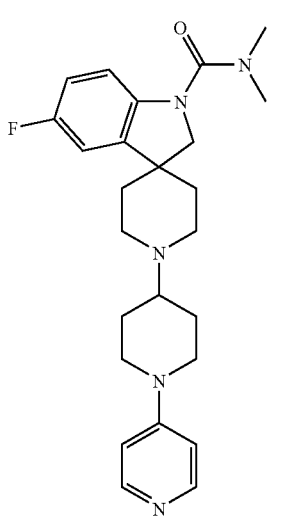

| 543 | 544 |
|---|---|
| -continued | -continued |
460 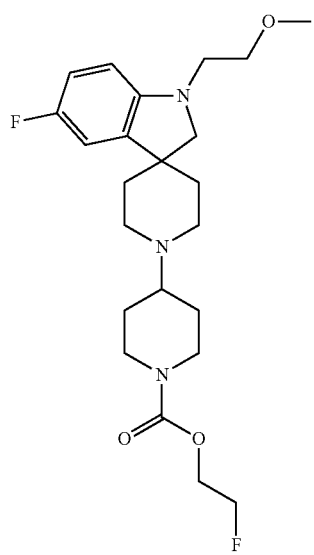
464 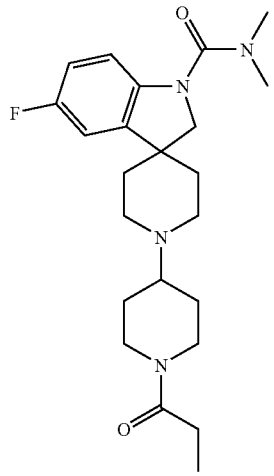
461 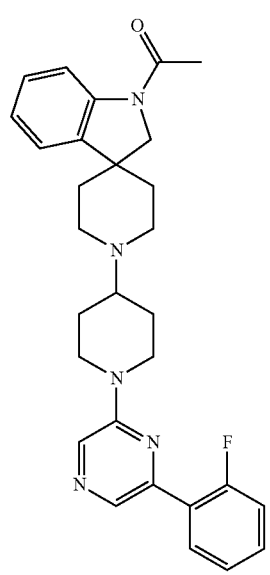
467 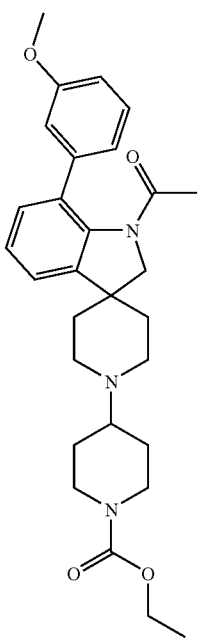
463 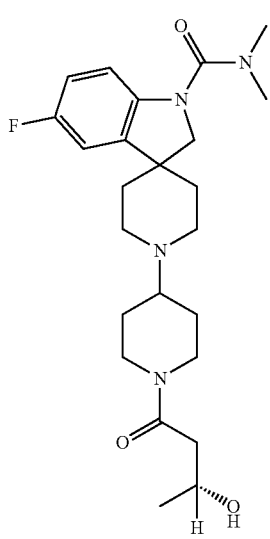
469 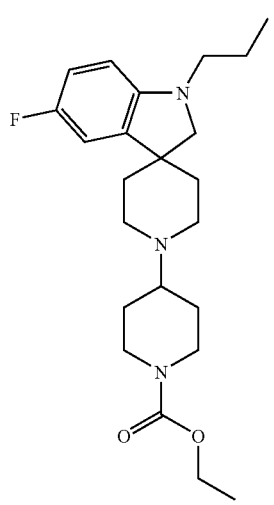

| 471 | 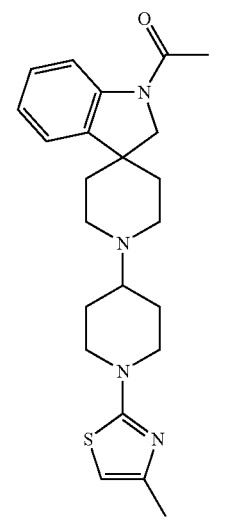 |
|---|---|
| 472 | 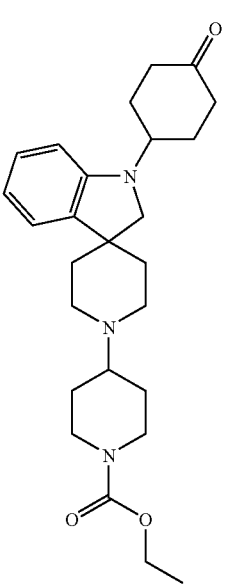 |
| 474 | 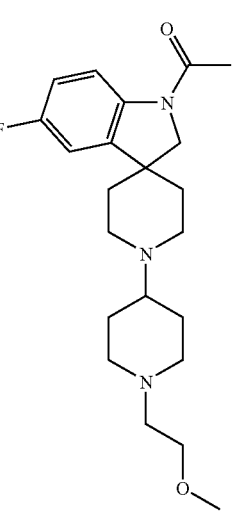 |
| 477 | 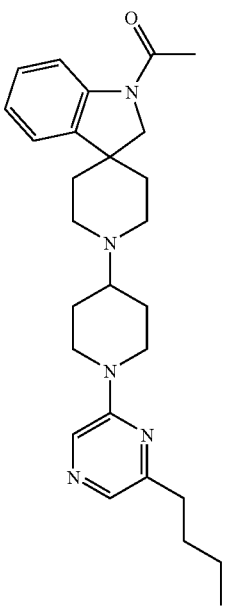 |
|---|---|
| 489 | 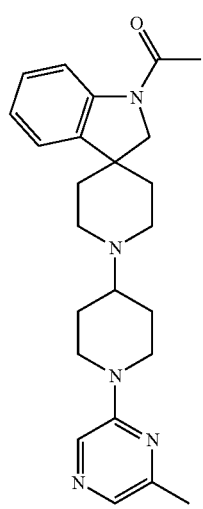 |

547
-continued
491
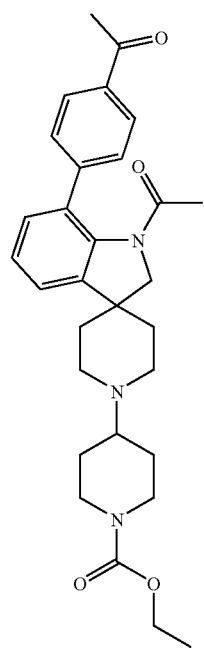
492
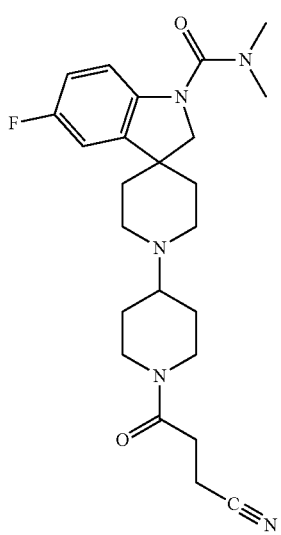
548
-continued
494
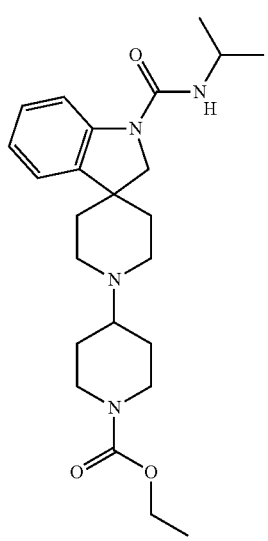
496
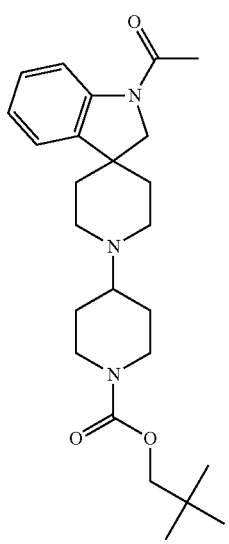
497
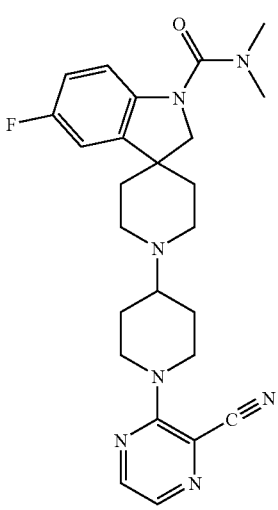

549
-continued
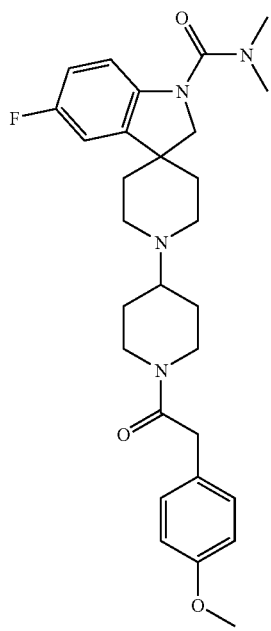
500
499
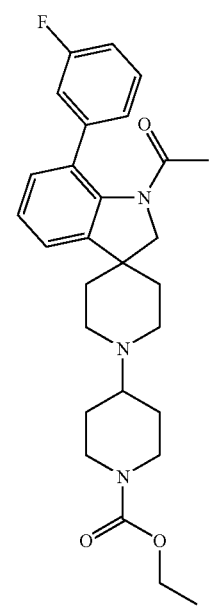
550
-continued
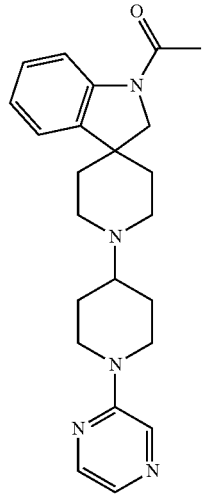
505
508
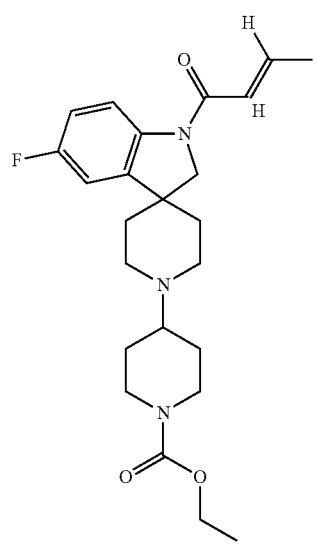
509
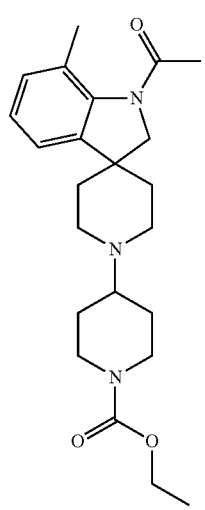

551
-continued
517
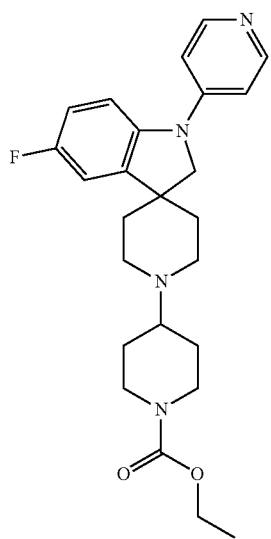
520
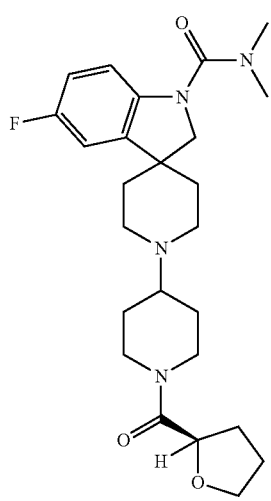
522
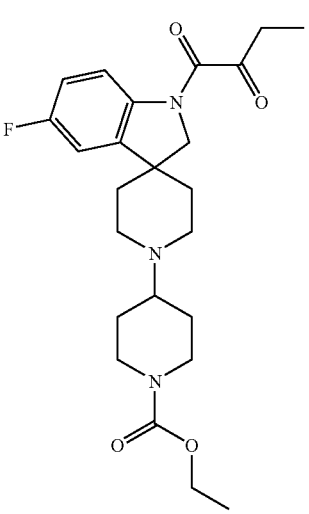
552
-continued
526
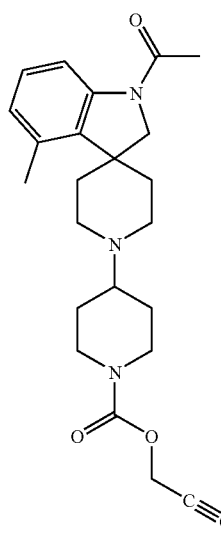
528
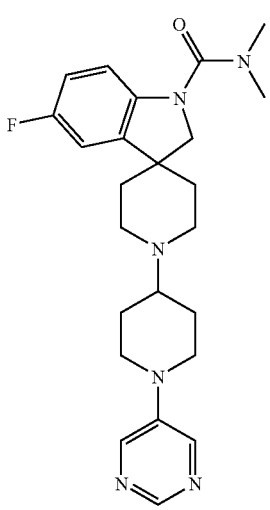
531
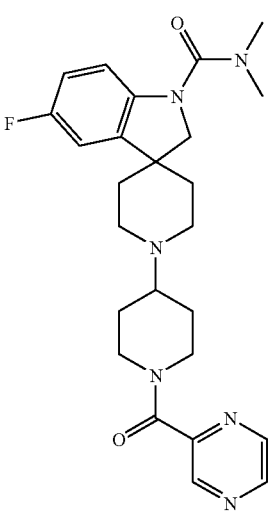

553
-continued
534
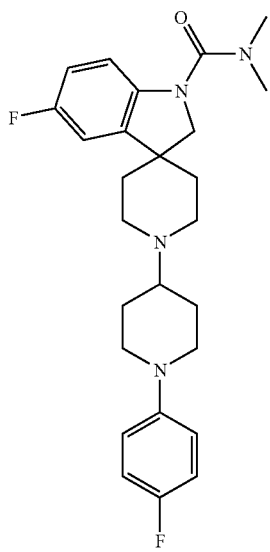
535
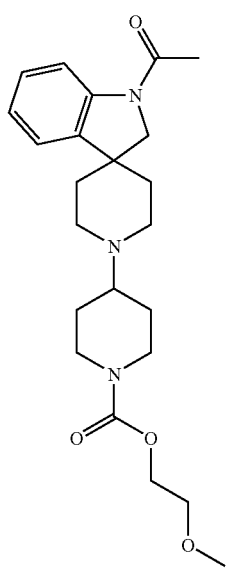
539
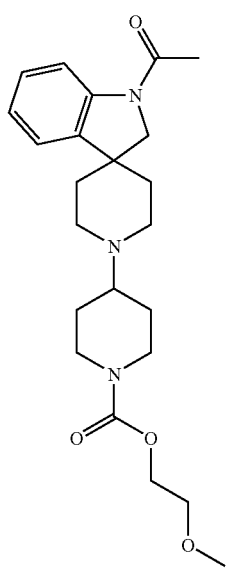
554
-continued
543
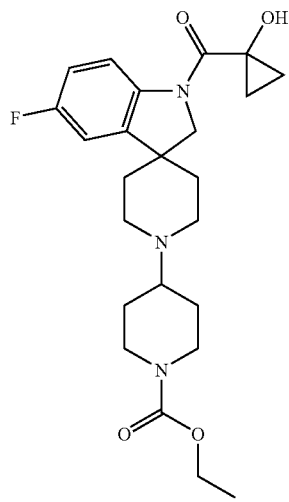
544
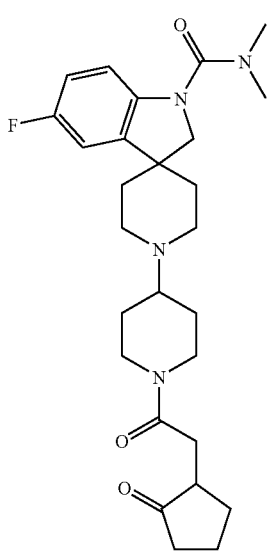
545
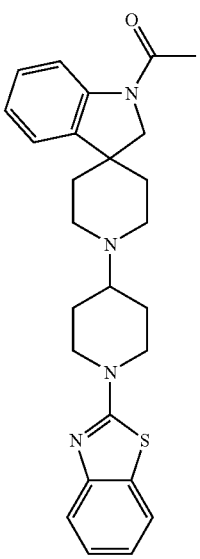

547
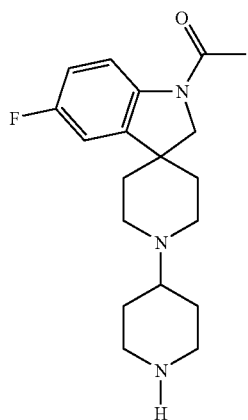
551
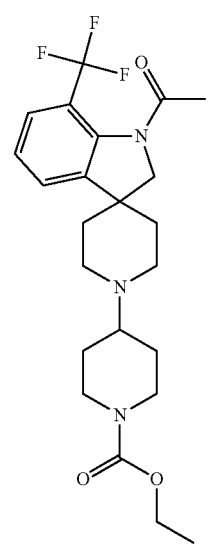
552
553
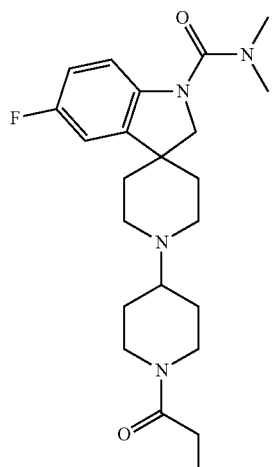
554
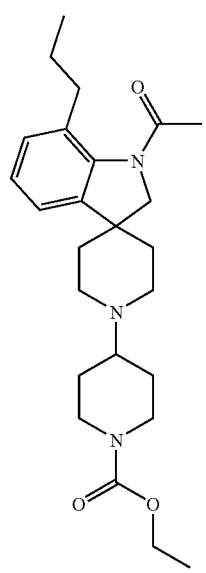
559
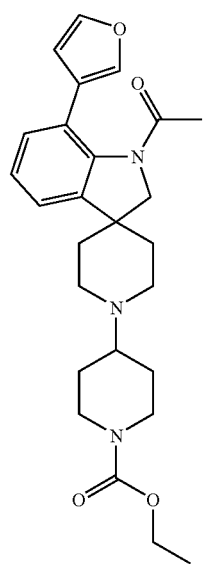

557
-continued
556
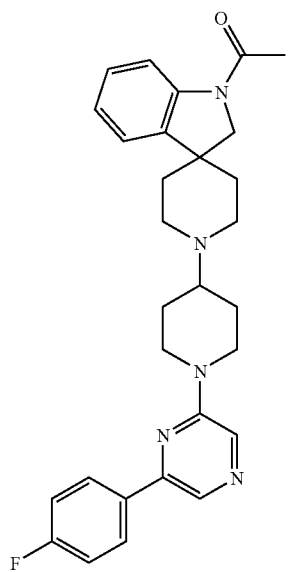
560
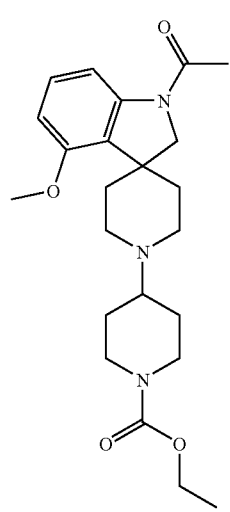
561
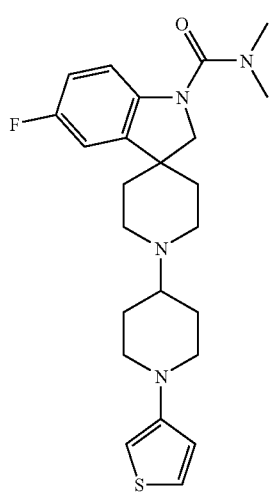
558
-continued
563
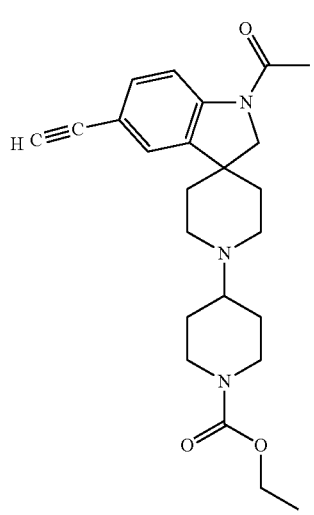
567
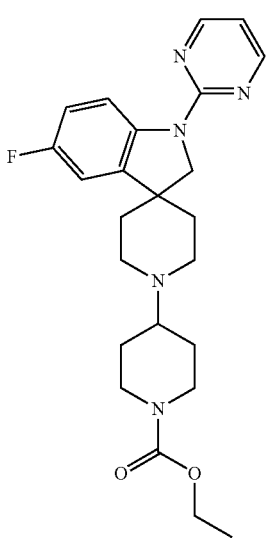
565
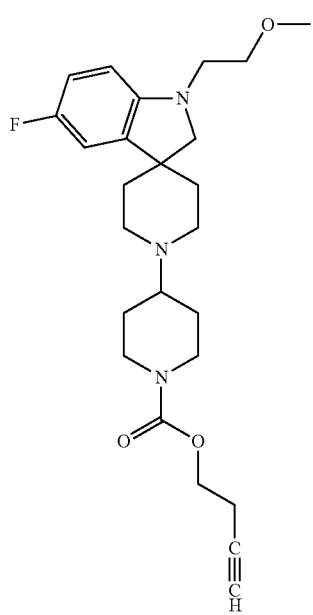

559
-continued
572
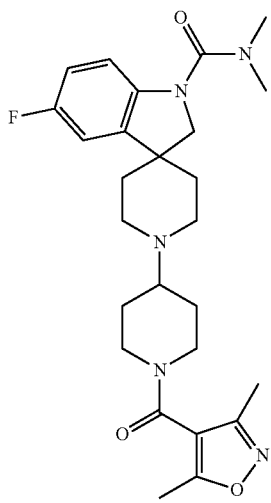
571
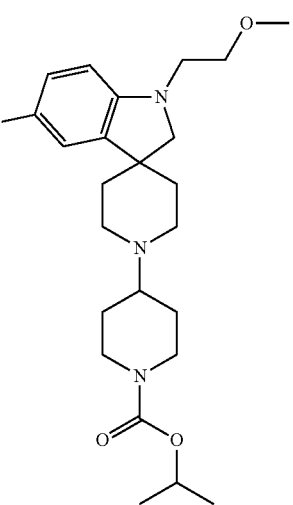
574
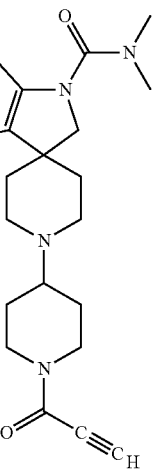
560
-continued
579
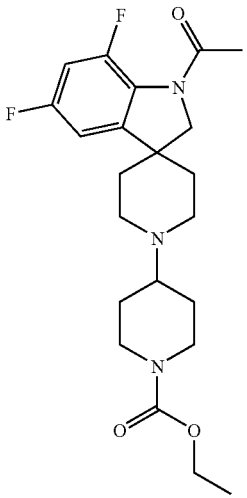
588
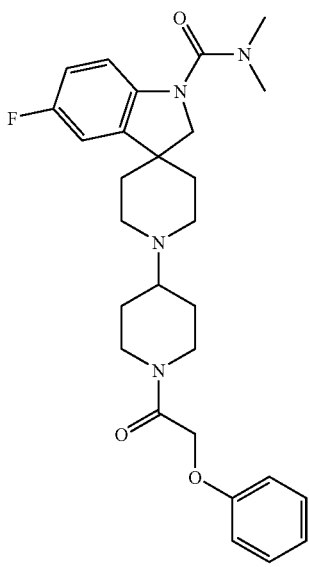
589
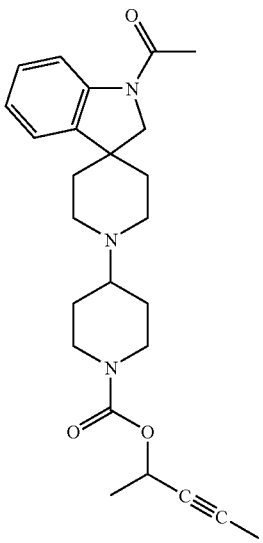

561
-continued
590
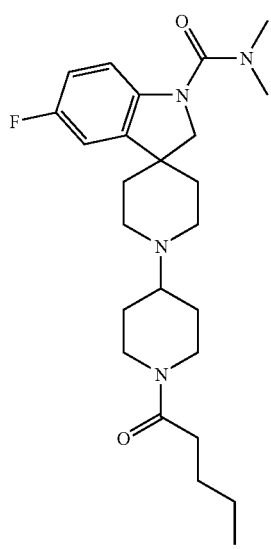
585
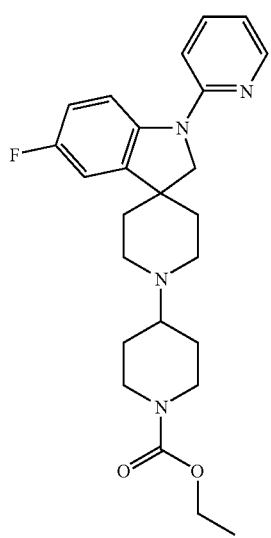
592
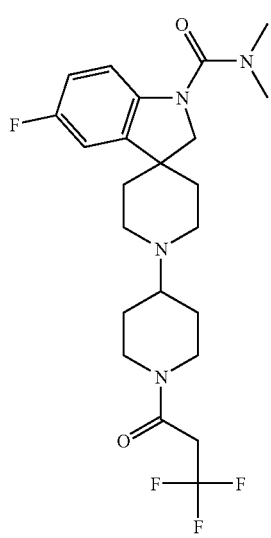
562
-continued
596
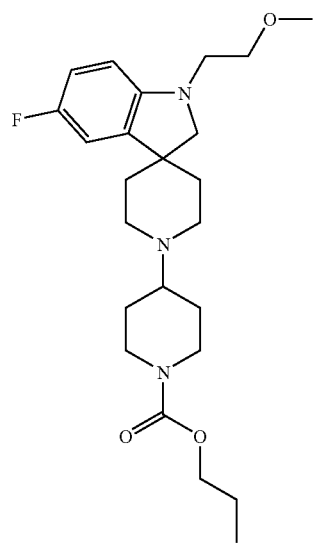
594
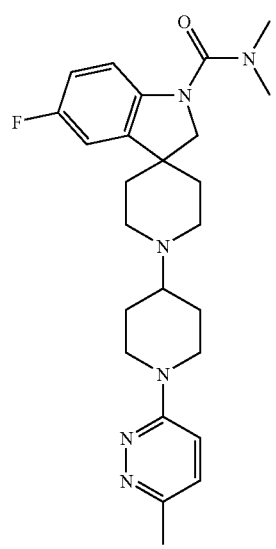
595
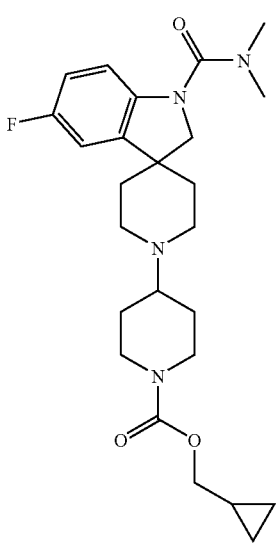

| 563 -continued | | 564 -continued | |
|---|---|---|---|
| 598 | 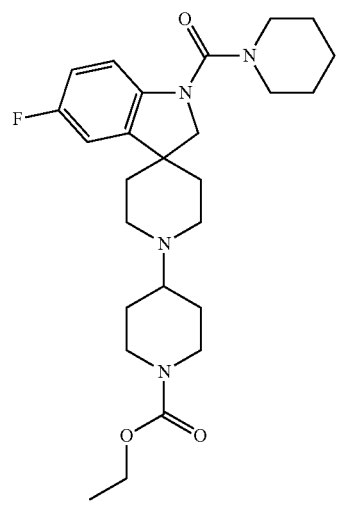 | 611 | 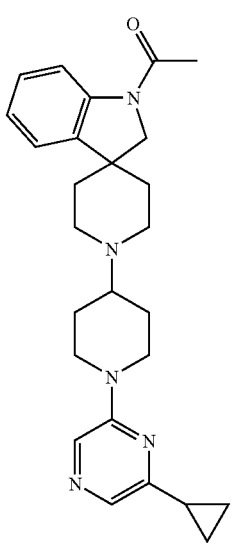 |
| 603 | 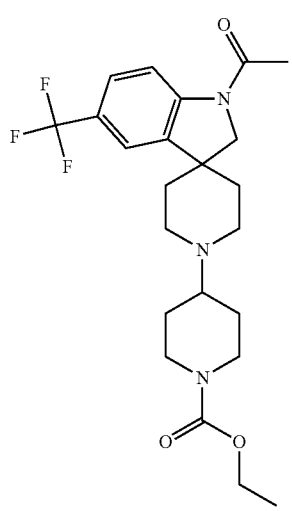 | 614 | 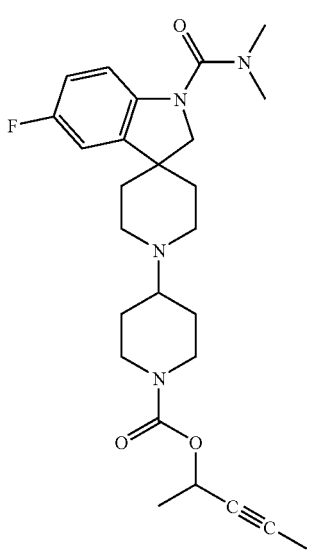 |
| 610 | 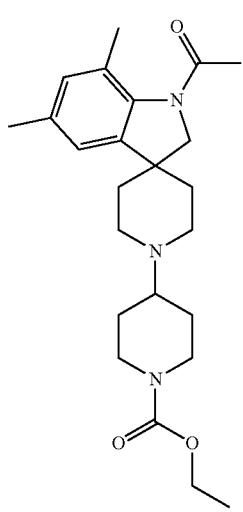 | 615 | 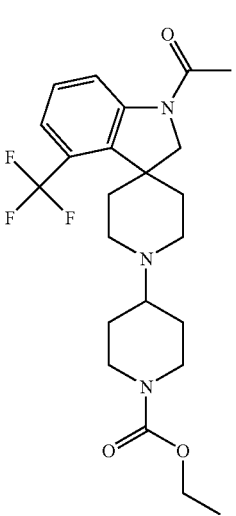 |

| 565 -continued | | 566 -continued | |
|---|---|---|---|
| | 619 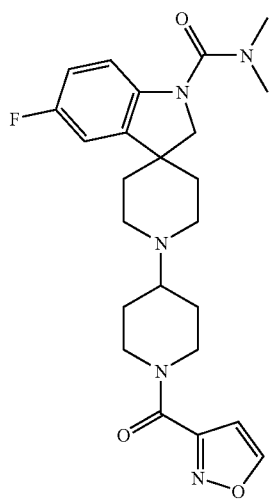 | | 629 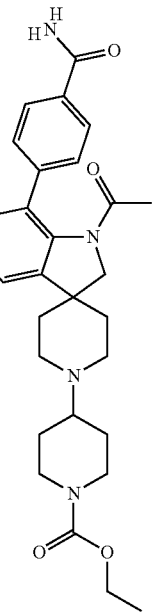 |
| | 620 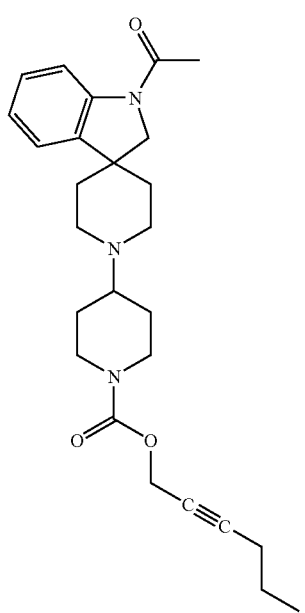 | | 630 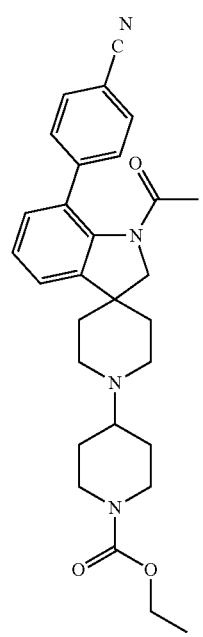 |
| | 626 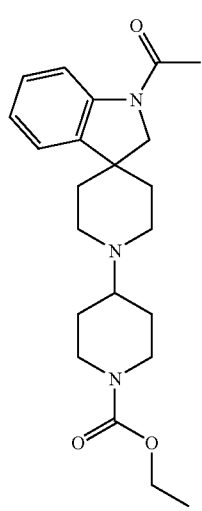 | | |

567
-continued
| | |
|---|---|
| 633 | 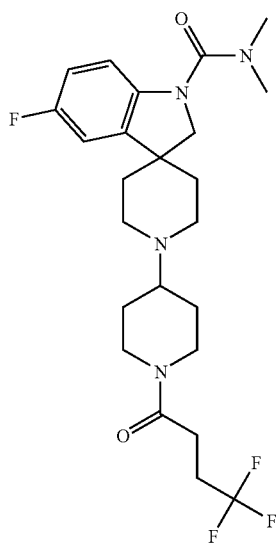 |
| 653 | 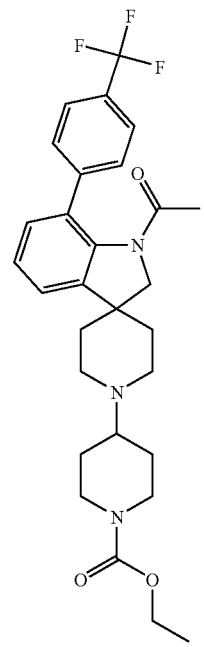 |
568
-continued
| | |
|---|---|
| 648 | 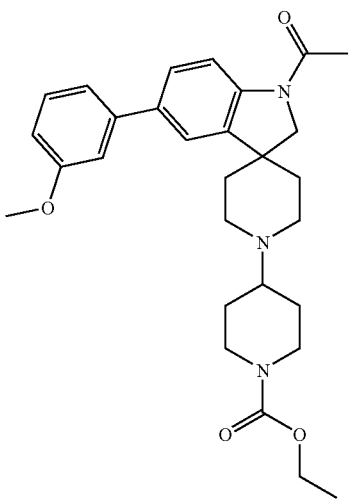 |
| 649 | 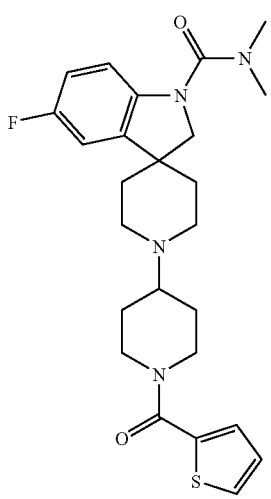 |
| 656 | 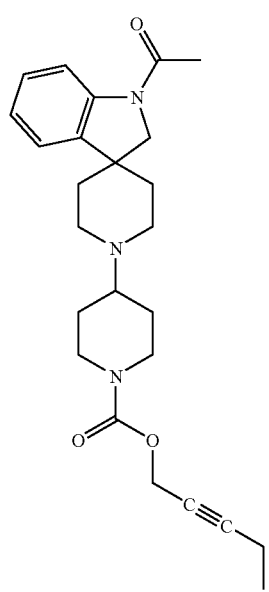 |

658
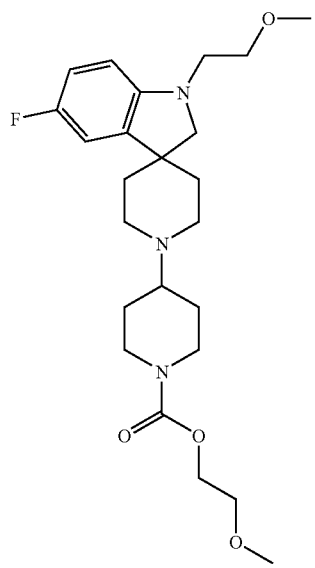
659
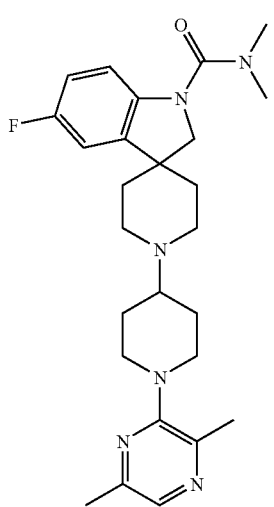
662
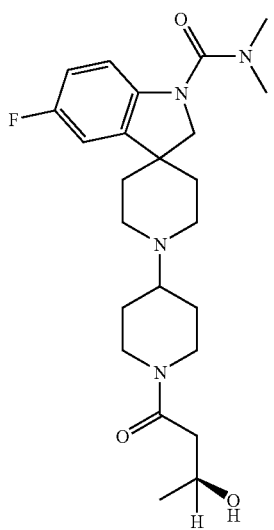
661
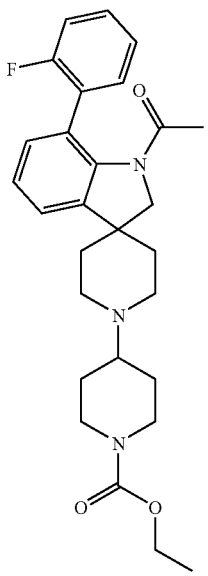
665
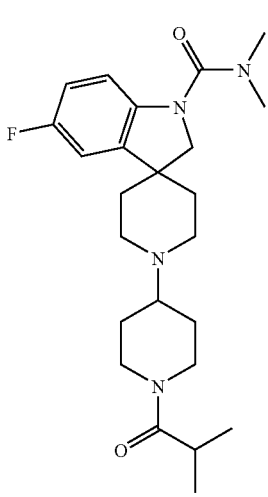
672
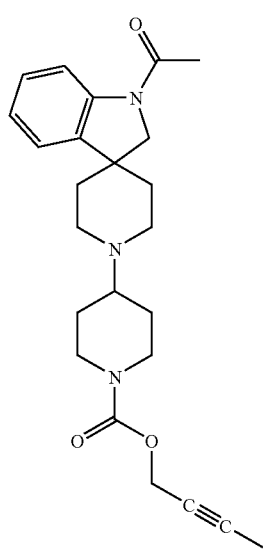

674
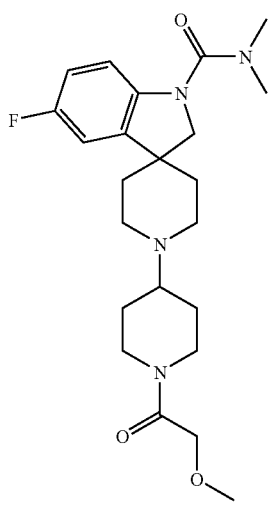
683
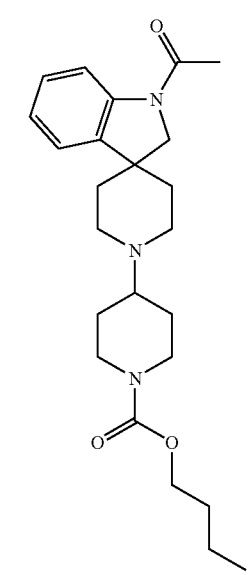
685
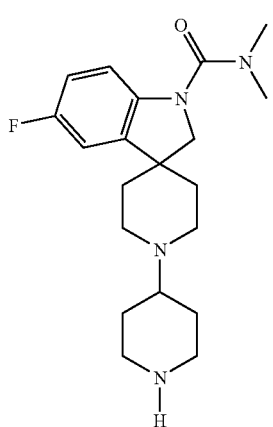
677
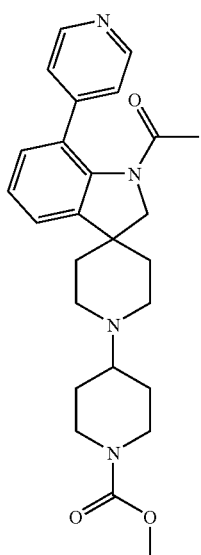
678
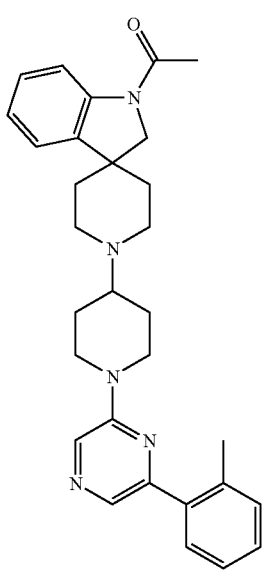
688
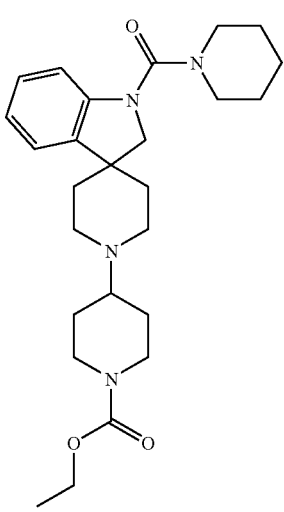

| | |
|---|---|
| 689 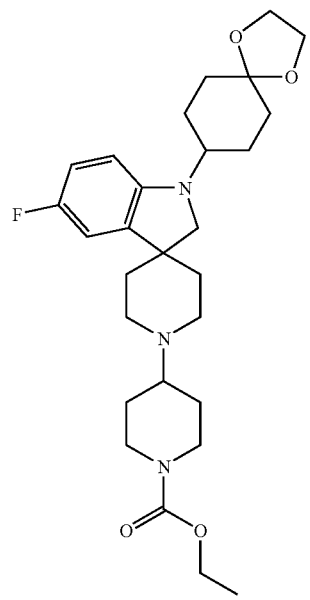 | 697 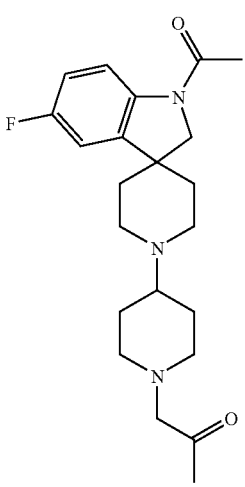 |
| 693 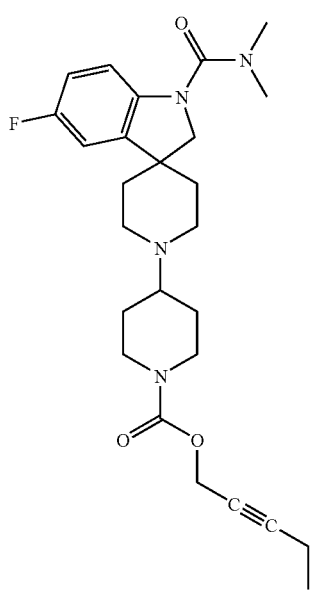 | 699 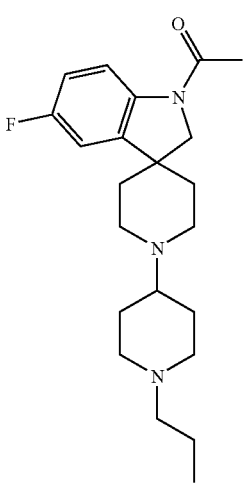 |
| 694 | 700 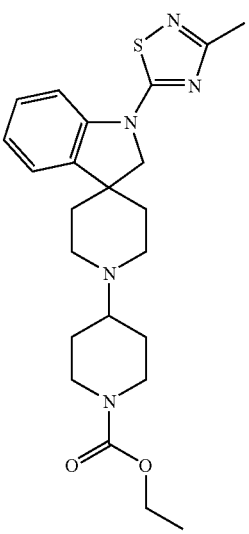 |

575
-continued
701
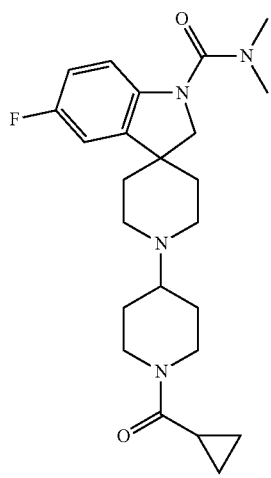
707
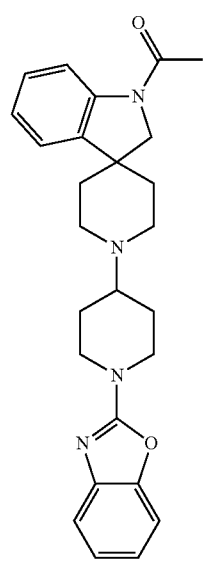
710
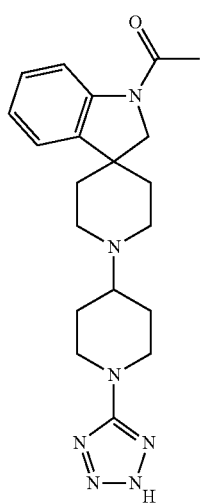
576
-continued
711
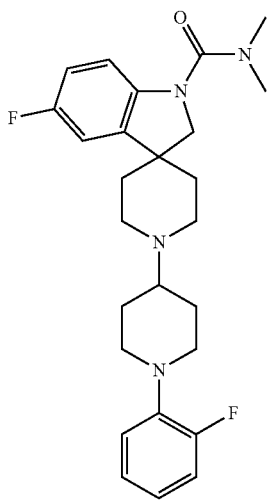
712
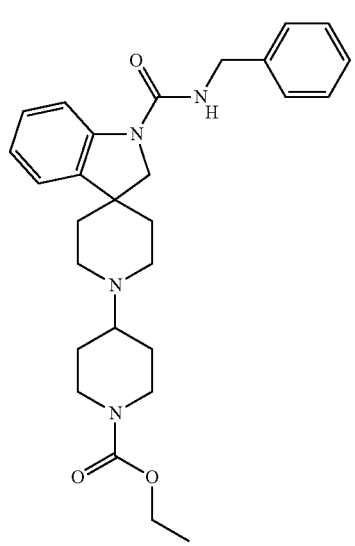
714
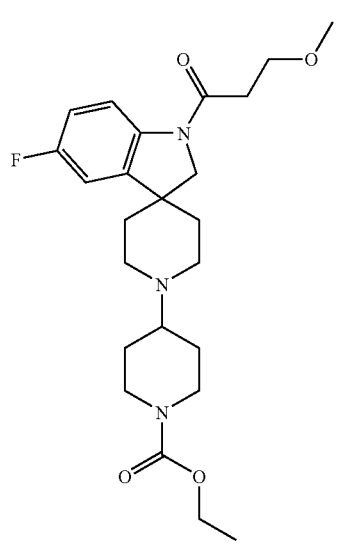

717 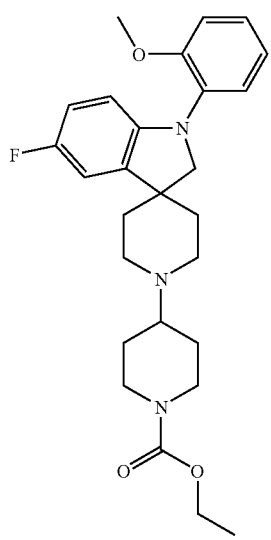
718 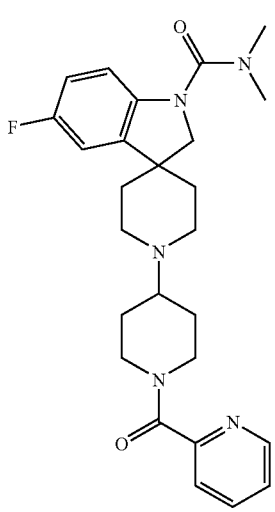
719 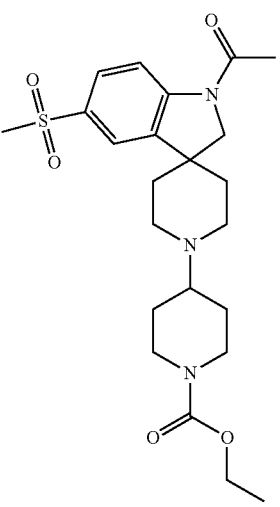
720 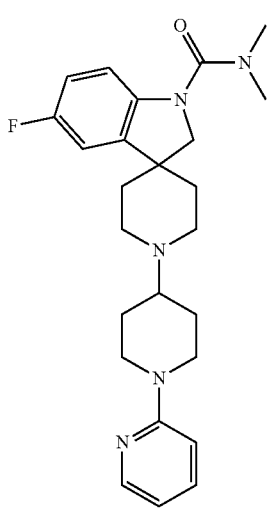
721 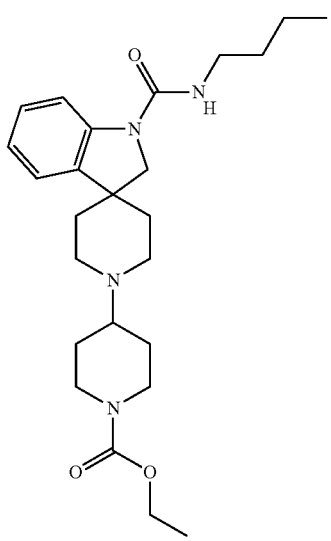
724 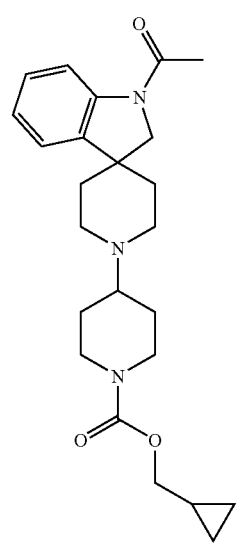

| 735 | 729 |
|---|---|
| 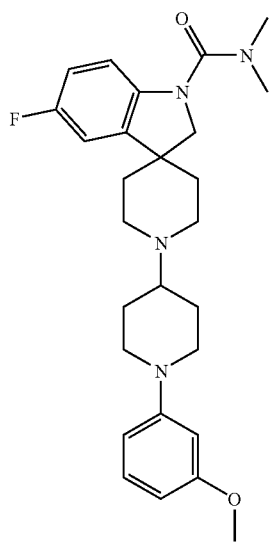 | 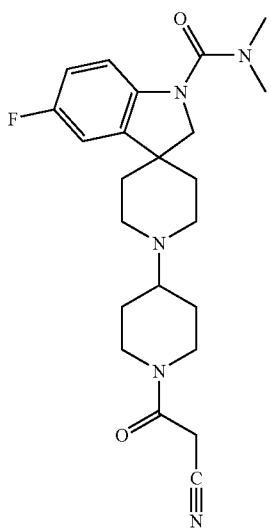 |
| 727 | |
| 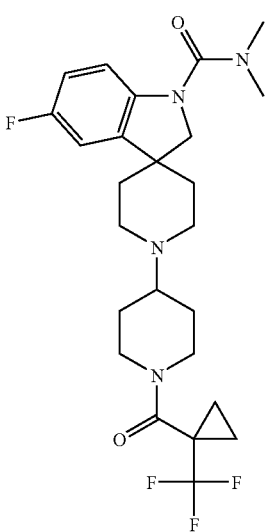 | 730 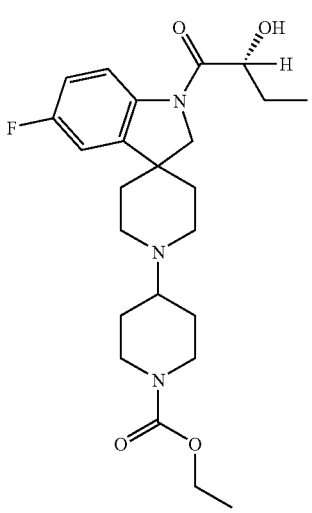 |
| 728 | 750 |
| 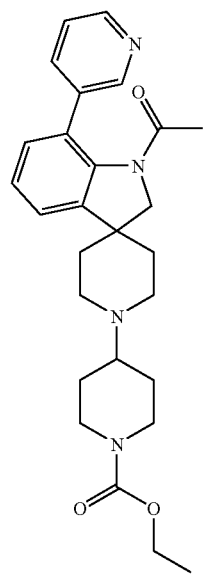 | 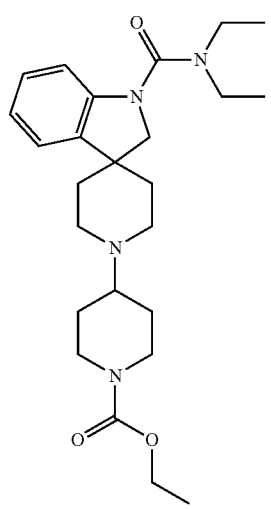 |

581
-continued
751
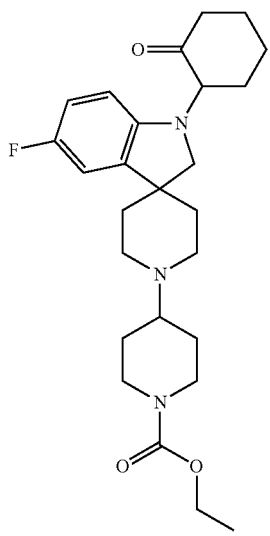
752
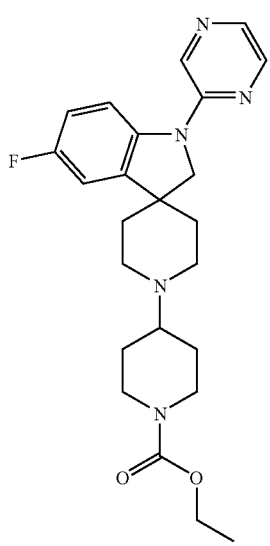
753
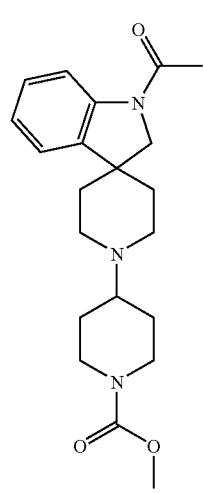
582
-continued
756
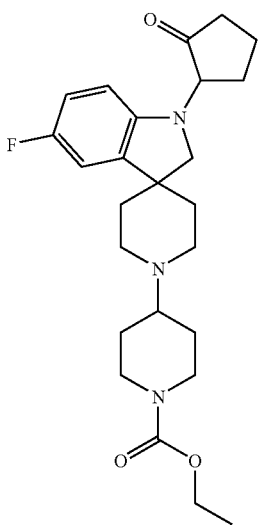
760
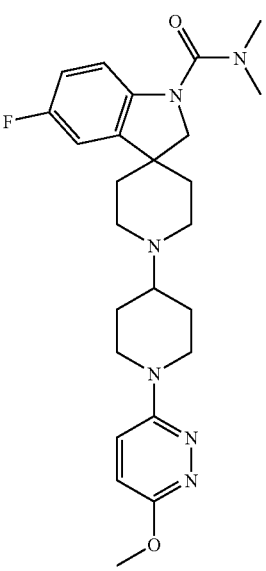
762
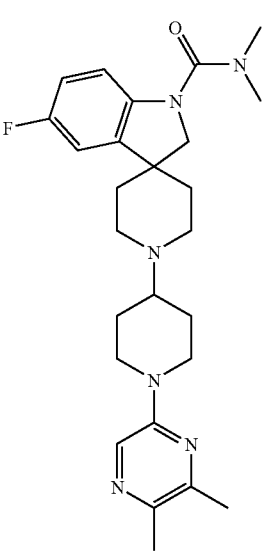

| 770 | 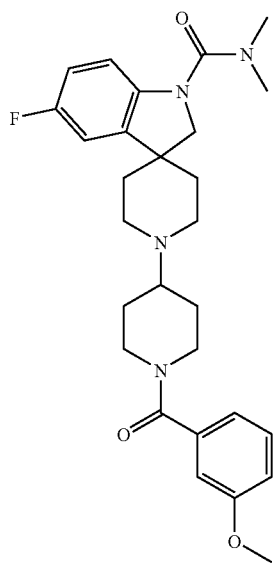 |
|---|---|
| 767 | 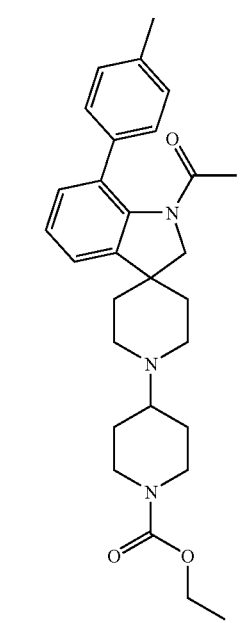 |
| 769 | 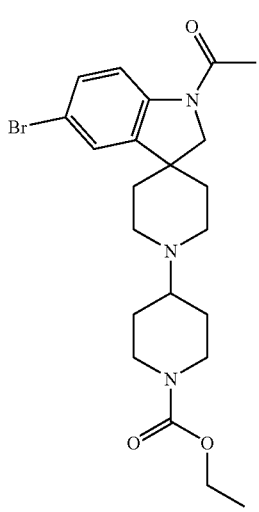 |
|---|---|
| 781 | 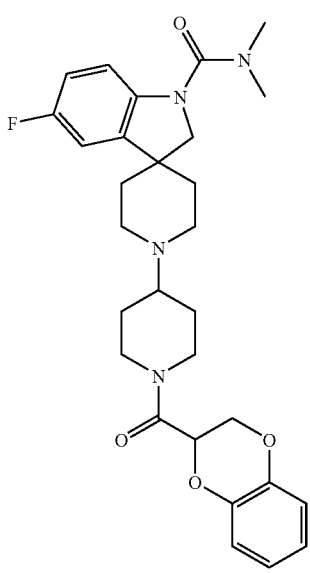 |
| 791 | 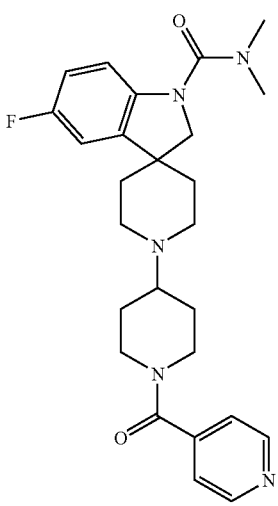 |

| 790 | 799 |
|---|---|
| 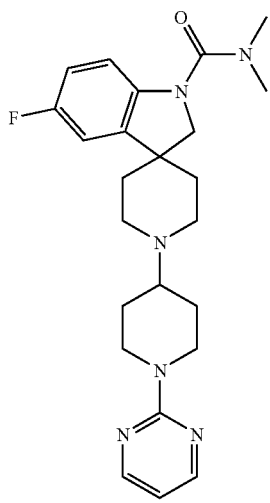 | 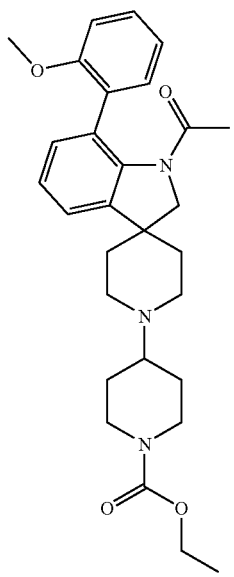 |
| 794 | 800 |
| 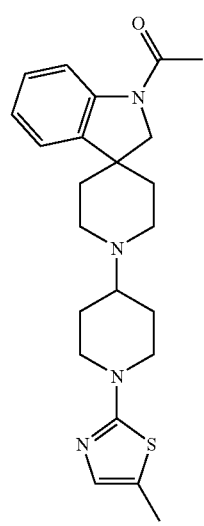 | 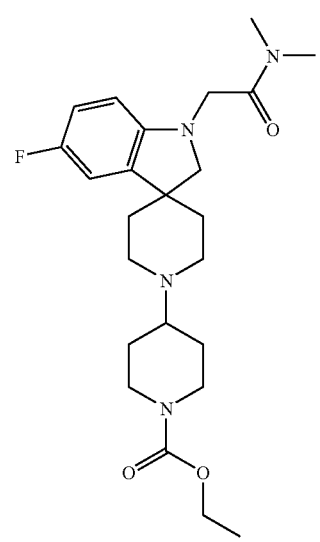 |
| 795 | 804 |
| | 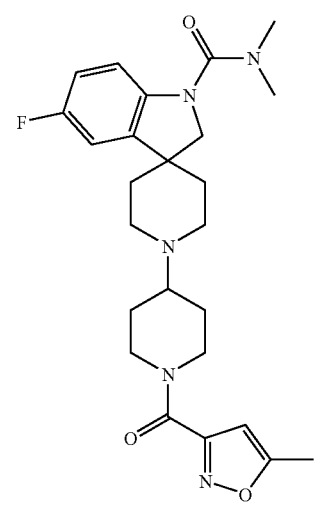 |

808 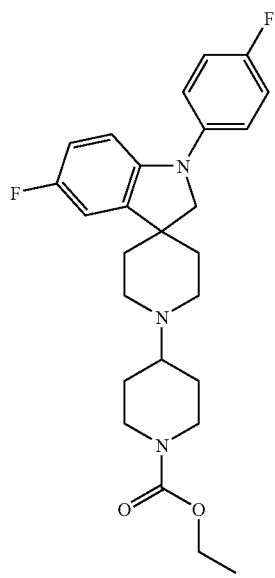
812 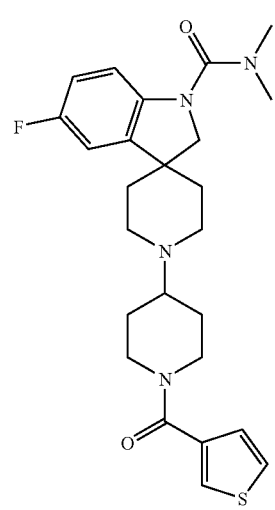
814 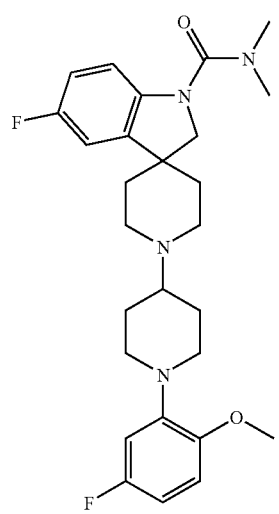
824 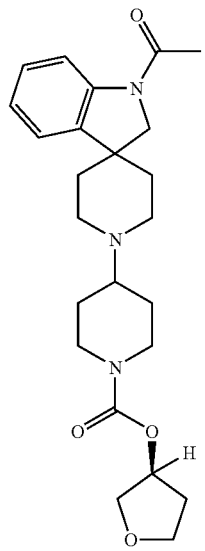
825 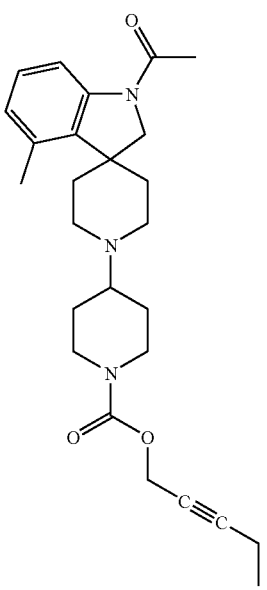
822 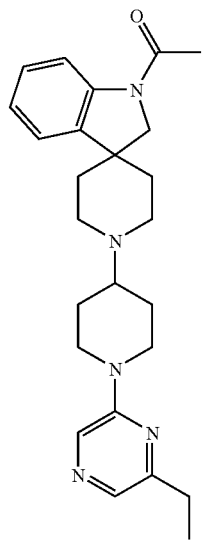

829 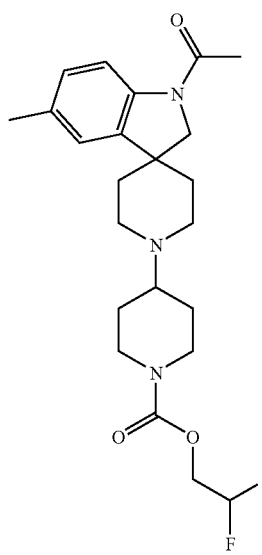
838 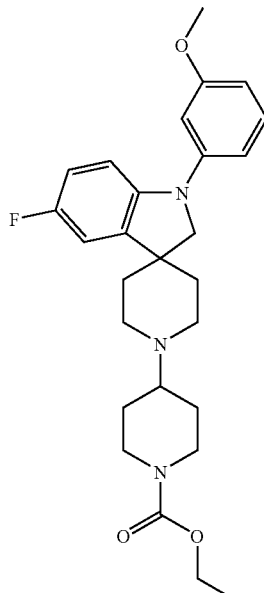
837 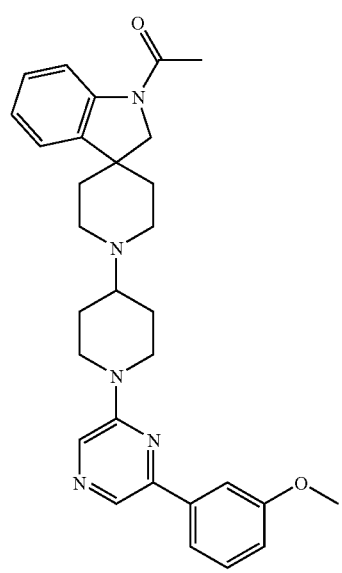
839 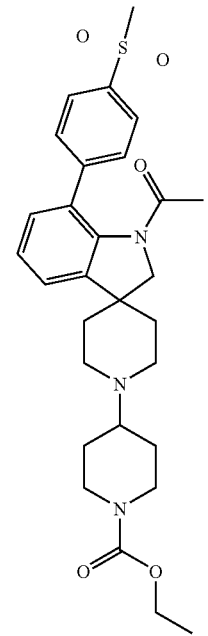

591
-continued
844
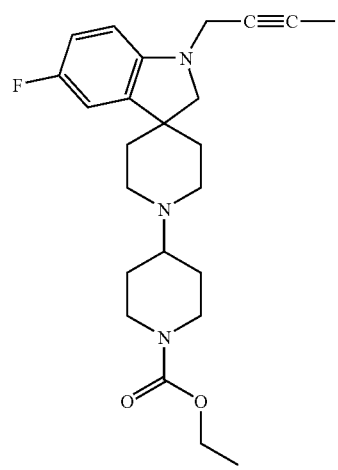
847
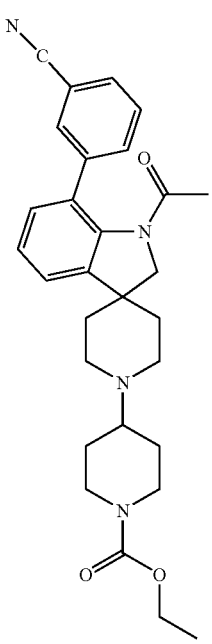
851
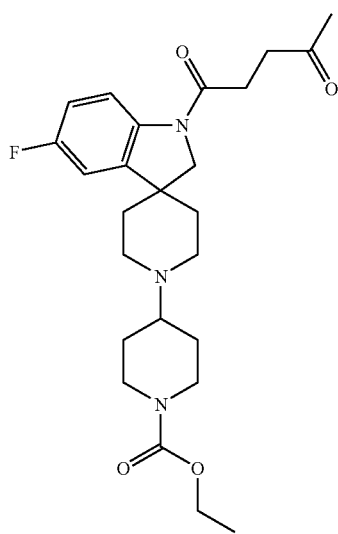
592
-continued
855
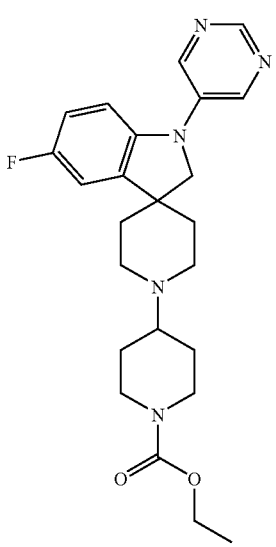
853
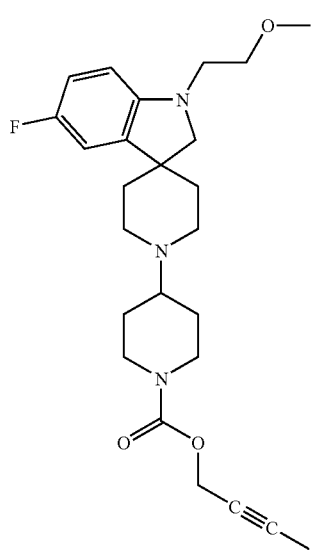
857
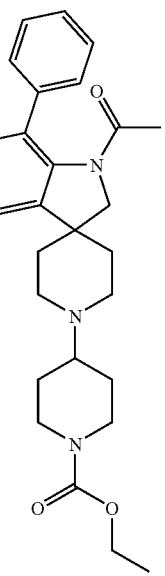

593
-continued
862
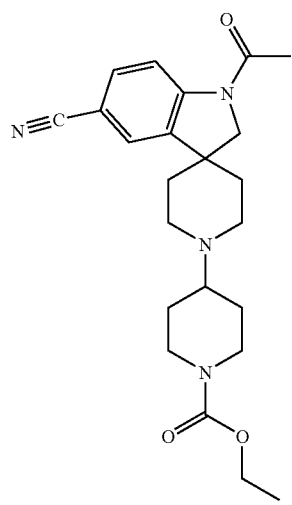
859
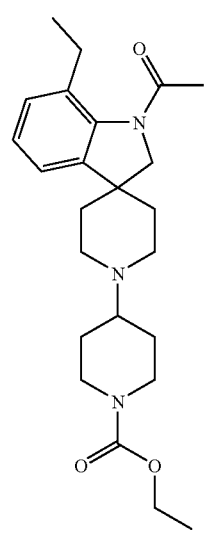
866
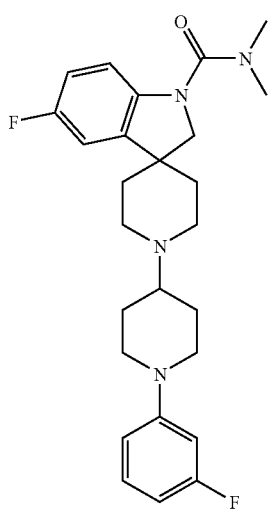
594
-continued
872
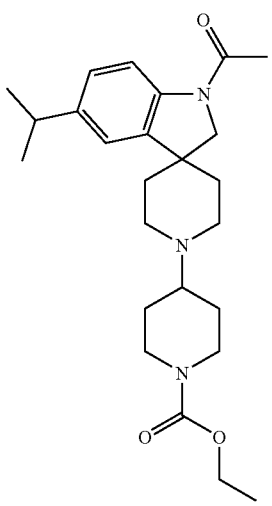
885
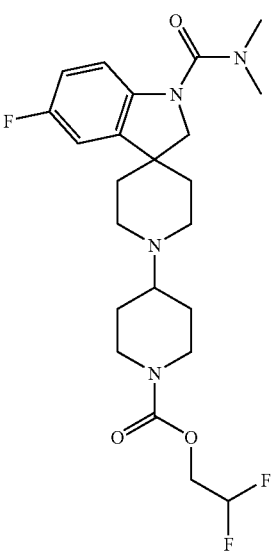
879
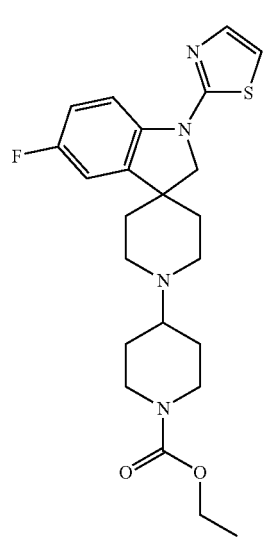

880 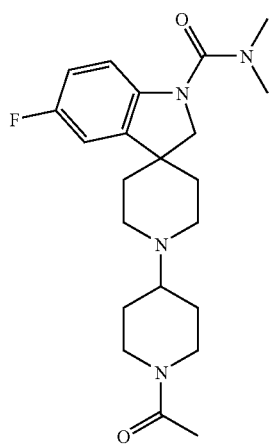
890 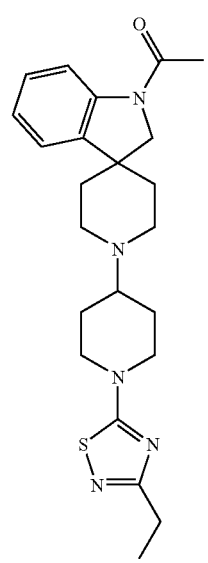
891 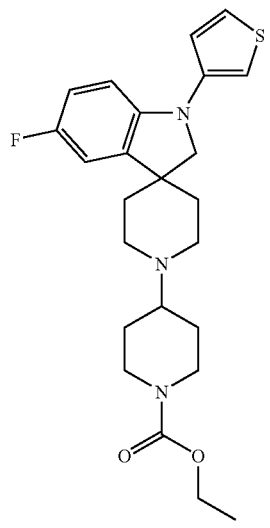
887 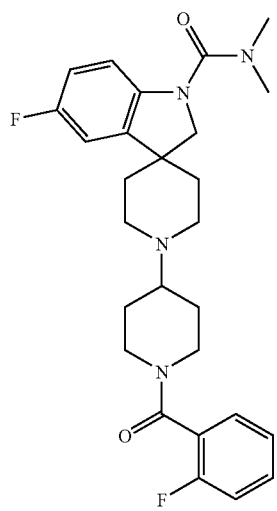
893 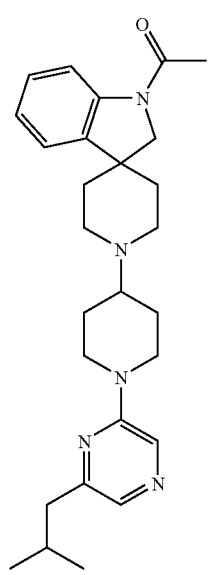
894 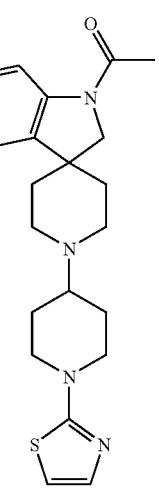

895 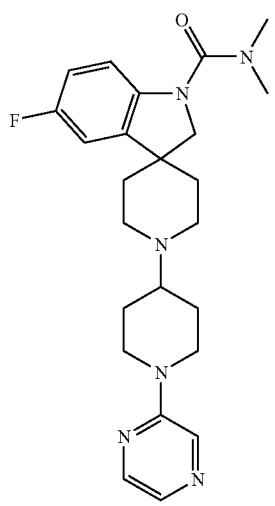
896 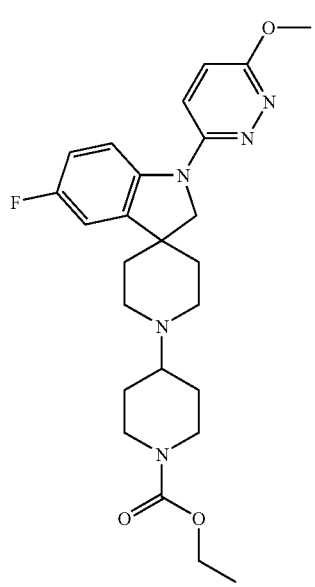
898 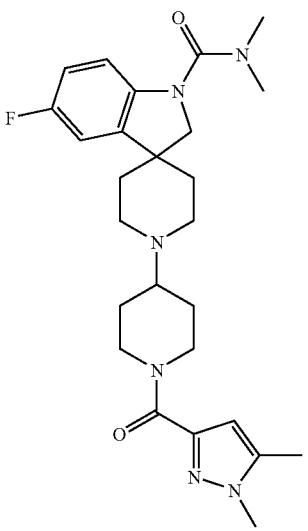
905 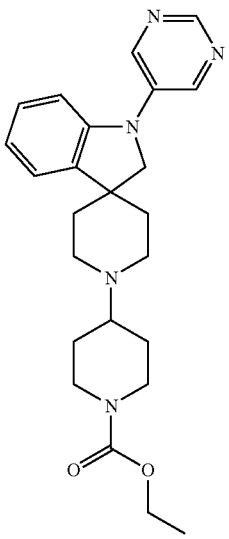
900 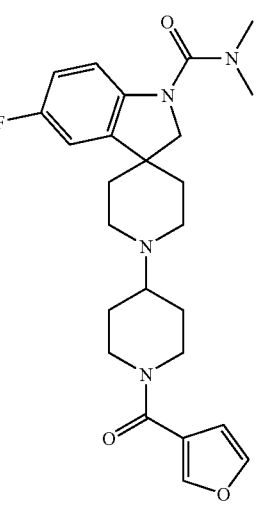
907 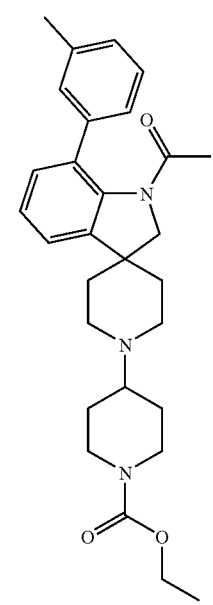

908
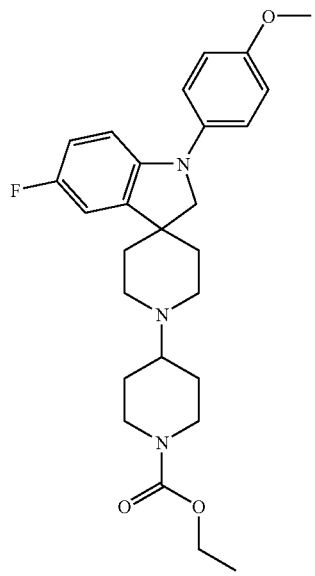
903
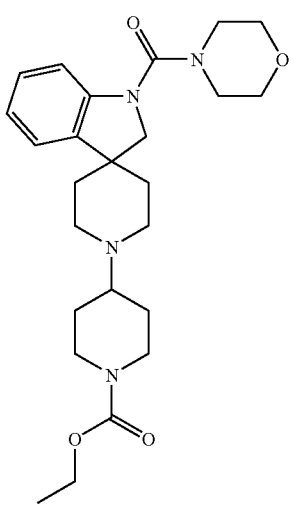
910
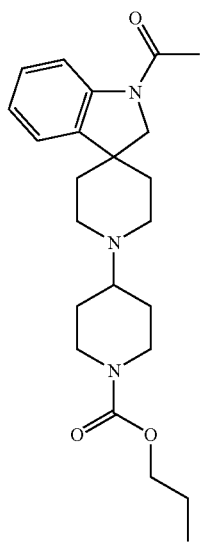
911
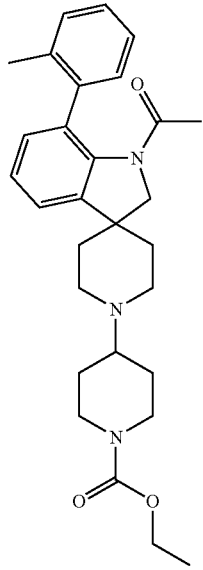
914
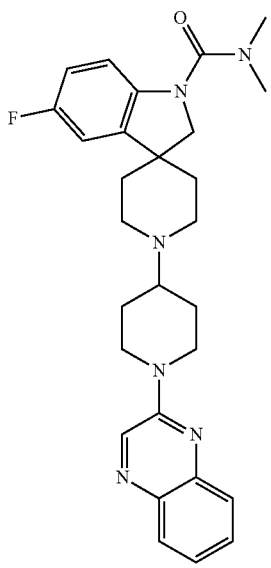
917
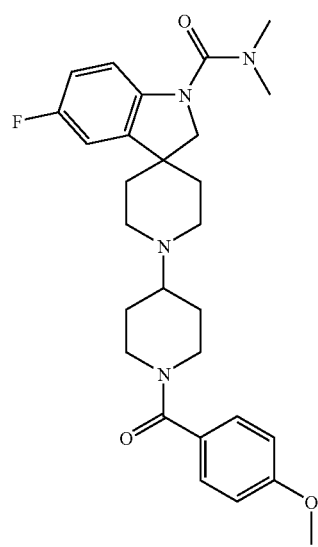

| 918 | 930 |
|---|---|
| 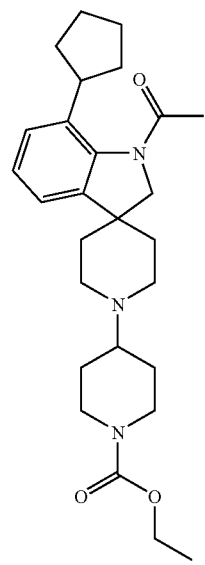 | 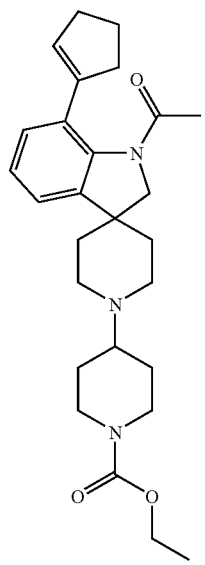 |
| 921 | 932 |
| 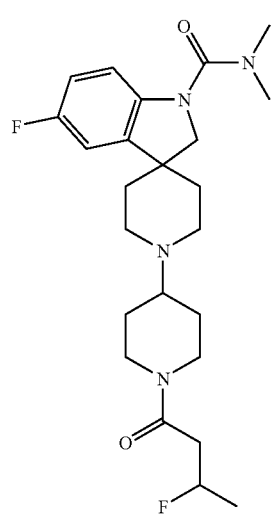 | 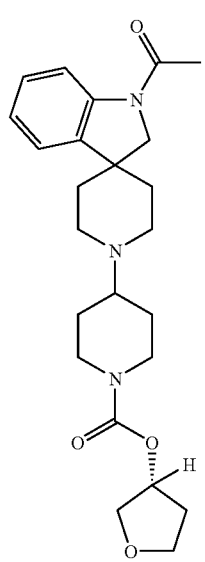 |
| 938 | 941 |
| 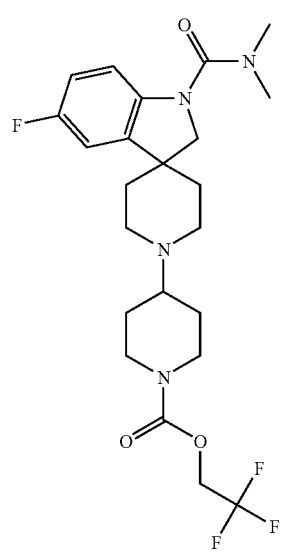 | 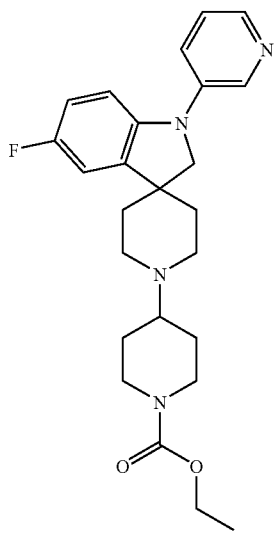 |

603
-continued
942
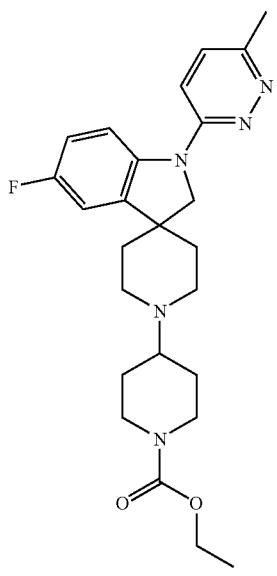
943
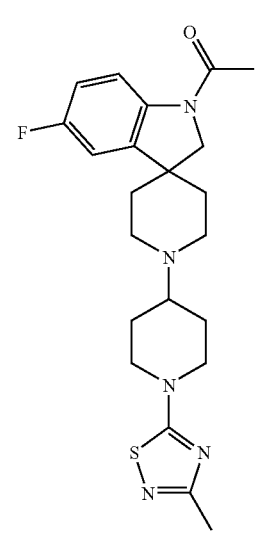
944
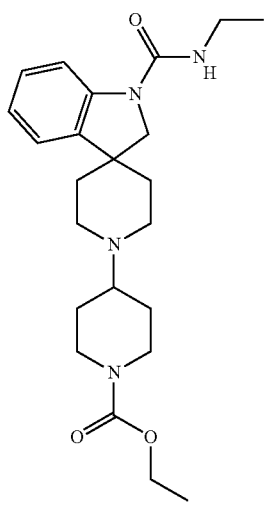
604
-continued
947
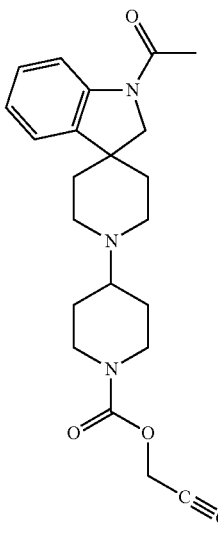
950
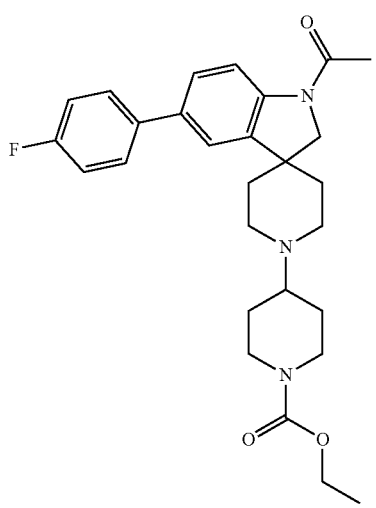
951
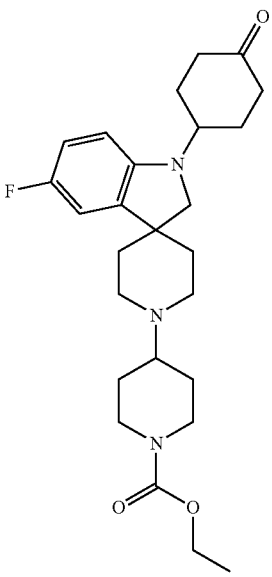

| 605 -continued | | 606 -continued | |
|---|---|---|---|
| 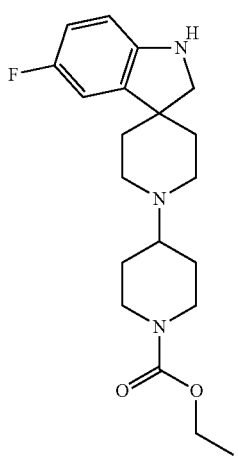 | 952 | 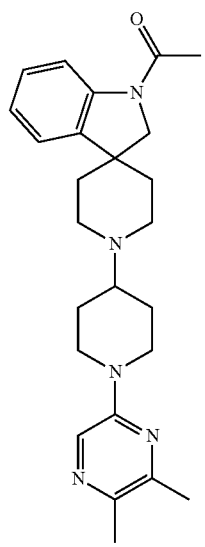 | 953 |
| 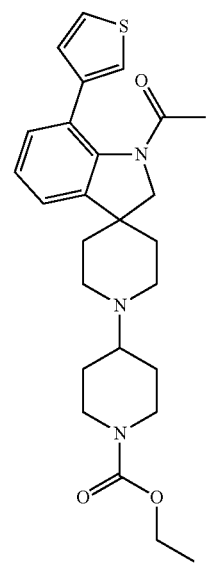 | 956 | 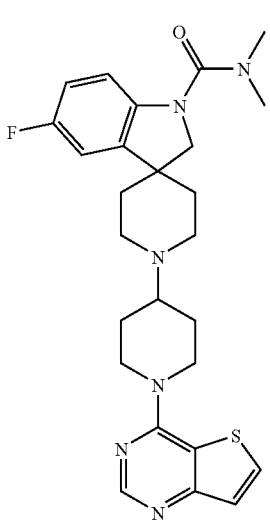 | 965 |
| 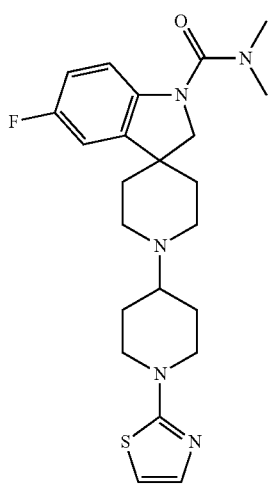 | 957 | 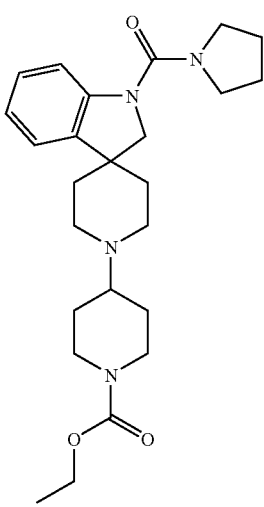 | 959 |

967 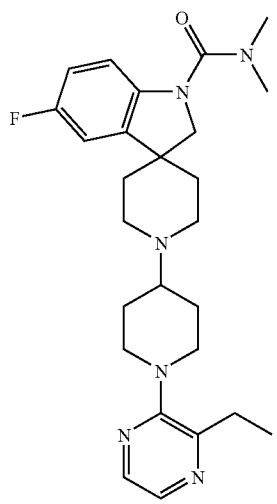
972 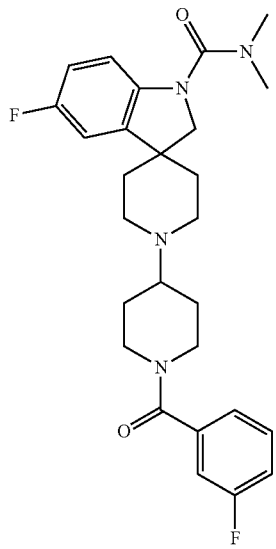
971 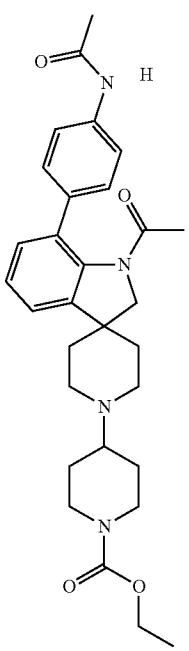
973 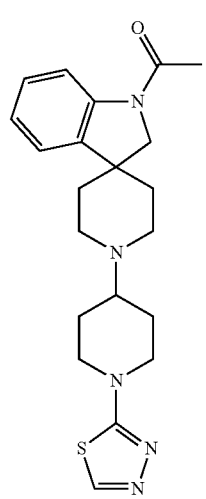
977 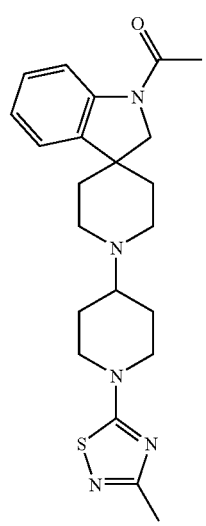

| 609 -continued | 610 -continued |
|---|---|
| 975 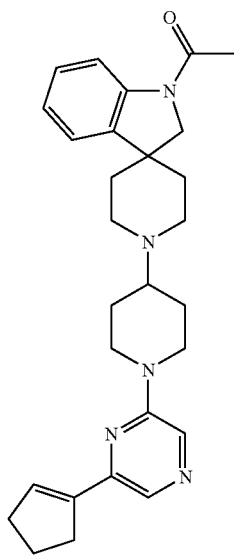 | 987 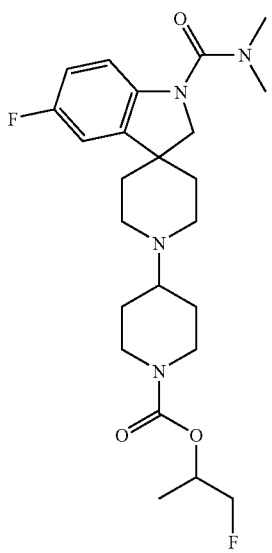 |
| 976 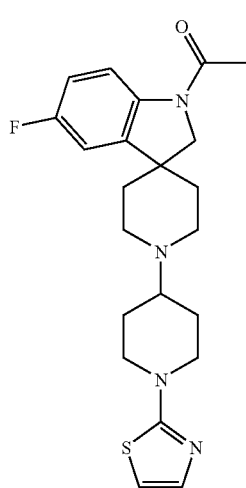 | 988 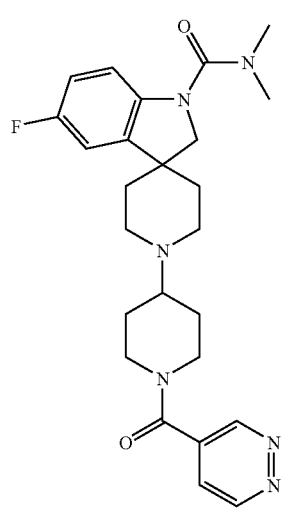 |
| 992 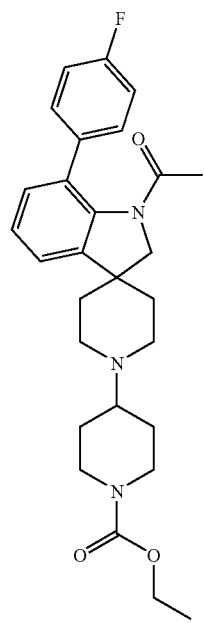 | 989 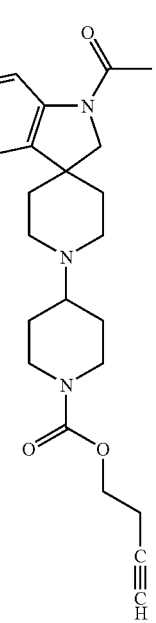 |

| 990 | 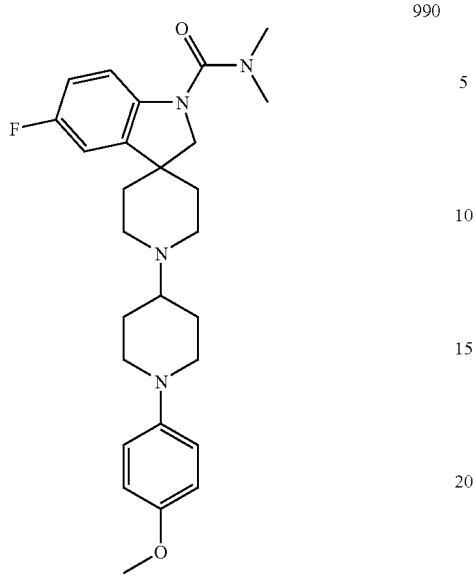 |
| --- | --- |
| 991 | 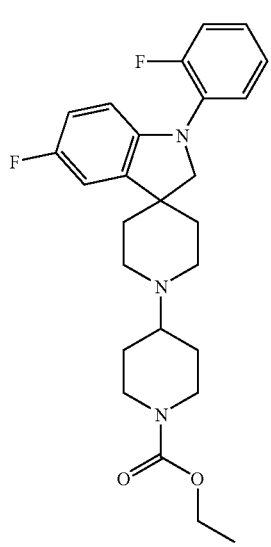 |
| 995 | 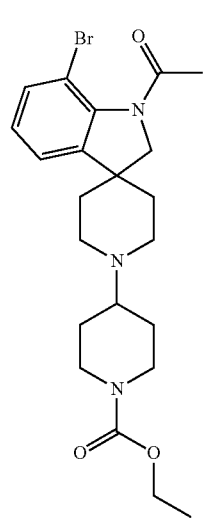 |
| 1000 | 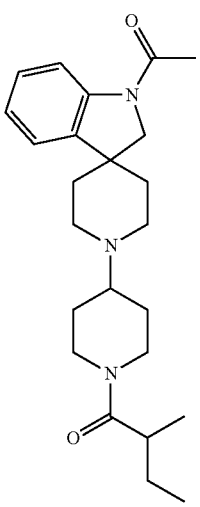 |
| --- | --- |
| 1004 | 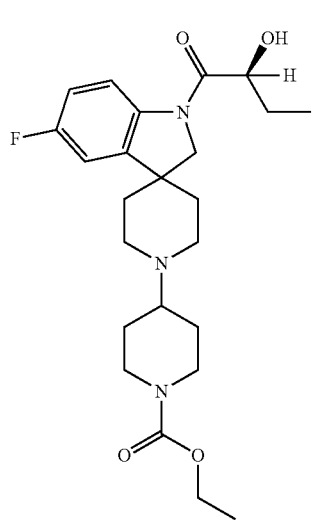 |
| 1018 | 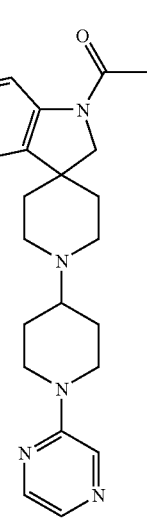 |

1019
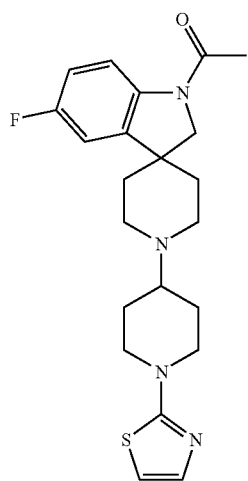
1006
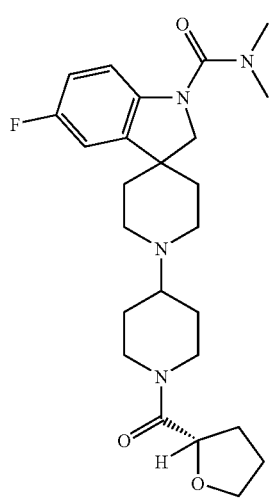
1021
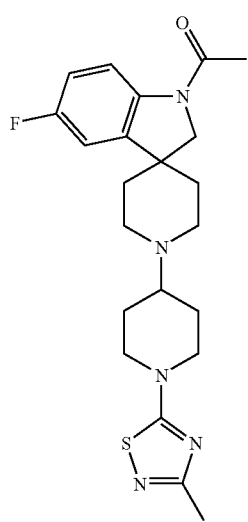
1022
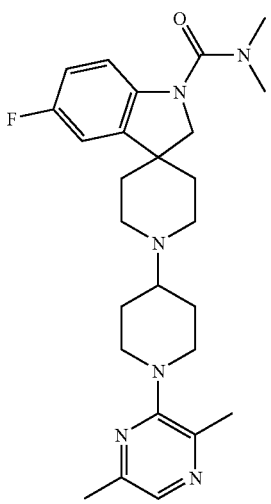
1023
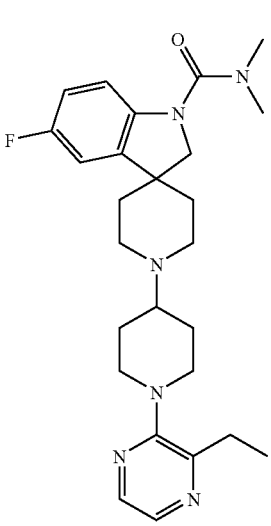
1024
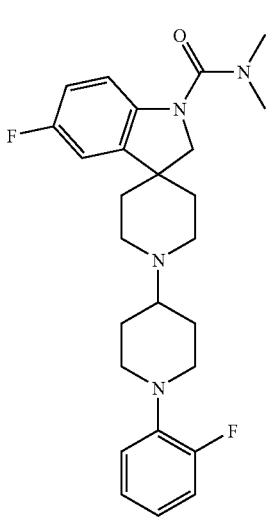

| | |
|---|---|
| 1025 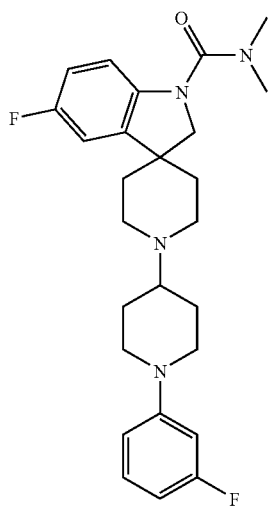 | 1028 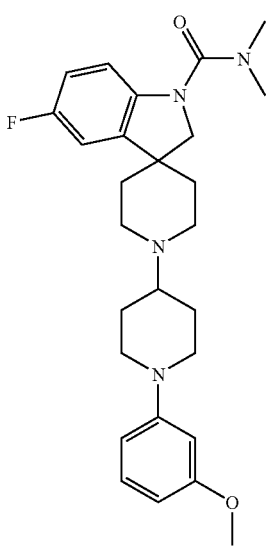 |
| 1026 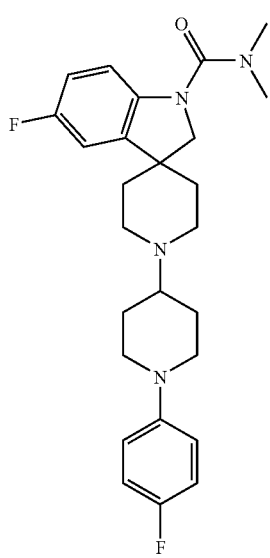 | 1029 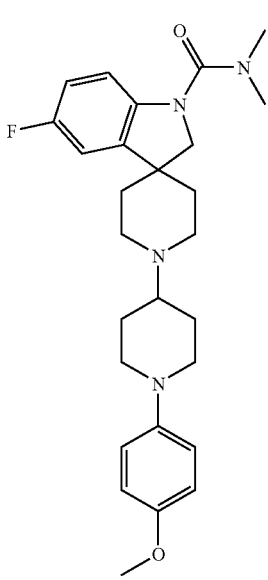 |
| 1027 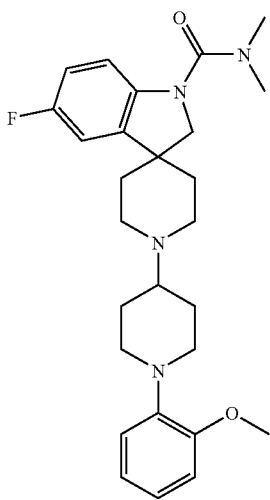 | 1030 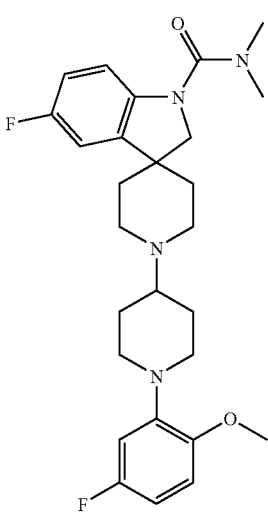 |

| | |
|---|---|
| 1031 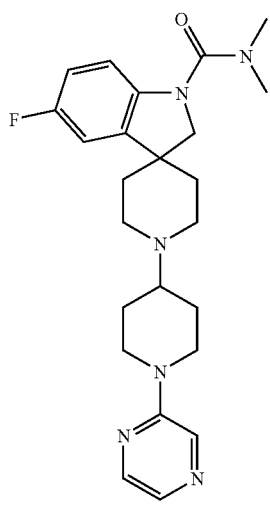 | 1034 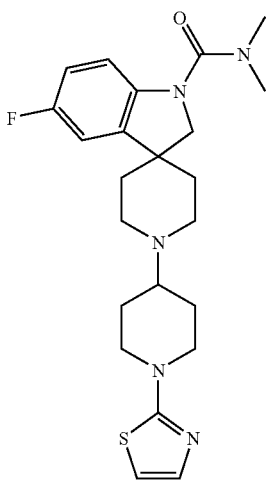 |
| 1032 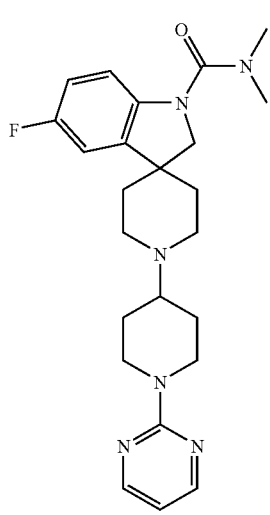 | 1039 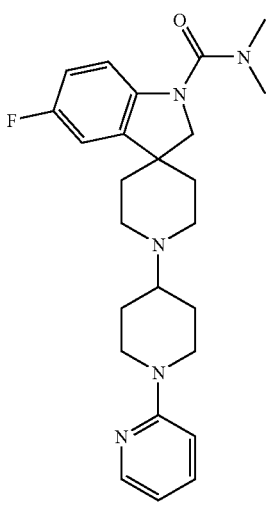 |
| 1033 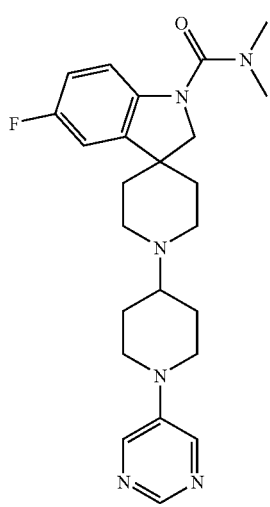 | 1040 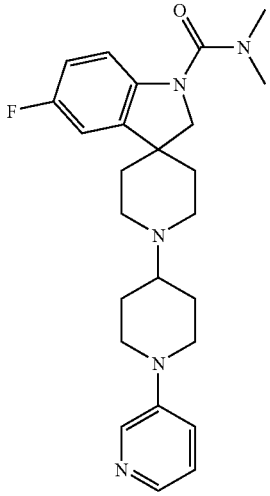 |

619
-continued
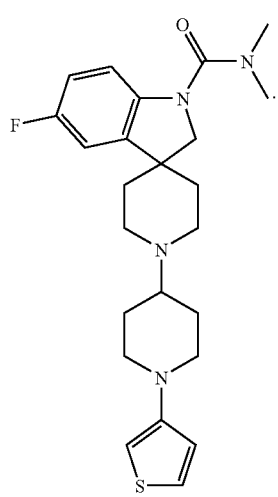
1041
620
-continued
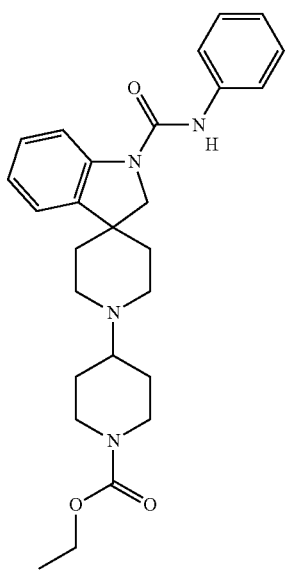
433
2. A pharmaceutical composition comprising a compound according to claim 1 and a pharmaceutical carrier.
3. A method of modulating activity of a muscarinic receptor, comprising the step of contacting said receptor with a compound selected from:
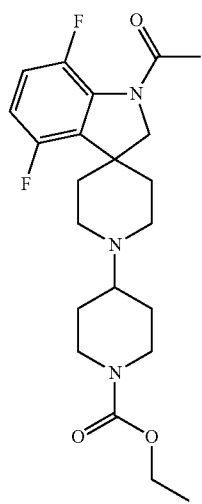
431
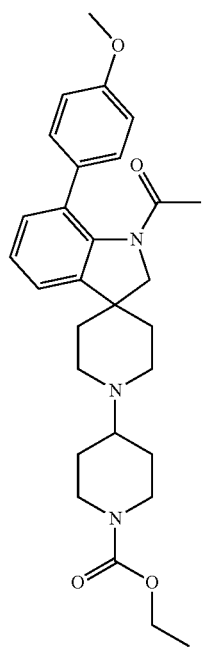
434

435
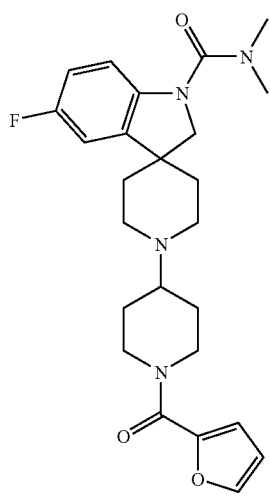
440
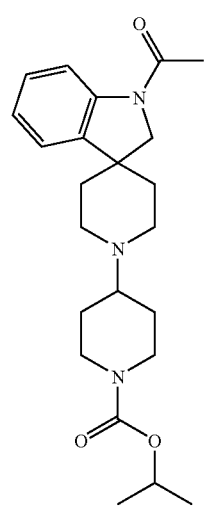
441
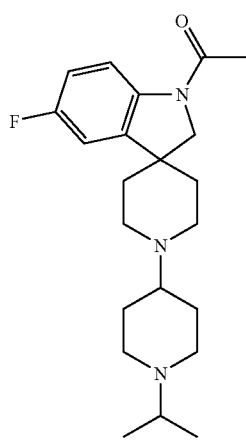
446
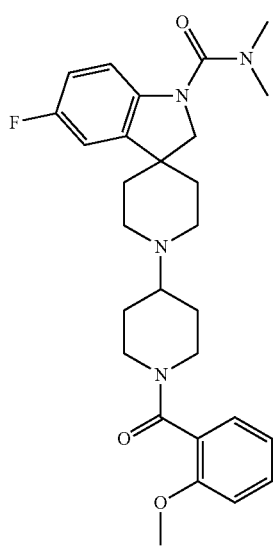
450
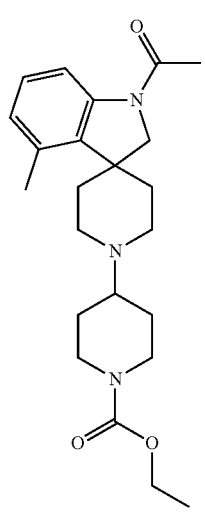
453
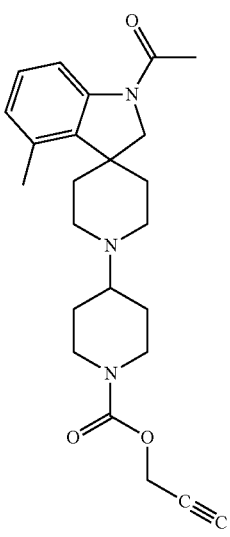

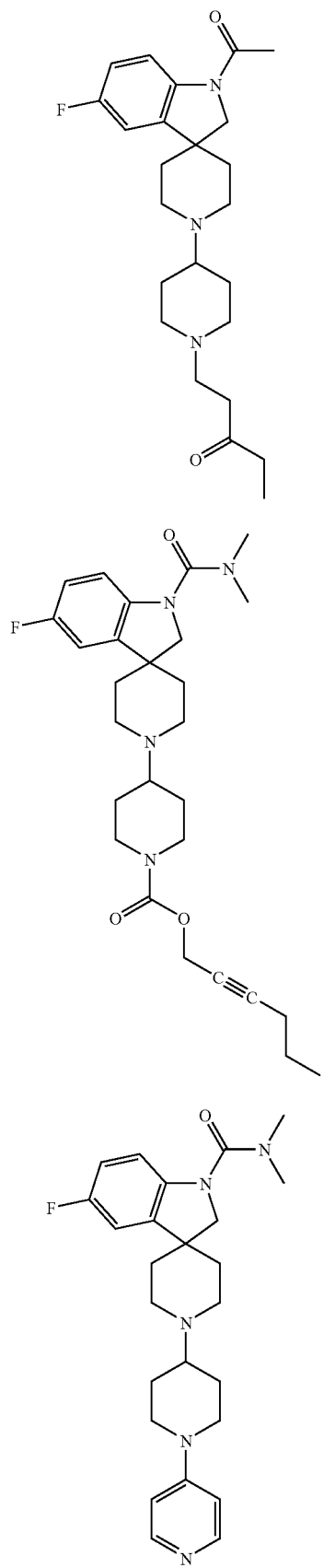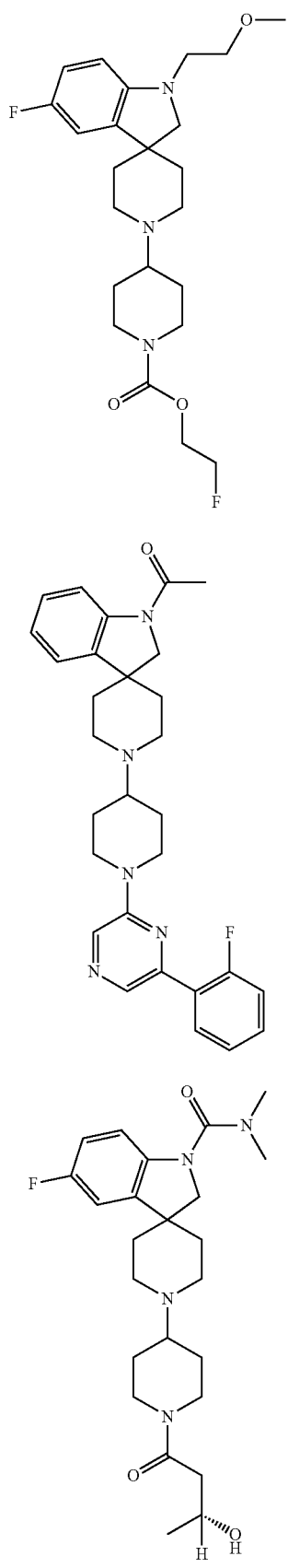

| 464 | 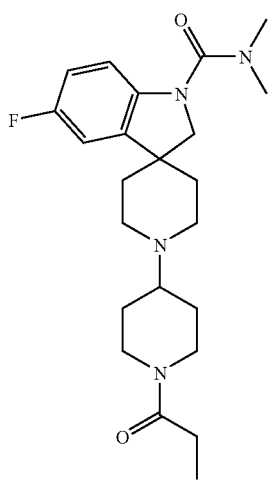 | 471 | 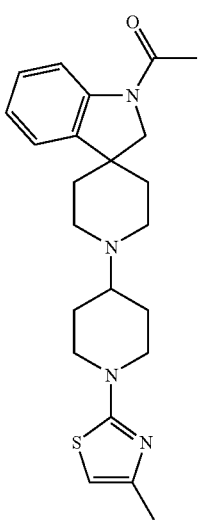 |
| 467 | 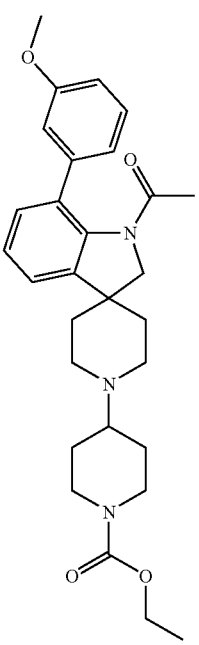 | 472 | 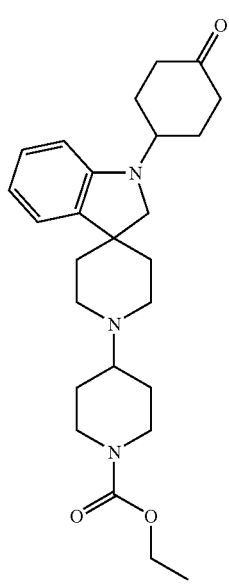 |
| 469 | 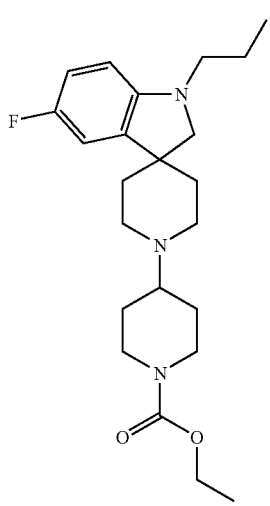 | 474 | 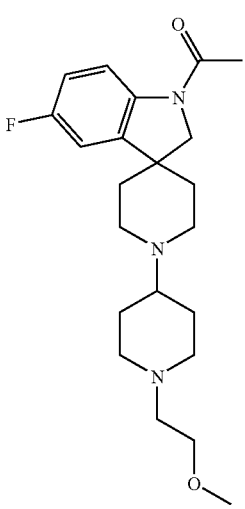 |

477
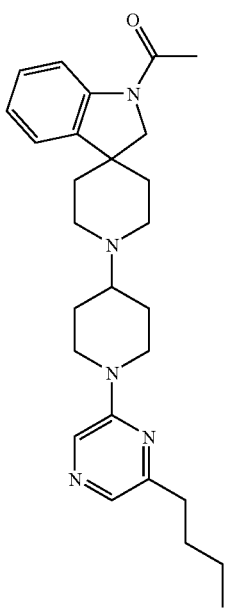
489
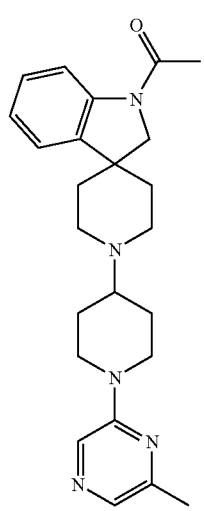
491
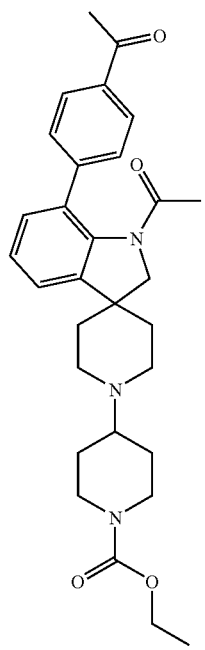
492
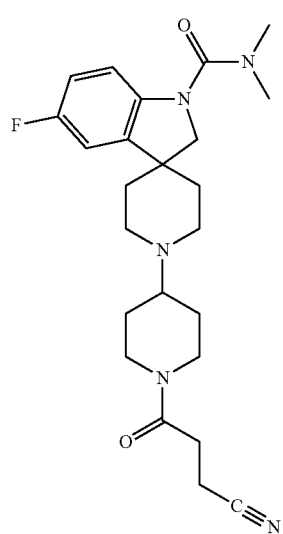

494 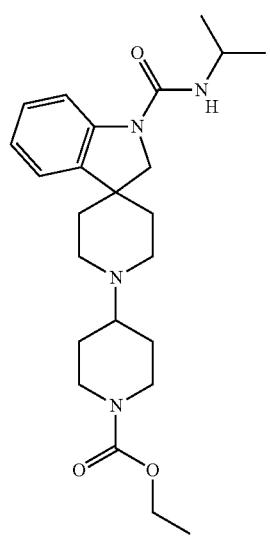
500 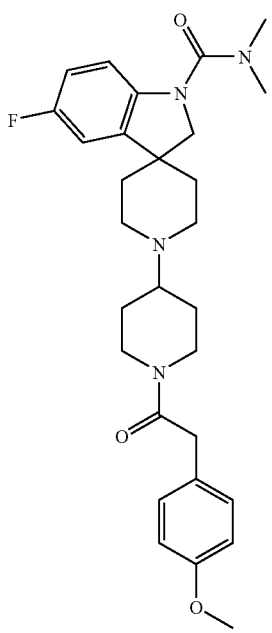
496 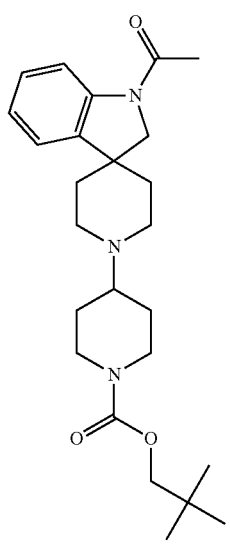
497 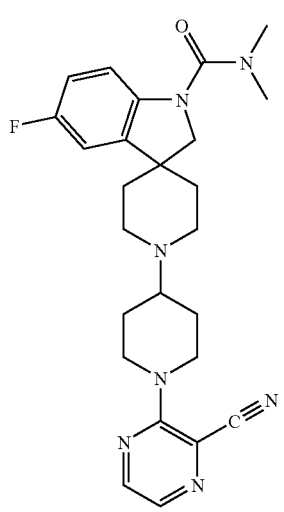
499 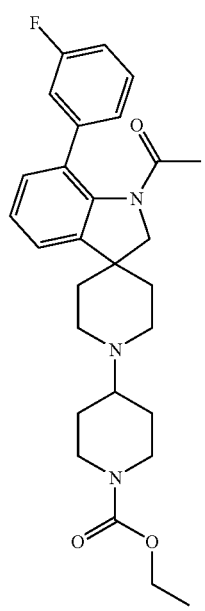

631
-continued
| 505 | 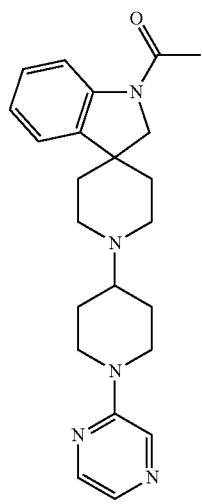 |
| --- | --- |
| 508 | 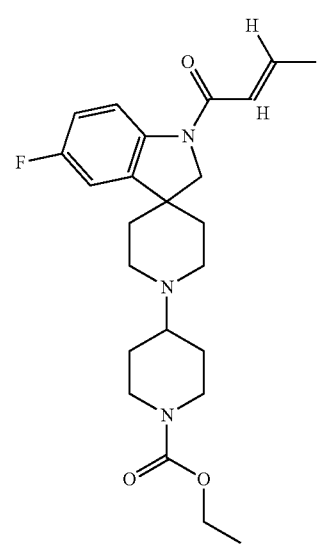 |
| 509 | 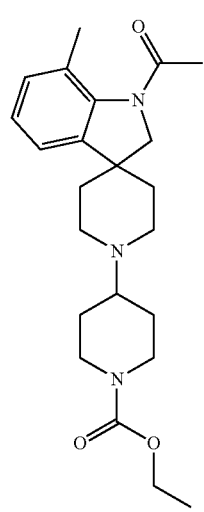 |
632
-continued
| 517 | 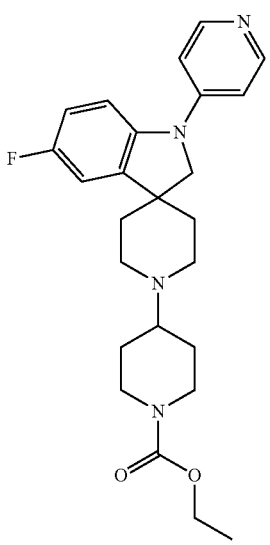 |
| --- | --- |
| 520 | 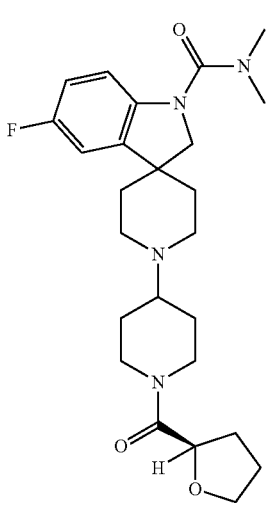 |
| 522 | 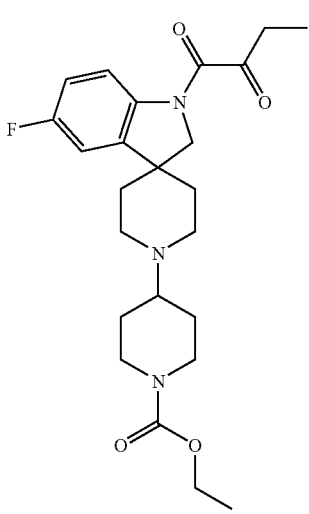 |

| 633 -continued | 634 -continued |
|---|---|
| 526 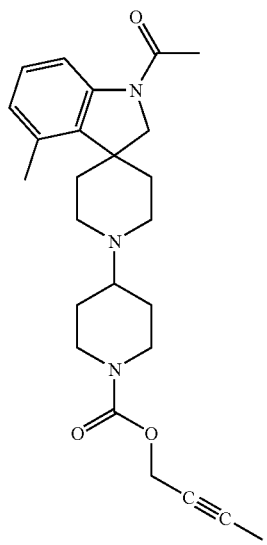 | 534 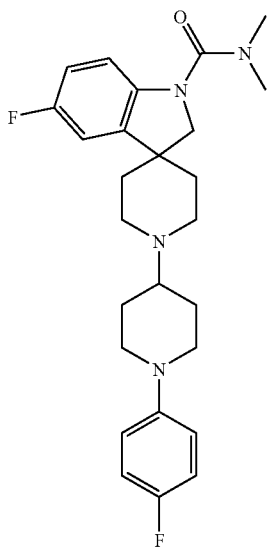 |
| 528 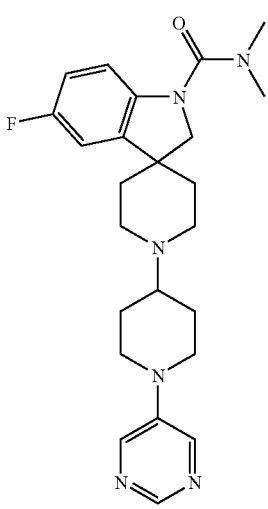 | 535 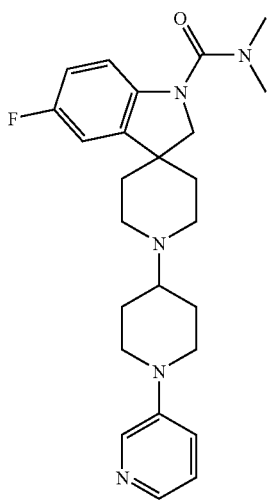 |
| 531 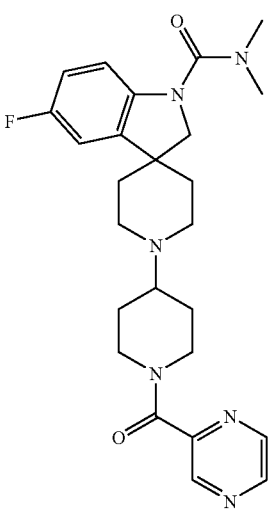 | 539 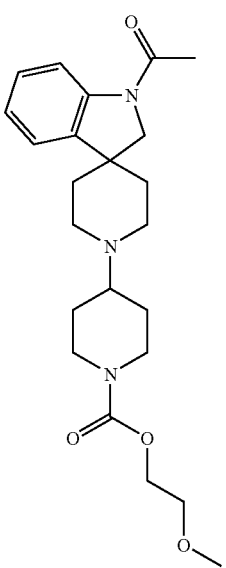 |

| 543 | 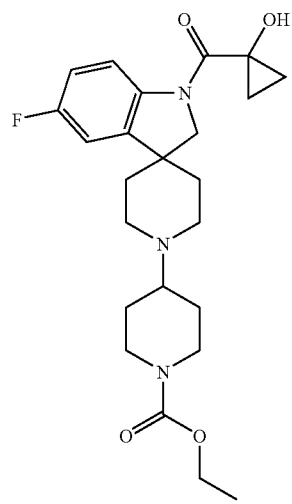 | 547 | 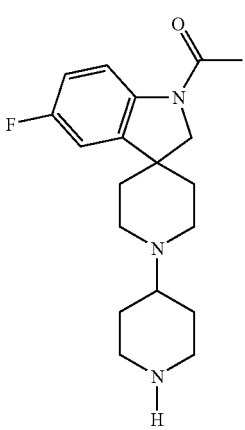 |
| 544 | 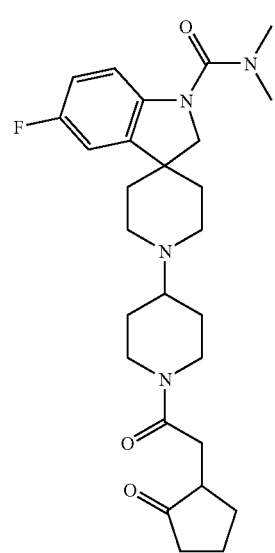 | 551 | 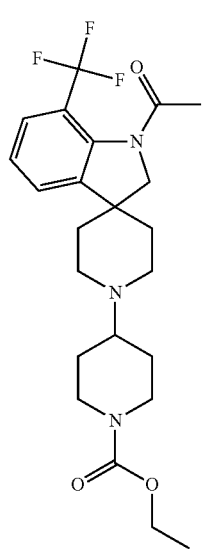 |
| 545 | 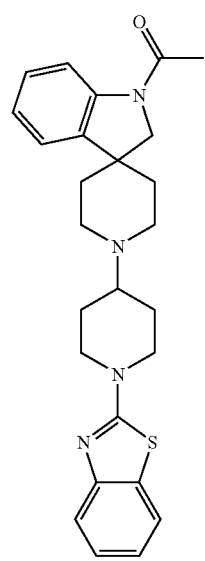 | 552 | 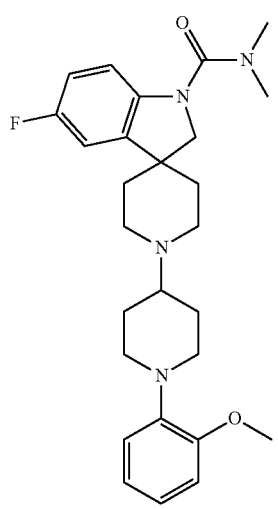 |

637
-continued
553
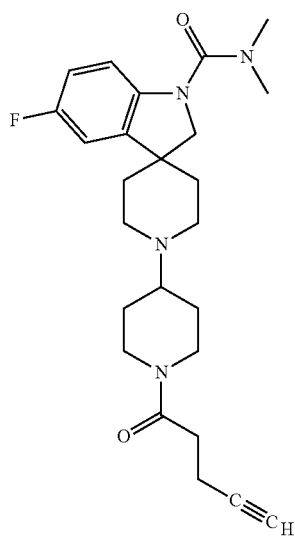
554
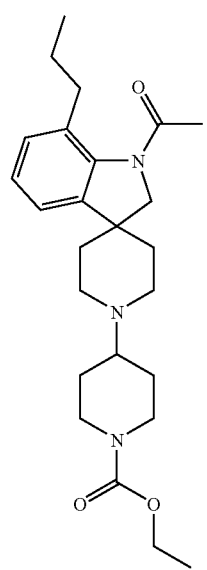
559
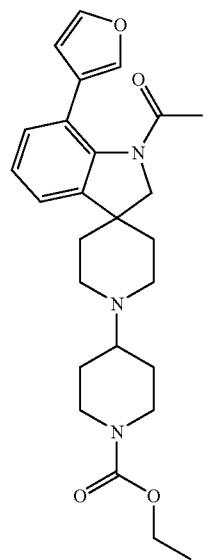
638
-continued
556
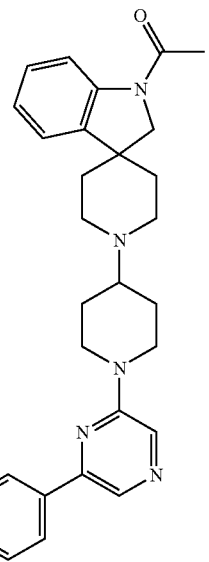
560
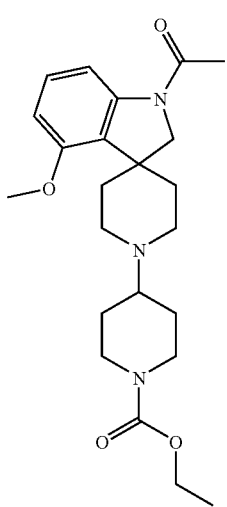
561
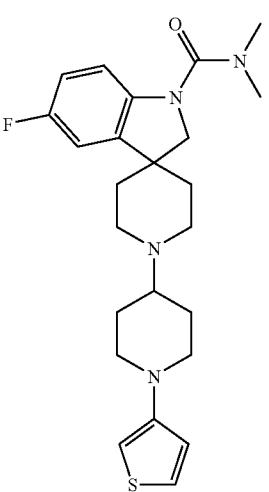

639
-continued
640
-continued
563
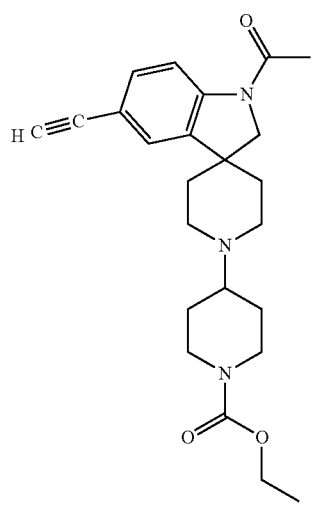
572
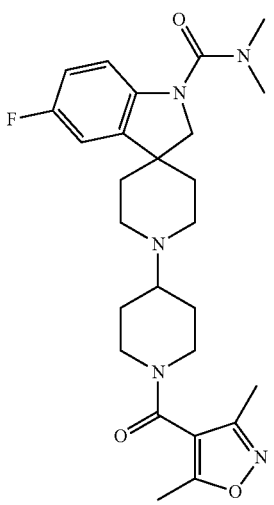
567
571
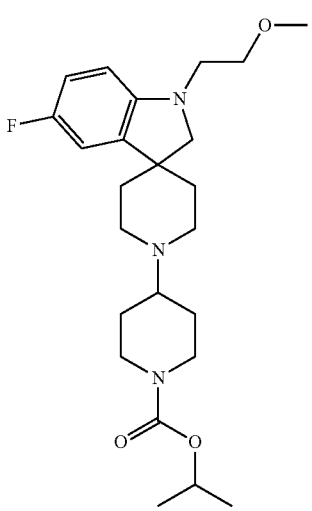
565
574
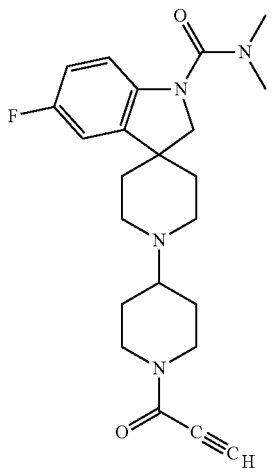

| 641 -continued | 642 -continued |
|---|---|
| 579 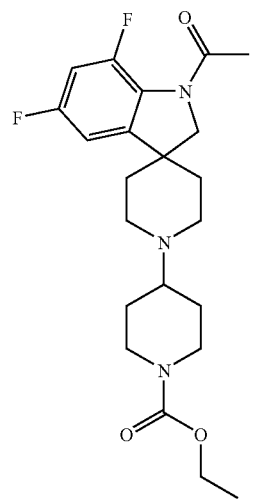 | 590 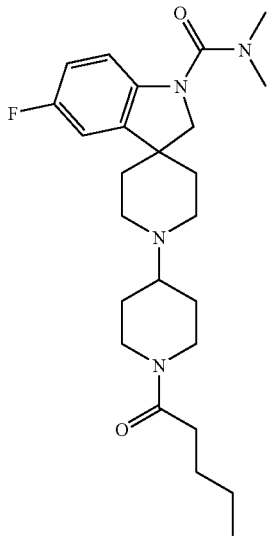 |
| 588 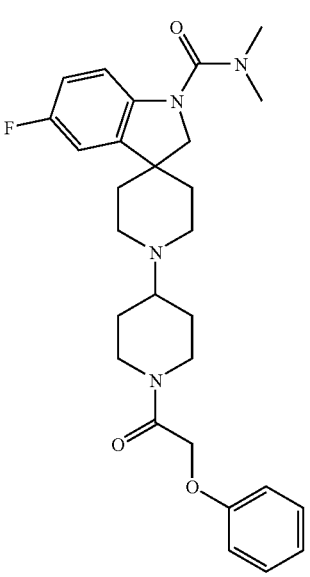 | 585 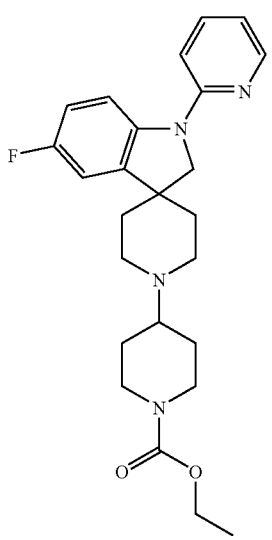 |
| 589 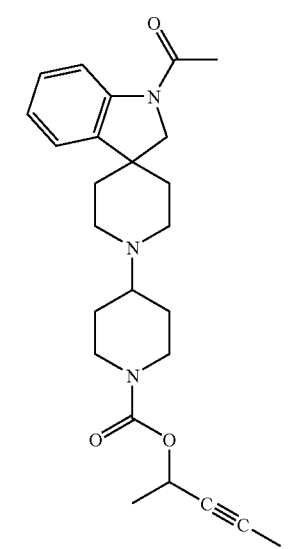 | 592 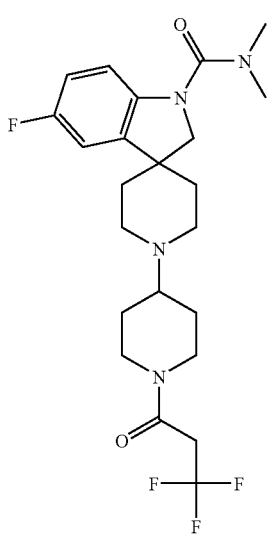 |

-continued

645
-continued
611
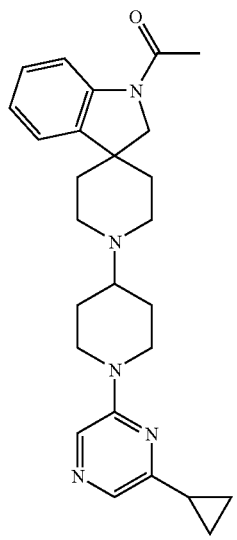
614
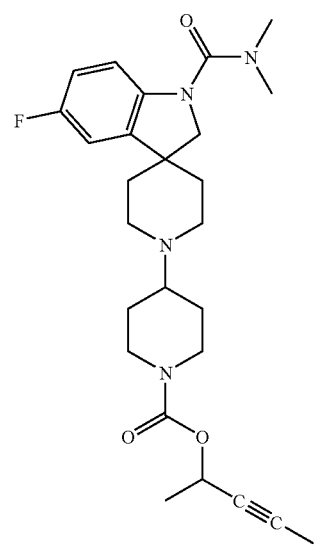
615
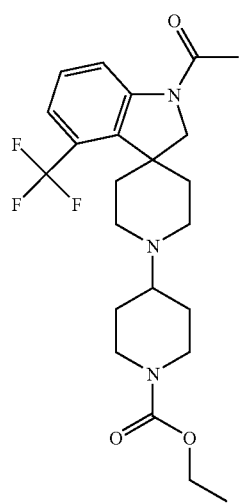
646
-continued
619
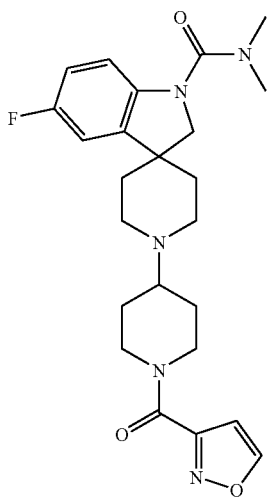
620
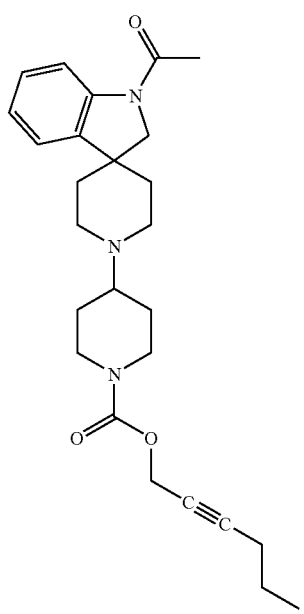
626
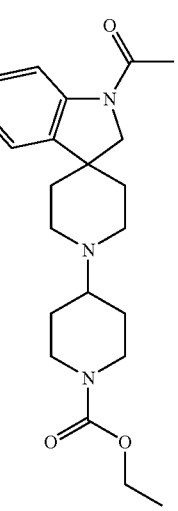

647
-continued
629
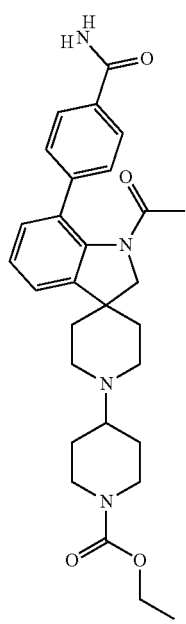
630
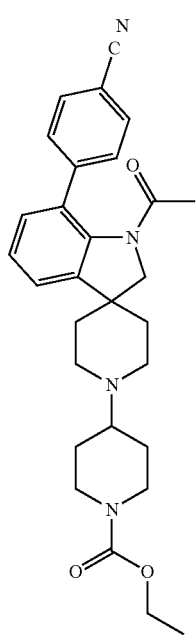
648
-continued
633
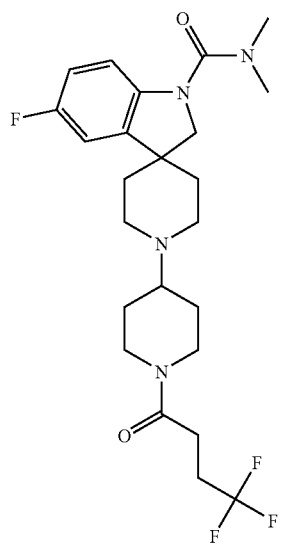
653
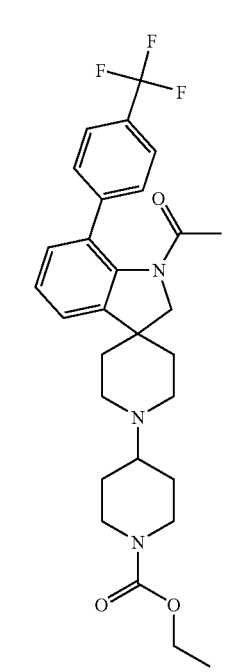

| 649 -continued | 650 -continued |
|---|---|
| 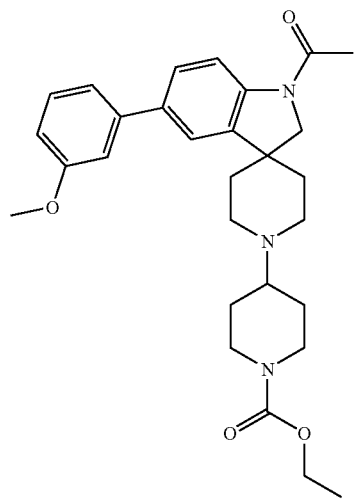 648 | 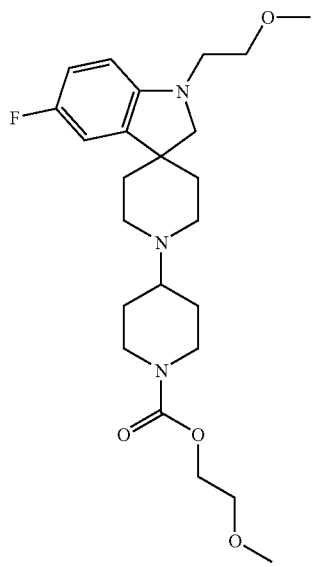 658 |
| 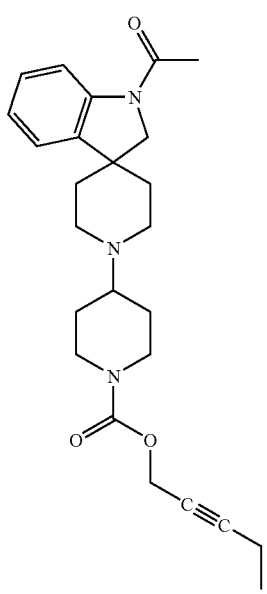 656 | 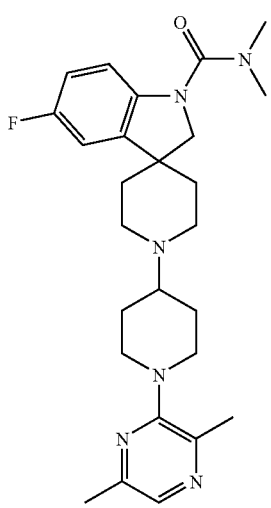 659 |
| | 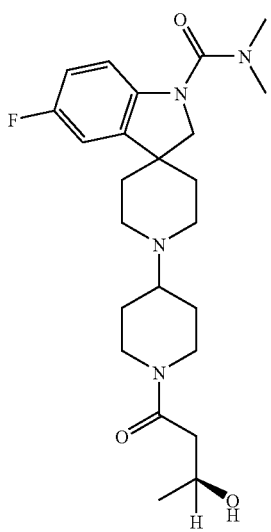 662 |

651
-continued
661 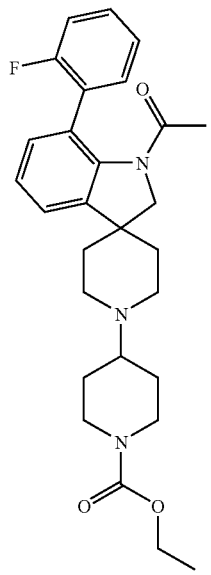
665 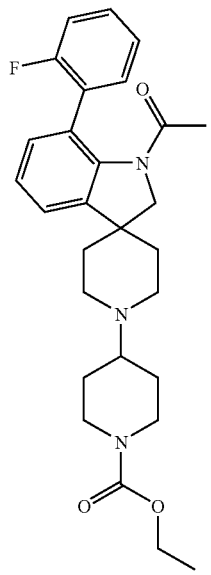
672 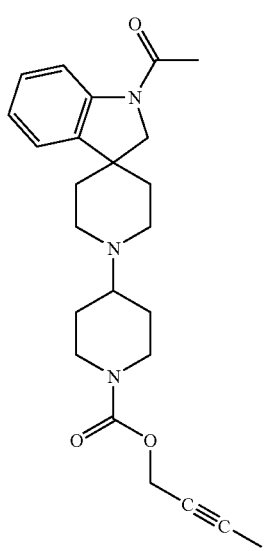
652
-continued
674 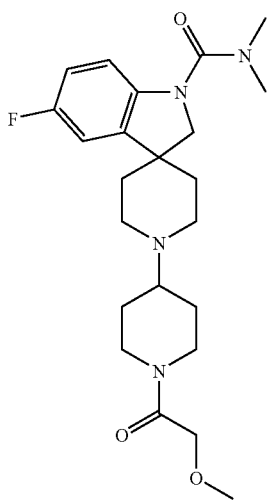
683 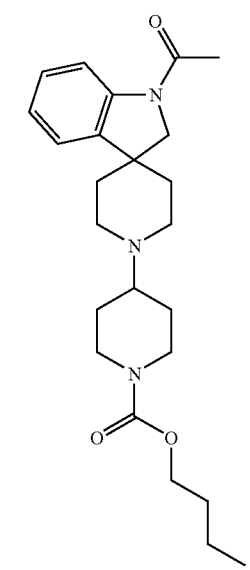
685 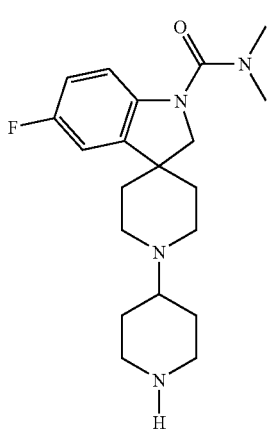

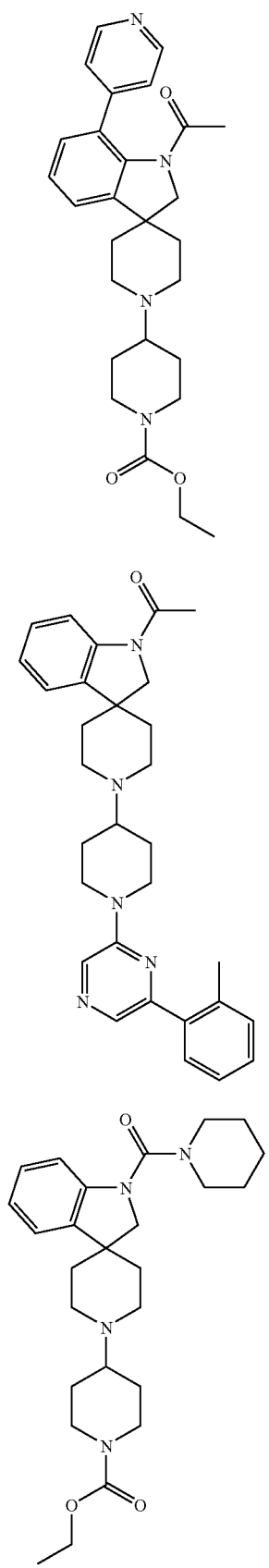
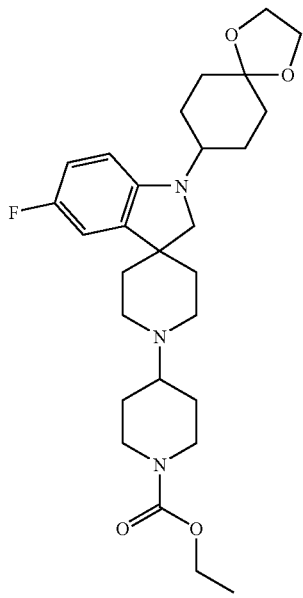
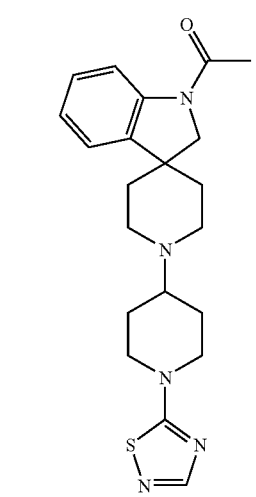
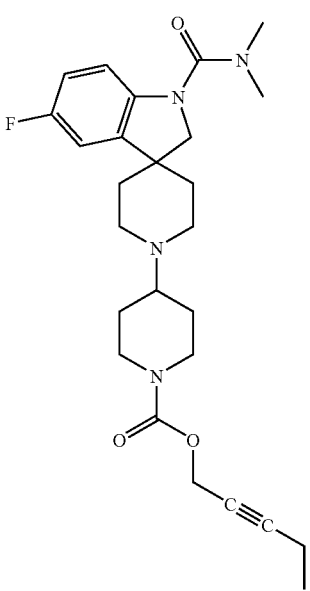

697 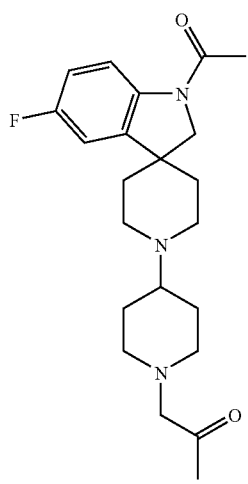
699 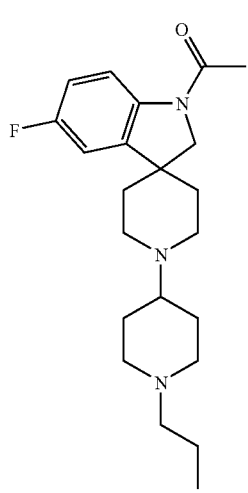
700 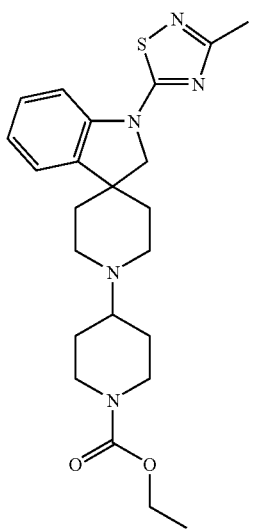
701 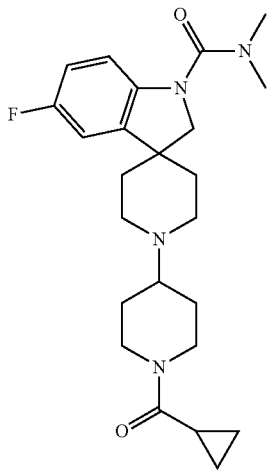
707 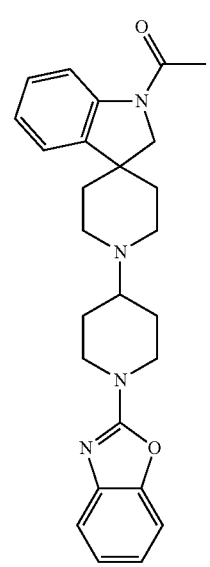
710 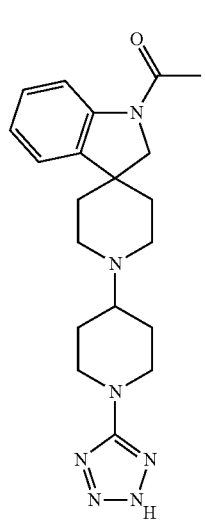

657
-continued
711
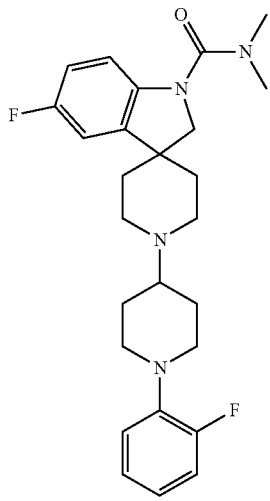
712
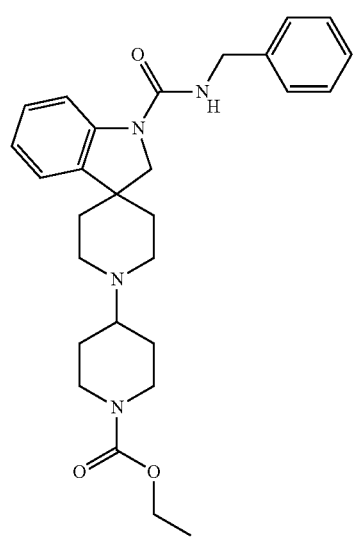
714
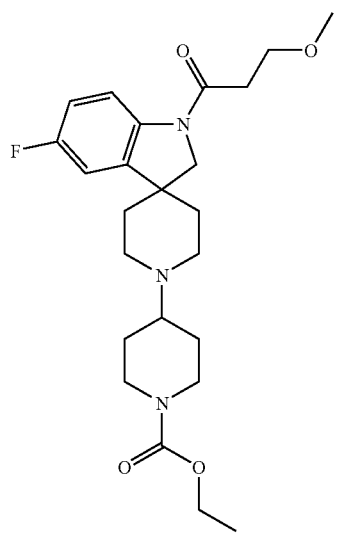
658
-continued
717
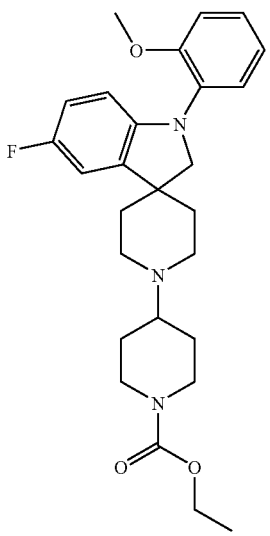
718
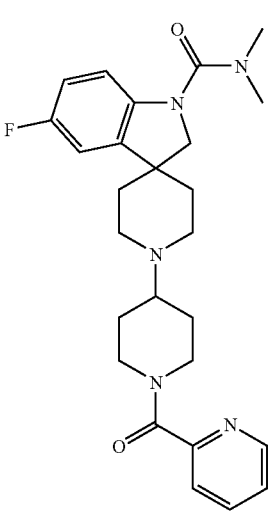
719
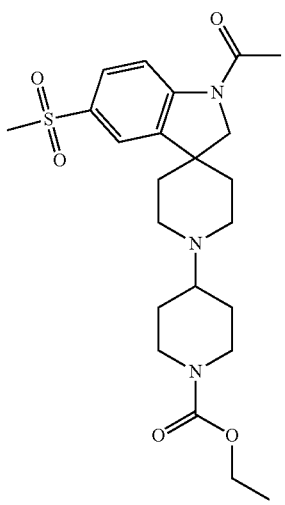

| 720 | 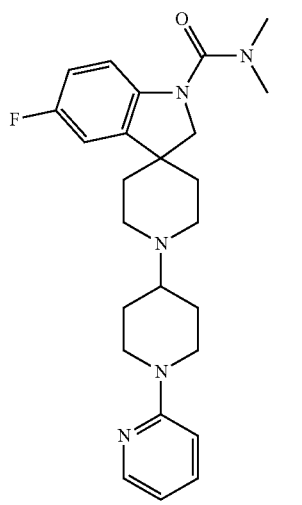 | 735 | 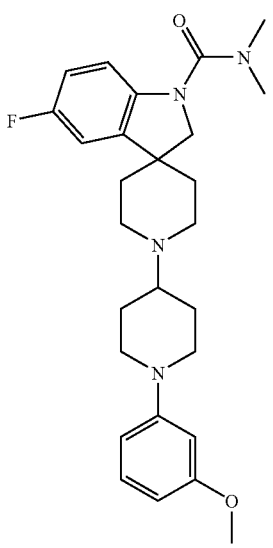 |
| 721 | 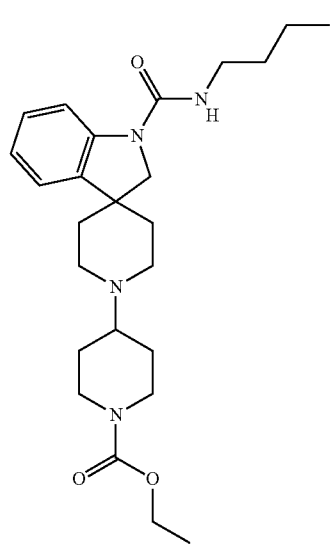 | 727 | 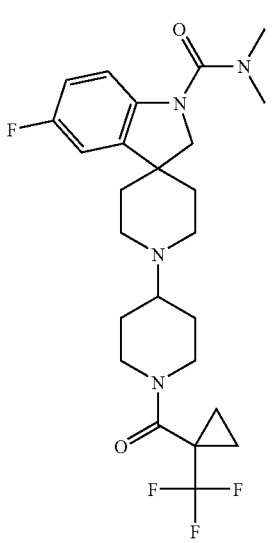 |
| 724 | 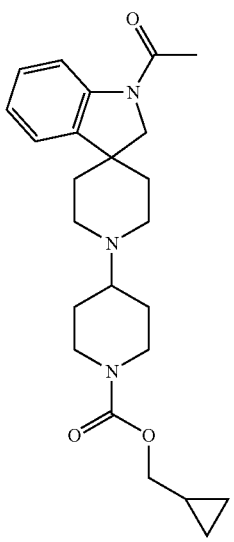 | 728 | 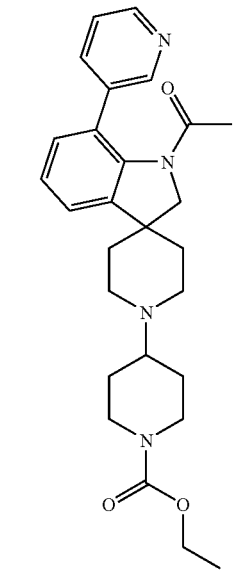 |

| 661 -continued | 662 -continued |
|---|---|
| 729 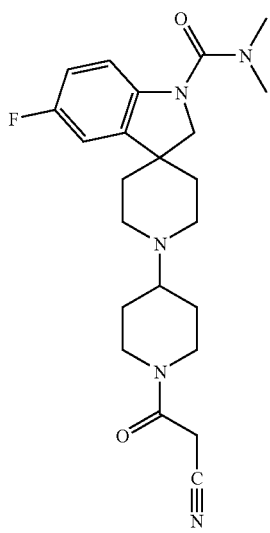 | 751 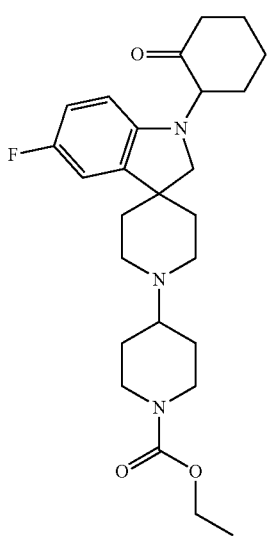 |
| 730 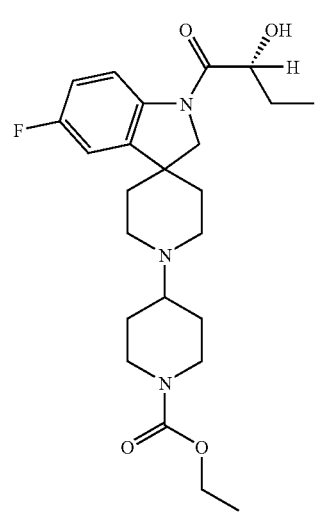 | 752 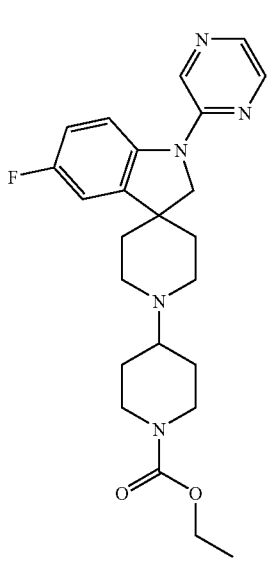 |
| 750 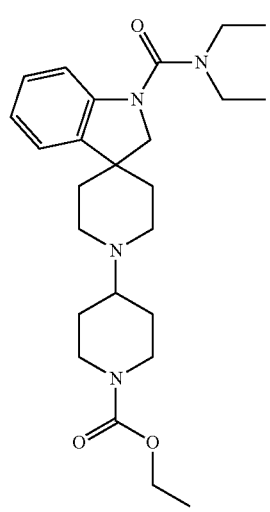 | 753 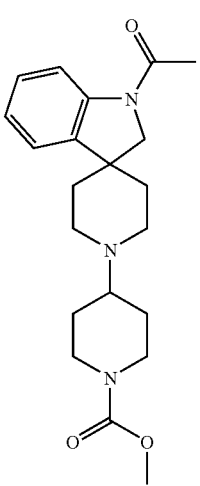 |

| 663 -continued | | 664 -continued | |
|---|---|---|---|
| 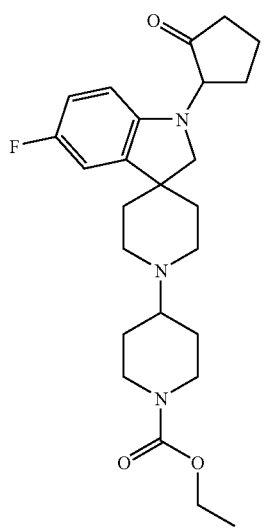 | 756 | 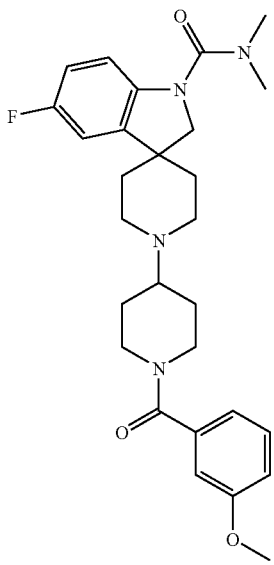 | 770 |
| 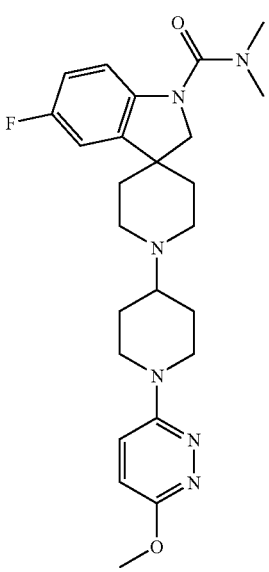 | 760 | 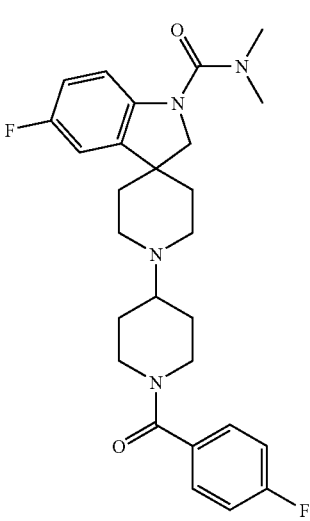 | 767 |
| 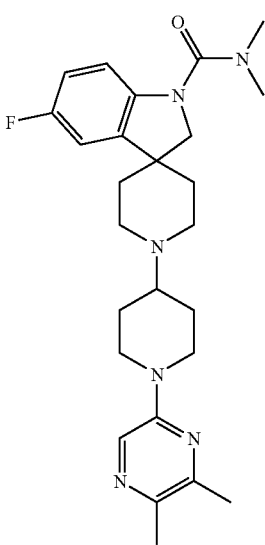 | 762 | 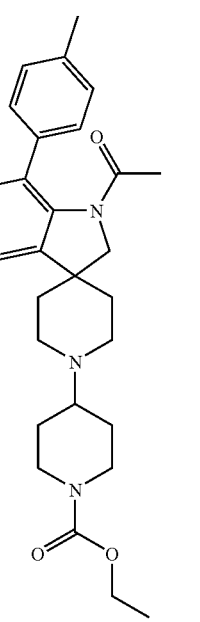 | 768 |

| 665 -continued | | 666 -continued | |
|---|---|---|---|
| 769 | 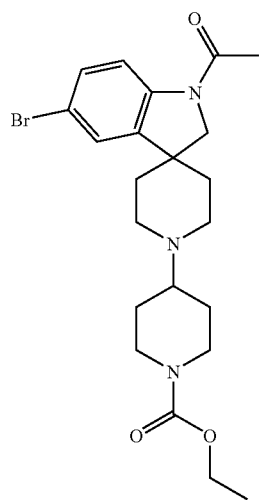 | 790 | 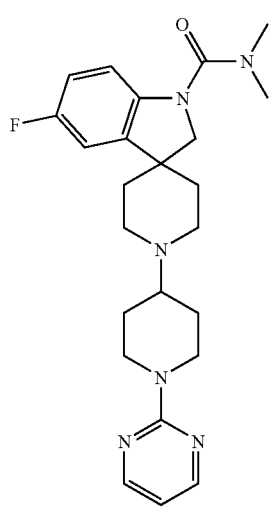 |
| 781 | | 794 | |
| 791 | | 795 | 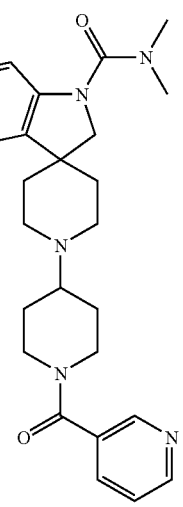 |

667
-continued
799
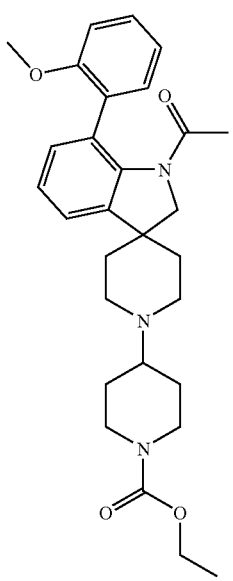
800
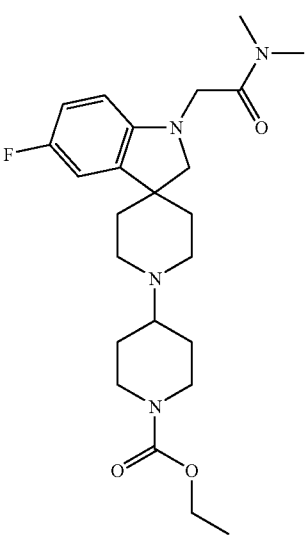
804
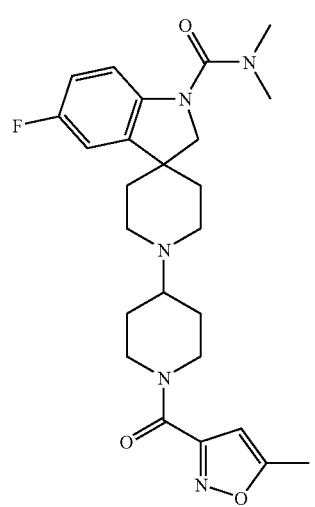
668
-continued
808
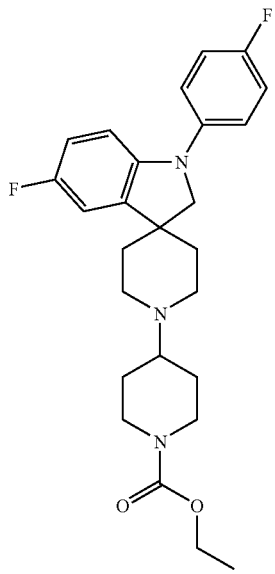
812
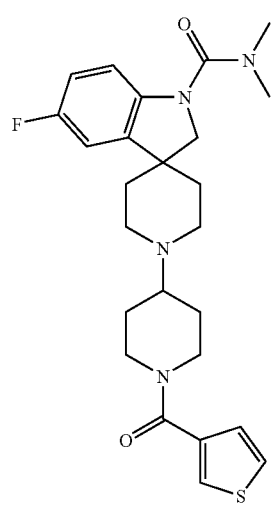
814
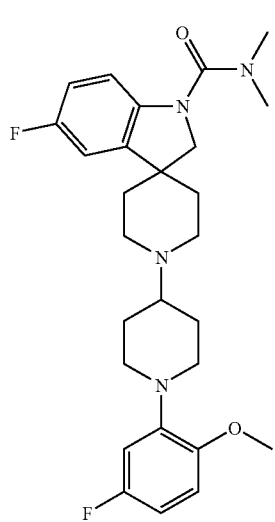

| 669 -continued | | 670 -continued | |
|---|---|---|---|
| 824 | 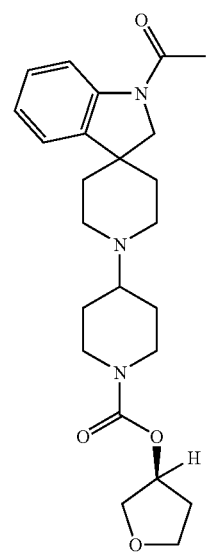 | 829 | 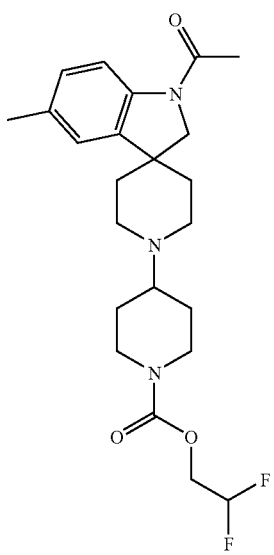 |
| 825 | 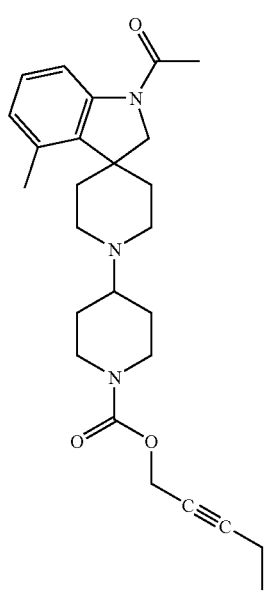 | 837 | 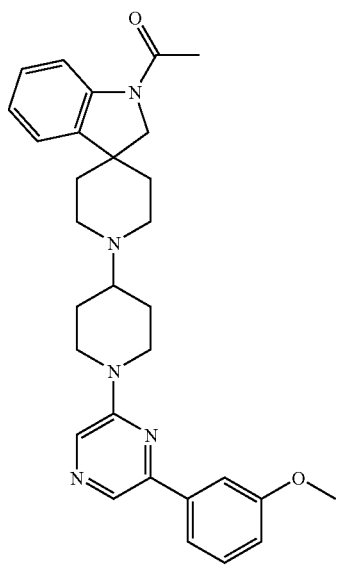 |
| 822 | 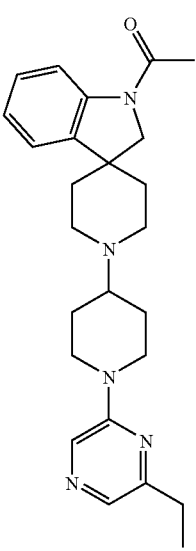 | | |

838
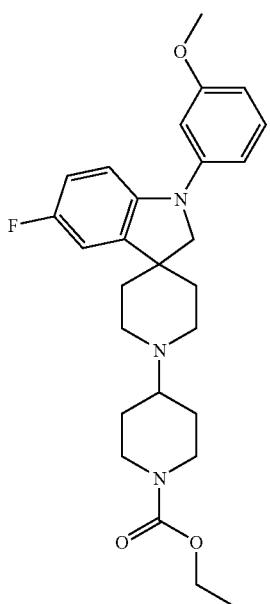
839
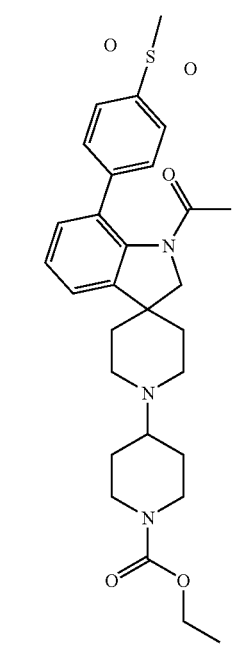
844
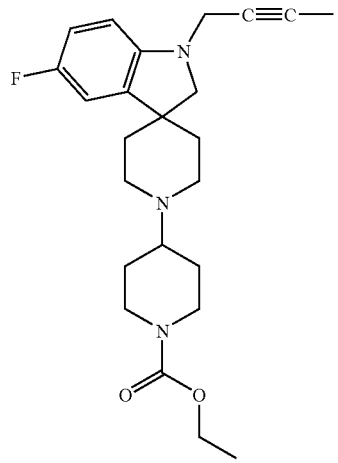
847
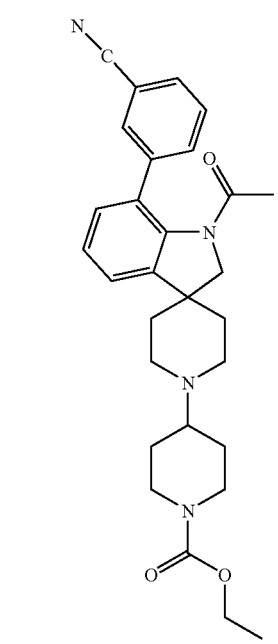
851
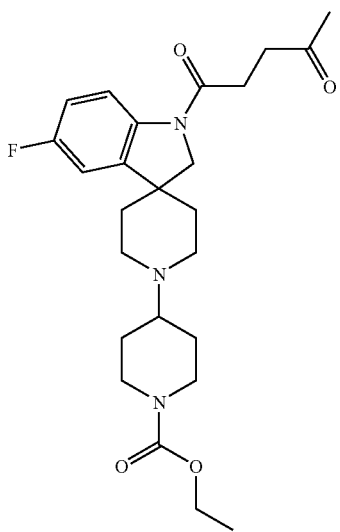

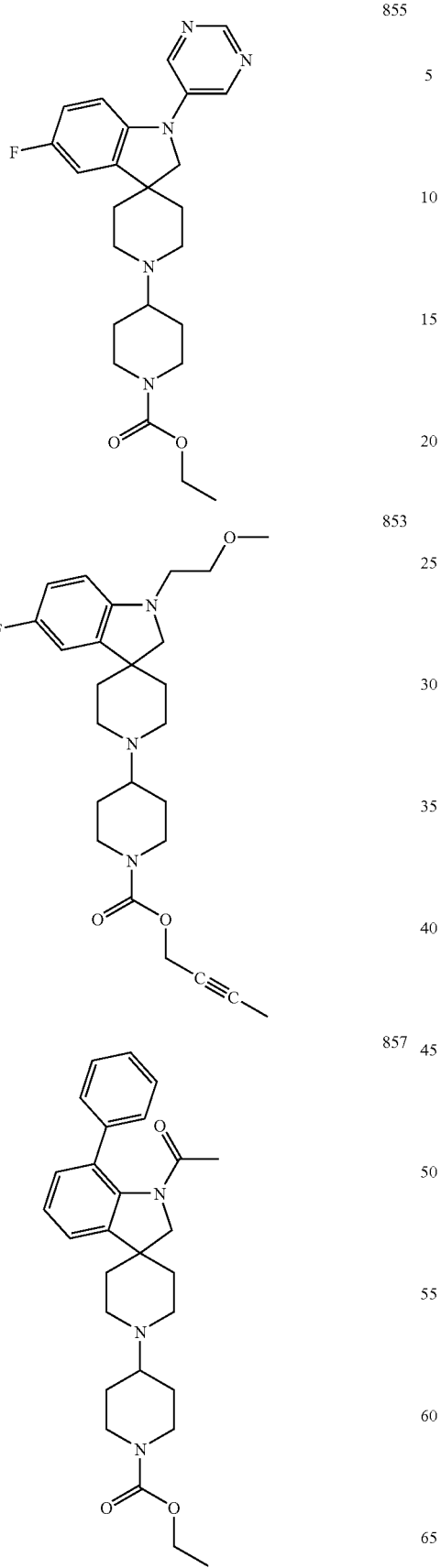
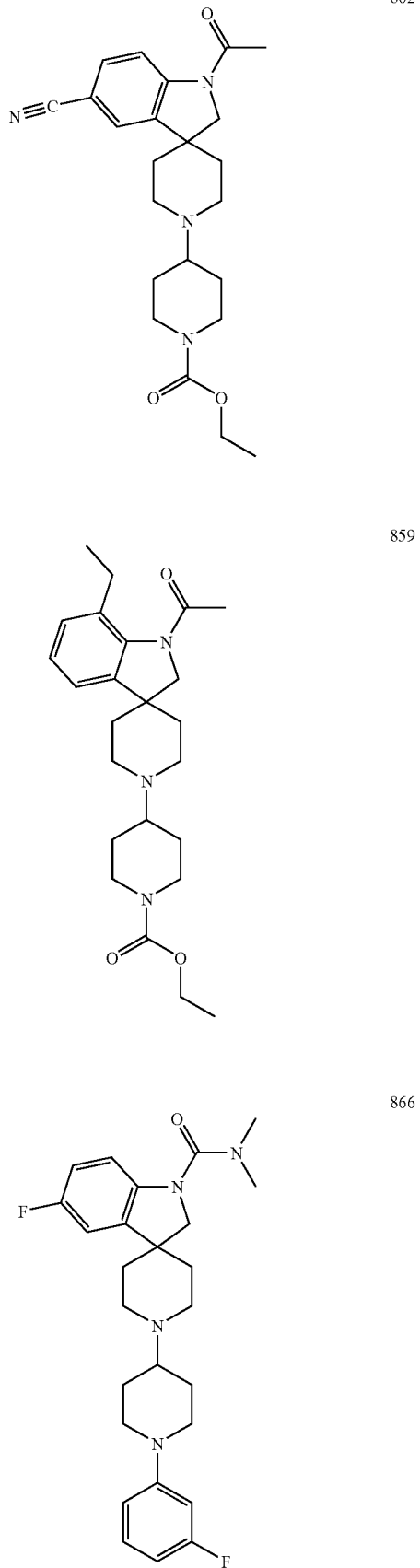

872
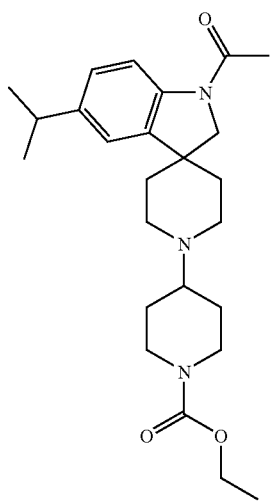
885
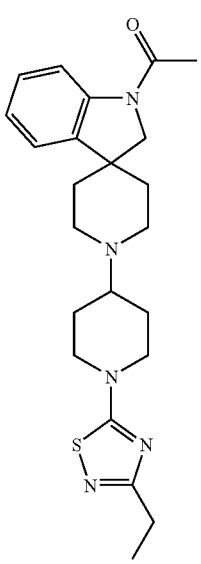
879
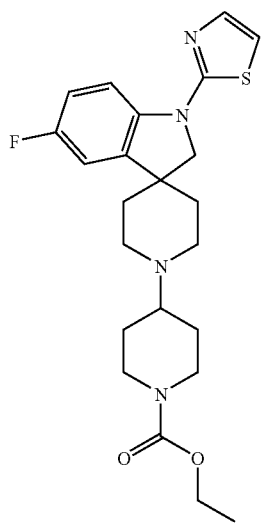
880
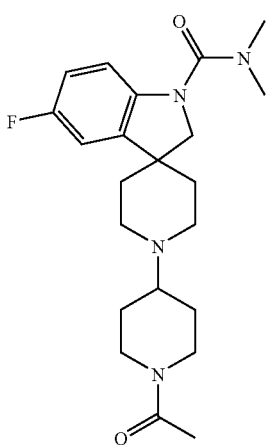
890
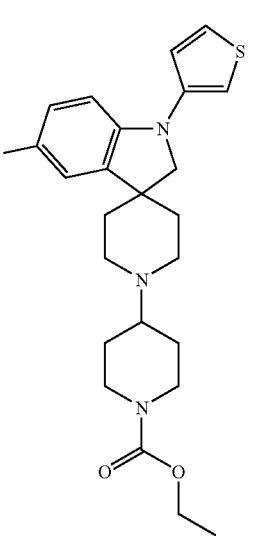
891

| 887 | 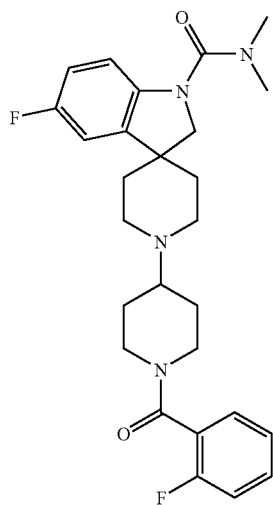 | 895 | 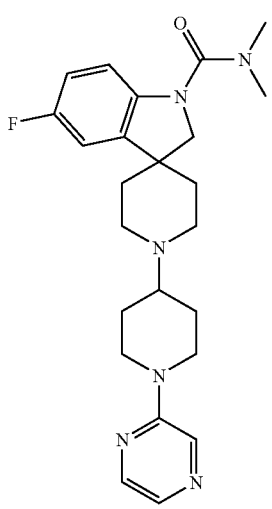 |
| --- | --- | --- | --- |
| 893 | 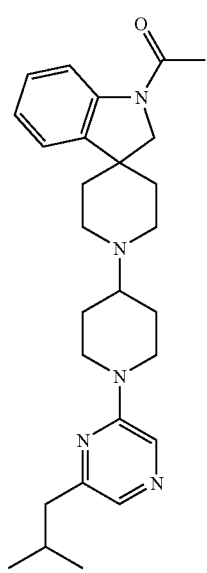 | 896 | 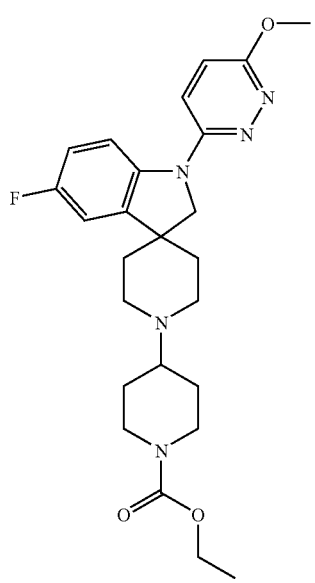 |
| 894 | 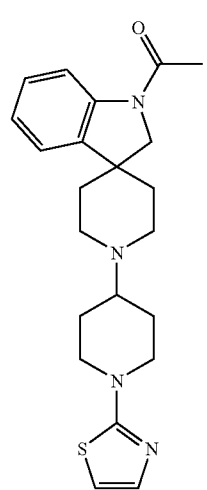 | 898 | 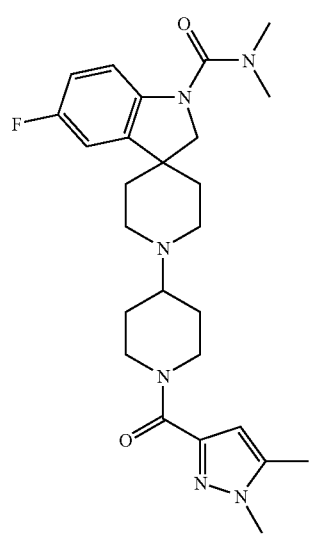 |

679
-continued
905
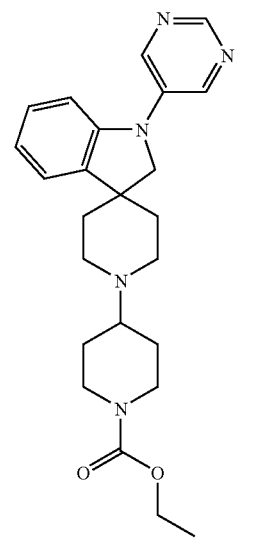
900
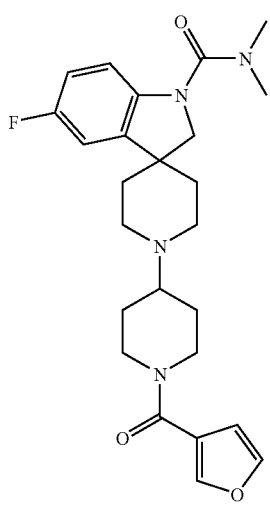
907
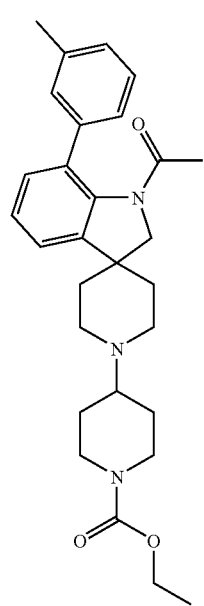
680
-continued
908
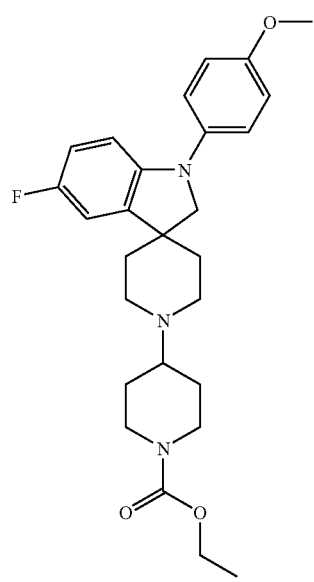
903
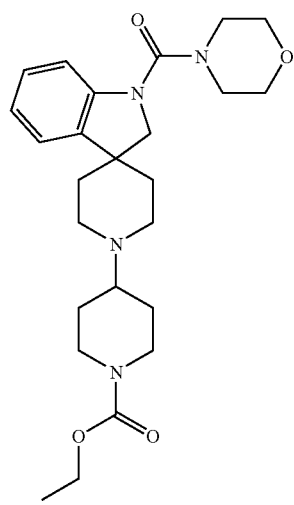
910
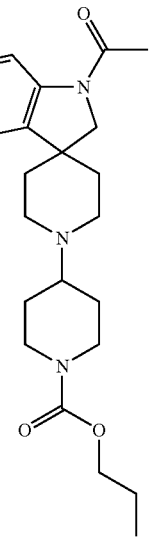

| 681 -continued | | 682 -continued | |
|---|---|---|---|
| 911 | 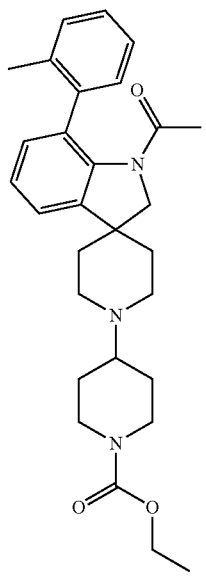 | 918 | 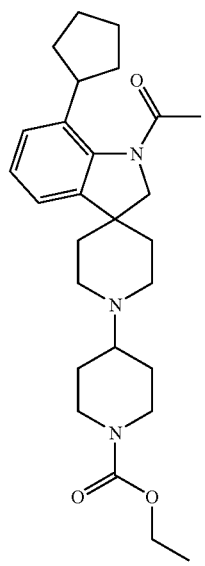 |
| 914 | 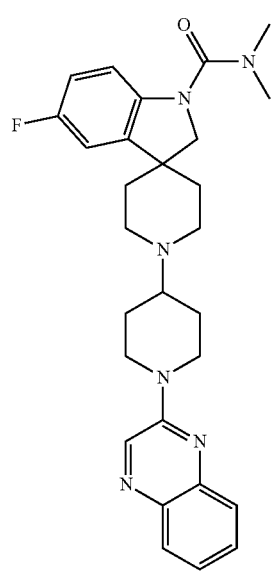 | 921 | 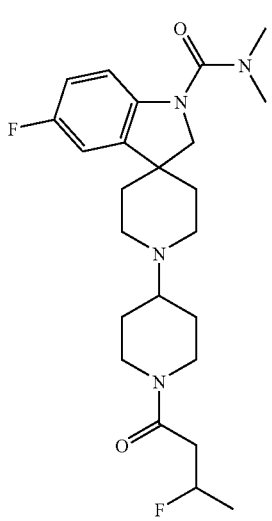 |
| 917 | 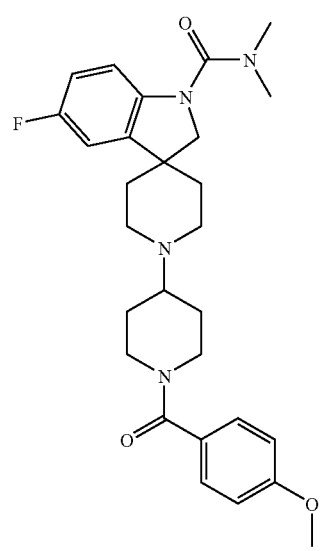 | 938 | 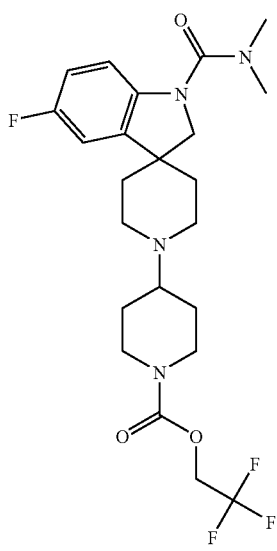 |

930 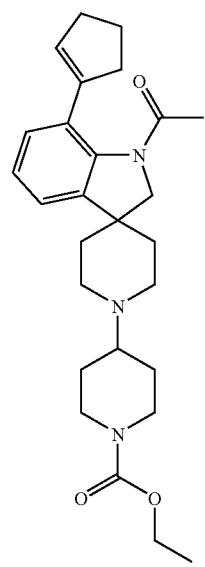
932 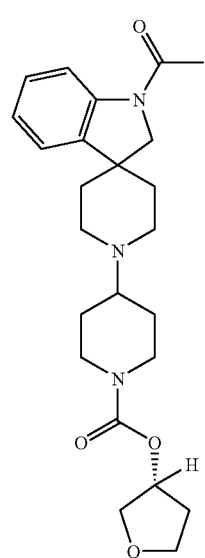
941 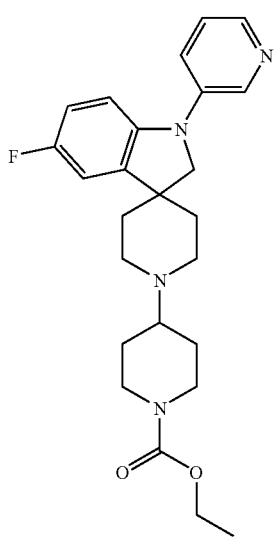
942 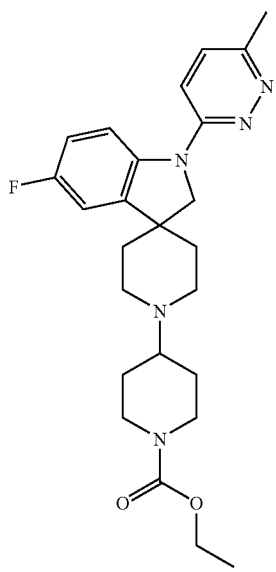
943 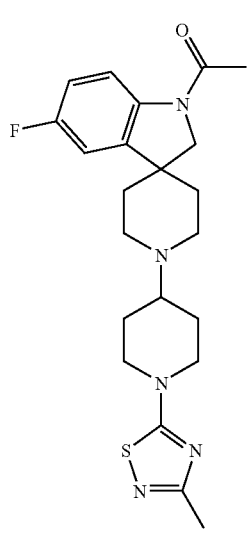
944 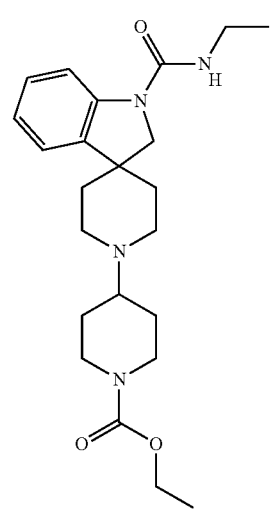

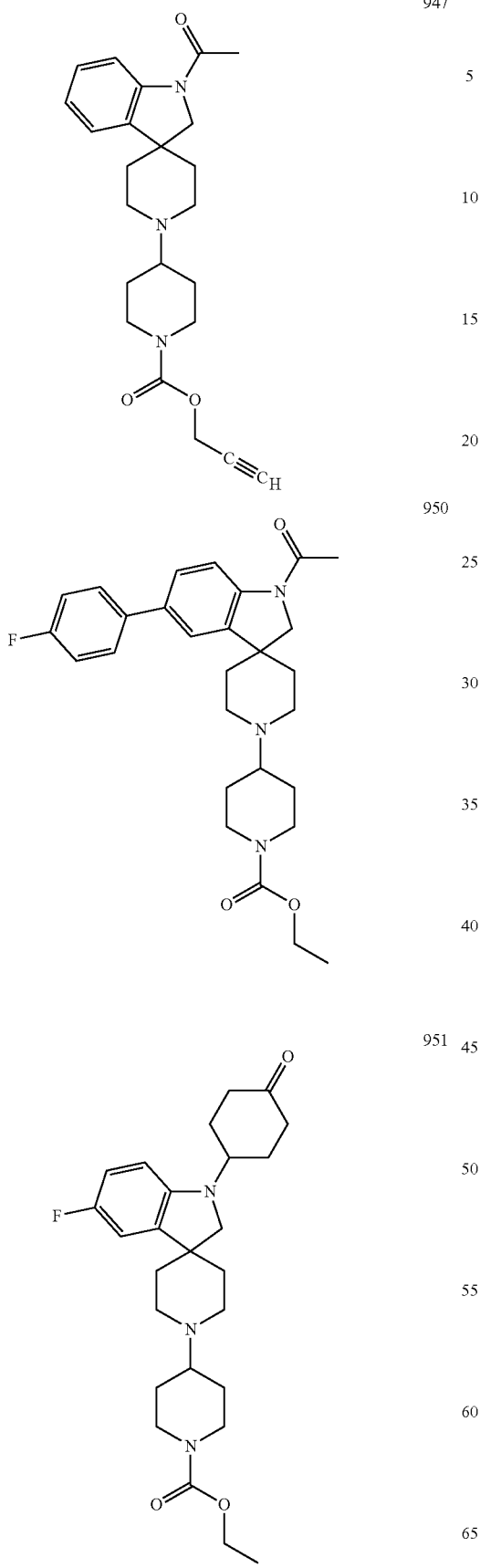
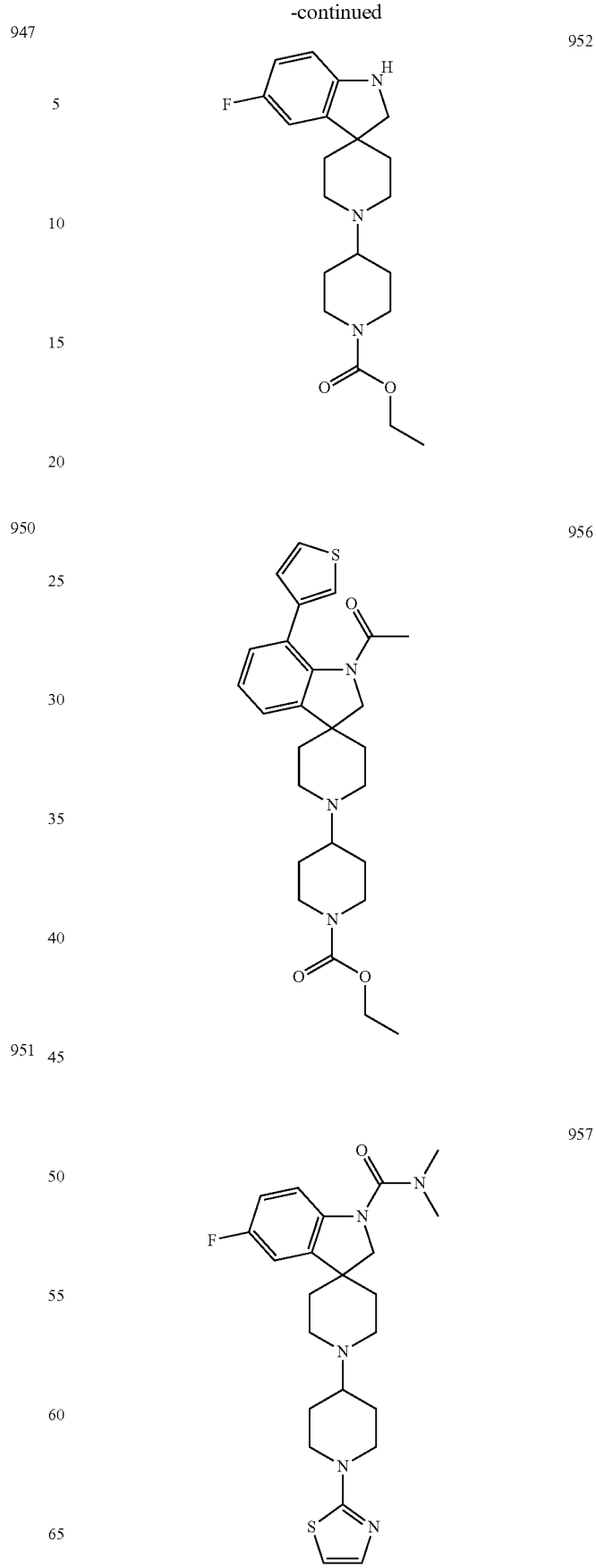

687
-continued
953 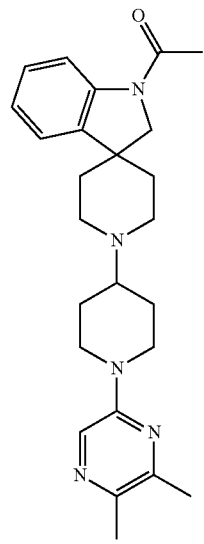
965 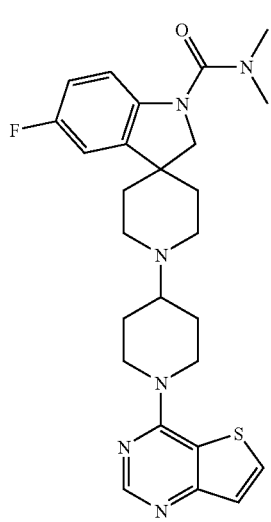
959 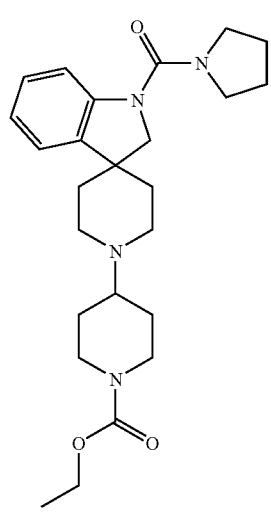
688
-continued
967 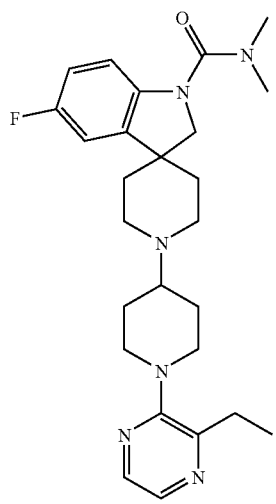
971 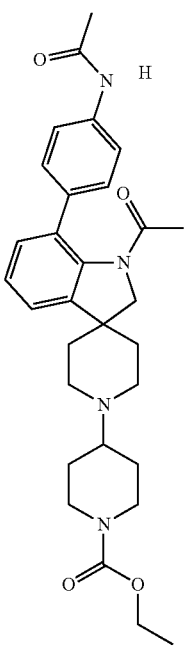

972
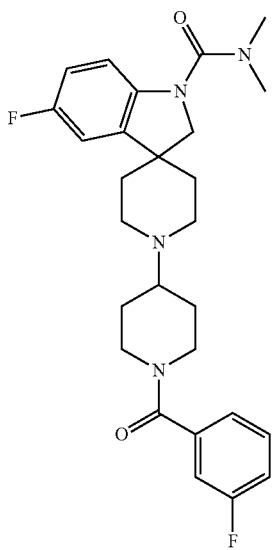
973
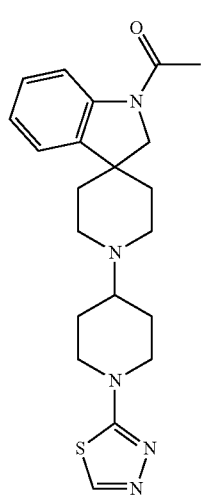
977
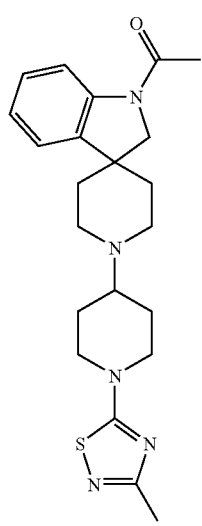
975
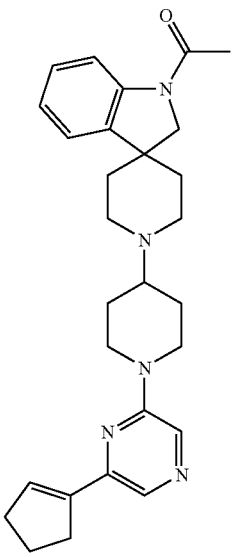
976
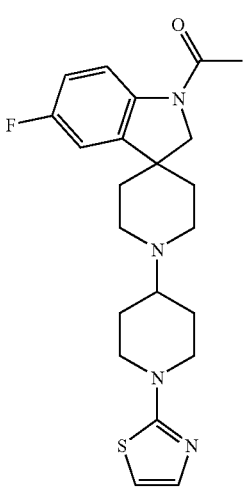
992
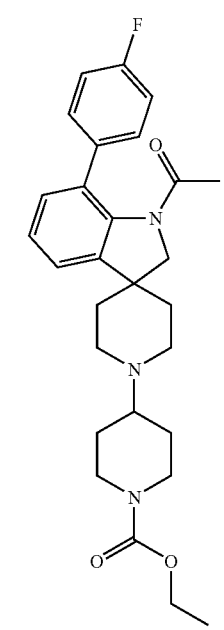

| 987 | 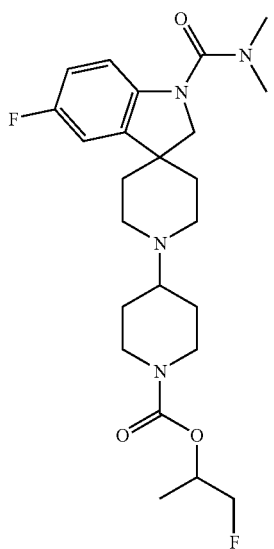 | 990 | 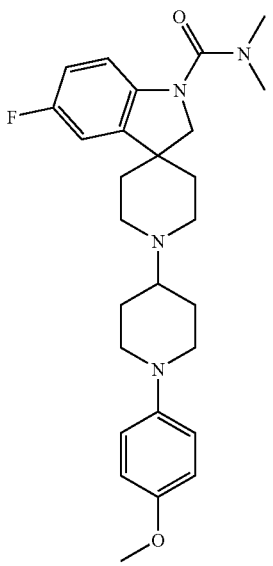 |
| 988 | 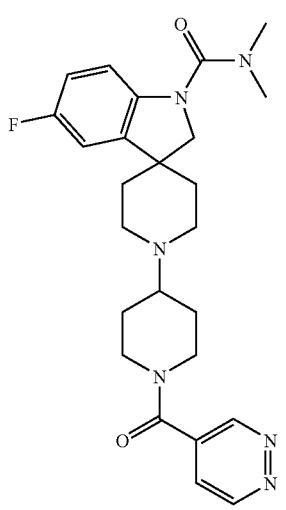 | 991 | 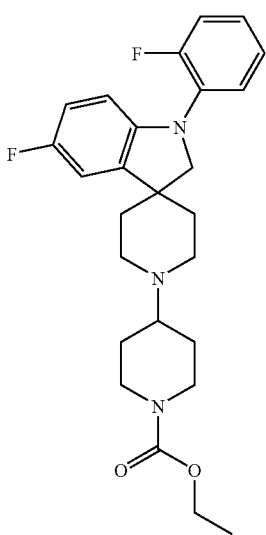 |
| 989 | 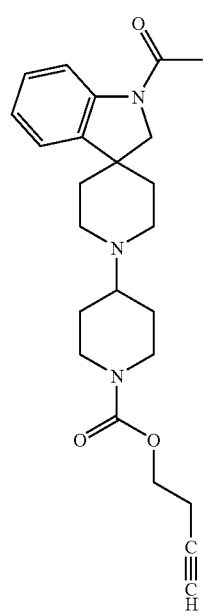 | 995 | 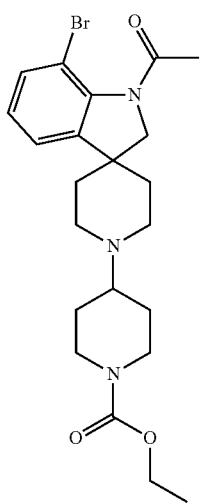 |

693
-continued
1000
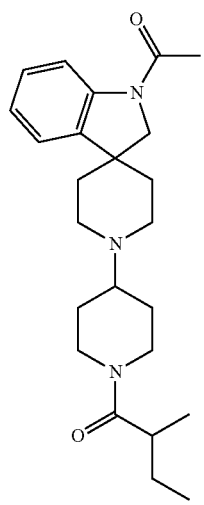
1004
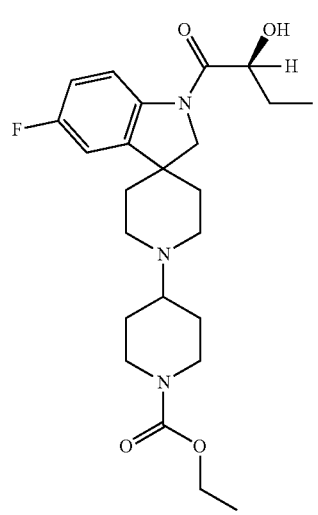
1018
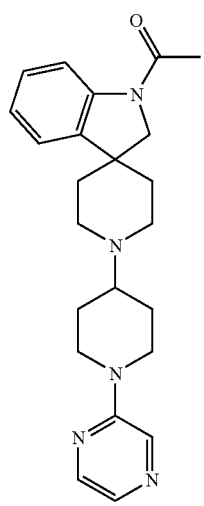
694
-continued
1019
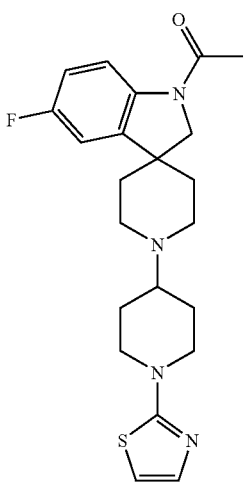
1006
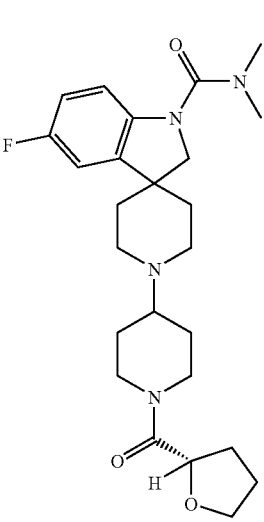
1021
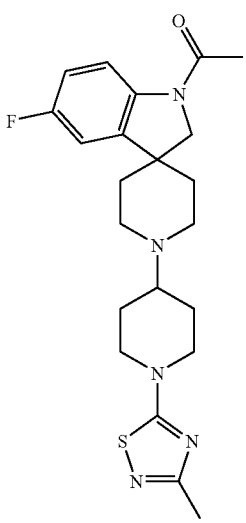

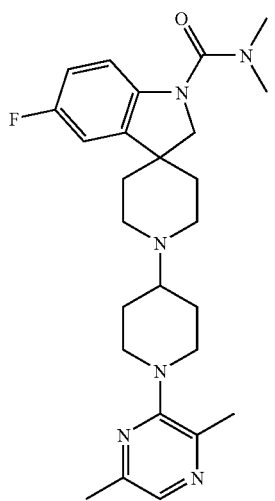
1022
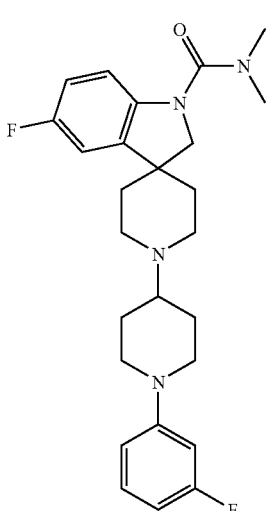
1025
1023
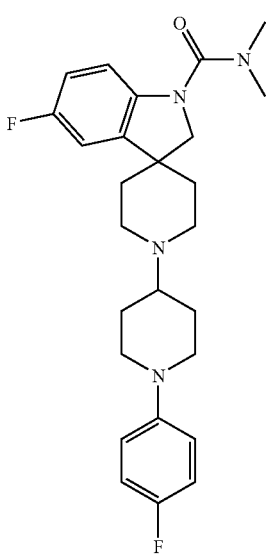
1026
1024
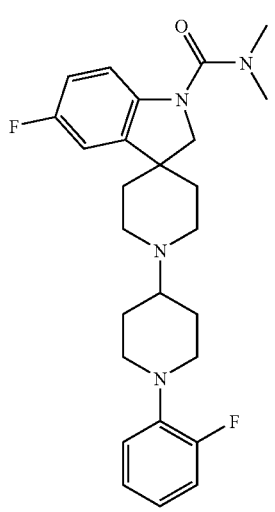
1027

| 1028 | 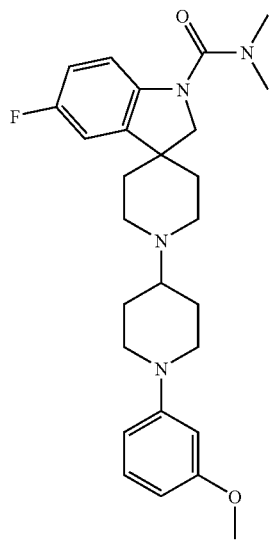 | 1031 | 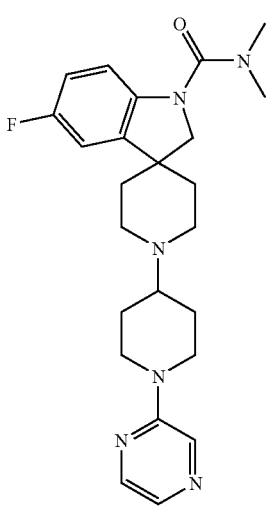 |
| 1029 | 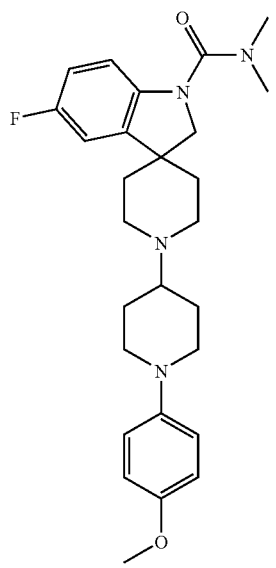 | 1032 | 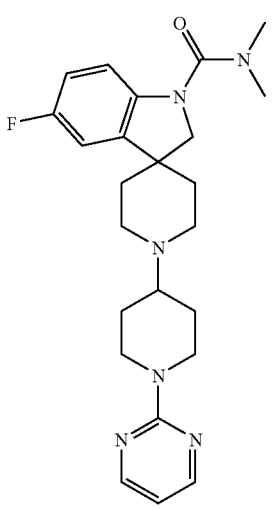 |
| 1030 | 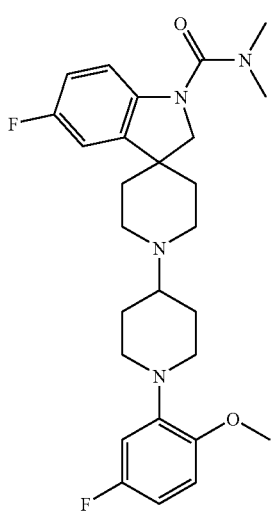 | 1033 | 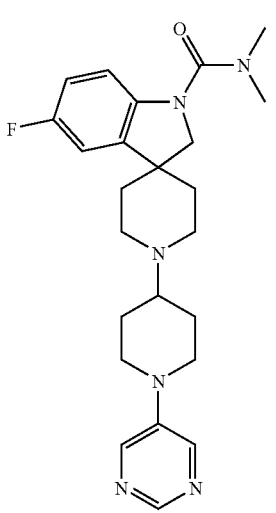 |

1034 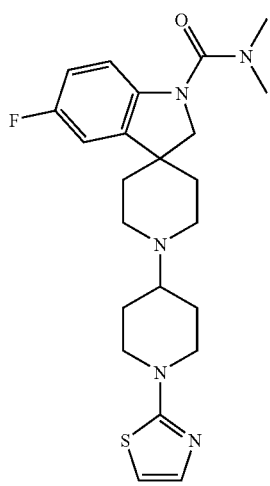

1039 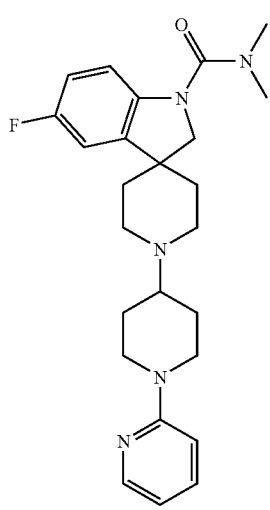

1040 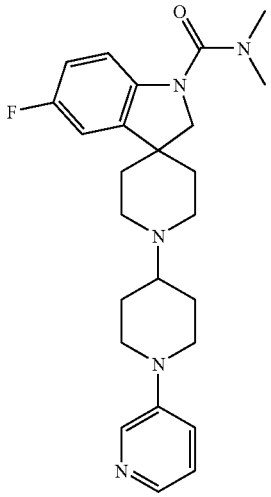

1041 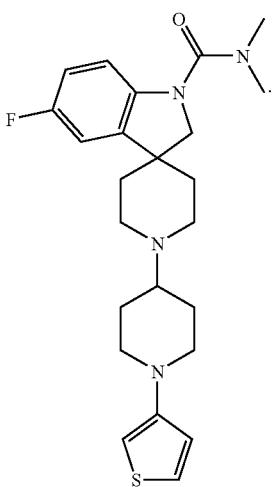

4. The method of claim 3, wherein the compound selectively modulates the $M_1$ or $M_4$ muscarinic receptor.

5. A method of treating or reducing the severity of a disease or condition in a patient, wherein said disease or condition is selected from Attention Deficit Hyperactivity Disorder (ADHD), schizophrenia, pain, Parkinson's disease, and Glaucoma, wherein said method comprises the step of contacting said patient with a compound as described in claim 3.

* * * * *